US006770259B2

(12) United States Patent
Carpenter, Jr.

(10) Patent No.: US 6,770,259 B2
(45) Date of Patent: Aug. 3, 2004

(54) SIMULTANEOUS DUAL ISOTOPE IMAGING OF CARDIAC PERFUSION AND CARDIAC INFLAMMATION

(75) Inventor: Alan P. Carpenter, Jr., Carlisle, MA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 42 days.

(21) Appl. No.: 10/002,359

(22) Filed: Nov. 2, 2001

(65) Prior Publication Data

US 2003/0003049 A1 Jan. 2, 2003

Related U.S. Application Data

(60) Provisional application No. 60/245,554, filed on Nov. 3, 2000.

(51) Int. Cl.$^7$ .............................................. A61K 49/00
(52) U.S. Cl. ...................... 424/9.1; 424/1.11; 424/1.65; 534/14
(58) Field of Search ............................... 424/1.11, 1.65, 424/9.1, 9.3, 9.4, 9.5, 9.6, 9.7, 9.8; 534/7; 562/10–16, 606; 554/1

(56) References Cited

U.S. PATENT DOCUMENTS

| 4,204,870 A | 5/1980 | Chapman et al. ........... 430/213 |
| 4,803,297 A | 2/1989 | Levenson et al. ........... 560/159 |
| 4,926,869 A | 5/1990 | Rubin et al. ................. 128/654 |
| 4,988,827 A | 1/1991 | Bergstein et al. ........... 549/451 |
| 5,281,704 A | 1/1994 | Love et al. ................... 540/465 |
| 5,376,356 A | 12/1994 | Morgan, Jr. ................. 424/1.41 |
| 5,412,148 A | 5/1995 | Keana ........................... 560/35 |
| 5,417,959 A | 5/1995 | Wallace ..................... 424/9.363 |
| 5,567,411 A | 10/1996 | Keana et al. ................. 434/9.1 |
| 5,679,810 A | 10/1997 | Love et al. ..................... 556/1 |
| 5,739,789 A | 4/1998 | Kronhamn .................. 342/465 |
| 5,744,120 A | 4/1998 | Edwards et al. ............ 424/1.64 |
| 5,750,088 A | 5/1998 | Sworin et al. .............. 424/1.69 |
| 5,760,191 A | 6/1998 | Snow et al. ................... 534/10 |
| 5,801,228 A | 9/1998 | Hollister et al. .............. 434/15 |
| 5,804,161 A | 9/1998 | Long et al. ................. 424/9.42 |

FOREIGN PATENT DOCUMENTS

| EP | 0 727 225 A2 | 8/1996 |
| WO | WO 83/03761 | 11/1983 |
| WO | WO 91/14460 | 10/1991 |
| WO | WO 92/04321 | 3/1992 |
| WO | WO 92/17215 | 10/1992 |
| WO | WO 93/15066 | 8/1993 |
| WO | WO 93/15067 | 8/1993 |
| WO | WO 94/22496 | 10/1994 |
| WO | WO 95/15956 | 6/1995 |

OTHER PUBLICATIONS

Barret et al (May 1998), Journal of Nuclear Medicine, vol. 39, No. 5, Suppl., pp. 215P.*

Arora, S.K. et al., "Preparation and biological evaluation of a potential photoaffinity lable for the prostaglandin H2/Thromboxane A2 receptor", J. Med. Chem., 1987, 30, 918–924.

Bertozzi, C. R. et al., "The synthesis of heterobifunctional linkers for the conjugation of ligands to molecular probes", J. Org. Chem., 1991, 56, 4326–4329.

Brooks, C. et al., "Modulators of leukotriene biosynthesis and receptor activation" J. Med Chem., 1996, 39, 2629–2654.

Cerqueira, M.D. et al., "Noninvasive arterial thrombus imaging with 99m Tc monoclonal antifibrin antibody", Circulation, 1992, 85(1), 298–304.

Chumpraidit, S. et al., "Synthesis and resolution of (+)-7-chloro-8-hydroxy-1(3'-iodophenyl)-3-methyl-2,3, 4,5-tetrahydro-1H-3-benzazepine(TISCH): A high affinity and selective iodinated ligand for CNS D1 dopamine receptor", J. Med Chem, 1991, 34, 877–883.

Chumpraidt, S. et al., "(+)-7-Chloro-8-hydroxy-1-(4'-[125I]iodophenyl)-3-methyl-2,3,4, 5-terahydro-1H-3-benz-azepine: A potential CNS D-1 dopamine receptor imaging agent", J. Med Chem, 1989, 32, 1431–1435.

Cohen, N. et al., "Recent progress in the development of leukotriene B4 antagonists" Curr. Opin. Invest. Drugs, 1994, 3, 13–22.

Cohen, et al., "Benzenepropanoic acids containing chromaanone or naphthalenone moieties are potent and orally active leukotriene B4 antagonists" Bioorg & Med. Chem. Lett., 1994, 4, 2883–2888.

Dean, R.T. et al., "Technetium (Tc–99m) labeled genetically engineered chimeric 17–1A G4K/Metallothionein antibody", J. Nucl. Med., 1989, 36$^{th}$ Ann. Meet. Soc. Nucl. Med., 30(5), 794.

Djuric, S.W. et al., "The leukotriene B4 receptor antagonists–A most discriminating class of antiinflammatory agent", Drugs of the Future, 1992, 17, 819–830.

Ellis, J. et al., "Synthesis of some new iodoquinolines", Aust J. Chem., 1973, 26, 907–11.

(List continued on next page.)

Primary Examiner—Dameron L. Jones
(74) Attorney, Agent, or Firm—Warren K. Volles; Paul D. Golian; Woodcock Washburn LLP

(57) ABSTRACT

The present invention provides novel diagnostic compositions comprising a radiolabeled LTB4 binding agent and a radiolabeled perfusion imaging agent, diagnostic kits comprising such compositions, and methods of concurrent imaging in a mammal comprising administering a radiolabeled LTB4 binding agent and a radiolabeled perfusion imaging agent, and concurrently detecting the radiolabeled LTB4 binding agent bound at the LTB4 receptor and the radiolabeled perfusion imaging agent.

49 Claims, No Drawings-

OTHER PUBLICATIONS

Epps, L.A. et al., "Technetium (Tc–99m) labeled genetically engineered chimeric 17–1A G4K/Metallothionein antibody", *J. Nucl. Med.,* 1989, 36th *Ann. Meet. Soc. Nucl. Med.,* 30(5), 794.

Fischman, A.J. et al., "Infection imaging with technetium–99–m–labeled chemotactic peptide analogs", *Semin. Nucl. Med.,* 1994, 154–168.

Fritzberg, A. R. et al., "Specific and stable labeling of anitbodies with technetium–99m with a diamide dithiolate chelating agent", *Proc. Natl Acad. Sci. U.S.A.,* 1988, 85, 4025–4029.

Harper, R.W. et al., "Leukotriene B4 (LTB4)receptor antagonist: A series of (Hydroxyphenyl) pyrazoles", *J. Med. Chem.,* 1994, 37, 2411–2420.

Harris, T.D. et al., "Tc–99m–Labeled fibrinogen receptor antagonists:Design and synthesis of cyclic rgd peptides for the detection of thrombi", *Bioorg. Med. Chem. Lett.,* 1996, 6, 1741–1746.

Hillel, P.G. et al., "The use of dual–isotope imaging to compare the gastrointestinal transit of food and pancreatic enzyme pellets in cystic fibrosis patients", *Nucl Med Commun.,* 1998, 19, 761–769.

Kabalka, G.W. et al., "Synthesis of iodine–125 labelled aryl and vinyl iodides", *J. Label. Compound. Radiopharm.,* 1982, 19, 795–799.

Koch, K. et al., "(+)–1–(3S,4R)–[3–(4–Phenylbenzyl)–4–hydroxychroman–7–y1]cyclopentane carboxylic acid, a highly potent, selective leukotriene B4 antagonist with oral activity in the murine collagen–induced arthritis model", *J. Med. Chem.,* 1994, 37, 3197–3199.

Labaudiniere, R. et al., "w–[(4,6–Diphenyl–2–pyridyl)oxy] alkanoic acid derivatives: A new family of potent and orally active LTB4 antagonists", *J. Med. Chem.,* 1992, 35, 4315–4324.

Larcheveque, M. et al., *Bull. Soc. Chim. Fr.,* 1974, 1710–1714 (English Language abstract not available).

Merkushev, E.B., "Advances in the synthesis of iodoaromatic compounds" *Synthesis,* 1988, 923–937.

Morin, C. et al., "Synthesis of a spermidine–derived conjugating agent", *Tetrahedron,* 1992, 48, 9277–9282.

Pak, K.Y. et al., "A rapid and efficient method for labeling IgG anti–bodies with Tc–99m and comparison to Tc–99m FAB' antibody fragments", *J. Nucl. Med.,* 1989, 36th *Ann. Meet. Soc. Nucl. Med.,* 30(5), 793.

Petter, R.C. et al., "Cooperative binding by aggregated mono–6–(alkylamino)–β–cyclodextrins", *J. Am. Chem. Soc.,* 1990, 112, 3860–3868.

Sawyer, J.S. et al., "Synthetic and structure/activity studies on acid–substituted 2–arylphenols: Discovery of 2–[2–Propyl–3[3–[2–ethyl–4(4–flurophenyl)–5–hydroxyphen oxy]–propoxy]phenoxy]benzoic Acid, a high–affinity leukotriene B4 receptor antagonist", *J. Med Chem,* 1995, 38, 4411–32.

Wilbur, D.S. et al., "Radiohalogenation of non activated aromatic compounds via aryltrimethtysilyl intermediates", *J. Label. Compound. Radiopharm,* 1982, 19, 1171–1188.

Eckart, K., et al., "Monitoring and optimization of deprotection reactions of peptides by direct sampling with fast atom bombardment mass spectrometry", *J. Org. Chem.,* 1986, 51, 483–486.

Wolf, C. et al., "Synthesis of Radiopharmaceuticals and labelled compounds using short–lived isotopes", *Radiopharmaceuticals and Labeled Compounds,* 1973, Vol 1, 345–381.

\* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence

<400> SEQUENCE: 1

Gly Lys Lys Lys
1

SIMULTANEOUS DUAL ISOTOPE IMAGING OF CARDIAC PERFUSION AND CARDIAC INFLAMMATION

This application claims benefit of provisional application No. 60/245,554, filed Nov. 3, 2000.

FIELD OF THE INVENTION

The present invention provides novel radiopharmaceuticals useful for the diagnosis of infection and inflammation, reagents and kits useful for preparing the radiopharmaceuticals, methods of imaging sites of infection and/or inflammation in a patient, and methods of diagnosing diseases associated with infection or inflammation in patients in need of such diagnosis. The radiopharmaceuticals bind in vivo to the leukotriene B4 (LTB4) receptor on the surface of leukocytes which accumulate at the site of infection and inflammation. The reagents provided by this invention are also useful for the treatment of diseases associated with infection and inflammation.

BACKGROUND OF THE INVENTION

The rapid diagnosis of diseases associated with focal infection and inflammation is a currently unmet clinical need. Inflammation is the result of the detection of an abnormality in the body, such as infection, by leukocytes. Leukocytes become activated and gravitate toward the site of the abnormality. When the leukocytes become fully activated they degranulate and release proteolytic enzymes as well as chemoattractants resulting in a chemotactic gradient and as a consequence the recruitment of additional leukocytes. The result is a concentration of activated leukocytes at the site. This localization provides a means for diagnosing diseases associated with infection and inflammation through the use of leukocytes labeled with an externally detectable radioisotope and gamma scintigraphy.

Two approaches have been taken to utilize this mechanism for imaging infection and inflammation. The first involves isolating leukocytes from a patient, labeling the leukocytes with a radioisotope and then reinjecting the radiolabeled autologous leukocytes into the patient. This approach has several drawbacks including the effect of the labeling methodology on the biological activity of the leukocytes manifest as a diminished number of competent leukocytes, and the hazards and inconvenience of handling the patient's blood. The second approach involves injecting into the patient a radiopharmaceutical that binds to activated leukocytes in vivo.

An example of the in vivo labeling approach is the use of radiolabeled monoclonal antibodies or fragments thereof that are directed against a leukocyte activation marker, as described in Morgan, Jr., U.S. Pat. No. 5,376,356. A leukocyte activation marker is an antigen on the surface of the leukocyte that is poorly expressed or not expressed at all until activation of the leukocyte. This approach suffers from the disadvantages associated with the use of many proteinaceous radiopharmaceuticals as diagnostics, namely, generally slow blood clearance which results in high background activity unless an inconveniently long period of time is allowed to pass between injection and imaging, and the possibility of an allergic reaction by the patient to a foreign protein.

It has been proposed that these problems can be overcome by using radiolabeled peptides that bind in vivo to surface receptors on activated leukocytes (Fischman et. al., Semin. Nucl. Med., 1994, 24, pp 154–168). The chemotactic peptide, fMLF, labeled with In-111 or Tc-99m have been shown to accumulate at sites of infection in experimental animal models. However, the peptide fMLF is a potent agonist for the leukocytes and thus has limited clinical applicability in a diagnostic radiopharmaceutical. The limitations include the potential for serious deleterious effects to the patient, such as a severe drop in white blood cell count, resulting from the activation of the leukocytes upon injection of even small amounts of the potent agonist peptide.

Another alternative approach has been described by Rubin et. al. in U.S. Pat. No. 4,926,869 involving the use of a radiolabeled immunoglobulin or fragment thereof. The immunoglobulin accumulates at the site of infection or inflammation by a non-specific mechanism attributed to the leakage of labeled immunoglobulin from the circulation into the greatly expanded protein space at the site. However, this approach suffers from the same disadvantages associated with the use of a proteinaceous substance as described above.

Therefore, there remains a need for new radiopharmaceuticals for imaging infection and inflammation that have improved pharmacokinetics, especially faster blood clearance, and do not cause serious side-effects in patients.

Leukotriene B4 (LTB4) is synthesized from arachidonic acid by the action of 5-lipoxygenase and leukotriene A4 hydrolase. LTB4 is released by polymorphonuclear leukocytes (PMN), macrophages, mast cells, basophils and monocytes with each cell type having an LTB4 surface receptor. Endothelial cells, eosinophils and platelets do not generate LTB4. The binding of LTB4 to its surface receptor promotes chemotaxis in PMN's, macrophages and eosinophils. It also induces PMN aggregation, adherence of PMNs to vascular endothelium and PMN diapedesis.

LTB4 in conjunction with PMN, macrophages, mast cells, basophils and monocytes has been implicated in a variety of diseases which involve undesirable inflammatory responses in diverse tissues, including infection, tissue injury and transient ischemia. In the case of reperfusion injury and transplant rejection, LTB4 together with PMN, macrophages and mast cells have been causally demonstrated to play a major role in the inflammatory processes associated with these phenomena. In addition, LTB4 in conjunction with PMN, macrophages, mast cells, basophils plays a pivotal role in the development of inflammatory bowel disease. Colonic mucosal scrapings from inflammatory bowel disease patients generate 6 fold more LTB4 than from corresponding normal subjects. Thus a radiopharmaceutical which binds to the LTB4 receptor at sub-therapeutic levels should be able to rapidly detect inflammatory disease processes throughout the body.

In the present invention it has been found that radiopharmaceuticals capable of binding to the LTB4 receptor are useful for imaging sites of infection and inflammation.

SUMMARY OF THE INVENTION

The present invention provides novel radiopharmaceuticals useful for the diagnosis of infection and inflammation, reagents and kits useful for preparing the radiopharmaceuticals, methods of imaging sites of infection and/or inflammation in a patient, and methods of diagnosing diseases associated with infection or inflammation in patients in need of such diagnosis. The radiopharmaceuticals bind in vivo to the leukotriene B4 (LTB4) receptor on the surface of leukocytes which accumulate at the site of infection and inflammation. The reagents of this invention are also useful in the treatment of diseases associated with infection and inflammation.

The radiopharmaceuticals of the present invention are small molecules and so do not suffer from the disadvantages associated with radiolabeled proteins or antibodies. As antagonists, the radiopharmaceuticals have significantly diminished risk of producing side-effects. The radiopharmaceuticals of the present invention have utility in the rapid detection of inflammatory or infectious diseases such as inflammatory bowel, fever of unknown origin, reperfusion injury and transplant rejection. The reagents of this invention are useful in the treatment of diseases associated with infection and inflammation.

The present invention also provides for novel dual isotope imaging methods utilizing LTB4-targeted imaging reagents in combination with perfusion imaging radiopharmaceuticals, such as cardiac or brain perfusion agents. The combination of imaging agents in the simultaneous dual isotope imaging method of this invention is useful for the concurrent imaging of organ blood flow and sites of inflammation which may be associated with disease processes such as reperfusion injury, atherosclerosis or infection in the organ of interest.

DETAILED DESCRIPTION OF THE INVENTION

[1] In an embodiment, the present invention provides a method of concurrent imaging in a mammal comprising:
  a) administering to said mammal a radiolabeled LTB4 binding agent and a radiolabeled perfusion imaging agent; and
  b) concurrently detecting the radiolabeled LTB4 binding agent bound at the LTB4 receptor and the radiolabeled perfusion imaging agent;
wherein said radiolabeled agents have spectrally separable energies.

[2] In an embodiment, the present invention provides a method according to embodiment [1] for use in concurrent imaging sites of inflammation and organ perfusion.

[3] In an embodiment, the present invention provides a method according to embodiment [1] for use in diagnosing and localizing sites of inflammation and perfusion abnormalities.

[4] In an embodiment, the present invention provides a method according to embodiment [1] for use in concurrent detection and localization of sites of ischemic tissue injury and perfusion abnormalities.

[5] In an embodiment, the present invention provides a method according to embodiment [1] for use in concurrent detection and localization of sites of ischemic tissue injury (e.g. reperfusion injury), vulnerable plaque, bacterial endocarditis or cardiac transplant rejection.

[6] In an embodiment, the present invention provides a method according to embodiment [1] for use in the concurrent detection and localization of sites of vulnerable plaque and perfusion abnormalities.

[7] In an embodiment, the present invention provides a method according to embodiment [1] for use in the concurrent detection and localization of sites of cardiac infection and perfusion abnormalities.

[8] In an embodiment, the present invention provides a method according to embodiment [1] for use in the concurrent detection and localization of sites of cardiac transplant rejection and perfusion abnormalities.

[9] In an embodiment, the present invention provides a method according to embodiment [1] wherein the method of detecting the radiolabeled agents is by scintigraphic imaging.

[10] In an embodiment, the present invention provides a method according to embodiment [1] wherein the method of detecting the radiolabeled agents is by radiation detecting probe.

[11] In an embodiment, the present invention provides a method according to embodiment [1] wherein the method of detecting the radiolabeled agents is by planar or ring gamma camera.

[12] In an embodiment, the present invention provides a method according to embodiment [1] wherein administering said radiolabeled LTB4 binding agent and radiolabeled perfusion imaging agent is concurrent.

[13] In an embodiment, the present invention provides a method according to embodiment [1] wherein administering said radiolabeled LTB4 binding agent and radiolabeled perfusion imaging agent is sequential.

[14] In an embodiment, the present invention provides a method according to embodiment [1] wherein the radiolabeled LTB4 binding agent is administered in a synergystically effective amount.

[15] In an embodiment, the present invention provides a method according to embodiment [1] wherein detecting the radiolabeled LTB4 binding agent and the radiolabeled perfusion imaging agent is enhanced to afford improved accuracy of the image registration.

[16] In an embodiment, the present invention provides a method according to embodiment [1] wherein the energies of the radiolabeled agents are spectrally separable by pulse-height analysis.

[17] In an embodiment, the present invention provides a method according to embodiment [1] wherein the difference in spectral energies of the radiolabeled agents is >10 Kev.

[18] In an embodiment, the present invention provides a method of any one of embodiments [1–17] wherein the radiolabeled LTB4 binding agent is radiolabeled with a radioisotope selected from the group consisting of $^{99m}$Tc, $^{111}$In, $^{95}$Tc, $^{62}$Cu, $^{67}$Ga, $^{68}$Ga, $^{123}$I, $^{125}$I, $^{18}$F, $^{11}$C, $^{13}$N, 15O, and 75Br.

[19] In an embodiment, the present invention provides a method of any one of embodiments [1–17] wherein the LTB4 binding agent is radiolabeled with In-111 Tc-99m or I-123.

[20] In an embodiment, the present invention provides a method of any one of embodiments [1–17] wherein the perfusion imaging agent is radiolabeled with Tc-99m or Tl-201.

[21] In an embodiment, the present invention provides a method of any one of embodiments [1–17] wherein the perfusion imaging agent is hexakis methoxyisobutyl isonitrile Technetium(I) ($^{99m}$Tc-Sestamibi), $^{210}$Tl, $^{99m}$Tc-tetrofosmin, $^{99m}$Tc-furifosmin, or $^{99m}$Tc-NOET.

[22] In an embodiment, the present invention provides a method of any one of embodiments [1–17] wherein the radiolabeled LTB4 binding agent is a reagent capable of direct transformation into a compound radiolabeled with a radioisotope selected from the group consisting of $^{99m}$Tc, $^{111}$In, $^{95}$Tc, $^{62}$Cu, $^{67}$Ga, and $^{68}$Ga and said reagent having the formula:

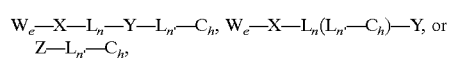

wherein, $W_e$ is selected from the group:

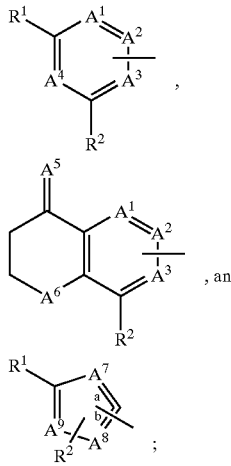

wherein, $A^1$ is N, C—OH, or CH;
$A^2$ and $A^3$ are independently N or CH;
$A^4$ is N or $CR^3$;
$A^5$ is O or S;
$A^6$ is O, $CH_2$, or S;
$A^7$ is C—OH, N, NH, O or S;
$A^8$ is NH, $CH_2$, O, S, N, or CH;
$A^9$ is N or CH;
a and b indicate the alternative positions of a double bond;
$R^1$ is selected from the group: H, —C(=NH)NH$_2$, $C_1$–$C_6$ alkyl substituted with 0–3 $R^4$, $C_1$–$C_6$ alkoxy substituted with 0–3 $R^4$, aryl substituted with 0–3 $R^5$, and heterocycle substituted with 0–3 $R^5$;
$R^2$ is selected from the group: H, $C_1$–$C_3$ alkyl, $C_2$–$C_3$ alkenyl, cyclopropyl, cyclopropylmethyl, and aryl substituted with 0–3 $R^5$;
$R^3$ is —H, —OH or $C_1$–$C_3$ alkoxy;
or alternatively, $R^1$ and $R^3$ can be taken together with the atoms to which they are attached to form a fused phenyl ring substituted with 0–3 $R^5$;
$R^4$ is independently selected from the group: —F, —Cl, —Br, —I, =O, —N($R^6$)($R^7$), and —CF$_3$;
$R^5$ is independently selected from the group: —F, —Cl, —Br, —I, —N($R^6$)($R^7$), —CF$_3$, $C_1$–$C_3$ alkyl, $C_1$–$C_3$ alkoxy, and methylenedioxy;
$R^6$ and $R^7$ are independently H or $C_1$–$C_3$ alkyl; provided that when $A^1$ and $A^2$ are CH, $A^3$ is C—X, and $A^4$ is $CR^3$, $R^1$ is selected from the group: $C_1$–$C_5$ alkyl substituted with 1–3 $R^4$, $C_1$–$C_5$ alkoxy substituted with 0–3 $R^4$, and aryl substituted with 0–3 $R^5$;
X is O, S, $CH_2$ or CH=CH;
$L_n$ is a linking group having the formula

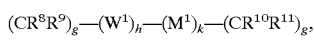

wherein, $R^8$, $R^9$, $R^{10}$ and $R^{11}$ are independently selected at each occurrence from the group: a bond to $L_{n'}$, H, $C_1$–$C_5$ alkyl, and $C_1$–$C_5$ alkoxy, or alternatively, $R^8$ and $R^9$ or $R^{10}$ and $R^{11}$ may be taken together to form a 3–6 membered cycloalkyl or heterocycle;
$W^1$ is independently selected from the group: O, S, C(=O)O, OC(=O), CH=CH, (OCH$_2$CH$_2$)$_p$ and (CH$_2$CH$_2$O)$_{p'}$, wherein p and p' are independently 1–3;

$M^1$ is selected from the group: phenyl substituted with 0–3 $R^{12}$, heterocycle substituted with 0–3 $R^{12}$, benzophenone substituted with 0–3 $R^{12}$, and diphenylether substituted with 0–3 $R^{12}$;
$R^{12}$ is independently selected from the group: a bond to $L_{n'}$, —COOR$^{13}$, $C_1$–$C_5$ alkyl substituted with 0–3 $R^{14}$, and $C_1$–$C_5$ alkoxy substituted with 0–3 $R^{14}$;
$R^{13}$ is H or $C_1$–$C_5$ alkyl;
$R^{14}$ is independently selected from the group: a bond to $L_{n'}$, and —COOH;
g is 0–10;
h is 0–3;
k is 0–1;
g' is 0–5;
provided that when h is 0 and k is 0, g is >1;
and provided that when $W^1$ is O or S and k is 0, g+g' is >1;
Y is selected from C(=O)NH, NHC(=O), C=O, C(=O)O, OC(=O), NHS(=O)$_2$, C(=O)NHS(=O)$_2$, COOH, C(=O)NH$_2$, NH(C=O)NH, or tetrazole;
provided that from 0–1 of $R^9$, $R^{10}$, $R^{11}$, $R^{12}$, and $R^{14}$ is a bond to $L_{n'}$ and when one of these variables is a bond to $L_{n'}$, then Y is COOH, C(=O)NH$_2$, or tetrazole;
$L_{n'}$ is a linking group having the formula:

wherein, $W^2$ is independently selected at each occurrence from the group: O, S, NH, NHC(=O), NHC(=O)M$^2$, C(=O)NH, C(=O), C(=O)O, OC(=O), NHC(=O)NH, SO$_2$, (OCH$_2$CH$_2$)s, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$, wherein aa is independently at each occurrence an amino acid, and s, s', s'', t, and ' are independently 1–10;
$M^2$ is selected from the group: aryl substituted with 0–3 $R^{19}$, cycloalkyl substituted with 0–3 $R^{19}$, and heterocycle substituted with 0–3 $R^{19}$;
$R^{15}$, $R^{16}$, $R^{17}$ and $R^{18}$ are independently selected at each occurrence from the group: =O, COOH, SO$_3$H, PO$_3$H, $C_1$–C5 alkyl substituted with 0–3 $R^{19}$, aryl substituted with 0–3 $R^{19}$, benzyl substituted with 0–3 $R^{19}$, and $C_1$–$C_5$ alkoxy substituted with 0–3 $R^{19}$, NHC(=O)R$^{20}$, C(=O)NHR$^{20}$, NHC(=O)NHR$^{20}$, NHR$^{20}$, $R^{20}$, and a bond to $C_h$;
$R^{19}$ is independently selected at each occurrence from the group: COOR$^{20}$, OH, NHR$^{20}$, SO$_3$H, PO$_3$H, aryl substituted with 0–3 $R^{20}$, heterocycle substituted with 0–3 $R^{20}$, $C_1$–$C_5$ alkyl substituted with 0–1 $R^{21}$, $C_1$–$C_5$ alkoxy substituted with 0–1 $R^{21}$ and a bond to $C_h$;
$R^{20}$ is independently selected at each occurrence from the group: H, aryl substituted with 0–1 $R^{21}$ heterocycle substituted with 0–1 $R^{21}$ cycloalkyl substituted with 0–1
$R^{21}$ polyalkylene glycol substituted with 0–1 $R^{21}$ carbohydrate substituted with 0–1 $R^{21}$ cyclodextrin substituted with 0–1 $R^{21}$ amino acid substituted with 0–1
$R^{21}$ polycarboxyalkyl substituted with 0–1 $R^{21}$, polyazaalkyl substituted with 0–1 $R^{21}$, peptide substituted with 0–1 $R^{21}$, wherein said peptide is comprised of 2–10 amino acids, and a bond to $C_h$;
$R^{21}$ is a bond to $C_h$;
k' is 0–2;
h' is 0–2;

h" is 0–5;

h'" is 0–2;

g" is 0–10;

g'" is 0–10;

$C_h$ is a metal bonding unit having a formula selected from the group:

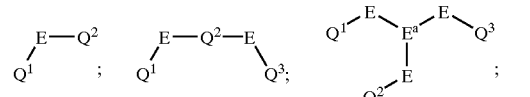
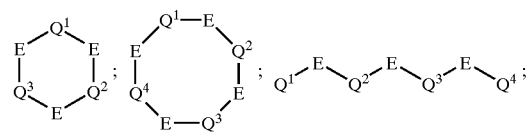
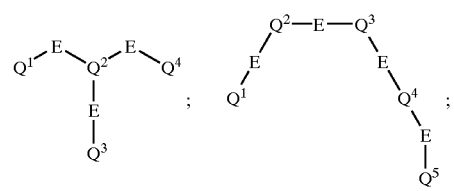
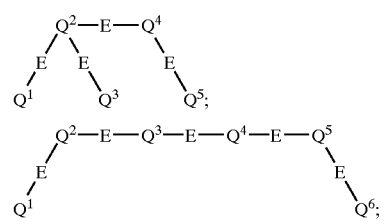
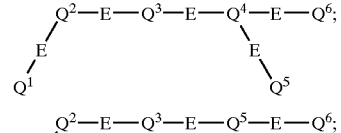
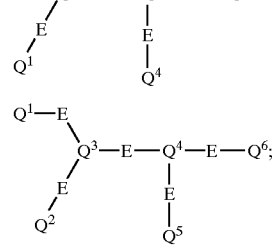
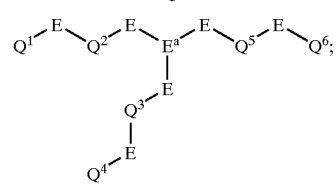
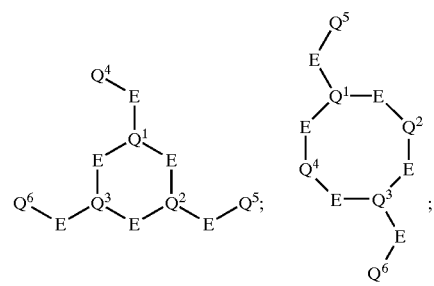

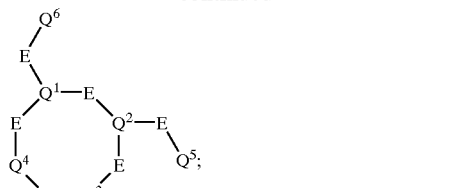
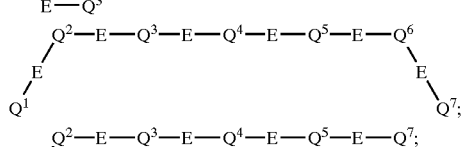
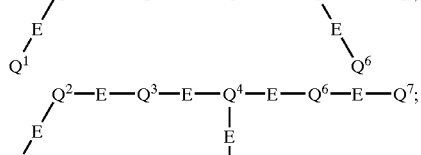
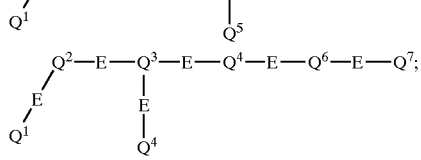
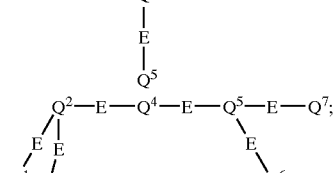
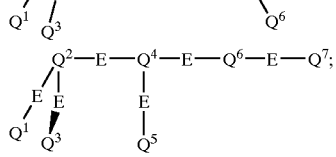
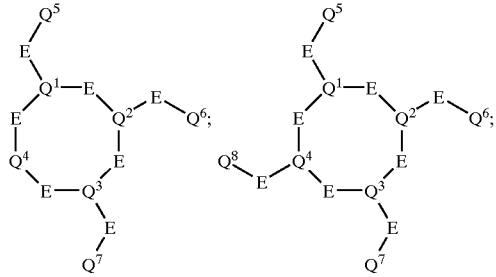

wherein:

$Q^1$, $Q^2$, $Q^3$, $Q^4$, $Q^5$, $Q^6$, $Q^7$, and $Q^8$ are independently selected at each occurrence from the group: $NR^{22}$, $NR^{22}R^{23}$, S, SH, O, OH, $PR^{22}$, $PR^{22}R^{23}$, $P(NR^{24})R^{25}R^{26}$, $P(O)R^{25}R^{26}$, and $P(S)R^{25}R^{26}$;

E is a bond, CH, or a spacer group selected from the group: $C_1$–$C_{10}$ alkyl substituted with 0–3 $R^{27}$, aryl substituted with 0–3 $R^{27}$, cycloalkyl substituted with 0–3 $R^{27}$, heterocycloalkyl substituted with 0–3 $R^{27}$, aralkyl substituted with 0–3 $R^{27}$, and alkaryl substituted with 0–3 $R^{27}$;

$E^a$ is a $C_1$–$C_{10}$ alkyl group or a $C_3$–$C_{14}$ carbocycle;

$R^{22}$, $R^{23}$, and $R^{24}$ are each independently selected from the group: a bond to $L_{n'}$, hydrogen, $C_1$–$C_{10}$ alkyl substituted with 0–3 $R^{27}$, aryl substituted with 0–3 $R^{27}$, cycloalkyl substituted with 0–3 $R^{27}$, heterocycloalkyl substituted with 0–3 $R^{27}$, aralkyl substituted with 0–3 $R^{27}$, alkaryl substituted with 0–3 $R^{27}$, heterocycle substituted with 0–3 $R^{27}$, and an electron, provided that when one of $R^{22}$ or $R^{23}$ is an electron, then the other is also an electron;

$R^{25}$ and $R^{26}$ are each independently selected from the group: a bond to $L_{n'}$, —OH, $C_1$–$C_{10}$ alkyl substituted with 0–3 $R^{27}$, $C_1$–$C_{10}$ alkyl substituted with 0–3 $R^{27}$, aryl substituted with 0–3 $R^{27}$, cycloalkyl substituted with 0–3 $R^{27}$, heterocycloalkyl substituted with 0–3 $R^{27}$, aralkyl substituted with 0–3 $R^{27}$, alkaryl substituted with 0–3 $R^{27}$, and heterocycle substituted with 0–3 $R^{27}$;

$R^{27}$ is independently selected at each occurrence from the group: a bond to $L_{n'}$, =O, F, Cl, Br, I, $CF_3$, CN, —$CO_2R^{28}$, —C(=O)$R^{28}$, —C(=O)N($R^{28}$)$_2$, —CHO, —$CH_2OR^{28}$, —OC(=O)$R^{28}$, —OC(=O)OR$^{28a}$, —OR$^{28}$, —OC(=O)N($R^{28}$)$_2$, —NR$^{29}$C(=O)$R^{28}$, —NR$^{29}$C(=O)OR$^{28a}$, —NR$^{29}$C(=O)N($R^{28}$)$_2$, —NR$^{29}SO_2$N($R^{28}$)$_2$, —NR$^{29}SO_2R^{28a}$, —$SO_3H$, —$SO_2R^{28a}$, —SR$^{28}$, —S(=O)$R^{28a}$, —$SO_2$N($R^{28}$)$_2$, —N($R^{28}$)$_2$, —NHC(=NH)NHR$^{28}$, —C(=NH)NHR$^{28}$, =NOR$^{28}$, $NO_2$, —C(=O)NHOR$^{28}$, —C(=O)NHNR$^{28}R^{28a}$, —OCH$_2CO_2$H, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{28}$, and a 5–10-membered heterocyclic ring system containing 1–4 heteroatoms independently selected from N, S, and O;

$R^{28}$, $R^{28a}$, and $R^{29}$ are independently selected at each occurrence from the group: a bond to $L_{n'}$, H, $C_1$–$C_6$ alkyl, phenyl, benzyl, $C_1$–$C_6$ alkoxy, halide, nitro, cyano, and trifluoromethyl;

Z is selected from the group:

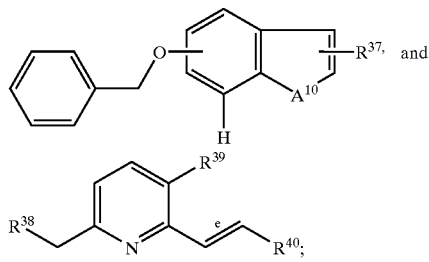

wherein, $A^{10}$ is $NR^{41}$ or —C($R^{41}$)=CH—;

$R^{37}$ is selected from the group: C(=O)—$R^{42}$, CH=CR$^{43}$C(=O)—$R^{42}$, $CH_2$C(=O)—$R^{42}$, and $CH_2CH_2$C(=O)—$R^{42}$;

$R^{38}$ is selected from the group: SR$^{44}$, SCH$_2R^{44}$, and S(=O)$R^{44}$;

$R^{39}$ is selected from the group: $C_1$–$C_{10}$ alkyl substituted with 0–3 $R^{44}$, and $C_1$–$C_{10}$ alkoxy substituted with 0–3 $R^{44}$;

$R^{40}$ is C(=O)—$R^{42}$;

$R^{41}$ is $CH_2$C(=O)N($CH_3$)$CH_2CH_2C_6H_5$;

$R^{42}$ is a bond to $L_{n'}$;

$R^{43}$ is selected from the group: H and $C_1$–$C_3$ alkyl;

$R^{44}$ is phenyl substituted with 0–4 $R^{45}$;

$R^{45}$ is independently selected at each occurrence from the group: $C_1$–$C_4$ alkyl, OR$^{46}$, C(=O)OR$^{46}$, —Cl, —Br, —F, and N($R^{46}$)$_2$;

$R^{46}$ is independently selected at each occurrence from the group: H, and $C_1$–$C_{10}$ alkyl; and e indicates the position of an optional double bond;

and pharmaceutically acceptable salts thereof.

[23] In an embodiment, the present invention provides a method according to embodiment [22] wherein:

$W_e$ is selected from the group:

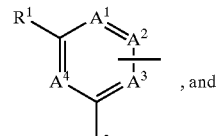, and

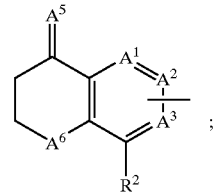;

wherein, $A^1$ is N, C—OH, or CH;

$A^2$ and $A^3$ are CH;

$A^4$ is $CR^3$;

$A^5$ is O;

$A^6$ is O or $CH_2$;

$R^4$ is independently selected from the group: —F, —Cl, =O, —N($R^6$)($R^7$), and —$CF_3$;

$R^5$ is independently selected from the group: —F, —Cl, —$CF_3$, $C_1$–$C_3$ alkyl, $C_1$–$C_3$ alkoxy, and methylenedioxy;

X is O, $CH_2$ or CH=CH;

$R^8$, $R^9$, $R^{10}$ and $R^{11}$ are independently selected at each occurrence from the group: a bond to $L_{n'}$, H, $C_1$–$C_5$ alkyl, and $C_1$–$C_5$ alkoxy;

or alternatively, $R^8$ and $R^9$ or $R^{10}$ and $R^{11}$ may be taken together to form a 3–6 membered cycloalkyl;

$C_h$ is selected from the group:

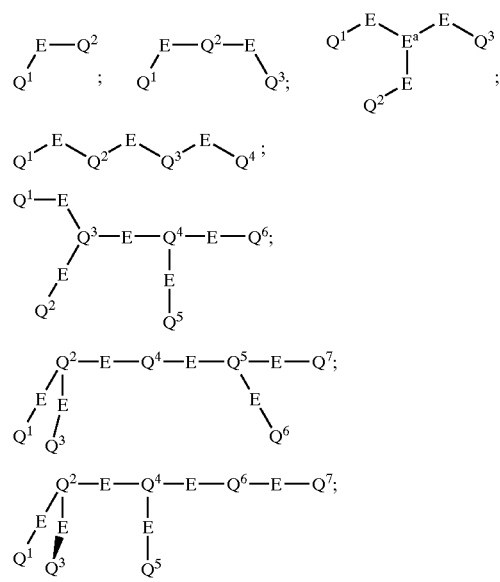

-continued

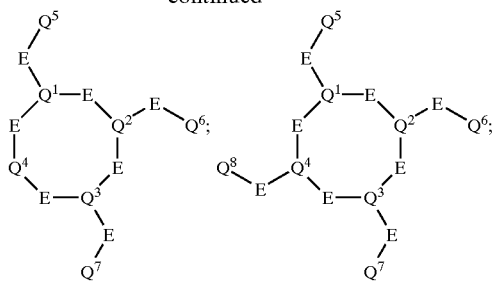

wherein:
Q$_1$, Q$^2$, Q$^3$, Q$^4$, Q$^5$, Q$^6$, Q$^7$, and Q$^8$ are independently selected at each occurrence from the group: NR$^{22}$, NR$^{22}$R$^{23}$, S, SH, OH;

E is a bond, CH, or a spacer group selected from the group: C$_1$–C$_{10}$ alkyl substituted with 0–3 R$^{27}$, aryl substituted with 0–3 R$^{27}$, cycloalkyl substituted with 0–3 R$^{27}$, and heterocycle substituted with 0–3 R$^{27}$;

E$^a$ is CH or a C$_3$–C$_6$ carbocycle;

R$^{22}$ and R$^{23}$ are each independently selected from the group: a bond to L$_{n'}$, hydrogen, C$_1$–C$_{10}$ alkyl substituted with 0–3 R$^{27}$, aryl substituted with 0–3 R$^{27}$, heterocycle substituted with 0–3 R$^{27}$, and an electron, provided that when one of R$^{22}$ or R$^{23}$ is an electron;

R$^{27}$ is independently selected at each occurrence from the group: a bond to L$_{n'}$, =O, F, Cl, Br, I, —CF$_3$, —CN, —CO$_2$R$^{28}$, —C(=O)R$^{28}$, —C(=O)N(R$^{28}$)$_2$, —CH$_2$OR$^{28}$, —OC(=O)R$^{28}$, —OC(=O)OR$^{28a}$, —OR$^{28}$, —OC(=O)N(R$^{28}$)$_2$, —NR$^{29}$C(=O)R$^{28}$, —NR$^{29}$C(=O)OR$^{28a}$, —NR$^{29}$C(=O)N(R$^{28}$)$_2$, —NR$^{29}$SO$_2$N(R$^{28}$)$_2$, —NR$^{29}$SO$_2$R$^{28a}$, —SO$_3$H, —SO$_2$R$^{28a}$, —SR$^{28}$, —S(=O)R$^{28a}$, —SO$_2$N(R$^{28}$)$_2$, —N(R$^{28}$)$_2$, —NHC(=NH)NHR$^{28}$, —C(=NH)NHR$^{28}$, =NOR$^{28}$, NO$_2$, —C(=O)NHOR$^{28}$, —C(=O)NHNR$^{28}$R$^{28a}$, —OCH$_2$CO$_2$H, and 2-(1-morpholino)ethoxy;

R$^{28}$, R$^{28a}$, and R$^{29}$ are independently selected at each occurrence from the group: a bond to L$_{n'}$, H, and C$_1$–C$_6$ alkyl;

R$^{39}$ is selected from the group: C$_1$–C$_{10}$ alkyl substituted with 0–1 R$^{44}$, and C$_1$–C$_{10}$ alkoxy substituted with 0–1 R$^{44}$;

R$^{43}$ is H; and

R$^{46}$ is independently selected at each occurrence from the group: H, and C$_1$–C$_5$ alkyl.

[24] In an embodiment, the present invention provides a reagent of Embodiment [22] wherein:

R$^1$ is selected from the group: H, —C(=NH)NH$_2$, C$_1$–C$_6$ alkyl substituted with 0–2 R$^4$, C$_1$–C$_6$ alkoxy substituted with 0–2 R$^4$, aryl substituted with 0–2 R$^5$, and heterocycle substituted with 0–2 R$^5$;

R$^3$ is —H, —OH or C$_1$–C$_3$ alkoxy;

or alternatively, R$^1$ and R$^3$ can be taken together with the atoms to which they are attached to form a fused phenyl ring substituted with 0–2 R$^5$;

R$^4$ is independently selected from the group: =O, and —N(R$^6$)(R$^7$);

R$^5$ is independently selected from the group: —F, C$_1$–C$_3$ alkyl, C$_1$–C$_3$ alkoxy, and methylenedioxy;

X is O, CH$_2$ or CH=CH;

R$^8$, R$^9$, R$^{10}$ and R$^{11}$ are independently selected at each occurrence from the group: a bond to L$_{n'}$, H, and C$_1$–C$_3$ alkyl;

or alternatively, R$^8$ and R$^9$ or R$^{10}$ and R$^{11}$ may be taken together to form a 3–6 membered cycloalkyl;

W$^1$ is O;

M$^1$ is selected from the group: phenyl substituted with 0–1 R$^{12}$, heterocycle substituted with 0–1 R$^{12}$, benzophenone substituted with 0–1 R$^{12}$, and diphenylether substituted with 0–1 R$^{12}$;

R$^{12}$ is independently selected from the group: a bond to L$_{n'}$, —COOR$^{13}$, C$_1$–C$_5$ alkyl substituted with 0–1 R$^{14}$, and C$_1$–C$_5$ alkoxy substituted with 0–1 R$^{14}$;

M$^2$ is selected from the group: aryl substituted with 0–1 R$^{19}$, cycloalkyl substituted with 0–3 R$^{19}$, and heterocycle substituted with 0–1 R$^{19}$;

C$_h$ is selected from:

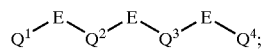

wherein,

Q$^1$ and Q$^4$ are SH;

Q$^2$ and Q$^3$ are NR$^{22}$;

E is independently selected from the group: CHR$^{27}$, CH$_2$CHR$^{27}$, CH$_2$CH$_2$CHR$^{27}$, and CHR$^{27}$C(=O);

R$^{22}$ is selected from the group: H, C$_1$–C$_6$ alkyl substituted with 0–1 R$^{27}$; and R$^{27}$ are independently selected from H and a bond to L$_{n'}$, and,

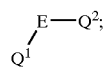

wherein

E is a bond;

Q$^2$ is NHR$^{23}$, wherein R$^{23}$ is heterocycle substituted with R$^{27}$, wherein the heterocycle is selected from pyridine and thiazole, R$^{27}$ is selected from C(=O)NHR$^{28}$ and C(=O)R$^{28}$, and R$^{28}$ is a bond to L$_{n'}$;

A$^{10}$ is NR$^{41}$;

R$^{39}$ is C$_1$–C$_{10}$ alkoxy substituted with 1 R$^{44}$; and

R$^{45}$ is independently selected at each occurrence from the group: C$_1$–C$_4$ alkyl, OH, C(=O)OH, —Cl, —F, and NH$_2$.

[25] In an embodiment, the present invention provides a method of embodiment [22] wherein the reagent is selected from the group:

4-ethyl-2-(4-fluorophenyl)-[5-[5,5-dimethyl-6-[[6-[[[(2-sulfonylphenyl)methylene]hydrazino]-3-pyridinyl]carbonyl]amino]hexyl]oxy]phenol;

4-ethyl-2-(4-fluorophenyl)-[5-[4-[[6-[[[(2-sulfonylphenyl)methylene]hydrazino]-3-pyridinyl]carbonyl]amino]butyl]oxy]phenol;

2-[[[5-[[(6-[(4,6-diphenyl-2-pyridinyl)oxy]-1-hexanamino] carbonyl]-2-pyridinyl]hydrazono]methyl]-benzenesulfonic acid;

2-[[[5-[[2,2-dimethyl-6-[(6-fluorophenyl-4-phenyl-2-pyridinyl)oxy]-1-hexanamino]carbonyl]-2-pyridinyl]hydrazono]methyl]-benzenesulfonic acid;

2-[[[5-[[N-[6-[(6-(4-fluorophenyl)-4-phenyl-2-pyridinyl)oxy]-hexanoyl]-tyrosine-O-[3-propanamino]]carbonyl]-2-pyridinyl]hydrazono]-methyl]-benzenesulfonic acid;

2-[[[5-[[N-[6-[(4,6-diphenyl-2-pyridinyl)oxy]-hexanoyl]-tyrosine-O-[3-propanamino]]carbonyl]-2-pyridinyl]hydrazono]-methyl]-benzenesulfonic acid;

2-[[[5-[[N-[6-[(4-(3,4-methylenedioxyphenyl)-6-phenyl-2-pyridinyl)oxy]-hexanoyl]-tyrosine-O-[3-propanamino]]-carbonyl]-2-pyridinyl]hydrazono]-methyl]-benzenesulfonic acid;

2-[[[5-[[alpha-N-[6-[(4,6-diphenyl-2-pyridinyl)oxy]-hexanoyl]-lysine-epsilon-N-amino]carbonyl]-2-pyridinyl]hydrazono]-methyl]-benzenesulfonic acid;

4-ethyl-2-(4-fluorophenyl)-5-[(5,5-dimethyl-6-aminohexyl)oxy]phenol N-[4-(carboxy)benzyl]-N,N'-bis[2-thioethyl]-glycinamide Conjugate;

Benzenesulfonic Acid, 2-[[[5-[[[6-[(4,6-diphenyl-2-pyridinyl)oxy]2,2-dimethyl-1-hexyl]aza]carbonyl]-2-pyridinyl]hydrazono]methyl];

2-[[[5-[[[[6-[(4,6-Diphenyl-2-pyridinyl)oxy]-hexanoyl]-4-sulfonamidyl]benzylamino]carbonyl]-2-pyridinyl]-hydrazono]methyl]-benzenesulfonic acid;

4-ethyl-2-(4-fluorophenyl)-[5-[6,6-dimethyl-7-[[6-[[[(2-sulfonylphenyl)methylene]hydrazino]-3-pyridinyl]carbonyl]amino]heptyl]oxy]phenol;

4-ethyl-2-(5-pyrazolyl)-[5-[5,5-dimethyl-6-[[6-[[[(2-sulfonylphenyl)methylene]hydrazino]-3-pyridinyl]carbonyl]amino]hexyl]oxy]phenol;

the Conjugate Between 2-[6-[(4,6-Diphenyl-2-pyridinyl)-oxy]pentyl]-6-(8-amino-5-aza-4-oxooctyloxy)-benzenepropanoic Acid and Benzenesulfonic Acid, 2-[[[5-[[(2,5-Dioxo-1-pyrrolidinyl)oxy]carbonyl]-2-pyridinyl]-hydrazono]methyl];

the Conjugate Between 6-(11-Amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid and Benzenesulfonic Acid, 2-[[[5-[[(2,5-Dioxo-1-pyrrolidinyl)oxy]carbonyl]-2-pyridinyl]-hydrazono]methyl];

4-ethyl-2-(4-fluorophenyl)-[5-[6,6-dimethyl-7-[[6-[[[phenylmethylene]hydrazino]-3-pyridinyl]carbonyl]amino]heptyl]oxy]phenol;

N-((6-(((1-aza-2-phenylvinyl)amino)(3-pyridyl))sulfonyl)-3-(1-((N-(2-phenylethyl)carbamoyl)methyl)-5-(phenylmethoxy)indol-3-yl)prop-2-enamide;

propyl 3-((7-(3-(6-ethyl-4-(4-fluorophenyl)-3-hydroxyphenoxy)propoxy)-8-propylchroman-2-yl)carbonylamino)propanoate, 2-(2-aza-2-((5-carbamoyl(2-pyridyl)amino)vinyl)benzenesulfonic acid;

3-((7-(-(6-ethyl-4-(4-fluorophenyl)-3-hydroxyphenoxy)propoxy)-8-propylchroman-2-yl)carbonylamino)propyl-2-methylpropanoate, 2-(2-aza-2((5-carbamoyl-(2-pyridyl)amino)vinyl)benzenesulfonic acid;

N-(3-((7-(3-(6-ethyl-4-(4-fluorophenyl)-3-hydroxyphenoxy)propoxy)-8-propylchroman-2-yl)carbonylamino)propyl)-2-methylpropanamide, 2-(2-aza-2-((5-carbamoyl-(2-pyridyl))amino)vinyl)benzenesulfonic acid;

2-(2-aza-2-((5-(N-(6-(6-ethyl-3-hydroxy-4-(1-methylpyrazol-5-yl)phenoxy)-22-dimethylhexyl)carbamoyl)(2-pyridyl))amino)vinyl)benzenesulfonic acid;

2-(2-aza-2-((5-(N-(6-(6-ethyl-3-hydroxy-4-(1-methylpyrazol-5-yl)phenoxy)-2,2-dimethylhexyl)carbamoyl)(2-pyridyl))amino)vinyl)benzenesulfonic acid;

2-(2-aza-2-((5-((3-((6-ethyl-4-(4-fluorophenyl)-3-hydroxyphenoxy)methyl)piperidyl)carbonyl)(2-pyridyl))amino)vinyl)benzenesulfonic acid;

2-(((4-(N-(6-(4,6-Diphenyl(2-pyridyloxy))-2,2-dimethylhexyl)carbamoyl)phenyl)methyl)(2-sulfanylethyl)amino)-N-(2-sulfanylethyl)ethanamide;

2-(2-Aza-2-((5-(N-(3-(2-(2-(3-(5-(5-(4,6-diphenyl-(2-pyridyloxy))-1,1-dimethylpentyl)(1,2,3,5-tetraazolyl)) pentanoylamino)propoxy)ethoxy)ethoxy)propyl) carbamoyl)(2-pyridyl))amino)vinyl)benzenesulfonic Acid;

2-(2-Aza-2-((5-(N-(3-(2-(2-(3-(5-(5-(4,6-diphenyl-(2-pyridyloxy))-1,1-dimethylpentyl)(1,2,3,4-tetraazolyl)) pentanoylamino)propoxy)ethoxy)ethoxy)propyl) carbamoyl)(2-pyridyl))amino)vinyl)benzenesulfonic Acid;

2-(2-Aza-2-((5-(N-(2-(2-(2-(2-(2-(2-(2-(2-(5-(4-(5-(4,6-diphenyl-(2-pyridyloxy))-1,1-dimethylpentyl)(1,2,3,5-tetraazolyl))pentanoylamino)ethoxy)ethoxy)ethoxy)ethoxy)ethoxy)ethoxy)ethoxy)ethyl)carbamoyl)(2-pyridyl))amino)vinyl)benzenesulfonic Acid;

2-(2-Aza-2-((5-(N-(5-(4-(5-(4,6-diphenyl-(2-pyridyloxy))-1,1-dimethylpentyl)(1,2,3,5-tetraazolyl)) pentanoylamino)-1-(6-deoxy-β-cyclodextryl)carbamoyl) pentyl)carbamoyl)(2-pyridyl))amino)vinyl) benzenesulfonic Acid;

2-(2-Aza-2-((5-(N-(3-(2-(2-(3-(2-(5-(5-(4,6-diphenyl-(2-pyridyloxy))-1,1-dimethylpentyl) (1,2,3,4-tetraazolyl)) acetylamino)propoxy)ethoxy)ethoxy)propyl)-carbamoyl) (2-pyridyl))amino)vinyl)benzenesulfonic Acid;

2-(2-Aza-2-((5-(N-(3-(2-(2-(3-(2-(4-(5-(4,6-diphenyl-(2-pyridyloxy))-1,1-dimethylpentyl)(1,2,3,5-tetraazolyl)) acetylamino)propoxy)ethoxy)ethoxy)propyl)-carbamoyl) (2-pyridyl))amino)vinyl)benzenesulfonic Acid;

3-(6-(3-(N-(5-((6-((1-Aza-2-(sulfophenyl)vinyl)amino)(3-pyridyl))carbonylamino)-5-(N-(ω-methoxypolyethylene-(750)glycoxyethyl)carbamoyl)pentyl) carbamoyl) propoxy)2(5-(4,6-diphenyl-(2-pyridyloxy))pentyloxy) phenyl)propanoic Acid;

3-(6-(3-(N-(3-(2-(2-(3-((6-((1-Aza-2-(2-sulfophenyl)vinyl) amino)(3-pyridyl))carbonylamino)propoxy)ethoxy) ethoxy)propyl)-carbamoyl)propoxy)2-(5-(4,6-diphenyl-(2-pyridyloxy))pentyloxy)phenyl)propanoic Acid;

3-(6-(3-(N-(5-((6-((1-Aza-2-(2-sulfophenyl)vinyl)amino) (3-pyridyl))carbonylamino)-5-(N-(2,3,4,5,6-pentahydroxyhexyl)carbamoyl)pentyl)carbamoyl) propoxy)2-(5-(4,6-diphenyl-(2-pyridyloxy))pentyloxy) phenyl)propanoic Acid;

3-(6-(3-(N-(3-((6-((1-Aza-2-(2-sulfophenyl)vinyl)amino) (3-pyridyl))carbonylamino) propyl)carbamoyl)propoxy)-2-(5-(5-oxo-1-prop-2-enyl-(2-6,7,8-trihydronaphthyloxy))pentyloxy)phenyl)propanoic Acid;

3-(6-(3-N-(2-(2-(2-(2-(2-(2-((6-((1-Aza-2-2-sulfophenyl)vinyl)amino)(3-pyridyl))carbonylamino) ethoxy)ethoxy)ethoxy)ethoxy)ethoxy)ethoxy)ethyl)carbamoyl)propoxy)-2-(5-(5-oxo-1-prop-2-enyl-(2-6,7,8-trihydronaphthyloxy))pentyloxy)phenyl)propanoic Acid;

3-(6-(3-N-(5-((6-((1-Aza-2-(2-sulfophenyl)vinyl)amino)(3-pyridyl))carbonylamino)-5-(N-(2,3,4,5,6-pentahydroxyhexyl)carbamoyl)pentyl)carbamoyl) propoxy-2-(5-(5-oxo-1-prop-2-enyl-(2-6,7,8-trihydronaphthyloxy))pentyloxy)phenyl)propanoic Acid;

3-(6-(3-N-(5-((6-((1-Aza-2-(2-sulfophenyl)vinyl)amino)(3-pyridyl))carbonylamino)-5-(N-(6-deoxy-β-cyclodextryl)carbamoyl)pentyl)carbamoyl)propoxy-2-(5-(5-oxo-1-prop-2-enyl-(2-6,7,8-trihydronaphthyloxy))pentyloxy)phenyl)propanoic Acid;

3-(6-(3-(N-(3-((6-((1-Aza-2-(2-sulfophenyl)vinyl)amino)(3-pyridyl))-Gly-Lys-Lys-Lys)aminopropyl)carbamoyl)propoxy)-2-(5-(5-oxo-1-prop-2-enyl-(2-6,7,8-trihydronaphthyloxy))pentyloxy)phenyl)propanoic Acid;

2-Sulfobenzaldehyde (E)-N-[3-(6-Hydrazinonicotinamido)propyl]-3-[6-[[(2,6-dichlorophenyl)thio]methyl]-3-(2-phenylethoxy)-2-pyridinyl]-2-propenamide Hydrazone;

2-Sulfobenzaldehyde (E)-N-[3-(6-Hydrazinonicotinamido) propyl]-3-[6-[(phenylthio)methyl]-3-(2-phenylethoxy)-2-pyridinyl]-2-propenamide Hydrazone;

2-Sulfobenzaldehyde (E)-N-[3-(6-Hydrazinonicotinamido) propyl]-3-[6-[[(2-chlorophenyl)thio]methyl]-3-(2-phenylethoxy)-2-pyridinyl]-2-propenamide Hydrazone;

2-Sulfobenzaldehyde (E)-N-[3-(6-Hydrazinonicotinamido) propyl]-3-[6-[[(2,6-dimethylphenyl)thio]methyl]-3-(2-phenylethoxy)-2-pyridinyl]-2-propenamide Hydrazone;

2-Sulfobenzaldehyde (E)-N-[3-(6-Hydrazinonicotinamido) propyl]-3-[6-[[(2,3,5,6-tetrafluorophenyl)thio]methyl]-3-(2-phenylethoxy)-2-pyridinyl]-2-propenamide Hydrazone;

2-Sulfobenzaldehyde (E)-N-[3-(6-Hydrazinonicotinamido) propyl]-3-[6-[[(4-hydroxyphenyl)thio]methyl]-3-(2-phenylethoxy)-2-pyridinyl]-2-propenamide Hydrazone;

2-Sulfobenzaldehyde (E)-N-[2-(6-Hydrazinonicotinamido) ethyl]-3-[6-[[(2,6-dichlorophenyl)thio]methyl]-3-(2-phenylethoxy)-2-pyridinyl]-2-propanamide Hydrazone;

2-Sulfobenzaldehyde N-[3-(6-Hydrazinonicotinamido) propyl]-1-[3-([1,1'-biphenyl]-4-ylmethyl)-2H-1-benzopyran-7-yl]-cyclopentanecarboxamide Hydrazone;

2-Sulfobenzaldehyde 6-[5-(6-Hydrazinonicotinamido) pentyloxy]-5-(2-propenyl)-1,2,3,4-tetrahydronaphthalen-1-one Hydrazone;

2-Sulfobenzaldehyde 6-[6-(6-Hydrazinonicotinamido) hexyloxy]-5-(2-propenyl)-1,2,3,4-tetrahydronaphthalen-1-one Hydrazone;

2-Sulfobenzaldehyde 6-[6-(6-Hydrazinonicotinamido)-4,4-dimethylpentyloxy]-5-(2-propenyl)-1,2,3,4-tetrahydronaphthalen-1-one Hydrazone;

2-Sulfobenzaldehyde 6-[6-(6-Hydrazinonicotinamido)-5,5-dimethylhexyloxy]-5-(2-propenyl)-1,2,3,4-tetrahydronaphthalen-1-one Hydrazone;

2-Sulfobenzaldehyde 6-[4-(6-Hydrazinonicotinamido) butoxy]-5-(2-propenyl)-1,2,3,4-tetrahydronaphthalen-1-one Hydrazone;

2-Sulfobenzaldehyde 6-[3-(6-Hydrazinonicotinamido) propoxy]-5-(2-propenyl)-1,2,3,4-tetrahydronaphthalen-1-one Hydrazone;

2-Sulfobenzaldehyde 6-[2-(6-Hydrazinonicotinamido) ethoxy]-5-(2-propenyl)-1,2,3,4-tetrahydronaphthalen-1-one Hydrazone;

2-[[[5-[[2,2-Dimethyl-6-[(4-(3,4-methylenedioxyphenyl)-6-phenyl-2-pyridinyl)oxy]-1-hexanamino]carbonyl]-2-pyridinyl]hydrazono]methyl]-benzenesulfonic acid;

N-[2,2-Dimethyl-6-[(4-(3,4-methylenedioxyphenyl)-6-phenyl-2-pyridinyl)oxy]-hexyl]-bis-S-(1-ethoxyethylmercapto-acetyl)pentanoate;

2-[[[5-[[N-[6-[(4,6-diphenyl-2-pyridinyl)oxy]-hexanoyl]-glycine-alpha-amino]carbonyl]-2-pyridinyl]hydrazono]-methyl]-benzenesulfonic acid;

2-Acetyl-4-ethyl-[5-[6-[[6-[[[(2-sulfonylphenyl)methylene] hydrazino]-3-pyridinyl]carbonyl]amino]hexyl]oxy] phenol;

2,4-Diethyl-[5-[5,5-dimethyl-6-[[6-[[[(2-sulfonylphenyl) methylene]hydrazino]-3-pyridinyl]carbonyl]amino] hexyl]oxy]phenol;

3-(4-(5-(4,6-diphenyl-(2-pyridyloxy))pentyloxy)-3-ethoxyphenyl)-N-((6-hydrazino(3-pyridyl))sulfonyl) prop-2-enamide;

2-((6-((1-aza-2-(2-sulfophenyl)vinyl)-amino)(3-pyridyl)) carbonyl)-7-(5-(4,6-diphenyl(2-pyridyl-oxy))pentyloxy)-1,2,3,4-tetrahydro-isoquinoline-3-carboxylic acid;

2-((6-((1-aza-2-(2-sulfophenyl)vinyl)-amino)(3-pyridyl) carbonylamino)-3-(4-(5-(4,6-diphenyl(2-pyridyloxy)) pentyloxy)phenyl)propanoic acid;

2-((6-((1-aza-2-(2-sulfophenyl)vinyl)-amino)(3-pyridyl) carbonylamino)-3-(2-(5-(4,6-diphenyl(2-pyridyloxy)) pentyloxy)phenyl)propanoic acid;

3-((6-((1-aza-2-(2-sulfophenyl)vinyl)amino)(3-pyridyl) carbonylamino)-3-(N-(6-(4,6-diphenyl(2-pyridyloxy))-2,2-dimethylhexyl)carbamoyl)propanoic acid;

2-(2-aza-2-((5-(N-(3-(2-(2-(3-((1-((N-methyl-N-(2-phenylethyl)carbamoyl)methyl)-5-(phenylmethoxy)-indol-2-yl)carbonylamino)propoxy)ethoxy)ethoxy) propyl)-carbamoyl)(2-pyridyl))amino)vinyl) benzenesulfonic acid;

2-(2-((6-((1-aza-2-(2-sulfophenyl)vinyl)-amino)(3-pyridyl) carbonylamino)-3-carboxypropanoylamino)-3-(2-(5-(4,6-diphenyl(2-pyridyloxy))pentyloxy)phenyl)propanoic acid;

2-(2-aza-2-((5-(N-(2-(N-(3-(2-(2-(3-(2-(2,5-dioxoimidazolidin-4-yl)acetylamino)-propoxy)ethoxy) ethoxy)-propyl)carbamoyl)-1-(N-(6-(4,6-diphenyl(2-pyridyloxy))-2,2-dimethylhexyl)carbamoyl)-ethyl) carbamoyl(2-pyridyl))amino)-vinyl)benzenesulfonic acid;

6-((6-((1-aza-2-(2-sulfophenyl)-vinyl)-amino)(3-pyridyl) carbonylamino)-2-((1-((N-methyl-N-(2-phenylethyl) carbamoyl)methyl)-5-(phenylmethoxy)indol-2-yl) carbonylamino)hexanoic acid;

1-(3-((6-((1-aza-2-(2-sulfophenyl)vinyl)amino)-(3-pyridyl) carbonylamino)-3-(N-(6-(4,6-diphenyl(2-pyridyloxy))-2,2-dimethylhexyl)carbamoyl)propanoylamino)-ethane-1,2-dicarboxylic acid;

1-(2-(3-((6-((1-aza-2-(2-sulfophenyl)vinyl)-amino)(3-pyridyl)carbonylamino)-3-(N-(6-(4,6-diphenyl(2-pyridyloxy))-2,2-dimethylhexyl)carbamoyl) propanoylamino)-3-carboxypropanoylamino)ethane-1,2-dicarboxylic acid;

2-(2-aza-2-((5-(N-(1-(N-(6-(4,6-diphenyl(2-pyridyloxy))-2,2-dimethylhexyl)carbamoyl)-2-(3-(((4,5,6-trihydroxy-3-(hydroxymethyl)(2-oxanyl))amino)carbonylamino)-propanoylamino)ethyl)carbamoyl(2-pyirdyl))amino) vinyl)-benzenesulfonic acid;

2-(2-aza-2-((5-((6-(4-benzo[d] 1,3-dioxolan-5-yl-6-phenyl (2-pyridyloxy))-2,2-dimethylhexanoyl-amino)sulfonyl)-(2-pyridyl))amino)vinyl)benzenesulfonic acid;

6-(4-benzo[d] 1,3-dioxolan-5-yl-6-phenyl(2-pyridyloxy))-N-(1-(N-((6-hydrazino(3-pyridyl))sulfonyl)cabamoyl)-2-(4-hydroxyphenyl)ethyl)-2,2-dimethylhexanamide;

4-(4,6-diphenyl(2-pyridyloxy))-N-(1-(N-(1-(N-((6-hydrazino(3-pyridyl))sulfonyl)cabamoyl)-2-(4-hydroxyphenyl)ethyl)-carbamoyl)-isopropyl)butanamide;

3-(4-(3-((6-((1-aza-2-(2-sulfophenyl)vinyl)amino)(3-pyridyl))carbonylamino)-propoxy)phenyl)-2-(2,2-dimethyl-6-(5-oxo-1-prop-2-enyl(2-6,7,8-trihydronaphthyloxy))hexanoylamino)propanoic acid;

3-((6-((1-aza-2-(2-sulfophenyl)vinyl)amino)(3-pyridyl) carbonylamino)-3-(N-(6-(4-benzo[d] 1,3-dioxolan-5-yl-6-phenyl(2-pyridyloxy))-2,2-dimethylhexyl)carbamoyl) propanoic acid;

2-(2-aza-2-((5-(N-(1-(N-(6-(4-benzo[d] 1,3-dioxolan-5-yl-6-phenyl(2-pyridyloxy))-2,2-dimethyl-hexyl) carbamoyl)-2-(4-hydroxyphenyl)ethyl)carbamoyl(2-pyridyl))amino)vinyl)-benzenesulfonic acid;

2-((6-((1-aza-2-(2-sulfophenyl)vinyl)amino)(3-pyridyl) carbonylamino)-2-(2,2-dimethyl-6-(5-oxo-1-prop-2-enyl (2-6,7,8-trihydronaphthyloyy))hexanoylamino)acetic acid;

2-((6-((1-aza-2-(2-sulfophenyl)vinyl)amino)(3-pyridyl) carbonylamino)-2-(2,2-dimethyl-6-(5-oxo-1-prop-2-enyl (2-6,7,8-trihydronaphthyloxy))hexanoylamino)acetic acid;

3-((6-((1-aza-2-(2-sulfophenyl)vinyl)amino)(3-pyridyl)carbonylamino)-3-(N-(6-(6-ethyl-3-hydroxy-4-phenylphenoxy)-2,2-dimethylhexyl)carbamoyl)propanoic acid;

2-((6-((1-aza-2-(2-sulfophenyl)vinyl)amino)(3-pyridyl)carbonylamino)-2-(6-(4-benzo[d] 1,3-dioxolan-5-yl-6-phenyl(2-pyridyloxy))-2,2-dimethylhexanoylamino)acetic acid;

2-(2-aza-2-((5-(N-(5-((3-((N-(6-(4,6-diphenyl(2-pyridyloxy))-2,2-dimethylhexanoylamino)-3-(4-hydroxyphenyl)propanoylamino)-1-(N-(2,3,4,5,6-pentahydroxyhexyl)carbamoyl)pentyl)carbamoyl(2-pyridyl))amino)vinyl)benzenesulfonic acid;

2-(2-aza-2-((5-(N-(5-((3-((N-(6-(4-benzo[d] 1,3-dioxolan-5-yl-6-phenyl(2-pyridyloxy))-2,2-dimethylhexyl)-carbamoyl)-2-(N-(2,3,4,5,6-pentahydroxyhexyl)carbamoyl)-ethyl)carbamoyl(2-pyridyl))amino)vinyl)benzenesulfonic acid;

2-(2-aza-2-((5-(N-(5-((3-((N-(6-(4-benzo[d] 1,3-dioxolan-5-yl-6-phenyl(2-pyridyloxy))-2,2-dimethylhexyl)carbamoyl)amino)phenyl)carbonylamino)-1-(N-(2,3,4,5,6-pentahydroxyhexyl)carbamoyl)pentyl)carbamoyl(2-pyridyl))amino)vinyl)benzenesulfonic acid;

2-((6-((1-aza-2-(2-sulfophenyl)vinyl)amino)(3-pyridyl))carbonylamino)-3-(N-(6-(4-benzo[d] 1,3-dioxolan-5-yl-6-phenyl(2-pyridyloxy))-2,2-dimethylhexyl)carbamoyl)-propanoylamino)-3-carboxypropanoylamino)-3-carboxypropanoylamino)-ethane-1,2-dicarboxylic acid;

2-((6-((1-aza-2-(2-sulfophenyl)vinyl)amino)(3-pyridyl))carbonylamino)-3-(2-(5-(4-benzo[d] 1,3-dioxolan-5-yl-6-phenyl(2-pyridyloxy))pentyloxy)phenyl)propanoic acid; and 2-({2-[((2S)-2-[Bis(carboxymethyl)amino]-3-{4-[({[3-(2-{2-[3-(5-{5-[5-(4,6-diphenyl(2-pyridyloxy))-1,1-dimethylpentyl](5H-1,2,3,4-tetraazolyl)}pentanoylamino)propoxy]ethoxy}ethoxy)propyl]amino}thioxomethyl)amino]phenyl}propyl)(carboxymethyl)amino]ethyl}-(carboxymethyl)amino)acetic acid.

In an embodiment, the present invention provides a method according to any one of embodiments [1–21] wherein the radiolabeled LTB4 binding agent is selected from the group consisting of:

$^{99m}$Tc(tricine)(TPPTS)(4-ethyl-2-(4-fluorophenyl)-[5-[5,5-dimethyl-6-[[[6-diazenido-3-pyridinyl]carbonyl]amino]hexyl]oxy]phenol);

$^{99m}$Tc(tricine)(TPPDS)(4-ethyl-2-(4-fluorophenyl)-[5-[5,5-dimethyl-6-[[[6-diazenido-3-pyridinyl]carbonyl]amino]hexyl]oxy]phenol);

$^{99m}$Tc(tricine)(TPPMS)(4-ethyl-2-(4-fluorophenyl)-[5-[5,5-dimethyl-6-[[[6-diazenido-3-pyridinyl]carbonyl]amino]hexyl]oxy]phenol);

$^{99m}$Tc(tricine)(3-sulfonatopyridine))(4-ethyl-2-(4-fluorophenyl)-[5-[5,5-dimethyl-6-[[[6-diazenido-3-pyridinyl]carbonyl]amino]hexyl]oxy]phenol);

$^{99m}$Tc(tricine)(TPPTS)(4-ethyl-2-(4-fluorophenyl)-[5-[4-[[[6-diazenido-3-pyridinyl]carbonyl]amino]butyl]oxy]phenol);

$^{99m}$Tc(tricine)(TPPTS)(2-[[5-[[(6-[(4,6-diphenyl-2-pyridinyl)oxy]-1-hexanamino]carbonyl]-2-pyridinyl]diazenido]);

$^{99m}$Tc(tricine)(TPPTS)(2-[[5-[[2,2-dimethyl-6-[(6-fluorophenyl-4-phenyl-2-pyridinyl)oxy]-1-hexanamino]carbonyl]-2-pyridinyl]diazenido]);

$^{99m}$Tc(tricine)(TPPTS)(2-[[5-[[N-[6-[(4,6-diphenyl-2-pyridinyl)oxy]-hexanoyl]-tyrosine-O-[3-propanamino]]carbonyl]-2-pyridinyl]diazenido]);

$^{99m}$Tc(tricine)(TPPTS)(2-[[[5-[[N-[6-[(4-(3,4-methylenedioxyphenyl)-6-phenyl-2-pyridinyl)oxy]-hexanoyl]-tyrosine-O-[3-propanamino]]-carbonyl]-2-pyridinyl]diazenido]);

$^{99m}$Tc(tricine)(TPPTS)(2-[[[5-[[alpha-N-[6-[(4,6-diphenyl-2-pyridinyl)oxy]-hexanoyl]-lysine-epsilon-N-amino]carbonyl]-2-pyridinyl]diazenido]);

$^{99m}$Tc(tricine)(TPPTS)(2-[[[5-[[[6-[(4,6-diphenyl-2-pyridinyl)oxy]-2,2-dimethyl-1-hexyl]aza]carbonyl]-2-pyridinyl]diazenido]);

$^{99m}$Tc(tricine)(TPPTS)(4-ethyl-2-(4-fluorophenyl)-[5-[6,6-dimethyl-7-[[6-[[6-diazenido]-3-pyridinyl]carbonyl]amino]heptyl]oxy]phenol);

$^{99m}$Tc(tricine)(TPPTS)(2-[6-[(4,6-Diphenyl-2-pyridinyl)oxy]pentyl]-6-(8-[[[6-diazenido]-3-pyridinyl]carbonyl]amino-5-aza-4-oxooctyloxy)-benzenepropanoic Acid);

$^{99m}$Tc(tricine)(3-pyridinesulfonic acid))(2-[6-[(4,6-Diphenyl-2-pyridinyl)oxy]pentyl]-6-(8-[[[6-diazenido]-3-pyridinyl]carbonyl]amino-5-aza-4-oxooctyloxy)benzenepropanoic Acid);

$^{99m}$Tc(tricine)(3,5-pyridinedicarboxylic acid)(2-[6-[(4,6-Diphenyl-2-pyridinyl)oxy]pentyl]-6-(8-[[[6-diazenido]-3-pyridinyl]carbonyl]amino-5-aza-4-oxooctyloxy)benzenepropanoic Acid);

$^{99m}$Tc(tricine)(TPPTS)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(TFP)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(3,5-pyridinedicarboxylic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(isonicotinic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(nicotinic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(3-pyridinesulfonic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(hydroxyethylisonicotinamide)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(4-methyl-5-imidazolemethanol)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(4-methyl-5-thiazoleethanol)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(pyridine)(6-(11-[[[6-diazenido]-3-pyridinyl]carbonyl]amino-3,6,9-trioxaundecyloxy)-2-[5-[(5-oxo-1-

(2-propenyl)-5,6,7,8-tetrahydro-2-naphthalenyl)oxy]pentyloxy]benzenepropanoic Acid);

$^{99m}$Tc(tricine)(4-pyridylethylsulfonic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(TPPTS)(N-((6-(diazenido)(3-pyridyl))sulfonyl)-3-(1-((N-(2-phenylethyl)carbamoyl)methyl)-5-(phenylmethoxy)indol-3-yl)prop-2-enamide);

$^{99m}$Tc(tricine)(TPPTS)((2-((5-carbamoyl(2-pyridyl)diazenido) ethyl 3-((7-(3-(6-ethyl-4-(4-fluorophenyl)-3-hydroxyphenoxy)propoxy)-8-propylchroman-2-yl)carbonylamino)propanoate);

$^{99m}$Tc(tricine)(TPPTS)(3-((7-(-(6-ethyl-4-(4-fluorophenyl)-3-hydroxyphenoxy)propoxy)-8-propylchroman-2-yl)carbonylamino)propyl-2-methylpropanoate, 2-(2((5-carbamoyl(2-pyridyl)diazenido);

$^{99m}$Tc(tricine)(TPPTS)(N-(3-((7-(3-(6-ethyl-4-(4-fluorophenyl)-3-hydroxyphenoxy)propoxy)-8-propylchroman-2-yl)carbonylamino)propyl)-2-methylpropanamide, 2-(2-((5-carbamoyl(2-pyridyl))diazenido);

$^{99m}$Tc(tricine)(TPPTS)(2-(2-((5-(N-(6-(6-ethyl-3-hydroxy-4-(1-methylpyrazol-5-yl)phenoxy)-2,2-dimethylhexyl)carbamoyl)(2-pyridyl))diazenido);

$^{99m}$Tc(tricine)(3-pyridinesulfonic acid)(2-(2-((5-(N-(6-(6-ethyl-3-hydroxy-4-(1-methylpyrazol-5-yl)phenoxy)-2,2-dimethylhexyl)carbamoyl)(2-pyridyl))diazenido);

$^{99m}$Tc(tricine)(TPPTS)(2-(2-((5-((3-((6-ethyl-4-(4-fluorophenyl)-3-hydroxyphenoxy)methyl)piperidyl)carbonyl)(2-pyridyl))diazenido);

$^{99m}$Tc(tricine)(TPPTS)(2-(2-((5-(N-(3-(2-(2-(3-(5-(5-(4,6-diphenyl(2-pyridyloxy))-1,1-dimethylpentyl)(1,2,3,4-tetraazolyl))pentanoylamino)propoxy)ethoxy)ethoxy)propyl)carbamoyl)(2-pyridyl))diazenido);

$^{99m}$Tc(tricine)(TPPTS)(2-(2-((5-(N-(2-(2-(2-(2-(2-(2-(2-(5-(4-(5-(4,6-diphenyl(2-pyridyloxy))-1,1-dimethylpentyl)(1,2,3,5-tetraazolyl))pentanoylamino)ethoxy)ethoxy)ethoxy)ethoxy)ethoxy)ethoxy)ethoxy)ethyl)carbamoyl)(2-pyridyl))diazenido);

$^{99m}$Tc(tricine)(TPPTS)(2-(2-((5-(N-(5-(4-(5-(4,6-diphenyl(2-pyridyloxy))-1,1-dimethylpentyl)(1,2,3,5-tetraazolyl))pentanoylamino)-1-(6-deoxy-β-cyclodextryl)carbamoyl)pentyl)carbamoyl)(2-pyridyl))diazenido);

$^{99m}$Tc(tricine)(TPPTS)(3-(6-(3-N-(5-((6-(diazenido)(3-pyridyl))carbonylamino)-5-(N-((ω-methoxypolyethylene(750)glycoxyethyl)carbamoyl)pentyl)carbamoyl)propoxy)2-(5-(4,6-diphenyl(2-pyridyloxy))pentyloxy)phenyl)propanoic Acid);

$^{99m}$Tc(tricine)(TPPTS)(3-(6-(3-N-(3-(2-(2-(3-((6-(diazenido)(3-pyridyl))carbonylamino)propoxy)ethoxy)ethoxy)propyl)-carbamoyl)propoxy)2-(5-(4,6-diphenyl(2-pyridyloxy))pentyloxy)phenyl)propanoic Acid);

$^{99m}$Tc(tricine)(TPPTS)(3-(6-(3-(N-(5-((6-(diazenido)(3-pyridyl))carbonylamino)-5-(N-(2,3,4,5,6-pentahydroxyhexyl)carbamoyl)pentyl)carbamoyl)propoxy)2-(5-(4,6-diphenyl(2-pyridyloxy))pentyloxy)phenyl)propanoic Acid);

$^{99}$mTc(tricine)(TFP)(3-(6-(3-(N-(5-((6-(diazenido)(3-pyridyl))carbonylamino)-5-(N-(2,3,4,5,6-pentahydroxyhexyl)carbamoyl)pentyl)carbamoyl)propoxy)2-(5-(4,6-diphenyl(2-pyridyloxy))pentyloxy)phenyl)propanoic Acid);

$^{99m}$Tc(tricine)(TPPTS)(3-(6-(3-(N-(3-((6-(diazenido)(3-pyridyl))carbonylamino)propyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(TFP)(3-(6-(3-(N-(3-((6-(diazenido)(3-pyridyl))carbonylamino)propyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(pyridine)(3-(6-(3-(N-(3-((6-(diazenido)(3-pyridyl))carbonylamino)propyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6-(3-N-(2-(2-(2-(2-(2-(2-(2-((6-(diazenido)(3-pyridyl))carbonylamino)ethoxy)ethoxy)ethoxy)ethoxy) ethoxy)ethoxy)ethyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6-(3-N-(5-((6-(diazenido)(3-pyridyl))carbonylamino)-5-(N-(2,3,4,5,6-pentahydroxyhexyl)carbamoyl)pentyl)carbamoyl)propoxy-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6-(3-N-(5-((6-(diazenido)(3-pyridyl))carbonylamino)-5-(N-(6-deoxy-p-cyclodextryl)carbamoyl)pentyl)carbamoyl)propoxy-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6-(3-(N-(3-((6-((diazenido)(3-pyridyl))-Gly-Lys-Lys-Lys)aminopropyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(TPPTS)((E)-N-[3-(6-diazenidonicotinamido)propyl]-3-[6-[[(2,6-dichlorophenyl)thio]methyl]-3-(2-phenylethoxy)-2-pyridinyl]-2-propenamide);

$^{99m}$Tc(tricine) (TPPTS)((E)-N-[3-(6-diazenidonicotinamido)propyl]-3-[6-[(phenylthio)methyl]-3-(2-phenylethoxy)-2-pyridinyl]-2-propenamide);

$^{99m}$Tc(tricine)(TPPTS)((E)-N-[3-(6-diazenidonicotinamido)propyl]-3-[6-[[(2-chlorophenyl)thio]methyl]-3-(2-phenylethoxy)-2-pyridinyl]-2-propenamide);

$^{99m}$Tc(tricine)(TPPTS)((E)-N-[3-(6-diazenidonicotinamido)propyl]-3-[6-[[(2,6-dimethylphenyl)thio]methyl]-3-(2-phenylethoxy)-2-pyridinyl]-2-propenamide);

$^{99m}$Tc(tricine)(TPPTS)((E)-N-[3-(6-diazenidonicotinamido)propyl]-3-[6-[[(2,3,5,6-tetrafluorophenyl)thio]methyl]-3-(2-phenylethoxy)-2-pyridinyl]-2-propenamide);

$^{99m}$Tc(tricine) (TPPTS)((E)-N-[3-(6-diazenidonicotinamido)propyl]-3-[6-[[(2,3,5,6-tetrafluorophenyl)thio]methyl]-3-(2-phenylethoxy)-2-pyridinyl]-2-propenamide);

$^{99m}$Tc(tricine) (TPPTS)((E)-N-[2-(6-diazenidonicotinamido)ethyl]-3-[6-[[(2,6-dichlorophenyl)thio]methyl]-3-(2-phenylethoxy)-2-pyridinyl]-2-propanamide);

$^{99m}$Tc(tricine)(TPPTS)(6-[6-(6-diazenidonicotinamido)-4,4-dimethylpentyloxy]-5-(2-propenyl)-1,2,3,4-tetrahydronaphthalen-1-one);

$^{99}$mTc(tricine)(TPPTS)(2-[[[5-[[2,2-Dimethyl-6-[(4-(3,4-methylenedioxyphenyl)-6-phenyl-2-pyridinyl)oxy]-1-hexanamino]carbonyl-2-pyridinyl]diazenido);

$^{99m}$Tc(tricine)(TPPTS)(2-[[[5-[[N-[6-[(4,6-diphenyl-2-pyridinyl)oxy]-hexanoyl]-glycine-alpha-amino]carbonyl]-2-pyridinyl]diazenido);

$^{99m}$Tc(tricine)(TPPTS)(2,4-Diethyl-[5-[5,5-dimethyl-6-[[6-[[diazenido]-3-pyridinyl]carbonyl]amino]hexyl]oxy]phenol);

$^{99m}$Tc(tricine)(TPPTS)(2-((6-(diazenido)(3-pyridyl)carbonylamino)-3-(2-(5-(4,6-diphenyl(2-pyridyloxy))pentyloxy)phenyl)propanoic acid);

$^{99}$mTc(tricine)(TPPTS)(3-((6-(diazenido)(3-pyridyl)carbonylamino)-3-(N-(6-(4,6-diphenyl(2-pyridyloxy))-2,2-dimethylhexyl)carbamoyl)propanoic acid);

<sup>99m</sup>Tc(tricine)(TPPTS)(2-(2-((6-(diazenido)(3-pyridyl)carbonylamino)-3-carboxypropanoylamino)-3-(2-(5-(4,6-diphenyl(2-pyridyloxy))pentyloxy)phenyl)propanoic acid);

<sup>99m</sup>Tc(tricine)(TPPTS)(2-(2-((5-(N-(2-(N-(3-(2-(2-(3-(2-(2,5-dioxoimidazolidin-4-yl)acetylamino)-propoxy)ethoxy)ethoxy)-propyl)carbamoyl)-1-(N-(6-(4,6-diphenyl(2-pyridyloxy))-2,2-dimethylhexyl)carbamoyl)-ethyl)carbamoyl(2-pyridyl))diazenido);

<sup>99m</sup>Tc(tricine)(TPPTS)(1-(3-((6-(diazenido)-(3-pyridyl)carbonylamino)-3-(N-(6-(4,6-diphenyl(2-pyridyloxy))-2,2-dimethylhexyl)carbamoyl)propanoylamino)-ethane-1,2-dicarboxylic acid);

<sup>99m</sup>Tc(tricine)(TPPTS)(2-(2-((5-(N-(1-(N-(6-(4,6-diphenyl(2-pyridyloxy))-2,2-dimethylhexyl)carbamoyl)-2-(3-(((4,5,6-trihydroxy-3-(hydroxymethyl)(2-oxanyl))amino)carbonylamino)-propanoylamino)ethyl)carbamoyl(2-pyridyl))diazenido);

<sup>99m</sup>Tc(tricine)(TPPTS)(2-(2-((5-((6-(4-benzo[d] 1,3-dioxolan-5-yl-6-phenyl(2-pyridyloxy))-2,2-dimethylhexanoyl-amino)sulfonyl)-(2-pyridyl))diazenido);

<sup>99m</sup>Tc(tricine)(TPPTS)(3-((6-((diazenido)(3-pyridyl)carbonylamino)-3-(N-(6-(4-benzo[d] 1,3-dioxolan-5-yl-6-phenyl(2-pyridyloxy))-2,2-dimethylhexyl)carbamoyl) propanoic acid);

<sup>99m</sup>Tc(tricine)(TFP)(3-((6-((diazenido)(3-pyridyl)carbonylamino)-3-(N-(6-(4-benzo[d] 1,3-dioxolan-5-yl-6-phenyl(2-pyridyloxy))-2,2-dimethylhexyl)carbamoyl) propanoic acid);

<sup>99m</sup>Tc(tricine)(TPPTS)(2-(2-((5-(N-(1-(N-(6-(4-benzo[d] 1,3-dioxolan-5-yl-6-phenyl(2-pyridyloxy))-2,2-dimethylhexyl)carbamoyl)-2-(4-hydroxyphenyl)ethyl)carbamoyl(2-pyridyl))diazenido);

<sup>99m</sup>Tc(tricine)(TPPTS)(2-((6-(diazenido)(3-pyridyl)carbonylamino)-2-(6-(4-benzo[d] 1,3-dioxolan-5-yl-6-phenyl(2-pyridyloxy))-2,2-dimethylhexanoylamino) acetic acid);

<sup>99m</sup>Tc(tricine)(TPPTS)(2-(2-((5-(N-(5-((3-((N-(6-(4,6-diphenyl(2-pyridyloxy))-2,2-dimethylhexanoylamino)-3-(4-hydroxyphenyl)propanoylamino)-1-(N-(2,3,4,5,6-pentahydroxyhexyl)carbamoyl)pentyl)carbamoyl(2-pyridyl))diazenido);

<sup>99m</sup>Tc(tricine)(TPPTS)(2-(2-((5-(N-(5-((3-((N-(6-(4-benzo[d] 1,3-dioxolan-5-yl-6-phenyl(2-pyridyloxy))-2,2-dimethylhexyl)-carbamoyl)-2-(N-(2,3,4,5,6-pentahydroxyhexyl)carbamoyl)-ethyl)carbamoyl(2-pyridyl))diazenido);

<sup>99m</sup>Tc(tricine)(TPPTS)(2-(2-((5-(N-(5-((3-((N-(6-(4-benzo[d] 1,3-dioxolan-5-yl-6-phenyl(2-pyridyloxy))-2,2-dimethylhexyl)carbamoyl)amino)phenyl)carbonylamino)-1-(N-(2,3,4,5,6-pentahydroxyhexyl)carbamoyl)pentyl)carbamoyl(2-pyridyl))diazenido);

<sup>99m</sup>Tc(tricine)(TPPTS)(2-((6-(diazenido)(3-pyridyl))carbonylamino)-3-(N-(6-(4-benzo[d] 1,3-dioxolan-5-yl-6-phenyl(2-pyridyloxy))-2,2-dimethylhexyl)carbamoyl)-propanoylamino)-3-carboxypropanoylamino)-3-carboxypropanoylamino)-ethane-1,2-dicarboxylic acid);

<sup>99m</sup>Tc(tricine)(TPPTS)(2-((6-(diazenido)(3-pyridyl))carbonylamino)-3-(2-(5-(4-benzo[d] 1,3-dioxolan-5-yl-6-phenyl(2-pyridyloxy))pentyloxy)phenyl)propanoic acid);

<sup>99m</sup>TcO(4-ethyl-2-(4-fluorophenyl)-5-[(5,5-dimethyl-6-aminohexyl)oxy]phenol N-[4-(carboxy)benzyl]-N,N'-bis[2-thiolatoethyl]-glycinamide);

<sup>99m</sup>TcO(N-[2,2-Dimethyl-6-[(4-(3,4-methylenedioxyphenyl)-6-phenyl-2-pyridinyl)oxy-hexyl]-bis(mercaptoacetyl)pentanoate); and <sup>111</sup>In(2-({2-[((2S)-2-[Bis(carboxymethyl)amino]-3-{4-[({[3-(2-{2-[3-(5-{5-[5-(4,6-diphenyl(2-pyridyloxy))-1,1-dimethylpentyl](5H-1,2,3,4-tetraazolyl)}pentanoylamino)-propoxy]ethoxy}ethoxy)propyl]amino}thioxomethyl)amino]phenyl}propyl)(carboxymethyl)amino]ethyl}-(carboxymethyl)amino)acetate).

[27] In an embodiment, the present invention provides a kit comprising a reagent of any one of Embodiment [22–26] and a perfusion imaging agent.

[28] In an embodiment, the present invention provides a kit of Embodiment [27] further comprising a reducing agent.

[29] In an embodiment, the present invention provides a kit of Embodiment [28] wherein the reducing agent is tin(II).

[30] In an embodiment, the present invention provides a kit of Embodiment [29] further comprising one or more ancillary ligands.

[31] In an embodiment, the present invention provides a kit of Embodiment [30] wherein the ancillary ligands are tricine and TPPTS.

[32] In an embodiment, the present invention provides a kit comprising radiolabeled LTB4 binding agent of Embodiment [18] and a perfusion imaging agent.

[33] In an embodiment, the present invention provides a kit of Embodiment [32] further comprising a reducing agent.

[34] In an embodiment, the present invention provides a kit of Embodiment [33] wherein the reducing agent is tin(II).

[35] In an embodiment, the present invention provides a kit of Embodiment [34] further comprising one or more ancillary ligands.

[36] In an embodiment, the present invention provides a kit of Embodiment [35] wherein the ancillary ligands are tricine and TPPTS.

[37] In an embodiment, the present invention provides a kit comprising radiolabeled LTB4 binding agent of Embodiment [18] and a radiolabeled perfusion imaging agent of any one of Embodiments [22–26].

[38] In an embodiment, the present invention provides a kit of Embodiment [37] further comprising a reducing agent.

[39] In an embodiment, the present invention provides a kit of Embodiment [38] wherein the reducing agent is tin(II).

[40] In an embodiment, the present invention provides a kit of Embodiment [39] further comprising one or more ancillary ligands.

[41] In an embodiment, the present invention provides a kit of Embodiment [40] wherein the ancillary ligands are tricine and TPPTS.

[42] In an embodiment, the present invention provides a method according to embodiment [1] further comprising forming an image from the detection of said agents.

[43] In an embodiment, the present invention provides a method according to embodiment [42] wherein the images are displayed side-by-side to faciliate interpretation of the localization of the radiolabeled LTB4 binding agent in the body, relative to the distribution of the radiolabeled perfusion agent in the body.

[44] In an embodiment, the present invention provides a method according to embodiment [42] wherein the images are are overlayed to faciliate interpretation of the localization of the radiolabeled LTB4 binding agent in the body, relative to the distribution of the radiolabeled perfusion agent in the body.

[45] In an embodiment, the present invention provides a method of diagnosing and localizing sites of inflammation and perfusion abnormalities in a single dual isotope imaging procedure.

[46] In an embodiment, the present invention provides a method of diagnostic imaging comprising the concurrent detection and localization of sites of ischemic tissue injury and perfusion abnormalities in a single imaging procedure.

[47] In an embodiment, the present invention provides a method according to embodiment [46] wherein the imaging procedure is one or more procedure selected from the group, CT imaging, ultrasound, and scintigraphy.

[48] In an embodiment, the present invention provides a method of diagnosing and localizing sites of inflammation and perfusion abnormalities in a single dual imaging procedure.

[49] In an embodiment, the present invention provides a method according to embodiment [48] wherein the imaging procedure is one or more procedure selected from the group, CT imaging, ultrasound, and scintigraphy.

[50] In an embodiment, the present invention provides a method of diagnostic imaging comprising the concurrent detection and localization of sites of of ischemic tissue injury (e.g. reperfusion injury), vulnerable plaque, bacterial endocarditis or cardiac transplant rejection in a single dual imaging procedure.

[51] In an embodiment, the present invention provides a method according to embodiment [50] wherein the imaging procedure is one or more procedure selected from the group, CT imaging, ultrasound, and scintigraphy.

[52] In an embodiment, the present invention provides a method of diagnostic imaging comprising the concurrent detection and localization of sites of vulnerable plaque and perfusion abnormalities in a single imaging procedure.

[53] In an embodiment, the present invention provides a method according to embodiment [52] wherein the imaging procedure is one or more procedure selected from the group, CT imaging, ultrasound, and scintigraphy.

[54] In an embodiment, the present invention provides a method of diagnostic imaging comprising the concurrent detection and localization of sites of cardiac infection and perfusion abnormalities in a single imaging procedure.

[55] In an embodiment, the present invention provides a method according to embodiment [54] wherein the imaging procedure is one or more procedure selected from the group, CT imaging, ultrasound, and scintigraphy.

[56] In an embodiment, the present invention provides a method of diagnostic imaging comprising the concurrent detection and localization of sites of cardiac transplant rejection and perfusion abnormalities in a single imaging procedure.

[57] In an embodiment, the present invention provides a method according to embodiment [56] wherein the imaging procedure is one or more procedure selected from the group, CT imaging, ultrasound, and scintigraphy.

[58] In an embodiment, the present invention provides a method according to embodiment [1] wherein the radiolabeled LTB4 binding agent is a reagent capable of direct transformation into a compound radiolabeled with a radioisotope selected from the group consisting of, $^{123}$I, $^{125}$I, $^{18}$F, $^{11}$C, $^{13}$N, $^{15}$O, and $^{75}$Br, and said reagent having the formula:

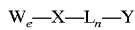

wherein,
$W_e$ is selected from the group:

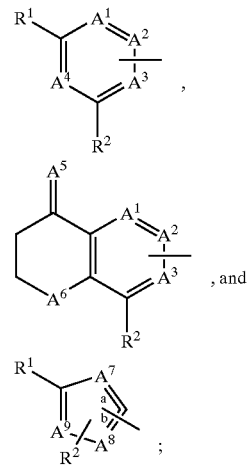

wherein,
$A^1$ is N, C—OH, or CH;
$A^2$ and $A^3$ are independently N or CH;
$A^4$ is N or $CR^3$;
$A^5$ is 0 or S;
$A^6$ is 0, $CH_2$ or S;
$A^7$ is C—OH, N, NH, 0 or S;
$A^8$ is NH, $CH_2$, O, S, N, or CH;
$A^9$ is N or CH;
a and b indicate the alternative positions of a double bond;
$R^1$ is selected from the group: H, —C(=NH)NH$_2$, $C_1$–$C_6$ alkyl substituted with 0–3 $R^4$, $C_1$–$C_6$ alkoxy substituted with 0–3 $R^4$, aryl substituted with 0–3 $R^5$, and heterocycle substituted with 0–3 $R^5$;
$R^2$ is selected from the group: H, $C_1$–$C_3$ alkyl, $C_2$–$C_3$ alkenyl, cyclopropyl, cyclopropylmethyl, and aryl substituted with 0–3 $R^5$;
$R^3$ is —H, —OH or $C_1$–$C_3$ alkoxy; or alternatively, $R^1$ and $R^3$ can be taken together with the atoms to which they are attached to form a fused phenyl ring substituted with 0–3 $R^5$;
$R^4$ is independently selected from the group: —F, —Cl, —Br, —I, =O, —N($R^6$)($R^7$), and —CF$_3$;
$R^5$ is independently selected from the group: —F, —Cl, —Br, —I, —N($R^6$)($R^7$), —CF$_3$, $C_1$–$C_3$ alkyl, $C_1$–$C_3$ alkoxy, and methylenedioxy;
$R^6$ and $R^7$ are independently H or $C_1$–$C_3$ alkyl; provided that when $A^1$ and $A^2$ are CH, $A^3$ is C—X, and $A^4$ is $CR^3$, $R^1$ is selected from the group: $C_1$–$C_5$ alkyl substituted with 1–3 $R^4$, $C_1$–$C_5$ alkoxy substituted with 0–3 $R^4$, and aryl substituted with 0–3 $R^5$;
X is O, S, $CH_2$ or CH=CH;
$L_n$ is a linking group having the formula

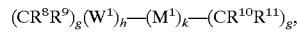

wherein,
$R^8$, $R^9$, $R^{10}$ and $R^{11}$ are independently selected at each occurrence from the group: H, $C_1$–$C_5$ alkyl, and $C_1$–$C_5$ alkoxy, or alternatively, $R^8$ and $R^9$ or $R^{10}$ and $R^{11}$ may be taken together to form a 3–6 membered cycloalkyl or heterocycle;
$W^1$ is independently selected from the group: O, S, C(=O)O, OC(=O), CH=CH, (OCH$_2$CH$_2$)$_p$ and (CH$_2$CH$_2$O)$_p$', wherein p and p' are independently 1–3;

M¹ is selected from the group: phenyl substituted with 0–3 R¹², heterocycle substituted with 0–3 R¹², benzophenone substituted with 0–3 R¹², and diphenylether substituted with 0–3 R¹²;

R¹² is independently selected from the group: —COOR¹³, $C_1$–$C_5$ alkyl substituted with 0–3 R¹⁴, and $C_1$–$C_5$ alkoxy substituted with 0–3 R¹⁴;

R¹³ is H or $C_1$–$C_5$ alkyl:

R¹⁴ is —COOH;

g is 0–10;

h is 0–3;

k is 0–1;

g' is 0–5;

provided that when h is 0 and k is 0, g is >1;

and provided that when W¹ is O or S and k is 0, g+g' is ≧1; and

Y is selected from C(=O)NH, NHC(=O), C=O, C(=O)O, OC(=O), NHS(=O)₂, C(=O)NHS(=O)₂, COOH, C(=O)NH₂, NH(C=O)NH, or tetrazole; or a pharmaceutically acceptable salts thereof.

[59] In an embodiment, the present invention provides a method according to embodiment [58] wherein:

$w_e$ is selected from the group:

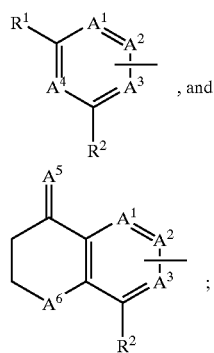

wherein,

A¹ is N, C—OH, or CH;

A² and A³ are CH;

A⁴ is CR³;

A⁵ is O;

A⁶ is O or CH₂;

R⁴ is independently selected from the group:

A⁵ is O;

A⁶ is O or CH₂;

R⁴ is independently selected from the group: —F, —Cl, =O, —N(R⁶)(R⁷), and —CF₃;

R⁵ is independently selected from the group: —F, —Cl, —CF₃, $C_1$–$C_3$ alkyl, $C_1$–$C_3$ alkoxy, and methylenedioxy;

X is O, CH₂ or CH=CH; and

R⁸, R⁹, R¹⁰ and R¹¹ are independently selected at each occurrence from the group: H, $C_1$–$C_5$ alkyl, and $C_1$–$C_5$ alkoxy;

or alternatively, R⁸ and R⁹ or R¹⁰ and R¹¹ may be taken together to form a 3–6 membered cycloalkyl.

[60] In an embodiment, the present invention provides a reagent of Embodiment [58] wherein:

R¹ is selected from the group:

H, —C(=NH)NH₂, $C_1$–$C_6$ alkyl substituted with 0–2 R⁴, $C_1$–$C_6$ alkoxy substituted with 0–2 R⁴, aryl substituted with 0–2 R⁵, and heterocycle substituted with 0–2 R⁵;

R³ is —H, —OH or $C_1$–$C_3$ alkoxy;

or alternatively, R¹ and R³ can be taken together with the atoms to which they are attached to form a fused phenyl ring substituted with 0–2 R⁵;

R⁴ is independently selected from the group: =O, and —N(R⁶)(R⁷);

R⁵ is independently selected from the group: —F, $C_1$–$C_3$ alkyl, $C_1$–$C_3$ alkoxy, and methylenedioxy;

X is O, CH₂ or CH=CH;

W¹ is O;

M¹ is selected from the group: phenyl substituted with 0–1 R¹², heterocycle substituted with 0–1 R¹², benzophenone substituted with 0–1 R¹², and diphenylether substituted with 0–1 R¹²;

R¹² is independently selected from the group: —COOR¹³, $C_1$–$C_5$ alkyl substituted with 0–1 R¹⁴, and $C_1$–$C_5$ alkoxy substituted with 0–1 R¹⁴; and M² is selected from the group: aryl substituted with 0–1 R¹⁹, cycloalkyl substituted with 0–3 R¹⁹, and heterocycle substituted with 0–1 R¹⁹.

[61] In an embodiment, the present invention provides a kit comprising a reagent of Embodiment [58] and a perfusion imaging agent.

In a further embodiment, the present invention provides a novel reagent capable of direct transformation into a radiopharmaceutical having a binding affinity for the LTB4 receptor of less than 1000 nM.

In a further embodiment, the present invention provides a novel method of detecting sites of infection and inflammation in a mammal comprising administering to said mammal a radiolabeled LTB4 binding agent and then detecting said sites using a radiation detecting probe.

In a further embodiment, the present invention provides a novel method of imaging sites of infection and inflammation in a mammal comprising administering to said mammal a radiolabeled LTB4 binding agent and then imaging said sites using a planar or ring gamma camera.

In a further embodiment, the present invention provides a novel method of diagnosing disease in a mammal associated with infection and inflamation comprising imaging said mammal using a radiolabeled LTB4 binding agent and determining the presence of said disease.

In a further embodiment, the present invention provides a novel method of dual isotope imaging utilizing an organ perfusion imaging agent and an inflammation image utilizing the LTB4-targeted radiopharmaceutical reagents described herein. The simultaneous imaging of organ perfusion and inflammation allows a more complete assessment of the underlying disease, both in terms of blood flow alterations and inflammatory changes, in a single imaging session on a patient. This simultaneous imaging procedure is more time-efficient than the serial/sequential imaging of perfusion and inflammation which is acquired in two separate imaging sessions. The simultaneous imaging process will save labor time of radiologists and imaging technologists, as well as reduce the time that imaging instruments are utilized in acquiring the perfusion and inflammation images. This procedure will also result in greater patient comfort by reducing the time needed for the subject to remain immobile relative to the situation of two separate imaging procedures. In addition, the simultaneous acquisition process will allow for improved accuracy in the spatial registration (i.e. overlay) of of two separate imaging procedures. In addition, the simultaneous acquisition process will allow for improved accuracy in the spatial registration (i.e. overlay) of perfusion and inflammation images in a patient versus the situation of serial images being co-registered expost-facto. This will allow a better spatial correlation of perfusion abnormalities and inflammatory processes in the tissue (e.g. in comparing areas of perfusion deficits in the heart to the location of inflammatory lesions associated with atherosclerotic plaques of the coronary arteries, and the like).

In a further embodiment, the invention provides a method of diagnostic imaging comprising the concurrent detection of inflammation and organ perfusion in a single imaging procedure. More particularly, a method of diagnostic imaging comprising the concurrent detection and localization of perfusion imaging agent and a LTB4 binding agent conjugated to an imageable moiety, such as a gamma ray or positron emitting radioisotope, a magnetic resonance imaging moiety, an X-ray imaging moiety, or an ultrasound imaging moiety.

An imaging moiety comprising a diagnostically radionuclide (i.e., a radioactive metal ion that has imageable gamma ray or positron emissions) are useful as radioimaging contrast agents.

An imaging moieties comprising a paramagnetic metal ion are useful as magnetic resonance imaging contrast agents An imaging moiety comprising one or more X-ray and a surfactant microsphere, are useful as ultrasound contrast agents.

In another preferred embodiment wherein the LTB4 binding agent conjugated to an X-ray imaging moiety, the metal is selected from the group: Re, Sm, Ho, Lu, Pm, Y, Bi, Pd, Gd, La, Au, Au, Yb, Dy, Cu, Rh, Ag, and Ir.

The frequently used heavy atom in X-ray imaging moieties is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215).

X-ray contrast imaging moieties of the present invention are comprised of one or more LTB4 binding agents attached to one or more X-ray absorbing or "heavy" atoms of atomic number 20 or greater. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215).

In another preferred embodiment wherein the LTB4 binding agent conjugated to a MRI imaging moiety of the present invention are comprised of one or more LTB4 binding agents attached to one or more paramagnetic metal ions. The paramagnetic metal ions are present in the form of metal complexes or metal oxide particles. U.S. Pat. Nos. 5,412,148, and 5,760,191, describes examples of chelators for paramagnetic metal ions for use in MRI contrast agents. U.S. Pat. Nos. 5,801,228, 5,567,411, and 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

In another preferred embodiment wherein the LTB4 binding agent conjugated to an ultrasound contrast imaging moiety of the present invention comprise a plurality of LTB4 binding agents attached to or incorporated into a microbubble of a biocompatible gas, a liquid carrier, and a surfactant microsphere. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein incorporated by reference. The term surfactant microsphere includes nanospheres, liposomes, vesicles and the like. The biocompatible gas can be air, or a fluorocarbon, such as a $C_3$–$C_5$ perfluoroalkane, which provides the difference in echogenicity and thus the contrast in ultrasound imaging. The gas is encapsulated or contained in the microsphere to which is attached the LTB4 binding agent, optionally via a linking group. The attachment can be covalent, ionic or by van der Waals forces. Specific examples of such contrast imaging moieties include lipid encapsulated perfluorocarbons with a plurality of tumor neovasculature receptor binding peptides, polypeptides or peptidomimetics.

When any variable occurs more than one time in any constituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —$N(R^{53})_2$, each of the two $R^{53}$ substituents on N is independently selected from the defined list of possible $R^{53}$. Combinations of substituents and/or variables are permissible only if such combinations result in stable compounds.

By "reagent" is meant a compound of this invention capable of direct transformation into a radiopharmaceutical of this invention. Reagents may utilized directly for the preparation of the radiopharmaceuticals of this invention or may be a component in a kit of this invention.

The term "binding agent" means a radiopharmaceutical of this invention having affinity for and capable of binding to LTB4. The binding agents of this invention have Ki<1000 nM.

By "stable compound" or "stable structure" is meant herein a compound that is sufficiently robust to survive isolation to a useful degree of purity from a reaction mixture, and formulation into an efficacious diagnostic agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65$^{th}$ Edition, CRC Press, Boca Raton, Fla., 1984, as any substance which yields ions, other than hydrogen or hydroxyl ions.

As used herein, "alkyl" is intended to include both branched and straight-chain saturated aliphatic hydrocarbon groups having the specified number of carbon atoms; "cycloalkyl" or "carbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" is intended to include saturated bicyclic ring groups such as [3.3.0]bicyclooctane, [4.3.0] bicyclononane, [4.4.0]bicyclodecane (decalin), [2.2.2] bicyclooctane, and so forth.

As used herein, the term "alkene" or "alkenyl" is intended to include both branched and straight-chain groups of the formula $C_nH_{2n-1}$ having the specified number of carbon atoms.

As used herein, the term "alkyne" or "alkynyl" is intended to include both branched and straight-chain groups of the formula $C_nH_{2n-3}$ having the specified number of carbon atoms.

As used herein, "aryl" or "aromatic residue" is intended to mean phenyl or naphthyl, which when substituted, the substitution can be at any position.

As used herein, the term "heterocycle" or "heterocyclic ring system" is intended to mean a stable 5- to 7-membered monocyclic or bicyclic or 7- to 14-membered bicyclic or tricyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H,6H-1,5,2-dithiazine, thiophene, tetrahydrothiophene, thianthrene, furan, pyran, isobenzofuran, chromene, xanthene, xanthone, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, chromanone, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl" means an aryl group bearing an alkyl group of 1–10 carbon atoms bearing an aryl group; and the term "heterocycloalkyl" means an alkyl group of 1–10 carbon atoms bearing a heterocycle.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to, α-cyclodextrin, hydroxyethyl-α-cyclodextrin, hydroxypropyl-α-cyclodextrin, β-cyclodextrin, hydroxypropyl-β-cyclodextrin, carboxymethyl-β-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-γ-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with the radionuclide, which is typically obtained as a relatively unreactive, high oxidation state compound, to lower its oxidation state by transfering electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with the radionuclide that is stable enough to prevent unwanted side-reactions but labile enough to be converted to the radiopharmaceutical. The formation of the intermediate complex is kinetically favored while the formation of the radiopharmaceutical is thermodynamically favored. Transfer ligands useful in the preparation of radiopharmaceuticals and in diagnostic kits useful for the preparation of said radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into the radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal radionuclide through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practising end user in a clinical or pharmacy setting to synthesize the radiopharmaceutical. The kit provides all the requisite components to synthesize and use the radiopharmaceutical except those that are commonly available to the practising end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

A "buffer" is a compound that is used to control the pH of the kit during its manufacture and during the synthesis of the radiopharmaceutical.

A "lyophilization aid" is a component that has favorable physical properties for lyophilization, such as the glass transition temperature, and is added to the diagnostic kit to improve the physical properties of the combination of all the components of the kit for lyophilization.

A "stabilization aid" is a component that is added to the radiopharmaceutical or to the diagnostic kit either to stabilize the radiopharmaceutical once it is synthesized or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid" is a component that improves the solubility of one or more other components in the medium required for the synthesis of the radiopharmaceutical.

A "bacteriostat" is a component that inhibits the growth of bacteria in the diagnostic kit either during its storage before use of after the kit is used to synthesize the radiopharmaceutical.

The term "dual isotope imaging" means the concurrent scintigraphic imaging of two spectrally-separable gamma emitting (including PET) isotopes wherein one isotope is associated with a LTB4-targeted radiopharmaceutical and the other isotope is associated with an organ perfusion imaging radiopharmaceutical.

The term "perfusion imaging agent" means a radiopharmaceutical which distributes within an organ (e.g. heart, brain, kidney) in proportion to the regional blood flow pattern within that organ, allowing for a scintigraphic image to be acquired which represents a picture of relative perfusion of the organ.

The term "site of endothelial damage" means a locus of vascular endothelium wherein the endothelial cells have been damaged by mechanical, hemodynamic or biochemical means.

The term "site of vulnerable plaque" means a vascular region of active atherosclerosis wherein the endothelium has been damaged and a localized cellular inflammatory process is ongoing.

In one embodiment this invention is a radiolabeled LTB4 antagonist radiopharmaceutical. The radiolabel is a suitable radioisotope having an emission that can be detected outside the body after injection of the radiolabeled LTB4 antagonist into a mammal. Detection using a gamma camera results in an image of the areas of localization of white blood cells bearing the LTB4 receptor to which is attached the radiopharmaceutical. Our approach in designing LTB4 antagonist radiopharmaceuticals was to identify common features in compounds known to have potential therapeutic uses, and then, assisted by a 3-dimensional map of the LTB4 receptor we developed, design radiopharmaceuticals having such features.

A number of therapeutic LTB4 compounds are known. These display a wide variety of structural types. One similarity shared by many of these compounds is the presence of two key regions in the molecule, described in the literature as the eastern and western ends of the molecule, connected by a flexible tethering group. Recent reviews of LTB4 antagonists include Djuric et. al., Drugs of the Future, 1992, 17, pp 819–830; Cohen, N. and Yagaloff, K., Curr. Opin. Invest. Drugs, 1994, 3, pp. 13–22; and Brooks, C. and Summers, J., J. Med. Chem., 1996, 39, pp 2629–2654, the disclosures of which are herein incorporated by reference in their entirety.

We have identified two concepts for designing radiolabeled LTB4 antagonists. In one concept the radioisotope bonding unit is incorporated into the structure in such a way that it participates in the binding of the compound to the receptor site even when bound to the radioisotope. In the second concept, the radioisotope bonding unit is incorporated into a site on the molecule which is not part of the recognition site, and is removed enough from the recognition site that its presence does not interfere with the binding of the compound to the receptor.

An example of the first concept is to design a LTB4 radiopharmaceutical wherein either the eastern or western end of a potential therapeutic LTB4 antagonist is replaced with an appropriate radionuclide bonding unit bound to Tc-99m or a radiohalogen substituent. Scheme 1 shows the potential therapeutic LTB4 antagonist, (I), which has excellent affinity for the LTB4 receptor (Sawyer et al.; J. Med. Chem., 1995, 38, 4411–32). In (I) the tetrazole substituent serves as a hydrogen bonding acceptor, thereby promoting binding of the compound to the receptor. When the tetrazole is absent, the compound has no affinity (7 $\mu$M) for the LTB4 receptor. Also shown in Scheme I is radiopharmaceutical (II), which is a LTB4 receptor antagonist labeled with Tc-99m. In this radiopharmaceutical, the tetrazole group of (I) is replaced with the HYNIC metal chelator complexed to Tc, whose coordination sphere is completed by two ancillary ligands. (II) retains good activity for the LTB4 receptor. (II) can be prepared from reagent (Iia), which bears a hydrazone protected hydrazonicotinamide group, by reaction of (Iia) with Tc-99m in the presence of a suitable reducing agent and appropriate ancillary ligands. (Iia) retains very good affinity for LTB4 (Ki=8 nM compared to 3 nM for I).

Scheme 1

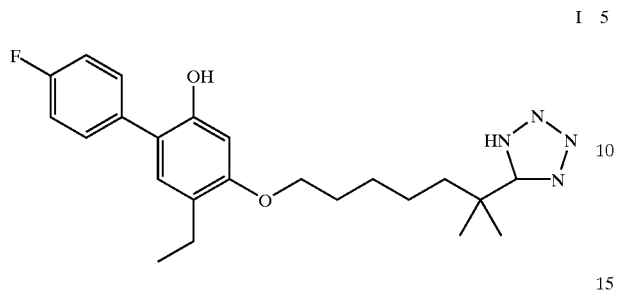

I

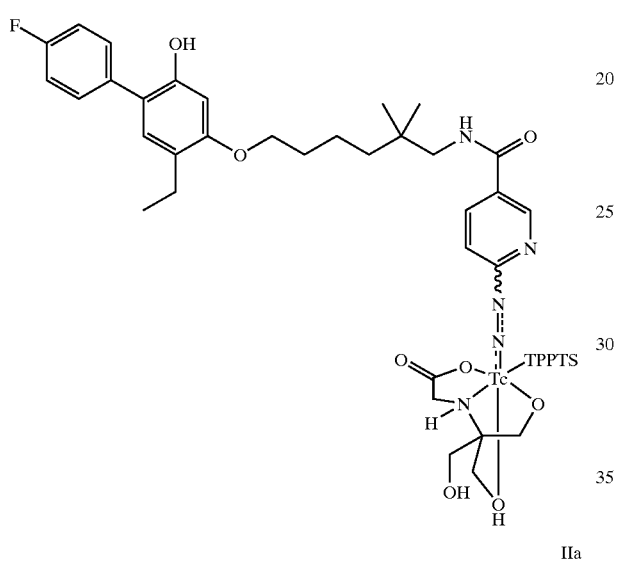

II

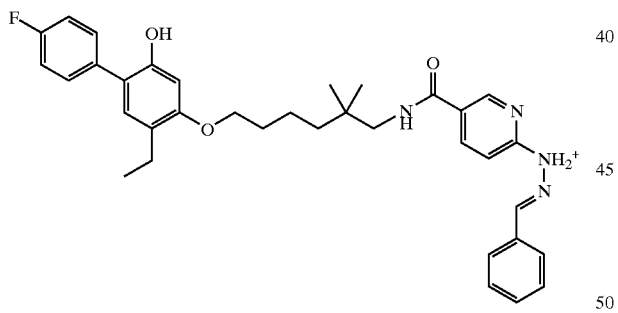

IIa

Scheme 2

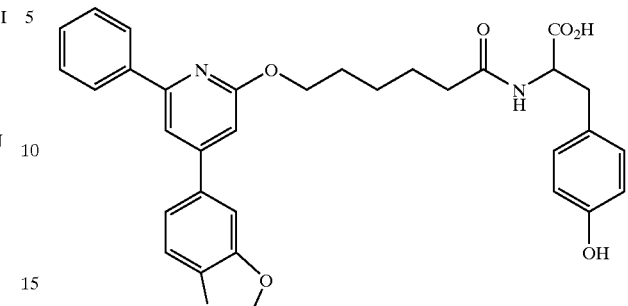

III

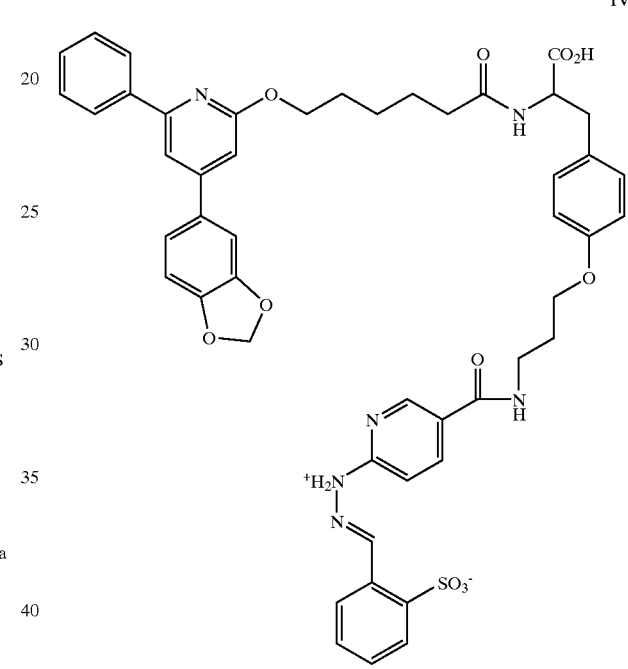

IV

An example of the second approach is shown in Scheme 2. Compound III is an active LTB4 antagonist (Ki=41 nm). This compound was elaborated into a reagent of this invention. This was accomplished by conjugation of a hydrazone protected hydrazinonicotinamide group via a three carbon tether to the tyrosine hydroxyl oxygen to provide a reagent for preparing a Tc-99m radiopharmaceutical of the present invention, reagent IV. Reagent (IV), with Ki=52 nM, has essentially the same affinity for LTB4 as does (III). Reagent IV is readily converted to the radiolabeled analog using the methods described below.

The tyrosine aromatic ring of (III) can also be radioiodinated to form a radiopharmaceutical of the present invention.

In the reagents of the present invention, compounds IIa and IV shown above, the three common structural features are: a western end comprised of a hydrogen bond acceptor, either phenolic oxygen or the pyridine nitrogen, and an aromatic substituent; a spacer or tether; and an eastern end comprised of a hydrogen bond acceptor, a carbonyl oxygen. Some examples of alternative western end moieties are shown in Scheme 3.

Scheme 3

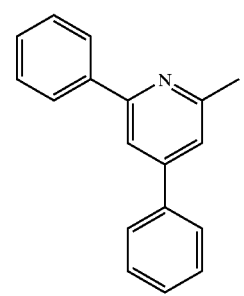 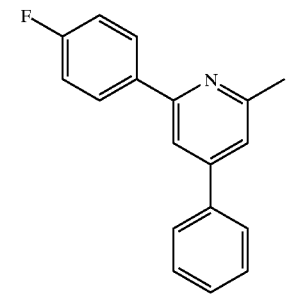

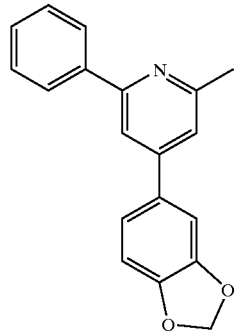
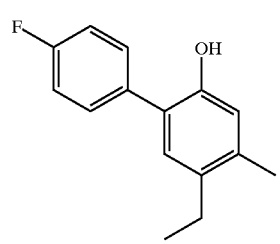
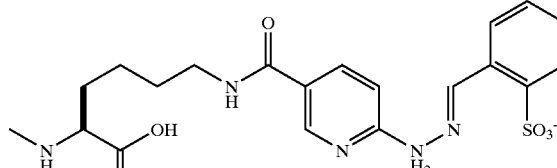
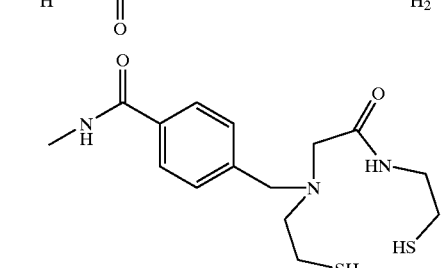
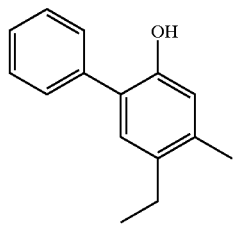
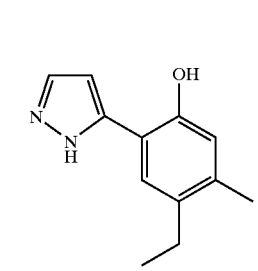
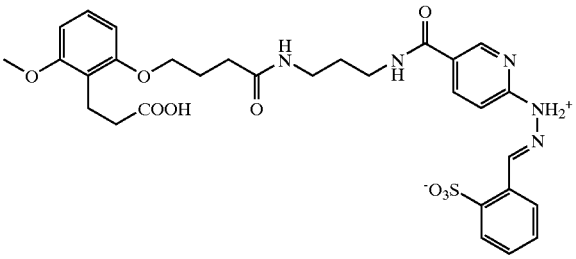
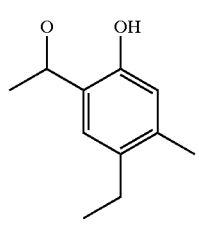
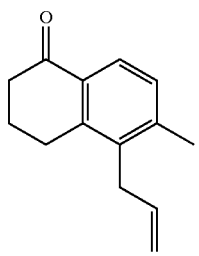
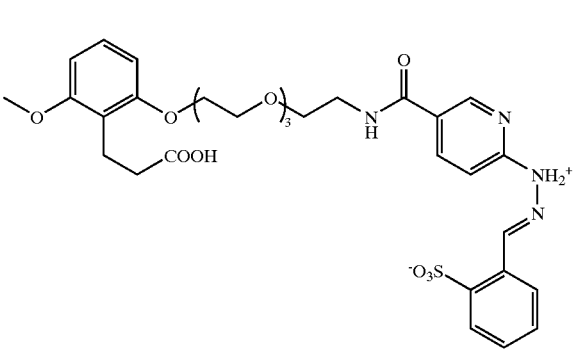

Some examples of alternative spacers or tethers include acyclic alkyl, either straight chain or branched and heterocycloalkyl. Some examples of alternative eastern ends bearing an optional second spacer or tether and a chelator or metal bonding unit are shown in Scheme 4.

Scheme 4

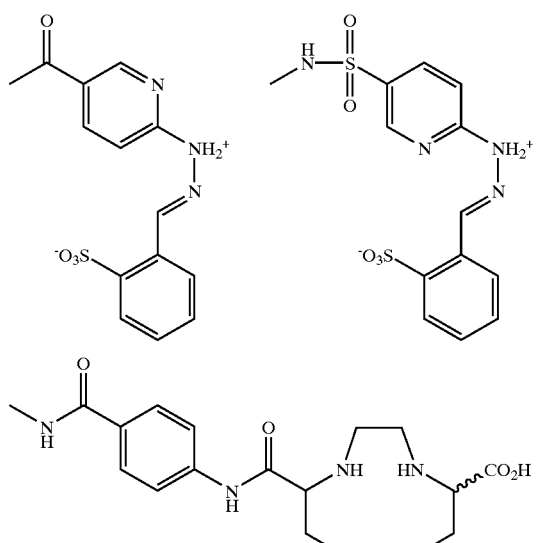

The second spacer or tether provide a means of incorporating a pharmacokinetic modifier into the radiopharmaceuticals of the present invention. The pharmacokinetic modifier serves to direct the biodistibution of the portion of the injected radiopharmaceutical that does not become associated with white blood cells. A wide variety of functional groups can serve as pharmacokinetic modifiers, including, but not limited to, carbohydrates, polyalkylene glycols, peptides or other polyamino acids, and cyclodextrins. The modifiers are generally characterized by a plurality of atoms selected from oxygen and nitrogen, which provide enhanced hydrophilicity to the radiopharmaceuticals and can thus affect their rate of blood clearance and the route of elimination. Preferred pharmacokinetic modifiers are those that result in moderate blood clearance and enhanced renal excretion.

Other radiopharmaceuticals of the present invention are comprised of more compact LTB4 antagonist moieties to which are attached an optional spacer or tether and a chelator or metal bonding unit. Examples of these compact LTB4 antagonist moieties are shown in Scheme 5.

Scheme 5

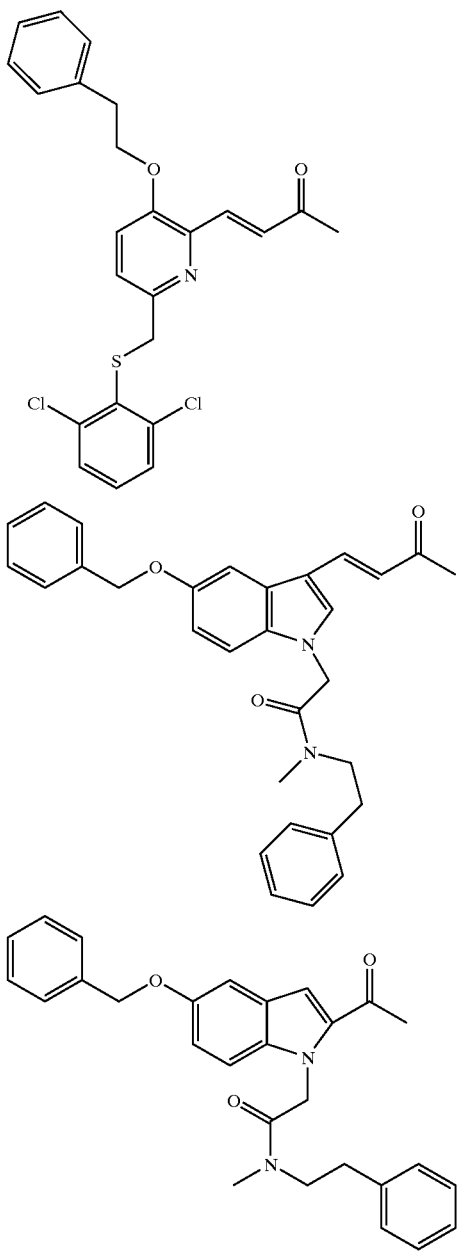

SYNTHESIS OF RADIOPHARMACEUTICALS

The radiolabeled LTB4 antagonist compounds of the present invention can be synthesized using standard synthetic methods known to those skilled in the art, using radioisotopes of halogens (such as chlorine, fluorine, bromine and iodine), technetium and indium, as well as others. Preferable radioisotopes include $^{123}$I, $^{125}$I, $^{131}$I, $^{99m}$Tc, and $^{111}$In.

The LTB4 antagonist compounds of the invention may be labeled either directly (that is, by incorporating the radiolabel directly into the compounds) or indirectly (that is, by incorporating the radiolabel into the compounds through a chelator which has been incorporated into the compounds). For direct labeling, as those skilled in the art will recognize, the labeling may be isotopic or nonisotopic. With isotopic labeling, one group already present in the cyclic compound is substituted with (exchanged for) the radioisotope. With nonisotopic labeling, the radioisotope is added to the cyclic compounds without substituting with (exchanging for) an already existing group.

Generally, labeled compounds are prepared by procedures which introduce the labeled atom at a late stage of the synthesis. This allows for maximum radiochemical yields, and reduces the handling time of radioactive materials. When dealing with short half-life isotopes, a major consideration is the time required to conduct synthetic procedures, and purification methods. Protocols for the synthesis of radiopharmaceuticals are described in Tubis and Wolf, Eds., "Radiopharmacy", Wiley-Interscience, New York (1976); Wolf, Christman, Fowler, Lambrecht, "Synthesis of Radiopharmaceuticals and Labeled Compounds Using Short-Lived Isotopes", in Radiopharmaceuticals and Labeled Compounds, Vol 1, p. 345–381 (1973), the disclosures of each of which are hereby incorporated herein by reference, in their entirety.

Various procedures may be employed in preparing the radiolabeled compounds of the invention where the radiolabel is a halogen. Some common synthetic methodologies for isotopic halogen labeling of aromatic compounds such as the type present here are iododediazonization, iododeborobation, iododestannylation, iododesilation, iododethallation, and halogen exchange reactions. The most common synthetic methodology for nonisotopic halogen labeling of aromatic compounds such as the type present here is iododeprotonation or electrophilic aromatic substitution reactions. These methods and additional procedures are described in Merkushev, Synthesis, 923 (1988), and Seevers et al, Chem. Rev., 82: 575 (1982), the disclosures of each of which are hereby incorporated herein by reference, in their entirety.

Alternatively, such compounds may prepared by way of isotopic labeling from the unlabeled bromo or iodo derivatives by various two step reaction sequences, such as through the use of trialkylsilyl synthons as described in Wilson et at J. Org. Chem., 51: 483 (1986) and Wilbur et al J. Label. Compound. Radiopharm., 19: 1171 (1982), the use of trialkylsilyl synthons as described in Chumpradit et al J. Med. Chem., 34: 877 (1991) and Chumpradit et al J. Med. Chem., 32: 1431 (1989), and the use of boronic acid synthons as described in Kabalka et al J. Label. Compound. Radiopharm., 19: 795 (1982) and Koch et al Chem. Ber., 124:2091 (1991).

The unlabeled iodo compounds are versatile precursors which can be converted to the labeled derivatives by any of the two step reaction sequences described above. Useful functionality to incorporate into the LTB4 antagonists includes the bromo, the nitro, the trialkylsilyl, the trialkyltin, and the boronic acid groups. The synthesis and application of each of these precursors is described in the references cited above.

The least complex means of radioiodination of the cyclic compounds of the present invention via isotopic labeling during the final stages of their preparation is the substitution of radioactive iodide for a stable iodine atom already present in the molecule. This can often be done by heating the compound with radioactive iodide in an appropriate solvent as described in Ellis et al., Aust. J. Chem., 26: 907 (1973). When applied to aromatic iodides, the extremely small quantities and low concentration of radioactive iodide employed leads to the incorporation of only modest specific activity.

The LTB4 antagonist compounds may also be isotopically iodo-labeled during the final stages of their preparation from the anilines by the Sandmeyer reaction as described in Ellis et al., Aust. J. Chem., 26: 907 (1973). This approach leads to a labeled cyclic compound with high specific activity. To avoid complications in the synthesis of the LTB4 antagonist compound, the nitro group provides an ideal synthon for the aniline.

Labeled iodo derivatives may also be readily prepared nonisotopically from the amino, hydroxy, or methoxy substituted cyclic compounds as described in Arora et al J. Med. Chem., 30:918 (1987). Electrophilic aromatic substitution reactions are enhanced by the presence of such electron-donating substituents.

Various procedures may also be employed in preparing the radiolabeled compounds of the invention where the radiolabel is a metal, such as where the radiolabel is technetium or indium. Exemplary procedures for such technetium or indium labeling are disclosed, for example, in Cerqueira et al., Circulation, Vol. 85, No. 1, pp. 298–304 (1992), Pak et al., J. Nucl. Med., Vol. 30, No. 5, p. 793, $36^{th}$ Ann. Meet. Soc. Nucl. Med. (1989), Epps et al., J. Nucl. Med., Vol. 30, No. 5, p. 794, $36^{th}$ Ann. Meet. Soc. Nucl. Med. (1989), Pak et al., J. Nucl. Med., Vol. 30, No. 5, p. 794, $36^{th}$ Ann. Meet. Soc. Nucl. Med. (1989), and Dean et al., J. Nucl. Med., Vol. 30, No. 5, p. 794, $36^{th}$ Ann. Meet. Soc. Nucl. Med. (1989), the disclosures of each of which are hereby incorporated herein by reference, in their entirety.

Preferred reagents of the present invention are comprised of chelators or radionuclide bonding units which are diaminedithiols, monoamine-monoamidedithiols, triamide-monothiols, monoamine-diamide-monothiols, diaminedioximes, or hydrazines. The chelators are generally tetradentate with donor atoms selected from nitrogen, oxygen and sulfur. More preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferrably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosue of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

The transition metal radionuclide is selected from the group: technetium-99 m, rhenium-186 and rhenium-188.

For diagnostic purposes Tc-99 m is the preferred isotope. Its 6 hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy, however, they also emit high energy beta particles that are more damaging to living tissues. These beta particle emissions can be utilized for therapeutic purposes, for example, cancer radiotherapy.

The coordination sphere of the radionuclide includes all the ligands or groups bound to the radionuclide. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and amine nitrogen ($sp^3$ hydribidized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris(hydroxymethyl)methylglycine).

The most preferred radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen (sp$^2$ hybridized), sulfur (sp$^2$ hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908, and U.S. Ser. Nos. 60/013360 and 08/646,886, the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

The radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $A_{L2}$ and reacting further at temperatures from 0 to 100° C.

The total time of preparation will vary depending on the identity of the radionuclide, the identities and amounts of the reactants and the procedure used for the preparation. The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amounts of the ancillary ligands $A_{L1}$ used can range from 0.1 mg to 1 g, or more preferrably from 1 mg to 100 mg. The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferrably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 µg/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistibution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

Another aspect of the present invention are diagnostic kits for the preparation of radiopharmaceuticals useful as imaging agents for the inflammation and infection. Diagnostic kits of the present invention comprise one or more vials containing the sterile, non-pyrogenic, formulation comprised of a predetermined amount of a reagent of the present invention, one or two ancillary and optionally other components such as reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practising end user, the ease of manufacturing the kit, the shelf-life of the kit, or the stability and shelf-life of the radiopharmaceutical. The one or more vials that contain all or part of the formulation can independently be in the form of a sterile solution or a lyophilized solid.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly (oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practising end user can synthesize the radiopharmaceutical and have a high degree of certainty that the radiopharmaceutical can be safely injected into a patient and will provide diagnostic information about the disease state of that patient.

Another aspect of the present invention contemplates a method of imaging the site of infection or inflammation in a patient involving: (1) synthesizing a radiopharmaceutical using a reagent of the present invention capable of localizing at sites of infection or inflammation; (2) administering said radiopharmaceutical to a patient by injection or infusion; (3) imaging the patient using either planar or SPECT gamma scintigraphy.

A further aim of the present invention is the use of LTB4-targeted radiopharmaceuticals in a dual isotope imaging procedure in conjunction with a perfusion imaging radiopharmaceutical. In this dual isotope procedure a scintigraphic image of the radiolabeled LTB4 receptor-binding compound is acquired at the same time as a scintigraphic image of a radiolabeled cardiac perfusion imaging agent. This simultaneous dual isotope imaging is done by utilizing radioisotopes bound to the LTB4 antagonist and the perfusion imaging agent which have spectrally separable gamma emission energies. For example, a Tc99m cardiac perfusion imaging agent (such as Tc99 m-Sestamibi) or T1201 (as Thallous Chloride), and an In111-labeled LTB4 antagonist compound are imaged simultaneously with a standard gamma camera. This is possible because the Tc99m gamma energy of ~140 KeV or the T1201 gamma energy of ~80 KeV are easily separable from the In111 gamma energies of ~160 KeV and 250 KeV. This simultaneous imaging of cardiac perfusion and cardiac inflammation (as evidenced by the LTB4 compound localization) is extremely useful for improved anatomic assessment of the location of LTB4 receptor distribution in the heart based on the comparison to the perfusion distribution seen on the Tc99 m-Sestamibi or T1201 image. It also allows for the evaluation of a match or mismatch between cardiac perfusion and the cardiac inflammation image. The simultaneous imaging of perfusion and inflammation allows a more complete assessment of the underlying cardiac disease, both in terms of blood flow alterations and inflammatory changes, in a single imaging session on a patient.

The simultaneous dual-isotope imaging of perfusion and inflammation allows for the localization of sites of ischemic tissue injury (e.g. reperfusion injury), vulnerable plaque, bacterial endocarditis or cardiac transplant rejection to be correlated with cardiac perfusion during one imaging session. In addition, the imaging of inflammatory response associated with ischemic tissue damage (such as in reperfusion injury) and myocardial blood flow (from the perfusion imaging agent) is extremely useful in characterizing the severity and extent/location of inflammation. This simultaneous imaging procedure is also useful in monitoring responses to therapy for reducing cardiac inflammation simultaneously with monitoring changes in myocardial blood flow.

The simultaneous imaging of different radioisotopes/ radiopharmaceuticals for localization of inflammation and cardiac perfusion allows a more exact registration of the images than would be possible when comparing two serially-acquired images. It is also a more efficient use of imaging equipment and health care personnel time and resources. This simultaneous imaging will save several hundred dollars per study relative to two separate imaging procedures.

The simultaneous imaging of different radioisotopically-labeled radiopharmaceuticals for organ perfusion and a biospecific target in patients is not new. For example, Antunes, et al., have demonstrated that it is possible to image myocardial infarction with an In111-antimyosin antibody along with the imaging of cardiac perfusion with T1201. However, the dual isotope imaging of the present invention is new, because it is the first reported approach to the simultaneous, dual isotope imaging of a radiolabeled inflammation imaging compound and a perfusion imaging compound. The combination of LTB4 antagonist scintigraphic imaging with perfusion imaging provides the imaging physician with an extraordinary amount of clinical information regarding, for example, reperfusion injury to transiently ischemic tissue or inflammation associated with active atherosclerotic plaque and organ blood flow changes in a single imaging session.

The radiopharmaceuticals are administered by intravenous injection, usually in saline solution, at a dose of 1 to 100 mCi per 70 kg body weight, or preferably at a dose of 5 to 50 mCi. Imaging is performed using known procedures.

EXAMPLES

The materials used to synthesize the following examples of the present invention were obtained from commercial sources or prepared as described in the following references.

Substituted (E)-3-[6-(arylthiomethyl)-3-(2-phenylethoxy)-2-pyridinyl]-2-propenoic acid and substituted 3-[6-(arylthiomethyl)-3-(2-phenylethoxy)-2-pyridinyl]propanoic acid derivatives useful as intermediates in the synthesis of the compounds of the invention are prepared using standard procedures, for example, as described in Daines et al., J. Med. Chem, 39: 3837 (1996); Daines et al J. Med. Chem, 37: 3327 (1994); Daines, PCT International Application WO 95/15752; Daines, PCT International Application WO 95/15950.

[3-(4-Phenylbenzyl)-4-hydroxychroman-7-yl] cyclopentane carboxylic acid derivatives useful as intermediates in the synthesis of the compounds of the invention are prepared using standard procedures, for example, as described in Koch et al., J. Med. Chem, 37: 3197 (1994); Koch et al., PCT International Application WO 93/15066; Koch et al., PCT International Application WO 93/15067.

5-Allyl-6-hydroxy-1-tetralone derivatives useful as intermediates in the synthesis of the compounds of the invention are prepared using standard procedures, for example, as described in Cohen et al., Bioorg. & Med. Chem. Lett., 4: 2883 (1994); Cohen et al., PCT International Application WO 95/15956.

6-Bromo-2,2-dimethylhexanenitrile was synthesized as described by Larcheveque, M. et. al., Bull. Soc. Chim. Fr., 1974, 1710–1714.

4,6-Diphenyl-2-pyridone, 4-(3,4-Methylenedioxyphenyl)-6-diphenyl-2-pyridone, 6-[(4,6-diphenyl-2-pyridinyl)oxy]-2,2-dimethylhexanenitrile, 6-(5-(2H-2,3,4,5-tetraazolyl)-5-methylhexyloxy)-2,4-diphenylpyridine and 6-(5-(2H-2,3,4,5-tetraazolyl)-5-methylhexyloxy)-2,4-diphenylpyridine were synthesized as described by Labaudiniere, R. et. al., J. Med. Chem., 1992, 35, 4315–4324.

t-Butyl 4-bromobutyrate was synthesized as described by Morin, C. et. al., Tetrahedron, 1992, 48, 9277–9282.

11-Amino-3,6,9-trioxaundecanol, 2-(2-(2-(3-aza-3-diazoprop-3-enyloxy)ethoxy)ethoxy)ethan-1-ol were synthesized as described by Bertozzi, C. R. et. al., J. Org. Chem., 1991, 56, 4326–4329.

2-Hydroxy-6-[(5-hydroxypentyl)oxy]benzenepropanoic acid methyl ester and 6-hydroxy-5-prop-2-enyl-2,3,4-trihydronaphthalen-1-one were synthesized as described by Cohen, N., European Patent Application EP 0531823A1.

2-Hydrazino-5-sulfamoylpyridine was prepared according to U.S. Pat. No. 4,204,870.

N-Methyl-N-phenethyl-2-[5-benzyloxy-3-(2-carboxyvinyl)indol-1-yl]acetamide was prepared according to F. C. Huang et al., PCT International Application WO 92/04321.

7-(3-(2-Ethyl-4-(4-flurophenyl)-5-(phenylmethoxy)phenoxy)propoxy)-8-propylchromane-2-carboxylic acid was prepared according to Sawyer, et al., J.Med.Chem., 1995, 38, 4411.

A mixture of 4-ethyl-2(1-methyl-1H-pyrazol-5-yl)-5-[[5-methyl-5-cyanohexyl]oxy]phenol and 4-ethyl-2(1-methyl-1H-pyrazol-3-yl)-5-[[5-methyl-5-cyanohexyl]oxy]phenol was prepared as described in R. W. Harper, et al., J.Med.Chem., 1994, 37, 2411.

N-[4-(Carboxy)benzyl]-N,N'-bis[(2-triphenylmethylthio)ethyl]glycinamide N-hydroxysuccinimide ester was synthesized as described by Harris, T. D. et. al., Bioorg. Med. Chem. Lett. 1996, 6, 1741–1746.

N-(2-(2-(2-(2-Aminoethoxy)ethoxy)ethoxy)-ethyl) (tert-butoxy)formamide (5.87 g, 20 mmol) was prepared as described by Levenson, C., U.S. Pat. No. 4,803,297.

6-Deoxy-6-amino-β-cyclodextrin was prepared as described by Petter, R. C. et. al., J. Am. Chem. Soc., 1990, 112, 3860–3868. Tetrafluorophenyl bis-S-(1-ethoxyethylmercapto-acetyl)pentanoate was prepared as described in Fritzberg, A. et. al., Proc. Natl. Acad. Sci. U.S.A., 1988, 85, 4025.

Abbreviations used in this section:
TEA: triethylamine
DCM: dichloromethane
ACN: acetonitrile
Z: benzyloxycarbonyl
Ms: mesylate
TFA: trifluoroacetic acid
DIEA: diisopropylethylamine
HATU: O-(7-azabenzotriazol-1-yl)-1,1,3,3-tetramethyluronium Hexafluorophosphate
HBTU: O-(Benzotriazol-1-yl)-1,1,3,3-tetramethyluronium Hexafluorophosphate
TMSI: trimethylsilyliodide
TPPTS: tris(3-sulfonatophenyl)phosphine, sodium salt
TPPDS: Bis(3-sulfonatophenyl)phenylphosphine, disodium salt
TPPMS: (3-sulfonatophenyl)diphenylphosphine, monosodium salt
TFP: tris(2-furanyl)phosphine Example 1

Synthesis of 4-ethyl-2-(4-fluorophenyl)-[5-[5,5-dimethyl-6-[[6-[[[(2-sulfonylphenyl)methylene]hydrazino]-3-pyridinyl]carbonyl]amino]hexyl]oxy] phenol

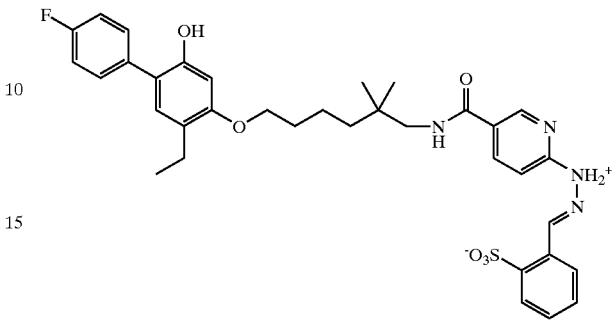

Step A: Preparation of 4-(benzyloxy)-2-[(5-methyl-5-cyanohexyl)oxy]-benzophenone A solution of 4-benzyloxy-2-hydroxyacetophenone (2.45 g), potassium carbonate (3.25 g), potassium iodide (0.42 g), and 5-cyano-5-methyl-1-bromohexane (2.6 g) in dimethylformamide (40 mL) was heated at 90° C. for 22 hours under nitrogen. The slurry was cooled, poured into water (150 mL) and extracted with ethyl acetate. The combined extracts were washed with water, dried (MgSO$_4$), filtered, and concentrated under reduced pressure to an orange oil. This was purified by flash chromatography (ethyl acetate:hexane) to afford the product (2.4 g) as a clear oil. NMR(CDCl$_3$): 1.37, s (6H); 1.64, m (4H); 1.89, m (2H); 2.58, s (3H); 4.03, t (3H); 5.09, s (2H); 6.50, s (1H); 6.58, d (1H); 7.37, m (5 H); 7.81, d (1H). Mass Spec (GC-MS) m/z=365 (M).

Step B: Preparation of 4-(benzyloxy)-2-[(5-methyl-5-cyanohexyl)oxy]-ethylbenzene The acetophenone (2.4 g) was dissolved in carbon tetrachloride (6 mL) and trifluoroacetic acid (6 mL) and triethylsilane (5.9 mL) added. The solution was stirred for 2 hours and poured into saturated sodium bicarbonate and ethyl acetate. The layers were separated and the organic layer was washed with saturated bicarbonate until washings remained basic, dried (MgSO$_4$), filtered, and concentrated under vacuum to a reddish oil (2.6 g). This was purified by flash chromatography (hexane:ethyl acetate) to afford the product (2.0 g) as a clear oil. NMR (CDCl$_3$): 1.15, t (3H); 1.34, s (6H); 1.5–1.9, m (6H); 2.55, q (2H); 3.94, t (2H); 5.02, s (2H); 6.48, m (2H); 7.02, d (1H); 7.37, m (5H). Mass Spec (GC-MS) m/z=351 (M).

Step C: Preparation of 1-bromo-2-(benzyloxy)-5-ethyl-4-[(5-methyl-5-cyanohexyl)oxy]benzene

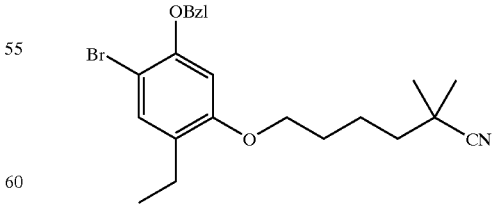

The ethylbenzene (2.0 g) was dissolved in carbon tetrachloride (25 mL) and N-bromosuccinimide (1.16 g) added. The solution was stirred 18 hours, diluted with dichloromethane (50 mL), washed with water, dried (MgSO$_4$), filtered and concentrated under vacuum to an orange solid.

This was recrystallized from hexane/ethyl acetate to yield the product as a white solid (1.65 g). NMR (CDCl$_3$): 1.14, t (3H); 1.35, s (6H) 1.5–1.9, m (6H); 2.52, q (2H); 3.88, t (2H); 5.12, s (2H); 6.45, s (1H); 7.2–7.5, m (6H). MS (EI) m/z=454.2 (M+Na).

Step D Preparation of 1-(benzyloxy)-4-ethyl-2-(4-fluorophenyl)-5-[(5-methyl-5-cyanohexyl)oxy]-benzene

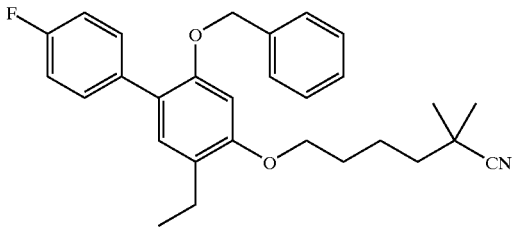

4-fluorophenylboronic acid (0.84 g) was added to ethanol (5 mL). To this was added toluene (15 mL), the bromonitrile (1.29 g), 1.82N sodium carbonate solution (4.9 mL), and tetrakis-triphenylphosphine palladium (0.35 g) under a nitrogen atmosphere. The mixture was heated at reflux for 18 hours, cooled, and poured into ethyl acetate (50 mL). The layers were separated and the organics washed with saturated ammonium chloride solution, dried (MgSO$_4$), filtered, and concentrated under vacuum to afford a green oil (1.75 g). This was purified by flash chromatography to afford the product (1.13 g) as a clear oil. NMR (CDCl$_3$): 1.19, t (3H); 1.36, s (6H) 1.5–1.9, m (6H); 2.612, q (2H); 3.97, t (2H); 5.02, s (2H); 6.55, s (1H); 7.06, m (3H); 7.32, m (5H); 7.50, dd (2H). MS (EI) m/z=468.2 (M+Na).

Step E: Preparation of 1-(benzyloxy)-4-ethyl-2-(4-fluorophenyl)-5-[(5,5-dimethyl-6-aminohexyl)oxy]benzene

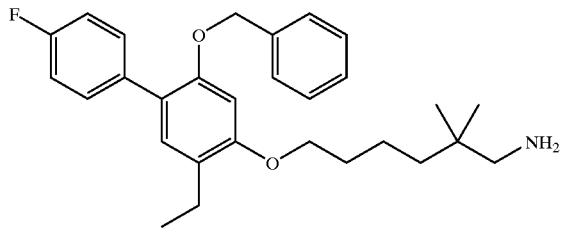

Dry ether (10 mL) was added to anhydrous aluminum chloride (670 mg) at 0° C. under nitrogen and stirred until dissolution was complete. Lithium aluminum hydride (190 mg) was added in one portion and the solution heated to reflux. 1-(benzyloxy)-4-ethyl-2-(4-fluorophenyl)-5-[(5-methyl-5-cyanohexyl)oxy]-benzene (1.05 g) dissolved in dry ether (5 mL) was added dropwise at reflux. The heat was removed and the mixture stirred at ambient temperature for 5 hours. The reaction was quenched by addition of water, followed by 6N sulfuric acid until a clear solution was obtained. This was extracted with ether. The aqueous solution was cooled and treated with 50% sodium hydroxide. The basic mixture was extracted with ether. The organic layers were dried over magnesium sulfate, filtered, and concentrated under reduced pressure to afford 900 mg of 1-(benzyloxy)-4-ethyl-2-(4-fluorophenyl)-5-[(6,6-dimethyl-6-aminohexyl)oxy]benzene as a white solid, which was not further purified but carried forward. NMR (CDCl$_3$) 0.83 s (6H); 1.17, t (3H); 1.25, m (2H); 1.42, m (2H); 1.55 broad (2H); 1.77, m (2H); 2.47, s (2H); 2.61 q (2H); 3.95, t (2H); 5.00, s (2H); 6.55, s (1H); 7.03, d (2H); 7.08, s (1H); 7.31, m (5H); 7.50, d of d (2H). Mass Spec (EI), m/e=450.3 (M+H)

Step F Preparation of 4-ethyl-2-(4-fluorophenyl)-5-[(5,5-dimethyl-6-aminohexyl)oxy]phenol 1-(benzyloxy)-4-ethyl-2-(4-fluorophenyl)-5-[(5,5-dimethyl-6-aminohexyl)oxy]benzene (900 mg) was dissolved in ethanol (7 mL) and added to a solution of 10% palladium on carbon (200 mg) in 10 mL ethanol. The flask was fitted with a balloon and pressurized with hydrogen gas to maintain inflation of the balloon. The reaction was stirred overnight. The solution was filtered through Celite and concentrated under reduced pressure to afford III as an amber oil, essentially pure by TLC. Trituration with 19:1 hexane/ethyl acetate afforded the product 4-ethyl-2-(4-fluorophenyl)-5-[(6,6-dimethyl-7-aminoheptyl)oxy]phenol (625 mg) as an off white solid. NMR (CDCl$_3$): 0.84, s, (6H); 1.17, t (3H); 1.24, m (2H); 1.76, m (2H); 2.43, s (2H); 2.57, q (2H); 2.82, broad (2H); 3.95, t (2H); 6.45, s (1H); 6.96, s (1H); 7.11, d of d (2H); 7.43, d of d (2H). Mass Spec (EI), m/e=360.2 (M+H).

Step G Preparation of Sodium 2-[[[5-[[(2,5-dioxo-1-pyrolidinyl)oxy]carbonyl]-2-pyridinyl]hydrazono]methyl]-benzenesulfonate

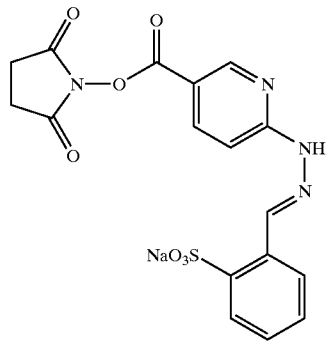

To a solution of 2-formylbenzenesulfonic acid sodium salt (13.6 g) in dimethylformamide (400 mL) was added 2-hydrazinonicotinic acid (10.0 g) and the mixture stirred for three hours. N-hydroxysuccinimide (7.52 g) and dicyclohexylcarbodiimide (27.6 g) were added to the reaction and it was stirred for 16 hours. The mixture was filtered through Celite and the filtrate concentrated under vacuum to a thick oil. This was triturated with ethyl acetate to afford a solid which was filtered to afford crude product (32.8 g). The solids were refluxed in hot methanol for 5 hours, filtered, washed with methanol, and dried under vacuum to afford Sodium 2-[[[5-[[(2,5-dioxo-1-pyrolidinyl)oxy]carbonyl]-2-pyridinyl]hydrazono]methyl]-benzenesulfonate (21.2 g) as a pale yellow solid. NMR (DMSO-d$_6$): 2.88, s (4H); 7.36, m (3H); 7.79, d of d (1H); 8.10, m (2H); 8.79, t (1H); 9.16, s (1H); 11.90, s (1H).

Step H Preparation of 4-ethyl-2-(4-fluorophenyl)-[5-[5,5-dimethyl-6-[[6-[[[(2-sulfonylphenyl)methylene]hydrazino]-3-pyridinyl]carbonyl]amino]heptyl]oxy]phenol Dry dimethylformamide (7 mL)was charged to a flask under nitrogen. To this was added 4-ethyl-2-(4-fluorophenyl)-5-[(5,5-dimethyl-6-aminohexyl)oxy]phenol (180 mg) and sodium 2-[[[5-[[(2,5-dioxo-1-pyrolidinyl)oxy]carbonyl]-2-pyridinyl]hydrazono]methyl]-benzenesulfonate (275 mg) followed by diisopropylethylamine (97 mg) and 4-dimethylaminopyridine (15 mg). The solution was stirred overnight. Solvent was concentrated under vacuum and the residual oil partitioned into water/ethyl acetate. The ethyl acetate was concentrated and the resulting solids triturated with hot ethanol. The crude product was purified by preparative HPLC (5×25 cm Vydac Pharmaceutical C18 column, 0.1% trifluoroacetic acid in water/acetonitrile gradient). NMR (DMSO-d$_6$): 0.88, s (6 H); 1.11, t (3H); 1.33, m (2H); 1.48, m (2H); 1.73, m (2H); 2.50, m (2H); 3.16, d (2H); 3.93, t (2H); 6.52, s (1H); 6.99, s (1H); 7.16, t (2H); 7.19, m (1H); 7.45, m (2H); 7.52, d of d (2H); 7.81, m (1H); 8.26, d (1H); 8.35, d (1H); 8.47, s (1H); 8.53, broad (1H); 9.33, broad (2H). m/e=661.3 (M−H).

Example 2

Synthesis of 4-ethyl-2-(4-fluorophenyl)-[5-[4-[[6-[[[(2-sulfonylphenyl)methylene]hydrazino]-3-pyridinyl]carbonyl]amino]butyl]oxy]phenol

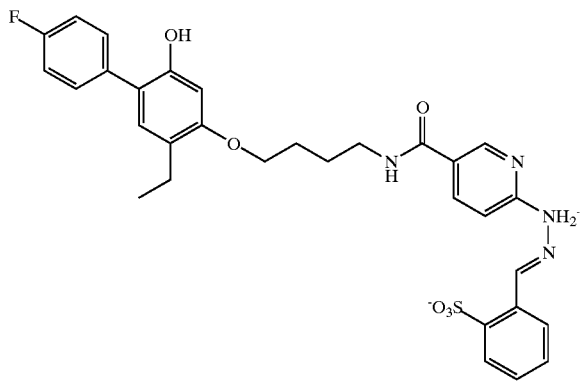

Step A Preparation of 4-(Benzyloxy)-2-[(3-cyanopropyl)oxy]-acetophenone 2-hydroxyl-4-benzyloxy-acetophenone (5 g), 4-bromobutyronitrile (3.66 g), powdered potassium carbonate (5.7 g), and potassium iodide (0.85 g) were added to dimethylformamide (100 mL) under nitrogen. The slurry was heated with stirring at 100° C. for 24 hours, cooled, and poured into water (200 mL) and ethyl acetate (50 mL). The layers were separated and the aqueous layer extracted with ethyl acetate. The combined organics were washed with sodium bisulfite solution and brine, dried over magnesium sulfate, filtered and concentrated under vacuum to an orange solid (5.8 g). This was recrystallized from ethanol to afford pure 4-(benzyloxy)-2-[(3-cyanopropyl)oxy]-acetophenone (5.2 g). NMR (DMSO-d$_6$): 2.10, m (2H); 2.50, s (3H); 2.70, t (2H); 4.16, t (2H); 5.19, s (2H); 6.69, m (1H); 6.75, d (1H); 7.40, m (5H); 7.67, d (1H). Mass Spec (EI), m/e=310.1 (M+H).

Step B Preparation of 4-(Benzyloxy)-2-[(3-cyanopropyl)oxy]-1-ethylbenzene 4-(Benzyloxy)-2-[(3-cyanopropyl)oxy]-acetophenone (5 g) was dissolved in carbon tetrachloride (12.5 mL) under nitrogen. To this was added trifluoroacetic acid (15 mL) and triethylsilane (15.5 mL) with stirring. The solution was stirred for three hours and then poured into 0.1N sodium hydroxide (190 mL)/ethyl acetate (50 mL) with cooling. The layers were separated and the aqueous reextracted with ethyl acetate. The combined organic layers were washed with sodium bicarbonate solution, brine, and dried over magnesium sulfate. The solvent was removed under vacuum after filtration to afford an orange oil. This was purified by flash chromatography on silica gel using hexane/ethyl acetate (9:1) as an eluant. After concentration, 4-(Benzyloxy)-2-[(3-cyanopropyl)oxy]-1-ethylbenzene was obtained as a clear oil (2.5 g). NMR (CDCl$_3$): 1.16, t (3H); 2.16, m (2H); 2.56, m (4H); 4.03, t (2H); 5.03, s (2H); 6.50, m (2H), 7.04, d (1H); 7.37, m (5H). Mass Spec (EI), m/e=296.3 (M+H).

Step C Preparation of 1-(benzyloxy)-2-bromo-4-ethyl-5-[(3-cyanopropyl)oxy]-benzene Carbon tetrachloride (30 mL) was used to dissolve 4-(Benzyloxy)-2-[(3-cyanopropyl)oxy]-1-ethylbenzene (2.5 g). N-bromosuccinimide (1.66 g) was added to the solution and it was stirred for 5.5 hours. The mixture was diluted with dichloromethane (50 mL), washed with water, dried over magnesium sulfate, filtered, and concentrated under vacuum. The resulting oil was crystallized from hexane/ethyl acetate at −20° C. to afford 1-(benzyloxy)-2-bromo-4-ethyl-5-[(3-cyanopropyl)oxy]-benzene as a white crystalline solid solution and it was stirred for 5.5 hours. The mixture was diluted with dichloromethane (50 mL), washed with water, dried over magnesium sulfate, filtered, and concentrated under vacuum. The resulting oil was crystallized from hexane/ethyl acetate at −20° C. to afford 1-(benzyloxy)-2-bromo-4-ethyl-5-[(3-cyanopropyl)oxy]-benzene as a white crystalline solid (1.5 g). NMR (CDCl$_3$) 1.14, t (3H); 2.14, m (2H); 2.55, m (4H); 3.98, t (2H); 5.12, s (2H); 6.45, s (1H); 7.37, m (6H).

Step D Preparation of 1-Benzyloxy-2-(4-fluorophenyl)-4-ethyl-5-[(3-cyanopropyl)oxy]-benzene 4-fluorobenzene boronic acid (1.14 g) was dissolved in ethanol (7 mL). To this was added 1-(benzyloxy)-2-bromo-4-ethyl-5-[(3-cyanopropyl)oxy]-benzene (1.5 g), toluene (20 mL), tetrakis-triphenylphosphine palladium (470 mg), and 2M sodium carbonate solution (6.1 mL). The resulting mixture was heated to reflux and held there for 24 hours. The solution was cooled, diluted with ethyl acetate, and the layers separated. The organic layer was washed with saturated ammonium chloride, dried over magnesium sulfate, filtered, and concentrated to afford a green oil. This was purified by flash chromatography on silica using hexane/ethyl acetate (9:1). The resulting fractions were concentrated under vacuum to afford 1-Benzyloxy-2-(4-fluorophenyl)-4-ethyl-5-[(3-cyanopropyl)oxy]-benzene (1.1 g) as a clear oil. NMR (CDCl$_3$): 1.18, t (3H); 2.15, m (2H); 2.59, m (4H); 4.06, t (2H); 5.00, s (2H); 6.53, s (1H); 7.06, t (2H); 7.09, s (1H); 7.30, m (5H); 7.49, d of d (2H).

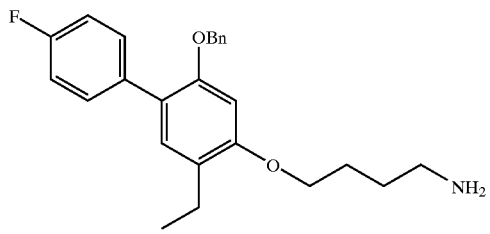

Dry ether (10 mL) was added to anhydrous aluminum chloride (693 mg) at 0° C. under nitrogen and stirred until dissolution was complete. Lithium aluminum hydride (197 mg) was added in one portion and the solution heated to reflux. 1-Benzyloxy-2-(4-fluorophenyl)-4-ethyl-5-[(3-cyanopropyl)oxy]-benzene (1.05 g) dissolved in dry ether (5 mL) was added dropwise at reflux. The heat was removed and the mixture stirred at ambient temperature for 4.5 hours.

The reaction was quenched by addition of water, followed by 6N sulfuric acid until a clear solution was obtained. This was extracted with ether. The aqueous solution was cooled and treated with 50% sodium hydroxide. The basic mixture was extracted with ether. The organic layers were dried over magnesium sulfate, filtered, and concentrated under reduced pressure to afford 500 mg of 1-Benzyloxy-2-(4-fluorophenyl)-4-ethyl-5-[(4-aminobutyl)oxy]-benzene as an oil, which was not further purified but carried forward. Mass Spec (EI), m/e=394.3 (M+H)

d (1H); 8.38, d (1H); 8.46, s (1H); 8.78, m (1H); 9.36, s (1H). Mass Spec (EI), m/e=605.2 (M−H).

Example 3

Synthesis of 2-[[[5-[[(6-[(4,6-diphenyl-2-pyridinyl)oxy]-1-hexanamino]carbonyl]-2-pyridinyl]hydrazono]methyl]-benzenesulfonic acid

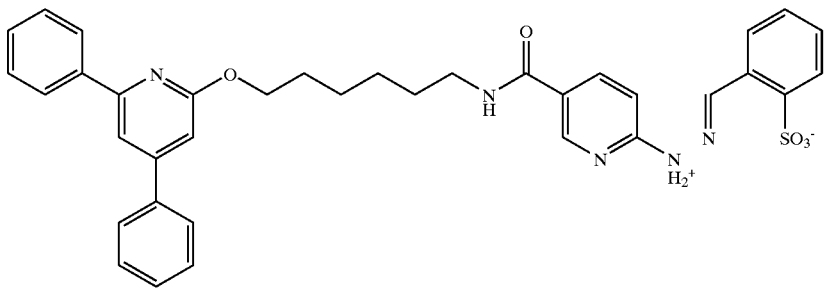

Step F Preparation of 4-Ethyl-2-(4-fluorophenyl)-5-[(4-aminobutyl)oxy]phenol

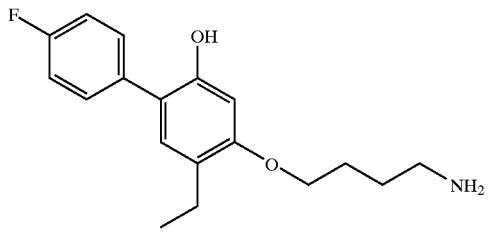

A flask was charged with 10% palladium on carbon (200 mg), ethanol (20 mL), and 1-benzyloxy-2-(4-fluorophenyl)-4-ethyl-5-[(4-aminobutyl)oxy]-benzene (500 mg). The flask was fitted with a balloon and pressurized with hydrogen to fully inflate the balloon. The reaction was stirred 3.5 hours, filtered through Celite, and the filtrate concentrated under vacuum to afford 4-ethyl-2-(4-fluorophenyl)-5-[(4-aminobutyl)oxy]phenol as a white powder (350 mg). HPLC showed that ~25% starting material remained. It was not purified but carried directly into the next step. Mass Spec (EI), m/e=304.1 (M+H).

Step G Preparation of 4-ethyl-2-(4-fluorophenyl)-[5-[4-[[6-[[[(2-sulfonylphenyl)methylene]hydrazino]-3-pyridinyl]carbonyl]amino]butyl]oxy]phenol 4-Ethyl-2-(4-fluorophenyl)-5-[(4-aminobutyl)oxy]phenol (300 mg) was dissolved in dimethylformamide (10 mL) under nitrogen. Sodium 2-[[[5-[[(2,5-dioxo-1-pyrolidinyl)oxy]carbonyl]-2-pyridinyl] hydrazono]methyl]-benzenesulfonate (440 mg) and triethylamine (324 mg) were added and the reaction stirred overnight at ambient temperature. The solvent was removed under vacuum to afford a brown oil, which was purified by preparative HPLC (5 cm×25 cm Vydac Pharmaceutical column, 0.1% trifluoroacetic acid/water (A): 90% acetonitrile/water (B) gradient, 50%→85% B in 25 minutes) and the product fractions lyophilized to afford a white powder (120 mg) (decomposes.250° C.). NMR (CDCl$_3$): 1.11, t (6H); 1.79, m (4H); 2.50, q (2H); 3.36, m (2H); 3.97, t (2H); 6.53, s (1H); 6.99, s (1H); 7.18, m (3H); 7.49, m (4H); 7.83, m (1H); 8.28, Part A Preparation of 1-Amino-6-[(4,6-diphenyl-2-pyridinyl)oxy]-hexane To a dry flask was added aluminum chloride (0.857 g, 6.42 mmol). The flask was cooled to less than 0° C. with an ice/ethanol bath. Ether (15 mL) was added, and the reaction was stirred for 5 min until the aluminum chloride dissolved. Lithium aluminum hydride (0.244 g, 6.42 mmol) was then added, and the reaction was heated to reflux. 6-[(4,6-Diphenyl-2-pyridinyl)oxy]-hexanenitrile (1.0 g, 2.92 mmol) was dissolved in ether (5 mL) and added dropwise to the refluxing solution. After addition was complete, the reaction was stirred overnight at room temperature. The reaction was then quenched with water. 6 N Aqueous sulfuric acid was added until a clear solution formed. This mixture was then extracted with ether (3×). The aqueous layer was then cooled in an ice bath and basified to pH 14 with 50% aq. NaOH. This was then extracted with ether (4×). The organic layer was then washed with saturated NaCl, dried over magnesium sulfate, and evaporated to give 0.7184 g (71%) of 1-amino-6-[(4,6-diphenyl-2-pyridinyl)oxy]-hexane as an oil. ESMS: Calcd. For $C_{23}H_{26}N_2O$, 346.20; Found, 347.3 $(M+H)^{+1}$ Part B Preparation of 2-[[[5-[[(6-[(4,6-diphenyl-2-pyridinyl)oxy]-1-hexanamino]carbonyl]-2-pyridinyl]hydrazono]methyl]-benzenesulfonic acid 1-Amino-6-[(4,6-diphenyl-2-pyridinyl)oxy]-hexane (0.200 g, 0.557 mmol) was dissolved in DMF (5 mL). Triethylamine (232.9 µL, 1.67 mmol) was added, and the reaction was stirred for 5 min. 2-[[[5-[[(2,5-Dioxo-1-pyrrolidinyl)oxy]carbonyl]-2-pyridinyl]hydrazono]methyl]-benzenesulfonic acid, monosodium salt (294.3 mg, 0.668 mmol) was then added, and the reaction mixture was stirred under nitrogen for 3 days. The reaction mixture was concentrated to an oil and triturated with ethyl acetate. The crude product was purified by preparative HPLC, using the following method to give 133 mg (35%) of the purified title compound. ESMS: Calcd. For $C_{36}H_{35}N_5O_5S$, 649.23; Found, 648.3 $(M-H)^{-1}$ HPLC Method 1
Instrument: Rainin Rabbit; Dynamax software
Column: Vydac C-18 (21.2 mm×25 cm)
Detector: Knauer VWM
Flow Rate: 15 mL/min
Column Temp: RT
Mobile Phase:
  A: 0.05 M ammonium acetate
  B: 90% ACN, 10% 0.05 M ammonium acetate

| Gradient | Time (min) | % A | % B |
|---|---|---|---|
| | 0 | 80 | 20 |
| | 20 | 0 | 100 |
| | 30 | 0 | 100 |
| | 31 | 80 | 20 |

Example 4

Synthesis of 2-[[[5-[[2,2-dimethyl-6-[(6-fluorophenyl-4-phenyl-2-pyridinyl)oxy]-1-hexanamino]carbonyl]-2-pyridinyl]hydrazono]methyl]-benzenesulfonic acid Part A Preparation of 2,2-Dimethyl-6-[(6-(4-fluorophenyl)-4-phenyl-2-pyridinyl)oxy]-hexanenitrile 6-(4-Fluorophenyl)-4-phenyl-2-pyridone (1.0 g, 3.77 mmol) was dissolved in toluene. Silver carbonate (1.04 g, 3.77 mmol) and 6-bromo-2,2-dimethyl-hexanenitrile (1.15 g, 5.66 mmol) were added, and the reaction was heated to reflux and kept in the dark for 2 days. The reaction was filtered and concentrated. The resulting residue was purified by flash column chromatography using 9:1 hexane:ethyl acetate to give 1.110 g (76%) of the purified nitrile. ESMS: Calcd. For $C_{25}H_{25}FN_2O$, 388.20; Found, 388 GCMS Part B Preparation of 1-Amino-2,2-dimethyl-6-[(6-fluorophenyl-4-phenyl-2-pyridinyl)oxy]-hexane

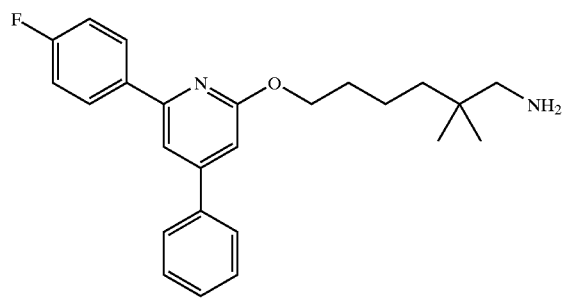

To a dry flask was added aluminum chloride (0.754 g, 5.65 mmol). The flask was cooled to less than 0° C. with an ice/ethanol bath. Ether (10 mL) was added, and the reaction was stirred for 5 min until the aluminum chloride dissolved. Lithium aluminum hydride (0.214 g, 5.65 mmol) was then added, and the reaction was heated to reflux. 2,2-Dimethyl-6-[(6-fluorophenyl)-4-phenyl-2-pyridinyl)oxy]-hexanenitrile (1.0 g, 2.57 mmol) was dissolved in ether (5 mL) and added dropwise to the refluxing solution. After addition was complete, the reaction was stirred for 5 h at room temperature. The reaction was then quenched with water. 6N Aqueous sulfuric acid was added until a clear solution formed. This mixture was then extracted with ether (3×). The aqueous layer was then cooled in an ice bath and basified to pH 14 with 50% aq. Sodium hydroxide. The resulting solution was then extracted with ether (4×). The organic layer was then washed with saturated NaCl, dried over magnesium sulfate, and evaporated to give 1.2 g (119%) of the amine product as an oil. ESMS: Calcd. For $C_{25}H_{29}FN_2O$, 392.23; Found, 393.2 $(M+H)+^{+1.}$ Part C Preparation of 2-[[[5-[[2,2-dimethyl-6-[(6-fluorophenyl-4-phenyl-2-pyridinyl)oxy]-1-hexanamino]carbonyl]-2-pyridinyl]hydrazono]methyl]-benzenesulfonic acid 1-Amino-2,2-dimethyl-6-[(6-fluorophenyl-4-phenyl-2-pyridinyl)oxy]-hexane (0.200 g, 0.51 mmol) was dissolved in dimethylformamide (5 mL). Triethylamine (213.2 µL, 1.53 mmol) was added and the reaction was stirred for 5 min. 2-[[[5-[[(2,5-Dioxo-1-pyrrolidinyl)oxy]carbonyl]-2-pyridinyl]hydrazono]methyl]-benzenesulfonic acid, monosodium salt (269.5 mg, 0.612 mmol) was added and the reaction was stirred for 24 h under nitrogen. The reaction was then concentrated to an oil under high vacuum. The oil was triturated with ethyl acetate. The crude product was then purified by the following method to give 10 mg (3%) of the title compound. ESMS: Calcd. For $C_{38}H_{38}FN_5O_5S$, 695.26; Found, 696.4 $(M+H)^{+1}$

| HPLC Method 2 | |
|---|---|
| Instrument | Rainin Rabbit; Dynamax software |
| Column | Vydac C-18 (21.2 mm × 25 cm) |
| Detector | Knauer VWM |
| Flow Rate | 15 mL/min |
| Column Temp | RT |
| Mobile Phase | A: 0.1% TFA in $H_2O$ |
| | B: 0.1% TFA in ACN/$H_2O$ (9:1) |

| Gradient | Time (min) | % A | % B |
|---|---|---|---|
| | 0 | 80 | 20 |
| | 20 | 0 | 100 |
| | 30 | 0 | 100 |
| | 31 | 80 | 20 |

Example 5

Synthesis of 2-[[[5-[[N-[6-[(6-(4-fluorophenyl)-4-phenyl-2-pyridinyl)oxy]-hexanoyl]-tyrosine-O-[3-propanamino]]carbonyl]-2-pyridinyl]hydrazono]-methyl]-benzenesulfonic acid

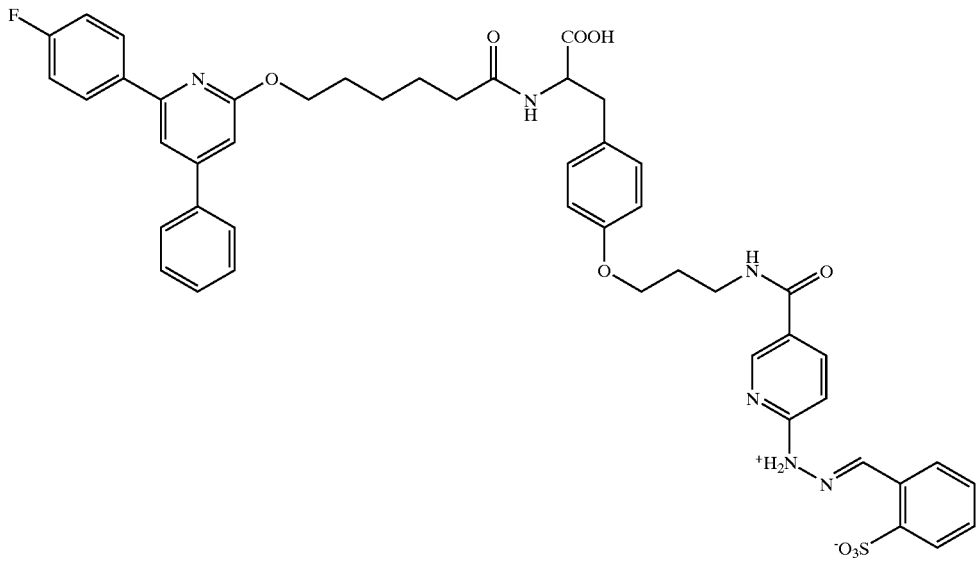

Part A Preparation of N-[6-[(6-(4-fluorophenyl)-4-phenyl-2-pyridinyl)oxy]-hexanoyl]tyrosine To a teabag (5×5 cm polypropylene filters, 0.75 μm mesh) was added 0.30 g of Fmoc-Tyr(OtBu)-Wang Resin. The teabag was washed with the following (10 mL/bag): DMF 2×3 min, 20% piperidine in DMF 1×3 min, 20% piperidine in DMF 1×30 min, DCM 8×3 min, and DMF 3×3 min. About 2.5 equivalents of 6-[(6-(4-fluorophenyl)-4-phenyl-2-pyridinyl)oxy]-hexanoic acid, five equivalents of each of the following; HBTU, HOBT, diisopropylethylamine (DIEA) and DMF (10 mL/bag) were added. The bag was then shaken overnight for about 18 h. The bag was then washed with the following (10 mL/bag): DMF 3×3 min, DCM 8×3 min. The bag was dried under high vacuum. The contents of the bag was then placed in a small erlenmeyer flask. To the flask was added 10 mL of cleavage cocktail (95% trifluoroacetic acid, 2.5% triisopropylsilane, and 2.5% water). The resin was allowed to sit for 2 h while occasionally being swirled. After each swirl the sides of the flasks were rinsed with additional cocktail until the total volume of cocktail added was 15 mL. After 2 h, the resin was filtered and washed with TFA (2×4 mL). The filtrates were then concentrated to an oil under high vacuum. The oils were then purified by prep HPLC using the method 2 described above, to give 36.2 mg of the title compound. ESMS: Calcd. For $C_{32}H_{31}FN_2O_5$, 542.22; Found, 543.4 $(M+H)^{+1}$

Part B Preparation of N-[6-[(6-(4-fluorophenyl)-4-phenyl-2-pyridinyl)oxy]-hexanoyl]-O-[N-tert-butyloxycarbonyl-3-aminopropyl]tyrosine

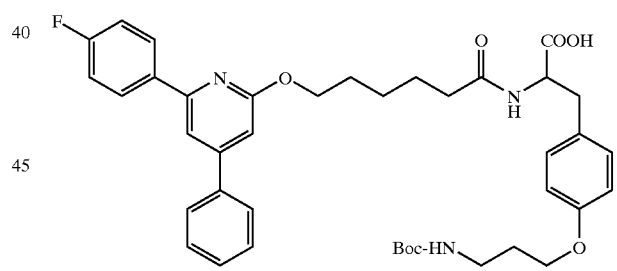

N-[6-[(6-(4-fluorophenyl)-4-phenyl-2-pyridinyl)oxy]-hexanoyl]tyrosine was dissolved in dimethyl formamide (0.5 mL) and cooled to 0° C. in an ice bath. Sodium hydride (2.2 equivalents) was added, and the reaction was stirred for 1 hour at 0° C. N-Boc-Bromopropylamine (1.1 equivalent) was dissolved in 0.2 mL of dimethylformamide and added dropwise to the solution. The reaction was stirred an additional 24 h under nitrogen. The reaction was then concentrated to an oil. The resulting residue was brought up in ethyl acetate. This was acidified with 10% potassium hydrogen sulfate. The organic layer was washed with brine, dried over magnesium sulfate, and evaporated to give 45.3 mg of the crude product as an oil. ESMS: Calcd. For $C_{40}H_{46}FN_3O_7S$, 699.33; Found, 698.4 $(M+H)^{+1}$ Part C Preparation of 2-[[[5-[[N-[6-[(6-(4-fluorophenyl)-4-phenyl-2-pyridinyl)oxy]-hexanoyl]-tyrosine-O-[3-propanamino]]carbonyl]-2-pyridinyl]hydrazono]-methyl]-benzenesulfonic acid To a solution of N-[6-[(6-(4-fluorophenyl)-4-phenyl-2-pyridinyl)oxy]-hexanoyl]-O-[N-tert-butyloxycarbonyl-3-aminopropyl]tyrosine dissolved in 1 mL of dichloromethane was added trifluoroacetic acid (1 mL), and the reaction mixture stirred for 2 h. The reaction mixture was then concentrated to an oil under high vacuum. The crude oil was dissolved in 1 mL of dimethylformamide. Triethylamine (3 equivalents) was added and the reaction stirred for 5 min. 2-[[[5-[[(2,5-Dioxo-1-pyrrolidinyl)oxy]carbonyl]-2-pyridinyl]hydrazono]-methyl]-benzenesulfonic acid, monosodium salt (1.2 equivalents) was added and the reaction was stirred for 24 h under nitrogen. The reaction was then concentrated to an oil under high vacuum. The oil was triturated with ethyl acetate. The crude product was then purified by method 2 described above to give 13.3 mg of the title product. ESMS: Calcd. For $C_{48}H_{47}FN_6O_9S$, 902.31; Found, 903.32 $(M+H)^{+1}$ Example 6

Synthesis of 2-[[[5-[[N-[6-[(4,6-diphenyl-2-pyridinyl)oxy]-hexanoyl]-tyrosine-O-[3-propanamino]]carbonyl]-2-pyridinyl]hydrazono]-methyl]-benzenesulfonic acid added 10 mL of cleavage cocktail (95% trifluoroacetic acid, 2.5% triisopropylsilane, and 2.5% water). The resin was allowed to sit for 2 h while occasionally being swirled. After each swirl the sides of the flasks were rinsed with additional cocktail until the total volume of cocktail added was 15 mL. After 2 h, the resin was filtered and washed with TFA (2×4 mL). The filtrates were then concentrated to an oil under high vacuum. The oils were then purified by prep HPLC method 2 described above, to give 43.6 mg of N-[6-[(4,6-diphenyl-2-pyridinyl)oxy]-hexanoyl]tyrosine. ESMS: Calcd. For $C_{32}H_{32}N_2O_5$, 524.23; Found, 525.4 $(M+H)^{+1}$ Part B Preparation of N-[6-[(4,6-diphenyl-2-pyridinyl)oxy]-hexanoyl]-O-[N-tert-butyloxycarbonyl-3-aminopropyl]tyrosine

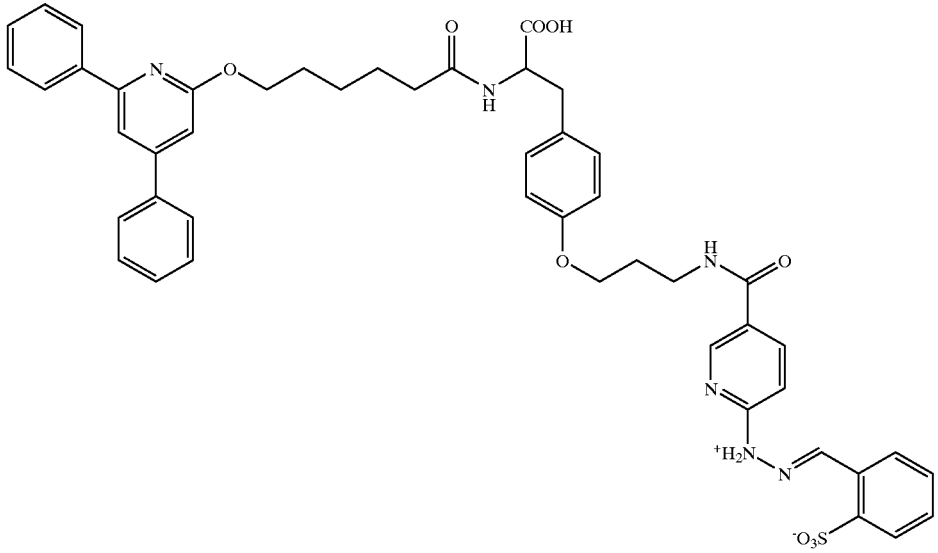

Part A Preparation of N-[6-[(4,6-diphenyl-2-pyridinyl)oxy]-hexanoyl]tyrosine

To a teabag (5×5 cm polypropylene filters, 0.75 μm mesh) was added 0.30 g of Fmoc-Tyr(OtBu)-Wang Resin. The teabag was washed with the following (10 mL/bag): DMF 2×3 min, 20% piperidine in DMF 1×3 min, 20% piperidine in DMF 1×30 min, DCM 8×3 min, and DMF 3×3 min. About 2.5 equivalents of 6-[(4,6-Diphenyl-2-pyridinyl)oxy]-hexanoic acid, five equivalents of each of the following; HBTU, HOBT, diisopropylethylamine(DIEA) and DMF (10 mL/bag) were added. The bag was then shaken overnight for about 18 h. The bag was then washed with the following (10 mL/bag): DMF 3×3 min, DCM 8×3 min. The bag was dried under high vacuum. The contents of the bag was then placed in a small erlenmeyer flask. To the flask was N-[6-[(4,6-diphenyl-2-pyridinyl)oxy]-hexanoyl]tyrosine was dissolved in dimethylformamide (0.5 mL) and cooled to 0° C. in an ice bath. Sodium hydride (2.2 equivalents) was added, and the reaction was stirred for 1 hour at 0° C. N-Boc-Bromopropylamine (1.1 equivalent) was dissolved in 0.2 mL of dimethylformamide and added dropwise to the solution. The reaction was stirred an additional 24 h under nitrogen. The reaction was then concentrated to an oil. The resulting residue was brought up in ethyl acetate. This was acidified with 10% potassium hydrogen sulfate. The organic layer was washed with brine, dried over magnesium sulfate, and evaporated to give the crude product as an oil. (35.0 mg)

ESMS: Calcd. For $C_{40}H_{47}N_3O_7$, 681.34; Found, 680.4 (M+H)+1

Part C Preparation of 2-[[[5-[[N-[6-[(4,6-diphenyl-2-pyridinyl)oxy]-hexanoyl]-tyrosine-O-[3-propanamino]]carbonyl]-2-pyridinyl]hydrazono]-methyl]-benzenesulfonic acid To a solution of N-[6-[(4,6-diphenyl-2-pyridinyl)oxy]-hexanoyl]-O-[N-tert-butyloxycarbonyl-3-aminopropyl] tyrosine dissolved in 1 mL of dichloromethane was added trifluoroacetic acid (1 mL), and the reaction mixture stirred for 2 h. The reaction mixture was then concentrated to an oil under high vacuum. The crude oil was dissolved in 1 mL of dimethylformamide. Triethylamine (3 equivalents) was added and the reaction stirred for 5 min. 2-[[[5-[[(2,5-Dioxo-1-pyrrolidinyl)oxy]carbonyl]-2-pyridinyl]hydrazono] methyl]-benzenesulfonic acid, monosodium salt (1.2 equivalents) was added and the reaction was stirred for 24 h under nitrogen. The reaction was then concentrated to an oil under high vacuum. The oil was triturated with ethyl acetate. The crude product was then purified by method 2 described above to give 17.1 mg of the product. ESMS: Calcd. For $C_{48}H_{48}N_6O_9S$, 884.32; Found, 885.33 $(M+H)^{+1}$ Example 7

Synthesis of 2-[[[5-[[N-[6-[(4-(3,4-methylenedioxyphenyl)-6-phenyl-2-pyridinyl)oxy]-hexanoyl]-tyrosine-O-[3-propanamino]]-carbonyl]-2-pyridinyl]hydrazono]-methyl]-benzenesulfonic acid Part A Preparation of N-[6-[(4-(3,4-methylenedioxyphenyl)-6-phenyl-2-pyridinyl)oxy]-hexanoyl]tyrosine To a teabag (5×5 cm polypropylene filters, 0.75 μm mesh) was added 0.30 g of Fmoc-Tyr(OtBu)-Wang Resin. The teabag was washed with the following (10 mL/bag): DMF 2×3 min, 20% piperidine in DMF 1×3 min, 20% piperidine in DMF 1×30 min, DCM 8×3 min, and DMF 3×3 min. About 2.5 equivalents of 6-[(4–6-Diaryl-2-pyridinyl)oxy]-hexanoic acid, five equivalents of each of the following; HBTU, HOBT, diisopropylethylamine(DIEA) and DMF (10 mL/bag) were added. The bag was then shaken overnight for about 18 h. The bag was then washed with the following (10 mL/bag): DMF 3×3 min, DCM 8×3 min. The bag was dried under high vacuum. The contents of the bag was then placed in a small erlenmeyer flask. To the flask was added 10 mL of cleavage cocktail (95% trifluoroacetic acid, 2.5% triisopropylsilane, and 2.5% water). The resin was allowed to sit for 2 h while occasionally being swirled. After each swirl the sides of the flasks were rinsed with additional cocktail until the total volume of cocktail added was 15 mL. After 2 h, the resin was filtered and washed with TFA (2×4 mL). The filtrates were then concentrated to an oil under high vacuum. The oils were then purified by prep HPLC using method 2 described above, to give 35.3 mg of the desired product. ESMS: Calcd. For $C_{33}H_{32}N_2O_7$, 568.22; Found, 569.4 $(M+H)^{+1}$

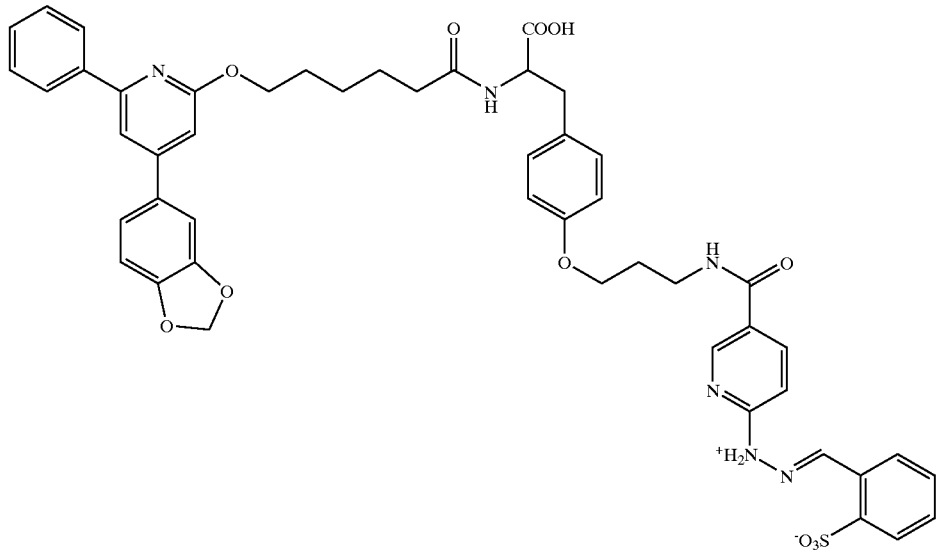

Part B Preparation of N-[6-[(4-(3,4-methylenedioxyphenyl)-6-phenyl-2-pyridinyl)oxy]-hexanoyl]-O-[N-tert-butyloxycarbonyl-3-aminopropyl]tyrosine

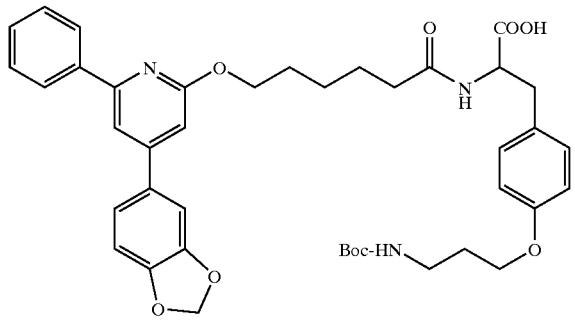

N-[6-[(4-(3,4-Methylenedioxyphenyl)-6-phenyl-2-pyridinyl)oxy]-hexanoyl]tyrosine was dissolved in dimethylformamide (0.5 mL) and cooled to 0° C. in an ice bath. Sodium hydride (2.2 equivalents) was added, and the reaction was stirred for 1 hour at 0° C. N-Boc-Bromopropylamine (1.1 equivalent) was dissolved in 0.2 mL of dimethylformamide and added dropwise to the solution. The reaction was stirred an additional 24 h under nitrogen. The reaction was then concentrated to an oil. The resulting residue was brought up in ethyl acetate. This was acidified with 10% potassium hydrogen sulfate. The organic layer was washed with brine, dried over magnesium sulfate, and evaporated to give 39.2 mg of the crude product as an oil. ESMS: Calcd. For $C_{41}H_{47}N_3O_9$, 725.33; Found, 726.3 $(M+H)^{+1}$ Part C Preparation of 2-[[[5-[[N-[6-[(4-(3,4-methylenedioxyphenyl)-6-phenyl-2-pyridinyl)oxy]-hexanoyl]-tyrosine-O-[3-propanamino]]-carbonyl]-2-pyridinyl]hydrazono]-methyl]-benzenesulfonic acid To a solution of N-[6-[(4-(3,4-methylenedioxyphenyl)-6-phenyl-2-pyridinyl)oxy]-hexanoyl]tyrosine dissolved in 1 mL of dichloromethane was added trifluoroacetic acid (1 mL), and the reaction mixture stirred for 2 h. The reaction mixture was then concentrated to an oil under high vacuum. The crude oil was dissolved in 1 mL of dimethylformamide. Triethylamine (3 equivalents) was added and the reaction stirred for 5 min. 2-[[[5-[[(2,5-Dioxo-1-pyrrolidinyl)oxy]carbonyl]-2-pyridinyl]hydrazono]methyl]-benzenesulfonic acid, monosodium salt (1.2 equivalents) was added and the reaction was stirred for 24 h under nitrogen. The reaction was then concentrated to an oil under high vacuum. The oil was triturated with ethyl acetate. The crude product was then purified by method 2 described above to give 3.8 mg of the product. ESMS: Calcd.for $C_{49}H_{48}N_6O_{11}S$, 928.31; Found, 929.32 $(M+H)^{+1}$ Example 8

Synthesis of 2-[[[5-[[alpha-N-[6-[(4,6-diphenyl-2-pyridinyl)oxy]-hexanoyl]-lysine-epsilon-N-amino]carbonyl]-2-pyridinyl]hydrazono]-methyl]-benzenesulfonic acid

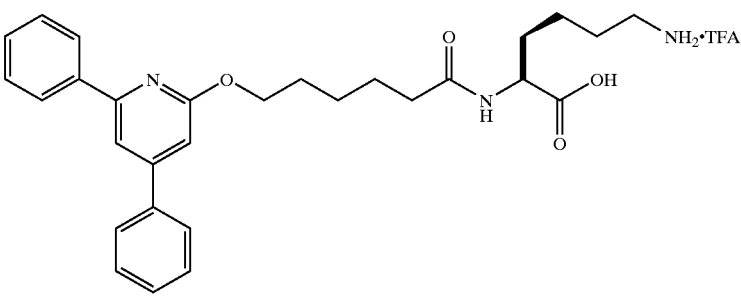

Part A Preparation of alpha-N-[6-[(4,6-diphenyl-2-pyridinyl)oxy]-hexanoyl]lysine

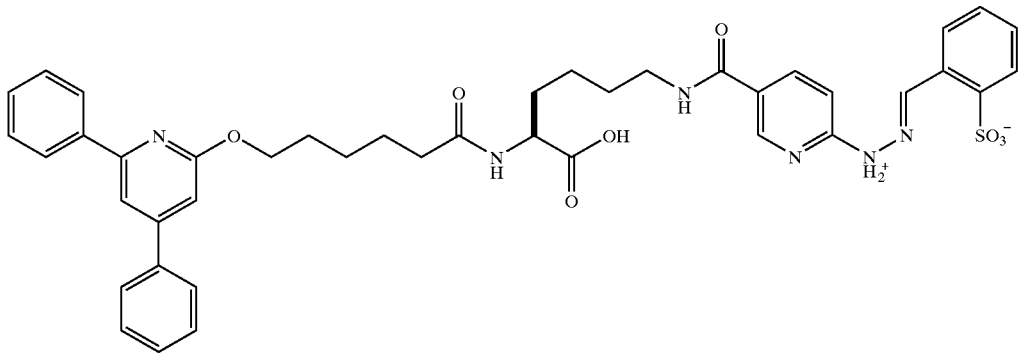

To the teabag (5×5cm polypropylene filters, 0.75 μm mesh) was added 0.88 g of Fmoc-Lys(boc)-Wang Resin. The teabag was washed with the following (10 mL/bag) DMF 2×3 min, 20% piperidine in DMF 1×3 min, 20% piperidine in DMF 1×30 min, DCM 8×3 min, and DMF 3×3 min. 2.2 Equivalents of 6-[(4,6-Diphenyl-2-pyridinyl)oxy]-hexanoic acid, five equivalents of each of the following; HBTU, HOBT, diisopropylethylamine(DIEA) and DMF (10 mL/bag) were added. The bag was then shaken overnight for about 18 h. The bag was then washed with the following (10 mL/bag): DMF 3×3 min, DCM 8×3 min. The bag was dried under high vacuum. The contents the bag was then placed in a small erlenmeyer flask. To the flask was added 10 mL of cleavage cocktail (95% trifluoracetic acid, 2.5% triisopropylsilane, and 2.5% water). The resin was allowed to sit for two h while occasionally being swirled. After each swirl the sides of the flasks were rinsed with additional cocktail until the total volume of cocktail added was 15 mL. After 2 h, the resin was filtered and washed with TFA (2×4 mL). The filtrate was then concentrated to an oil under high vacuum. The oil was then purified by prep HPLC using the method 2 described above, to give 115 mg of product. ESMS: Calcd. For $C_{29}H_{35}N_3O_4$, 489.26; Found, 490.4 $(M+H)^{+}1$.

Part B Preparation of 2-[[[5-[[alpha-N-[6-[(4,6-diphenyl-2-pyridinyl)oxy]-hexanoyl]-lysine-epsilon-N-amino]carbonyl]-2-pyridinyl]hydrazono]-methyl]-benzenesulfonic acid The lysine derivative (30 mg, 0.061 mmol) was dissolved in 0.5 mL of dimethylformamide. Triethylamine (25.5 μL, 0.183 mmol) was added and the reaction was stirred for 5 min. 2-[[[5-[[(2,5-dioxo-1-pyrrolidinyl)oxy]carbonyl]-2-pyridinyl]hydrazono]methyl]-benzenesulfonic acid, monosodium salt (32.2 mg, 0.073 mmol) was added and the reaction was stirred for 24 h under nitrogen. The reaction was then concentrated to an oil under high vacuum. The oil was triturated with ethyl acetate. The crude product was then purified by method 2 described above to give 4.8 mg (10%) of the title compound. ESMS: Calcd. For $C_{42}H_{44}N_6O_8S$, 792.29; Found, 793.30 $(M+H)^{+1}$.

Example 9

Synthesis of 4-ethyl-2-(4-fluorophenyl)-5-[(5,5-dimethyl-6-aminohexyl)oxy]phenol N-[4-(carboxy)benzyl]-N,N'-bis[2-thioethyl]-glycinamide Conjugate

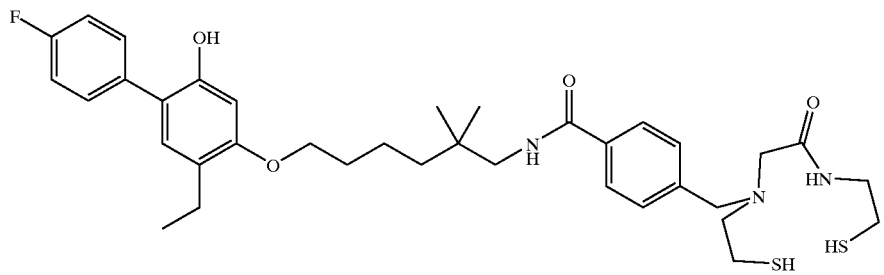

Part A Preparation of S-Triphenylmethyl-2-aminoethanethiol

A solution of cysteamine hydrochloride (79.5 g, 0.7 mol) in TFA (500 ml) was treated with triphenylmethanol (182 g, 0.7 mol), and stirred at room temperature for one hour. TFA was removed under reduced pressure at a temperature of 45° C. and the resulting dark orange oil was dissolved in EtOAc (700 ml). The EtOAc solution was washed with cold 2N NaOH (3×350 ml), H₂O (2×350 ml), saturated NaHCO₃ (350 ml), and saturated NaCl (350 ml). The combined aqueous washings were back extracted with EtOAc (350 ml). The combined organic layers were dried (MgSO₄) and concentrated to a yellow solid. Trituration with ether (500 ml) gave product (97.2 g, 43%) as a colorless solid, MP 90–92° C. Concentration of the ether triturant to a volume of 100 ml and cooling produced an additional 40.9 g of product, MP 89–91° C., for a combined yield of 62%.

Part B Preparation of N-2-Bromoacetyl-S-triphenylmethyl-2-aminoethanethiol

A solution S-triphenylmethyl-2-aminoethanethiol (48 g, 0.15 mol) and Et₃N (20.9 ml, 0.15 mol) in DCM (180 ml)

was slowly added to a stirred solution of bromoacetyl bromide (13.9 ml, 0.15 mol) in DCM (100 ml) at a temperature of −20° C. The reaction was allowed to warm to room temperature over a one hour period. The reaction was washed with 500 ml portions of H₂O, 0.2 N HCl, saturated NaHCO₃, and saturated NaCl. The organic solution was dried (MgSO₄) and concentrated to an oil. This oil was crystallized from DCM-hexane to give product (54.9 g, 83%) as a colorless solid, MP 137–139.5° C.

Part C Preparation of N,N'-Bis[(2-triphenylmethylthio) ethyl]glycinamide

A solution of N-2-Bromoacetyl-S-triphenylmethyl-2-aminoethanethiol (35.2 g, 0.08 mol), S-triphenylmethyl-2-aminoethanethiol (25.5 g, 0.08 mol), and Et₃N (16.7 ml, 0.12 mol) in DCM (375 ml) was kept at room temperature for 24 hours. The solution was washed with 200 ml portions of H₂O (1×), saturated NaHCO₃ (2×), H₂O (1×), and saturated NaCl (1×), dried (MgSO₄), and concentrated to give a viscous oil. The oil was dissolved in 70:30 DCM:EtOAc (150 ml) and cooled in an ice bath. The solid which formed was removed by filtration. The filtrate was concentrated to a viscous oil. This oil was purified by flash chromatography over 200–400 mesh, 60A silica gel using 70:30 DCM:EtOAc mobile phase to give product (34.4 g, 63%) as a colorless, amorphous foamy solid. ¹H NMR (CDCl₃) 7.42–7.18 (m, 30H), 3.12–3.01 (m, 4H), 2.48–2.27 (m, 6H).

Part D Preparation of Methyl 4-(Methanesulfonylmethyl)benzoate

A solution of methyl 4-(hydroxymethyl)benzoate (10.8 g, 0.065 mol) and proton sponge (19.5 g, 0.091 mol) in DCM (200 ml) was treated with methanesulfonic anhydride (13.94 g, 0.08 mol) and stirred at room temperature for 20 hours. The reaction mixture was washed with 100 ml portions of H₂O (1×), 1N HCl (2×), H₂O (1×), saturated NaHCO₃ (1×), and H₂O (1×). The organic phase was dried (MgSO₄) and concentrated to give 15.5 g of pale yellow solid. Recrystallization from CCl₄ (150 ml) using decolorizing carbon gave product (14.2 g, 90%) as colorless needles, MP 91–94° C.

Part E Preparation of N-[4-(Carbomethoxy)benzyl]-N,N'-bis[(2-triphenylmethylthio)ethyl]glycinamide A solution of N,N'-Bis[(2-triphenylmethylthio)ethyl]-glycinamide (16.27 g, 0.024 mol) and methyl 4-(methanesulfonylmethyl)benzoate (4.88 g, 0.02 mol) in ethylene dichloride (200 ml) was heated to reflux for 28 hours. The reaction was washed with 200 ml portions of saturated NaHCO₃ and H₂O, dried (MgSO₄), and concentrated to a light brown oil (30 g). This oil was purified by flash chromatography over 200–400 mesh, 60 Å silica gel using DCM:EtOAc mobile phase to give product (9.9 g, 60%) as a colorless, amorphous foamy solid. ¹H NMR (CDCl₃) 7.90 (d, 2H, J=6.5 Hz), 7.49–7.18 (m, 32H), 3.91 (s, 3H), 3.47 (s, 2H), 3.01 (q, 2H, J=6.2 Hz), 2.88 (s, 2H), 2.43 (t, 2H, J=6.2 Hz), 2.39–2.27 (m, 4H).

Part F Preparation of N-[4-(Carboxy)benzyl]-N,N'-bis[(2-triphenylmethylthio)ethyl]glycinamide A mixture of N-[4-(carbomethoxy)benzyl]-N,N'-bis[(2-triphenylmethylthio)ethyl]glycinamide (6.00 g, 7.26 mmol) in dioxane (65 ml) and 1N NaOH (65 ml) was stirred at room temperature for 24 hours. The mixture was acidified with 2.5 M citric acid (100 ml) and the gummy precipitate which formed was extracted into EtOAc (400 ml). The EtOAc solution was washed with H₂O (3×200 ml) and saturated NaCl (100 ml), dried (MgSO₄), and concentrated to give product (5.90 g, 100%) as a colorless, amorphous foamy solid. ¹H NMR (CDCl₃) 7.96 (d, 2H, J=8.1 Hz), 7.40–7.16 (m, 32H), 3.71 (s, 3H), 3.49 (s, 2H), 3.00 (q, 2H, J=5.4 Hz), 2.91 (s, 2H), 2.44 (t, 2H, J=5.4 Hz), 2.38–2.30 (m, 4H).

Part G Preparation of N-[4-(Carboxy)benzyl]-N,N'-bis[(2-triphenylmethylthio)ethyl]glycinamide N-Hydroxysuccinimide Ester A solution of N-[4-(carboxy)benzyl]-N,N'-bis[(2-triphenylmethylthio)ethyl]glycinamide (450 mg, 0.55 mmol) and N-hydroxysuccinimide (76 mg, 0.66 mmol) in DCM (10 ml) was treated with a solution of WSCD.HCl (122 mg, 0.66 mmol) in DCM (7 ml) and stirred at room temperature for 22 hours. The reaction mixture was concentrated and the solids redissolved in EtOAc (60 ml). The EtOAc solution was washed with H₂O (2×25 ml), 0.1 N NaOH (35 ml), H₂O (2×25 ml), and saturated NaCl (35 ml), dried (Na₂SO₄), and concentrated to give product (469 mg, 93%) as a colorless solid.

Part H Preparation of 4-ethyl-2-(4-fluorophenyl)-5-[(5,5-dimethyl-6-aminohexyl)oxy]phenol N-[4-(carboxy)benzyl]-N,N'-bis[(2-triphenylmethylthio)ethyl]-glycinamide Conjugate

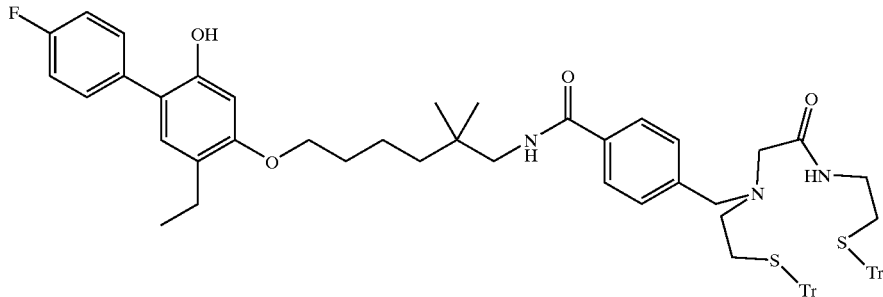

4-ethyl-2-(4-fluorophenyl)-5-[(5,5-dimethyl-6-aminohexyl)oxy]phenol (100 mg) was dissolved in dimethylformamide (5 mL) under nitrogen. To this was added triethylamine (84 mg), N-[4-(carboxy)benzyl]-N,N'-bis[(2-triphenylmethylthio)ethyl]-glycinamide N-hydroxysuccinimide ester (254 mg), and 4-dimethylaminopyridine (7 mg). The mixture was stirred overnight at ambient temperature. The reaction mixture was diluted with water (20 mL) and extracted with ethyl acetate. The combined organics were dried (magnesium sulfate), filtered, and concentrated to dryness to yield an oil (205 mg). This was purified by preparative HPLC (5 cm×25 cm Vydac Pharmaceutical column, 0.1% trifluoroacetic acid/water (A):90% acetonitrile/water (B) gradient,) and the fractions lyophilized to yield the product (118 mg) as a white powder. NMR (CDCl₃): 0.93, s (6H); 1.15, t (3H); 1.34, m (2H); 1.51, m (2H); 1.78, m (2H); 2.31, t (2H); 2.45, m (2H); 2.55, m (4H); 2.95, m (2H); 2.45, s (2H); 3.28, d (2H); 3.73, s (2H); 3.96, t (2H); 6.05, t (1H); 6.48, s (1H); 6.94, s (1H);

7.07, t (2H); 7.20, m (20H); 7.38, m (15H); 7.56, d (2H): Mass Spec (EI), m/e=1154.7 (M+H).

Part I Preparation of 4-ethyl-2-(4-fluorophenyl)-5-[(5,5-dimethyl-6-aminohexyl)oxy]phenol N-[4-(carboxy)benzyl]-N,N'-bis[2-thioethyl]-glycinamide Conjugate 4-ethyl-2-(4-fluorophenyl)-5-[(5,5-dimethyl-6-aminohexyl)oxy]phenol N-[4-(carboxy)benzyl]-N,N'-bis[(2-triphenylmethylthio)ethyl]-glycinamide Conjugate (92 mg) was mixed with trifluoroacetic acid (4.6 mL) and triethylsilane (36 mg) and stirred for 3 hours under nitrogen. The solution was filtered and concentrated under vacuum. The resulting solid was dissolved in chloroform, loaded onto a SepPak® (SiO$_2$) and flushed with chloroform (5 mL). It was then flushed with methanol and the methanol collected and concentrated under vacuum to afford the product (25 mg). NMR (CDCl$_3$): 0.97, s (6H); 1.15, t (3H); 1.36, m (2H); 1.49, m (2H); 1.80, m (2H); 2.58, m (4H); 2.78, t (2H); 2.97, t (2H); 3.31, m (2H); 3.39, m (2H); 3.91, s (2H); 3.97, t (2H); 6.16, t (1H); 6.48, s (1H); 6.96, s (1H); 7.11, t (2H); 7.43, m (4H); 7.69, d (2H); 7.79, b (1H): Mass Spec (EI), m/e=670.3 (M+H).

Example 10

Synthesis of Benzenesulfonic Acid, 2-[[[5-[[[6-[(4,6-diphenyl-2-pyridinyl)oxy]-2,2-dimethyl-1-hexyl]aza]carbonyl]-2-pyridinyl]hydrazono]methyl]

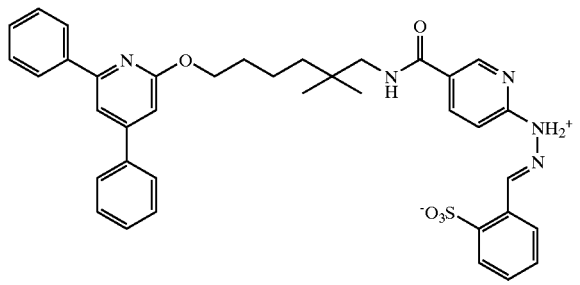

Part A Preparation of 6-[(4,6-Diphenyl-2-pyridinyl)oxy]-2,2-dimethyl-1-hexylamine A stirred suspension of NaBH$_4$ (255 mg, 6,75 mmol) in THF (4 mL) was treated with TFA (52 ul, 6.75 mmol). To the resulting solution was added dropwise a solution of 6-[(4,6-diphenyl-2-pyridinyl)oxy]-2,2-dimethylhexanenitrile (500 mg, 1.35 mmol) in THF (5 mL). The solution was stirred at ambient temperatures for 4 hr, and the excess reagent was decomposed at 0° C. by the cautious addition of water. The solution was concentrated to dryness and the residue was partitioned between DCM (30 mL) and water (30 mL). The aqueous layer was further extracted with DCM (3×30 mL). The combined DCM extracts were washed with water (50 mL) and sat. NaCl (50 Ml), dried (MgSO$_4$), and concentrated to give a yellow oil. Purification by preparative HPLC on a Vydac C-18 column (21.2×25 cm) using a 1.35%/min gradient of 50 to 80% ACN containing 0.1% TFA at a flow rate of 15 mL/min gave the title compound as a colorless oil (321 mg, 63.5%). $^1$H NMR (CDCl$_3$): 8.00–7.93 (m, 2H), 7.71–7.62 (m, 2H), 7.56–7.41 (m, 7H), 6.96 (s, 1H), 4.64–4.38 (m, 4H), 2.82–2.70 (m, 2H), 1.90–1.75 (m, 2H), 1.58–1.32 (m 4H), 0.97 (s, 6H); MS: m/e 375.2 [M+H].

Part B Preparation of Benzenesulfonic Acid, 2-[[[5-[[[6-[(4,6-diphenyl-2-pyridinyl)oxy]-2,2-dimethyl-1-hexyl]aza]carbonyl]-2-pyridinyl]hydrazono]methyl]

A solution of 6-[(4,6-diphenyl-2-pyridinyl)oxy]-2,2-dimethyl-1-hexylamine (64.8 mg, 0.17 mmol), benzenesulfonic acid, 2-[[[5-[[(2,5-dioxo1-pyrrolidinyl)oxy]carbonyl]-2-pyridinyl]hydrazono]methyl] (76.2 mg, 0.17 mmol), and TEA (96 ul, 0.53 mmol) in DMF (2 mL) was stirred at ambient temperature under nitrogen for 24 h. The DMF was removed under vacuum and the residue was purified by preparative HPLC on a Vydac C-18 column (21.2×25 cm) using a 1.8%/min gradient of 20 to 90% ACN containing 0.05 M NH$_4$OH at a flow rate of 15 mL/min. A second HPLC purification on the same column and gradient using ACN gave the title compound as a colorless oil (9.6 mg, 8.4%). ES-MS: m/e 676.3 [M−H].

Example 11

Synthesis of 2-[[[5-[[[[6-[(4,6-Diphenyl-2-pyridinyl)oxy]-hexanoyl]-4-sulfonamidyl]benzylamino]carbonyl]-2-pyridinyl]-hydrazono]methyl]-benzenesulfonic acid

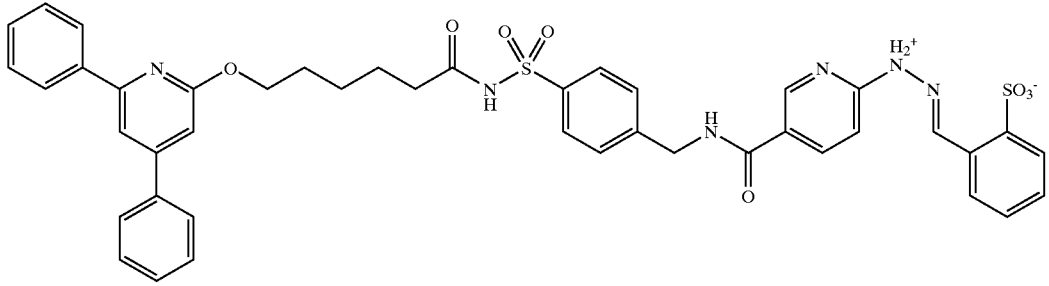

Part A Preparation of 4-(tert-butyl-aminomethyl)benzene sulfonamide

Commercially available 4-aminomethylbenzene sulfonamide hydrochloride hydrate (0.5 g, 2.25 mmol) was dissolved in dioxane (10 mL). Triethylamine (0.627 mL, 4.5 mmol) was added and the reaction was stirred for 5 min. Di-tert-butyl-dicarbonate (0.490 g, 2.25 mmol) was added, and the reaction was stirred overnight at room temperature. The reaction was then concentrated under high vacuum. The resulting oil was brought up in water and extracted with dichloromethane. The organic layer was then washed with brine, dried over magnesium sulfate, and evaporated to a small volume. Hexane was added and the product precipitated. The product was filtered, washed with hexane, and dried to give 0.476 g (74%) of 4-(tert-butyl-aminomethyl) benzene sulfonamide. ESMS: Calcd. For $C_{12}H_{18}N_2O_4S$, 286.10; Found, 285.1 $(M-H)^{-1}$ Part B Preparation of 4-(Aminomethyl)-benzosulfonimide of 6-[(4,6-Diphenyl-2-pyridinyl)oxy]-hexanoic acid, trifluoroacetic acid salt

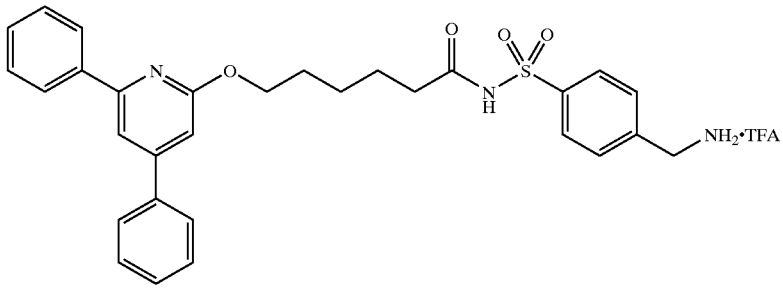

6-[(4,6-Diphenyl-2-pyridinyl)oxy]-hexanoic acid (0.100 g, 0.276 mmol) was dissolved in dichloromethane (8 mL). 4-Dimethylaminopyridine (43.8 mg, 0.358 mmol), 1-(3-dimethylaminopropyl)-3-ethylcarbodiimide hydrochloride (50.9 mg, 0.276 mmol), and 4-(Tert-butyl-aminomethyl) benzene sulfonamide (79.0 mg, 0.276 mmol) were added. 4 Å Molecular sieves were added, and the reaction was stirred overnight for 22 h. The reaction was then filtered, and washed with dichloromethane. The filtrate was washed with 1N HCl (1×), water (2×), saturated NaCl (2×), dried over magnesium sulfate, and concentrated to give a white solid which was recrystallized from hexane/ethyl acetate to give 106.7 mg (61%) of the boc protected sulfonimide product. ESMS: Calcd. For $C_{35}H_{39}N_3O_6S$, 629.26; Found, 628.3 $(M-H)^1$ The boc protected product (97.3 mg, 0.154 mmol) was then dissolved in dichloromethane (1.5 mL). Trifluoroacetic acid (1.5 mL) was added, and the reaction was stirred for 2 h at room temperature. The reaction mixture was then concentrated to an oil and triturated with ether. The product was filtered, washed with ether, and dried to give 97.2 mg (119%) of 4-(aminomethyl)-benzosulfonimide of 6-[(4,6-Diphenyl-2-pyridinyl)oxy]-hexanoic acid, trifluoroacetic acid salt. ESMS: Calcd. For $C_{30}H_{31}N_3O_4S$, 529.20; Found, 530.2 $(M+H)^{+1}$ Part C Preparation of 2-[[[5-[[[[6-[(4,6-Diphenyl-2-pyridinyl)oxy]-hexanoyl]-4-sulfonamidyl]benzylamino] carbonyl]-2-pyridinyl]-hydrazono]methyl]-benzenesulfonic acid The sulfonimido-amine (0.080 g, 0.124 mmol) was dissolved in dimethylformamide (3 mL). Triethylamine (51.8 μl, 0.372 mmol) was added and the reaction was stirred for 5 minutes. 2-[[[5-[[(2,5-Dioxo1-pyrrolidinyl)oxy]-carbonyl]-2-pyridinyl]hydrazono]methyl]-benzenesulfonic acid, monosodium salt (65.5 mg, 0.149 mmol) was added and the reaction was stirred for 36 h under nitrogen. The reaction was then concentrated to an oil under high vacuum. The oil was triturated with ethyl acetate to give 100.9 mg (98%) of the title compound. ESMS: Calcd. For $C_{43}H_{40}N_6O_8S_2$, 832.23; Found, 831.4 $(M+H)^{+1}$.

Example 12

Synthesis of 4-ethyl-2-(4-fluorophenyl)-[5-[6,6-dimethyl-7-[[6-[[[(2-sulfonylphenyl)methylene] hydrazino]-3-pyridinyl]carbonyl]amino]heptyl]oxy] phenol

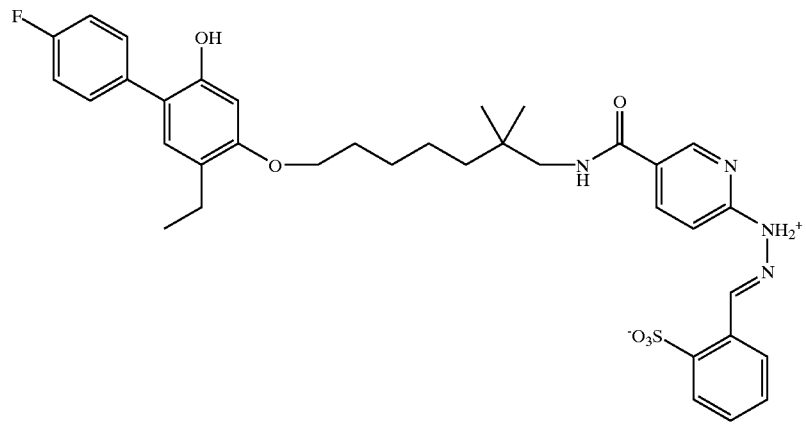

Part A Preparation of 1-(benzyloxy)-4-ethyl-2-(4-fluorophenyl)-5-[(6-methyl-6-cyanoheptyl)oxy]-benzene 1-(Benzyloxy)-4-ethyl-2-(4-fluorophenyl)-5-[(6-methyl-6-cyanoheptyl)oxy]-benzene was prepared as described in Example 1 for the synthesis of 1-(benzyloxy)-4-ethyl-2-(4- fluorophenyl)-5-[(5-methyl-5-cyanohexyl)oxy]-benzene substituting 6-cyano-6-methyl-1-bromoheptane for 5-cyano-5-methyl1-bromohexane.

Part B Preparation of 4-ethyl-2-(4-fluorophenyl)-5-[(6,6-dimethyl-7-aminoheptyl)oxy]phenol

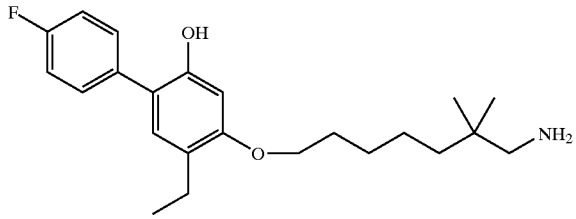

1-(benzyloxy)-4-ethyl-2-(4-fluorophenyl)-5-[(6-methyl-6-cyanoheptyl)oxy]-benzene (485 mg) was dissolved in ethanol (15 mL) and added to a solution of platinum oxide (20 mg) in 10 mL ethanol in a Parr bottle. The bottle was pressurized to 55 psi with hydrogen and shaken for 20 hours. Additional catalyst (120 mg) was added and bottle shaken at 55 psi of hydrogen for an additional 18 hours. The solution was filtered through Celite and concentrated under vacuum to afford crude 4-ethyl-2-(4-fluorophenyl)-5-[(6,6-dimethyl-7-aminoheptyl)oxy]phenol (475 mg) as an oil. It was purified by chromatography on silica gel with chloroform/methanol eluant. The product fractions were combined and concentrated under vacuum (120 mg). NMR (CDCl₃): 1.00, s, (6H); 1.15, t (3H); 1.33, m (2H); 1.44, m (2H); 1.77, m (2H); 2.55, q (2H); 2.74, s (2H); 3.92, t (2H); 6.52, s (1H); 6.96, s (1H); 7.11, d of d (2H); 7.43, d of d (2H). Mass Spec (EI), m/e=374.3 (M+H).

Part C Preparation of 4-ethyl-2-(4-fluorophenyl)-[5-[6,6-dimethyl-7-[[6-[[[(2-sulfonylphenyl)methylene]hydrazino]-3-pyridinyl]carbonyl]amino]heptyl]oxy]phenol Dry dimethyl formamide (5 mL) was charged to a flask under nitrogen. To this was added 4-ethyl-2-(4-fluorophenyl)-5-[(6,6-dimethyl-7-aminoheptyl)oxy]phenol (85 mg) and sodium 2-[[[5-[[(2,5-dioxo-1-pyrolidinyl)oxy]carbonyl]-2-pyridinyl]hydrazono]methyl]-benzenesulfonate (100 mg) followed by diisopropylethylamine (94 mg) and 4-dimethylaminopyridine (5 mg). The solution was stirred overnight. Solvent was concentrated under vacuum and the residual oil purified by preparative HPLC (5×25 cm Vydac C₁₈ pharmaceutical column, 0.1% trifluoroacetic acid in water/acetonitrile gradient) and lyophilized to afford the product (30 mg) as an off-white powder. NMR (DMSO-d₆): 0.88, s (6H); 1.10, t (3H); 1.33, m (6H); 1.76, m (2H); 2.50, m (2H); 3.16, d (2H); 3.93, t (2H); 6.52, s (1H); 6.99, s (1H); 7.16, t (2H); 7.19, m (1H); 7.41, m (2H); 7.53, d of d (2H); 7.80, m (1H); 8.19, b (2H); 8.51, s (1H); 9.18, broad (1H); 9.33, broad (1H). Mass Spec (EI), m/e=675.3 (M–H).

Example 13

Preparation of 4-ethyl-2-(5-pyrazolyl)-[5-[5,5-dimethyl-6-[[6-[[[[(2-sulfonylphenyl)methylene]hydrazino]-3-pyridinyl]carbonyl]amino]hexyl]oxy]phenol

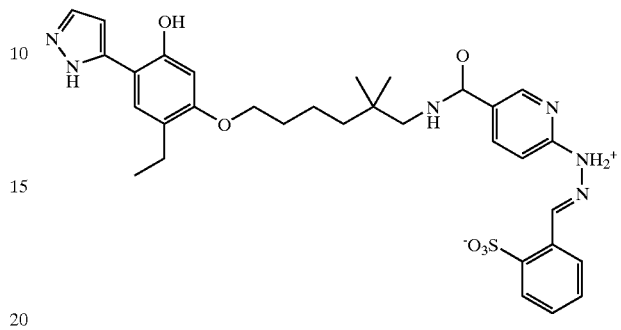

Part A Preparation of 2-hydroxy-5-ethyl-4-[(5-methyl-5-cyanohexyl)oxy]-acetophenone A solution of 2,4-dihydroxy-5-ethyl-acetophenone (2.65 g), potassium carbonate (3.6 g), potassium iodide (0.49 g), and 5-cyano-5-methyl-1-bromohexane (3.0 g) in dimethylsulfoxide (4 mL) and 2-butanone (15 mL) was heated at 110° C. for 18 hours under nitrogen. The mixture was cooled, diluted with water (40 mL), and extracted with toluene. The combined organics were washed with water, dried (magnesium sulfate), filtered, and concentrated under vacuum to a yellow oil (3.6 g). This was flash chromatographed (6:1 hexane/ethyl acetate) and the combined fractions concentrated to afford the product as an oil (3.3 g). NMR (CDCl₃): 1.17, t (3H); 1.35, s (6H); 1.6–1.9, m (6H); 2.55, s (3H); 2.56, q (2H); 4.01, t (2H); 6.35, s (1H); 7.41, s (1H); 12.69, s (1H); Mass Spec (GC/MS), m/e=303 (M).

Part B Preparation of 3-[(5-methyl-5-cyanohexyl)oxy]-4-ethyl-6-pyrazoyl-phenol:

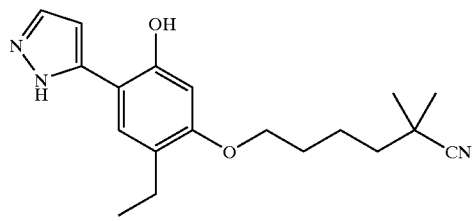

2-hydroxy-5-ethyl-4-[(5-methyl-5-cyanohexyl)oxy]-acetophenone (1.0 g) was mixed with dimethylformamide dimethylacetal (1.6 g) and heated in a 100° C. oil bath, where the solid dissolved. After 3 hours, a yellow precipitate had formed and the volatiles were removed under vacuum. The solids were suspended in ethanol (20 mL) and hydrazine hydrate (375 mg) added. The mixture was stirred for 18 hours at ambient temperature and then for 24 hours at reflux. The solution was filtered and the filtrate concentrated to an oil which was purified by flash chromatography (Hexane/chloroform/acetonitrile/methanol, 6:2:1:1). The desired fractions were combined and concentrated to afford the product as an oil (600 mg). NMR (CDCl₃): 1.19, t (3H); 1.35, s (6H); 1.6–1.9, m (6H); 2.60, q (2H); 4.01, t (2H);

6.51, s (1H); 6.62, d (1H; 7.31, s (1H); 7.60, d (1H); 10.2, b (1H); Mass Spec (EI), m/e=326.2 (M−H).

Part C Preparation of 3-[(5,5-dimethyl-6-aminohexyl)oxy]-4-ethyl-6-pyrazoyl-phenol

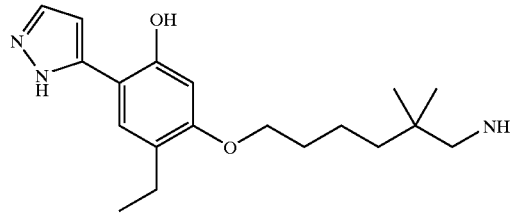

3-[(5-methyl-5-cyanohexyl)oxy]-4-ethyl-6-pyrazoyl-phenol (285 mg) was dissolved in methanol (25 mL) in a Parr bottle and platinum oxide (100 mg) and concentrated hydrochloric acid (270 µL) added. The vessel was capped, pressurized at 54 psi of hydrogen and shaken for 24 hours. The reaction was filtered through Celite and the filtrate concentrated to afford the product as an oil (265 mg). NMR (DMSO-$d_6$): 0.92, s (6H); 1.14, t (3H); 1.2–1.5, m (4H); 1.6–1.8, m (2H); 2.48, q (2H); 2.64, m (2H); 3.97, t (2H); 6.51, s (1H); 6.76, d (1H); 7.45, s (1H); 7.85, d (1H); Mass Spec (EI), m/e=332.2 (M+H)

Part D Preparation of 4-ethyl-2-(5-pyrazolyl)-[5-[5,5-dimethyl-6-[[6-[[[(2-sulfonylphenyl)methylene]hydrazino]-3-pyridinyl]carbonyl]amino]hexyl]oxy]phenol 3-[(5,5-dimethyl-6-aminohexyl)oxy]-4-ethyl-6-pyrazoyl-phenol (260 mg) was dissolved in dimethylformamide (12 mL) and triethylamine (230 mg) added, followed by sodium 2-[[[5-[[(2,5-dioxo1-pyrrolidinyl)oxy]carbonyl]-2-pyridinyl]hydrazono]methyl]-benzenesulfonate (398 mg) and dimethylaminopyridine (8 mg). The purple reaction was stirred overnight, concentrated under vacuum, and the resulting oil (840 mg) purified by preparative HPLC (5 cm×25 cm Vydac Pharmaceutical column, 0.1% trifluoroacetic acid/water (A):90% acetonitrile/water (B) gradient). The fractions were lyophilized to yield the product as a grey powder (140 mg). NMR (DMSO-$d_6$): NMR (DMSO-$d_6$): 0.88, s (6H); 1.12, t (3H); 1.2–1.9, m (6H); 2.53, q (2H); 3.15, m (2H); 3.95, t (2H); 4.2, b (5H); 6.46, s (1H); 6.75, s (1H); 7.17, d (1H); 7.43, m (3H); 7.84, m (2H); 8.29, d (1H); 8.38, d (1H); 8.45, s (1H)8.54, t (1H); 9.34, s(1H); 13.10, b (1H); Mass Spec (EI), m/e=633.2 (M−H);

Example 14

Synthesis of the Conjugate Between 2-[6-[(4,6-Diphenyl-2-pyridinyl)oxy]pentyl]-6-(8-amino-5-aza-4-oxooctyloxy)benzenepropanoic Acid and Benzenesulfonic Acid, 2-[[[5-[[(2,5-Dioxo-1-pyrrolidinyl)oxy]carbonyl]-2-pyridinyl]-hydrazono] methyl]

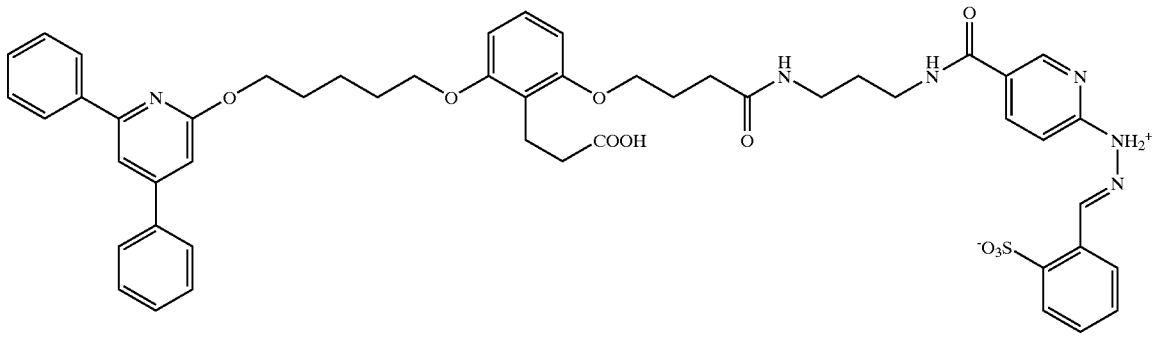

Part A Preparation of 6-[(5-Hydroxypentyl)oxy]-2-(4-t-butoxy-4-oxobutyloxy)benzenepropanoic Acid Methyl Ester A mixture of 2-hydroxy-6-[(5-hydroxypentyl)oxy]-benzenepropanoic acid methyl ester (2.04 g, 7.23 mmol) (as described by Cohen, N. EP Appl. 531,823), t-butyl 4-bromobutyrate (1.93 g, 8.67 mmol), and $K_2CO_3$ (2.29 g, 16.6 mmol) in DMSO (60 mL) was stirred at ambient temperatures under nitrogen for 21 h. The solids were removed by filtration and the filtrate was diluted with water (100 mL), and extracted with EtOAc (3×100 mL). The combined organic extracts were washed with water and sat. NaCl, dried ($MgSO_4$), and concentrated to give product as a yellow oil (2.98 g). A portion (487 mg) was purified by silica gel flash chromatography (40:60 EtOAc/hexanes) to give the title compound as a colorless oil (367 mg, 73.3%). $^1$H NMR ($CDCl_3$): 7.08 (t, J=8.2 Hz, 1H), 6.48 (d, J=8.2 Hz, 2H), 4.00–3.89 (m, 4H), 3.70–3.62 (m, 5H), 3.04–2.93 (m, 2H), 2.50–2.39 (m, 4H), 2.11–1.99 (m, 2H), 1.88–1.75 (m, 2H), 1.72–1.52 (m, 5H), 1.43 (s, 9H); MS: m/e 447.3 [M+Na].

Part B Preparation of 6-(4-t-Butoxy-4-oxobutoxy)-2-[[5-(methylsulfonyl)oxy]pentyl]oxy]benzenepropanoic Acid Methyl Ester A solution of 6-[(5-hydroxypentyl)oxy]-2-(4-t-butoxy-4-oxobutyloxy)benzenepropanoic acid methyl ester (1.68 g, 3.96 mmol), TEA (1.10 ml, 11.8 mmol), and methanesulfonyl chloride (0.46 mL, 5.9 mmol) in DCM (30 mL) was stirred at ambient temperature under nitrogen for 1 hr. The solution was diluted with DCM (50 mL) and water (30 mL), and the aqueous layer was further extracted with DCM (3×50 mL). The combined DCM extracts were washed successively with 0.1N HCl (100 mL), sat. $NaHCO_3$ (50 mL), and sat. NaCl (50 mL), dried ($MgSO_4$), and concentrated to give product as a pale yellow oil (1.99 g, 100%). $^1$H NMR ($CDCl_3$): 7.08 (t, J=8.3 Hz, 1H), 6.48 (d, J=8.3 Hz, 2H), 4.25 (t, J=6.4 Hz, 2H), 4.00–3.90 (m, 4H), 3.67 (s, 3H), 3.01–2.91 (m, 5H), 2.50–2.37 (m, 4H), 2.13–2.00 (m, 2H), 1.89–1.75 (m, 4H), 1.68–1.56 (m, 2H), 1.43 (s, 9H); MS: m/e 520.3 [M+NH$_4$].

Part C Preparation of 2-[6-[(4,6-Diphenyl-2-pyridinyl)oxy]hexyl]-6-(4-t-butoxy-4-oxobutoxy)benzenepropanoic Acid Methyl Ester

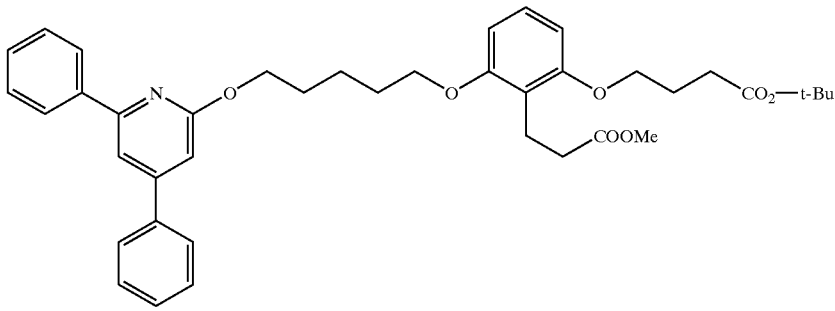

A mixture of 6-(4-t-butoxy-4-oxobutoxy)-2-[[5-(methylsulfonyl)oxy]pentyl]oxy]benzenepropanoic acid methyl ester (2.08 g, 3.6 mmol), 4,6-diphenyl-2-pyridinone (0.89 g, 3.6 mmol), and K$_2$CO$_3$ (1.19 g, 8.64 mmol) in DMSO (40 mL) was stirred at ambient temperature under nitrogen for 23 h. The reaction mixture was diluted with water (50 mL) and extracted with EtOAc (3×70 mL). The combined organic extracts were washed successively with water, and sat. NaCl, dried (MgSO$_4$), and concentrated to give a yellow oil. Purification by silica gel flash chromatography (1:6 EtOAc/hexanes) gave the title compound as a colorless oil (1.56 g, 66.4%). $^1$H NMR (CDCl$_3$): 8.07 (d, J=6.7 Hz, 2H), 7.70–7.63 (m, 2H), 7.54–7.35 (m, 7H), 7.08 (t, J=8.1 Hz, 1H), 6.89 (s, 1H), 6.52–6.43 (m, 1H), 4.50 (t, J=6.3 Hz, 2H), 4.05–3.93 (m, 4H), 3.63 (s, 3H), 3.05–2.94 (m, 2H), 2.54–2.39 (m, 4H), 2.11–1.98 (m, 2H), 1.98–1.83 (m, 4H), 1.76–1.61 (m, 2H), 1.43 (s, 9H); MS: m/e 654.5 [M+H].

Part D Preparation of 2-[6-[(4,6-Diphenyl-2-pyridinyl)oxy]hexyl]-6-(3-carboxypropoxy)benzenepropanoic Acid Methyl Ester A solution of 2-[6-[(4,6-diphenyl-2-pyridinyl)oxy]-hexyl]-6-(4-t-butoxy-4-oxobutoxy)benzenepropanoic acid methyl ester (200 mg, 0.3 mmol) and anisole (65 ul, 0.6 mmol) in TFA (5 mL) was stirred at ambient temperatures for 2 h. The solution was evaporated to dryness and the residue was partitioned between EtOAc (40 mL) and H$_2$O (40 mL). The aqueous layer was extracted with additional EtOAc (3×20 mL). The combined organic extracts were washed successively with sat. NaHCO$_3$ (30 mL) and sat. NaCl (2×30 mL), dried (MgSO$_4$), and concentrated to give a colorless solid. Lyophilization from 70% ACN gave the title compound as a colorless solid (170 mg, 94.8%). High Resolution MS: Calcd for C$_{36}$H$_{39}$NO$_7$: 598.2805, Found: 598.2813.

Part E Preparation of 2-[6-[(4,6-Diphenyl-2-pyridinyl)oxy]hexyl]-6-(5-aza-8-t-butoxycarbonylamino-4-oxooctyloxy)benzenepropanoic Acid Methyl Ester

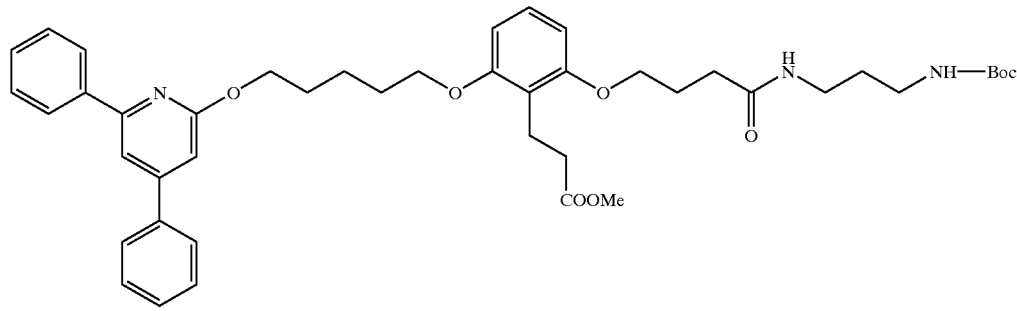

A solution of 2-[6-[(4,6-diphenyl-2-pyridinyl)oxy]-hexyl]-6-(3-carboxypropoxy)benzenepropanoic acid methyl ester (118 mg, 0.197 mmol) in DMF (4 mL) was treated with HBTU (82 mg, 0.217 mmol). After 5 min a solution of mono-N-Boc-1,3-diaminopropane (34.3 mg, 0.197 mmol) and DIEA (86 ul, 0.49 mmol) in DMF (1 mL) was added and stirring was continued at ambient temperatures for 10 min. The DMF was removed by evaporation and the residue was dissolved in a mixture of EtOAc (40 mL) and H$_2$O (30 mL). The aqueous layer was adjusted to pH 2 with 0.2 N HCl and the layers were thoroughly mixed. The EtOAc layer was washed consecutively with sat. NaHCO$_3$ (30 mL) and sat. NaCl (2×30 mL), dried (MgSO$_4$), and concentrated to give the title compound as a colorless oil (129 mg, 86.8%). High Resolution MS: Calcd for C$_{44}$H$_{55}$N$_3$O$_8$: 754.4067, Found: 754.4077.

Part F Preparation of 2-[6-[(4,6-Diphenyl-2-pyridinyl)oxy]hexyl]-6-(8-amino-5-aza-4-oxooctyloxy)benzenepropanoic Acid

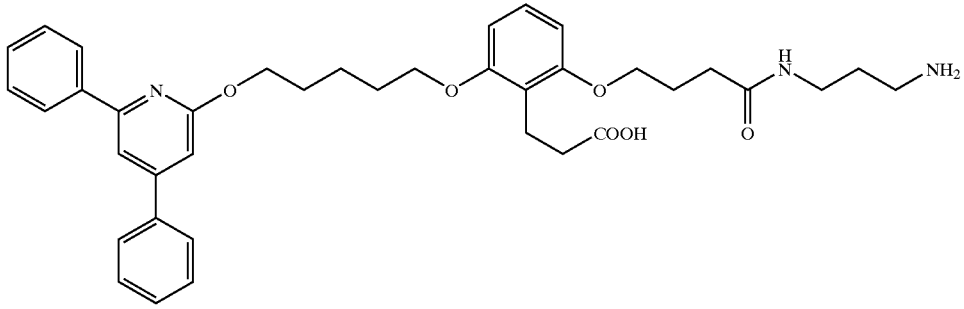

A mixture of 2-[6-[(4,6-diphenyl-2-pyridinyl)oxy]hexyl]-6-(5-aza-8-t-butoxycarbonylamino-4-oxooctyloxy)benzenepropanoic acid methyl ester (120 mg, 0.159 mmol) and 3 M LiOH (0.77 mL, 2.3 mmol) in THF (7.6 mL) was stirred at ambient temperatures for 4 days. The THF and H$_2$O were removed by vacuum evaporation and the residue was taken up cautiously with cooling in TFA (4 mL). The resulting solution was stirred at ambient temperature for 70 min and the TFA was removed by evaporation. The residue was treated with EtOAc (30 mL) and sat. NaHCO$_3$ (30 mL) causing a colorless solid to form in the EtOAc layer. This solid/EtOAc mixture was washed with water (2×10 mL) and filtered to remove the solid. The solid was dried to give the title compound as a colorless solid (77 mg, 76%). High Resolution MS: Calcd for C$_{38}$H$_{45}$N$_3$O$_6$: 640.3387, Found: 640.3384.

Part G Preparation of Conjugate between 2-[6-[(4,6-Diphenyl-2-pyridinyl)oxy]hexyl]-6-(8-amino-5-aza-4-oxooctyloxy)benzenepropanoic Acid and Benzenesulfonic Acid, 2-[[[5-[[(2,5-Dioxo1-pyrrolidinyl)oxy]carbonyl]-2-pyridinyl]hydrazono]methyl]

A mixture of 2-[6-[(4,6-diphenyl-2-pyridinyl)oxy]hexyl]-6-(8-amino-5-aza-4-oxooctyloxy)benzenepropanoic acid (55 mg, 0.086 mmol), benzenesulfonic acid, 2-[[[5-[[(2,5-dioxo-1-pyrrolidinyl)oxy]carbonyl]-2-pyridinyl]hydrazono]methyl] (45.4 mg, 0.103 mmol), and TEA (56 ul, 0.344 mmol) in DMF (0.6 mL) was stirred at ambient temperatures for 17 h. The reaction mixture was purified directly by preparative HPLC on a Vydac C-18 column (21.2×25 cm) using a 1.33%/min gradient of 40 to 80% ACN containing 0.05 M NH$_4$OH at a flow rate of 15 mL/min. Lyophilization of the product-containing fraction gave title compound as a colorless solid (50 mg, 61.7%). High Resolution MS: Calcd for C$_{51}$H$_{54}$N$_6$O$_{10}$S: 943.3700, Found: 943.3701.

Example 15

Synthesis of the Conjugate Between 6-(11-Amino-3,6,9-trioxaundecyloxy)-2-[5-[(5-oxo1-(2-propenyl)-5,6,7,8-tetrahydro-2-naphthalenyl)oxy]pentyloxy] benzenepropanoic Acid and Benzenesulfonic Acid, 2-[[[5-[[(2,5-Dioxo1-pyrrolidinyl)oxy]carbonyl]-2-pyridinyl]hydrazono]methyl]

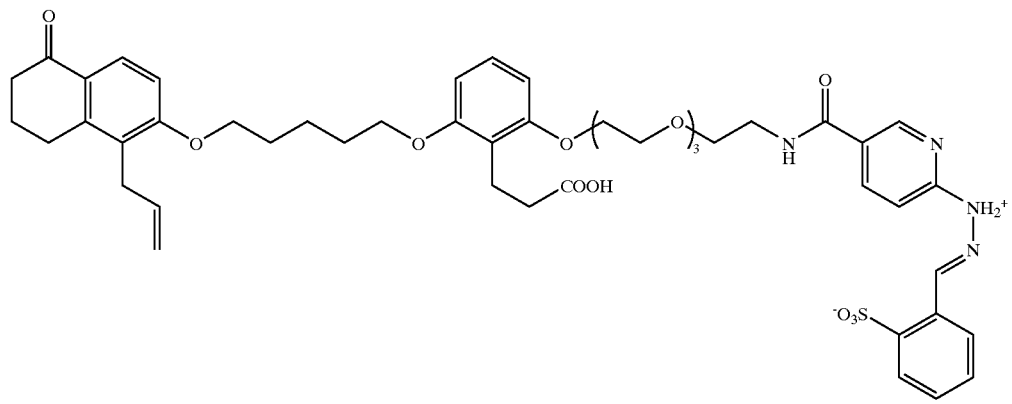

Part A Preparation of 11-Benzyloxycarbonylamino-3,6,9-trioxaundecanol

A solution of 11-amino-3,6,9-trioxaundecanol (6.56 g, 0.034 mol) and TEA (5.2 mL, 0.037 mol) in DCM (200 mL) was treated with benzyl chloroformate (5.1 mL, 0.036 mol) in one portion. After 18 h the solution was concentrated to a viscous oil and triturated with ether (3×100 mL). The combined triturants were concentrated to give an amber oil (9.4 g). Flash chromatoraphy on silica gel (6% MeOH/EtOAc) gave the title compound as a colorless viscous oil (7.0 g, 63%). $^1$H NMR (CDCl$_3$): 7.36–7.25 (m, 5H), 6.04 (bs, 1H), 5.08 (s, 2H), 3.72 –3.48 (m, 14H), 3.41–3.31 (m, 2H).

Part B Preparation of 11-Benzyloxycarbonylamino-3,6,9-trioxaundecyl Mesylate

A solution of 11-benzyloxycarbonylamino-3,6,9-trioxaundecanol (2.10 g, 6.4 mmol), TEA (2.7 mL, 19.2 mmol), and methanesulfonyl chloride (0.8 mL, 10.2 mmol) in DCM (20 mL). After 2 h the solution was diluted with DCM (80 mL), washed successively with 0.2 M HCl (40 mL), water (40 mL), sat. NaHCO$_3$ (40 mL) and sat. NaCl (2×40 mL), and dried (MgSO$_4$). Concentration gave the title compound as a viscous oil (2.3 g, 88.6%). $^1$H NMR (CDCl$_3$): 7.37–7.23 (m, 5H), 5.34 (bs, 1H), 5.08 (s, 2H), 4.35–4.26 (m, 2H), 3.72–3.50 (m, 12H), 3.41–3.32 (m, 2H), 3.02 (s, 3H); MS: m/e 406.2 [M+H].

Part C Preparation of N-Benzyloxycarbonyl-11-iodo-3,6,9-trioxaundecylamine

A mixture of 11-benzyloxycarbonylamino-3,6,9-trioxaundecyl mesylate (3.0 g, 7.4 mmol) and NaI (2.2 g, 14.8 mmol) in ACN (45 mL) was heated at 80° C. with stirring for 3 h. The mixture was partitioned between ether (140 mL) and water (80 mL). The aqueous phase was further extracted with ether (2×100 mL). The combined ether extracts were washed successively with water (60 mL), 10% sodium thiosulfate (60 mL), and sat. NaCl (2×60 mL). The ether solution was dried (MgSO4) and concentrated to give the title compound as a colorless oil (3.20 g, 98.9%). $^1$H NMR (CDCl$_3$): 7.39–7.26 (m, 5H), 5.35 (bs, 1H), 5.08 (s, 2H), 3.73–3.50 (m, 12H), 3.42–3.32 (m, 2H), 3.27–3.16 (m, 2H); MS: m/e 438.1 [M+H].

Part D Preparation of 6-[(5-Hydroxypentyl)oxy]-2-(11-benzyloxycarbonylamino-3,6,9-trioxaundecyloxy)benzenepropanoic Acid Methyl Ester

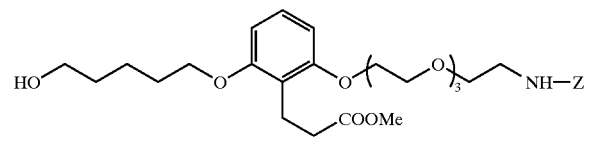

A mixture of 2-hydroxy-6-[(5-hydroxypentyl)oxy]-benzenepropanoic acid methyl ester (1.39 g, 4.93 mmol), N-benzyloxycarbonyl-11-iodo-3,6,9-trioxaundecylamine (1.96 g, 4.48 mmol), and K$_2$CO$_3$ (1.24 mg, 8.96 mmol) in DMSO (6 mL) was stirred at ambient temperature under nitrogen for 6 d. The reaction mixture was used directly for purification on a Vydac C-18 column (21.2×25 cm) using a 1.5%/min gradient of 30 to 80% ACN at a flow rate of 15 mL/min. The product fractions from nine injections were collected together and lyophilized to give the title compound as a colorless oil (626 mg, 23.6%). $^1$H NMR (CDCl$_3$): 7.34–7.25 (m, 5H), 7.07 (t, J=8.3 Hz, 1H), 6.48 (d, J=8.3 Hz, 1H), 6.46 (d, J=8.3 Hz, 1H), 5.4 (s, 1H), 5.08 (s, 2H), 4.07–3.35 (m, 23H), 2.98 (t, J=8.1 Hz, 2H), 2.48 (t, J=8.1 Hz, 2H), 1.83–1.61 (m, 8H); MS: m/e 592.3 [M+H].

Part E Preparation of 6-(11-benzyloxycarbonylamino-3,6,9-trioxaundecyloxy)-2-[[5-(methylsulfonyl)oxy]pentyl]oxy]benzenepropanoic Acid Methyl Ester A solution of 6-[(5-hydroxypentyl)oxy]-2-(11-benzyloxycarbonylamino-3,6,9-trioxaundecyloxy)benzenepropanoic acid methyl ester (75 mg, 0.13 mmol), TEA (51 mg, 0.51 mmol), and methanesulfonyl chloride (29 mg, 0.25 mmol) in DCM (1.0 mL) was stirred at ambient temperatures for 1 h. The solution was diluted with DCM (6 mL), and washed successively with water (3 mL), pH 2.0 HCl (3 mL), sat. NaHCO$_3$ (3 mL), and sat. NaCl (2×3 mL). The DCM solution was dried (MgSO$_4$) and concentrated to give product as a viscous oil (67 mg, 79%). MS: m/e 670.3 [H+H].

Part F Preparation of 6-(11-Benzyloxycarbonylamino-3,6,9-trioxaundecyloxy)-2-[5-[(5-oxo1-(2-propenyl)-5,6,7,8-tetrahydro-2-naphthalenyl)oxy]pentyloxy]benzenepropanoic Acid Methyl Ester

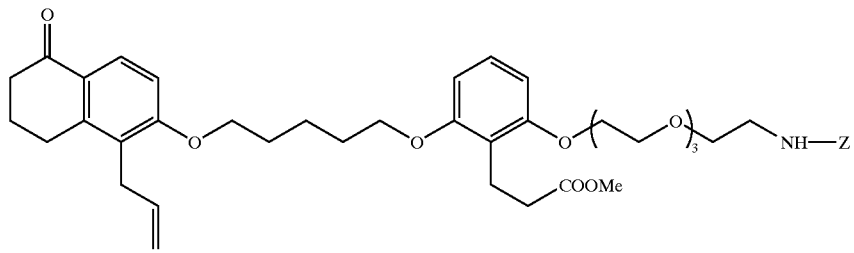

A mixture of the mesylate prepared in Part C (67 mg, 0.10 mmol), 6-hydroxy-5-(2-propenyl)-1,2,3,4-tetrahydronaphthalen-1-one (22.5 mg, 0.11 mmol), and anhydrous K$_2$CO$_3$ (27 mg, 0.20 mmol) in DMSO (500 ul) was stirred at ambient temperature under nitrogen for 96 h. The reaction solution was used directly for preparative HPLC purification on a Vydac C-18 column (21.2×25 cm) using a 1.8%/min gradient of 27 to 81% ACN at a flow rate of 15 mL/min. Lyophilization of the product fraction gave the title compound as a viscous oil (38 mg, 49%). $^1$H NMR (CDCl$_3$): 7.99 (d, J=8.8 Hz, 1H), 7.40–7.20 (m, 5H), 7.08 (t, J=8.3 Hz, 1H), 6.83 (d, J=8.8 Hz, 1H), 6.49 (d, J=8.3 Hz, 1H), 6.46 (d, J=8.3 Hz, 1H), 5.94–5.79 (m, 1H), 5.35 (s, 1H), 5.08 (s, 2H), 4.97–4.87 (m, 2H), 4.07–3.94 (m, 6H), 3.80–3.38 (m, 18H), 2.98–2.85 (m, 4H), 2.59–2.48 (m, 4H), 2.08–1.65 (m, 8H); $^{13}$C NMR (CDCl$_3$): 197.74, 174.06, 160.64, 157.62, 157.44, 156.40, 144.39, 136.61, 135.50, 128.43, 128.05, 128.00, 127.800, 127.16, 126.30, 125.19, 117.34, 114.72, 109.14, 104.59, 70.86, 70.63, 70.49, 70.24, 69.96, 69.73, 68.00, 67.91, 66.57, 51.31, 40.86, 38.43, 33.32, 29.86, 28.98, 28.86, 26.31, 22.87, 22.73, 18.84; DCI-MS: m/e 793.6 [M+NH$_4$]; High Resolution MS: Calcd for C$_{44}$H$_{58}$N$_1$O$_{11}$ [M+H]: 776.4010, Found: 776.4011.

Part G Preparation of 6-(11-Benzyloxycarbonylamino-3,6, 9-trioxaundecyloxy)-2-[5-[(5-oxo-1-(2-propenyl)-5,6,7,8-tetrahydro-2-naphthalenyl)oxy]pentyloxy] benzenepropanoic Acid

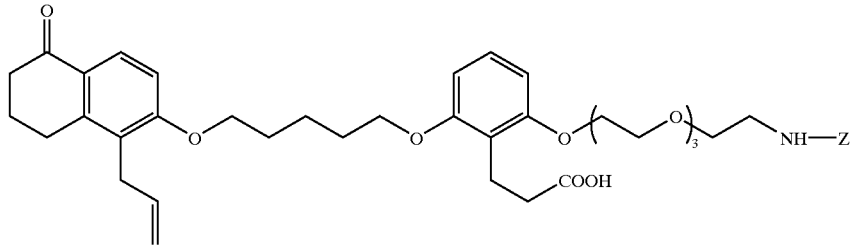

The ester prepared in Part C (28.5 mg, 0.037 mmol) was treated with THF (1.8 mL) and 3N aqueous LiOH (0.18 mL). The mixture was stirred at ambient temperatures under nitrogen for 6 d. The resulting yellow solution was concentrated to dryness, the residue was treated with water (4 mL), and adjusted to pH 2 with 1N HCl. The milky solution was extracted with EtOAc (3×8 mL). The combined organic layers were washed with water (20 mL), and then sat. NaCl (15 mL), dried (MgSO$_4$), and concentrated to give the title compound as a colorles oil (27.0 mg, 95.7%). DCI-MS: m/e 779.5 [M+NH$_4$]; High Resolution MS: Calcd for C$_{43}$H$_{55}$NO$_{11}$ [M+H]: 762.3853, Found: 762.3859.

Part H Preparation of 6-(11-Amino-3,6,9-trioxaundecyloxy)-2-[5-[(5-oxo1-(2-propenyl)-5,6,7,8-tetrahydro-2-naphthalenyl)oxy]pentyloxy] benzenepropanoic Acid A solution of 6-(11-benzyloxycarbonylamino-3,6,9-trioxaundecyloxy)-2-[5-[(5-oxo1-(2-propenyl)-5,6,7,8-tetrahydro-2-naphthalenyl)oxy]pentyloxy]benzenepropanoic acid (22 mg, 0.0289 mmol) and TMSI (58 ul, 0.0458 mmol) in ACN (1 mL) was stirred at ambient temperatures for 30 min. HPLC analysis indicated approximately 50% starting material remaining and additional TMSI (58 ul) was added. After an additional 30 min the solution was concentrated and the residue was partitioned between 5% NaHCO$_3$ (10 mL) and EtOAc (10 mL). The aqueous layer was extracted with additional EtOAc (2×5 mL). The combined EtOAc extracts were washed with 10% sodium thiosulfate (5 mL), dried (MgSO$_4$), and concentrated to give the title compound as a pale yellow oil (9.8 mg, 54%). MS: m/e 628.4 [H+H].

Part I Preparation of Conjugate Between 6-(11-Amino-3,6, 9-trioxaundecyloxy)-2-[5-[(5-oxo1-(2-propenyl)-5,6,7,8-tetrahydro-2-naphthalenyl)oxy]pentyloxy] benzenepropanoic Acid and Benzenesulfonic Acid, 2-[[[5-[[(2,5-Dioxo1-pyrrolidinyl)oxy]carbonyl]-2-pyridinyl]-hydrazono]methyl]

A solution of 6-(11-amino-3,6,9-trioxaundecyloxy)-2-[5-[(5-oxo1-(2-propenyl)-5,6,7,8-tetrahydro-2-naphthalenyl)oxy]pentyloxy]benzenepropanoic acid (7 mg, 0.0111 mmol), benzenesulfonic acid, 2-[[[5-[[(2,5-dioxo-1-pyrrolidinyl)oxy]carbonyl]-2-pyridinyl]hydrazono]methyl] (5.6 mg, 0.0134 mmol), and TEA (6.2 ul, 0.0444 mmol) in DMF (0.3 mL) was stirred at ambient temperatures for 16 h. The reaction mixture was purified directly by preparative HPLC on a Vydac C-18 column (21.2×25 cm) using a 2.0%/min gradient of 20 to 80% ACN containing 0.05 M NH$_4$OH at a flow rate of 15 mL/min. Lyophilization of the product-containing fraction gave title compound as a colorless solid. MS: m/e 931.4 [H+H].

Example 16

Synthesis of 4-ethyl-2-(4-fluorophenyl)-[5-[6,6-dimethyl-7-[[6-[[[phenylmethylene]hydrazino]-3-pyridinyl]carbonyl]amino]heptyl]oxy]phenol

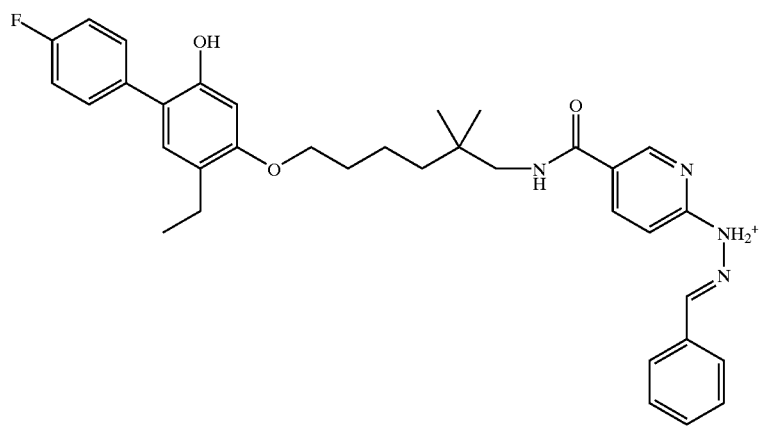

Step A: Preparation of 2-[[[5-[[(2,5-dioxo1-pyrolidinyl)oxy]carbonyl]-2-pyridinyl]hydrazono]methyl]-benzene

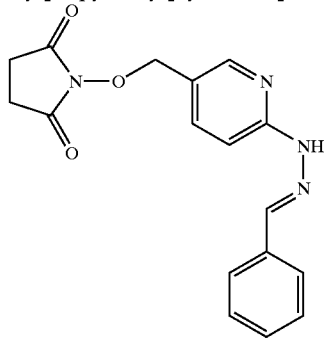

This was prepared in an identical fashion to Example 1, Part G, substituting benzaldehyde for 2-formylbenzensulfonic acid. Clean solid 2-[[[5-[[(2,5-dioxo1-pyrolidinyl)oxy]carbonyl]-2-pyridinyl]hydrazono]methyl]-benzene was obtained by simple rotary evaporation without trituration. NMR (DMSO-$d_6$): 2.88, s (4H); 7.36, m (3H); 7.79, d of d (1H); 8.10, m (2H); 8.79, t (1H); 9.16, s (1H); 11.90, s (1H). Mass Spec (EI): m/z=(M+H)

Step B: Preparation of 4-ethyl-2-(4-fluorophenyl)-[5-[6,6-dimethyl-7-[[6-[[[phenylmethylene]hydrazinobenzene]-3-pyridinyl]carbonyl]amino]heptyl]oxy]phenol Dry dimethylformamide (10 mL) was charged to a flask under nitrogen. To this was added 4-ethyl-2-(4-fluorophenyl)-5-[(5,5-dimethyl-6-aminohexyl)oxy]phenol (Example 1, Part C) (188 mg) and 2-[[[5-[[(2,5-dioxo1-pyrolidinyl)oxy]carbonyl]-2-pyridinyl]hydrazono]methyl]-benzene (200 mg) followed by diisopropylethylamine (231 mg) and 4-dimethylaminopyridine (15 mg). The solution was stirred 18 hours and then concentrated under reduced pressure. The residual oil was partitioned into water/ethyl acetate. The ethyl acetate was concentrated and the resulting crude purified by preparative HPLC (5×25 cm Vydac C18 pharmaceutical column; water/acetonitrile/0.1% trifluoroacetic acid gradient) and lyophilized to yield 98 mg of product. NMR (CDCl$_3$): 0.96, s (6H); 1.15, t (3H); 1.37, m (2H); 1.53, m (2H); 1.80, m (2H); 2.53, q (2H); 3.31, d (2H); 4.00, t (2H); 6.50, s (1H); 6.92, s (1H); 7.06, t (2H); 7.38, m (5H); 7.71, m (31H); 8.21, m (3H); 13.81, b (1H). LRMS (EI): m/z=583.3 (M+H); HRMS(FAB): Calc. For $C_{35}H_{40}N_4O_3F$—583.3084; Found—583.3070

Example 17

Synthesis of N-((6-((1-aza-2-phenylvinyl)amino)(3-pyridyl))sulfonyl)-3-(1-((N-(2-phenylethyl)carbamoyl)methyl)-5-(phenylmethoxy)indol-3-yl)prop-2-enamide

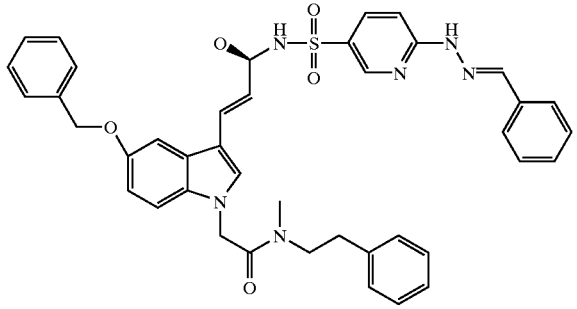

Step A: Preparation of Sodium 2-[[[5-[[(2,5-dioxo1-pyrolidinyl)oxy]carbonyl]-2-pyridinyl]hydrazono]methyl]-benzenesulfonate

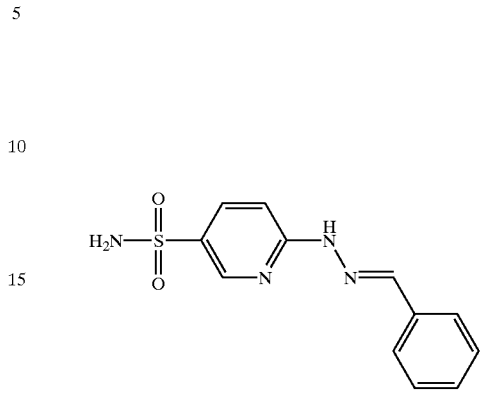

2-Hydrazino-5-sulfamoylpyridine (0.2 g, 1.06 mmol), benzaldehyde (170 mg, 1.6 mmol), and DMF (3 mL) were combined and stirred overnight. The solution was concentrated to a yellow solid, which was triturated with ethyl acetate, filtered, and dried under vacuum to yield 240 mg (82%) of product as a yellow solid. NMR (DMSO-$d_6$): 7.40, m (6H); 7.75, d (2H); 8.02, dd (1H); 8.16, s (1H); 8.47, d (1H); 11.85, b (exchange). Mass Spec (EI) m/z=277.1 (M+H).

Step B: Preparation of N-((6-((1-aza-2-phenylvinyl)amino)(3-pyridyl))sulfonyl)-3-(1-((N-(2-phenylethyl)carbamoyl)methyl)-5-(phenylmethoxy)indol-3-yl)prop-2-enamide N-Methyl-N-phenethyl-2-[5-benzyloxy-3-(2-carboxyvinyl)indol-1-yl]acetamide (70 mg, 0.15 mmol), sodium 2-[[[5-[[(2,5-dioxo1-pyrolidinyl)oxy]carbonyl]-2-pyridinyl]hydrazono]methyl]-benzenesulfonate (43 mg, 0.155 mmol), ethyldimethylaminopropyl carbodiimide (EDC) (30.7 mg, 0.16 mmol). And 4-dimethylaminopyridine (25 mg, 0.021 mmol) were added to dry DMF (3 mL) in a dry flask under nitrogen with stirring. Additional EDC (31 mg, 0.16 mmol) was added after 24 hours. After an additional 16 hr of stirring, water (15 mL) was added, and the mixture extracted with ethyl acetate. The combined organics were washed with 0.1N HCl, sat. NaHCO3, and brine. The solution was dried (MgSO$_4$), filtered, and concentrated to a yellow oil, which was purified by flash chromatography (ethyl acetate/hexane) to afford 21 mg of product. NMR(CDCl$_3$+D$_2$O): 2.88, m (2H); 2.94, d (3H); 3.58, m (2H); 4.27, s, (1H); 4.82, d (2H); 4.86, d (2H); 6.01, dd (1H); 6.67, dd (1H); 6.91, s (1H); 6.94, s (1H); 7.17, m (5H); 7.34, m (10H); 7.63, m (3H); 7.78, s (1H); 8.23, d (1H); 8.74, s, (1H). HRMS (FAB): Calc. For $C_{41}H_{39}N_6O_5S$—727.270266; Found—727.271253.

Example 18

Synthesis of (2-sulfonato-(2-aza-2-((5-carbamoyl(2-pyridyl)amino)vinyl)benzene)ethyl 3-((7-(3-(6-ethyl-4-(4-fluorophenyl)-3-hydroxyphenoxy)propoxy)-8-propylchroman-2-yl)carbonylamino)propanoate

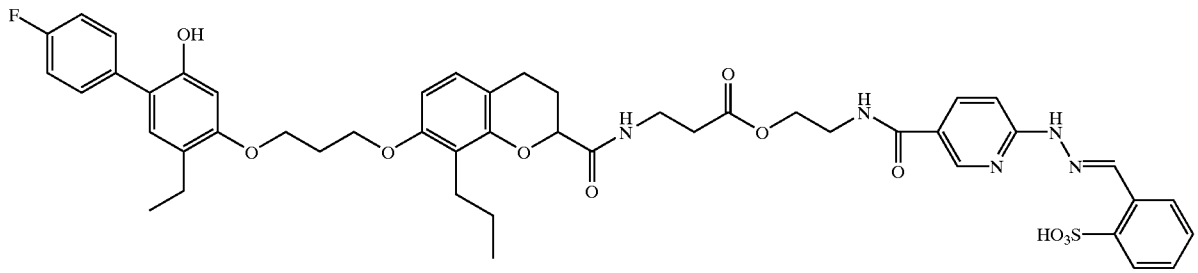

Step A: Preparation of 2-[N-(t-butoxycarbonyl)ethyl]3-carbobenzyloxyaminopropionate N-(t-butoxycarbonyl)-2-hydroxyethylamine (2.2 g, 13.7 mmol), N-benzyloxycarbonyl-β-alanine (3.05 g, 13.7 mmol), and 4-dimethylaminopyridine (0.84 g, 6.85 mmol) were dissolved in dry DMF (45 mL) under nitrogen and cooled to −5° C. Ethyl dimethylaminopropyl carbodiimide (2.9 g, 15.1 mmol) was added and the reaction allowed to warm to room temperature. It was stirred 18 hours, and diluted with water (300 mL). The mixture was extracted with ethyl acetate and the combined organics were washed with 10% citric acid, brine, dried (MgSO$_4$), filtered, and concentrated under vacuum. The resulting oil was purified by flash chromatography (hexane/ethyl acetate) to afford 3.7 g (74%) of product as a clear oil. NMR (CDCl$_3$): 1.42, s (9H); 2.54, t (2H); 3.35, m (2H); 3.46, m (2H); 4.12, t (2H); 4.85, b (1H); 5.08, s (2H); 5.40, b (1H); 7.33, s (5H). Mass spec (EI): m/z=384.3 (M+NH$_4$)

Step B: Preparation of 2-[N-t-butoxycarbonylaminoethyl]-3-aminopropionate acetate salt 2-[N-(t-butoxycarbonyl)ethyl]3-carbobenzyloxyaminopropionate (3.7 g, 10.1 mmol) was dissolved in ethanol (50 mL) with one equivalent of acetic acid and 10% palladium on carbon (500 mg). Hydrogen gas was bubbled into the slurry for four hours, the mixture filtered on Celite®, rinsed with ethanol, and concentrated under reduced pressure. The oil was taken up in toluene (50 mL) and reconcentrated to afford 2.4 g of a clear oil. NMR (CDCl$_3$): 1.42, s (9H); 1.95, s (3H); 2.63, t (2H); 3.09, t (2H); 3.37, m (2H); 4.14, dd (2H); 5.38, b (1H); 6.32, s (3H). Mass spec (EI): m/z=233.0 (M+H).

Step C: Preparation of 2-((tert-butoxy)carbonylamino)ethyl-3-((7-(3-(2-ethyl-4-(4-fluorophenyl)-5-(phenylmethoxy)phenoxy)propoxy)-8-propylchroman-2-yl)carbonylamino)propanoate

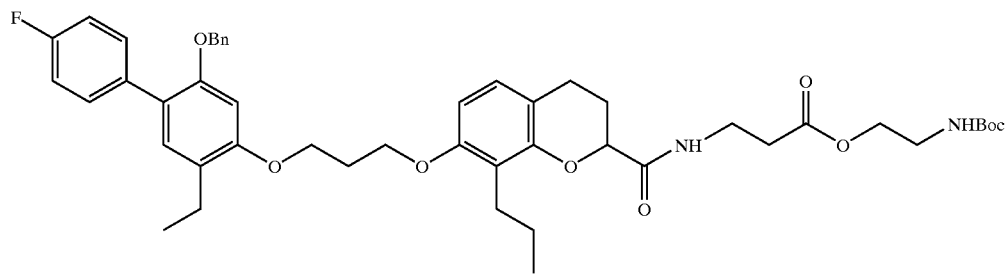

7-(3-(2-ethyl-4-(4-flurophenyl)-5-(phenylmethoxy)phenoxy)propoxy)-8-propylchromane-2-carboxylic acid (200 mg, 0.33 mmol), 2-[N-t-butoxycarbonylaminoethyl]-3-aminopropionate acetate salt (122 mg, 0.42 mmol), hydroxybenzotriazole (76.6 mg, 0.50 mmol), HBTU (190 mg, 0.50 mmol), and diisopropylethylamine (1.32 mmol, 233 μL) were added to dry DMF (1.7 mL) and stirred under nitrogen for 24 hours. An additional 50% of HOBT, HBTU, and diisopropylethylamine were added and the reaction stirred another 24 hours. The mixture was added to water (7 mL) and extracted with ethyl acetate. The combined organics were washed with 0.1N HCl, bicarbonate, and brine, dried over MgSO$_4$, filtered, and concentrated under vacuum. The resulting oil was purified by flash chromatography (hexane/ethyl acetate) to afford 120 mg of product. Mass Spec (EI) m/z=830.6 (M+NH$_4$)

Step D: Preparation of 2-((tert-butoxy)carbonylamino)ethyl-3-((7-(3-(6-ethyl-4-(4-fluorophenyl)-3-hydroxyphenoxy)propoxy)-8-propylchroman-2-yl)carbonylamino)propanoate

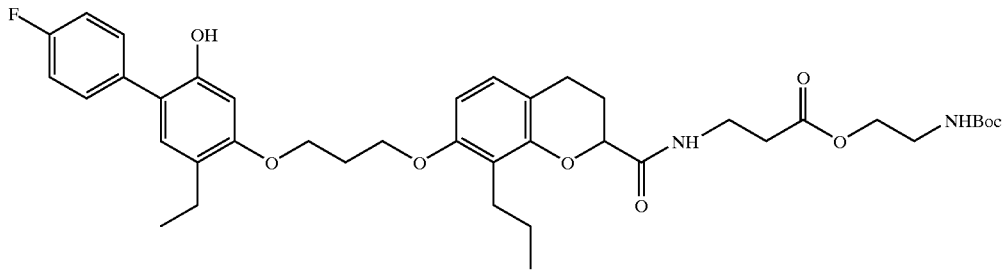

2-((tert-butoxy)carbonylamino)ethyl-3-((7-(3-(2-ethyl-4-(4-fluorophenyl)-5-(phenylmethoxy)phenoxy)propoxy)-8-propylchroman-2-yl)carbonylamino)propanoate (110 mg) was dissolved in methanol/chloroform (2:1, 5 mL) with 10% Pd/C (24 mg) and hydrogen gas bubbled in for 2 hours. The mixture was filtered through Celite®, rinsed with methanol, and concentrated under vacuum to afford 80 mg of 2-((tert-butoxy)carbonylamino)ethyl-3-((7-(3-(6-ethyl-4-(4-fluorophenyl)-3-hydroxyphenoxy)propoxy)-8-propylchroman-2-yl)carbonylamino)propanoate. Mass Spec (EI): 723.5 (M+H).

Step E: Preparation of 2-aminoethyl-3-((7-(3-(6-ethyl-4-(4-fluorophenyl)-3-hydroxyphenoxy)propoxy)-8-propylchroman-2-yl)carbonylamino)propanoate 2-((tert-butoxy)carbonylamino)ethyl-3-((7-(3-(6-ethyl-4-(4-fluorophenyl)-3-hydroxyphenoxy)propoxy)-8-propylchroman-2-yl)carbonylamino)propanoate (55.4 mg, 0.07 mmol) was added to dichloromethane (4 mL), followed by anisole (30 mg, 0.28 mmol) and trifluoroacetic acid (4 mL). The solution was stirred for 2 hours, concentrated under reduced pressure, and purified on a short silica column (chloroform/methanol) to afford 48 mg of product. NMR (CDCl$_3$): 0.90, t (3H); 1.14, t (3H), 1.50, m (2H); 1.62, m (2H); 1.87, m (2H); 2.27, m(3H); 2.54, q (2H); 2.58, m (4H); 3.42, b (2H); 4.14, m (6H); 4.44, b (1H); 6.47, d (1H); 6.57, s (1H); 6.80, m (2H); 6.95, s (1H); 7.10, dd (2H); 7.40, dd (2H); 8.81, b (3H). Mass Spec (EI): m/z=623.4 (M+H).

Step F: Preparation of propyl 3-((7-(3-(6-ethyl-4-(4-fluorophenyl)-3-hydroxyphenoxy)propoxy)-8-propylchroman-2-yl)carbonylamino)propanoate, 2-(2-aza-2-((5-carbamoyl(2-pyridyl)amino)vinyl)benzenesulfonic acid 2-aminoethyl-3-((7-(3-(6-ethyl-4-(4-fluorophenyl)-3-hydroxyphenoxy)propoxy)-8-propylchroman-2-yl)carbonylamino)propanoate (43 mg, 0.072 mmol), Sodium 2-[[[5-[[(2,5-dioxo-1-pyrolidinyl)oxy]carbonyl]-2-pyridinyl]hydrazono]methyl]-benzenesulfonate (32 mg, 0.08 mmol), and diisopropyethylamine (23.4 mg, 0.18 mmol) were added to dry DMF (0.3 mL) and stirred 18 hr. The solution was diluted with water and acetonitrile and purified by direct injection onto a Vydac C18 using acetonitrile/water/0.01% trifluoroacetic acid gradient. The collected fractions were lyophilized to afford 20 mg of product. NMR (DMSO-d6): 0.82, t (3H); 1.14, t (3H), 1.42, m (2H); 1.80, m (1H); 2.18, m (3H); 2.50, m (6H); 3.42, t (2H); 4.09, m (6H); 4.42, d (1H); 6.51, d (1H); 6.55, s (1H); 6.80, d (1H); 6.98, s (1H); 7.16, m (4H); 7.41, t (2H); 7.51, dd (2H); 7.72, t (1H); 7.79 d (1H); 8.21, b (2H); 8.50, s (1H); 8.72, b (1H); 9.35, d (2H). LRMS (EI): m/z=926.5 (M+H). HRMS (FAB): Calc. For $C_{48}H_{53}N_5O_{11}FS$: 926.344633; Found: 926.346995

Example 19

Synthesis of 3-((7-(-(6-ethyl-4-(4-fluorophenyl)-3-hydroxyphenoxy)propoxy)-8-propylchroman-2-yl)carbonylamino)propyl-2-methylpropanoate, 2-(2-aza-2((5-carbamoyl(2-pyridyl)amino)vinyl)benzenesulfonic acid

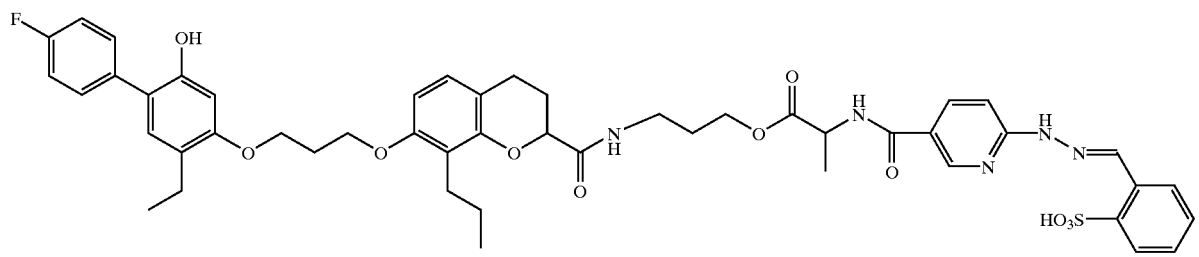

Step A: Preparation of 3-(N-tert-butoxycarbonylaminopropyl)-2-(N-carbobenzyoxyamino)propionate The procedure used in example Example 18, Part A was followed, using N-carbobenzyloxyalanine and 3-(N-tert-butoxycarbonyl)-aminopropanol to afford 1.8 g of 3-(N-tert-butoxycarbonylaminopropyl)-2-(N-carbobenzyoxyamino)propionate after flash chromatography (ethyl acetate/hexane). NMR (CDCl$_3$): 1.40, d (3H); 1.43, s (9H); 1.80, t (2H); 3.15, m (2H); 4.14, t (2H); 4.35, m (1H); 4.68, b (1H); 5.09, s (2H); 5.38, b (1H); 7.33, s (5H). Mass spec (EI): m/z=381.2 (M+H)

Step B: Preparation of 3-aminopropyl-2-(N-carbobenzyloxy) aminopropionate trifluoroacetate

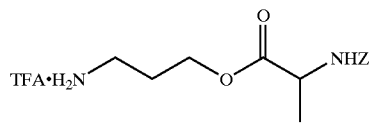

3-(N-tert-butoxycarbonylaminopropyl)-2-(N-carbobenzyoxyamino)propionate (510 mg) was dissolved in dichloromethane (10 mL) and trifluoroacetic acid (10 mL) added. The solution was stirred for 2.5 hours and concentrated under reduced pressure to a clear oil. NMR (CDCl3): 1.37, d (3H); 2.04, m (2H); 3.12, m (2H); 4.24, m (3H); 5.06, dd (2H); 5.44, b (1H); 7.32, m (5H); 12.67, s (3H). Mass Spec (EI): m/z=281.0 (M+H).

Step C: Preparation of 3-((7-(3-(2-ethyl-4-(4-fluorophenyl)-5-(phenylmethyloxy)phenoxy)propoxy)-8-propylchroman-2-yl)carbonylamino)propyl 2-((phenylmethoxy)carbonylamino)propanoate

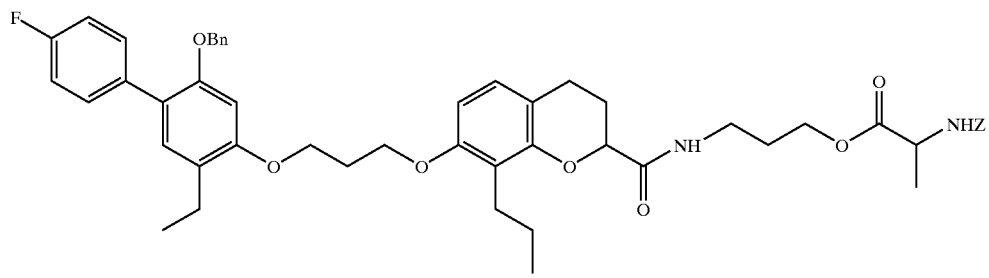

This was carried out in identical fashion to Example 18, Part C, using 3-aminopropyl-2-(N-carbobenzyloxy) aminopropionate, to afford 125 mg of product. Mass Spec (EI) m/z=861.5 (M+H)

Step D: Preparation of 3-((7-(3-(6-ethyl-4-(4-fluorophenyl)-3-hydroxyphenoxy)propoxy)-8-propylchroman-2-yl) carbonylamino)propyl 2-aminopropanoate 3-((7-(3-(2-ethyl-4-(4-fluorophenyl)-5-(phenyl-methyloxy)phenoxy)propoxy)-8-propylchroman-2-yl) carbonylamino)propyl 2-((phenylmethoxy)carbonylamino) propanoate (125 mg) is dissolved in methanol/chloroform (2:1, 7 mL) with 50 mg 10% Pd/C catalyst. Hydrogen gas is bubbled in for 3 hours, when the mixture is filtered through Celite® and concentrated to yield 88 mg of product as a white crunchy foam. Mass Spec (EI) m/z=637.5 (M+H)

Step E: Preparation of 3-((7-(-(6-ethyl-4-(4-fluorophenyl)-3-hydroxyphenoxy)propoxy)-8-propylchroman-2-yl) carbonylamino)propyl-2-methylpropanoate, 2-(2-aza-2((5-carbamoyl(2-pyridyl)amino)vinyl)benzenesulfonic acid This procedure was carried out with 3-((7-(3-(6-ethyl-4-(4-fluorophenyl)-3-hydroxyphenoxy)propoxy)-8-propylchroman-2-yl)carbonylamino)propyl 2-aminopropanoate as in Example 18, Part F to afford 41 mg of product after lyophilization. NMR (DMSO-$d_6$): 0.82, t (3H); 1.07, t (3H), 1.42, m (5H); 1.76, m (3H); 2.18, m (3H); 2.70, m (6H); 3.25, m (2H); 4.09, m (6H); 4.43, m (2H); 6.53, d (1H); 6.55, s (1H); 6.82, d (1H); 6.99, s (1H); 7.16, m (3H); 7.51, m (4H); 7.78, t (1H); 7.80 d (1H); 8.21, b (2H); 8.31, b (1H); 8.53, s (1H); 9.05, b (1H); 9.35, d (2H). Mass Spec (EI): m/z=940.4 (M+H).

Example 20

Synthesis of N-(3-((7-(3-(6-ethyl-4-(4-fluorophenyl)-3-hydroxyphenoxy)propoxy)-8-propylchroman-2-yl)carbonylamino)propyl)-2-methylpropanamide, 2-(2-aza-2-((5-carbamoyl(2-pyridyl))amino)vinyl)benzenesulfonic acid

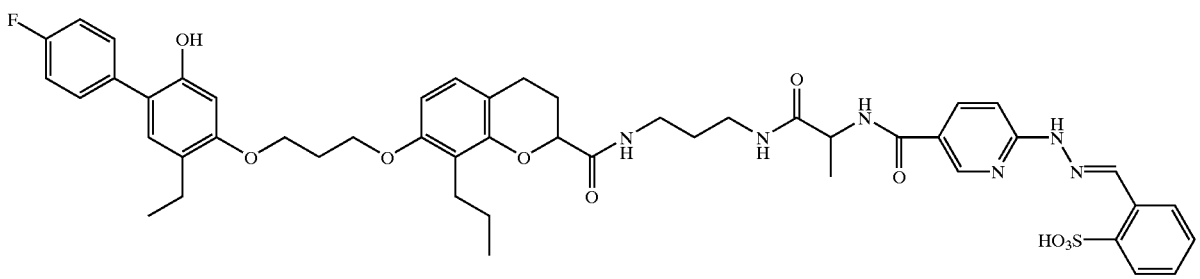

Step A: Preparation of N-(3-((tert-butoxy)carbonylamino)propyl)-2-((phenylmethoxy)carbonylamino)-2-methylpropanamide

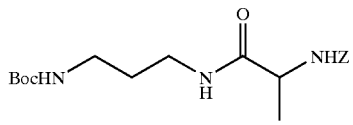

N-carbobenzyloxyalanine (1.3 g, 5.7 mmol), 3-(N-tertbutoxycarbonylamino)-1,3-propanediamine (1 g, 5.7 mmol), hydroxybenzotriazole (0.88 g, 5.8 mmol), HBTU (2.4 g, 0.63 mmol), and diisopropylethylamine (1.48 g, 11.5 mmol) were added to dry DMF (25 mL) under nitrogen and stirred 16 hours, when the reaction was poured into water (100 mL) and extracted with ethyl acetate. The combined organics were washed with 0.1N HCl and saturated bicarbonate, dried over magnesium sulfate, filtered, and concentrated under reduced pressure. The reaction mixture was not further purified but carried directly into the next step. Mass Spec (EI): m/z=380.3 (M+H)

Step B: Preparation of N-(3-aminopropyl)-2-((phenylmethoxy)carbonylamino)-2-methylpropanamide trifluoroacetate salt This procedure was carried out as in Example 19, Part B, using N-(3-((tert-butoxy)carbonylamino)propyl)-2-((phenylmethoxy)carbonylamino)-2-methylpropanamide (2 g) to yield 1.4 g N-(3-aminopropyl)-2-((phenylmethoxy)carbonylamino)-2-methylpropanamide trifluoroacetate salt. Mass Spec (EI): m/z=280.1 (M+H)

Step C: Preparation of N-(3-((7-(3-(2-ethyl-4-(4-fluorophenyl)-5-(phenylmethoxy)phenoxy)propoxy)-8-propylchroman-2-yl)carbonylamino)propyl)-2-((phenylmethoxy)carbonylamino)-2-methylpropanamide This procedure was carried out as in Example 18, Part C, using N-(3-aminopropyl)-2-((phenylmethoxy)carbonylamino)-2-methylpropanamide trifluoroacetate salt (82 mg, 0.3 mmol) to yield 165 mg of product, which was not purified but carried forward directly. Mass Spec (EI): m/z=860.5 (M+H)

Step D: Preparation of 2-amino-N-(3-((7-(3-(6-ethyl-4-(4-fluorophenyl)-3-hydroxyphenoxy)propoxy)-8-propylchroman-2-yl)carbonylamino)propyl)-2-methylpropanamide This step was carried out as in Example 19, Part D, using N-(3-((7-(3-(2-ethyl-4-(4-fluorophenyl)-5-(phenylmethoxy)phenoxy)propoxy)-8-propylchroman-2-yl)carbonylamino)propyl)-2-((phenylmethoxy)carbonylamino)-2-methylpropanamide (160 mg) to yield 100 mg of product, which was not purified but carried forward directly. Mass Spec (EI): m/z=636.3 (M+H)

Step E: Preparation of N-(3-((7-(3-(6-ethyl-4-(4-fluorophenyl)-3-hydroxyphenoxy)propoxy)-8-propylchroman-2-yl)carbonylamino)propyl)-2-methylpropanamide, 2-(2-aza-2-((5-carbamoyl(2-pyridyl))amino)vinyl)benzenesulfonic acid This procedure was carried out as in Example 18, Part F, using 2-amino-N-(3-((7-(3-(6-ethyl-4-(4-fluorophenyl)-3-hydroxyphenoxy)propoxy)-8-propylchroman-2-yl)carbonylamino)propyl)-2-methylpropanamide (100 mg) to afford 74 mg of product after lyophilization. NMR (DMSO-d6): 0.81, t (3H); 1.07, t (3H), 1.33, d (2H); 1.42, m (2H); 1.55, t (2H); 1.80, m (1H); 2.18, m (3H); 2.70, m (6H); 3.09, m (3H); 4.09, m (4H); 4.40, m (2H); 6.53, d (1H); 6.54, s (1H); 6.83, d (1H); 6.99, s (1H); 7.16, m (3H); 7.51, m (4H); 7.80 m (2H); 8.04, t (1H); 8.25, d (1H); 8.40, b (1H); 8.54, s (1H); 9.35, b (2H). Mass Spec (EI): m/z 956.4 (M+NH₄)

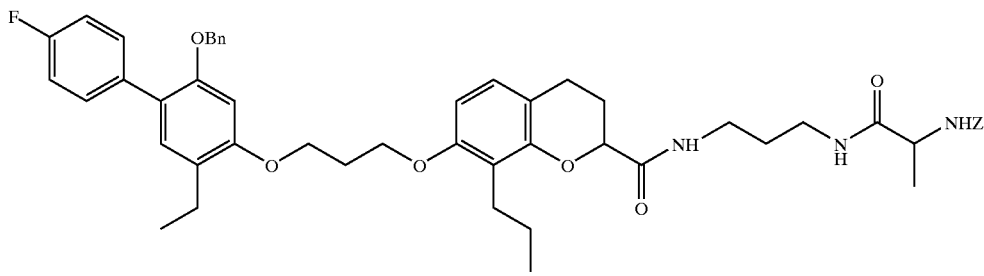

Example 21

Synthesis of 2-(2-aza-2-((5-(N-(6-(6-ethyl-3-hydroxy-4-(1-methylpyrazol-5-yl)phenoxy)-2,2-dimethylhexyl)carbamoyl)(2-pyridyl))amino)vinyl) benzenesulfonic acid

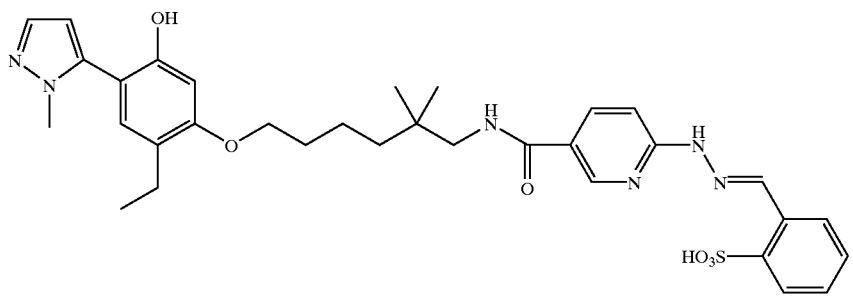

Step A: Preparation of 4-Ethyl-2-(1-methyl-1H-pyrazol-3-yl)-5-[[5,5-dimethyl-6-aminohexyl]oxy]phenol and 4-Ethyl-2-(1-methyl-1H-pyrazol-5-yl)-5-[[5,5-dimethyl-6-aminohexyl]oxy]phenol

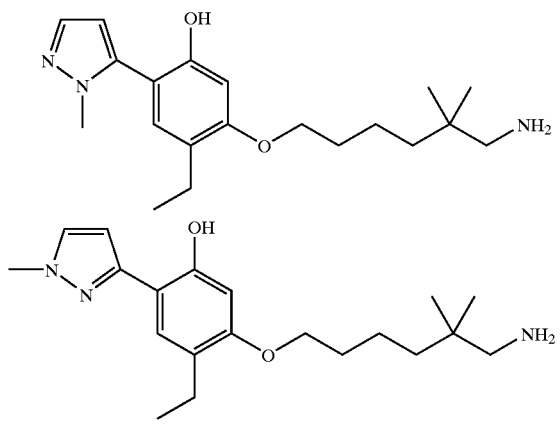

A mixture of 4-ethyl-2(1-methyl-1H-pyrazol-5-yl)-5-[[5-methyl-5-cyanohexyl]oxy]phenol and 4-ethyl-2(1-methyl-1H-pyrazol-3-yl)-5-[[5-methyl-5-cyanohexyl]oxy]phenol (350 mg, 1.05 mmol) was added to methanol (20 mL) containing platinum oxide (120 mg, 0.53 mmol) in a Parr bottle. Four equivalents of conc. Hydrochloric acid were then added and the mixture hydrogenated at 55 psi for 18 hours. The slurry was filtered on Celite®, rinsed with methanol, and concentrated under reduced pressure to afford 318 mg of an off-white solid. Analysis by HPLC showed two peaks, in a ratio of 4:1, consisting of the two isomeric products. These were not separated, but carried directly into the next reaction.

Step B: Preparation of 2-(2-aza-2-((5-(N-(6-(6-ethyl-3-hydroxy-4-(1-methylpyrazol-5-yl)phenoxy)-22-dimethylhexyl)carbamoyl)(2-pyridyl))amino)vinyl) benzenesulfonic acid The mixture obtained in Step A (318 mg, 0.92 mmol) was reacted in the same manner as described in Example 18, Part F. HPLC purification (acetonitrile/water/0.1% trifluoroacetic acid, Vydac C18) afforded two clean products. The earlier eluting product (66 mg after lyophilization) was identified as the 1-methyl-5-pyrazolyl compound by NMR. NMR (DMSO-d6): 0.88, s (6H); 1.09, t (3H), 1.33, m (2H); 1.49, m (2H); 1.73, m (2H); 2.47, m (2H); 3.16, s (2H); 3.64, s (3H); 3.95, t (2H); 6.14, s (1H); 6.53, s (1H); 6.89, s (1H); 7.19, d (1H); 7.38, s (1H); 7.46, m (2H); 7.80 d (1H); 8.30, d (1H); 8.39, d (1H); 8.47, s (1H); 8.53, m (1H); 9.34, s (1H); 9.65, b (1H). LRMS(EI): m/z=647.3 (M−H). HRMS(FAB): Calc. For $C_{33}H_{41}N_6O_6S$—649.2808; Found—649.2834.

Example 22

Synthesis of 2-(2-aza-2-((5-(N-(6-(6-ethyl-3-hydroxy-4-(1-methylpyrazol-5-yl)phenoxy)-2,2-dimethylhexyl)carbamoyl)(2-pyridyl))amino)vinyl) benzenesulfonic acid

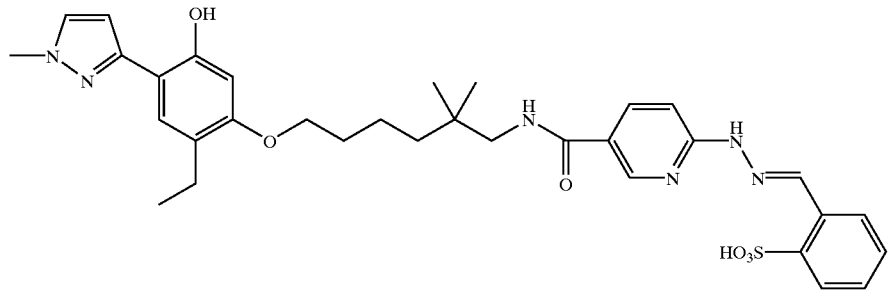

The 1-methyl-3-pyrazolyl isomer was isolated as the second eluting peak in Example 21, Part B (8 mg). NMR (DMSO-d6): 0.88, s (6H); 1.09, t (3H), 1.33, m (2H); 1.49, m (2H); 1.73, m (2H); 2.47, m (2H); 3.15, bs (2H); 3.83, s (3H); 3.95, t (2H); 6.14, s (1H); 6.44, s (1H); 6.68, s (1H); 7.17, d (1H); 7.38, s (1H); 7.46, m (2H); 7.75 m (1H); 8.30, d (1H); 8.39, d (1H); 8.53, m (2H); 9.34, s (1H); 9.65, b (1H). LRMS (EI): m/z=649.3 (M+H); HRMS(FAB): Calc. For $C_{33}H_{41}N_6O_6S$—649.2808; Found—649.2831

Example 23

Synthesis of 2-(2-aza-2-((5-((3-((6-ethyl-4-(4-fluorophenyl)-3-hydroxyphenoxy)methyl)piperidyl)carbonyl)(2-pyridyl))amino)vinyl)benzenesulfonic acid

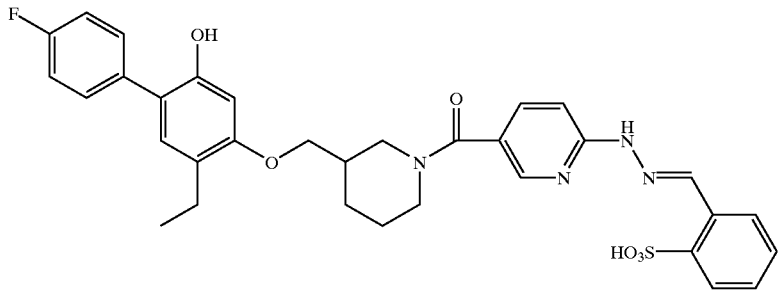

Step A: Preparation of 2-mesyloxy-4-benzyloxyacetophenone

4-Benzyloxy-2-hydroxyacetophenone (25 g, 0.1 mol) and diisopropylethylamine (17.3 g, 0.134 mol) were dissolved in chloroform (200 mL). Methanesulfonyl chloride (14.2 g, 0.124 mol) was added slowly and the reaction stirred for 24 hours. The chloroform was poured into water (150 mL), the layers seperated, and the organic layer washed with 0.1N NaOH, water, 0.1N HCl, water, dried over magnesium sulfate, filtered and concentrated to a crude brown solid. Flash chromatography (hexane:ethyl acetate) afforded 15.1 g of product as an orange solid. NMR (CDC13): 2.57, s (3H); 3.23, s, (dH); 5.11, s (2H); 6.94, dd (1H); 7.01, d (1H); 7.40, m (5H); 7.77, d (1H). Mass Spec (GCMS): 320 (M).

Step B: Preparation of 2-mesyloxy-4-benzyloxyethylbenzene 2-mesyloxy-4-benzyloxyacetophenone (15 g, 47 mmol) is dissolved in carbon tetrachloride (40 mL). To this stirring solution under nitrogen is added trifluoroacetic acid (45 mL) and triethylsilane (45 mL) and the reaction stirred 24 hours. The volatiles are removed under reduced pressure and the residue redissolved in dichloromethane, washed with 0.1N NaOH, dried over sodium sulfate, filtered and concentrated to afford an orange oil which solidified to afford 10.8 g (75%) of a light orange solid. NMR (CDC13): 1.21, t, (3H); 2.66, q (2H); 3.14, s (3H); 5.04, s (2H); 6.88, dd (1H); 6.95, d (1H); 7.19, d (1H); 7.38, m (5H). Mass Spec (GCMS): 306 (M).

Step C: Preparation of 2-mesyloxy-4-benzyloxy-5-bromoethylbenzene 2-mesyloxy-4-benzyloxyethylbenzene (10.3 g, 33.7 mmol) is dissolved in carbon tetrachloride (25 mL) with stirring. N-bromosuccinimide (6.6 g, 37 mmol) is added and the reaction stirred 18 hours under nitrogen. The slurry is diluted with dichloromethane (100 mL) and washed with water, dried over magnesium sulfate, filtered and concentrated. The crude solids are recrystallized from hexane to afford 6 g of 2-mesyloxy-4-benzyloxy-5-bromoethylbenzene as an off-white solid. NMR (CDC13): 1.20, t, (3H); 2.60, q (2H); 3.09, s (3H); 5.13, s (2H); 6.93, s (1H); 7.38, m (6H). Mass Spec (GCMS): 384 (M).

Step D: Preparation of 5-(4-fluorophenyl)-4-benzyloxy-2-mesyloxyethylbenzene

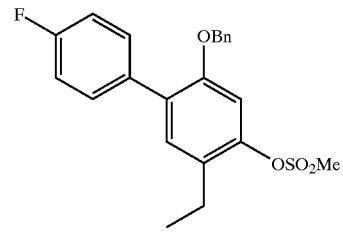

4-Fluorophenylboronic acid (2.18 g, 15.6 mmol) is slurried in ethanol (13 mL). To this is added the 2-mesyloxy-4-benzyloxy-5-bromoethylbenzene dissolved in toluene (40 mL), followed by palladium tetrakistriphenylphosphine (150 mg) and a solution of sodium carbonate (0.2M, 12 mL). The mixture is heated to reflux under nitrogen and the temperature maintained for 24 hours. The mixture is cooled and diluted with ethyl acetate. The organic layer is separated and washed with saturated ammonium chloride, dried over magnesium sulfate, filtered, and concentrated under reduced pressure to afford a light orange solid, which was recrystallized from hexane to afford 5-(4-fluorophenyl)-4-benzyloxy-2-mesyloxyethylbenzene (2.5 g) as an off-white solid. NMR (DMSO-d6): 1.17, t, (3H); 2.66, q (2H); 3.48, s (3H); 5.14, s (2H); 7.38, m (8H); 7.59, dd (2H); 7.83, dd (1H). Mass Spec (GCMS): 400 (M).

Step E: Preparation of 5-(4-fluorophenyl)-4-benzyloxy-2-hydroxyethylbenzene

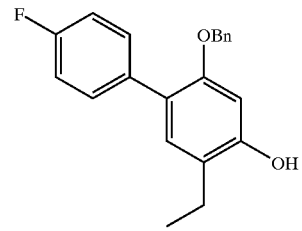

5-(4-fluorophenyl)-4-benzyloxy-2-mesyloxyethylbenzene (2.5 g, 6.24 mmol) was dissolved in methanol (80 mL). To this was added sodium hydroxide (300 mg, 7.5 mmol) dissolved in water (20 mL). The solution was heated to reflux and heating maintained for 24 hours, when an additional equivalent of sodium hydroxide was added, and reflux maintained for an additional 16 hours. The mixture was cooled, acidified with 1N HCl, and extracted with ethyl acetate. The organic layers were dried over magnesium sulfate, filtered, and concentrated under reduced pressure to afford an orange solid which was triturated with hexane to yield 5-(4-fluorophenyl)-4-benzyloxy-2-hydroxyethylbenzene (1.4 g) as an off-white powder. NMR (DMSO-d6): 1.11, t, (3H); 2.50, q (2H); 3.34, s (3H); 5.02, s (2H); 6.60, d (1H); 6.98, s (1H); 7.16, t (2H); 7.35, m (5H); 7.50, dd (2H); 9.44, s (1H). Mass Spec (GCMS): 322 (M).

Step F: Preparation of 3-(methanesulfonyloxymethyl)-N-(tertbutoxycarbonyl)-piperidine 3-Hydroxymethyl-N-(tert-butoxycarbonyl)-piperidine (4.3 g, 20 mmol) was dissolved in dichloroethane (50 mL) with Proton Sponge® (6.08 g, 28.3 mmol). Triflic anhydride (4.94 g, 28.4 mmol) was dissolved in dichloroethane (50 mL) and added dropwise to this solution. The reaction was stirred for 3 days, quenched with water (100 mL), the layers separated, and the combined organics washed with 1N HCl, water, bicarbonate, water, and brine. The solution was dried over sodium sulfate, filtered, and concentrated under reduced pressure to afford 3-(methanesulfonyloxymethyl)-N-(tertbutoxycarbonyl)-piperidine (6 g) as a yellow oil. NMR (CDC13): 1.39, m (1H); 1.42, s (9H); 1.65, m (2H); 1.85, m (2H); 2.77, m (1H); 2.89, t (1H); 2.99, s (3H); 3.81, m (1H); 3.92, m (1H); 4.06, m (2H). Mass Spec (EI): 316.10 (M+Na).

Step G: Preparation of tert-butyl 3-((2-ethyl-4-(4-fluorophenyl)-5-(phenylmethoxy)phenoxy)methyl)piperidinecarboxylate

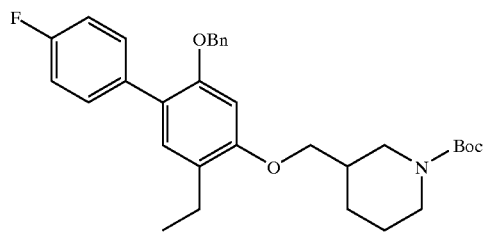

3-(Methanesulfonyloxymethyl)-N-(tertbutoxycarbonyl)-piperidine (143 mg, 0.49 mmol) and 5-(4-fluorophenyl)-4-benzyloxy-2-hydroxyethylbenzene (150 mg, 0.47 mmol) were added to methyl ethyl ketone (7 mL) followed by potassium carbonate (113 mg, 0.82 mmol), potassium iodide (15.5 mg, 93 μmol), and dimethylsulfoxide (4 mL). The slurry was heated at reflux for 40 hours, when it was cooled, diluted with water (50 mL) and extracted with ethyl acetate. The combined organic layers were dried over magnesium sulfate, filtered, and concentrated under reduced pressure to a clear oil which was not purified but used as is in the following step. Mass Spec (EI): 537.4 (M+NH$_4$)

Step H: Preparation of 5-(4-fluorophenyl)-4-benzyloxy-2-[(3-piperidinyl)methoxy]ethylbenzene The crude product of tert-butyl 3-((2-ethyl-4-(4-fluorophenyl)-5-(phenylmethoxy)phenoxy)methyl)piperidinecarboxylate (125 mg) was dissolved in ethanol (5 mL) containing 10% Pd/C catalyst (55 mg). The slurry was hydrogenated at balloon pressure for 28 hours, filtered through Celite®, and concentrated under reduced pressure to afford 80 mg of an oil. This was dissolved in dichloromethane (5 mL) and trifluoroacetic acid (5 mL) added. The solution was stirred 3 hours, and concentrated under reduced pressure to afford 85 mg of 5-(4-fluorophenyl)-4-benzyloxy-2-[(3-piperidinyl)methoxy]ethylbenzene as an oil. Mass spec. (EI): 330.2 (M+H)

Step I: Preparation of 2-(2-aza-2-((5-((3-((6-ethyl-4-(4-fluorophenyl)-3-hydroxyphenoxy)methyl)piperidyl)carbonyl)(2-pyridyl))amino)vinyl)benzenesulfonic acid The crude 5-(4-fluorophenyl)-4-benzyloxy-2-[(3-piperidinyl)methoxy]ethylbenzene (60 mg, ~70% pure) was reacted according to the procedure in Example 18, Part F and purified by preparative HPLC (acetonitrile/water/0.1% trifluoroacetic acid gradient). The product fractions were combined and lyophilized to afford 20 mg of a yellow powder. NMR (DMSO-d6): 0.86, b (2H); 1.08, m (3H); 1.43, m (2H); 1.72, m (1H); 1.85, m (1H); 2.06, m (1H); 2.21, m (1H); 2.45, m (2H); 3.06, m (1H); 3.88, m (2H); 6.42, m (1H); 6.93, m (1H); 7.15, m (4H); 7.45, m (5H); 7.78, s (1H); 7.79, d (1H); 7.97, d (1H); 8.13, s (1H); 8.24, m (1H); 9.19, s (1H). LRMS(EI): 631.1 (M–H). HRMS (FAB): Calc. For $C_{33}H_{34}FN_4O_6S$ (M+H)—633.2183; Found—633.2160

Example 24

Synthesis of 2-(((4-(N-(6-(4,6-Diphenyl(2-pyridyloxy))-2,2-dimethylhexyl)carbamoyl)phenyl)methyl)(2-sulfanylethyl)amino)-N-(2-sulfanylethyl)ethanamide

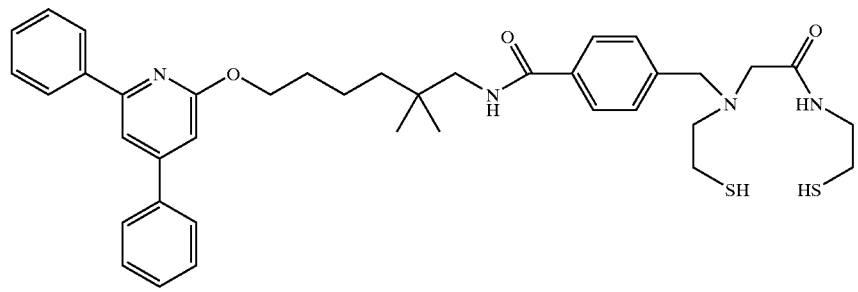

Part A: Preparation of 2-(((4-(N-(6-(4,6-Diphenyl(2-pyridyloxy))-2,2-dimethylhexyl)carbamoyl)phenyl)methyl)(2-triphenylmethylthio)ethyl)amino)-N-(2-triphenylmethylthio)ethyl)ethanamide A solution of 6-[(4,6-diphenyl(2-pyridinyl)oxy]-2,2-dimethyl-1-hexylamine (37.6 mg, 0.077 mmol), N-[4-(carboxy)benzyl]-N,N'-bis[(2-triphenylmethylthio)ethyl]-glycinamide N-hydroxysuccinimide ester (70.0 mg, 0.077 mmol), and TEA (32 ul, 0.23 mmol) in DMF (1.0 mL) was stirred at ambient temperature for 18 h. The reaction solution was used directly for HPLC purification on a Vydac C-18 column (22×250 mm) using a 3.6%/min gradient of 72 to 90% ACN containing 0.1% TFA followed by isocratic elution at 90% ACN containing 0.1% TFA at a flow rate of 15 mL/min to give the title compound as a colorless solid (27 mg, 19%). $^1$H NMR (CDCl$_3$): 8.11–8.03 (m, 2H), 7.70–7.12 (m, 43H), 6.88 (s, 1H), 5.96–5.85 (m, 1H), 4.53–4.43 (m, 2H), 3.44 (s, 2H), 3.33–3.25 (m, 2H), 3.08–2.96 (m, 2H), 2.86 (s, 2H), 2.48–2.24 (m, 6H), 1.90–1.73 (m, 2H), 1.61–1.22 (m, 4H), 0.91 (s, 6H); $^{13}$C NMR (CDCl$_3$): δ170.23, 167.27, 164.34, 155.16, 151.97, 144.68, 144.63, 140.97, 139.24, 138.81, 134.25, 129.50, 129.06, 128.94, 128.84, 128.59, 127.92, 127.04, 126.80, 126.72, 111.69, 107.12, 66.86, 66.65, 65.80, 58.17, 57.61, 53.31, 49.54, 39.86, 37.74, 34.63, 32.05, 29.96, 29.76, 29.68, 24.94, 20.66; MS: m/e 1191.8 [M+Na]; High Resolution MS: Calcd for C$_{77}$H$_{76}$N$_4$O$_3$S$_2$: 1169.5437, Found: 1169.5448.

Part B: Preparation of 2-(((4-(N-(6-(4,6-Diphenyl(2-pyridyloxy))-2,2-dimethylhexyl)carbamoyl)phenyl)methyl)(2-sulfanylethyl)amino)-N-(2-sulfanylethyl)ethanamide 2-(((4-(N-(6-(4,6-Diphenyl(2-pyridyloxy))-2,2-dimethylhexyl)carbamoyl)phenyl)methyl)(2-triphenylmethylthio)ethyl)amino)-N-(2-triphenylmethylthio)ethyl)ethanamide (64 mg, 0.092 mmol) was dissolved in TFA (4 mL) along with triethylsilane (57 μL) and stirred under nitrogen atmosphere for 2 h at ambient temperatures. The precipitate of triphenylmethane was removed by filtration and the filtrate was concentrated. The crude product was purified by HPLC on a Vydac C-18 column (22×250 mm) using a 2.1%/min gradient of 27 to 90% ACN containing 0.1% TFA at a flow rate of 15 mL/min to give the title compound as a colorless oil (18 mg, 28%). MS: m/e 685.4 [M+H].

Example 25

Synthesis of 2-(2-Aza-2-((5-(N-(3-(2-(2-(3-(5-(4-(5-(4,6-diphenyl(2-pyridyloxy))-1,1-dimethylpentyl)(1,2,3,5-tetraazolyl))pentanoylamino)propoxy)ethoxy)ethoxy)propyl)carbamoyl)(2-pyridyl))amino)vinyl)benzenesulfonic Acid

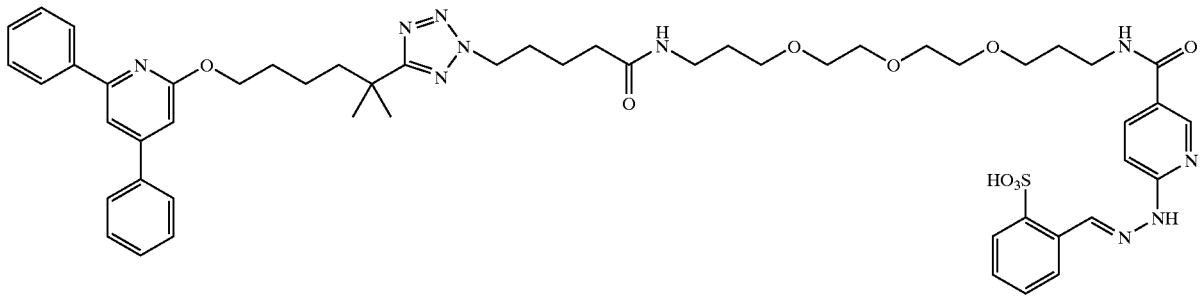

Part A: Preparation of Ethyl 5-(5-(5-(4,6-Diphenyl(2-pyridyloxy))-1,1-dimethylpentyl)-1,2,3,4-tetraazolyl)pentanoate and Ethyl 5-(4-(5-(4,6-Diphenyl(2-pyridyloxy))-1,1-dimethylpentyl)-1,2,3,5-tetraazolyl)pentanoate

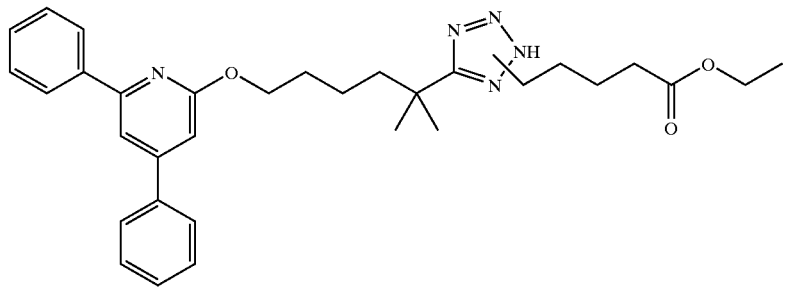

A solution of 6-(5-(2H-2,3,4,5-tetraazolyl)-5-methylhexyloxy)-2,4-diphenylpyridine (880 mg, 2.13 mmol), ethyl 5-bromovalerate (1.35 mL, 8.51 mmol), and TEA (1.31 mL, 9.36 mmol) in ACN (50 mL) was heated to reflux under nitrogen for 3 h. The solution was concentrated and the residue was partitioned between EtOAc (150 mL) and water (50 mL). The EtOAc layer was washed with 0.1 N HCl (50 mL), dried (MgSO$_4$), and concentrated to an amber oil. Flash chromatography on silica gel (25% EtOAc/hexanes) gave N2 isomer ethyl 5-(4-(5-(4,6-diphenyl(2- pyridyloxy))-1,1-dimethylpentyl)-1,2,3,5-tetraazolyl)pentanoate as a colorless oil (925 mg, 80.2%). $^1$H NMR (CDCl$_3$): 8.10–8.01 (m, 2H), 7.69–7.61 (m, 2H), 7.55–7.35 (m, 7H), 6.86 (s, 1H), 4.54 (t, J=7.1 Hz, 2H), 4.42 (t, J=6.6 Hz, 2H), 4.09 (q, J=7.1 Hz, 2H), 2.31 (t, J=7.3 Hz, 2H), 2.09–1.95 (m, 2H), 1.90–1.70 (m, 4H), 1.70–1.56 (m, 2H), 1.45–1.28 (m, 8H), 1.21 (t, J=7.1 Hz, 3H); $^{13}$C NMR (CDCl$_3$): 173.50, 172.81, 164.32, 155.12, 151.97, 139.18, 138.82, 128.94, 128.84, 128.57, 127.03, 126.81, 111.66, 107.10, 65.83, 60.40, 52.32, 42.40, 34.77, 33.32, 29.59, 28.63, 27.21, 21.74, 21.31, 14.18; MS: m/e 542.4 [M+H]; High Resolution MS: Calcd for C$_{32}$H$_{40}$N$_5$O$_3$ [M+H]: 542.3131, Found: 542.3143; CHN Calcd: C, 70.95; H, 7.26; N, 12.93; Found: C, 71.02; H, 6.89; N, 13.04.

After eluting the above compound from the flash column the eluting solvent was changed to 40% EtOAc/hexanes to give N1 isomer ethyl 5-(5-(5-(4,6-diphenyl(2-pyridyloxy))-1,1-dimethylpentyl)-1,2,3,4-tetraazolyl)pentanoate as a colorless oil (113 mg, 9.8%). $^1$H NMR (CDCl$_3$): 8.10–8.01 (m, 2H), 7.69–7.62 (m, 2H), 7.55–7.36 (m, 7H), 6.85 (s, 1H), 4.43 (t, J=6.3 Hz, 2H), 4.34 (t, J=7.5 Hz, 2H), 4.09 (q, J=7.1 Hz, 2H), 2.32 (t, J=7.2 Hz, 2H), 2.07–1.92 (m, 2H), 1.91–1.60 (m, 8H), 1.50 (s, 6H), 1.21 (t, J=7.1 Hz, 3H); MS: m/e 542.4 [M+H]; High Resolution MS: Calcd for C$_{32}$H$_{40}$N$_5$O$_3$ [M+H]: 542.3131, Found: 542.3140.

Part B: Preparation of 5-(4-(5-(4,6-Diphenyl(2-pyridyloxy))-1,1-dimethylpentyl)-1,2,3,5-tetraazolyl)pentanoic Acid

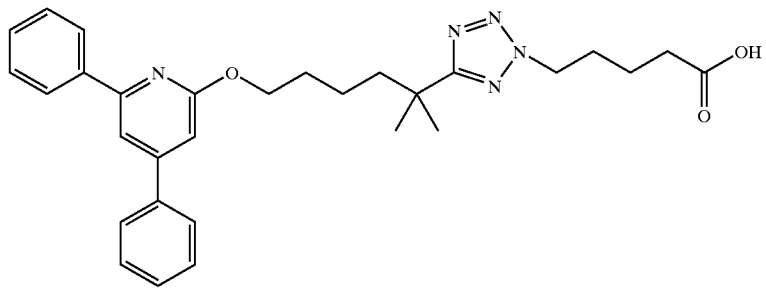

A mixture of ethyl 5-(4-(5-(4,6-diphenyl(2-pyridyloxy))-1,1-dimethylpentyl)-1,2,3,5-tetraazolyl)pentanoate (464 mg, 0.858 mmol), 3 M LiOH (3.0 mL), and THF (25 mL) was stirred at ambient temperatures for 45 h. The mixture was concentrated to a volume of 5 mL and partitioned between ether (25 mL) and water (75 mL). The layers were separated and the aqueous layer was acidified to pH=4.0 with 1 N HCl. The aqueous layer was extracted with EtOAc (3×25 mL). The combined organic extracts were dried (MgSO$_4$) and concentrated to give the title compound as a colorless oil (418 mg, 94.8%). $^1$H NMR (CDCl$_3$): 8.04 (d, J=6.8 Hz, 2H), 7.65 (d, J=8.4 Hz, 2H), 7.55–7.31 (m, 7H), 6.84 (s, 1H), 4.53 (t, J=6.9 Hz, 2H), 4.40 (t, J=6.6 Hz, 2H), 2.40–2.25 (m, 2H), 2.09–1.94 (m, 2H), 1.86–1.70 (m, 4H), 1.70–1.52 (m, 2H), 1.50–1.25 (m, 8H).

Part C: Preparation of N-(3-(2-(2-(3-Aminopropoxy)ethoxy)ethoxy)propyl)(tert-butoxy)formamide A 1 L 3-neck round bottom flask was fitted with a 500 mL addition funnel with nitrogen line, a thermometer, and a mechanical stirrer. The flask was charged with 4,7,10-trioxa-1,13-tridecanediamine (72.5 g, 0.329 mol), anhydrous THF (250 mL), and anhydrous MeOH (100 mL). The addition funnel was charged with a solution of di-tert-butyl dicarbonate (22.4 g, 0.103 mol) in anhydrous THF (100 mL). The contents of the addition funnel were added to the flask with rapid stirring at ambient temperatures over 30 min, causing a slight rise in temperature from 21° C. to 32° C. The reaction was stirred an additional 3 h at ambient temperatures and the solvents were removed under reduced pressure. The resulting thick syrup was taken up in sat. NaCl (1500 mL) and extracted with ether (5×1000 mL). The combined ether extracts were dried (MgSO$_4$) and concentrated to give a colorless oil (29.8 g). A 5.00 g sample of this oil was purified by flash chromatography on silica gel (DCM:MeOH:TEA, 20:15:0.75) to give the title compound as a colorless oil (4.00 g, 72.2%). 1H NMR (CDCl$_3$): 5.13 (s, 1H), 3.63–3.47 (m, 12H), 3.17 (q, J=6.2 Hz, 2H), 2.75 (t, J=6.7 Hz, 2H), 1.75–1.64 (m, 4H), 1.39 (s, 9H), 1.36 (s, 2H); MS: m/e 321.2 [M+H].

Part D: Preparation of N-(3-(2-(2-(3-((tert-Butoxy)carbonylamino)propoxy)ethoxy)ethoxy)propyl)-5-(4-(5-(4,6-diphenyl(2-pyridyloxy))-1,1-dimethylpentyl)(1,2,3,5-tetraazolyl))pentanamide

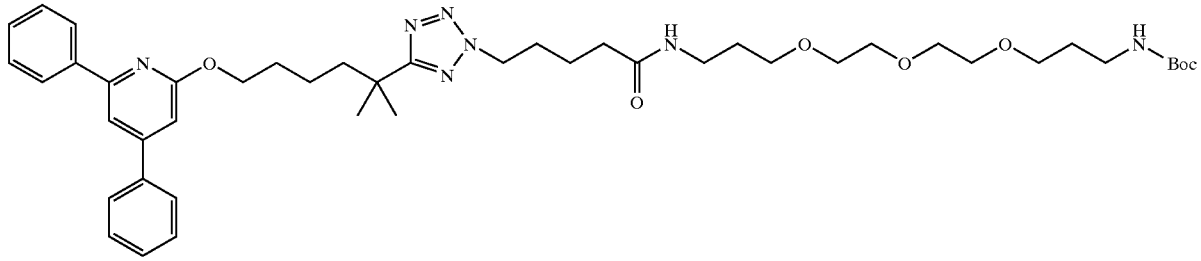

A solution of 5-(4-(5-(4,6-diphenyl(2-pyridyloxy))-1,1-dimethylpentyl)-1,2,3,5-tetraazolyl)pentanoic acid (185 mg (0.360 mmol) and TEA (208 uL, 1.50 mmol) in anhydrous DMF (2.5 mL) was pre-activated by treatment with HBTU (218 mg, 0.576 mmol). After 5 min at ambient temperatures, a solution of N-(3-(2-(2-(3-aminopropoxy)ethoxy)ethoxy)propyl)(tert-butoxy)formamide (180 mg, 0.562 mmol) in DMF (500 uL) was added and the solution was stirred at ambient temperatures for 2 h. The DMF was removed under reduced pressure and the resulting oil was partitioned between EtOAc (20 mL) and 0.1 N HCl (5 mL). The organic phase was washed consecutively with 0.1 N HCl (5 mL) and sat. NaHCO$_3$ (2×5 mL), dried (MgSO$_4$), and concentrated to give an amber oil (177 mg). This oil was purified by flash chromatography on silica gel (hexane:EtOAc:CHCl$_3$) to give the title compound as a pale yellow oil (162 mg, 55%). MS: 816.5 [M+H].

Part E: Preparation of 2-(2-Aza-2-((5-(N-(3-(2-(2-(3-(5-(4-(5-(4,6-diphenyl(2-pyridyloxy))-1,1-dimethylpentyl)(1,2,3,5-tetraazolyl))pentanoylamino) propoxy)ethoxy)ethoxy)propyl)carbamoyl)(2-pyridyl))amino)vinyl)benzenesulfonic Acid N-(3-(2-(2-(3-((tert-Butoxy)carbonylamino)propoxy)ethoxy)ethoxy)propyl)-5-(4-(5-(4,6-diphenyl(2-pyridyloxy))-1,1-dimethylpentyl)(1,2,3,5-tetraazolyl)) pentanamide (60 mg, 0.074 mmol) was dissolved in TFA and stirred at ambient temperatures for 45 min. The TFA was removed under reduced pressure and the resulting thick oil was dissolved in anhydrous DMF (0.70 mL) and the solution was made basic to pH paper with TEA (82 uL, 0.588 mmol). The solution was treated with 2-(2-aza-2-((5-((2,5-dioxopyrrolidinyl)carbonyl)(2-pyridyl))amino)vinyl)benzenesulfonic acid (48.5 mg, 0.110 mmol) and stirred at ambient temperatures for 24 h. The DMF was removed under vacuum, and the resulting oil was dissolved in 80% ACN and purified by preparative HPLC on a Vydac C-18 column (22×250 mm) using a 1.80%/min gradient of 18 to 72% ACN containing 0.05 M NH$_4$Oac at a flow rate of 15 mL/min. The main product peak eluting at 26.3 min was collected and lyophilized to give the title compound as a colorless powder (54.5 mg, 72.8%). MS: 1019.5 [M+H]; High Resolution MS: Calcd for C$_{53}$H$_{67}$N$_{10}$O$_9$S [M+H]: 1019.4813, Found: 1019.4842.

Example 26

Synthesis of 2-(2-Aza-2-((5-(N-(3-(2-(2-(3-(5-(5-(4,6-diphenyl(2-pyridyloxy))-1,1-dimethylpentyl)(1,2,3,4-tetraazolyl))pentanoylamino)propoxy)ethoxy)ethoxy)propyl)carbamoyl)(2-pyridyl))amino)vinyl)benzenesulfonic Acid Part A: Preparation of 5-(5-(5-(4,6-Diphenyl(2-pyridyloxy))-1,1-dimethylpentyl)-1,2,3,4-tetraazolyl) pentanoic Acid

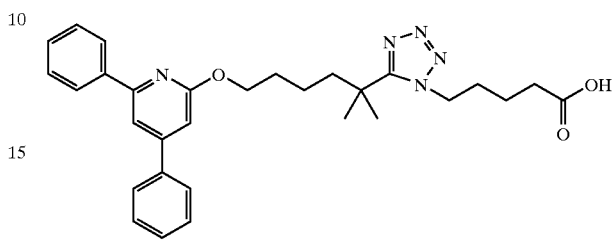

A mixture of ethyl 5-(5-(5-(4,6-diphenyl(2-pyridyloxy))-1,1-dimethylpentyl)-1,2,3,4-tetraazolyl)pentanoate (113 mg, 0.21 mmol), 3 M LiOH (1.0 mL), and THF (6 mL) was stirred at ambient temperatures for 45 h. The mixture was partitioned between EtOAc (50 mL) and water (25 mL). The aqueous layer was acidified to pH=3.0 with 1 N HCl and the layers were separated. The aqueous layer was extracted with EtOAc (25 mL). The combined organic extracts were dried (MgSO$_4$) and concentrated to give the title compound as a colorless oil (106 mg, 98.3%). $^1$H NMR (CDCl$_3$): 8.02 (d, J=8.4 Hz, 2H), 7.65(d, J=8.2 Hz, 2H), 7.55–7.35 (m, 7H), 6.84 (s, 1H), 4.43–4.31 (m, 4H), 2.36 (t, J=7.0 Hz, 2H), 2.10–1.92 (m, 2H), 1.89–1.62 (m, 6H), 1.49 (s, 6H), 1.42–1.20 (m, 2H); MS: m/e 512.5 [M−H]; High Resolution MS: Calcd for C$_{30}$H$_{36}$N$_5$O$_3$ [M+H]: 514.2818, Found: 514.2819.

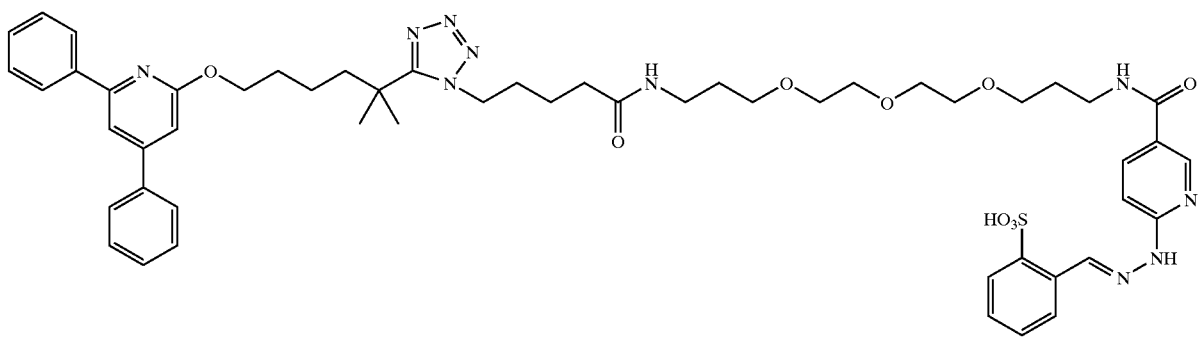

Part B: Preparation of N-(3-(2-(2-(3-((tert-Butoxy)carbonylamino)propoxy)ethoxy)ethoxy)propyl)-5-(5-(5-(4,6-diphenyl(2-pyridyloxy))-1,1-dimethylpentyl)(1,2,3,4-tetraazolyl))pentanamide

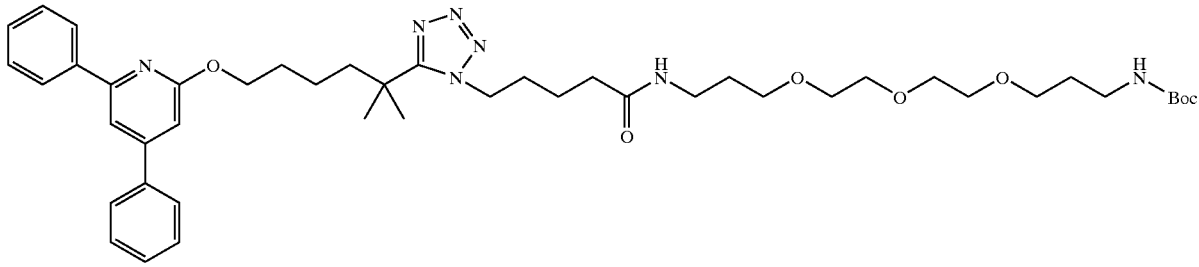

A solution of 5-(5-(5-(4,6-diphenyl(2-pyridyloxy))-1,1-dimethylpentyl)-1,2,3,4-tetraazolyl)pentanoic acid (90 mg, 0.175 mmol) and DIEA (122 uL, 0.70 mmol) in anhydrous DMF (8 mL) was treated with HBTU (73 mg, 0.192 mmol) and stirred at ambient temperatures for 1 min. A solution of N-(3-(2-(2-(3-aminopropoxy)ethoxy)ethoxy)propyl)(tert-butoxy)formamide (63.2 mg, 0.197 mmol) in DMF 4 mL) was added and the solution was stirred for 2.5 h. The DMF was removed by vacuum evaporation and the resulting thick oil was partitioned between EtOAc (50 mL) and water (10 mL). The aqueous layer was adjusted to pH=3 with 1.0 N HCl, the layers were mixed thoroughly and separated. The organic phase was washed with 1N NaOH (2×10 mL) and sat. NaCl (10 mL), dried (MgSO$_4$), and concentrated to give the title compound as a pale amber oil (144 mg, 100%). MS: m/e 816.6 [M+H]; High Resolution MS: Calcd for $C_{45}H_{66}N_7O_7$ [M+H]: 816.5024, Found: 816.5044.

Part C: Preparation of 2-(2-Aza-2-((5-(N-(3-(2-(2-(3-(5-(5-(4,6-diphenyl(2-pyridyloxy))-1,1-dimethylpentyl)(1,2,3,4-tetraazolyl))pentanoylamino)propoxy)ethoxy)ethoxy)propyl)carbamoyl)(2-pyridyl))amino)vinyl)benzenesulfonic Acid N-(3-(2-(2-(3-((tert-Butoxy)carbonylamino)propoxy)ethoxy)ethoxy)propyl)-5-(5-(5-(4,6-diphenyl(2-pyridyloxy))-1,1-dimethylpentyl)(1,2,3,4-tetraazolyl))pentanamide (146 mg, 0.179 mmol) was dissolved in TFA (5 mL) and stirred at ambient temperatures for 45 min. The TFA was removed under vacuum and the thick amber oil was dissolved in anhydrous DMF (3 mL) and made basic to pH paper with TEA (200 uL). The solution was treated with 2-(2-aza-2-((5-((2,5-dioxopyrrolidinyl)carbonyl)(2-pyridyl))amino)vinyl)benzenesulfonic acid (94.6 mg, 0.215 mmol) and stirred at ambient temperatures for 18 h under a nitrogen atmosphere. The reaction solution was concentrated to a volume of 1.0 mL, diluted with ACN (4 mL), and purified by preparative HPLC on a Vydac C-18 column (22×250 mm) using a 1.80%/min gradient of 18 to 72% ACN containing 0.05 M NH$_4$Oac at a flow rate of 15 mL/min. The main product peak eluting at 24.7 min was collected and lyophilized to give the title compound as a colorless powder (131 mg, 71.8%). MS: m/e 1019.5 [M+H]; High Resolution MS: Calcd for $C_{53}H_{67}N_{10}O_9S$ [M+H]: 1019.4813, Found: 1019.4839.

Example 27

Synthesis of 2-(2-Aza-2-((5-(N-(2-(2-(2-(2-(2-(2-(2-(2-(5-(4-(5-(4,6-diphenyl(2-pyridyloxy))-1,1-dimethylpentyl)(1,2,3,5-tetraazolyl))pentanoylamino)ethoxy)ethoxy)ethoxy)ethoxy)ethoxy)ethoxy)ethoxy)ethyl)carbamoyl)(2-pyridyl))amino)vinyl)benzenesulfonic Acid

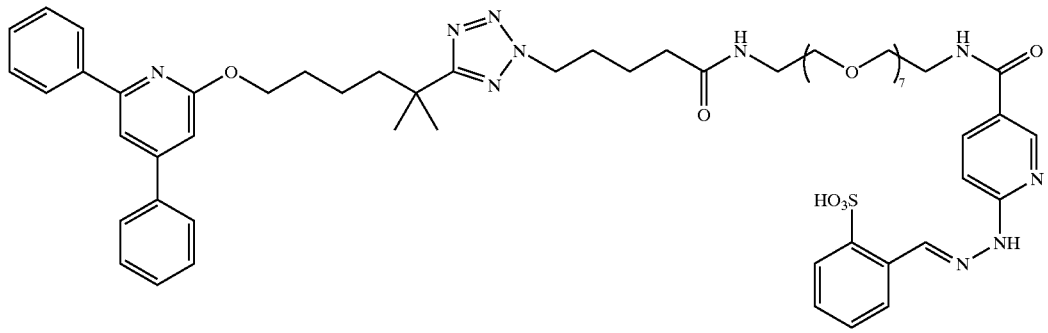

Part A: Preparation of (tert-Butoxy)-N-(2-(2-(2-(2-((4-methylphenyl)sulfonyloxy)ethoxy)ethoxy)ethoxy)ethyl)formamide A solution of N-(2-(2-(2-(2-aminoethoxy)ethoxy)ethoxy)ethyl)(tert-butoxy)formamide (5.87 g, 20 mmol) and TEA (6.12 mL, 44 mmol) in ether was treated with p-toluenesulfonyl chloride (4.00 g, 21 mmol) and stirred at reflux under a nitrogen atmosphere for 24 h, and for another 24 h at ambient temperatures. The solution was concentrated and the oily residue was shaken with sat. NaCl (200 mL) and ether (400 mL), causing a crystalline solid to form in the aqueous layer. The aqueous layer was extracted with a second portion of ether (400 mL). The combined ether extracts were dried (MgSO$_4$), and concentrated to a dark oil. This oil was purified by flash chromatography on silica gel (hexane:EtOAc) to give the title compound as a pale yellow oil (2.85 g, 31.8%). $^1$H NMR (CDCl$_3$): 7.78 (d, J=8.0 Hz, 2H), 7.32 (d, J=8.0 Hz, 2H), 4.18–4.08 (m, 2H), 3.71–3.46 (m, 12H), 3.32–3.22 (m, 2H), 2.43 (s, 3H), 1.42 (s, 9H); MS: m/e 465.4 [M+NH$_4$].

2H), 1.40 (s, 2H), 1.38 (s, 9H); MS: m/e 469.3 [M+H]; High Resolution MS: Calcd for C$_{21}$H$_{45}$N$_2$O$_9$ [M+H]: 469.3126, Found: 469.3125.

Part D: Preparation of N-(2-(2-(2-(2-(2-(2-(2-(2-((tert-Butoxy)carbonylamino)ethoxy)ethoxy)ethoxy)ethoxy)ethoxy)ethoxy)ethoxy)ethyl)-5-(4-(5-(4,6-diphenyl(2-pyridyloxy))-1,1-dimethylpentyl) (1,2,3,5-tetraazolyl))pentanamide

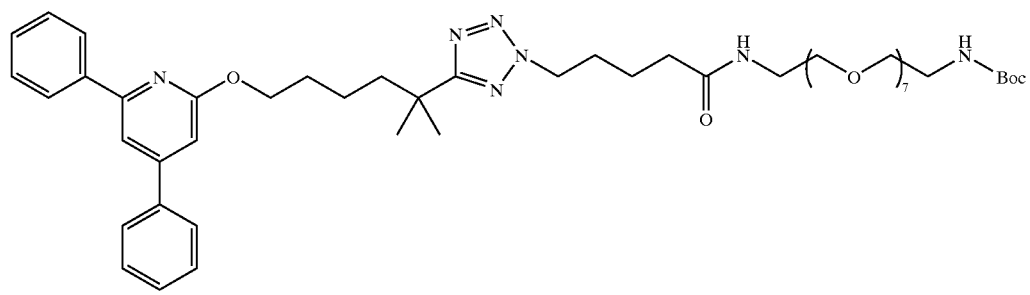

Part B: Preparation of N-(2-(2-(2-(2-(2-(2-(2-(3-Aza-3-diazoprop-3-enyloxy)ethoxy)ethoxy)ethoxy)ethoxy)ethoxy)ethoxy)ethyl)(tert-butoxy)formamide A solution of 2-(2-(2-(3-aza-3-diazoprop-3-enyloxy)ethoxy)ethoxy)ethan-1-ol (0.723 g, 3.30 mmol) in anhydrous THF (20 mL) was treated with NaH (144 mg of 60% dispersion, 3.6 mmol) and stirred at ambient temperatures under a nitrogen atmosphere until gas evolution ceased. A solution of (tert-butoxy)-N-(2-(2-(2-(2-((4-methylphenyl)sulfonyloxy)ethoxy)ethoxy)ethoxy)ethyl)formamide (1.61 g, 3.6 mmol) in anhydrous THF (20 mL) was added and the mixture was stirred 48 hr at ambient temperatures under nitrogen. The THF was removed under vacuum and the residue was triturated with ether (3×50 mL). The combined triturants were concentrated to give an amber oil. This oil was purified by flash chromatography on silica gel (hexane:EtOAc:MeOH, 47.5:47.5:5) to give the title compound as a colorless oil (1.11 g, 68%). $^1$H NMR (CDCl$_3$): 5.00 (s, 1H), 3.67 –3.51 (m, 26H), 3.49 (t, J=5.2 Hz, 2H), 3.34 (t, J=5.1 Hz, 2H) 3.30–3.20 (m, 2H), 1.40 (s, 9H); MS: m/e 512.4 [M+NH$_4$]; High Resolution MS: Calcd for C$_{21}$H$_{43}$N$_4$O$_8$ [M+H]: 495.3030, Found: 495.3047.

Part C: Preparation of N-(2-(2-(2-(2-(2-(2-(2-(2-Aminoethoxy)ethoxy)ethoxy)ethoxy)ethoxy)ethoxy)ethoxy)ethyl)(tert-butoxy)formamide A solution of 5-(4-(5-(4,6-diphenyl(2-pyridyloxy))-1,1-dimethylpentyl)-1,2,3,5-tetraazolyl)pentanoic acid (99 mg, 0.193 mmol) and DIEA (134 uL, 0.772 mmol) in anhydrous DMF (8 mL) was activated by treatment with HBTU (80.5 mg, 0.212 mmol) for 2 min at ambient temperatures. To this solution was added N-(2-(2-(2-(2-(2-(2-(2-(2-aminoethoxy)ethoxy)ethoxy)ethoxy)ethoxy)ethoxy)ethoxy)ethyl)(tert-butoxy)formamide (103 mg, 0.220 mmol) in DMF (4 mL) and the resulting solution was stirred 2 h at ambient temperatures under nitrogen. The DMF was removed under reduced pressure and the thick oil was partitioned between EtOAc (50 mL) and water (10 mL). The aqueous layer was adjusted to pH=2.0 with 0.1 N HCl and the layers were mixed. The organic phase was washed with sat. NaHCO$_3$ (10 mL) and sat. NaCl (10 mL), dried (MgSO$_4$), and concentrated to give the title compound as an amber oil (208 mg, 92.2%). MS: m/e 981.7 [M+NH$_4$]; High Resolution MS: Calcd for C$_{51}$H$_{78}$N$_7$O$_{11}$ [M+H]: 964.5759, Found: 964.5788.

Part E: Preparation of 2-(2-Aza-2-((5-(N-(2-(2-(2-(2-(2-(2-(2-(2-(5-(4-(5-(4,6-diphenyl(2-pyridyloxy))-1,1-

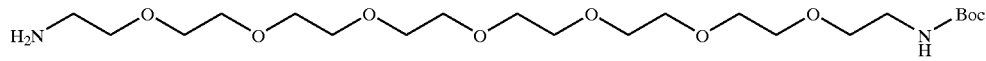

A solution of N-(2-(2-(2-(2-(2-(2-(2-(3-aza-3-diazoprop-3-enyloxy)ethoxy)ethoxy)ethoxy)ethoxy)ethoxy)ethoxy)ethyl)(tert-butoxy)formamide (960 mg, 1.94 mmol) in MeOH (100 mL) was hydrogenated over PtO$_2$ (100 mg) at a pressure of 60 psi for 2 hr at ambient temperatures. The catalyst was removed by filtration through filter aid and the filtrate was concentrated to give the title compound as a pale amber oil (953 mg). $^1$H NMR (CDCl$_3$): 5.06 (s, 1H), 3.67–3.40 (m, 28H), 3.28–3.18 (m, 2H), 2.79 (t, J=5.2 Hz, dimethylpentyl)(1,2,3,5-tetraazolyl))pentanoylamino)ethoxy)ethoxy)ethoxy)ethoxy)ethoxy)ethoxy)ethoxy)ethyl)-carbamoyl)(2-pyridyl))amino)vinyl)benzenesulfonic Acid N-(2-(2-(2-(2-(2-(2-(2-(2-((tert-Butoxy)carbonylamino)ethoxy)ethoxy)ethoxy)ethoxy)ethoxy)ethoxy)ethoxy)ethyl)-5-(4-(5-(4,6-diphenyl(2-pyridyloxy))-1,1-dimethylpentyl)(1,2,3,5-tetraazolyl))pentanamide (170 mg, 0.193 mmol) was dissolved in TFA (5 mL) and stirred at ambient temperatures for 45 min. The TFA was removed under reduced pressure and the resulting thick oil was taken up in anhydrous DMF and made basic to pH paper by the addition of TEA (315 uL, 2.32 mmol). This solution was treated with 2-(2-aza-2-((5-((2,5-dioxopyrrolidinyl)carbonyl)(2-pyridyl))amino)vinyl)-benzenesulfonic acid (102 mg, 0.232 mmol) and stirred at ambient temperatures for 20 h. The DMF was removed under reduced pressure and the thick oil was dissolved in ACN (3 mL) and purified by preparative HPLC on a Vydac C-18 column (22×250 mm) using a 1.80%/min gradient of 18 to 72% ACN containing 0.05 M NH$_4$Oac at a flow rate of 15 mL/min. The main product peak eluting at 27.5 min was collected and lyophilized to give the title compound as a pale yellow powder (151 mg, 67.1%). MS: m/e 1167.8 [M+H]; High Resolution MS: Calcd for $C_{59}H_{79}N_{10}O_{13}S$ [M+H]: 1167.5549, Found: 1167.5577.

Example 28

Synthesis of 2-(2-Aza-2-((5-(N-(5-(4-(5-(4,6-diphenyl(2-pyridyloxy))-1,1-dimethylpentyl)(1,2,3,5-tetraazolyl))pentanoylamino)-1-(6-deoxy-β-cyclodextryl)carbamoyl)pentyl)carbamoyl)(2-pyridyl))amino)vinyl)benzenesulfonic Acid Part A: Preparation of 6-Amino-2-((tert-butoxy)carbonylamino)-N-(6-deoxy-β-cyclodextryl)hexanamide A solution of 6-deoxy-6-amino-β-cyclodextrin (70 mg, 0.062 mmol), Boc-Lys(Z)-Osu (29.5 mg, 0.062 mmol), and TEA (12.6 uL, 0.092 mmol) in anhydrous DMF (3 mL) was stirred under a nitrogen atmosphere at ambient temperatures for 90 min. The solvent was removed under reduced pressure. The slightly green solid was taken up in MeOH (6 mL) and water (0.5 mL), treated with anisole (100 uL), and hydrogenolyzed over 10% Pd/C (50 mg) at 30 psi and ambient temperatures for 18 h. The catalyst was removed by filtration through filter aid and the filtrate was concentrated under vacuum to give the title compound as a slightly green solid (87 mg). MS: 1362.7 [M+H].

Part B: Preparation of 2-((tert-Butoxy)carbonylamino)-6-(5-(4-(5-(4,6-diphenyl(2-pyridyloxy))-1,1-dimethylpentyl)(1,

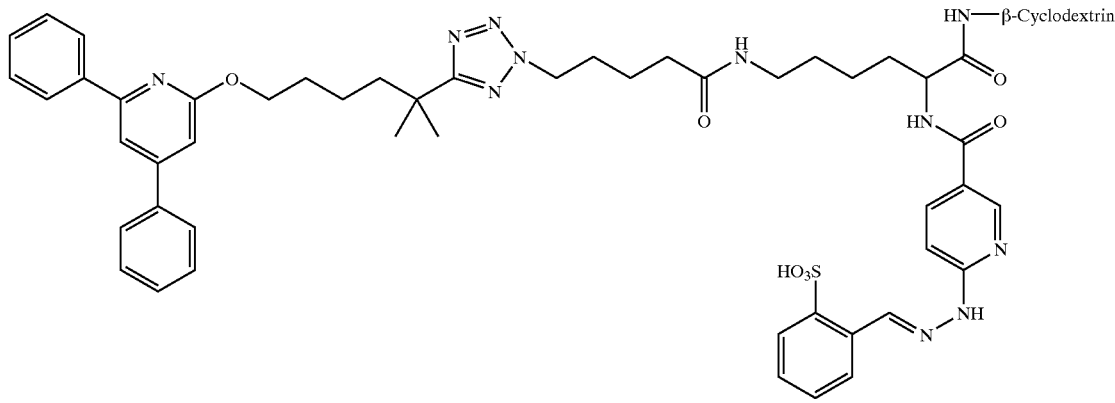

2,3,5-tetraazolyl))pentanoylamino)-N-(6-deoxy-β-cyclodextryl)hexanamide

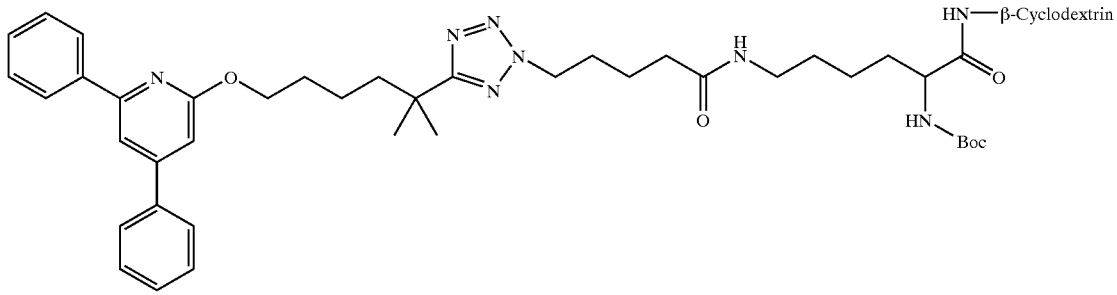

5-(4-(5-(4,6-Diphenyl(2-pyridyloxy))-1,1-dimethylpentyl)-1,2,3,5-tetraazolyl)pentanoic acid (31.6 mg, 0.062 mmol) was dissolved in anhydrous DMF (3 mL) and preactivated by the addition of HBTU (25.6 mg, 0.068 mmol) and DIEA (28 uL, 0.186 mmol). After 5 min a solution of 6-amino-2-((tert-butoxy)carbonylamino)-N-(6-deoxy-β-cyclodextryl)hexanamide (84 mg, 0.062 mmol) and DIEA (28 uL, 0.186 mmol) in DMF (3 mL) was added and the resulting mixture was stirred at ambient temperatures under nitrogen for 18 h. Solvents were removed under reduced pressure and the residue was dissolved in MeOH:water:DMF, 10:2:2 (1.4 mL). This solution was used for preparative HPLC purification on a Vydac C-18 column (22×250 mm) using a 1.80%/min gradient of 18 to 72% ACN at a flow rate of 15 mL/min. The main product peak eluting at 27.3 min was collected and lyophilized to give the title compound as a colorless powder (52 mg, 45.5%). MS: 1857.9 [M+H]; High Resolution MS: Calcd for $C_{83}H_{125}N_8O_{39}$ [M+H]: 1857.8044, Found: 1857.8068.

a colorless powder (30 mg, 52%). MS: 2061.6 [M+H]; High Resolution MS: Calcd for $C_{91}H_{126}N_{11}O_{41}S$ [M+H]: 2060.7833, Found: 2060.7874.

Example 29

Synthesis of 2-(2-Aza-2-((5-(N-(3-(2-(2-(3-(2-(5-(5-(4,6-diphenyl(2-pyridyloxy))-1,1-dimethylpentyl) (1,2,3,4-tetraazolyl))acetylamino)propoxy)ethoxy) ethoxy)propyl)-carbamoyl)(2-pyridyl))amino)vinyl) benzenesulfonic Acid

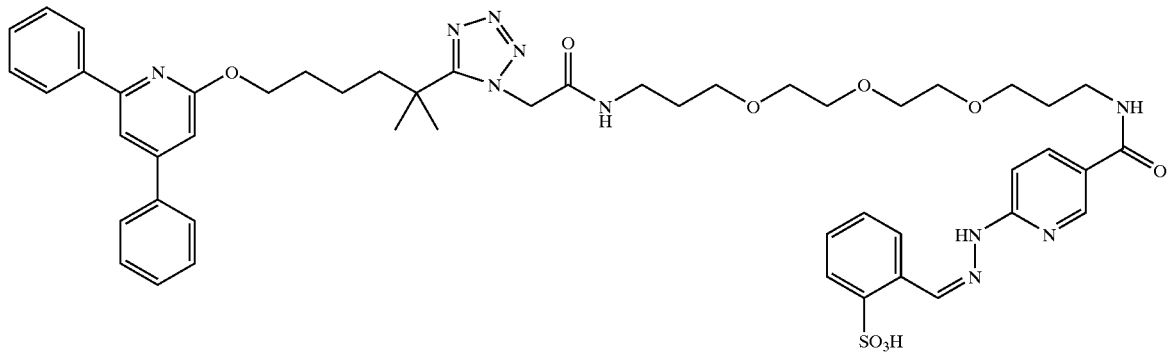

Part C Preparation of 2-(2-Aza-2-((5-(N-(5-(4-(5-(4,6-diphenyl(2-pyridyloxy))-1,1-dimethylpentyl)(1,2,3,5-tetraazolyl))pentanoylamino)-1-(6-deoxy-β-cyclodextryl) carbamoyl)pentyl)carbamoyl)(2-pyridyl))amino)vinyl) benzenesulfonic Acid 2-((tert-Butoxy)carbonylamino)-6-(5-(4-(5-(4,6-diphenyl (2-pyridyloxy))-1,1-dimethylpentyl)(1,2,3,5-tetraazolyl)) pentanoylamino)-N-(6-deoxy-β-cyclodextryl)hexanamide (52 mg, 0.028 mmol) was dissolved in TFA and stirred 45 min at ambient temperatures. The TFA was removed under vacuum, and the residue was dissolved in anhydrous DMF (3 mL) and made basic to pH paper with TEA (58 uL, 0.42 mmol). The solution was treated with active ester 2-(2-aza-2-((5-((2,5-dioxopyrrolidinyl)carbonyl)(2-pyridyl))amino) vinyl)benzenesulfonic acid (14.8 mg, 0.034 mmol) and stirred under a nitrogen atmosphere at ambient temperatures. Additional active ester was added at 72 h (17 mg) and at 96 h (20 mg). After a total reaction time of 8 days the solution was concentrated to give a thick oil. This oil was dissolved in 50% MeOH and purified by preparative HPLC on a Vydac C-18 column (22×250 mm) using a 1.50%/min gradient of 18 to 63% ACN containing 0.05 M NH₄Oac at a flow rate of 15 mL/min. The main product peak eluting at 27.1 min was collected and lyophilized to give the title compound as Part A Preparation of Ethyl 2-(5-(5-(4,6-diphenyl(2-pyridyloxy))-1,1-dimethylpentyl)-1,2,3,4-tetraazolyl)acetate and Ethyl 2-(4-(5-(4,6-diphenyl(2-pyridyloxy))-1,1-dimethylpentyl)-1,2,3,5-tetraazolyl)acetate

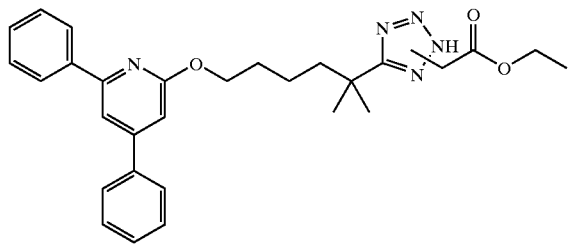

A solution of 6-(5-(2H-2,3,4,5-tetraazolyl)-5-methylhexyloxy)-2,4-diphenylpyridine (827 mg, 2.00 mmol) and bis-tri-n-butyltin oxide (596 mg, 1.00 mmol) in EtOH (50 mL) was stirred at reflux under a nitrogen atmosphere for 20 min and concentrated to a pale yellow oil under reduced pressure. The oil was dissolved in ACN (25 mL), treated with ethyl bromoacetate (333 uL, 3.00 mmol) and heated to reflux under nitrogen for 60 h. The ACN was removed under vacuum and the resulting amber oil was taken up in EtOAc (50 mL). This organic solution was washed consecutively with 0.1 N HCl (10 mL), sat. NaHCO₃ (15 mL), sat. NaCl (15 mL), dried (MgSO₄), and concentrated to give an amber oil (1.662 g). The oil was dissolved in ether (60 mL) and washed with 10% KF (2×30 mL). The precipitate was removed by filtration and the two layers of the filtrate were separated. The organic layer was dried (MgSO₄) and concentrated to give a yellow solid (0.957 g). Flash chromatography on silica gel (20% EtOAc/hexanes) gave N2 isomer ethyl 2-(4-(5-(4,6-diphenyl(2-pyridyloxy))-1,1-dimethylpentyl)-1,2,3,5-tetraazolyl) acetate as a colorless solid (617 mg). Recrystallization from hexanes afforded product as colorless solid (490 mg, 49.1%). MP: 76–79° C.; 1H NMR (CDCl₃): 8.06 (d, J=6.8 Hz, 2H), 7.66 (d, J=8.1 Hz, 2H), 7.58–7.34 (m, 7H), 6.86 (s, 1H), 5.33 (s, 2H), 4.42 (t, J=6.6 Hz, 2H), 4.22 (q, J=7.1 Hz, 2H), 1.90–1.72 (m, 4H), 1.50–1.28 (m, 8H), 1.22 (t, J=7.1 Hz, 3H); MS: m/e 500.3 [M+H]; High Resolution MS: Calcd for C₂₉H₃₄N₅O₃ [M+H]: 500.2662, Found: 500.2668; CHN Calcd: C, 69.72; H, 6.66; N, 14.02; Found: C, 69.43; H, 6.69; N, 13.90.

After eluting the above compound from the flash column the eluting solvent was changed to 30% EtOAc/hexanes to give N1 isomer ethyl 2-(5-(5-(4,6-diphenyl(2-pyridyloxy))-1,1-dimethylpentyl)-1,2,3,4-tetraazolyl)acetate as a pale yellow oil (142 mg, 14.2%). ¹H NMR (CDCl₃): 8.05 (d, J 6.8 Hz, 2H), 7.66 (d, J 6.5 Hz, 2H), 7.60–7.33 (m, 7H), 6.85 (s, 1H), 5.20 (s, 2H), 4.43 (t, J=6.4 Hz, 2H), 4.22 (q, J=7.1 Hz, 2H), 1.89–1.70 (m, 4H), 1.52–1.38 (m, 8H), 1.24 (t, J=7.1 Hz, 3H); MS: m/e 500.3 [M+H]; High Resolution MS: Calcd for C₂₉H₃₄N₅O₃ [M+H]: 500.2662, Found: 500.2653.

Part B Preparation of 2-(5-(5-(4,6-Diphenyl(2-pyridyloxy))-1,1-dimethylpentyl)-1,2,3,4-tetraazolyl)acetic Acid

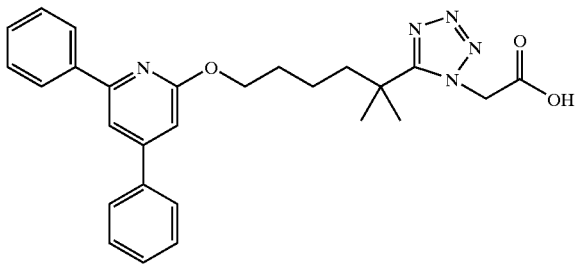

A mixture of ethyl 2-(5-(5-(4,6-diphenyl(2-pyridyloxy))-1,1-dimethylpentyl)-1,2,3,4-tetraazolyl)acetate (97 mg, 0.194 mmol) and 3N LiOH (1.2 mL, 3.6 mmol) in THF (2 mL) was stirred at 50° C. for 23 h under a nitrogen atmosphere. The THF was removed under vacuum and the residue was dissolved in EtOAc (20 mL), washed with dilute HCl (pH=2, 5 mL)) and then with water (5 mL). The organic solution was dried (MgSO₄) and concentrated to give the title compound as a colorless solid. MS: 470.3 [M–H].

Part C Preparation of 2-(2-Aza-2-((5-(N-(3-(2-(2-(3-(2-(5-(5-(4,6-diphenyl(2-pyridyloxy))-1,1-dimethylpentyl)(1,2,3,4-tetraazolyl))acetylamino)propoxy)ethoxy)ethoxy)-propyl)carbamoyl)(2-pyridyl))amino)vinyl)benzenesulfonic Acid A solution of 2-(5-(5-(4,6-diphenyl(2-pyridyloxy))-1,1-dimethylpentyl)-1,2,3,4-tetraazolyl)acetic acid (76 mg, 0.161 mmol), TEA (181 uL, 1.30 mmol), N-(3-(2-(2-(3-aminopropoxy)ethoxy)ethoxy)propyl)(tert-butoxy)formamide (157 mg, 0.488 mmol), and HBTU (195 mg, 0.512 mmol) in anhydrous DMF (3 mL) was stirred at ambient temperatures under nitrogen for 27 h. The solution was concentrated under reduced pressure and the resulting dark amber oil was dissolved in EtOAc (20 mL), washed with 0.1 N HCl (10 mL) and sat. NaCl (2×10 mL), dried (MgSO₄), and concentrated to give the crude linker conjugate as an amber oil (280 mg). The presence of the desired conjugate was confirmed by low resolution mass spectroscopy (MS: 774.4 [M+H]).

The above oil was dissolved in TFA (3 mL) and stirred at ambient temperatures for 45 min. The TFA was removed under vacuum, the resulting oil was dissolved in DMF (1 mL) and made basic to pH paper with TEA (385 uL, 2.76 mmol). The solution was treated with active ester 2-(2-aza-2-((5-((2,5-dioxopyrrolidinyl)carbonyl)(2-pyridyl))-amino)vinyl)benzenesulfonic acid (264 mg, 0.598 mmol) and stirred at ambient temperatures for 48 h. The solution was diluted with 50% ACN (2.5 mL) and purified by preparative HPLC on a Vydac C-18 column (22×250 mm) using a 1.50%/min gradient of 18 to 63% ACN containing 0.05 M NH₄Oac at a flow rate of 15 mL/min. The main product peak eluting at 29.4 min was collected and lyophilized to give the title compound as a pale yellow powder (49 mg, 31.2%). MS: 977.4 [M+H]; High Resolution MS: Calcd for C₅₀H₆₁N₁₀O₉S [M+H]: 977.4344, Found: 977.4333.

Example 30

Synthesis of 2-(2-Aza-2-((5-(N-(3-(2-(2-(3-(2-(4-(5-(4,6-diphenyl(2-pyridyloxy))-1,1-dimethylpentyl)(1,2,3,5-tetraazolyl))acetylamino)propoxy)ethoxy)ethoxy)propyl)-carbamoyl)(2-pyridyl))amino)vinyl)benzenesulfonic Acid

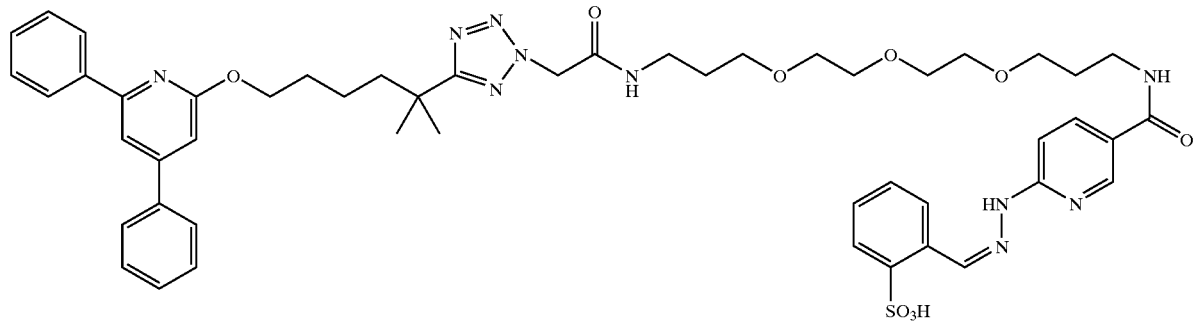

Part A: Preparation of 2-(4-(5-(4,6-Diphenyl(2-pyridyloxy))-1,1-dimethylpentyl)-1,2,3,5-tetraazolyl)acetic Acid

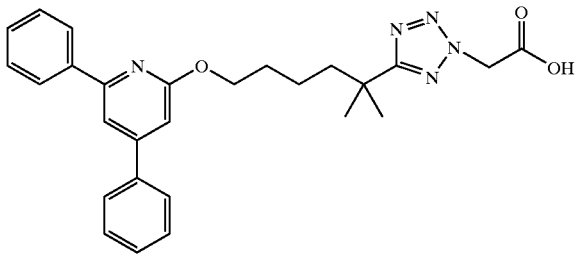

A mixture of ethyl 2-(4-(5-(4,6-diphenyl(2-pyridyloxy))-1,1-dimethylpentyl)-1,2,3,5-tetraazolyl)acetate (370 mg, 0.739 mmol) and 3 N LiOH (3.6 mL, 10.8 mmol) in THF (1 mL) was stirred at 50° C. for 17 h and concentrated to dryness. The residue was partitioned between EtOAc (20 mL) and dilute HCl (pH 2, 5 mL). The organic phase was washed with water (5 mL), dried ($MgSO_4$), and concentrated to give the title compound as a colorless solid (278 mg, 75.1%). MS: 470.3 [M–H].

Part B Preparation of 2-(2-Aza-2-((5-(N-(3-(2-(2-(3-(2-(4-(5-(4,6-diphenyl(2-pyridyloxy))-1,1-dimethylpentyl)(1,2,3,5-tetraazolyl))acetylamino)-propoxy)ethoxy)ethoxy)propyl)carbamoyl)(2-pyridyl))amino)vinyl)benzenesulfonic Acid A solution of 2-(4-(5-(4,6-diphenyl(2-pyridyloxy))-1,1-dimethylpentyl)-1,2,3,5-tetraazolyl)acetic acid (261 mg, 0.553 mmol), TEA (920 uL, 6.60 mmol), HBTU (754 mg, 1.99 mmol), and N-(3-(2-(2-(3-aminopropoxy)-ethoxy)ethoxy)propyl)(tert-butoxy)formamide (398 mg, 1.24 mmol) in anhydrous DMF 1.5 mL) was stirred at ambient temperatures under nitrogen for 21 h. The solution was concentrated under reduced pressure and the resulting dark amber oil was dissolved in EtOAc (20 mL), washed with 0.1 N HCl (10 mL) and sat. $NaHCO_3$ (2×10 mL), dried ($MgSO_4$), and concentrated to give the crude N-(3-(2-(2-(3-((tert-butoxy)carbonylamino)propoxy)ethoxy)ethoxy)propyl)-2-(4-(5-(4,6-diphenyl(2-pyridyloxy))-1,1-dimethylpentyl)(1,2,3,5-tetraazolyl))ethanamide as a pale amber oil (430 mg). The presence of this conjugate was confirmed by low resolution mass spectroscopy (MS: 774.4 [M+H]).

The above oil was dissolved in TFA and stirred at ambient temperatures for 45 min. The TFA was removed under reduced pressure, the resulting oil was dissolved in DMF (2 mL) and made basic to pH paper with TEA (464 uL, 3.34 mmol). The solution was treated with active ester 2-(2-aza-2-((5-(((2,5-dioxopyrrolidinyl)carbonyl)(2-pyridyl))amino)vinyl)benzenesulfonic acid (490 mg, 1.11 mmol) and stirred at ambient temperatures for 93 h. The solution was diluted with 50% ACN (2.5 mL) and purified by preparative HPLC on a Vydac C-18 column (22–250 mm) using a 1.80%/min gradient of 18 to 72% ACN containing 0.05 M $NH_4Oac$ at a flow rate of 15 mL/min. The main product peak eluting at 26.8 min was collected and lyophilized to give the title compound as a pale yellow powder (120 mg, 22.2%). MS: 977.4 [M+H]; High Resolution MS: Calcd for $C_5OH_{61}N_{10}O_9S$ [M+H]: 977.4344, Found: 977.4341.

Example 31

Synthesis of 3-(6-(3-(N-(5-((6-((1-Aza-2-(sulfophenyl)vinyl)amino)(3-pyridyl))carbonylamino)-5-(N-((ω-methoxypolyethylene(750)glycoxyethyl)carbamoyl)pentyl)carbamoyl)propoxy)2-(5-(4,6-diphenyl(2-pyridyloxy))pentyloxy)phenyl)propanoic Acid

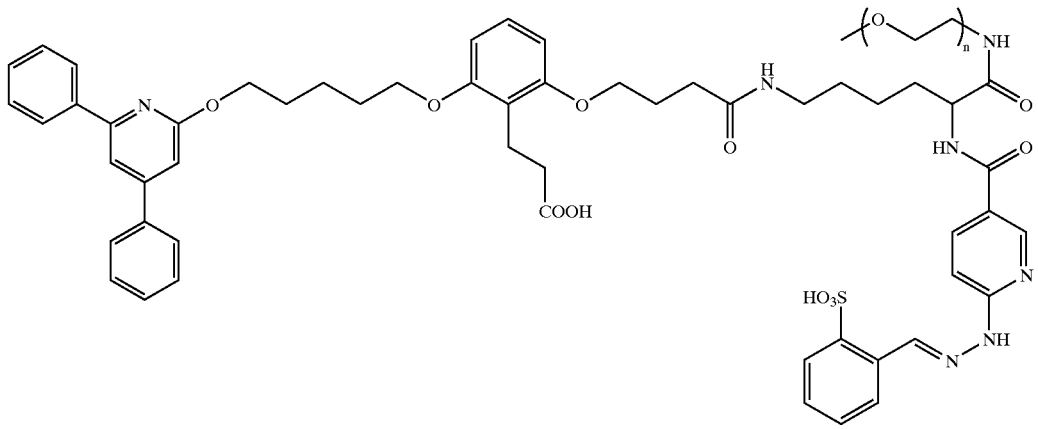

Part A: Preparation of 3-Aza-3-diazo-1-((ω-methoxypolyethylene(750)glycoxy)prop-3-ene A 1000 mL 3-neck flask was equipped with a mechanical stirrer, an addition funnel with nitrogen line, and a thermometer. The flask was charged with (ω-methoxypolyethylene(750)glycoxyethanol (75 g, 0.10 mol), TEA (28 mL, 0.20 mol), anhydrous ether (300 mL), and anhydrous THF (200 mL). The solution was cooled to 5° C. in an ice bath. The addition funnel was charged with methanesulfonyl chloride (11.6 mL, 0.15 mol), ether (250 mL), and THF (250 mL). The contents of the addition funnel were added to the flask dropwise with stirring while maintaining the flask contents at 5–10° C. When addition was complete, the ice bath was removed and stirring was continued at ambient temperatures for 1 h. The mixture was filtered to remove TEA.HCl salt and the filtrate was concentrated to give a pale yellow oil. This oil was triturated with hexanes (6×100 mL) and dried under vacuum to give the mesylate as a pale yellow oil (86.8 g).

The mesylate was dissolved in anhydrous EtOH (600 mL) and treated with sodium azide (6.8 g, 0.104 mmol). The mixture was heated at reflux under nitrogen for 24 h, at which time additional sodium azide (2.0 g) was added, and heating was continued another 24 h. The EtOH was removed under vacuum giving a mixture of oil and solid. The oil was dissolved in ether (500 mL) and filtered, and the filtrate was concentrated to give the title compound as a pale yellow oil (74.6 g, 96%). $^{13}$C NMR (CDCl$_3$): 58.8 (O—CH$_2$CH$_2$NH$_2$), 50.5 (CH$_2$—N$_3$); IR (neat/KBr cm$^{-1}$): 2100 (s).

Part B: Preparation of 2-(ω-Methoxypolyethylene(750)glycoxy)ethylamine

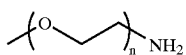

3-Aza-3-diazo-1-((ω-methoxypolyethylene(750)glycoxy)prop-3-ene (14.0 g, 18.0 mmol) in MeOH (200 mL) was hydrogenated over PtO$_2$ (1.0 g) at 60 psi and ambient temperatures for 15 h. Catalyst was removed by filtration through filter aid and the filtrate was concentrated to give the title compound as a pale yellow oil (11.3 g, 83.3%). $^{13}$C NMR (CDCl$_3$): 58.8 (O—CH$_2$CH$_2$NH$_2$), 41.4 (CH$_2$—NH$_2$); IR (neat/KBr cm$^{-1}$): 3350 (s); MS: 516.4 (n=11), 560.4 (n=12), 604.4 (n=13), 648.4 (n=14), 692.4 (n=15), 736.5 (n=16), 780.5 (n=17), 824.5 (n=18) [M+H].

Part C: Preparation of 2-((tert-Butoxy)carbonylamino)-N-(ω-methoxypolyethylene(750)glycoxyethyl)-6-((phenylmethoxy)carbonylamino)hexanamide

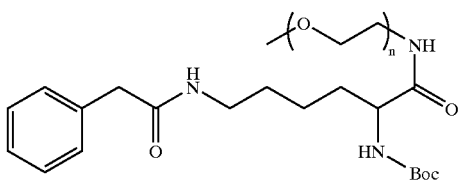

A solution of 2-(ω-methoxypolyethylene(750)glycoxy)ethylamine (11.2 g, 14.9 mmol), Boc-Lys(Z)-Osu (6.2 g, 0.13.0 mmol), and TEA (2.7 mL, 0.19.5 mmol) in anhydrous THF (500 mL) was stirred at ambient temperatures for 24 h. The solution was diluted with 70:30 ether CHCl$_3$ (1200 mL) and washed with sat. NaCl (500 mL). The NaCl wash was back extracted with 70:30 ether CHCl$_3$ (500 mL). The combined organic extracts were dried (MgSO$_4$) and concentrated to give a colorless oil (15.1 g). A 2.0 g sample of this oil was purified by flash chromatography on silica gel (CHCl$_3$:MeOH) to give the title compound as a colorless oil (1.30 g, 65%). MS: 939.5 (n=12), 983.7 (n=13), 1027.7 (n=14), 1071.8 (n=15), 1115.7 (n=16), 1159.7 (n=17), 1203.8 (n=18) [M+NH$_4$]; High Resolution MS: Calcd for C$_{50}$H$_{92}$N$_3$O$_{20}$ (n=15) [M+H]: 1054.6274, Found: 1054.6224; Calcd for C$_{52}$H$_{96}$N$_3$O$_{21}$ (n=16) [M+H]: 1098.6536, Found: 1098.6476.

Part D: Preparation of 6-Amino-2-((tert-butoxy)carbonylamino)-N-(ω-methoxypolyethylene(750)glycoxyethyl)hexanamide

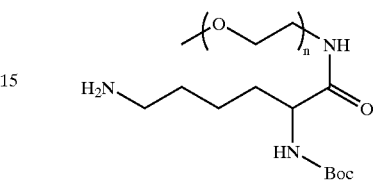

2-((tert-Butoxy)carbonylamino)-N-(ω-methoxypolyethylene-(750)glycoxyethyl)-6-((phenylmethoxy)carbonylamino)hexanamide (1.00 g, 0.86 mmol) in MeOH (20 mL) was hydrogenolyzed over 10% Pd/C (200 mg) at 1 atm and ambient temperatures for 4 h. The catalyst was removed by filtration through filter aid and the filtrate was concentrated to give the title compound as a colorless oil (0.79 g, 89%). MS: 832.6 (n=13), 876.7 (n=14), 920.8 (n=15), 964.8 (n=16), 1008.7 (n=17), 1052.6 (n=18), 1096.8 (n=19) [M+H].

Part E; Preparation of Methyl 3-(6-(3-(N-(5-((tert-Butoxy)carbonylamino)-5-(N-(ω-methoxypolyethylene(750)glycoxyethyl)carbamoyl)pentyl)carbamoyl)propoxy)2-(5-(4,6-diphenyl(2-pyridyloxy))pentyloxy)phenyl)propanoate

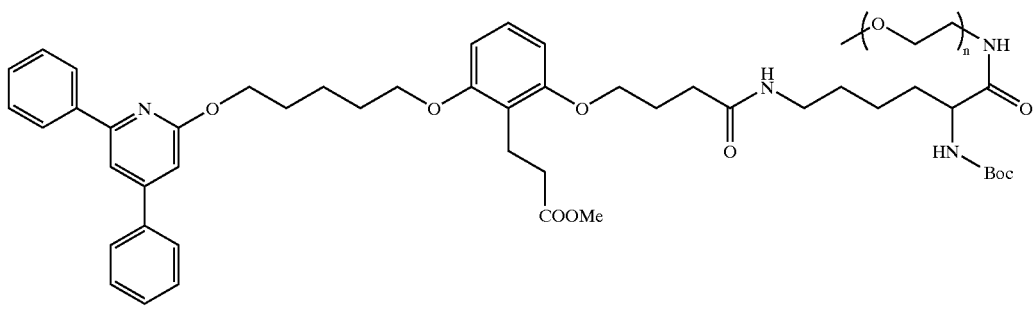

A solution of 4-(3-(5-(4,6-diphenyl(2-pyridyloxy))-pentyloxy)-2-(2-(methoxycarbonyl)ethyl)phenoxy)butanoic acid (27.5 mg, 0.045 mmol) and TEA (12 uL) in anhydrous DMF (2.5 mL) was treated with HBTU (18.9 mg, 0.049 mmol) under a nitrogen atmosphere. The solution was stirred 5 min at ambient temperatures and treated with a solution of 6-amino-2-((tert-butoxy)carbonylamino)-N-(ω-methoxypolyethylene(750)glycoxyethyl)hexanamide (55.7 mg, 0057 mmol) in DMF (3.0 mL). The solution was stirred 3 h at ambient temperatures under a nitrogen atmosphere and concentrated to a colorless oil. This oil was dissolved in ACN (1.5 mL) and purified by preparative HPLC on a Vydac C-18 column (22×250 mm) using a 1.80%/min gradient of 36 to 90% ACN containing 0.1% TFA at a flow rate of 15 mL/min. The main product peak eluting at 20.4 min was collected and lyophilized to give the title compound as a colorless oil (40 mg, 56.5%). MS: 1478.0 (n=14), 1521.8 (n=15), 1565.9 (n=16), 1610.0 (n=17), 1654.1 (n=18) [M+Na]; High Resolution MS: Calcd for $C_{78}H_{123}N_4O_{24}$ (n=15) [M+H]: 1499.8527, Found: 1499.8579; Calcd for $C_{82}H_{131}N_4O_{26}$ (n=17) [M+H]: 1587.9052, Found: 1587.9026.

Part F: Preparation of 3-(6-(3-(N-(5-((6-((1-Aza-2-(2-sulfophenyl)vinyl)amino)(3-pyridyl))carbonylamino)-5-(N-(ω-methoxypolyethylene(750)glycoxyethyl)-carbamoyl)pentyl)carbamoyl)propoxy)2-(5-(4,6-diphenyl(2-pyridyloxy))pentyloxy)phenyl)propanoic Acid A mixture of methyl 3-(6-(3-(N-(5-((tert-butoxy)-carbonylamino)-5-(N-(ω-methoxypolyethylene(750-glycoxyethyl)carbamoyl)pentyl)carbamoyl)propoxy)2-(5-(4,6-diphenyl(2-pyridyloxy))pentyloxy)phenyl)propanoate (35.7 mg, 0.0226 mmol) and 3 N LiOH (609 uL) in THF (3.5 mL) was stirred at ambient temperatures under nitrogen for 96 h. The solution was concentrated under reduced pressure and the colorless solid was taken up in TFA (4 mL) and stirred at ambient temperatures for 45 min. The TFA was removed under vacuum to give 3-(6-(3-(N-(5-amino-5-(N-(ω-methoxypolyethylene(750)glycoxyethyl)carbamoyl)pentyl)carbamoyl)propoxy)2-(5-(4,6-diphenyl(2-pyridyloxy))-pentyloxy)phenyl)propanoic acid as an orange solid (32.2 mg).

A solution of the above orange solid (32.2 mg, 0.0245 mmol), TEA (101 uL), and 2-(2-aza-2-((5-((2,5-dioxopyrrolidinyl)carbonyl)(2-pyridyl))amino)vinyl)-benzenesulfonic acid (20.0 mg, 0.0454 mmol) in anhydrous DMF (2 mL) was stirred at ambient temperatures under nitrogen for 72 h. The DMF was removed under vacuum and the resulting thick oil was dissolved in ACN (1.0 mL) and purified by preparative HPLC on a Vydac C-18 column (22×250 mm) using a 1.80%/min gradient of 18 to 72% ACN containing 0.05 M $NH_4Oac$ at a flow rate of 15 mL/min. The main product peak eluting at 25.7 min was collected and lyophilized to give the title compound as a pale yellow oil (21.0 mg, 57.9%). MS: 1643.5 (n=14), 1687.6 (n=15), 1731.7 (n=16), 1775.2 (n=17), 1819.2 (n=18), 1863.2 (n=19), 1907.5 (n=20) [M+H].

Example 32

Synthesis of 3-(6-(3-(N-(3-(2-(2-(3-((6-((1-Aza-2-(2-sulfophenyl)vinyl)amino)(3-pyridyl))carbonylamino)propoxy)ethoxy)ethoxy)propyl)-carbamoyl)propoxy)2-(5-(4,6-diphenyl(2-pyridyloxy))pentyloxy)phenyl)propanoic Acid

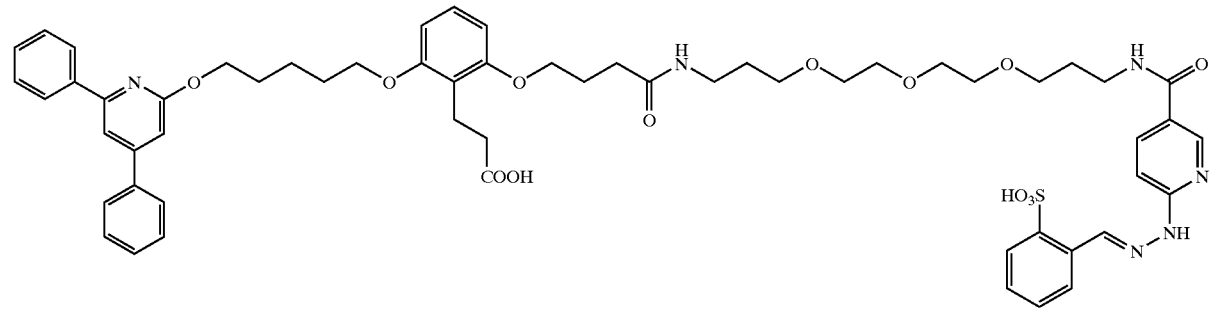

Part A: Preparation of Methyl 3-(6-(3-(N-(3-(2-(2-(3-((tert-Butoxy)carbonylamino)propoxy)ethoxy)ethoxy)propyl)-carbamoyl)propoxy)2-(5-(4,6-diphenyl(2-pyridyloxy))pentyloxy)phenyl)propanoate

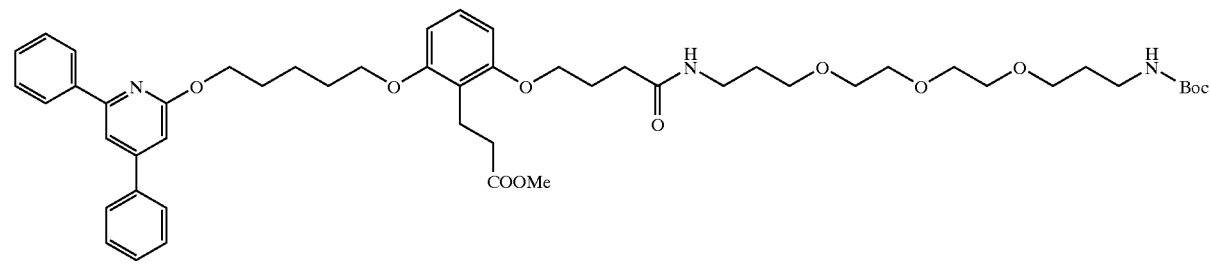

A solution of 4-(3-(5-(4,6-diphenyl(2-pyridyloxy)) pentyloxy)-2-(2-(methoxycarbonyl)ethyl)phenoxy)butanoic acid (100 mg, 0.167 mmol) in anhydrous DMF (0.75 mL) was treated with HBTU (90 mg, 0.237 mmol) under a nitrogen atmosphere. The solution was stirred 5 min at ambient temperatures and treated with a solution of N-(3-(2-(2-(3-aminopropoxy)ethoxy)ethoxy)propyltert-butoxy) formamide (59 mg, 0.184 mmol) in anhydrous DMF (0.75 mL), followed by DIEA (73 mg, 0.418 mmol). The solution was stirred 3 h at ambient temperatures under nitrogen. The reaction solution was purified directly by preparative HPLC on a Vydac C-18 column (22×250 mm) using a 1.80%/min gradient of 36 to 90% ACN at a flow rate of 15 mL/min. The main peak eluting at 33.9 min was collected and lyophilized to give the title compound as a colorless oil (105 mg, 69.7%). $^1$H NMR (CDCl$_3$): 8.10–8.06 (m, 2H), 7.70–7.62 (m, 2H), 7.56–7.35 (m 7H), 7.08 (t, J=8.1 Hz, 1H), 6.89 (d, J=1.2 Hz, 1H), 6.53–6.44(m, 3H), 4.95 (s, 1H), 4.51 (t, J=6.5 Hz, 2H), 3.97 (q, J=6.2 Hz, 2H), 3.62–3.45 (m, 15H), 3.33 (q, J=6.2 Hz, 2H), 3.23–3.15 (m, 2H), 3.05–2.95 (m, 2H), 2.59–2.34 (m, 4H), 2.16–2.04 (m, 2H), 1.98–1.63 (m, 10H), 1.42 (s, 9H); MS: m/e 900.7 [M+H]; High Resolution MS: Calcd for $C_{51}H_{70}N_3O_{11}$ [M+H]: 900.5010, Found: 900.5012.

Part B: Preparation of 3-(6-(3-(N-(3-(2-(2-(3-((tert-Butoxy) carbonylamino)propoxy)ethoxy)ethoxy)propyl)-carbamoyl) propoxy)2-(5-(4,6-diphenyl(2-pyridyloxy))pentyloxy) phenyl)propanoic Acid A mixture of methyl 3-(6-(3-(N-(3-(2-(2-(3-((tert-butoxy) carbonylamino)propoxy)ethoxy)ethoxy)propyl)carbamoyl) propoxy)2-(5-(4,6-diphenyl(2-pyridyloxy))pentyloxy) phenyl)propanoate (107 mg, 0.119 mmol) and 3M LiOH (0.57 mL, 1.72 mmol) in THF (5.8 mL) was stirred at ambient temperatures for 4 days. The THF was removed by vacuum evaporation and the resulting mixture was treated with water (20 mL). The aqueous mixture was adjusted to pH=2 with 1.0 N HCl, and extracted with EtOAc (3×40 mL). The combined organic layers were washed consecutively with water (20 mL) and sat. NaCl (20 mL), dried (MgSO4), and concentrated to give the title compound as a colorless oil (93.0 mg, 88.3%). MS: m/e 886.6 [M+H]; High Resolution MS: Calcd for $C_{50}H_{68}N_3O_{11}$ [M+H]: 886.4854, Found: 886.4872.

Part C Preparation of 3-(6-(3-(N-(3-(2-(2-(3-((6-((1-Aza-2-(2-sulfophenyl)vinyl)amino)(3-pyridyl))carbonylamino) propoxy)ethoxy)ethoxy)propyl)-carbamoyl)propoxy)2-(5-(4,6-diphenyl(2-pyridyloxy))pentyloxy)phenyl)propanoic Acid A solution of 3-(6-(3-(N-(3-(2-(2-(3-((tert-butoxy)-carbonylamino)propoxy)ethoxy)ethoxy)propyl)carbamoyl) propoxy)2-(5-(4,6-diphenyl(2-pyridyloxy))pentyloxy) phenyl)propanoic acid (89 mg, 0.100 mmol) in TFA (4 mL) was stirred under a nitrogen atmosphere for 60 min at ambient temperatures. The TFA was removed by vacuum evaporation and the resulting oil was dissolved in DMF (0.7 mL). TEA was added until the solution was basic to pH paper (106 uL, 0.76 mmol), and 2-(2-aza-2-((5-((2,5-dioxopyrrolidinyl)carbonyl)(2-pyridyl))amino)vinyl) benzenesulfonic acid (53.0 mg, 0.12 mmol) was added. The resulting solution was stirred 17 h at ambient temperatures under a nitrogen atmosphere. The solution was purified directly by preparative HPLC on a Vydac C-18 column (22×250 mm) using a 1.80%/min gradient of 20 to 80% ACN containing 0.05 M NH$_4$Oac at a flow rate of 15 mL/min. The main product peak eluting at 25.8 min was collected and lyophilized to give the title compound as a colorless solid (75.6 mg, 69%). MS: m/e 1087.5 [M−H]; High Resolution MS: Calcd for $C_{58}H_{69}N_6O_{13}S$ [M+H]: 1089.4643, Found: 1089.4661.

Example 33

Synthesis of 3-(6-(3-(N-(5-((6-((1-Aza-2-(2-sulfophenyl)vinyl)amino)(3-pyridyl)) carbonylamino)-5-(N-(2,3,4,5,6-pentahydroxyhexyl) carbamoyl)pentyl)carbamoyl)propoxy)2-(5-(4,6-diphenyl(2-pyridyloxy))pentyloxy)phenyl)propanoic Acid

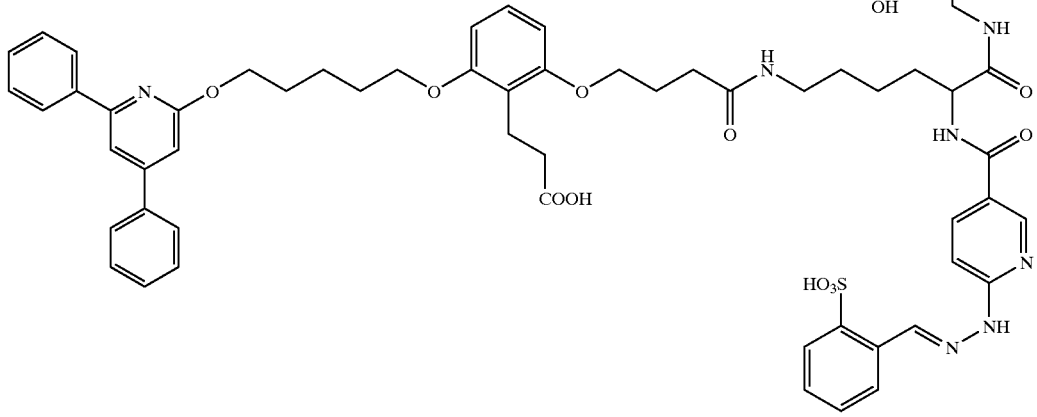

Part A: Preparation of 2-((tert-Butoxy)carbonylamino)-N-(2,3,4,5,6-pentahydroxyhexyl)-6-((phenylmethoxy)carbonylamino)hexanamide

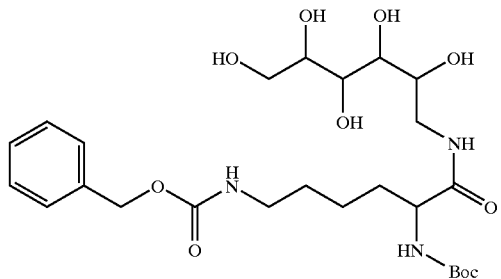

A mixture of 1-amino-1-deoxysorbitol (1.99 g, 11.0 mmol), Boc-Lys-(Z)-Osu (4.77 g, 10.0 mmol), TEA (0.556 g, 4.0 mmol), THF (50 mL), and water (10 mL) was stirred at ambient temperatures for 2 h followed by concentration to a volume of 10 mL. Water (100 mL) was added, and the mixture was extracted with EtOAc (3×200 mL). The combined organic extracts were washed consecutively with 0.05 N HCl (50 mL), water (50 mL), and sat. NaCl (50 mL), dried (MgSO$_4$), and concentrated by vacuum evaporation until crystals began to form. The mixture was diluted with ether, causing additional crystallization. The solid was collected by filtration and dried to give the title compound as colorless crystals (1.08 g, 19.9%). $^1$H NMR (CD$_3$OD): 7.41–7.26 (m, 5H), 5.09 (s, 2H), 4.05–3.94 (m, 2H), 3.88–3.45 (m, 7H), 3.14 (t, J=6.6 Hz, 2H), 1.87–1.31 (m, 16H); MS: m/e 544.4 [M+H]; High Resolution MS: Calcd for C$_{25}$H$_{42}$N$_3$O$_{10}$ [M+H]: 544.2870, Found: 544.2895.

Part B: Preparation of 6-Amino-2-((tert-butoxy)carbonylamino)-N-(2,3,4,5,6-pentahydroxyhexyl)hexanamide 2-((tert-Butoxy)carbonylamino)-N-(2,3,4,5,6-pentahydroxyhexyl)-6-((phenylmethoxy)carbonylamino)hexanamide (450 mg, 0.829 mmol) was dissolved in MeOH (10 mL) and hydrogenolyzed over 10% Pd/C (85 mg) at atmospheric pressure for 90 min. The catalyst was removed by filtration through filter aid and the filtrate was concentrated under reduced pressure to give the title compound as a pale yellow oil (331 mg, 97.7%). MS: m/e 410.3 [M+H].

Part C: Preparation of Methyl 3-(6-(3-(N-(5-((tert-Butoxy)carbonylamino)-5-(N-(2,3,4,5,6-pentahydroxyhexyl)carbamoyl)pentyl)carbamoyl)propoxy)-2-(5-(4,6-diphenyl(2-pyridyloxy))pentyloxy)phenyl)propanoate A solution of 4-(3-(5-(4,6-diphenyl(2-pyridyloxy))pentyloxy)-2-(2-(methoxycarbonyl)ethyl)phenoxy)butanoic acid (90 mg, 0.152 mmol), and DIEA (66 uL, 0.380 mmol) in anhydrous DMF (2 mL) was preactivated with HBTU (69.2 mg, 0.182 mmol) for 5 min at ambient temperatures, and then treated with a solution of 6-amino-2-((tert-butoxy)carbonylamino)-N-(2,3,4,5,6-pentahydroxyhexyl)hexanamide (74.7 mg, 0.182 mmol) in anhydrous DMF (2 mL). The solution was stirred at ambient temperatures for 45 min and purified directly by preparative HPLC on a Vydac C-18 column (22×250 mm) using a 2.10%/min gradient of 27 to 90% ACN at a flow rate of 15 mL/min. The main product peak eluting at 29.5 min was collected and lyophilized to give the title compound as a colorless oil (88 mg, 58.5%). MS: m/e 989.5 [M+H]; High Resolution MS: Calcd for C$_{53}$H$_{73}$N$_4$O$_{14}$ [M+H]: 989.5123, Found: 989.5145.

Part D: Preparation of 3-(6-(3-(N-(5-Amino-5-(N-(2,3,4,5,6-pentahydroxyhexyl)carbamoyl)pentyl)carbamoyl)propoxy)-2-(5-(4,6-diphenyl(2-pyridyloxy))pentyloxy)phenyl)propanoic Acid A mixture of methyl 3-(6-(3-(N-(5-((tert-butoxy)carbonylamino)-5-(N-(2,3,4,5,6-pentahydroxyhexyl)carbamoyl)pentyl)carbamoyl)propoxy)-2-(5-(4,6-diphenyl(2-pyridyloxy))pentyloxy)phenyl)propanoate (37 mg, 0.037 mmol) and 3M LiOH (181 uL) in THF (1.8 mL) was stirred at ambient temperatures for 3 h and then concentrated to dryness under vacuum. The solid residue was cooled at −10° C. and treated with TFA (4 mL). The resulting solution was stirred 60 min at ambient temperatures and concentrated under reduced pressure to give the TFA salt of the title compound as an amber oil. MS: m/e 875.5 [M+H].

Part E Preparation of 3-(6-(3-(N-(5-((6-((1-Aza-2-(2-sulfophenyl)vinyl)amino)(3-pyridyl))carbonylamino)-5-(N-(2,3,4,5,6-pentahydroxyhexyl)carbamoyl)pentyl)carbamoyl)propoxy)-2-(5-(4,6-diphenyl(2-pyridyloxy))pentyloxy)phenyl)propanoic Acid A solution of 3-(6-(3-(N-(5-amino-5-(N-(2,3,4,5,6-pentahydroxyhexyl)carbamoyl)pentyl)carbamoyl)propoxy)-2-(5-(4,6-diphenyl(2-pyridyloxy))pentyloxy)phenyl)propanoic acid in anhydrous DMF (0.5 mL) was treated with TEA until basic to pH paper (57 uL, 0.41 mmol). This solution was treated with 2-(2-aza-2-((5-((2,5-dioxopyrrolidinyl)carbonyl)(2-pyridyl))amino)vinyl)benzenesulfonic acid (18.2 mg, 0.041 mmol) and stirred at ambient temperatures for 17 h under a nitrogen atmosphere. The solution was diluted with 80% ACN (0.5 mL) and purified directly by preparative HPLC on a Vydac C-18 column (22×250 mm) using a 1.80%/min gradient of 18 to 72% ACN containing 0.05 M NH$_4$Oac at a flow rate of 15

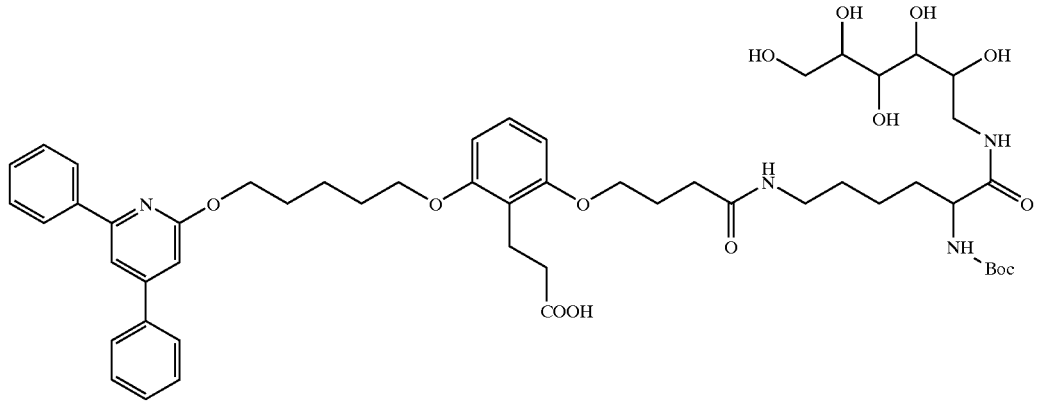

mL/min. The main product peak eluting at 23 min was collected and lyophilized to give the title compound as a colorless powder (11.5 mg, 28.7%). MS: m/e 1176.7 [M−H]; High Resolution MS: Calcd for $C_{60}H_{72}N_7O_{16}S$ [M+H]: 1178.4756, Found: 1178.4792.

Example 34

Synthesis of 3-(6-(3-(N-(3-((6-((1-aza-2-(2-sulfophenyl)vinyl)amino3-pyridyl))carbonylamino)propyl)carbamoyl)propoxy)-2-(5-(5-oxo-1-prop-2-enyl(2-6,7,8-trihydronaphthyloxy))pentyloxy)phenyl)propanoic Acid

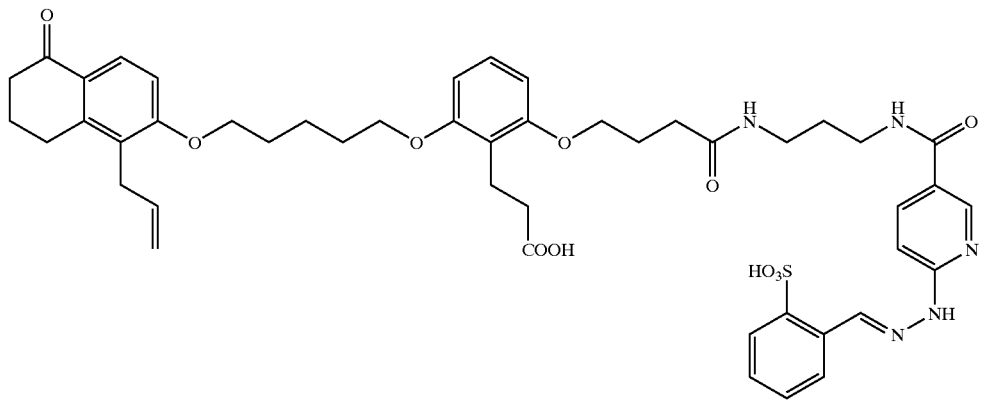

Part A: Preparation of tert-Butyl 4-(2-(2-(Methoxycarbonyl)ethyl)-3-(5-(5-oxo-1-prop-2-enyl(2-6,7,8-trihydronaphthyloxy))pentyloxy)phenoxy)butanoate

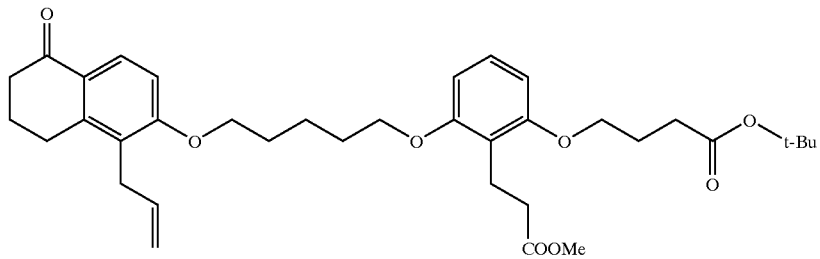

A mixture of tert-butyl 4-(2-(2-(methoxycarbonyl)ethyl)-3-(5-(methylsulfonyloxy)pentyloxy)phenoxy)butanoate (482 mg, 0.959 mmol), 6-hydroxy-5-prop-2-enyl-2,3,4-trihydro-naphthalen-1-one (204 mg, 1.01 mmol), and anhydrous $K_2CO_3$ (265 mg, 1.92 mmol) in anhydrous DMSO (4.5 mL) was stirred at ambient temperatures under a nitrogen atmosphere for 67 h. The reaction mixture was diluted with 80% ACN and used directly for preparative HPLC purification on a Vydac C-18 column (22×250 mm) using a 1.80%/min gradient of 36 to 90% ACN at a flow rate of 15 mL/min. The main product peak eluting at 32 min was collected and lyophilized to give the title compound as a pale yellow oil (330 mg, 57%). $^1$H NMR (CDCl$_3$): 8.00 (d, J=8.7 Hz, 1H), 7.08 (t, J=8.3 Hz, 1H), 6.83 (d, J=8.7 Hz, 1H), 6.48 (d, J=8.3 Hz, 2H), 5.95–5.78 (m, 1H), 5.00–4.84 (m, 2H), 4.05 (t, J=6.2 Hz, 2H), 4.01–3.91 (m, 4H), 3.64 (s, 3H), 3.43 (d, J=5.9 Hz, 2H), 2.98 (t, J=8.2 Hz, 2H), 2.88 (t, J=6.1 Hz, 2H), 2.57 (t, J=6.5 Hz, 2H), 2.53–2.37 (m, 4H), 2.16–1.57 (m, 10H), 1.43 (s, 9H); MS: m/e 609.4 [M+H]; High Resolution MS: Calcd for $C_{36}H_{49}O_8$ [M+H]: 609.3427, Found: 609.3398.

Part B Preparation of 4-(2-(2-(Methoxycarbonyl)ethyl)-3-(5-(5-oxo-1-prop-2-enyl(2-6,7,8-trihydronaphthyloxy))pentyloxy)phenoxy)butanoic Acid A solution of tert-butyl 4-(2-(2-(methoxycarbonyl)ethyl)-3-(5-(5-oxo-1-prop-2-enyl(2-6,7,8-trihydro-naphthyloxy))pentyloxy)phenoxy)butanoate (252 mg, 0.414 mmol) and anisole (90 uL, 0.823 mmol) in TFA (6 mL) was stirred 15 min at ambient temperatures. The TFA was removed by vacuum evaporation, the resulting oil was dissolved in 70% ACN and lyophilized to give the title compound as a colorless powder (224 mg, 97%). $^1$H NMR (CDCl$_3$): 7.99 (d, J=8.7 Hz, 1H), 7.05 (t, J=8.2 Hz, 1H), 6.83 (d, J=8.7 Hz, 1H), 6.48 (t, J=8.2 Hz, 2H), 5.94-5.78 (m, 1H), 4.99–4.84 (m, 2H), 4.10–3.92 (m, 6H), 3.67 (s, 3H), 3.42 (d, J=5.9 Hz, 2H), 3.01–2.84 (m, 4H), 2.62–2.42 (m, 6H), 2.22–2.01 (m, 4H), 1.95–1.80 (m, 4H), 1.73–1.59 (m, 2H); MS: m/e 553.3 [M+H]; High Resolution MS: Calcd for $C_{32}H_{37}O_8$ [M+H]: 553.2801, Found: 553.2796.

Part C Preparation of Methyl 3-(6-(3-(N-(3-((tert-Butoxy)carbonylamino)propyl)carbamoyl)propoxy)-2-(5-(5-oxo-1-prop-2-enyl(2-6,7,8-trihydronaphthyloxy))pentyloxy)phenyl)propanoate Part E Preparation of 3-(6-(3-(N-(3-((6-((1-aza-2-(2-sulfophenyl)vinyl)amino)(3-pyridyl))carbonylamino)propyl)carbamoyl)propoxy)-2-(5-(5-oxo-1-prop-2-enyl(2-6,7,8-trihydronaphthyloxy))pentyloxy)phenyl)propanoic Acid

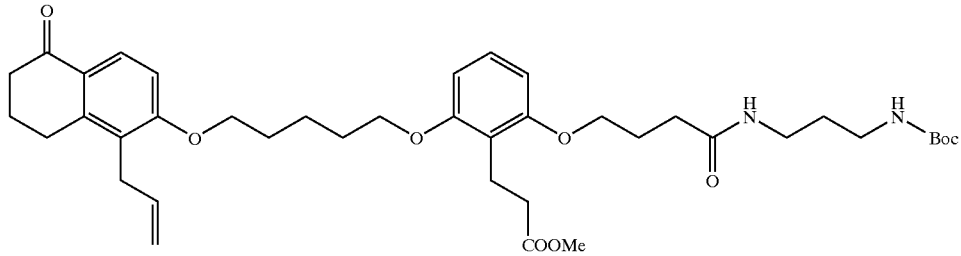

A solution of 4-(2-(2-(methoxycarbonyl)ethyl)-3-(5-(5-oxo-1-prop-2-enyl(2-6,7,8-trihydronaphthyloxy))pentyloxy)phenoxy)butanoic acid (110 mg, 0.191 mmol) in anhydrous DMF (3 mL) was preactivated by treatment with HBTU (79.7 mg, 0.21 mmol) for 5 min at ambient temperatures. A solution of N-(3-aminopropyl)(tert-butoxy)formamide (33.3 mg, 0.191 mmol) and DIEA (83 uL, 0.478 mmol) in anhydrous DMF (1 mL) was added and stirring was continued at ambient temperatures for 15 min. The DMF was removed by vacuum evaporation and the resulting yellow oil was taken up in a mixture of EtOAc (40 mL) and water (30 mL). The aqueous phase was adjusted to pH=2 with 0.2 N HCl and the layers were thoroughly mixed. The organic phase was washed consecutively with sat. NaHCO$_3$, (30 mL), and sat NaCl (2×30 mL), dried (MgSO$_4$), and concentrated to give the title compound as a pale yellow oil (129 mg, 95.3%). MS: m/e 709.4 [M+H].

Part D Preparation of 3-(6-(3-(N-(3-((tert-Butoxy)carbonylamino)propyl)carbamoyl)propoxy)-2-(5-(5-oxo-1-prop-2-enyl(2-6,7,8-trihydronaphthyloxy))pentyloxy)phenyl)propanoic Acid A mixture of methyl 3-(6-(3-(N-(3-((tert-butoxy)carbonylamino)propyl)carbamoyl)propoxy)-2-(5-(5-oxo-1-prop-2-enyl(2-6,7,8-trihydronaphthyloxy))pentyloxy)phenyl)propanoate (105 mg, 0.148 mmol), and 3 M LiOH (0.72 mL) in THF (7.2 mL) was stirred at ambient temperatures for 4 days and concentrated to dryness under vacuum. Water (20 mL) was added to the oily residue and adjusted to pH=2.0 with 1.0 N HCl. The cloudy solution was extracted with EtOAc (3×40 mL). The combined organic extracts were washed with water (20 mL) and with sat. NaCl (20 mL), dried (MgSO$_4$), and concentrated to give the title compound as a colorless solid (93.5 mg, 91%). MS: m/e 693.4 [M−H].

A solution of 3-(6-(3-(N-(3-((tert-butoxy)carbonylamino)propyl)carbamoyl)propoxy)-2-(5-(5-oxo-1-prop-2-enyl(2-6,7,8-trihydronaphthyloxy))pentyloxy)phenyl)propanoic acid (72 mg, 0.104 mmol) in TFA (3 mL) was stirred at ambient temperatures for 70 min and concentrated to a viscous oil under reduced pressure. This oil was dissolved in anhydrous DMF (0.7 mL) and treated with TEA until basic (58 uL, 0.415 mmol). This solution was treated with 2-(2-aza-2-((5-((2,5-dioxopyrrolidinyl)carbonyl)(2-pyridyl))amino)vinyl)benzenesulfonic acid (55 mg, 0.125 mmol) and stirred at ambient temperatures for 16 h under a nitrogen atmosphere. The solution was diluted with 80% ACN (0.7 mL) and purified directly by preparative HPLC on a Vydac C-18 column (22×250 mm) using a 1.80%/min gradient of 18 to 72% ACN containing 0.05 M NH$_4$Oac at a flow rate of 15 mL/min. The main product peak eluting at 20.7 min was collected and lyophilized to give the title compound as a colorless powder (52 mg, 57%). MS: m/e 896.4 [M−H]; High Resolution MS: Calcd for C$_{47}$H$_{56}$N$_5$O$_{11}$S [M+H]: 898.3697, Found: 898.3699.

Example 35

Synthesis of 3-(6-(3-N-(2-(2-(2-(2-(2-(2-(2-(2-((6-((1-Aza-2-(2-sulfophenyl)vinyl)amino)(3-pyridyl))carbonylamino)ethoxy)ethoxy)ethoxy)ethoxy)ethoxy)ethoxy)ethoxy)ethyl)carbamoyl)propoxy )-2-(5-(5-oxo-1-prop-2-enyl(2-6,7,8-trihydronaphthyloxy))pentyloxy)phenyl)propanoic Acid

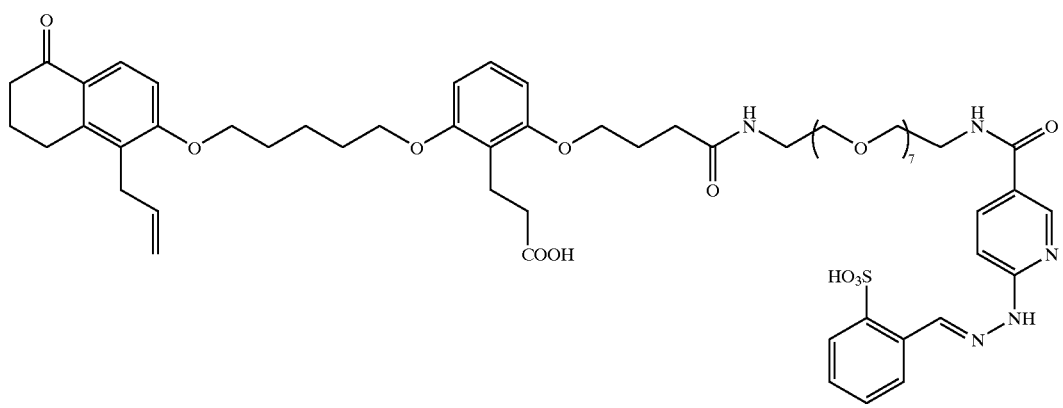

Part A Preparation of Methyl 3-(6-(3-N-(2-(2-(2-(2-(2-(2-(2-(2-((tert-Butoxy)carbonylamino)ethoxy)ethoxy)ethoxy)ethoxy)ethoxy)ethoxy)ethoxy)ethyl)carbamoyl)propoxy)-2-(5-(5-oxo-1-prop-2-enyl(2-6,7,8-trihydronaphthyloxy))pentyloxy)phenyl)propanoate

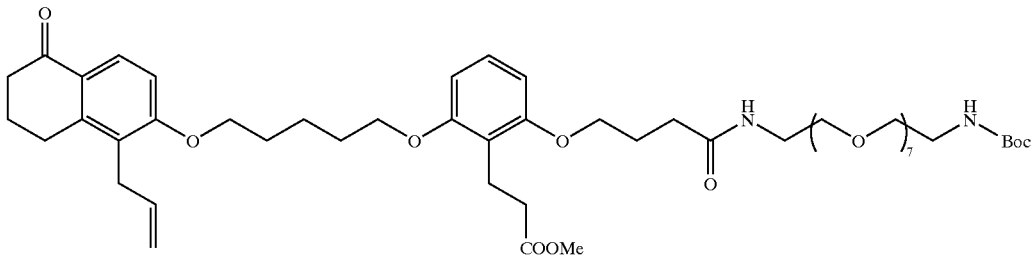

A solution of 4-(2-(2-(methoxycarbonyl)ethyl)-3-(5-(5-oxo-1-prop-2-enyl(2-6,7,8-trihydronaphthyloxy))pentyloxy)phenoxy)butanoic acid (80 mg, 0.139 mmol) in anhydrous DMF (1 mL) was treated with HBTU (58 mg, 0.152 mmol). After 5 min a solution of N-(2-(2-(2-(2-(2-(2-(2-(2-aminoethoxy)ethoxy)ethoxy)ethoxy)ethoxy)ethoxy)ethoxy)ethyl)(tert-butoxy)formamide (71.2 mg, 0.152 mmol) and DIEA (60.5 uL, 0.348 mmol) in anhydrous DMF (2 mL) was added and the resulting solution was stirred at ambient temperatures under a nitrogen atmosphere for 15 min. The DMF was removed by vacuum evaporation and the resulting oil was dissolved in a mixture of EtOAc (40 mL) and water (30 mL). The aqueous layer was adjusted to pH=2.0 with 0.2 N HCl and the phases were thoroughly mixed. The organic phase was washed consecutively with at. NaHCO₃ (30 mL), and sat. NaCl (2×30 mL), dried (MgSO₄), and concentrated to give the title compound as a colorless oil (114 mg, 81.7%). MS: m/e 1020.7 [M+NH₄].

Part B: Preparation of 3-(6-(3-N-(2-(2-(2-(2-(2-(2-(2-(2-((tert-Butoxy)carbonylamino)ethoxy)ethoxy)ethoxy)ethoxy)ethoxy)ethoxy)ethoxy)ethyl)carbamoyl)propoxy)-2-(5-(5-oxo-1-prop-2-enyl(2-6,7,8-trihydronaphthyloxy))pentyloxy)phenyl)propanoic Acid

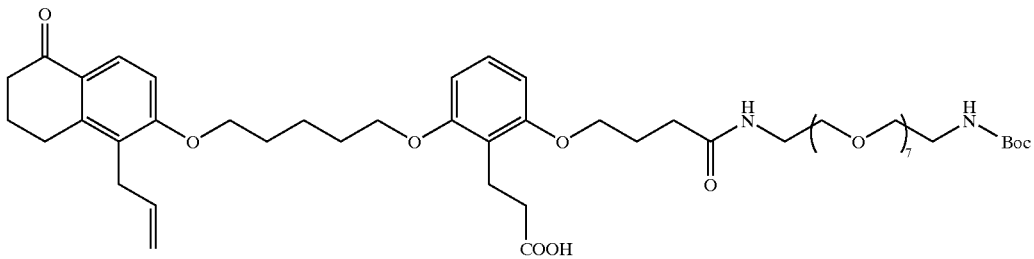

A mixture of methyl 3-(6-(3-N-(2-(2-(2-(2-(2-(2-(2-(2-((tert-butoxy)carbonylamino)ethoxy)ethoxy)ethoxy)ethoxy)ethoxy)ethoxy)ethoxy)ethyl)carbamoyl)propoxy)-2-(5-(5-oxo-1-prop-2-enyl(2-6,7,8-trihydronaphthyloxy))pentyloxy)phenyl)propanoate (110 mg, 0.11 mmol) and 3 M LiOH (0.53 mL, 1.59 mmol) in THF (5.3 mL) was stirred at ambient temperatures under a nitrogen atmosphere for 3 days and concentrated to dryness under reduced pressure. Water (20 mL) was added to the mixture and adjusted to pH=2.0 using 1.0 N HCl. The mixture was extracted with EtOAc (3×40 mL). The combined organic extracts were washed with water (20 mL) and with sat. NaCl (20 mL), dried (MgSO₄), and concentrated to give the title compound as a colorless oil (93 mg, 85.8%). MS: m/e 1006.7 [M+NH₄].

Part C Preparation of 3-(6-(3-N-(2-(2-(2-(2-(2-(2-(2-(2-((6-((1-Aza-2-(2-sulfophenyl)vinyl)amino)(3-pyridyl))carbonylamino)ethoxy)ethoxy)ethoxy)ethoxy)ethoxy)ethoxy)ethoxy)ethyl)carbamoyl)propoxy )-2-(5-(5-oxo-1-prop-2-enyl(2-6,7,8-trihydronaphthyloxy))pentyloxy)phenyl)propanoic Acid A solution of 3-(6-(3-N-(2-(2-(2-(2-(2-(2-(2-(2-((tert-butoxy)carbonylamino)ethoxy)ethoxy)ethoxy)ethoxy)ethoxy)ethoxy)ethoxy)ethyl)carbamoyl)propoxy)-2-(5-(5-oxo-1-prop-2-enyl(2-6,7,8-trihydronaphthyloxy))pentyloxy)phenyl)propanoic acid (83 mg, 0.084 mmol) in TFA (4 mL) was stirred at ambient temperatures under a nitrogen atmosphere for 60 min. The TFA was removed under reduced pressure to give an amber oil. This oil was dissolved in anhydrous DMF (0.7 mL) and treated with TEA until basic to pH paper (71 uL, 0.511 mmol). This solution was treated with 2-(2-aza-2-((5-((2,5-dioxopyrrolidinyl)carbonyl)(2-pyridyl))amino)vinyl)-benzenesulfonic acid (45 mg, 0.102 mmol) and stirred at ambient temperatures for 19 h under a nitrogen atmosphere. The solution was diluted with 80% ACN (0.7 mL) and purified directly by preparative HPLC on a Vydac C-18 column (22×250 mm) using a 1.80%/min gradient of 18 to 72% ACN containing 0.05 M NH₄Oac at a flow rate of 15 mL/min. The main product peak was collected and lyophilized to give the title compound as a colorless powder (64 mg, 63%). MS: m/e 1209.7 [M+NH₄]; High Resolution MS: Calcd for $C_{60}H_{82}N_5O_{18}S$ [M+H]: 1192.5376, Found: 1192.5394.

Example 36

Synthesis of 3-(6-(3-N-(5-((6-((1-Aza-2-(2-sulfophenyl)vinyl)amino)(3-pyridyl))carbonylamino)-5-(N-(2,3,4,5,6-pentahydroxyhexyl)carbamoyl)pentyl)carbamoyl)propoxy-2-(5-(5-oxo-1-prop-2-enyl(2-6,7,8-trihydronaphthyloxy))pentyloxy)phenyl)propanoic Acid

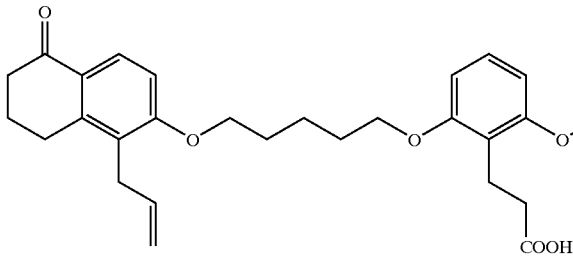

Part A Preparation of Methyl 3-(6-(3-N-(5-((tert-Butoxy)carbonylamino)-5-(N-(2,3,4,5,6-pentahydroxyhexyl)carbamoyl)pentyl)carbamoyl)propoxy-2-(5-(5-oxo-1-prop-2-enyl(2-6,7,8-trihydronaphthyloxy))pentyloxy)phenyl)propanoate

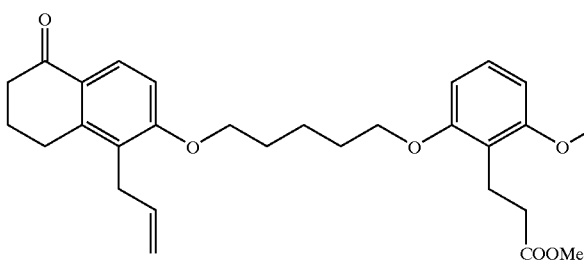

A solution of 4-(2-(2-(methoxycarbonyl)ethyl)-3-(5-(5-oxo-1-prop-2-enyl(2-6,7,8-trihydronaphthyloxy))pentyloxy)phenoxy)butanoic acid (55 mg, 0.096 mmol) in anhydrous DMF (0.8 mL) was treated with HBTU (43.5 mg, 0.115 mmol) and the solution was stirred at ambient temperatures for 5 min. To this solution was added a solution of 6-amino-2-((tert-butoxy)carbonylamino)-N-(2,3,4,5,6-pentahydroxyhexyl)hexanamide (47 mg, 0.115 mmol) and DIEA (42 uL, 0.239 mmol) in anhydrous DMF (0.8 mL) and stirring was continued at ambient temperatures for 45 min. The solution was concentrated to 25% of its original volume and diluted with 80% ACN (1.2 mL). This solution was purified directly by preparative HPLC on a Vydac C-18 column (22×250 mm) using a 2.10%/min gradient of 27 to 90% ACN at a flow rate of 15 mL/min. The main product peak eluting at 22.1 min was collected and lyophilized to give the title compound as a colorless powder (70 mg, 77.5%). $^1$H NMR (CDCl$_3$): 7.98 (d, J=8.8 Hz, 1H), 7.25 (s, 1H), 7.07 (t, J=8.4 Hz, 1H), 6.90 (s, 1H), 6.83 (d, J=8.8 Hz, 1H), 6.47 (d, J=8.4 Hz, 2H), 5.94–5.77 (m, 2H), 4.98–4.84 (m, 2H), 4.40–3.10 (m, 27H), 3.05–2.81 (m, 4H), 2.61–2.36 (m, 6H), 2.16–1.98 (m, 4H), 1.94–1.25 (m, 21H); MS: m/e 961.6 [M+NH$_4$]; High Resolution MS: Calcd for C$_{49}$H$_{74}$N$_3$O$_{15}$ [M+H]: 944.5120, Found: 944.5117.

Part B Preparation of 3-(6-(3-N-(5-((6-((1-Aza-2-(2-sulfophenyl)vinyl)amino)(3-pyridyl))carbonylamino)-5-(N-(2,3,4,5,6-pentahydroxyhexyl)carbamoyl)pentyl)carbamoyl)propoxy-2-(5-(5-oxo-1-prop-2-enyl(2-6,7,8-trihydronaphthyloxy))pentyloxy)phenyl)propanoic Acid A mixture of methyl 3-(6-(3-N-(5-((tert-butoxy)-carbonylamino)-5-(N-(2,3,4,5,6-pentahydroxyhexyl)carbamoyl)pentyl)carbamoyl)propoxy-2-(5-(5-oxo-1-prop-2-enyl(2-6,7,8-trihydronaphthyloxy))pentyloxy)phenyl)propanoate (55 mg, 0.058 mmol) and 3 M LiOH (280 uL) in THF (2.8 mL) was stirred at ambient temperatures for 2.5 h and concentrated to dryness under reduced pressure. The presence of the expected hydrolysis product was confirmed by low resolution mass spectroscopy. MS: m/e 928.5 [M−H].

The solid resulting from the above hydrolysis was cooled to 0° C., dissolved in TFA (5 mL), and stirred at ambient temperatures 25 min. The TFA was removed under reduced pressure and the resulting amber oil was used directly in the next reaction.

The oil was dissolved in anhydrous DMF (0.75 mL) and made basic to pH paper with TEA (49 uL, 0.35 mmol). The solution was treated with 2-(2-aza-2-((5-((2,5-dioxopyrrolidinyl)carbonyl)(2-pyridyl))amino)vinyl)-benzenesulfonic acid (31 mg, 0.070 mmol) and stirred at ambient temperatures for 22 h. The solution was diluted with 80% ACN (0.75 mL) and purified directly by preparative HPLC on a Vydac C-18 column (22×250 mm) using a 1.80%/min gradient of 18 to 72% ACN containing 0.05 M NH$_4$Oac at a flow rate of 15 mL/min. The main product peak eluting at 18.7 min was collected and lyophilized to give the title compound as a pale yellow powder (31.5 mg, 47.7%). MS: m/e 1131.7 [M−H]; High Resolution MS: Calcd for C$_{56}$H$_{73}$N$_6$O$_{17}$S [M+H]: 1133.4753, Found: 1133.4722.

Example 37

Synthesis of 3-(6-(3-N-(5-((6-((1-Aza-2-(2-sulfophenyl)vinyl)amino)(3-pyridyl))carbonylamino)-5-(N-(6-deoxy-β-cyclodextryl)carbamoyl)pentyl)carbamoyl)propoxy-2-(5-(5-oxo-1-prop-2-enyl(2-6,7,8-trihydronaphthyloxy))pentyloxy)phenyl)propanoic Acid pentyloxy)phenoxy)butanoic acid (21.3 mg, 0.0386 mmol) in anhydrous DMF (1.0 mL) was preactivated by treatment with HBTU (14.6 mg, 0.0386 mmol) and TEA (80 uL, 0.579 mmol) for 5 min at ambient temperatures. A solution of 6-amino-2-((tert-butoxy)carbonylamino)-N-(6-deoxy-β-cyclodextryl)hexanamide (52.5 mg, 0.0386 mmol) in DMF (1.5 mL) was added and stirring was continued ofr 17 h at ambient temperatures under a nitrogen atmosphere. The DMF was removed by vacuum evaporation and the resulting colorless solid (90 mg) was dissolved in a combination of 80% ACN (800 uL), MeOH (200 uL), and DMF (300 uL). This solution was purified by preparative HPLC on a Vydac C-18 column (22×250 mm) using a 1.80%/min gradient of 18 to 72% ACN at a flow rate of 15 mL/min. The main product peak eluting at 24.2 min was collected and lyophilized to give the title compound as a colorless powder (28.2 mg, 38.5%). MS: 1897.0 [M+H].

Part B Preparation of 3-(6-(3-N-(5-((6-((1-Aza-2-(2-sulfophenyl)vinyl)amino)(3-pyridyl))carbonylamino)-5-(N-(6-deoxy-β-cyclodextryl)carbamoyl)pentyl)carbamoyl)propoxy-2-(5-(5-oxo-1-prop-2-enyl(2-6,7,8-trihydronaphthyloxy))pentyloxy)phenyl)propanoic Acid A mixture of methyl 3-(6-(3-N-(5-((tert-butoxy)-carbonylamino)-5-(N-(6-deoxy-β-cyclodextryl)carbamoyl)-pentyl)carbamoyl)propoxy-2-(5-(5-oxo-1-prop-2-enyl(2-6,7,8-trihydronaphthyloxy))pentyloxy)phenyl)propanoate

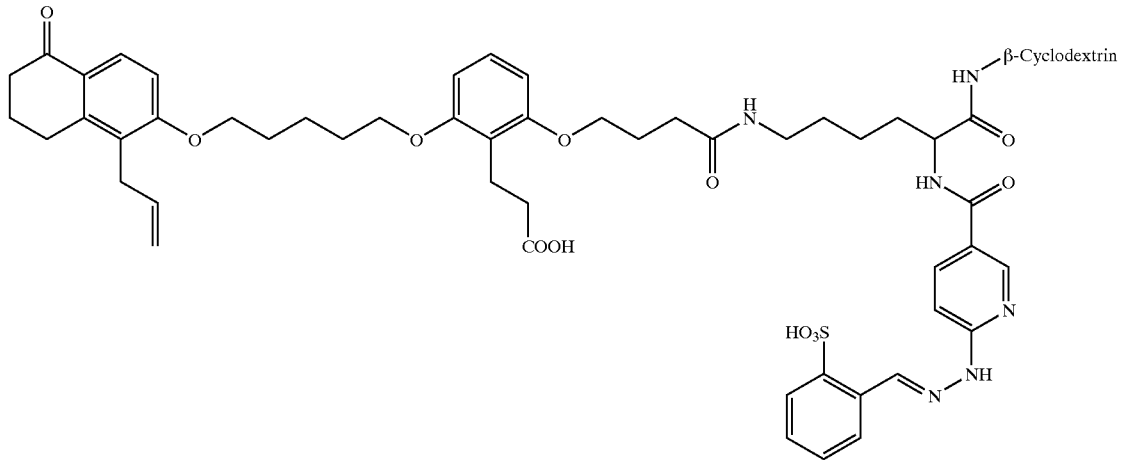

Part A Preparation of Methyl 3-(6-(3-N-(5-((tert-Butoxy)carbonylamino)-5-(N-(6-deoxy-β-cyclodextryl)carbamoyl)pentyl)carbamoyl)propoxy-2-(5-(5-oxo-1-prop-2-enyl(2-6,7,8-trihydronaphthyloxy))pentyloxy)phenyl)propanoate (28.2 mg, 0.0149 mmol) and 3 N LIOH (138 uL, 0.416 mmol) in THF was stirred at ambient temperatures under nitrogen for 4.5 h. The solution was concentrated and the colorless solid was dissolved in TFA (3 mL), and stirred at

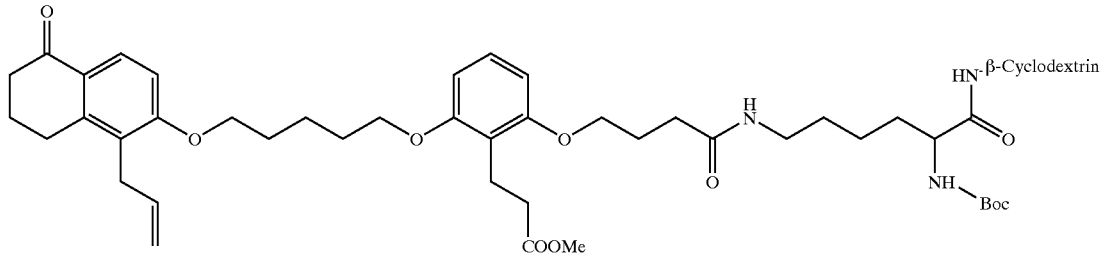

A solution of 4-(2-(2-(methoxycarbonyl)ethyl)-3-(5-(5-oxo-1-prop-2-enyl(2-6,7,8-trihydronaphthyloxy))

ambient temperatures under nitrogen for 1.5 h. The TFA was removed to give 3-(6-(3-N-(5-amino-5-(N-(6-deoxy-β- cyclodextryl)carbamoyl)-pentyl)carbamoyl)propoxy-2-(5-(5-oxo-1-prop-2-enyl(2-6,7,8-trihydronaphthyloxy))pentyloxy)phenyl)propanoic acid as a pink oil (35.4 mg).

The above oil was dissolved in anhydrous DMF (500 uL), made basic to pH paper with TEA (130 uL), and treated with 2-(2-aza-2-((5-((2,5-dioxopyrrolidinyl)carbonyl)(2-pyridyl))amino)vinyl)benzenesulfonic acid (20.1 mg, 0.0444 mmol). This solution was stirred under nitrogen at ambient temperatures for 7 days. The sample was concentrated under reduced pressure, the oily residue was dissolved in 50% ACN (1.5 mL), and purified by preparative HPLC on a Vydac C-18 column (22×250 mm) using a 1.50%/min gradient of 18 to 63% ACN containing 0.05 M NH$_4$Oac at a flow rate of 15 mL/min. The main product peak eluting at 18.4 min was collected and lyophilized to give the title compound as a colorless powder (1.0 mg, 3.22%). MS: 1041.7 [M-2H].

Example 38

Synthesis of 3-(6-(3-(N-(3-((6-((1-Aza-2-(2-sulfophenyl)vinyl)amino)(3-pyridyl))-Gly-Lys-Lys-Lys)aminopropyl)carbamoyl)propoxy)-2-(5-(5-oxo-1-prop-2-enyl (2-6,7,8-trihydronaphthyloxy))pentyloxy)phenyl)propanoic Acid treatment with benzoyl chloride (3 mL) and pyridine (3 mL) in DCM for 2 hours, and the resin was washed with 180 mL portions of DCM (3×), MeOH (1×), DCM (3×), MeOH (2×), and DCM (3×).

The following steps were then performed: (Step 1) The resin was washed with 70 ml portions of DMF (3×). (Step 2) The resin was washed with 80 mL of 20% piperidine in DMF, and the Fmoc group was removed using 80 ml of 20% piperidine in DCM for 30 minutes. (Step 3) The resin was washed thoroughly with 180 mL portions of DCM (3×), MeOH (1×), DCM (2×), MeOH (3×), and DMF (3×). (Step 4) Fmoc-Lys(Dde)-OH (8.0 g, 15 mmol), HATU (5.7 g, 15 mmol), DIEA (5.0 ml, 28 mmol), and DMF (70 ml) were added to the resin and the reaction was allowed to proceed for 18 hours. (Step 5) The completeness of the coupling reaction was monitored by the ninhydrin test. Steps 1–5 were repeated until the desired sequence had been attained. The resin was washed thoroughly with 180 mL portions of DCM (3×), MeOH (133), DCM (2×), MeOH (3×), and DCM (3×), and dried under reduced pressure to give 15.1 g of tan solid.

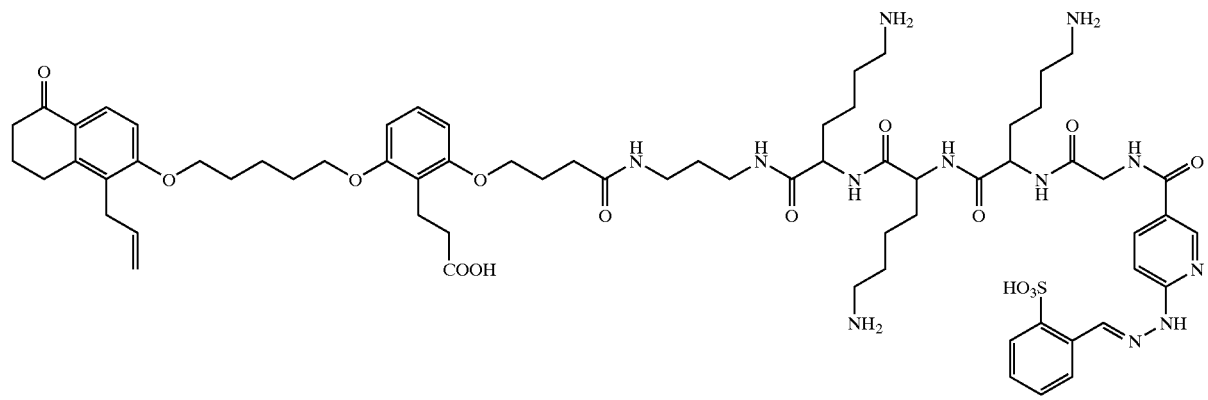

Part A: Preparation of Boc-Gly-Lys(Dde)-Lys(Dde)-Lys(Dde)-OH

To a 250 ml peptide reaction vessel was added HMPB-BHA resin (9.0 g, substitution level=0.86 mmol/g). The resin was pre-washed with anhydrous DMF (3×100 ml). The resin was suspended in DMF (60 mL), treated with Fmoc-Lys(Dde)-OH (8.25 g, 15.5 mmol), and after gentle mixing for 15 min was treated with anhydrous pyridine (2.1 mL, 25.5 mmol) and 2,6-dichlorobenzoyl chloride (2.36 mL, 15.5 mmol). The mixture was gently shaken at ambient temperatures for 22 h and the resin was washed thoroughly with 180 mL portions of DMF (3×), MeOH (1×), DCM (3×), MeOH (2×), and DCM (3×). The substitution level was determined to be 0.73 mmol/g by the fulvene-piperidine adduct test. Unreacted hydroxyl groups were blocked by The fully protected linear peptide was cleaved from the resin using 1% TFA. Peptide-resin (3.0 g) was placed in a sintered glass funnel and washed with DCM (30 mL) to swell the resin. The resin was treated with 1% TFA in DCM (20 mL) for 2 min and filtered directly into 10% pyridine in MeOH (4 mL). This procedure was repeated until all of the desired peptide had been cleaved from the resin. Filtrates were monitored by TLC (silica gel, CHCl$_3$:MeOH, 10:1) with product peptide having an Rf=0.75. Fractions containing product were combined and concentrated to give a thick oil. Trituration with ether (3×100 mL) gave an orange solid (1.5 g). Purification was accomplished using reversed-phase HPLC on a Vydac C-18 column (22×250 mm) using a 2.10%/min gradient of 18 to 81% ACN at a flow rate of 15 mL/min. The main product peak eluting at 22.7 min was collected and lyophilized to give the title compound as a colorless solid (350 mg, 35%). MS: m/e 1069.6 [M+NH$_4$].

Part B: Preparation of Methyl 3-(6-(3-(N-(3-(tert-Butoxycarbonyl-Gly-Lys(Dde)-Lys(Dde)-Lys(Dde))aminopropyl)carbamoyl)propoxy)-2-(5-(5-oxo-1-prop-2-enyl(2-6,7,8-trihydronaphthyloxy))pentyloxy)phenyl) propanoate aminopropyl)carbamoyl)propoxy)-2-(5-(5-oxo-1-prop-2-enyl(2-6,7,8-trihydronaphthyloxy))pentyloxy)phenyl) propanoic Acid Methyl 3-(6-(3-(N-(3-(tert-butoxycarbonyl-Gly-Lys(Dde)-Lys(Dde)-Lys(Dde))aminopropyl)carbamoyl)

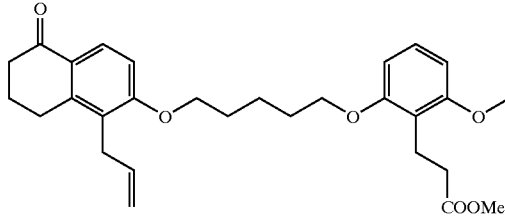
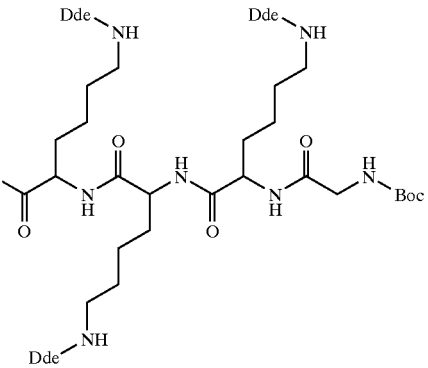

Methyl 3-(6-(3-(N-(3-((tert-butoxy)carbonylamino)propyl)carbamoyl)propoxy)-2-(5-(5-oxo-1-prop-2-enyl(2-6,7,8-trihydronaphthyloxy))pentyloxy)phenyl)propanoate (100 mg, 0.141 mmol) was dissolved in TFA (2 mL) and stirred at ambient temperatures for 20 min. The TFA was removed under reduced pressure to give a pale yellow oil. This oil was dissolved in anhydrous DMF (1.5 mL) and preactivated by the addition of HBTU (58.8 mg, 0.155 mmol). After 5 min the solution was treated with a solution of Boc-Gly-Lys(Dde)-Lys(Dde)-Lys(Dde)-OH (148 mg, 0.141 mmol) and DIEA (147 uL, 0.89 mmol) in DMF (1.5 mL). After 10 min at ambient temperatures the DMF was removed and the pale yellow oil was dissolved in a mixture of EtOAc (50 mL) and water 40 mL). The aqueous layer was adjusted to pH=2.0 using 0.2 N HCl and the layers were thoroughly mixed. The organic phase was washed with consecutively with sat. NaHCO$_3$ (5 mL) and sat. NaCl (2×4 mL), dried (MgSO$_4$), and concentrated to give colorless solid (155 mg). This solid was purified by preparative HPLC on a Vydac C-18 column (22×250 mm) using a 1.80%/min gradient of 36 to 90% ACN at a flow rate of 15 mL/min. The main product peak eluting at 27.3 min was collected and lyophilized to give the title compound as a colorless solid. $^1$H NMR (CDCl$_3$): 13.40–13.17 (m, 3H), 7.97 (d, J=8.8 Hz, 1H), 7.82 (s, 1H), 7.55 (d, J=8.3 Hz, 1H), 7.04 (t, J=8.3 Hz, 1H), 6.97 (s, 1H), 6.90–6.70 (m, 2H), 6.47 (d, J=8.3 Hz, 2H), 6.00–5.75 (, 2H), 4.95–4.80 (m 2H), 4.29 (s, 3H), 4.15–3.90 (m, 6H), 3.90–3.55 (m, 5H), 3.55–3.10 (m, 11H), 3.10–2.75 (m, 4H), 2.75–2.20 (m, 29H), 2.20–1.25 (m, 39H), 1.25–0.90 (m, 18H); MS: m/e 1660.9 [M+NH$_4$]; High Resolution MS: Calcd for C$_{90}$H$_{132}$N$_9$O$_{19}$ [M+H]: 1642.9640, Found: 1642.9602.

Part C: Preparation of 3-(6-(3-(N-(3-((6-((1-aza-2-(2-sulfophenyl)vinyl)amino)(3-pyridyl))-Gly-Lys-Lys-Lys)propoxy)-2-(5-(5-oxo-1-prop-2-enyl(2-6,7,8-trihydronaphthyloxy))pentyloxy)-phenyl)propanoate (37 mg, 0.0225 mmol) was dissolved in TFA (3 mL) and stirred at ambient temperatures for 15 min. The TFA was removed under vacuum and the oily residue was taken up in anydrous DMF (0.5 mL) and made basic to pH paper with TEA (19 uL, 0.135 mmol). The solution was treated with 2-(2-aza-2-((5-((2,5-dioxopyrrolidinyl)carbonyl)(2-pyridyl))amino)vinyl)-benzenesulfonic acid (10.9 mg, 0.025 mmol) and stirred at ambient temperatures for 20 h. The DMF was removed under vacuum. The residue was taken up in 3 M LiOH (110 uL) and THF (1.1 mL) and the mixture was stirred at ambient temperatures for 21 h. The THF was removed by vacuum evaporation, the mixture was dissolved in 50% ACN (1.0 mL) and adjusted to pH 7.0 with acetic acid. The solution was purified by preparative HPLC on a Vydac C-18 column (22×250 mm) using a 1.80%/min gradient of 18 to 72% ACN containing 0.05 M NH$_4$Oac at a flow rate of 15 mL/min. The main product peak eluting at 18.6 min was collected and lyophilized to give the title compound as a colorless powder (10 mg, 35%). MS: m/e 1339.6 [M+H].

Example 39

Synthesis of 2-Sulfobenzaldehyde (E)-N-[3-(6-Hydrazinonicotinamido)propyl]-3-[6-[[(2,6-dichlorophenyl)thio]methyl]-3-(2-phenylethoxy)-2-pyridinyl]-2-propenamide Hydrazone

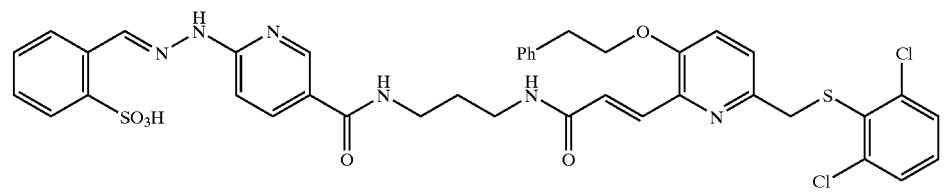

Part A Synthesis of (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide

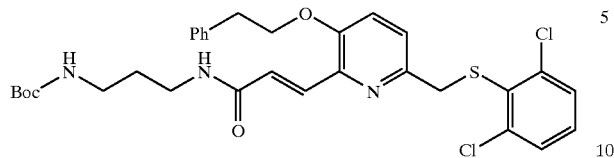

To a solution of (E)-3-[6-[[(2,6-dichlorophenyl)thio]methyl]-3-(2-phenylethoxy)-2-pyridinyl]-2-propenoic acid (702 mg, 1.52 mmol), tert-butyl N-(3-aminopropyl) carbamate (341 mg, 1.96 mmol), and TBTU (596 mg, 1.86 mmol) in DMF (10 ml) was added diisopropylethylamine (2.00 ml, 11.48 mmol). The reaction mixture was allowed to stir at room temperature for 3 hours, was concentrated, diluted with EtOAc, washed with water, saturated NaHCO₃, brine, dried (Na₂SO₄) and concentrated. The residue was purified by column chromatography (silica gel) using 3:1 EtOAc/CH₂Cl₂. Recovered the title compound (805 mg, 86%) as a dried white foam. ¹H NMR (D₆-DMSO) 8.18 (br t, NH), 7.63 (d, =CH), 7.51 (d, 2Ar—H), 7.45–7.10 (m, 8 Ar—H), 6.85 (m, NH), 6.79 (d, =CH), 4.23 (t, CH₂O), 4.15 (s, CH₂S), 3.16 (q, CH₂N), 3.07 (t, CH₂Ph), 2.95 (q, CH₂N), 1.57 (quintet, CH₂), 1.38 (s, t-Bu); ES-MS: [M+H]⁺=616.2; FAB-HRMS: [M+H]⁺=616.1815 (Calcd for C₃₁H₃₆Cl₂N₃O₄S=616.1804).

Part B Synthesis of 2-Sulfobenzaldehyde (E)-N-[3-(6-Hydrazinonicotinamido)propyl]-3-[6-[[(2,6-dichlorophenyl)thio]methyl]-3-(2-phenylethoxy)-2-pyridinyl]-2-propenamide Hydrazone To a solution of (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide (502 mg, 0.81 mmol) in CH₂Cl₂ (8 ml) was added TFA (4 ml, 51.92 mmol). The reaction mixture was allowed to stir at RT overnight, then was concentrated, diluted with CH₂Cl₂, concentrated, and dried under high-vacuum for 3 hours.

The crude residue and succinimidyl 2-sulfobenzaldehyde 6-hydrazinonicotinate hydrazone (410 mg, 0.93 mmol) was dissolved in DMF (5 ml), followed by the addition of Et₃N (1 ml, 7.18 mmol). The reaction mixture was allowed to stir at room temperature for 24 hours, and was concentrated to provide a dark oil. Purification of a portion of the crude product was accomplished by reversed-phase HPLC on a preparative Vydac C18 column (2.5×25 cm) using a gradient of 40 to 100% of solution B (90% acetonitrile/10% 0.05 M NH₄Oac) over 30 minutes, and solution A (100% 0.05 M NH₄Oac) to give the title compound (306 mg) as a pale yellow powder. Proton NMR spectral data indicated the presence of some triethylammonium salts, therefore, a second preparative HPLC under identical conditions was run to provide the title compound (126 mg) as a pale yellow powder. ¹H NMR (D₆-DMSO) 11.75 (br s, OH), 9.15 (br s, NH), 8.58 (s, 1H), 8.50 (br s, 1H), 8.27 (t, 1H), 8.15 (m, 2H), 7.80 (d, 1H), 7.64 (d, =CH), 7.55–7.00 (m, 15H), 6.90 (s, 1H), 6.81 (d, =CH), 4.23 (t, CH₂O), 4.15 (s, CH₂S), 3.31 (m, 2CH₂N), 3.07 (t, CH₂Ph), 1.74 (quintet, CH₂); ES-MS: [M–H]⁻=817.2; FAB-HRMS: [M+H]⁺=819.1577 (Calcd for C₃₉H₃₇Cl₂N₆O₆S₂=819.1593).

Example 40

Synthesis of 2-Sulfobenzaldehyde (E)-N-[3-(6-Hydrazinonicotinamido)propyl]-3-[6-[(phenylthio)methyl]-3-(2-phenylethoxy)-2-pyridinyl]-2-propenamide Hydrazone

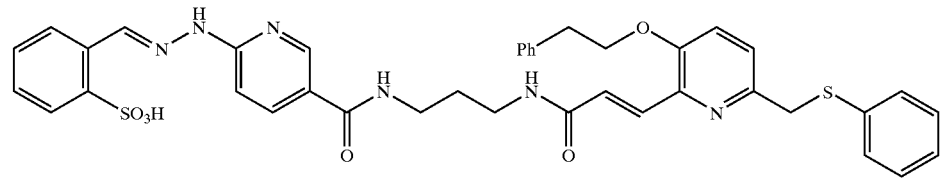

Part A Synthesis of (E)-N-[N-(tert-Butyloxycarbonyl)-3-aminopropyl]-3-[6-[(phenylthio)methyl]-3-(2-phenylethoxy)-2-pyridinyl]-2-propenamide

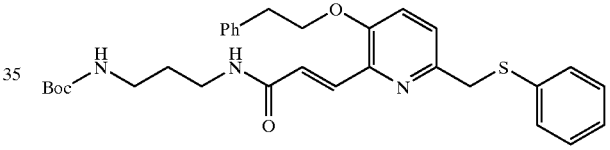

The title compound was prepared by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting (E)-3-[6-[(phenylthio)methyl]-3-(2-phenylethoxy)-2-pyridinyl]-2-propenoic acid. Recovered the title compound (773 mg, 98%) as a pale yellow solid which was used without further purification. ¹H NMR (D₆-DMSO) 8.30 (br t, NH), 7.71 (d, =CH), 7.48 (d, Ar—H), 7.40–7.10 (m, 11 Ar—H), 7.03 (d, =CH), 6.80 (t, NH), 4.28 (s, CH₂S), 4.25 (t, CH₂O), 3.17 (q, CH₂N), 3.08 (t, CH₂Ph), 2.96 (m, CH₂N), 1.57 (quintet, CH₂), 1.38 (s, t-Bu); ES-MS: [M+H]⁺=548.3.

Part B Synthesis of 2-Sulfobenzaldehyde (E)-N-[3-(6-Hydrazinonicotinamido)propyl]-3-[6-[(phenylthio)methyl]-3-(2-phenylethoxy)-2-pyridinyl]-2-propenamide Hydrazone The title compound was prepared by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2-pyridinyl]-2-propenamide Hydrazone, substituting (E)-N-[N-(tert-Butyloxycarbonyl)-3-aminopropyl]-3-[6-[(phenylthio)methyl]3(2 phenylethoxy)2 pyridinyl]-2-propenamide. Purification of a portion of the crude product was accomplished by reversed-phase HPLC on a preparative Vydac C18 column (2.5×25 cm) using a gradient of 40 to 100% of solution B (90% acetonitrile/10% 0.05 M NH₄Oac) over 30 minutes, and solution A (100% 0.05 M NH₄Oac) to give the title compound as a pale yellow powder. ¹H NMR (D$_6$-DMSO) 11.75 (br s, OH), 9.11 (br s, NH), 8.63 (s, 1H), 8.50 (br s, 1H), 8.39 (t, 1H), 8.12 (m, 2H), 7.81 (d, 1H), 7.74 (d, =CH), 7.50 –7.00 (m, 18H), 6.91 (s, 1H), 4.28 (s, CH$_2$S), 4.25 (t, CH$_2$O), 3.34 (m, 2CH$_2$N), 3.08 (t, CH$_2$Ph), 1.75 (quintet, CH$_2$); ES-MS: [M+H]$^+$=751.4; FAB-HRMS: [M+H]$^+$=751.2357 (Calcd for C$_{39}$H$_{39}$N$_6$O$_6$S$_2$=751.2372).

Example 41

Synthesis of 2-Sulfobenzaldehyde (E)-N-[3-(6-Hydrazinonicotinamido)propyl]-3-[6-[[(2-chlorophenyl)thio]methyl]-3-(2-phenylethoxy)-2-pyridinyl]-2-propenamide Hydrazone pyridinyl]-2-propenamide Hydrazone, substituting (E)-N-[N-(tert-Butyloxycarbonyl)-3-aminopropyl]-3-[6-[[(2-chlorophenyl)thio]methyl]-3-(2-phenylethoxy)-2-pyridinyl]-2-propenamide. Purification of a portion of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.75 (br s, OH), 9.13 (br s, NH), 8.61 (s, 1H), 8.50 (br s, 1H), 8.40 (t, 1H), 8.13 (m, 2H), 7.81 (d, 1H), 7.75 (d, =CH), 7.55–7.00 (m, 18H), 6.90 (s, 1H), 4.33 (s, CH$_2$S), 4.26 (t, CH$_2$O), 3.28 (m, 2CH$_2$N), 3.08

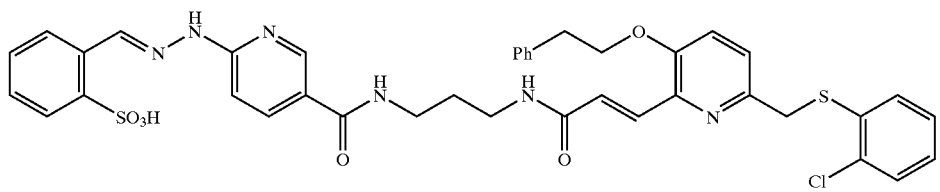

Part A Synthesis of (E)-N-[N-(tert-Butyloxycarbonyl)-3-aminopropyl]-3-[6-[[(2-chlorophenyl)thio]methyl]-3-(2-phenylethoxy)-2-pyridinyl]-2-propenamide

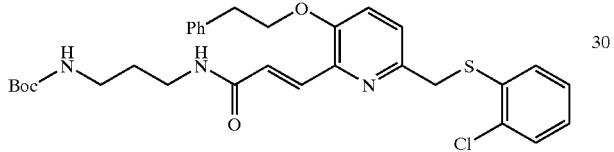

The title compound was prepared by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting (E)-3-[6-[[(2-chlorophenyl)thio]methyl]-3-(2-phenylethoxy)-2-pyridinyl]-2-propenoic acid. Recovered the title compound (847 mg, 97%) as a dried pale reddish foam which was used without further purification. $^1$H NMR (D$_6$-DMSO) 8.31 (br t, NH), 7.72 (d, =CH), 7.55–7.40 (m, 4Ar—H), 7.40–7.10 (m, 7 Ar—H), 7.04 (d, =CH), 6.85 (t, NH), 4.33 (s, CH$_2$S), 4.26 (t, CH$_2$O), 3.17 (q, CH$_2$N), 3.09 (t, CH$_2$Ph), 2.96 (m, CH$_2$N), 1.57 (quintet, CH$_2$), 1.38 (s, t-Bu); ES-MS: [M+H]$^+$=582.3.

Part B Synthesis of 2-Sulfobenzaldehyde (E)-N-[3-(6-Hydrazinonicotinamido)propyl]-3-[6-[[(2-chlorophenyl)thio]methyl]-3-(2-phenylethoxy)-2-pyridinyl]-2-propenamide Hydrazone The title compound was prepared by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2-

(t, CH$_2$Ph), 1.75 (quintet, CH$_2$); ES-MS: [M+H]$^+$=785.3; FAB-HRMS: [M+H]$^+$=785.2013 (Calcd for C$_{39}$H$_{38}$ClN$_6$O$_6$S$_2$=785.1983).

Example 42

Synthesis of 2-Sulfobenzaldehyde (E)-N-[3-(6-Hydrazinonicotinamido)propyl]-3-[6-[[(2,6-dimethylphenyl)thio]methyl]-3-(2-phenylethoxy)-2-pyridinyl]-2-propenamide Hydrazone H

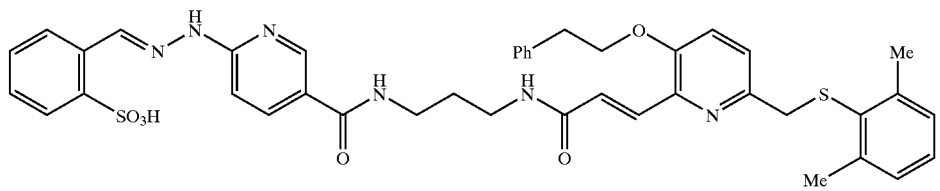

Part A Synthesis of (E)-N-[N-(tert-Butyloxycarbonyl)-3-aminopropyl]-3-[6-[[(2,6-dimethylphenyl)thio]methyl]-3-(2-phenylethoxy)-2-pyridinyl]-2-propenamide

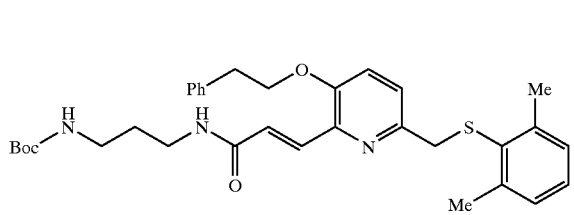

The title compound was prepared by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting (E)-3-[6-[[(2,6-dimethylphenyl)thio]methyl]-3-(2-phenylethoxy)-2-pyridinyl]-2-propenoic acid. Recovered the title compound (847 mg, 97%) as a dried pale reddish foam which was used without further purification. $^1$H NMR (D$_6$-DMSO) 8.25 (br t, NH), 7.69 (d, =CH), 7.40–7.15 (m, 6Ar—H), 7.15–7.00 (m, 3Ar—H), 6.95 (d, =CH), 6.88 (d, Ar—H), 6.80 (t, NH), 4.21 (t, CH$_2$O), 3.89 (s, CH$_2$S), 3.17 (q, CH$_2$N), 3.07 (t, CH$_2$Ph), 2.96 (q, CH$_2$N), 2.32 (s, 2Me), 1.57 (quintet, CH$_2$), 1.38 (s, t-Bu); ES-MS: [M+H]$^+$=576.4.

Part B Synthesis of 2-Sulfobenzaldehyde (E)-N-[3-(6-Hydrazinonicotinamido)propyl]-3-[6-[[(2,6-dimethylphenyl)thio]methyl]-3-(2-phenylethoxy)-2-pyridinyl]-2-propenamide Hydrazone The title compound was prepare by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2-pyridinyl]-2-propenamide Hydrazone, substituting (E)-N-[N-(tert-Butyloxycarbonyl)-3-aminopropyl]-3-[6-[[(2,6-dimethylphenyl)thio]methyl]-3-(2-phenylethoxy)-2-pyridinyl]-2-propenamide. Purification of a portion of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.75 (br s, OH), 9.12 (br s, NH), 8.63 (s, 1H), 8.50 (br s, 1H), 8.36 (t, 1H), 8.13 (m, 2H), 7.82 (d, 1H), 7.71 (d, =CH), 7.40–7.15 (m, 10H), 7.15–6.85 (m, 7H), 4.22 (t, CH$_2$O), 3.89 (s, CH$_2$S), 3.32 (m, 2CH$_2$N), 3.07 (t, CH$_2$Ph), 2.32 (s, 2CH$_3$), 1.75 (quintet, CH$_2$); ES-MS: [M+H]$^+$=779.4; FAB-HRMS: [M+H]$^+$=779.2691 (Calcd for C$_{41}$H$_{43}$N$_6$O$_6$S$_2$=779.2686).

Example 43

Synthesis of 2-Sulfobenzaldehyde (E)-N-[3-(6-Hydrazinonicotinamido)propyl]-3-[6-[[(2,3,5,6-tetrafluorophenyl)thio]methyl]-3-(2-phenylethoxy)-2-pyridinyl]-2-propenamide Hydrazone Part A Synthesis of (E)-N-[N-(tert-Butyloxycarbonyl)-3-aminopropyl]-3-[6-[[(2,3,5,6-tetrafluorophenyl)thio]methyl]-3-(2-phenylethoxy)-2-pyridinyl]-2-propenamide

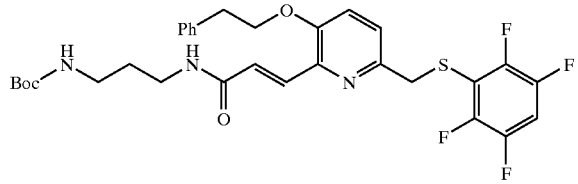

The title compound was prepared by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting (E)-3-[6-[[(2,3,5,6-tetrafluorophenyl)thio]methyl]-3-(2-phenylethoxy)-2-pyridinyl]-2-propenoic acid. Recovered the title compound (865 mg, 98%) as a dried pale yellow foam which was used without further purification. $^1$H NMR (D$_6$-DMSO) 8.22 (br t, NH), 7.89 (m, Ar—H), 7.63 (d, =CH), 7.48 (d, Ar—H), 7.35–7.20 (m, 6Ar—H), 6.83 (d, =CH), 6.80 (m, NH), 4.26 (t, CH$_2$O), 4.19 (s, CH$_2$S), 3.16 (q, CH$_2$N), 3.08 (t, CH$_2$Ph), 2.96 (m, CH$_2$N), 1.57 (quintet, CH$_2$), 1.38 (s, t-Bu); ES-MS: [M+H]$^+$=620.3.

Part B Synthesis of 2-Sulfobenzaldehyde (E)-N-[3-(6-Hydrazinonicotinamido)propyl]-3-[6-[[(2,3,5,6-tetrafluorophenyl)thio]methyl]-3-(2-phenylethoxy)-2-pyridinyl]-2-propenamide Hydrazone The title compound was prepared by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2-pyridinyl]-2-propenamide Hydrazone, substituting (E)-N-[N-(tert-Butyloxycarbonyl)-3-aminopropyl]-3-[6-[[(2,3,5,6-tetrafluorophenyl)thio]methyl]-3-(2-phenylethoxy)-2-pyridinyl]-2-propenamide. Purification of a portion of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.75 (br s, OH), 9.11 (br s, NH), 8.63 (s, 1H), 8.52 (br s, 1H), 8.32 (t, 1H), 8.12 (m, 2H), 7.90 (m, 2H), 7.65 (d, =CH), 7.50–7.15 (m, 11H), 7.10 (s, 1H), 6.90 (s, 1H), 6.87 (d, =CH), 4.25 (t, CH$_2$O), 4.19 (s, CH$_2$S), 3.34 (m, 2CH$_2$N), 3.08 (t, CH$_2$Ph), 1.75 (quintet, CH$_2$); ES-MS: [M+H]$^+$=823.4; FAB-HRMS: [M+H]$^+$=823.2014 (Calcd for C$_{39}$H$_{35}$F$_4$N$_6$O$_6$S$_2$=823.1996).

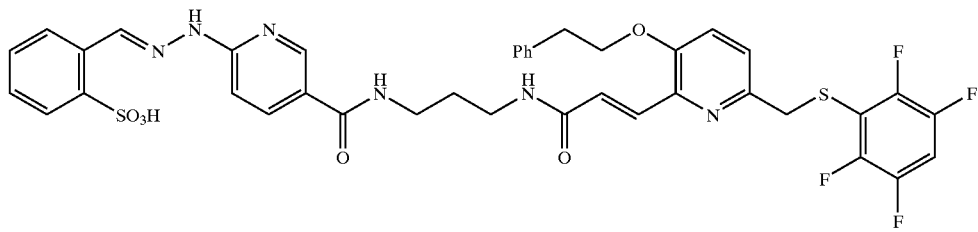

Example 44

Synthesis of 2-Sulfobenzaldehyde (E)-N-[3-(6-Hydrazinonicotinamido)propyl]-3-[6-[[(4-hydroxyphenyl)thio]methyl]-3-(2-phenylethoxy)-2-pyridinyl]-2-propenamide Hydrazone

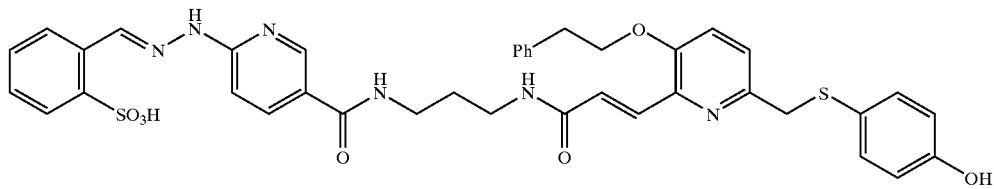

Part A Synthesis of (E)-N-[N-(tert-Butyloxycarbonyl)-3-aminopropyl]-3-[6-[[(4-hydroxyphenyl)thio]methyl]-3-(2-phenylethoxy)-2-pyridinyl]-2-propenamide

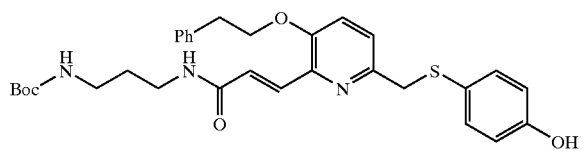

The title compound was prepared by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting (E)-N-[N-(tert-Butyloxycarbonyl)-3-aminopropyl]-3-[6-[[(4-hydroxyphenyl)thio]methyl]-3-(2-phenylethoxy)-2-pyridinyl]-2-propenamide. Recovered the title compound (675 mg, 99%) as a dried pale reddish foam which was used without further purification. $^1$H NMR (D$_6$-DMSO) 9.55 (s, OH), 8.28 (br t, NH), 7.71 (d, =CH), 7.44 (d, Ar—H), 7.35–7.10 (m, 8Ar—H), 7.00 (d, =CH), 6.82 (t, NH), 6.68 (d, Ar—H), 4.25 (t, CH$_2$O), 4.08 (s, CH$_2$S), 3.17 (q, CH$_2$N), 3.08 (t, CH$_2$Ph), 2.96 (q, CH$_2$N), 1.56 (quintet, CH$_2$), 1.38 (s, t-Bu); ES-MS: [M+H]$^+$=564.4.

Part B Synthesis of 2-Sulfobenzaldehyde (E)-N-[3-(6-Hydrazinonicotinamido)propyl]-3-[6-[[(4-hydroxyphenyl)thio]methyl]-3-(2-phenylethoxy)-2-pyridinyl]-2-propenamide Hydrazone The title compound was prepared by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2-pyridinyl]-2-propenamide Hydrazone, substituting (E)-N-[N-(tert-Butyloxycarbonyl)-3-aminopropyl]-3-[6-[[(4-hydroxyphenyl)thio]methyl]-3-(2-phenylethoxy)-2-pyridinyl]-2-propenamide. Purification of a portion of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.75 (br s, OH), 9.57 (br s, OH), 9.13 (br s, NH), 8.64 (s, 1H), 8.50 (br s, 1H), 8.38 (t, 1H), 8.14 (m, 2H), 7.82 (d, 1H), 7.73 (d, =CH), 7.45–6.90 (m, 15H), 6.70 (d, 2H), 4.24 (t, CH$_2$O), 4.07 (s, CH$_2$S), 3.35 (m, 2CH$_2$N), 3.08 (t, CH$_2$Ph), 1.75 (quintet, CH$_2$); ES-MS: [M+H]$^+$=767.3; FAB-HRMS: [M+H]$^+$=767.2335 (Calcd for C$_{39}$H$_{39}$N$_6$O$_7$S$_2$=767.2322).

Example 45

Synthesis of 2-Sulfobenzaldehyde (E)-N-[2-(6-Hydrazinonicotinamido)ethyl]-3-[6-[[(2,6-dichlorophenyl)thio]methyl]-3-(2-phenylethoxy)-2-pyridinyl]-2-propanamide Hydrazone

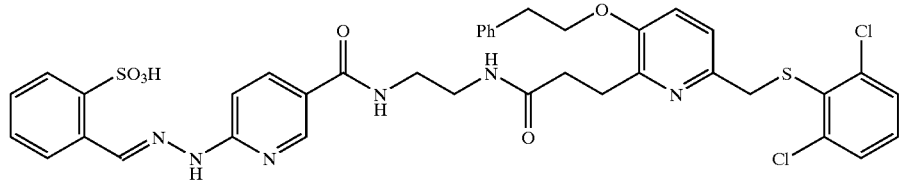

Part A Synthesis of (E)-N-[N-(tert-Butyloxycarbonyl)-2-aminoethyl]-3-[6-[[(2,6-dichlorophenyl)thio]methyl]-3-(2-phenylethoxy)-2-pyridinyl]-2-propanamide

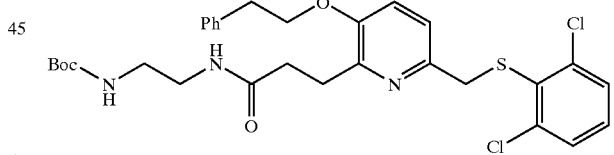

The title compound was prepared by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propanamide and tert-butyl N-(3-aminoethyl) carbamate and was used without further purification. ES-MS: [M+H]$^+$=604.2.

Part B Synthesis of 2-Sulfobenzaldehyde (E)-N-[2-(6-Hydrazinonicotinamido)ethyl]-3-[6-[[(2,6-dichlorophenyl)thio]methyl]-3-(2-phenylethoxy)-2-pyridinyl]-2-propanamide Hydrazone The title compound was prepare by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2- pyridinyl]-2-propenamide Hydrazone, substituting (E)-N-[N-(tert-Butyloxycarbonyl)-2-aminoethyl]-3-[6-[[(2,6-dichlorophenyl)thio]methyl]-3-(2-phenylethoxy)-2-pyridinyl]-2-propanamide. Purification of a portion of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.75 (br s, OH), 9.01 (br s, NH), 8.61 (s, 1H), 8.40 (t, 1H), 8.03 (t, 2H), 7.92 (t, 1H), 7.77 (d, 1H), 7.48 (d, 2H), 7.40–7.10 (m, 11H), 6.94 (d, 1H), 4.15 (t, CH$_2$O), 4.08 (s, CH$_2$S), 3.29 (m, 2CH$_2$N), 3.17 (t, CH$_2$Ph), 3.02 (m, CH$_2$Ar), 2.26 (m, CH$_2$CO); ES-MS: [M+H]$^+$=807.2; FAB-HRMS: [M+H]$^+$=807.1609 (Calcd for C$_{38}$H$_{37}$Cl$_2$N$_6$O$_6$S$_2$=807.1593).

Example 46

Synthesis of 2-Sulfobenzaldehyde N-[3-(6-Hydrazinonicotinamido)propyl]-1-[3-([1,1'-biphenyl]-4-ylmethyl)-2H-1-benzopyran-7-yl]-cyclopentanecarboxamide Hydrazone 1-benzopyran-7-yl]-cyclopentanecarboxylic acid. Recovered the title compound (530 mg, 98%) as a colorless glass which was used without further purification. $^1$H NMR (D$_6$-DMSO) 7.62 (m, 4ArH), 7.50–7.30 (m, 3Ar—H, NH), 7.25 (m, 3ArH), 6.86 (d, ArH), 6.74 (s, ArH), 6.70 (m, NH), 5.45 (d, OH), 4.29 (t, CHO), 4.03 (dABq, CH$_2$O), 2.95 (q, CH$_2$N), 2.80 (q, CH$_2$N), 2.70 (m, 1H), 2.45 (m, CH$_2$Ar), 2.10 (m, 1H), 1.80–1.50 (m, 6H), 1.40 (m, 2H), 1.35 (s, t-Bu); ES-MS: [M+H]$^+$=585.4; FAB-HRMS: [M+H]$^+$=585.3345 (Calcd for C$_{36}$H$_{45}$N$_2$O$_5$=585.3328).

Part B Synthesis of 2-Sulfobenzaldehyde N-[3-(6-Hydrazinonicotinamido)propyl]-1-[3-([1,1'-biphenyl]-4-ylmethyl)-2H-1-benzopyran-7-yl]-cyclopentanecarboxamide Hydrazone The title compound was prepared by the general procedure described above for 2-Sulfobenzaldehyde (E)-N-[3-(6-Hydrazinonicotinamide)propyl]-3-[6-[[(2,6-dichlorophenyl)thio]methyl]-3-(2-phenylethoxy)-2-pyridinyl]-2-propenamide Hydrazone, substituting (trans)-N-[N-(tert-Butyloxycarbonyl)-3-aminopropyl]-1-[3-([1,1'-biphenyl]-4-ylmethyl)-3,4-dihydro-4-hydroxy-2H-1-benzopyran-7-yl]-cyclopentanecarboxamide. Purification of

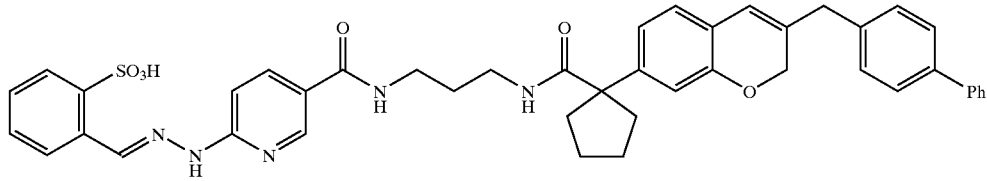

Part A Synthesis of (trans)-N-[N-(tert-Butyloxycarbonyl)-3-aminopropyl]-1-[3-([1,1'-biphenyl]-4-ylmethyl)-3,4-dihydro-4-hydroxy-2H-1-benzopyran-7-yl]-cyclopentanecarboxamide

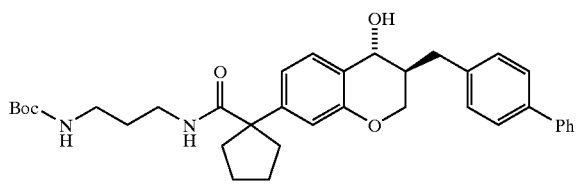

The title compound was prepare by the general procedure described above for (E)-N-[N-(tert-Butyloxycarbonyl)-3-aminopropyl]-3-[6-[[(2,6-dichlorophenyl)thio]methyl]-3-(2-phenylethoxy)-2-pyridinyl]-2-propenamide, substituting [3-([1,1'-biphenyl]-4-ylmethyl)-3,4-dihydro-4-hydroxy-2H- a portion of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.50 (br s, OH), 9.00 (br s, NH), 8.56 (s, 1H), 8.30 (br s, 1H), 8.04 (m, 2H), 7.78 (d, 1H), 7.65 (m, 4H), 7.50–6.80 (m, 14H), 6.70 (s, 1H), 6.24 (s, =CH), 4.63 (s, CH$_2$O), 3.08 (m, 2CH$_2$N), 2.45 (m, 2H), 1.80–1.50 (m, 8H); ES-MS: [M–H]$^-$=768.3.

Example 47

Synthesis of 2-Sulfobenzaldehyde 6-[5-(6-Hydrazinonicotinamido)pentyloxy]-5-(2-propenyl)-1,2,3,4-tetrahydronaphthalen-1-one Hydrazone

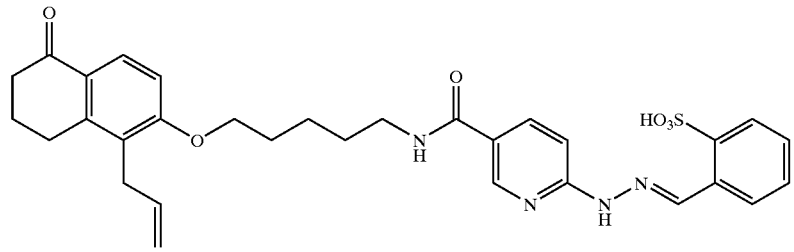

151

Part A Synthesis of 6-[N-(tert-Butyloxycarbonyl)-5-aminopentyloxy]-5-(2-propenyl)-1,2,3,4-tetrahydronaphthalen-1-one

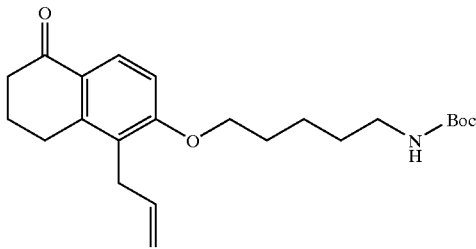

To a solution of 6-hydroxy-5-(2-propenyl)-1,2,3,4-tetrahydronaphthalen-1-one (1.00 g, 4.94 mmol), tert-butyl N-(5-hydroxypentyl)carbamate (1.10 g, 4.97 mmol), and PPh₃ (1.30 g, 4.96 mmol) in anhydrous THF (31 ml), cooled in an ice-bath, was added diethyl azodicarboxylate (2.00 ml, 11.48 mmol) over 15 minutes. The reaction mixture was allowed to stir at 0° C. for 15 minutes, then slowly warm to room temperature over 1 hour. The reaction mixture was concentrated, triturated with hexane/EtOAc (4:1), cooled to 0° C., filtered, and the filtrate was concentrated. The residue was purified by column chromatography (silica gel) using 3:1 hexane/EtOAc. Recovered the title compound (1.55 g, 81%) as a white solid. ¹H NMR (CDCl₃) 7.99 (d, ArH), 6.81 (d, ArH), 5.86 (m, =CH), 4.96 (dd, =CHH), 4.89 (dd, =CHH), 4.50 (br s, NH), 4.01 (t, CH₂O), 3.42 (m, CH₂C=), 3.12 (q, CH₂N), 2.88 (t, CH₂Ar), 2.57 (t, CH₂CO), 2.08 (quintet, CH₂), 1.81 (quintet, CH₂), 1.51 (m, 2CH₂), 1.43 (s, t-Bu); ES-MS: [M+H]⁺=388.3.

Part B Synthesis of 2-Sulfobenzaldehyde 6-[5-(6-Hydrazinonicotinamido)pentyloxy]-5-(2-propenyl)-1,2,3,4-tetrahydronaphthalen-1-one Hydrazone To a solution of 6-[N-(tert-Butyloxycarbonyl)-5-aminopentyloxy]-5-(2-propenyl)-1,2,3,4-tetrahydronaphthalen-1-one (502 mg, 0.81 mmol) in CH₂Cl₂ (8 ml) was added TFA (4 ml, 51.92 mmol). The reaction mixture was allowed to stir at RT for 3 hours, then was concentrated, diluted with CH₂Cl₂, concentrated, and dried under high-vacuum overnight. ¹H NMR (CDCl₃) 8.86 (br s, NH₃), 7.94 (d, ArH), 7.44 (br s, 2H), 6.77 (d, ArH), 5.83 (m, =CH), 4.94 (dd, =CHH), 4.84 (dd, =CHH), 4.01 (t, CH₂O), 3.40 (m, CH₂C=), 3.06 (q, CH₂N), 2.86 (t, CH₂Ar), 2.60 (t, CH₂CO), 2.07 (quintet, CH₂), 1.80 (m, 2CH₂), 1.51 (m, CH₂); ES-MS: [M+H]⁺=288.3.

The crude amine.TFA salt (100 mg, 0.25 mmol) and succinimidyl 2-sulfobenzaldehyde 6-hydrazinonicotinate hydrazone (131.6 mg, 0.30 mmol) was dissolved in DMF (2 ml), followed by the addition of Et₃N (200 μl, 1.44 mmol). The reaction mixture was allowed to stir at room temperature for 48 hours, and was concentrated. Purification of the crude product was accomplished by reversed-phase HPLC on a preparative Vydac C18 column (2.5×25 cm) using a gradient of 40 to 100% of solution B (90% acetonitrile/10% 0.05 M NH₄Oac) over 30 minutes, and solution A (100% 0.05 M NH₄Oac) to give the title compound (39 mg) as a yellow solid. Proton NMR spectral data indicated the presence of some triethylammonium salts. ¹H NMR (D₆-DMSO) 9.05 (br s, NH), 8.58 (s, 1H), 8.35 (br s, 1H), 8.05 (br d, 2H), 7.82 (d, ArH), 7.78 (dd, 1H), 7.34 (m, 1H), 7.23 (d, 1H), 7.01 (d, ArH), 5.81 (m, =CH), 4.90 (m, =CHH), 4.07 (t, CH₂O), 3.37 (m, CH₂C=, CH₂N), 3.10 (m, CH₂N salt), 2.85 (t, CH₂), 2.50 (m, CH₂), 1.98 (quintet, CH₂), 1.78 (quintet, CH₂), 1.55 (m, 2CH₂), 1.18 (t, CH₃CH₂N salt); ES-MS: [M+H]⁺=591.4; FAB-HRMS: [M+H]⁺=591.2276 (Calcd for C₃₁H₃₅N₄O₆S=591.2277).

Example 48

Synthesis of 2-Sulfobenzaldehyde 6-[6-(6-Hydrazinonicotinamido)hexyloxy]-5-(2-propenyl)-1,2,3,4-tetrahydronaphthalen-1-one Hydrazone

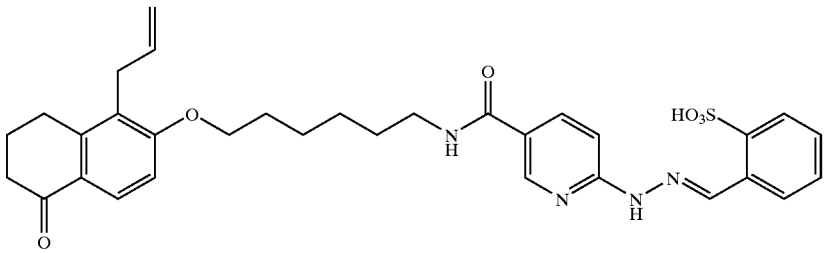

Part A Synthesis of 6-[N-(tert-Butyloxycarbonyl)-6-amninohexyloxy]-5-(2-propenyl)-1,2,3,4-tetrahydronaphthalen-1-one

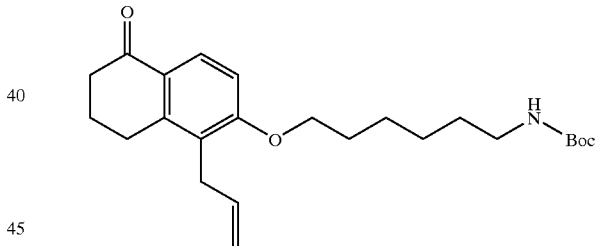

The title compound was prepare by the general procedure described above for 6-[N-(tert-Butyloxycarbonyl)-5-aminopentyloxy]-5-(2-propenyl)-1,2,3,4-tetrahydronaphthalen-1-one substituting tert-butyl N-(6-hydroxyhexyl) carbamate. Recovered the title compound as a white solid. ¹H NMR (D₆-DMSO) 7.82 (d, ArH), 6.99 (d, ArH), 6.76 (br t, NH), 5.84 (m, =CH), 4.96 (dd, =CHH), 4.91 (dd, =CHH), 4.04 (t, CH₂O), 3.40 (d, CH₂C=), 2.86 (m, 2CH₂), 2.50 (m, CH₂), 1.98 (quintet, CH₂), 1.71 (quintet, CH₂), 1.36 (m, 3CH₂), 1.36 (s, t-Bu); ES-MS: [M+H]⁺=402.5.

Part B Synthesis of 2-Sulfobenzaldehyde 6-[6-(6-Hydrazinonicotinamido)hexyloxy]-5-(2-propenyl)-1,2,3,4-tetrahydronaphthalen-1-one Hydrazone The title compound was prepare by the general procedure described above for 2-Sulfobenzaldehyde 6-[5-(6-Hydrazinonicotinamido)pentyloxy]-5-(2-propenyl)-1,2,3,4-tetrahydronaphthalen-1-one Hydrazone, substituting 6-[N-(tert-Butyloxycarbonyl)-6-aminohexyloxy]-5-(2-propenyl)-1,2,3,4-tetrahydronaphthalen-1-one. Purification of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. Proton NMR spectral data indicated the presence of some triethylammonium salts. $^1$H NMR (D$_6$-DMSO) 11.45 (br s, OH), 9.04 (br s, NH), 8.57 (s, 1H), 8.35 (br s, 1H), 8.06 (br d, 2H), 7.82 (d, ArH), 7.78 (dd, 1H), 7.34 (m, 1H), 7.22 (d, 1H), 7.00 (d, ArH), 5.83 (m, =CH), 4.94 (m, =CHH), 4.06 (t, CH$_2$O), 3.38 (m, CH$_2$C=), 3.26 (q, CH$_2$N), 3.10 (m, CH$_2$N salt), 2.85 (t, CH$_2$), 2.50 (m, CH$_2$), 1.98 (quintet, CH$_2$), 1.75 (quintet, CH$_2$), 1.50 (m, 3CH$_2$), 1.17 (t, CH$_3$CH$_2$N salt); ES-MS: [M−H]$^-$=603.2; FAB-HRMS: [M+H]$^+$=605.2433 (Calcd for C$_{32}$H$_{37}$N$_4$O$_6$S=605.2434).

Example 49

Synthesis of 2-Sulfobenzaldehyde 6-[6-(6-Hydrazinonicotinamido)-4,4-dimethylpentyloxy]-5-(2-propenyl)-1,2,3,4-tetrahydronaphthalen-1-one Hydrazone

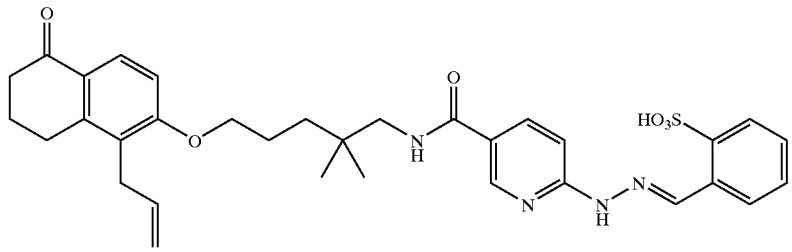

Part A Synthesis of 5-(tert-Butyldimethylsilyloxy)-2,2-dimethylpentanenitrile

To a solution of LDA.THF in cyclohexane (1.5 M, 100 ml, 150 mmol) and anhydrous THF (100 ml) cooled to −78° C. was added isobutyronitrile (10.00 g, 144.70 mmol) over 15 minutes. The reaction mixture was allowed to warm to −40° C. over 30 minutes, recooled to −78° C., then 3-(tert-butyldimethylsilyloxy)propyl bromide (26.08 g, 102.98 mmol) was added dropwise over 30 minutes. The reaction mixture was allowed to warm to 0° C. over 1 hour, quenched with 1 N HCl, extracted with ether, and the combined extracts were washed with H$_2$O, saturated NaHCO$_3$, brine, dried (Na$_2$SO$_4$), and concentrated. Recovered the title compound (22.23 g, 89.4%) as a pale yellow liquid which was used without further purification. $^1$H NMR (CDCl$_3$) 3.64 (t, CH$_2$O), 1.60 (m, 2CH$_2$), 1.34 (s, 2CH$_3$), 0.88 (s, t-Bu), 0.04 (s, 2CH$_3$Si); ES-MS: [M+H]$^+$=242.1.

Part B Synthesis of (5-Hydroxyl-2,2-dimethylpentyl)ammonium chloride

To a solution of 5-(tert-Butyldimethylsilyloxy)-2,2-dimethylpentanenitrile (5.00 g, 20.71 mmol) in MeOH (50 ml)/H$_2$O (5 ml) was added concentrated HCl (2.5 ml, 30.0 mmol) followed by PtO$_2$ (100 mg). The mixture was hydrogenated on a Parr apparatus at 60 psi for 36 hours, the catalyst was removed by filtration, and the reaction mixture was concentrated. Recovered the title compound (4.72 g, contained residual methanol) as a colorless oil which which was used without further purification. $^1$H NMR (D$_6$-DMSO) 7.97 (br s, NH$_3$), 3.36 (t, CH$_2$O), 2.59 (q, CH$_2$N), 1.30 (m, 2CH$_2$), 0.90 (s, 2CH$_3$); ES-MS: [M+H]$^+$=132.0.

Part C Synthesis of N-(tert-Butyloxycarbonyl)-5-amino-4,4-dimethylpentanol

To a suspension of (5-Hydroxyl-2,2-dimethylpentyl) ammonium chloride (crude, 20.78 mmol) in CH$_2$Cl$_2$ (50 ml), cooled in an ice-bath, was added Et$_3$N (3 ml, 21.52 mmol) followed by Boc$_2$O (5.1 ml, 22.20 mmol). The cooling bath was removed and the reaction mixture was allowed to stir at room temperature for 18 hours. The reaction mixture was concentrated, partitioned between EtOAc/H$_2$O, and the organic layer was washed with 5% citric acid, H$_2$O, saturated NaHCO$_3$, brine, dried (Na$_2$SO$_4$), and concentrated. The residue was purified by column chromatography (silica gel) using 3:1 to 1:1 hexane/EtOAc. Recovered the title compound (4.45 g, 93%) as a colorless oil. $^1$H NMR (CDCl$_3$) 4.60 (br s, NH), 3.60 (t, CH$_2$O), 2.92 (d, CH$_2$N), 1.74 (br s, OH), 1.51 (m, CH$_2$), 1.42 (s, t-Bu), 1.25 (m, CH$_2$), 0.84 (s, 2CH$_3$); ES-MS: [M+H]$^+$=232.1.

Part D Synthesis of 6-[N-(tert-Butyloxycarbonyl)-5-amino-4,4-dimethylpentyloxy]-5-(2-propenyl)-1,2,3,4-tetrahydronaphthalen-1-one The title compound was prepared by the general procedure described above for 6-[N-(tert-Butyloxycarbonyl)-5-aminopentyloxy]-5-(2-propenyl)-1,2,3,4-tetrahydronaphthalen-1-one, substituting N-(tert-Butyloxycarbonyl)-5-amino-4,4-dimethylpentanol. Recovered the title compound as a crude pale yellow oil. ES-MS: [M+H]$^+$=416.2.

Part E Synthesis of 2-Sulfobenzaldehyde 6-[5-(6-Hydrazinonicotinamido)-4,4-dimethylpentyloxy]-5-(2-propenyl)-1,2,3,4-tetrahydronaphthalen-1-one Hydrazone The title compound was prepare by the general procedure described above for 2-Sulfobenzaldehyde 6-[5-(6-Hydrazinonicotinamido)pentyloxy]-5-(2-propenyl)-1,2,3,4-tetrahydronaphthalen-1-one Hydrazone, substituting 6-[N-(tert-Butyloxycarbonyl)-5-amino-4,4-dimethylpentyloxy]-5-(2-propenyl)-1,2,3,4-tetrahydronaphthalen-1-one. Purification of the crude product was accomplished by reversed-phase HPLC on a preparative Vydac C18 column (2.5×25 cm) using a gradient of 40 to 100% of solution B (90% acetonitrile/10% 0.05 M NH$_4$Oac) over 30 minutes, and solution A (100% 0.05 M NH$_4$Oac) to give the title compound as a pale yellow powder. $^1$H NMR (D$_6$-DMSO) 11.40 (br s, OH), 9.01 (s, NH), 8.61 (s, 1H), 8.17 (br t, 1H), 8.03 (t, 2H), 7.82 (d, ArH), 7.78 (dd, 1H), 7.40–7.20 (m, 3H), 6.99 (d, ArH), 5.82 (m, =CH), 4.89 (m, =CHH), 4.03 (br t, CH$_2$O), 3.36 (m, CH$_2$C=), 3.14 (d, CH$_2$N), 2.84 (m, CH$_2$), 2.50 (m, CH$_2$), 1.97 (m, CH$_2$), 1.75 (m, CH$_2$), 1.40 (m, CH$_2$), 0.89 (s, 2CH$_3$); ES-MS: [M+H]$^+$=619.3; FAB-HRMS: [M+H]$^+$=619.2610 (Calcd for C$_{33}$H$_{39}$N$_4$O$_6$S=619.2590).

Example 50

Synthesis of 2-Sulfobenzaldehyde 6-[6-(6-Hydrazinonicotinamido)-5,5-dimethylhexyloxy]-5-(2-propenyl)-1,2,3,4-tetrahydronaphthalen-1-one Hydrazone

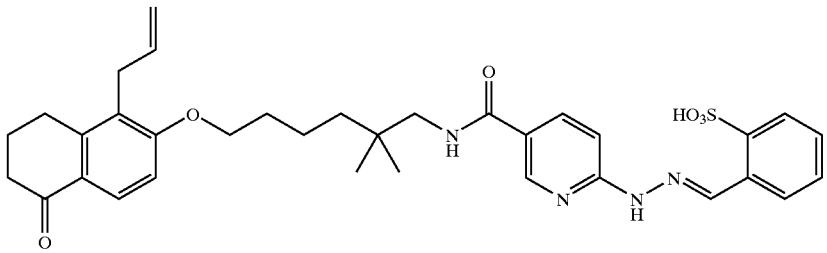

Part A Synthesis of 6-(tert-Butyldimethylsilyloxy)-2,2-dimethylhexanenitrile

The title compound was prepare using the procedure described above for 5-(tert-Butyldimethylsilyloxy)-2,2-dimethylpentanenitrile. Recovered the title compound as a pale yellow liquid which was used without further purification. $^1$H NMR (CDCl$_3$) 3.62 (br t, CH$_2$O), 1.52 (br s, 3CH$_2$), 1.32 (s, 2CH$_3$), 0.88 (s, t-Bu), 0.04 (s, 2CH$_3$Si); ES-MS: [M+H]$^+$=256.1.

Part B Synthesis of (6-Hydroxyl-2,2-dimethylhexyl) ammonium chloride

The title compound was prepare using the procedure described above for (5-Hydroxyl-2,2-dimethylpentyl) ammonium chloride. Recovered the title compound as a colorless oil which which was used without further purification. $^1$H NMR (D$_6$-DMSO) 8.02 (br s, NH$_3$), 3.38 (t, CH$_2$O), 2.58 (q, CH$_2$N), 1.38 (m, CH$_2$), 1.22 (m, 2CH$_2$), 0.89 (s, 2CH$_3$); ES-MS: [M+H]$^+$=146.0.

Part C Synthesis of N-(tert-Butyloxycarbonyl)-6-amino-5,5-dimethylhexanol

The title compound was prepare using the procedure described above for N-(tert-Butyloxycarbonyl)-5-amino-4,4-dimethylpentanol. Recovered the title compound as a colorless oil. $^1$H NMR (CDCl$_3$) 4.60 (br s, NH), 3.58 (t, CH$_2$O), 2.88 (d, CH$_2$N), 2.19 (br s, OH), 1.49 (m, CH$_2$), 1.40 (s, t-Bu), 1.40–1.10 (m, 2CH$_2$), 0.81 (s, 2CH$_3$); ES-MS: [M+H]$^+$=246.1.

Part D Synthesis of 6-[N-(tert-Butyloxycarbonyl)-6-amino-5,5-dimethylhexyloxy]-5-(2-propenyl)-1,2,3,4-tetrahydronaphthalen-1-one The title compound was prepare by the general procedure described above for 6-[N-(tert-Butyloxycarbonyl)-5-aminopentyloxy]-5-(2-propenyl)-1,2,3,4-tetrahydronaphthalen-1-one, substituting N-(tert-Butyloxycarbonyl)-6-amino-5,5-dimethylhexanol. Recovered the title compound as a pale yellow oil. $^1$H NMR (CDCl$_3$) 7.69 (d, ArH), 6.81 (d, ArH), 6.75 (br m, NH), 5.85 (m, =CH), 4.94 (m, =CHH), 4.04 (t, CH$_2$O), 3.37 (m, CH$_2$C=), 3.35 (m, CH$_2$N), 2.82 (t, CH$_2$), 2.46 (t, CH$_2$), 1.96 (quintet, CH$_2$), 1.68 (m, CH$_2$), 1.36 (s, t-Bu), 1.17 (m, 2CH$_2$), 0.76 & 0.74 (2s, 2CH$_3$); ES-MS: [M+H]$^+$=430.3.

Part E Synthesis of 2-Sulfobenzaldehyde 6-[6-(6-Hydrazinonicotinamido)-5,5-dimethylhexyloxy]-5-(2-propenyl)-1,2,3,4-tetrahydronaphthalen-1-one Hydrazone The title compound was prepare by the general procedure described above for 2-Sulfobenzaldehyde 6-[5-(6-Hydrazinonicotinamido)pentyloxy]-5-(2-propenyl)-1,2,3,4-tetrahydronaphthalen-1-one Hydrazone, substituting 6-[N-(tert-Butyloxycarbonyl)-6-amino-5,5-dimethylhexyloxy]-5-(2-propenyl)-1,2,3,4-tetrahydronaphthalen-1-one. Purification of the crude product was accomplished by reversed-phase HPLC on a preparative Vydac C18 column (2.5×25 cm) using a gradient of 40 to 100% of solution B (90% acetonitrile/10% 0.05 M NH4Oac) over 30 minutes, and solution A (100% 0.05 M NH4Oac) to give the title compound as a pale yellow powder. $^1$H NMR (D$_6$-DMSO) 11.50 (br s, OH), 9.09 (br s, NH), 8.56 (s, 1H), 8.20 (br s, 1H), 8.09 (m, 2H), 7.82 (d, ArH), 7.78 (dd, 1H), 7.40–7.15 (m, 4H), 7.08 (s, 1H), 6.99 (d, ArH), 6.89 (s, 1H), 5.85 (m, =CH), 4.94 (m, =CHH), 4.06 (br t, CH$_2$O), 3.35 (m, CH$_2$C=), 3.13 (d, CH$_2$N), 2.84 (br t, CH$_2$), 2.50 (m, CH$_2$), 1.98 (m, CH$_2$), 1.71 (m, CH$_2$), 1.45 (m, CH$_2$), 1.30 (m, CH$_2$), 0.86 (s, 2CH$_3$); ES-MS: [M+H]$^+$=633.3; FAB-HRMS: [M+H]$^+$=633.2752 (Calcd for C$_{34}$H$_{41}$N$_4$O$_6$S= 633.2747).

Example 51

Synthesis of 2-Sulfobenzaldehyde 6-[4-(6-Hydrazinonicotinamido)butoxy]-5-(2-propenyl)-1,2,3,4-tetrahydronaphthalen-1-one Hydrazone

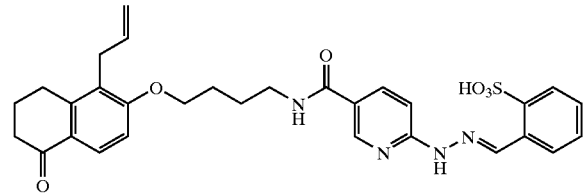

Part A Synthesis of 6-[N-(tert-Butyloxycarbonyl)-4-aminobutoxy]-5-(2-propenyl)-1,2,3,4-tetrahydronaphthalen-1-one The title compound was prepare by the general procedure described above for 6-[N-(tert-Butyloxycarbonyl)-5-aminopentyloxy]-5-(2-propenyl)-1,2,3,4-tetrahydronaphthalen-1-one, substituting N-(tert-Butyloxycarbonyl)-4-aminobutanol. Recovered the title compound as a white solid. $^1$H NMR (CDCl$_3$) 7.98 (d, ArH), 6.80 (d, ArH), 5.85 (m, =CH), 4.94 (dd, =CHH), 4.88 (dd, =CHH), 4.55 (br s, NH), 4.03 (t, CH$_2$O), 3.42 (m, CH$_2$C=), 3.17 (q, CH$_2$N), 2.87 (t, CH$_2$), 2.57 (t, CH$_2$), 2.07 (quintet, CH$_2$), 1.82 (quintet, CH$_2$), 1.68 (quintet, CH$_2$), 1.43 (s, t-Bu); ES-MS: [M+H]$^+$=374.4.

Part B Synthesis of 2-Sulfobenzaldehyde 6-[4-(6-Hydrazinonicotinamido)butoxy]-5-(2-propenyl)-1,2,3,4-tetrahydronaphthalen-1-one Hydrazone The title compound was prepare by the general procedure described above for 2-Sulfobenzaldehyde 6-[5-(6-Hydrazinonicotinamido)pentyloxy]-5-(2-propenyl)-1,2,3,4-tetrahydronaphthalen-1-one Hydrazone, substituting 6-[N-(tert-Butyloxycarbonyl)-

4-aminobutoxy]-5-(2-propenyl)-1,2,3,4-tetrahydronaphthalen-1-one. Purification of the crude product was accomplished by reversed-phase HPLC on a preparative Vydac C18 column (2.5×25 cm) using a gradient of 40 to 100% of solution B (90% acetonitrile/10% 0.05 M NH₄Oac) over 30 minutes, and solution A (100% 0.05 M NH₄Oac) to give the title compound as a pale yellow powder. Proton NMR spectral data indicated the presence of some triethylammonium salts. $^1$H NMR (D$_6$-DMSO) 11.45 (br s, OH), 9.04 (br s, NH), 8.56 (s, 1H), 8.40 (br s, 1H), 8.05 (br s, 2H), 7.82 (d, ArH), 7.77 (dd, 1H), 7.35 (m, 1H), 7.22 (d, 1H), 7.02 (d, ArH), 5.84 (m, =CH), 4.93 (m, =CHH), 4.10 (t, CH$_2$O), 3.40 (m, CH$_2$C=), 3.25 (m, CH$_2$N), 3.10 (m, CH$_2$N salt), 2.84 (t, CH$_2$), 2.50 (m, CH$_2$), 1.98 (quintet, CH$_2$), 1.80–1.55 (m, 2CH$_2$), 1.17 (t, CH$_3$CH$_2$N salt); ES-MS: [M−H]−=575.3; FAB-HRMS: [M+H]⁺=577.2130 (Calcd for C$_{30}$H$_{33}$N$_4$O$_6$S=577.2121).

Example 52

Synthesis of 2-Sulfobenzaldehyde 6-[3-(6-Hydrazinonicotinamido)propoxy]-5-(2-propenyl)-1,2,3,4-tetrahydronaphthalen-1-one Hydrazone

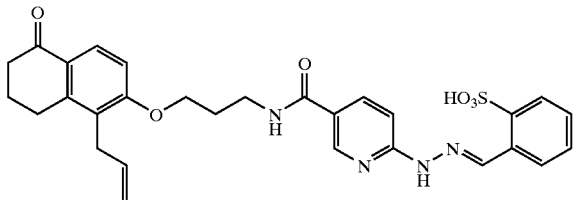

Part A Synthesis of 6-[N-(tert-Butyloxycarbonyl)-3-aminopropoxy]-5-(2-propenyl)-1,2,3,4-tetrahydronaphthalen-1-one The title compound was prepare by the general procedure described above for 6-[N-(tert-Butyloxycarbonyl)-5-aminopentyloxy]-5-(2-propenyl)-1,2,3,4-tetrahydronaphthalen-1-one, substituting N-(tert-Butyloxy- carbonyl)-3-aminopropanol. Recovered the title compound as a white solid. $^1$H NMR (CDCl$_3$) 8.00 (d, ArH), 6.82 (d, ArH), 5.90 (m, =CH), 4.98 (dd, =CHH), 4.86 (dd, =CHH), 4.75 (br s, NH), 4.08 (t, CH$_2$O), 3.43 (d, CH$_2$C=), 3.32 (q, CH$_2$N), 2.88 (t, CH$_2$), 2.58 (t, CH$_2$), 2.08 (quintet, CH$_2$), 2.02 (quintet, CH$_2$), 1.43 (s, t-Bu); ES-MS: [M+H]⁺=360.3.

Part B Synthesis of 2-Sulfobenzaldehyde 6-[3-(6-Hydrazinonicotinamido)propoxy]-5-(2-propenyl)-1,2,3,4-tetrahydronaphthalen-1-one Hydrazone The title compound was prepare by the general procedure described above for 2-Sulfobenzaldehyde 6-[5-(6-Hydrazinonicotinamido)pentyloxy]-5-(2-propenyl)-1,2,3,4-tetrahydronaphthalen-1-one Hydrazone, substituting 6-[N-(tert-Butyloxycarbonyl)-3-aminopropoxy]-5-(2-propenyl)-1,2,3,4-tetrahydronaphthalen-1-one. Purification of the crude product was accomplished by reversed-phase HPLC on a preparative Vydac C18 column (2.5×25 cm) using a gradient of 40 to 100% of solution B (90% acetonitrile/10% 0.05 M NH₄Oac) over 30 minutes, and solution A (100% 0.05 M NH₄Oac) to give the title compound as an off-white powder. Proton NMR spectral data indicated the presence of some triethylammonium salts. $^1$H NMR (D$_6$-DMSO) 9.04 (br s, NH), 8.58 (s, 1H), 8.45 (br s, 1H), 8.05 (br t, 2H), 7.83 (d, ArH), 7.77 (dd, 1H), 7.34 (m, 1H), 7.23 (d, 1H), 7.02 (d, ArH), 5.82 (m, =CH), 4.97 (m, =CHH), 4.13 (t, CH$_2$O), 3.44 (br d, CH$_2$C=), 3.32 (m, CH$_2$N), 3.10 (m, CH$_2$N salt), 2.87 (t, CH$_2$), 2.50 (m, CH$_2$), 2.01 (m, 2CH$_2$), 1.17 (t, CH$_3$CH$_2$N salt); ES-MS: [M+H]⁺=563.4; FAB-HRMS: [M+H]⁺=563.1978 (Calcd for C$_{29}$H$_{31}$N$_4$O$_6$S 563.1964).

Example 53

Synthesis of 2-Sulfobenzaldehyde 6-[2-(6-Hydrazinonicotinamido)ethoxy]-5-(2-propenyl)-1,2,3,4-tetrahydronaphthalen-1-one Hydrazone

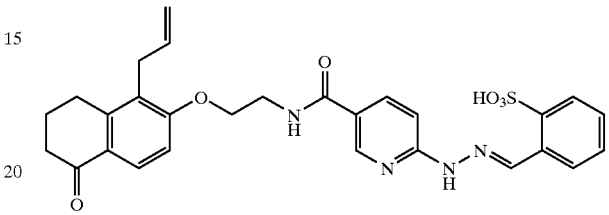

Part A Synthesis of 6-[N-(tert-Butyloxycarbonyl)-2-aminoethoxy]-5-(2-propenyl)-1,2,3,4-tetrahydronaphthalen-1-one The title compound was prepared by the general procedure described above for 6-[N-(tert-Butyloxycarbonyl)-5-aminopentyloxy]-5-(2-propenyl)-1,2,3,4-tetrahydronaphthalen-1-one, substituting N-(tert-Butyloxycarbonyl)-2-aminoethanol. Recovered the title compound as a white solid. $^1$H NMR (CDCl$_3$) 8.00 (d, ArH), 6.81 (d, ArH), 5.90 (m, =CH), 5.00 (dd, =CHH), 4.90 (br s, NH), 4.89 (dd, =CHH), 4.08 (t, CH$_2$O), 3.54 (q, CH$_2$), 3.44 (d, CH$_2$C=), 2.88 (t, CH$_2$), 2.58 (t, CH$_2$), 2.09 (quintet, CH$_2$), 1.36 (m, 3CH$_2$), 1.43 (s, t-Bu); ES-MS: [M+H]⁺=346.2.

Part B Synthesis of 2-Sulfobenzaldehyde 6-[2-(6-Hydrazinonicotinamido)ethoxy]-5-(2-propenyl)-1,2,3,4-tetrahydronaphthalen-1-one Hydrazone The title compound was prepare by the general procedure described above for 2-Sulfobenzaldehyde 6-[5-(6-Hydrazinonicotinamido)pentyloxy]-5-(2-propenyl)-1,2,3,4-tetrahydronaphthalen-1-one Hydrazone, substituting 6-[N-(tert-Butyloxycarbonyl)-2-aminoethoxy]-5-(2-propenyl)-1,2,3,4-tetrahydronaphthalen-1-one. Purification of the crude product was accomplished by reversed-phase HPLC on a preparative Vydac C18 column (2.5×25 cm) using a gradient of 40 to 100% of solution B (90% acetonitrile/10% 0.05 M NH₄Oac) over 30 minutes, and solution A (100% 0.05 M NH₄Oac) to give the title compound as a pale yellow powder. Proton NMR spectral data indicated the presence of some triethylammonium salts. $^1$H NMR (D$_6$-DMSO) 9.21 (br s, NH), 8.80 (br s, 1H), 8.52 (s, 1H), 8.18 (br m, 2H), 7.82 (d, ArH), 7.79 (dd, 1H), 7.41 (m, 1H), 7.22 (d, 1H), 7.05 (d, ArH), 5.80 (m, =CH), 4.88 (m, =CHH), 4.21 (t, CH$_2$O), 3.67 (m, CH$_2$C=), 3.40 (m, CH$_2$N), 3.10 (m, CH$_2$N salt), 2.85 (t, CH$_2$), 2.50 (m, CH$_2$), 1.97 (quintet, CH$_2$), 1.17 (t, CH$_3$CH$_2$N salt); ES-MS: [M+H]⁺=549.2; FAB-HRMS: [M+H]⁺=549.1792 (Calcd for C$_{28}$H$_{29}$N$_4$O$_6$S=549.1808).

Example 54

Synthesis of 2-[[[5-[[2,2-Dimethyl-6-[(4-(3,4-methylenedioxyphenyl)-6-phenyl-2-pyridinyl)oxy]-1-hexanamino]carbonyl]-2-pyridinyl]hydrazono]methyl]-benzenesulfonic acid

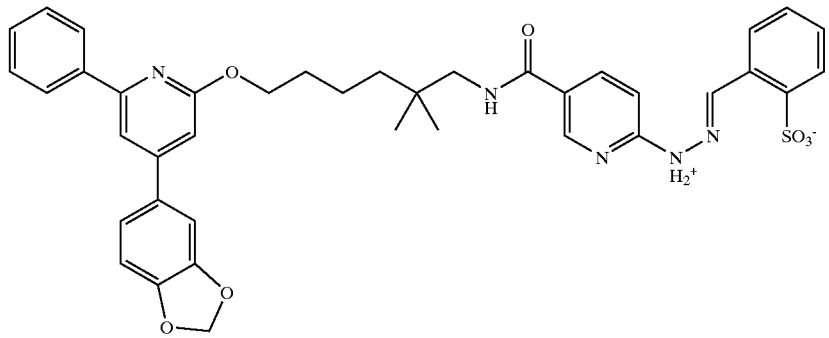

Part A Preparation of 2,2-Dimethyl-6-[(4-(3,4-methylenedioxyphenyl)-6-phenyl-2-pyridinyl)oxy]-hexanenitrile

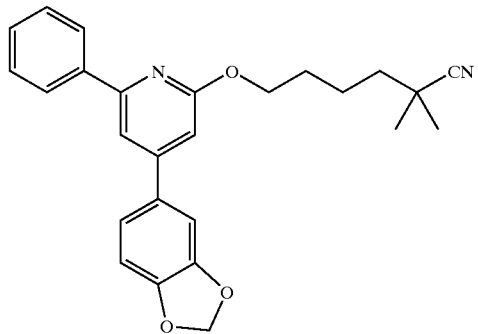

4-(3,4-Methylenedioxyphenyl)-6-phenyl-2-pyridone (1.1 g, 3.77 mmol) was dissolved in dimethylformamide (60 mL). 6-Bromo-2,2-dimethylhexanenitrile (1.54 g, 7.54 mmol) and silver carbonate (1.04 g, 3.77 mmol) were added, and the reaction was refluxed in the dark for 36 h. The reaction was then cooled, filtered, and concentrated under high vacuum. The residue was brought up in methylene chloride and passed through silica gel. The filtrate was concentrated under high vacuum. The resulting residue was recrystallized from hexane:ethyl acetate to give 1.18 g (76%) of product. ESMS: Calcd. For $C_{26}H_{26}N_2O_3$, 414.19; Found 415.3 [M+H]+1

Part B Preparation of 1-Amino-2,2-dimethyl-6-[(4-(3,4-methylenedioxyphenyl)-6-phenyl-2-pyridinyl)oxy]-hexane To a dry flask was added aluminum chloride (0.707 g, 5.30 mmol). The flask was cooled to less than 0° C. with an ice/ethanol bath. Ether (10 mL) was added, and the reaction was stirred for 5 minutes until the aluminum chloride dissolved. Lithium aluminum hydride (0.201 g, 5.30 mmol) was then added, and the reaction was heated to reflux. 2,2-Dimethyl-6-[(4-(3,4-methylenedioxyphenyl)-6-phenyl-2-pyridinyl)oxy]-hexanenitrile (1.0 g, 2.41 mmol) was dissolved in ether (5 mL) and added dropwise to the refluxing solution. After addition was complete, the reaction was stirred for 5 hours at room temperature. The reaction was then quenched with water. Aqueous sulfuric acid (6 N) was added until a clear solution formed. This mixture was then extracted with ether (3x). The aqueous layer was then cooled in an ice bath and basified to pH 14 with 50% aq. Sodium hydroxide. The resulting solution was then extracted with ether (4x). The organic layer was washed with saturated NaCl, dried over magnesium sulfate, and evaporated to give an oil. The oil was crystallized from hexane:ethyl acetate to give 0.3184 g (31%) of product. ESMS: Calcd. For $C_{26}H_{30}N_2O_3$, 418.23; Found, 419.3 [M+H]+1

Part C Preparation of 2-[[[5-[[2,2-dimethyl-6-[(4-(3,4-methylenedioxyphenyl)-6-phenyl-2-pyridinyl)oxy]-1-hexanamino]carbonyl]-2-pyridinyl]hydrazono]methyl]-benzenesulfonic acid 1-Amino-2,2-dimethyl-6-[(4-(3,4-methylenedioxyphenyl)-6-phenyl-2-pyridinyl)oxy]-hexane (0.100 g, 0.239 mmol) was dissolved in dimethylformamide (5 mL). Triethylamine (99.7 µL, 0.717 mmol) was added and the reaction was stirred for 5 minutes. 2-[[[5-[[(2,5-Dioxo-1-pyrrolidinyl)oxy]carbonyl]-2-pyridinyl]hydrazono]methyl]-benzenesulfonic acid, monosodium salt (0.126 g, 0.287 mmol) was added and the reaction was stirred for 24 hours under nitrogen. The reaction was then concentrated to an oil under high vacuum. The oil was triturated with ethyl acetate. The crude product was then purified by preparative HPLC Method 1 to give 16 mg (9%) of product. HRMS: Calcd. For $C_{39}H_{39}N_5O_7S$+H, 722.2648; Found, 722.2669.

Example 55

Synthesis of N-[2,2-Dimethyl-6-[(4-(3,4-methylenedioxyphenyl)-6-phenyl-2-pyridinyl)oxy]-hexyl]-bis-S-(1-ethoxyethylmercapto-acetyl) pentanoate

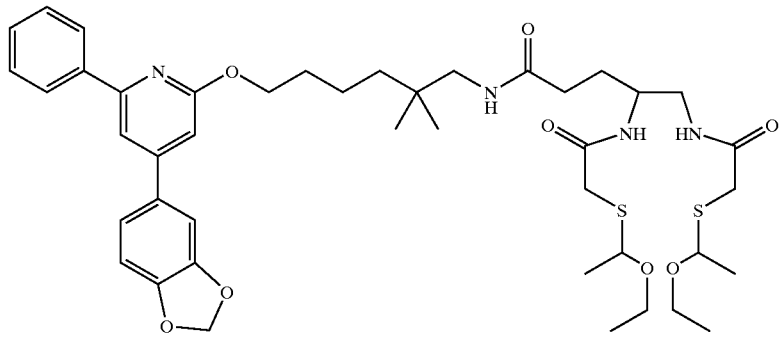

1-Amino-2,2-dimethyl-6-[(4-(3,4-methylenedioxyphenyl)-6-phenyl-2-pyridinyl)oxy]-hexane (0.010 g, 0.0238 mmol), as described in Example 54, Part B, was dissolved in dimethylformamide (1 mL). Triethylamine (10.0 µL, 0.0286 mmol) was added and the reaction was stirred for 5 minutes. Tetrafluorophenyl bis-S-(1-ethoxyethylmercapto-acetyl)pentanoate (MAPT, 0.015 g, 0.0262 mmol) was added and the reaction was stirred for 24 hours under nitrogen. The reaction was then concentrated to an oil under high vacuum. The oil was triturated with ethyl acetate to give 20.0 mg (100%) of product. HRMS: Calc. For $C_{43}H_{60}N_4O_8S_2$+H, 825.3931; Found, 825.3959.

Example 56

Synthesis of 2-[[[5-[[N-[6-[(4,6-diphenyl-2-pyridinyl)oxy]-hexanoyl]-glycine-alpha-amino] carbonyl]-2-pyridinyl]hydrazono]-methyl]-benzenesulfonic acid

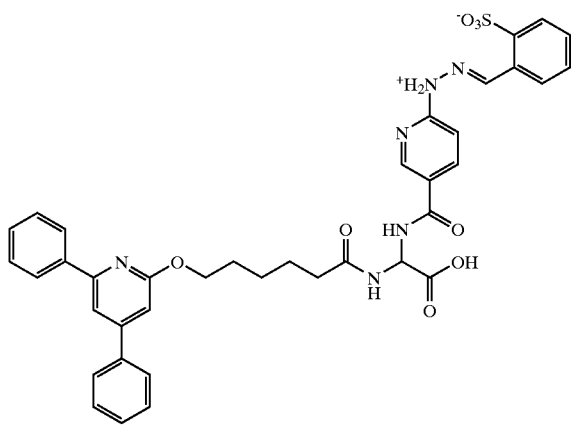

Part A Preparation of 2-amino-[2'-N'-[6-[(4,6-diphenyl-2-pyridinyl)oxy]-hexanoyl]-amino]ethanoic acid trifluoroacetic acid salt

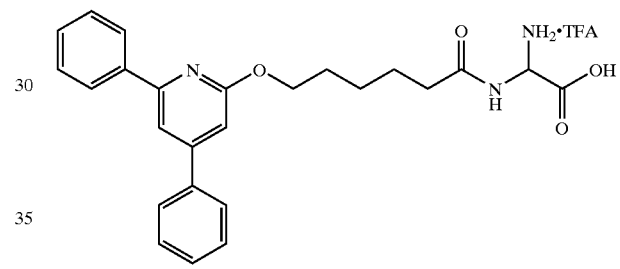

Wang Resin (0.60 mmol/g) (5 g, 3.0 mmol) was placed in a reaction vessel. To this was added dimethylformamide (100 mL) and the reaction was rotated for 10 min. The DMF was removed, and the following were added: Fmoc-Gly(NH-Boc)-OH (2.46 g, 6.0 mmol); HATU (2.85 g, 7.5 mmol); diisopropylethylamine (3.13 mL, 18.0 mmol); dimethylformamide (50 mL). The reaction was rotated for 24 h. The resin was then washed with 100 mL of DMF 3×, MeOH 1×, DCM 3×, MeOH 2×, DCM 3×. The resin was dried under vacuum. The new substitution was determined using the picric acid assay (0.495 mmol/g). The resin was then capped: to the resin was added pyridine (3 mL), benzoyl chloride (3 mL), in dichloroethane (80 mL), and the reaction was rotated for 2 h. The resin was then washed with 100 mL of DCE 3×, DCM 3×, MeOH 1×, DCM 2×, MeOH 2×, DCM 2×. The resin was dried under high vacuum.

To a teabag (5×5 cm polypropylene filter, 0.75 µm mesh) was added 0.50 g of Fmoc-Gly(NH-Boc)-Wang Resin prepared above. The teabag was washed with the following (10 ml/bag) DMF 2×3 min, 20% piperidine in DMF solution 1×3 min, 20% piperidine in DMF solution 1×30 min, DCM 8×3 min, and DMF 3×3 min. To the reactor was added 3 equivalents of 6-[(4,6-diphenyl-2-pyridinyl)oxy]-hexanoic acid, five equivalents of each of the following; HBTU, HOBT, diisopropylethylamine (DIEA) and DMF (10 ml/bag). The bag was then shaken overnight for about 18 hours. The bag was then washed with the following (10 ml/bag): DMF 3×3 min, DCM 8×3 min. The bag was dried under high vacuum. The contents of the bag was then placed in a small erlenmeyer flask. To the flask was added cleavage cocktail (10 mL) (95% trifluoroacetic acid, 2.5% triisopropylsilane, and 2.5% water). The resin was allowed to sit for two hours while occasionally being swirled. After each swirl the side of the flask was rinsed with additional cocktail until the total volume of cocktail added was 15 mL. After two hours, the resin was filtered and washed with TFA 2×4 mL. The filtrate was concentrated to an oil under high vacuum. The oil was triturated with ether to give 96 mg of product. ESMS: Calcd. For $C_{25}H_{27}N_3O_4$, 433.20; Found, 434.3 [M+H]+1

Part B Preparation of 2-[[[5-[[N-[6-[(4,6-diphenyl-2-pyridinyl)oxy]-hexanoyl]-glycine-alpha-amino]carbonyl]-2-pyridinyl]hydrazono]-methyl]-benzenesulfonic acid 2-Amino-[2'-N'-[6-[(4,6-diphenyl-2-pyridinyl)oxy]-hexanoyl]-amino]ethanoic acid trifluoroacetic acid salt (0.040 g, 0.0731 mmol) was dissolved in dimethylformamide (2 mL). Triethylamine (30.6 μL, 0.219 mmol) was added and the reaction was stirred for 5 minutes. 2-[[[5-[[(2,5-Dioxo-1-pyrrolidinyl)oxy]carbonyl]-2-pyridinyl]hydrazono]methyl]-benzenesulfonic acid, monosodium salt (0.0386 g, 0.0877 mmol) was added and the reaction was stirred for 24 hours under nitrogen. The reaction was then concentrated to an oil under high vacuum. The oil was triturated with ethyl acetate. The crude product was then purified by preparative HPLC Method 3 to give 12 mg (22%) of product. HRMS: Calcd. For $C_{38}H_{36}N_6O_8S+H$, 737.2394; Found, 737.2420.

| HPLC Method 3 | | | |
|---|---|---|---|
| Instrument | Rainin Rabbit; Dynamax software | | |
| Column | Vydac C-18 (21.2 mm × 25 cm) | | |
| Detector | Knauer VWM | | |
| Flow Rate | 15 ml/min | | |
| Column Temp | RT | | |
| Mobile Phase | A: $H_2O$ | | |
| | B: ACN/$H_2O$ (9:1) | | |
| Gradient | Time (min) | % A | % B |
| | 0 | 60 | 40 |
| | 20 | 40 | 60 |
| | 21 | 0 | 100 |
| | 30 | 0 | 100 |
| | 31 | 60 | 40 |

Example 57

Synthesis of 2-Acetyl-4-ethyl-[5-[6-[[6-[[[(2-sulfonylphenyl)methylene]hydrazino]-3-pyridinyl]carbonyl]amino]hexyl]oxy]phenol

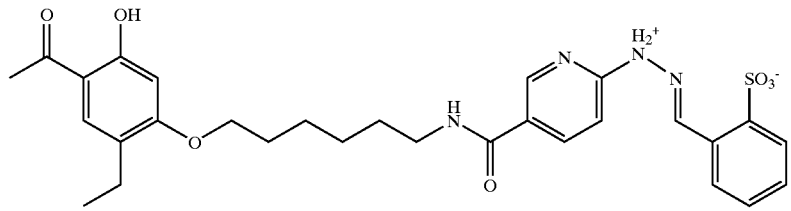

Part A Preparation of 2-Hydroxy-5-ethyl-4-[[6-(N-tert-butyloxycarbonyl)aminohexyl]oxy]acetophenone

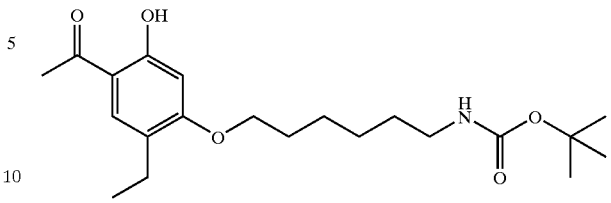

2,4-Dihydroxy-5-ethyl-acetophenone (1.5 g, 8.32 mmol) and N-tert-butyloxycarbonyl-6-bromohexylamine (2.45 g, 8.73 mmol) were dissolved in methylethylketone (5.5 mL). Potassium carbonate (2.01 g, 14.6 mmol), potassium iodide (0.276 g, 1.66 mmol) and methyl sulfoxide (1.2 mL) were added and the reaction was heated to reflux for 30 h. The reaction was cooled, brought up in water, and extracted with toluene. The organic layer was washed with 1.0 N NaOH (3×), 1N HCl (1×), and water. The organic layer was then stirred with silica gel for 15 min. The silica was removed by filtration. The filtrate was concentrated. The resulting solid was brought up in hexane and filtered and dried to give 1.63 g (52%) of product. ESMS: Calcd. For $C_{21}H_{33}NO_5$, 379.24; Found, 380.3 [M+H]+1

Part B Preparation of 2-Hydroxy-5-ethyl-4-[[6-aminohexyl]oxy]acetophenone trifluoroacetate salt 2-Hydroxy-5-ethyl-4-[[6-(N-tert-butyloxycarbonyl)aminohexyl]oxy]acetophenone (0.100 g, 0.264 mmol) was dissolved in methylene chloride (1.5 mL). Trifluoroacetic acid (1.5 mL) was added, and the reaction was stirred for 2 h. The reaction was concentrated under high vacuum. The resulting oil was brought up 50:50 acetonitrile/water and lyophilized to give 100.2 mg (97%) of product. ESMS: Calcd. For $C_{16}H_{25}NO_3$, 279.18; Found, 280.2 [M+H]+1

Part C Preparation of 2-Acetyl-4-ethyl-[5-[6-[[6-[[[(2-sulfonylphenyl)methylene]hydrazino]-3-pyridinyl]carbonyl]amino]hexyl]oxy]phenol 2-Hydroxy-5-ethyl-4-[[6-aminohexyl]oxy]acetophenone trifluoroacetate salt (0.095 g, 0.241 mmol) was dissolved in dimethylformamide (5 mL). Triethylamine (100.9 μL, 0.723 mmol) was added and the reaction was stirred for 5 minutes. 2-[[[5-[[(2,5-Dioxo-1-pyrrolidinyl)oxy]carbonyl]-2-pyridinyl]hydrazono]methyl]-benzenesulfonic acid, monosodium salt (0.127 g, 0.289 mmol) was added and the reaction was stirred for 24 hours under nitrogen. The reaction was then concentrated to an oil under high vacuum. The oil was triturated with ethyl acetate. The crude product was then purified by preparative HPLC Method 2 to give 3.1 mg (2%) of product. HRMS: Calcd. For $C_{29}H_{34}N_4O_7S+H$, 583.2226; Found, 583.2213.

Example 58

Synthesis of 2,4-Diethyl-[5-[5,5-dimethyl-6-[[6-[[[(2-sulfonylphenyl)methylene]hydrazino]-3-pyridinyl]carbonyl]amino]hexyl]oxy]phenol

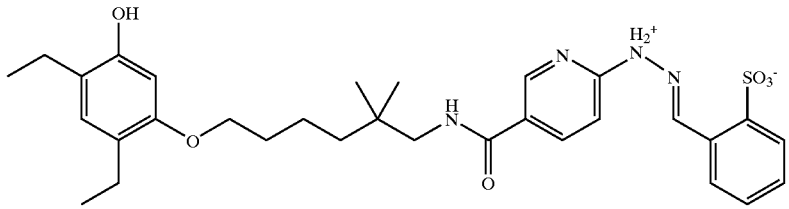

Part A: Preparation of 2-Benzyloxy-5-ethyl-4-[(5-methyl-5-cyanohexyl)oxy-acetophenone

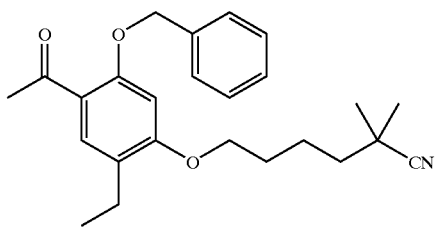

2-Hydroxy-5-ethyl-4-[(5-methyl-5-cyanohexyl)oxy-acetophenone (2.8 g, 9.22 mmol), as described in Example 13, Part A, was dissolved in dimethylformamide (40 mL). Potassium carbonate (2.04 g, 14.8 mmol) and benzyl bromide (2.19 mL, 18.4 mmol) were added and the reaction was heated to 75° C. for 18 h. The reaction was cooled, filtered and concentrated. The resulting oil was brought up in ethyl acetate. The organic layer was washed with water, brine, dried over magnesium sulfate, filtered and concentrated. The crude product was purified by flash chromatography using 6:1 hexane:ethyl acetate followed by 3:1:0.05 hexane:ethyl acetate:methanol to give 1.79 g (49%) of product. ESMS: Calcd. For $C_{25}H_{31}NO_3$, 393.23; Found 394.3 [M+H]+1

Part B: Preparation of 1-Benzyloxy-2,4-diethyl-5-[(5,5-dimethyl-6-aminohexyl)oxy]benzene To a dry flask was added aluminum chloride (0.186 g, 13.9 mmol). The flask was cooled to less than 0° C. with an ice/ethanol bath. Ether (5 mL) was added, and the reaction was stirred for 5 minutes until the aluminum chloride dissolved. Lithium aluminum hydride (0.0531 g, 13.9 mmol) was then added, and the reaction was heated to reflux. 2-Benzyloxy-5-ethyl-4-[(5-methyl-5-cyanohexyl)oxy-acetophenone (0.250 g, 0.635 mmol) was dissolved in ether (2 mL) and added dropwise to the refluxing solution. After addition was complete, the reaction was stirred for 5 hours at room temperature. The reaction was then quenched with water. 5N hydrosulfuric acid was added until a clear solution formed. This mixture was then extracted with ether (3×). The aqueous layer was then cooled in an ice bath and basified to pH 14 with 50% aq. Sodium hydroxide. The resulting solution was then extracted with ether (4×). The organic layer was washed with water, saturated NaCl, dried over magnesium sulfate, and evaporated to give 0.140 g (57%) of product as an oil. ESMS: Calcd. For $C_{25}H_{37}NO_2$, 383.28; Found, 384.4 [M+H]+1

Part C Preparation of 2,4-Diethyl-5-[(5,5-dimethyl-6-aminohexyl)oxy]phenol

A small round bottom was purged with nitrogen. To this was added palladium on carbon (10 mg, 10% w/w) followed by ethanol (5 mL). 1-Benzyloxy-2,4-diethyl-5-[(5,5-dimethyl-6-aminohexyl)oxy]benzene (0.100 g, 0.527 mmol) was dissolved in ethanol (5 mL) and added to the reaction. The reaction was evacuated and purged with nitrogen twice, and then evacuated and opened to hydrogen twice. The reaction was stirred under hydrogen for 1 h. The reaction was filtered through celite, washed with ethanol. The filtrate was concentrated under high vacuum to give 67.4 mg (88%) as an oil. ESMS: Calcd. For $C_{18}H_{31}NO2$, 293.24; Found, 294.3 [M+H]+1

Part D Preparation of 2,4-Diethyl-[5-[5,5-dimethyl-6-[[6-[[[(2-sulfonylphenyl)methylene]hydrazino]-3-pyridinyl]carbonyl]amino]hexyl]oxy]phenol 2,4-Diethyl-5-[(5,5-dimethyl-6-aminohexyl)oxy]phenol (0.040 g, 0.136 mmol) was dissolved in dimethylformamide (2 mL). Triethylamine (56.8 µL, 0.408 mmol) was added and the reaction was stirred for 5 minutes. 2-[[[5-[[(2,5-Dioxo-1-pyrrolidinyl)oxy]carbonyl]-2-pyridinyl]hydrazono]methyl]-benzenesulfonic acid, monosodium salt (0.072 g, 0.163 mmol) was added and the reaction was stirred for 24 hours under nitrogen. The reaction was then concentrated to an oil under high vacuum. The oil was triturated with ethyl acetate. The crude product was then purified by preparative HPLC Method 2 to give 15.1 mg (19%) of product. MS: Calcd. For $C_{31}H_{40}N_4O_6S+H$, 597.2747; Found, 597.2754

Example 59

Synthesis of 2-(5-Carboxypentyloxy)-6-[6-[[4-acetyl-2-ethyl-5-hydroxyphenyl]oxy]hexyl]benzenepropanoic acid

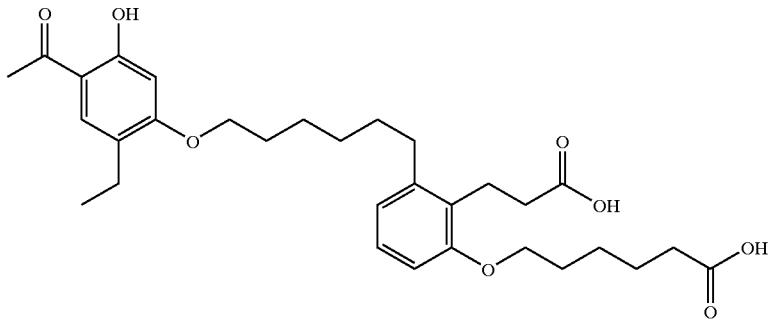

Part A Preparation of 2-(6-Methoxy-6-oxohexyloxy)-6-[6-[[4-acetyl-2-ethyl-5-hydroxyphenyl]oxy]hexyl]benzenepropanoic acid methyl ester

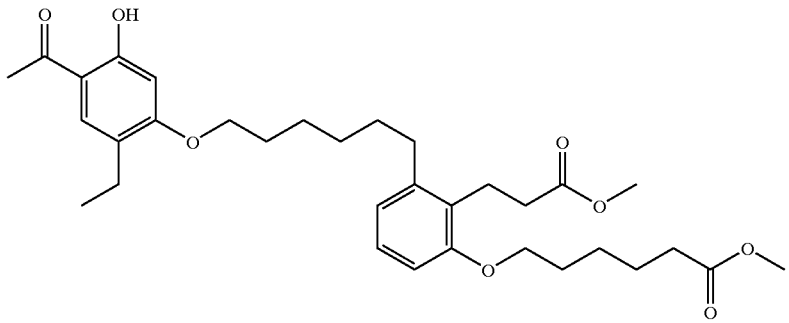

2,4-Dihydroxy-5-ethyl-acetophenone (20.8 mg, 0.117 mmol) and 2-(6-Methoxy-6-oxohexyloxy)-6-[6-iodohexyl]benzene-propanoic acid methyl ester (50 mg, 0.0964 mmol) were dissolved in acetonitrile (5 mL). Potassium carbonate (53.3 mg, 0.386 mmol) was added, and the reaction was heated to 80° C. overnight. The reaction was concentrated under high vacuum. The resulting residue was brought up in ethyl acetate and washed with water, brine, dried over magnesium sulfate, filtered, and evaporated. The resulting crude product was purified by flash column chromatography (5:1 hexane:ethyl acetate) to give 38.1 mg (69%) of product. MS: Calcd. For $C_{33}H_{46}O_8$, 570.32; Found, 571.4 [M+H]+1

Part B Preparation of 2-(5-Carboxypentyloxy)-6-[6-[[4-acetyl-2-ethyl-5-hydroxyphenyl]oxy]hexyl]benzenepropanoic acid 2-(6-Methoxy-6-oxohexyloxy)-6-[6-[[4-acetyl-2-ethyl-5-hydroxyphenyl]oxy]hexyl]benzenepropanoic acid methyl ester (25.8 mg, 0.0452 mmol) was dissolved in tetrahydrofuran (5 mL). Lithium hydroxide monohydrate (18.9 mg, 0.452 mmol) was dissolved in water (1 mL) and added to the reaction. The reaction was stirred for 18 h. The reaction was then concentrated, brought up in water, acidified to pH 5 with 1N HCl, and extracted with ethyl acetate. The organic layer was washed with water, brine, dried over magnesium sulfate, filtered, and evaporated. The resulting oil recrystallized with hexane:ethyl acetate to give 24.5 mg (100%) of product. MS: Calcd. For $C_{31}H_{42}O_8$+H, 543.2958; Found, 543.2946

Example 60

Synthesis of 2-((tert-butyl)oxycarbonyl)-7-(5-(4,6-diphenyl(2-pyridyloxy))pentyloxy)-1,2,3,4-tetrahydro-isoquinoline-3-carboxylic acid

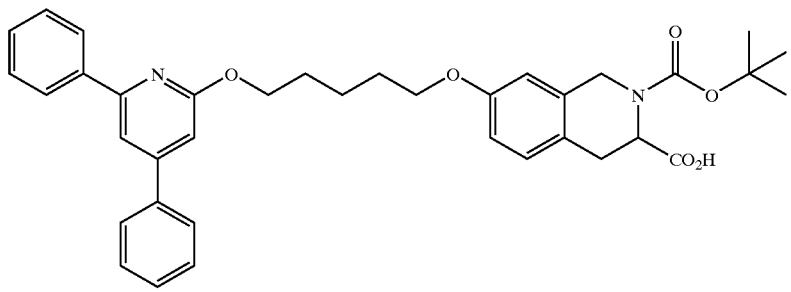

Part A: Preparation of 5-(4,6-diphenyl-2-pyridyloxy)-pentyl acetate

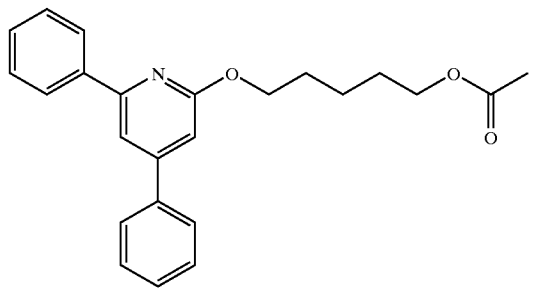

A mixture of 4,6-diphenyl-2-pyridone (2.5 g, 10.1 mmol), N,N-dimethylformaide (137.5 mL), methyl 6-bromohexanoate (3.17 g, 15.15 mmol) and silver carbonate (2.9 g, 7.58 mmol) was heated at 110° C. in the dark for 48 h. The mixture was allowed to cool to room temperature, filtered, and concentrated under high vacuum. The residue was purified by silica gel flash chromatography (hexane/ethyl acetate, 10:1) to give 2.85 g (75%) of product. $^1$H NMR (CDCl3): 8.12–6.90 (m, 12H), 4.52 (t, 2H), 4.18 (t, 2H), 2.05 (s, 3H), 1.98–1.50 (m, 6H); ESMS: Calculated for $C_{24}H_{25}NO3$, 375.18 Found 376.3 [M+H]+1; $R_t$=21.013 min (88.5% pure, Vydac C18 column; gradient 20 to 100% acetonitrile/water+0.1% TFA over 30 min).

Part B: Preparation of 5-(4,6-Diphenyl-2-pyridyloxy)-pentan-1-ol

A solution of 5-(4,6-diphenyl-2-pyridyloxy)-pentyl acetate (2.85 g, 7.59 mmol) in MeOH (107 mL) was treated with 1N NaOH (26.82 mL) and stirred at room temperature for 16 h. The solvent was evaporated in vacuo, and the residue was acidified with 10% $KHSO_4$ and extracted with EtOAc (3×). The combined organic extracts were washed with saturated NaCl, dried over $MgSO_4$, filtered and concentrated under high vacuum to afford 2.3 g (91%) of a yellowish solid. The product was used without further purification. $^1$H NMR (CDCl$_3$): 8.15–6.90 (m, 12H), 4.56 (t, 2H), 3.76 (t, 2H), 1.95–1.50 (m, 7H); ESMS: Calculated for $C_{22}H_{23}NO_2$, 333.17 Found 334.3 [M+H]+1; $R_t$=17.468 min (96.6% pure, Vydac C18 column; gradient 20 to 100% acetonitrile/water+0.1% TFA over 30 min).

Part C: Preparation of (5-(4,6-diphenyl(2-pyridyloxy))pentyl)(methylsulfonyl)oxy A mixture of 5-(4,6-diphenyl-2-pyridyloxy)-pentan-1-ol (2.3 g, 6.9 mmol), ethyl acetate (50 mL), triethylamine (7.4 mL) and methanesulfonyl chloride (3.4 g, 29.7 mmol) was stirred at 0–5° C. for 4 h and refrigerated for 24 h. The mixture was acidified with 1N HCl and extracted with ether. The ether extract was washed with water and brine, dried over $MgSO_4$, filtered and concentrated in vacuo to give 2.8 g (98%) of a yellowish solid which was used without further purification. $^1$H NMR (CDCl$_3$): 8.14–6.90 (m, 12H), 4.56 (t, 2H), 4.34 (t, 2H), 3.05 (s, 3H), 1.98–1.52 (m, 7H); ESMS: Calculated for $C_{23}H_{25}NO_4S$, 411.15 Found 412.3 [M+H]+1; Rt=18.935 min (97.0% pure, Vydac C18 column; gradient 20 to 100% acetonitrile/water+0.1% TFA over 30 min).

Part D: Preparation of 2-((tert-butyl)oxycarbonyl)-7-hydroxy-1,2,3,4-tetrahydroisoquinoline-3-carboxylic acid

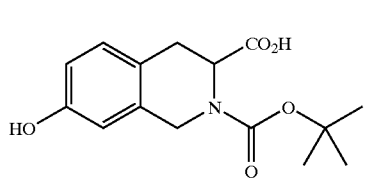

To a solution of L-1,2,3,4-tetrahydro-7-hydroxylisoquinoline-3-carboxylic acid (1 g, 5.18 mmol) in DMF (5.3 mL) was added triethylamine (0.87 mL, 6.23 mmol) followed by di-t-butyl-dicarbonate (1.13 g, 5.18 mmol). The mixture was stirred at room temperature for 17 h, evaporated in vacuo, dissolved in a minimum amount of ethyl acetate and filtered through silica gel using ethyl acetate as eluent. The filtrate was concentrated under high vacuum to give 1.2 g (79%) of a yellowish solid which was used without further purification. ESMS: Calculated for $C_{15}H_{19}NO_5$, 293.13 Found 292.2 [M–H]-1; $R_t$=9.091 min (92.1% pure, Vydac C18 column; gradient 20 to 100% acetonitrile/water+0.1% TFA over 30 min).

Part E: Preparation of 2-((tert-butyl)oxycarbonyl)-7-(5-(4,6-diphenyl(2-pyridyloxy))pentyloxy)-1,2,3,4-tetrahydroisoquinoline-3-carboxylic acid A solution of 2-((tert-butyl)oxycarbonyl)-7-hydroxy-1,2,3,4-tetrahydroisoquinoline-3-carboxylic acid (72 mg, 0.244 mmol) in DMF (0.53 mL) was treated with NaH (50% dispersion in oil, 6.4 mg, 0.268 mmol) and stirred at 0° C. for 1 h. A solution of (5-(4,6-diphenyl(2-pyridyloxy))pentyl)(methylsulfonyl)oxy (50 mg, 0.122 mmol) in DMF (0.20 mL) was added dropwise and the mixture was stirred at room temperature for 24 h. The solvent was removed in vacuo, and the residue was purified by reverse-phase HPLC (water-acetonitrile gradient containing 0.1% TFA) to afford 47 mg (63%) of a white powdered solid. $^1$H NMR (CDCl$_3$): 8.18–6.60 (m, 15H), 4.50–4.38 (m, 3H), 4.05 (m, 11H), 3.18 (t, 2H), 1.98–1.60 (m, 6H), 1.50 (m, 9H). ESMS: Calculated for $C_{37}H_{40}N_2O_6$, 608.29 Found 607.3 [M–H]-1; $R_t$=22.403 min (96.5% pure, Vydac C18 column; gradient 20 to 100% acetonitrile/water+0.1% TFA over 30 min).

Example 61

Synthesis of 3-(4-(5-(4,6-diphenyl(2-pyridyloxy))pentyloxy)-3-ethoxyphenyl)-N-((6-hydrazino(3-pyridyl))sulfonyl)prop-2-enamide

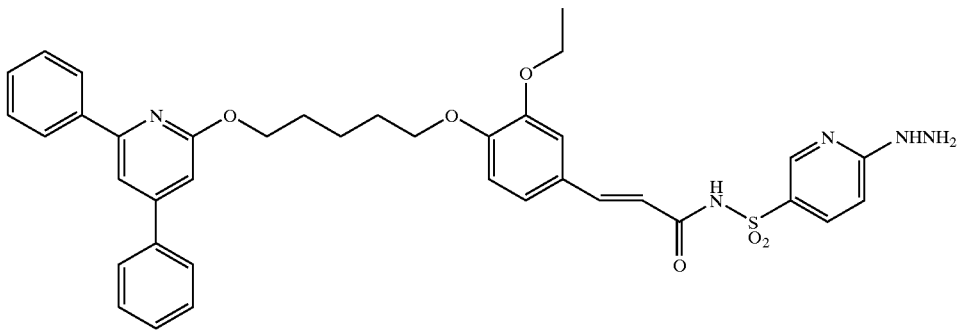

Part A: Preparation of 4-(5-(4,6-diphenyl(2-pyridyl-oxy))pentyloxy)-3-ethoxybenzaldehyde

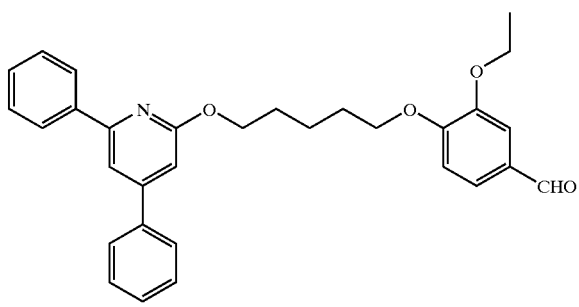

A mixture of (5-(4,6-diphenyl(2-pyridyloxy))pentyl)-(methylsulfonyl)oxy (0.5 g, 1.21 mmol), 3-ethoxy-4-hydroxyl benzaldehyde (0.2 g, 1.21 mmol), N,N-dimethylforamide (17 mL) and cesium carbonate (0.79 g, 2.43 mmol) was heated at 60° C. for 18 h. The mixture was concentrated under high vacuum, taken up in water, and extracted with EtOAc (3×). The combined organic extracts were washed with saturated NaCl, dried over $MgSO_4$, filtered and evaporated in vacuo to afford 0.38 g (65%) of product which was used without further purification. ESMS: Calculated for $C_{31}H_{31}NO_4$, 481.23 Found 482.4 [M+H]+1; $R_t$=22.024 min (83.4% pure, Vydac C18 column; gradient 20 to 100% acetonitrile/water+0.1% TFA over 30 min).

Part B: Preparation of ethyl 3-(4-(5-(4,6-diphenyl(2-pyridyloxy))pentyloxy)-3-ethoxyphenyl)prop-2-enoate

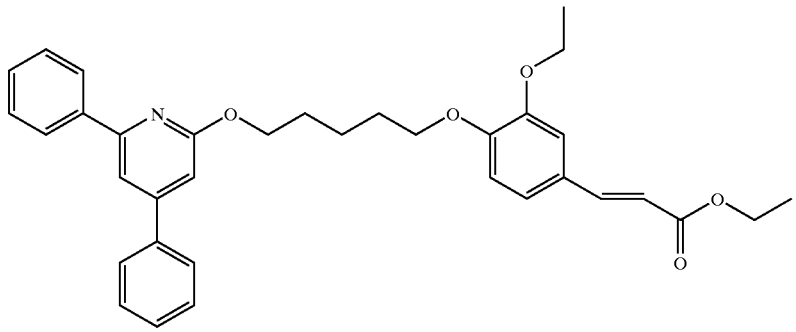

A mixture of NaH (50% dispersion in oil, 29 mg, 1.22 mmol), tetrahydrofuran (3.75 mL), triethyl phosphonoacetate (0.24 mL, 1.18 mmol) was stirred at 0° C. for 15 min. A solution of 4-(5-(4,6-diphenyl(2-pyridyl-oxy))pentyloxy)-3-ethoxybenzaldehyde (380 mg, 0.789 mmol) in tetrahydrofuran (2 mL) was added. The mixture was stirred at room temperature for 18 h, concentrated under high vacuum, and partitioned between EtOAc and water. The organic phase was washed with brine, dried over $MgSO_4$, filtered and evaporated in vacuo. Purification by silica gel flash chromatography (hexane/ethyl acetate, 4:1) yielded 310 mg (71%) of a white solid. $^1H$ NMR ($CDCl_3$): 8.14 (d, 2H), 7.73–6.30 (m, 15H), 4.58 (t, 2H), 4.30 (q, 2H), 4.04 (m, 5H), 2.00 (m, 5H), 1.78 (m, 2H), 1.45 (m, 12H); ESMS: Calculated for $C_{35}H_{37}NO_5$, 551.27 Found 552.4 [M+H]+1; $R_t$=23.450 min (96.5% pure, Vydac C18 column; gradient 20 to 100% acetonitrile/water+0.1% TFA over 30 min).

Part C: Preparation of 3-(4-(5-(4,6-diphenyl(2-pyridyloxy))pentyloxy)-3-ethoxyphenyl)prop-2-enoic acid To a solution of ethyl 3-(4-(5-(4,6-diphenyl(2-pyridyloxy))pentyloxy)-3-ethoxyphenyl)prop-2-enoate (250 mg, 0.453 mmol) in ethanol (7 mL) was treated with KOH (2.24 M, 0.68 mL) and heated to 50° C. for 72 h. The mixture was concentrated under high vacuum, diluted with water, acidified to pH 7 with 1N HCl and extracted with ether (3×). The ether extract was washed with saturated NaCl, dried over MgSO$_4$, filtered and concentrated in vacuo to give 140 mg (59%) of product which was used without further purification. $^1$H NMR (DMSO-d$_6$): 8.25 (d, 2H), 7.98–6.30 (m, 15H), 4.50 (t, 2H), 4.0 (t, 5H), 1.90–1.25 (m, 9H); ESMS: Calculated for C$_{33}$H$_{33}$NO$_5$, 523.24 Found 524.3 [M+H]+1; R$_t$=20.436 min (96.5% pure, Vydac C18 column; gradient 20 to 100% acetonitrile/water+0.1% TFA over 30 min).

Part D Preparation of 3-(4-(5-(4,6-diphenyl(2-pyridyloxy))pentyloxy)-3-ethoxyphenyl)-N-((6-hydrazino(3-pyridyl))sulfonyl)prop-2-enamide To a solution of 3-(4-(5-(4,6-diphenyl(2-pyridyloxy))pentyloxy)-3-ethoxyphenyl)prop-2-enoic acid (0.231 mmol) in methylene chloride, is added 2-chloro-pyridine-5-sulfonamide (0.243 mmol), dimethylaminopyridine (0.300 mmol), 1-(3-dimethylaminopropyl)-3-ethyl carbodiimide hydrochloride (0.231 mmol), and 4 A molecular sieves. The reaction mixture is stirred overnight for 18 h and is then filtered. The filtrate is washed with 1N HCl, water, brine. The organic layer is dried over magnesium sulfate, filtered, and concentrated to a small volume. The resulting concentrated solution is triturated with hexane. The product is filtered, washed with hexane and dried under high vacuum to give the chloropyridine intermediate. This intermediate (0.164 mmol) is brought up in hydrazine hydrate (5 mL). The reaction is heated to 70° C. for 18 h. The precipitate is dissolved in ethanol (10 mL) and the reaction is heated at 80° C. for another 20 h. The reaction is then concentrated under high vacuum to give the crude product, which is purified by flash chromatography.

Example 62

Synthesis of 2-((6-((1-aza-2-(2-sulfophenyl)vinyl)-amino)(3-pyridyl))carbonyl)-7-(5-(4,6-diphenyl(2-pyridyl-oxy))pentyloxy)-1,2,3,4-tetrahydro-isoquinoline-3-carboxylic acid

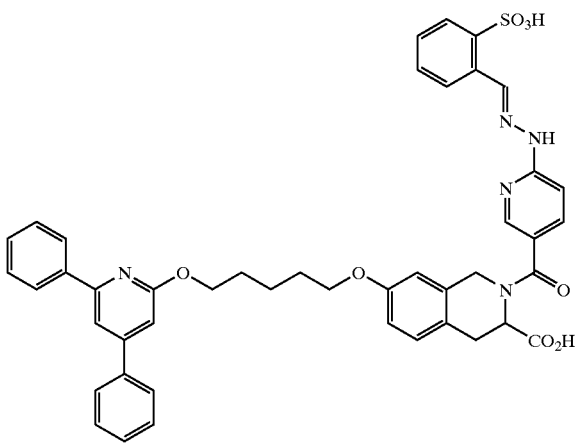

Part A Preparation of 7-(5-(4,6-diphenyl(2-pyridyl-oxy))pentyloxy)-1, 2,3,4-tetrahydroisoquinoline-3-carboxylic acid (trifluoroacetic acid salt)

A solution of 2-((tert-butyl)oxycarbonyl)-7-(5-(4,6-diphenyl(2-pyridyloxy))pentyloxy)-1,2,3,4-tetrahydro-isoquinoline-3-carboxylic acid (30 mg, 0.049 mmol), the compound of Example 60, in dichloromethane (2.5 mL) was treated with trifluoroacetic acid (2.5 mL) and stirred at room temperature for 2 h. The solution was concentrated under high vacuum, and the residue was lyophilized to afford 21 mg (84%) of a white powdered solid. $^1$H NMR (CD$_3$OD): 8.20–6.80 (m, 16H), 4.61 (t, 2H), 4.42 (s, 2H), 4.14 (m, 3H), 3.70 (m, 2H), 2.02–1.66 (m, 6H); ESMS: Calculated for C$_{32}$H$_{32}$N$_2$O$_4$, 508.24 Found 509.3 [M+H]+1; R$_t$=16.871 min (85.2% pure, Vydac C18 column; gradient 20 to 100% acetonitrile/water+0.1% TFA over 30 min).

Part B Preparation of 2-((6-((1-aza-2-(2-sulfophenyl)vinyl)-amino)(3-pyridyl))carbonyl)-7-(5-(4,6-diphenyl(2-pyridyl-oxy))pentyloxy)-1,2,3,4-tetrahydro-isoquinoline-3-carboxylic acid A mixture of 7-(5-(4,6-diphenyl(2-pyridyl-oxy))pentyloxy)-1,2,3,4-tetrahydroisoquinoline-3-carboxylic acid (trifluoroacetic acid salt) (0.0805 mmol), N,N-dimethyl formamide (2 mL), and triethylamine (0.2478 mmol) is stirred at room temperature for 15 min. 2-[[[5-[[(2,5-Dioxo-1-pyrrolidinyl)oxy]carbonyl]-2-pyridinyl]hydrazono]methyl]-benzenesulfonic acid, monosodium salt (0.0991 mmol) is added and the mixture is stirred under nitrogen. After 24 h, the mixture is concentrated under high vacuum. Purification by reverse-phase HPLC (water-acetonitrile gradient containing 0.1% TFA) yields the desired product.

Example 63

Synthesis of 2-((6-((1-aza-2-(2-sulfophenyl)vinyl)-amino)(3-pyridyl)carbonylamino)-3-(4-(5-(4,6-diphenyl(2-pyridyloxy))pentyloxy)phenyl)propanoic acid

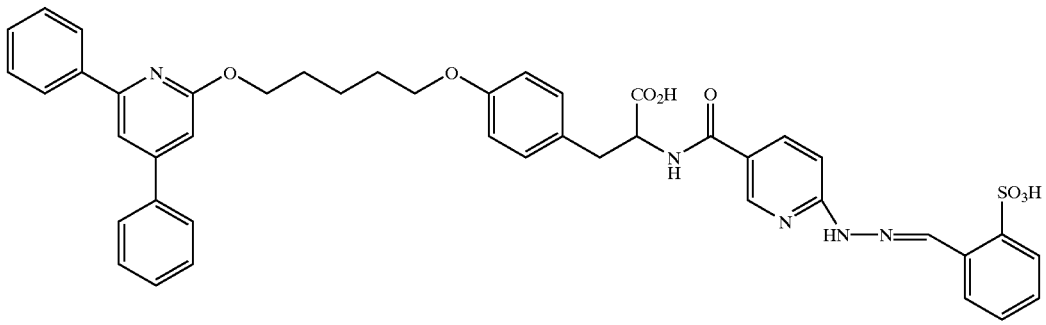

Part A: Preparation of benzyl 2-((tert-butoxy)-carbonylamino)-3-(4-(5-(4,6-diphenyl(2-pyridyloxy))-pentyloxy)phenyl)propanoate

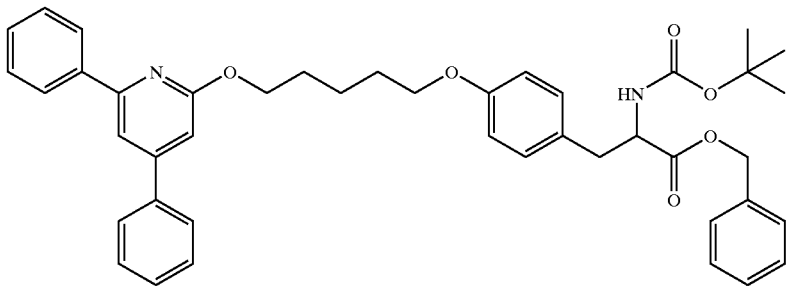

A mixture of (5-(4,6-diphenyl(2-pyridyloxy))pentyl)-(methylsulfonyl)oxy (200 mg, 0.487 mmol), Boc-Tyr-Obzl (181 mg, 0.487 mmol), N,N-dimethylforamide (7 mL) and cesium carbonate (317 mg, 0.974 mmol) was heated to 60° C. for 18 h. The mixture was concentrated under high vacuum, diluted with water and extracted with EtOAc (3×). The combined organic extracts were washed with water and saturated NaCl, dried over $MgSO_4$, and concentrated in vacuo. Purification by reverse-phase HPLC (water-acetonitrile gradient containing 0.1% TFA) yielded 140 mg (42%) of a white powdered solid. $^1$H NMR ($CDCl_3$): 8.14–6.66 (m, 22H), 5.11 (m, 3H), 4.59 (t, 2H), 4.00 (t, 2H), 3.08 (d, 2H), 1.88 (m, 10H), 1.40 (m, 12H); ESMS: Calculated for $C_{43}H_{46}N_2O_6$, 686.34 Found 687.4 [M+H]+1; $R_t$=23.460 min (99.6% pure, Vydac C18 column; gradient 20 to 100% acetonitrile/water+0.1% TFA over 30 min).

Part B: Preparation of 2-((tert-butoxy)-carbonylamino)-3-(4-(5-(4,6-diphenyl(2-pyridyloxy))-pentyloxy)phenyl)propanoic acid A mixture of 10% Pd on carbon (13 mg) and ethyl acetate (5 mL) was added to a dry flask and stirred at room temperature for 10 min. A solution of benzyl 2-((tert-butoxy)-carbonylamino)-3-(4-(5-(4,6-diphenyl(2-pyridyloxy))-pentyloxy)phenyl)propanoate (130 mg, 0.189 mmol) in 5 mL of ethyl acetate was added dropwise. The mixture was stirred under atmospheric hydrogen for 24 h and filtered through Celite using ethyl acetate as eluent. The filtrate concentrated under high vacuum to give 52 mg (46%) of a yellowish oil which was used without further purification. ESMS: Calculated for $C_{36}H_{40}N_2O_6$, 596.29 Found 597.3 [M+H]+1; $R_t$=20.989 min (100% pure, Vydac $C_{18}$ column; gradient 20 to 100% acetonitrile/water+0.1% TFA over 30 min).

Part C: Preparation of 2-amino-3-(4-(5-(4,6-diphenyl(2-pyridyloxy))-pentyloxy)phenyl)propanoic acid (trifluoroacetic acid salt)

A solution of 2-((tert-butoxy)-carbonylamino)-3-(4-(5-(4,6-diphenyl(2-pyridyloxy))-pentyloxy)phenyl)propanoic acid (53 mg, 0.088 mmol) in dichloromethane (4.9 mL) was treated with trifluoroacetic acid (4.9 mL) and stirred at room temperature for 1 h. The solution was concentrated under high vacuum, and the residue was lyophilized to give 43 mg (97%) of a white powdered solid. $^1$H NMR (DMSO-$d_6$): 8.25–6.80 (m, 16H), 4.54 (t, 2H), 4.12 (m, 3H), 3.06 (d, 2H), 1.80 (m, 6H); ESMS: Calculated for $C_{31}H_{32}N_2O_4$, 496.24 Found 497.3 [M+H]+1; $R_t$=16.257 min (100% pure, Vydac C18 column; gradient 20 to 100% acetonitrile/water+0.1% TFA over 30 min).

Part D: Preparation of 2-((6-((1-aza-2-(2-sulfophenyl)vinyl)amino)(3-pyridyl)carbonylamino)-3-(4-(5-(4,6-diphenyl(2-pyridyloxy))pentyloxy)phenyl)propanoic acid A mixture of 2-amino-3-(4-(5-(4,6-diphenyl(2-pyridyloxy))-pentyloxy)phenyl)propanoic acid (40 mg, 0.0805 mmol), N,N-dimethyl formamide (2 mL), and triethylamine (34.5 mL, 0.2478 mmol) was stirred at room temperature for 15 min. 2-[[[5-[[(2,5-Dioxo-1-pyrrolidinyl)oxy]carbonyl]-2-pyridinyl]hydrazono]methyl]-benzenesulfonic acid, monosodium salt (43.6 mg, 0.0991 mmol) was added and the mixture was stirred under nitrogen. After 24 h, the mixture was concentrated under high vacuum. Purification by reverse-phase HPLC (water-acetonitrile gradient containing 0.1% TFA) yielded 25 mg (39%) of a white powdered solid. $^1$H NMR (DMSO-$d_6$): 9.40 (s, 1H), 9.02 (s, 1H), 8.54 (s, 1H), 8.30–6.76 (m, 26H), 4.58 (m, 3H), 4.00 (t, 2H), 3.10 (m, 2H), 1.78 (m, 6H); ESMS: Calculated for $C_{44}H_{41}N_5O_8S$, 799.26 Found 800.3

[M+H]+1; $R_t$=16.691 min (98.0% pure, Vydac C18 column; gradient 20 to 100% acetonitrile/water+0.1% TFA over 30 min).

Example 64

Synthesis of 2-((6-((1-aza-2-(2-sulfophenyl)vinyl)-amino)(3-pyridyl)carbonylamino)-3-(2-(5-(4,6-diphenyl(2-pyridyloxy))pentyloxy)phenyl)propanoic acid

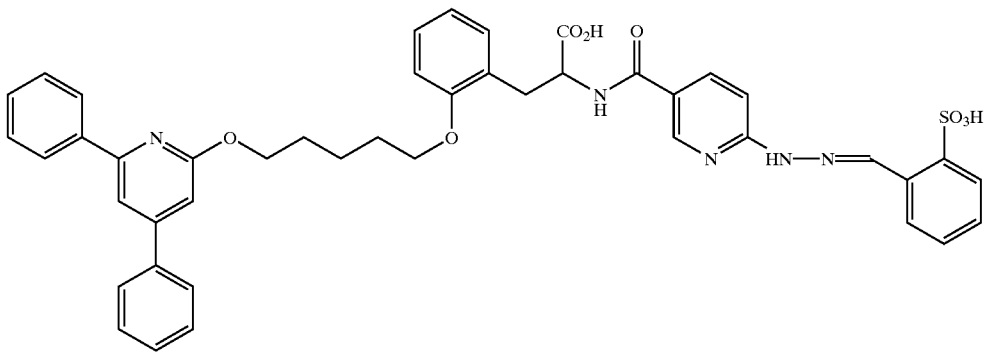

Part A: Preparation of methyl 2-amino-3-(2-hydroxyphenyl)propanoate (hydrochloride)

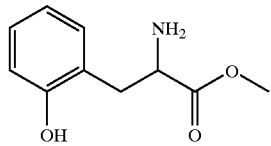

A solution of DL-o-tyrosine (2 g, 11.04 mmol) in methanol (40 mL) was treated with concentrated HCl (0.67 mL, 22.08 mmol) and refluxed for 24 h. The solution was cooled to room temperature and concentrated under high vacuum to give 2 g (93%) of a brownish solid which was used without further purification. $^1$H NMR (DMSO-$d_6$): 7.15–6.12 (m, 4H), 4.22 (t, $^1$H), 3.75 (s, 3H), 3.08 (d, 2H); ESMS: Calculated for $C_{10}H_{13}NO_3$, 195.09 Found 196.1 [M+H]+1; $R_t$=2.956–3.850 min (100% pure, Vydac C18 column; gradient 20 to 100% acetonitrile/water+0.1% TFA over 30 min).

Part B: Preparation of methyl 2-((tert-butoxy)-carbonylamino)-3-(2-hydroxyphenyl)propanoate To a solution of methyl 2-amino-3-(2-hydroxyphenyl)-propanoate (1.5 g, 7.68 mmol) in DMF (10 mL) was added triethylamine (2.14 mL, 15.36 mmol) followed by di-tert-butyl-di-carbonate (1.68 g, 7.68 mmol), and the mixture was stirred at room temperature for 18 h. The mixture was concentrated under high vacuum dissolved in a minimal amount of EtOAc, filtered through silica gel using EtOAc as eluent. The filtrate was concentrated in vacuo and purified by silica gel flash chromatography (hexane/ethyl acetate, 7:3) to provide 1.1 g (48%) of a white solid. $^1$H NMR (CDCl$_3$): 7.20–6.76 (m, 4H), 4.47 (s, $^1$H), 3.77 (s, 3H), 3.12 (m, 2H), 1.47 (m, 9H); ESMS: Calculated for $C_{15}H_{21}NO_5$, 295.14 Found 294.2 [M–H]–1; $R_t$=11.471 min (89.1% pure, Vydac C18 column; gradient 20 to 100% acetonitrile/water+0.1% TFA over 30 min).

Part C: Preparation of methyl 2-((tert-butoxy)-carbonylamino)-3-(2-(5-(4,6-diphenyl(2-pyridyloxy))-pentyloxy)phenyl)propanoate A mixture of (5-(4,6-diphenyl(2-pyridyloxy))pentyl)-(methylsulfonyl)oxy (400 mg, 0.972 mmol) and methyl 2-((tert-butoxy)-carbonylamino)-3-(2-hydroxyphenyl) propanoate (287 mg, 0.972 mmol), N,N-dimethylforamide (20 mL), cesium carbonate (633 mg, 1.944 mmol) was heated to 79° C. for 18 h. The mixture was concentrated under high vacuum, diluted with water and extracted with EtOAc (3×). The combined organic extracts were washed with water and saturated NaCl, dried over MgSO$_4$, filtered and concentrated in vacuo. Purification by reverse-phase HPLC (water-acetonitrile gradient containing 0.1% TFA) yielded 350 mg (57%) of a white powdered solid. ESMS: Calculated for $C_{37}H_{42}N_2O_6$, 610.30 Found 611.3 [M+H]+1; $R_t$=23.124 min (100% pure, Vydac C18 column; gradient 20 to 100% acetonitrile/water+0.1% TFA over 30 min).

Part D: Preparation of 2-((tert-butoxy)-carbonylamino)-3-(2-(5-(4,6-diphenyl(2-pyridyloxy))-pentyloxy)phenyl)propanoic acid

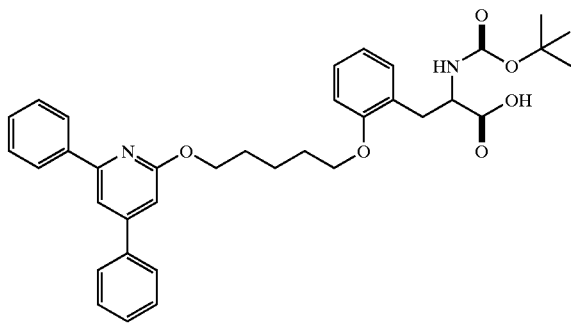

A solution of methyl 2-((tert-butoxy)-carbonylamino)-3-(2-(5(416-diphenyl(2-pyridyloxy))pentyloxy)phenyl)propanoate (145 mg, 0.237 mmol) in THF (15.8 mL) was treated with lithium hydroxide monohydrate (0.6 M, 4 mL) and stirred at room temperature for 18 h. The mixture was concentrated under high vacuum, diluted with water, acidified to pH 3 with 1N HCl and extracted with EtOAc (3×). The EtOAc extract was washed with water and brine, dried over MgSO$_4$, filtered and concentrated in vacuo to yield 125 mg (88%) of a white solid which was used without further purification. ESMS: Calculated for $C_{36}H_{40}N_2O_6$, 596.29 Found 597.3 [M+H]+1; R$_t$=21.353 min (95.8% pure, Vydac C18 column; gradient 20 to 100% acetonitrile/water+0.1% TFA over 30 min).

Part E: Preparation of 2-amino-3-(2-(5-(4,6-diphenyl(2-pyridyloxy))-pentyloxy)phenyl)propanoic acid (trifluoroacetic acid salt)

A solution of 2-((tert-butoxy)-carbonylamino)-3-(2-(5-(4,6-diphenyl(2-pyridyloxy))-pentyloxy)phenyl)propanoic acid (95 mg, 0.159 mmol) in dichloromethane (5 mL) was treated with trifluoroacetic acid (5 mL) and stirred at room temperature for 30 min. The solution was concentrated under high vacuum, and the residue lyophilized to give 79 mg (100%) of a white powdered solid. ESMS: Calculated for $C_{31}H_{32}N_2O_4$, 496.24 Found 497.3 [M+H]+1; R$_t$=16.002 min (97.1% pure, Vydac C18 column; gradient 20 to 100% acetonitrile/water+0.1% TFA over 30 min).

Part F: Preparation of 2-((6-((1-aza-2-(2-sulfophenyl)vinyl)amino)(3-pyridyl)carbonylamino)-3-(2-(5-(4,6-diphenyl(2-pyridyloxy))pentyloxy)phenyl)propanoic acid A solution of 2-amino-3-(2-(5-(4,6-diphenyl(2-pyridyloxy))-pentyloxy)phenyl)propanoic acid (53 mg, 0.106 mmol) in DMF (2 mL) was added triethylamine (44.3 mL, 0.318 mmol) and stirred at room temperature for 15 min. 2-[[[5-[[(2,5-Dioxo-1-pyrrolidinyl)oxy]carbonyl]-2-pyridinyl]hydrazono]methyl]-benzenesulfonic acid, mono-sodium salt (56.4 mg, 0.128 mmol) was added. The mixture was stirred for 4 h, concentrated under high vacuum, and purified by reverse-phase HPLC (water-acetonitrile gradient containing 0.1% TFA) to afford 41 mg (48%) of a white powdered solid. $^1$H NMR (DMSO-d$_6$): 8.54 (s, 1H), 8.28–6.70 (m, 22H), 4.80 (d, 1H), 4.55 (t, 2H), 4.12 (t, 2H), 3.00 (t, 1H), 1.85 (m, 6H); ESMS: Calculated for $C_{44}H_{41}N_5O_8S$, 799.27 Found 800.3 [M+H]+1; R$_t$=16.407 min (100% pure, Vydac C18 column; gradient 20 to 100% acetonitrile/water+0.1% TFA over 30 min).

Example 65

Synthesis of 3-((6-((1-aza-2-(2-sulfophenyl)vinyl)amino)(3-pyridyl)carbonylamino)-3-(N-(6-(4,6-diphenyl(2-pyridyloxy))-2,2-dimethylhexyl)carbamoyl)propanoic acid

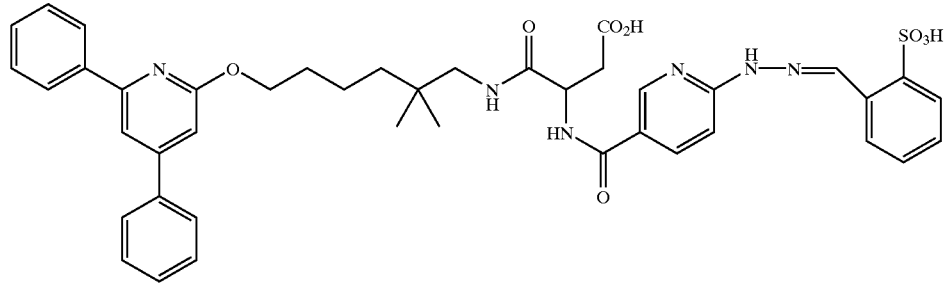

Part A: Preparation of tert-butyl 3-((tert-butoxy)carbonylamino)-3-(N-(6-(4,6-diphenyl(2-pyridyloxy))-2,2-dimethylhexyl)carbamoyl)propanoate

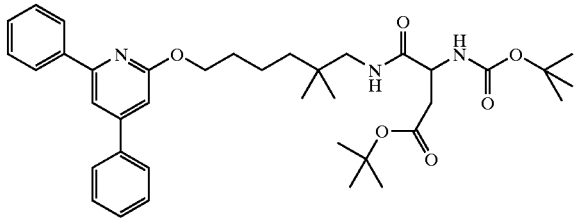

A solution of 6-(4,6-diphenyl(2-pyridyloxy))-2,2-dimethylhexylamine (100 mg, 0.267 mmol), as described in Example 10, Part C, in DMF (5 mL) was added triethylamine (112 mL, 0.801 mmol) and stirred at room temperature for 15 min. Boc-Asp(OtBu)-Osu (124 mg, 0.320 mmol) was added, and the mixture was stirred for 4 h. The mixture was concentrated under high vacuum, taken up in water and extracted with EtOAc. The EtOAc extract was washed with water and saturated NaCl, dried over MgSO$_4$, filtered and evporated in vacuo. The resulting residue was lyophilized to give 155 mg (90%) of product. The product was used without further purification. ESMS: Calculated for $C_{38}H_{51}N_3O_6$, 645.38 Found 646.3 [M+H]+1; R$_t$=23.397 min (94.1% pure, Vydac C18 column; gradient 20 to 100% acetonitrile/water+0.1% TFA over 30 min).

Part B: Preparation of 3-amino-3-(N-(6-(4,6-diphenyl(2-pyridyloxy))-2,2-dimethylhexyl)carbamoyl)propanoic acid (trifluoroacetic acid salt)

A solution of tert-butyl 3-((tert-butoxy)carbonylamino)-3-(N-(6-(4,6-diphenyl(2-pyridyloxy))-2,2-dimethylhexyl)-carbamoyl)propanoate (150 mg, 0.232 mmol) in dichloromethane (5 mL) was treated with trifluoroacetic acid (7 mL) and stirred at room temperature for 30 min. The solution was concentrated under high vacuum, and the residue was lyophilized to give 180 mg of product which

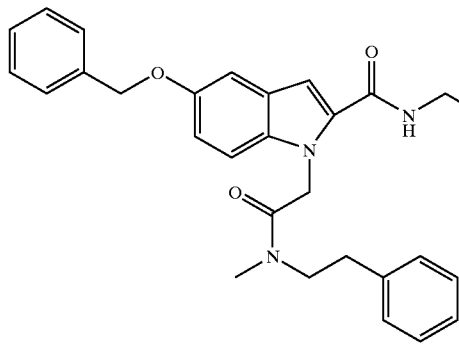

was used without further purification. ESMS: Calculated for $C_{29}H_{35}N_3O_4$, 489.26 Found 490.3 [M+H]+1; $R_t$=15.685 min (95.2% pure, Vydac C18 column; gradient 20 to 100% acetonitrile/water+0.1% TFA over 30 min).

Part C: Preparation of 3-((6-((1-aza-2-(2-sulfophenyl)vinyl)amino)(3-pyridyl)carbonylamino)-3-(N-(6-(4,6-diphenyl(2-pyridyloxy))-2,2-dimethylhexyl)-carbamoyl)propanoic acid A mixture of 3-amino-3-(N-(6-(4,6-diphenyl(2-pyridyloxy))-2,2-dimethylhexyl)carbamoyl)propanoic acid (20 mg, 0.0408 mmol), N,N-dimethylformamide (1 mL) and triethylamine (17 mL, 0.122 mmol) was stirred at room temperature for 15 min. 2-[[[5-[[(2,5-Dioxo-1-pyrrolidinyl)oxy]carbonyl]-2-pyridinyl]hydrazono]methyl]-benzenesulfonic acid, monosodium salt (21.6 mg, 0.0492 mmol) was added, and the mixture was stirred for 25 h. The mixture was concentrated under high vacuum, and the residue was purified by reverse-phase HPLC (water-acetonitrile gradient containing 0.1% TFA) to afford 15 mg (46%) of a white powdered solid. $^1$H NMR (DMSO-d$_6$): 9.45 (s, 1H), 9.00 (s, 1H), 8.50–7.15 (m, 19H), 7.10 (s, 1H), 4.95 (t, 1H), 4.51 (t, 2H), 3.25–2.50 (m, 4H), 1.80–1.25 (m, 6H), 0.80 (s, 6H); ESMS: Calculated for $C_{42}H_{44}N_6O_8S$, 792.29 Found 793.4 [M+H]+1; $R_t$=15.488 min (98.3% pure, Vydac C18 column; gradient 20 to 100% acetonitrile/water+0.1% TFA over 30 min).

Example 66

Synthesis of 2-(2-aza-2-((5-(N-(3-(2-(2-(3-((1-((N-methyl-N-(2-phenylethyl)carbamoyl)methyl)-5-(phenylmethoxy)-indol-2-yl)carbonylamino)propoxy)ethoxy)ethoxy)propyl)-carbamoyl)(2-pyridyl))amino)vinyl)benzenesulfonic acid

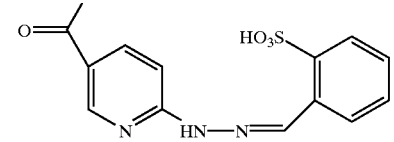

Part A: Preparation of 2-(2-(N-(3-(2-(2-(3-((tert-butoxy)carbonylamino)propoxy)ethoxy)ethoxy)propyl)carbamoyl)-5-(phenylmethoxy)indolyl)-N-methyl-N-(2-phenylethyl)-ethanamide

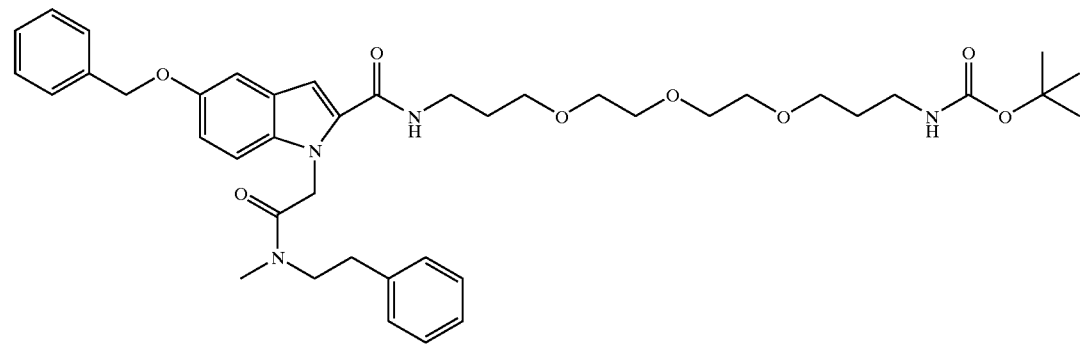

To a solution of 1-((N-methyl-N-(2-phenylethyl)-carbamoyl)methyl-5-(benzyloxy)indole-2-carboxylic acid (133 mg, 0.3 mmol), as described in Example 25, Part C, in DMF (3 mL) was added diisopropylethylamine (130 mL, 0.75 mmol) followed by 2-(1H-benzotriazole-1-yl)-1,1,3,3-tetramethyluronium hexafluorophosphate (114 mg, 0.3 mmol). The solution was stirred at room temperature for 5 min, and N-(3-(2-(2-(3-amino)propoxy)ethoxy)ethoxy)propyl)-(tert-butoxyl)formamide (80 mg, 0.250 mmol) was added. The mixture was stirred for 18 h, concentrated under high vacuum and purified by reverse-phase HPLC (water-acetonitrile gradient containing 0.1% TFA) to afford 140 mg (75%) of product. ESMS: Calculated for $C_{42}H_{56}N_4O_8$, 744.41 Found 745.5 [M+H]+1; $R_t$=18.006 min (96.2% pure, Vydac C18 column; gradient 20 to 100% acetonitrile/water+0.1% TFA over 30 min).

Part B: Preparation of 2-(2-(N-(3-(2-(2-(3-aminopropoxy)ethoxy)ethoxy)propyl)carbamoyl)-5-(phenylmethoxy)indolyl)-N-methyl-N-(2-phenylethyl)-ethanamide (trifluoroacetic acid salt)

A solution of 2-(2-(N-(3-(2-(2-(3-((tert-butoxy)-carbonylamino)propoxy)ethoxy)ethoxy)propyl)carbamoyl)-5-(phenylmethoxy)indolyl)-N-methyl-N-(2-phenylethyl)-ethanamide (140 mg, 0.188 mmol) in dichloromethane (7 mL) was treated with trifluoroacetic acid (7 mL) and stirred at room temperature for 30 min. The solution was concentrated under high vacuum, and the residue was lyophilized to give 130 mg (91%) of a white powdered solid. ESMS: Calculated for $C_{37}H_{48}N_4O_6$, 644.36 Found 645.4 [M+H]+1; $R_t$=13.737 min (94.6% pure, Vydac C18 column; gradient 20 to 100% acetonitrile/water+0.1% TFA over 30 min).

Part C: Preparation of 2-(2-aza-2-((5-(N-(3-(2-(2-(3-((1-((N-methyl-N-(2-phenylethyl)carbamoyl)methyl)-5-(phenylmethoxy)-indol-2-yl)carbonylamino)propoxy)-ethoxy)ethoxy)propyl)-carbamoyl)(2-pyridyl))amino)-vinyl)benzenesulfonic acid A solution of 2-(2-(N-(3-(2-(2-(3-aminopropoxy)ethoxy)ethoxy)propyl)carbamoyl)-5-(phenylmethoxy)indolyl)-N-methyl-N-(2-phenylethyl)-ethanamide (130 mg, 0.171 mmol) in DMF (4 mL) was added triethylamine (84 mL, 0.606 mmol) and stirred at room temperature for 15 min. 2-[[[5-[[(2,5-Dioxo-1-pyrrolidinyl)oxy]carbonyl]-2-pyridinyl]hydrazono]methyl]-benzenesulfonic acid, monosodium salt (107 mg, 0.242 mmol) was added, and the mixture was stirred for 24 h. The mixture was concentrated under high vacuum and purified by reverse-phase HPLC (water-acetonitrile gradient containing 0.1% TFA) to provide 116 mg (71%) of a white powdered solid. $^1$H NMR (DMSO-$d_6$): 8.60–6.75 (m, 24H), 5.5 (s, $^1$H), 5.36 (s, 1H), 5.18 (t, 2H), 3.60 (m, 16H), 3.15–2.64 (m, 7H), 1.80 (m, 4H), 1.25 (t, 1H); ESMS: Calculated for $C_{50}H_{57}N_7O_{10}S$, 947.39 Found 948.4 [M+H]+1; $R_t$=13.750 min (98.1% pure, Vydac C18 column; gradient 20 to 100% acetonitrile/water+0.1% TFA over 30 min).

Example 67

Synthesis of 2-(2-((6-((1-aza-2-(2-sulfophenyl)vinyl)-amino)(3-pyridyl)carbonylamino)-3-carboxypropanoylamino)-3-(2-(5-(4,6-diphenyl(2-pyridyloxy))pentyloxy)phenyl)propanoic acid

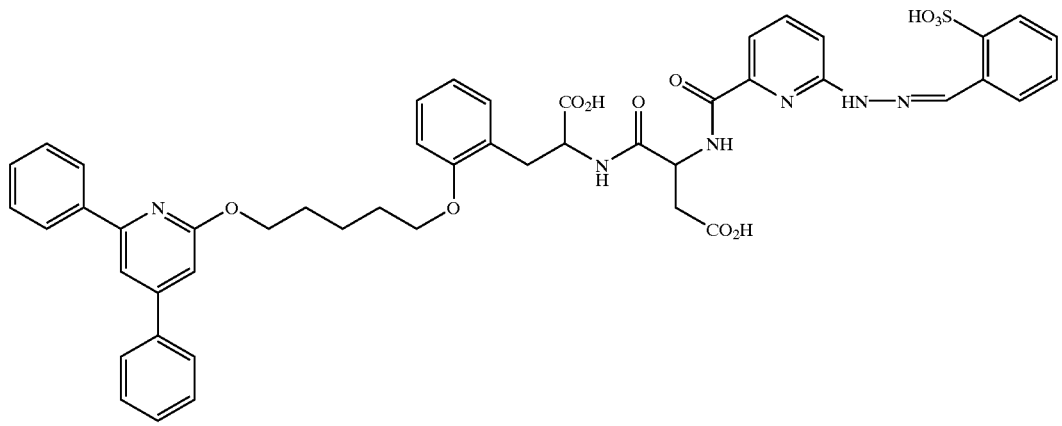

Part A: Preparation of 2-(3-((tert-butyl)oxycarbonyl)-2-((tert-butoxy)-carbonylamino)propanoylamino)-3-(2-(5-(4,6-diphenyl(2-pyridyloxy))-pentyloxy)phenyl)propanoate

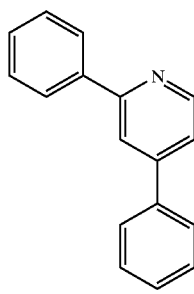

A mixture of 2-amino-3-(2-(5-(4,6-diphenyl(2-pyridyloxy))-pentyloxy)phenyl)propanoic acid (166 mg, 0.334 mmol), N,N-dimethylformamide (4 mL) and triethylamine (0.14 mL, 1.00 mmol) was stirred at room temperature for 15 min. Boc-Asp(OtBu)-Osu (155 mg, 0.401 mmol) was added and the mixture was stirred for 2 h. The mixture was concentrated under high vacuum, diluted with water and extracted with EtOAc (3×). The combined organic extracts were washed with water and saturated NaCl, dried over $MgSO_4$ and filtered. The filtrate was concentrated in vacuo and lyophilized to give 228 mg (89%) of product which was used without further purification. ESMS: Calculated for $C_{44}H_{53}N_3O_9$, 767.38 Found 768.4 [M+H]+1; $R_t$=17.484 min (88.7% pure, Vydac C18 column; gradient 20 to 100% acetonitrile/water+0.1% TFA over 30 min).

Part B: Preparation of 2-(amino-3-carboxypropanoyl-amino)-3-(2-(5-(4,6-diphenyl(2-pyridyloxy))pentyloxy)-phenyl)propanoic acid (trifluoroacetic acid salt)

A solution of 2-(3-((tert-butyl)oxycarbonyl)-2-((tert-butoxy)-carbonylamino)propanoylamino)-3-(2-(5-(4,6-diphenylamino)(2-pyridyloxy))-pentyloxy)phenyl)propanoate (205 mg, 0.267 mmol) in dichloromethane (5 mL) was treated with trifluoroacetic acid (7 mL) and stirred at room temperature for 1 h. The solution was concentrated under high vacuum, and the residue was lyophilized to give 210 mg of product. ESMS: Calculated for $C_{35}H_{37}N_3O_7$, 611.26 Found 612.4 [M+H]+1; $R_t$=15.413 min (91.0% pure, Vydac C18 column; gradient 20 to 100% acetonitrile/water+0.1% TFA over 30 min).

Part C: Preparation of 2-(2-((6-((1-aza-2-(2-sulfophenyl) vinyl)amino)(3-pyridyl)carbonylamino)-3-carboxypropanoylamino)-3-(2-(5-(4,6-diphenyl(2-pyridyl-oxy))pentyloxy)phenyl)propanoic acid A solution of 2-(amino-3-carboxypropanoylamino)-3-(2-(5-(4,6-diphenyl(2-pyridyloxy))pentyloxy)phenyl) propanoic acid (84 mg, 0.137 mmol) in DMF (2 mL) was added triethylamine (57 mL) and stirred at room temperature for 15 min. 2-[[[5-[[(2,5-Dioxo-1-pyrrolidinyl)oxy]carbonyl]-2-pyridinyl]hydrazono]methyl]-benzenesulfonic acid, monosodium salt (73 mg, 0.165 mmol) was added and the mixture was stirred for 48 h. The reaction was monitored by analytical HPLC, and the chromatogram showed that there were two diastereoisomers in the reaction. The mixture was concentrated under high vacuum, and the two diaster-oisomers were separated by reverse-phase HPLC (water-acetonitrile gradient containing 0.1% TFA) to afford 11 mg (9%) of each isomer. ESMS: Calculated for $C_{48}H_{46}N_6O_{11}S$, 914.29 Found 915.4 [M+H]+1; For SK983: $R_t$–14.686 min (88.5% pure, Vydac $C_{18}$ column; gradient 20 to 100% acetonitrile/water+0.1% TFA over 30 min); For SK894: $R_t$=15.129 min (95.7% pure, Vydac C18 column; gradient 20 to 100% acetonitrile/water+0.1% TFA over 30 min).

Example 68

Synthesis of 2-(2-aza-2-((5-(N-(2-(N-(3-(2-(2-(3-(2-(2,5-dioxoimidazolidin-4-yl)acetylamino)-propoxy) ethoxy)ethoxy)-propyl)carbamoyl)-1-(N-(6-(4,6-diphenyl(2-pyridyloxy))-2,2-dimethylhexyl) carbamoyl)-ethyl)carbamoyl(2-pyridyl))amino)-vinyl)benzenesulfonic acid Part A: Preparation of N-(3-(2-(2-(3-((tert-butoxy)carbonylamino)propoxy)ethoxy)ethoxy)propyl-2-(2,5-dioxoimidazolidin-4-yl)ethanamide.

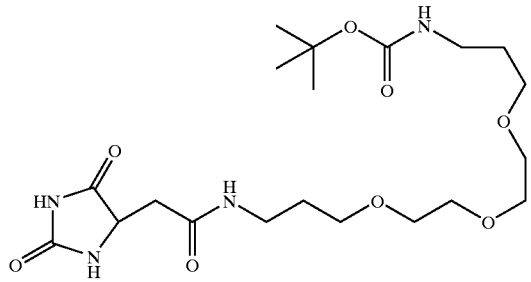

A mixture of 5-hydrantoinacetic acid (0.44 g, 2.78 mmol), N,N-dimethylformamide (10 mL), diisopropylethylamine (1.2 mL, 6.96 mmol) and 2-(1H-benzotriazole-1-yl)-1,1,3,3-tetramethyl uronium hexafluoro-phosphate (2.64 g, 6.96 mmol) was stirred at room temperature for 5 min. N-(3-(2-(2-(3-amino)propoxy)ethoxy)ethoxy)propyl)(tert-butoxyl) formamide (0.744 g, 2.32 mmol) was added and the mixture was stirred for 24 h. The mixture was concentrated under high vacuum, and the residue was purified by silica gel flash chromatography (chloroform/methanol, 4:1) to give 0.75 g (70%) of a brownish oil. ESMS: Calculated for $C_{20}H_{36}N_4O_8$, 460.25 Found 461.3 [M+H]+1

Part B: Preparation of N-(3-(2-(2-(3-aminopropoxy)-ethoxy)ethoxy)propyl-2-(2,5-dioxoimidazolidin-4-yl)-ethanamide.(trifluoroacetic acid salt)

A solution of N-(3-(2-(2-(3-((tert-butoxy)-carbonylamino)propoxy)ethoxy)ethoxy)propyl-2-(2,5-dioxoimidazolidin-4-yl)ethanamide (0.75 g, 1.64 mmol) in dichloromethane (10 mL) was treated with trifluoroacetic acid (10 mL) and stirred at room temperature for 1 h. The solution was concentrated under high vacuum, and the residue was lyophilized to give 0.75 g (96%) of product. ESMS: Calculated for $C_{15}H_{28}N_4O_6$, 360.20 Found 361.2 [M+H]+1

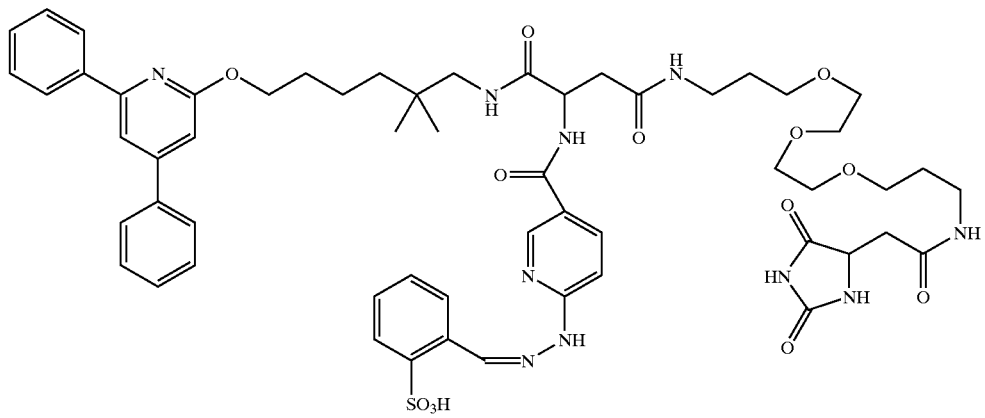

Part C: Preparation of 3-((tert-butoxy)carbonylamino-3-(N-(6-(4,6-diphenyl(2-pyridyloxy))-2,2-dimethylhexyl)-carbamoyl)-propanoic acid

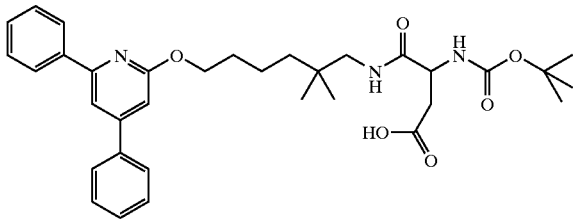

To a solution of 3-amino-3-(N-(6-(4,6-diphenyl(2-pyridyloxy))-2,2-dimethylhexyl)carbamoyl)propanoic acid (120 mg, 0.253 mmol) in acetonitrile (3 mL) was added triethylamine (42.4 mL) followed by di-tert-butyl-dicarbonate (55 mg, 0.253 mmol). The mixture was stirred at room temperature for 4 h, concentrated under high vacuum and filtered through silica gel using ethyl acetate as eluent. The filtrate was evaporated in vacuo and lyophilized to provide 163 mg of product which was used without further purification. ESMS: Calculated for $C_{34}H_{43}N_3O_6$, 589.32 Found 590.2 [M+H]+1; $R_t$=20.268 min (94.2% pure, Vydac C18 column; gradient 20 to 100% acetonitrile/water+0.1% TFA over 30 min).

Part D: Preparation of 2-((tert-butoxy)carbonylamino-N'-(3-(2-(2-(3-(2-(2,5-dioxoimidazolidin-4-yl)acetylamino)-propoxy)ethoxy)ethoxy)propyl)-N-(6-(4,6-diphenyl(2-pyridyloxy))-2,2-dimethylhexyl)butane-1,4-diamide

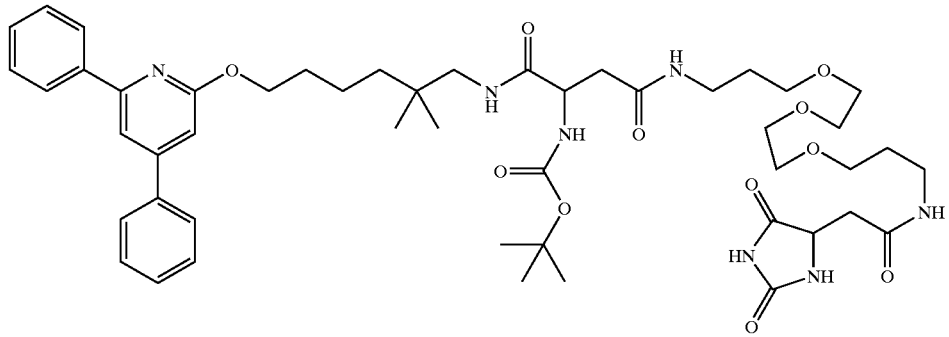

A mixture of 3-((tert-butoxy)carbonylamino-3-(N-(6-(4,6-diphenyl(2-pyridyloxy))-2,2-dimethylhexyl)carbamoyl)-propanoic acid (141 mg, 0.239 mmol), N,N-dimethylformamide (6 mL), diisopropylethylamine (0.1 mL, 0.60 mmol) and 2-(1H-benzotriazole-1-yl)-1,1,3,3-tetramethyluronium hexafluorophosphate (90 mg, 0.239 mmol) was stirred at room temperature for 15 min. N-(3-(2-(2-(2-(3-aminopropoxy)ethoxy)-ethoxy)propyl-2-(2,5-dioxoimidazolidin-4-yl)ethanamide (94 mg, 0.199 mmol) was added and the mixture was stirred for 18 h. The mixture was concentrated under high vacuum and purified by reverse-phase HPLC (water-acetonitrile containing 0.1% TFA) to afford 68 mg (37%) of a white powdered solid. ESMS: Calculated for $C_{49}H_{69}N_7O_{11}$, 931.50 Found 932.6 [M+H]+1; $R_t$=17.822 min (82.3% pure, Vydac C18 column; gradient 20 to 100% acetonitrile/water+0.1% TFA over 30 min).

Part E: Preparation of 2-amino-N'-(3-(2-(2-(3-(2-(2,5-dioxoimidazolidin-4-yl)acetylamino)-propoxy)ethoxy)-ethoxy)propyl)-N-(6-(4,6-diphenyl(2-pyridyloxy))-2,2-dimethylhexyl)butane-1,4-diamide (trifluoroacetic acid salt)

A solution of 2-((tert-butoxy)carbonylamino-N'-(3-(2-(2-(3-(2-(2,5-dioxoimidazolidin-4-yl)acetylamino)-propoxy)ethoxy)ethoxy)propyl)-N-(6-(4,6-diphenyl(2-pyridyloxy))-2,2-dimethylhexyl)butane-1,4-diamide (68 mg, 0.073 mmol) in dichloromethane (4 mL) was treated with trifluoroacetic acid (4 mL) and stirred at room temperature for 1 h. The solution was concentrated under high vacuum, and the residue was lyophilized to give 60 mg (98%) of product. ESMS: Calculated for $C_{44}H_{61}N_7O_9$, 831.45 Found 832.5 [M+H]+1; $R_t$=14.308 min (75.8% pure, Vydac C18 column; gradient 20 to 100% acetonitrile/water+0.1% TFA over 30 min).

Part F: Preparation of 2-(2-aza-2-((5-(N-(2-(N-(3-(2-(2-(3-(2-(2,5-dioxoimidazolidin-4-yl)acetylamino)-propoxy)ethoxy)ethoxy)propyl)carbamoyl)-1-(N-(6-(4,6-diphenyl(2-pyridyloxy))-2,2-dimethylhexyl)carbamoyl)-ethyl)carbamoyl(2-pyridyl))amino)vinyl)benzenesulfonic acid A solution of 2-amino-N'-(3-(2-(2-(3-(2-(2,5-dioxoimidazolidin-4-yl)acetylamino)-propoxy)ethoxy)-ethoxy)propyl)-N-(6-(4,6-diphenyl(2-pyridyloxy))-2,2-dimethylhexyl)butane-1,4-diamide (60 mg, 0.072 mmol) in DMF (2 mL) was added triethylamine (30 mL, 0.216 mmol) was added and stirred at room temperature for 15 min. 2-[[[5[[(2,5-Dioxo-1-pyrrolidinyl)oxy]carbonyl]-2-pyridinyl]hydrazono]-methyl]-benzenesulfonic acid, monosodium salt (73 mg, 0.165 mmol) was added and the mixture was stirred for 48 h. The mixture was concentrated under high vacuum, and the residue was purified by reverse-phase HPLC (water-acetonitrile gradient containing 0.1% TFA) to afford 12.8 mg (16%) of a white powdered solid. ESMS: Calculated for $C_{57}H_{70}N_{10}O_{13}S$, 1134.48 Found 1135.6 [M+H]+1; $R_t$=14.167 min (86.1% pure, Vydac C18 column; gradient 20 to 100% acetonitrile/water+0.1% TFA over 30 min).

Example 69

Synthesis of 6-((6-(((1-aza-2-(2-sulfophenyl)-vinyl)amino)(3-pyridyl)carbonylamino)-2-((1-((N-methyl-N-(2-phenylethyl)carbamoyl)methyl)-5-(phenylmethoxy)indol-2-yl)carbonylamino)hexanoic acid

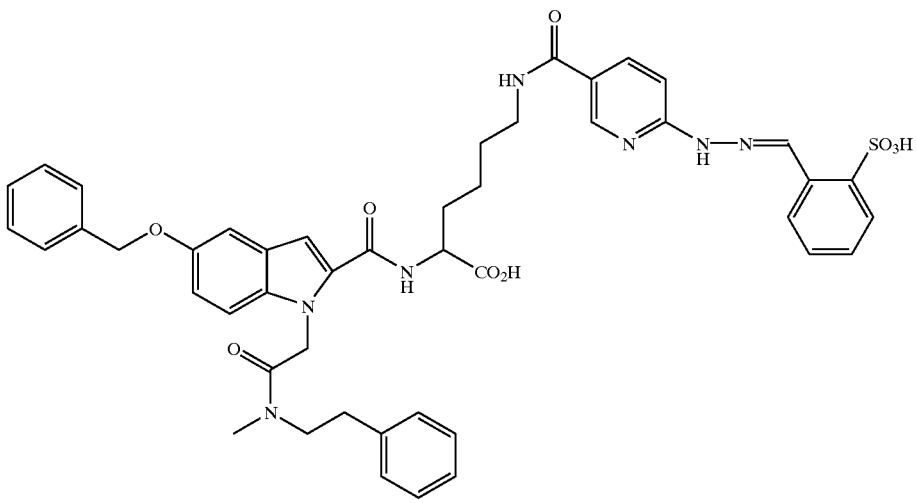

Part A: Preparation of tert-butyl 6-((tert-butoxy)-carbonylamino)-2-((1-((N-methyl-N-(2-phenylethyl)carbamoyl)-methyl)-5-(phenylmethoxy)indol-2-yl)carbonylamino)hexanoic acid

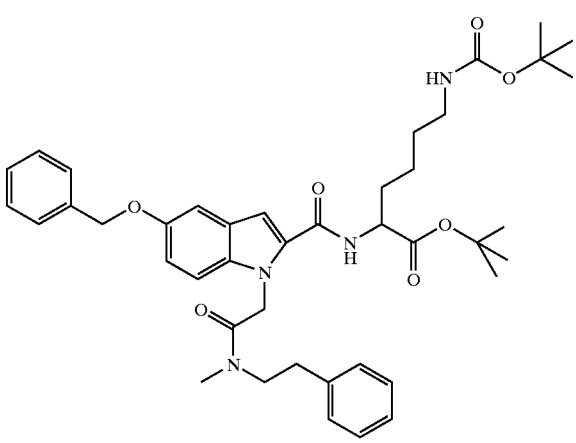

To a mixture of 1-((N-methyl-N-(2-phenylethyl)-carbamoyl)methyl-5-(benzyloxy)indole-2-carboxylic acid (180 mg, 0.407 mmol), N,N-dimethylformamide (4 mL). Diisopropylethylamine (0.18 mL, 1.02 mmol) was added 2-(1H-benzotriazole-1-yl)-1,1,3,3-tetramethyluronium hexafluorophosphate (154 mg, 0.407 mmol). After stirring at room temperature for 5 min, H-Lys(Boc)-OtBu.HCl (103 mg, 0.339 mmol) was added and the mixture was stirred for 24 h. The mixture was concentrated under high vacuum and purified by reverse-phase HPLC (water-acetonitrile gradient containing 0.1% TFA) to afford 137 mg (56%) of a white powdered solid. ESMS: Calculated for $C_{42}H_{54}N_4O_7$, 726.40 Found 744.6 [M+NH$_4$]+1; $R_t$=19.783 min (98.6% pure, Vydac C18 column; gradient 20 to 100% acetonitrile/water+ 0.1% TFA over 30 min).

Part B: Preparation of 6-amino-2-((1-((N-methyl-N-(2-phenylethyl)carbamoyl)methyl)-5-(phenylmethoxy)indol-2-yl)carbonylamino)hexanoic acid (trifluoroacetic acid salt)

A solution of tert-butyl 6-((tert-butoxy)carbonylamino)-2-((1-((N-methyl-N-(2-phenylethyl)carbamoyl)methyl)-5-(phenylmethoxy)indol-2-yl)carbonylamino)hexanoic acid (137 mg, 0.188 mmol) in dichloromethane (7 mL) was treated with trifluoroacetic acid (7 mL) and stirred at room temperature for 1 h. The solution was concentrated under high vacuum, and the residue was lyophilized to give 103 mg (80%) of product. ESMS: Calculated for $C_{33}H_{38}N_4O_5$, 570.28 Found 569.3 [M–H]–1; $R_t$=12.423 min (93.1% pure, Vydac C18 column; gradient 20 to 100% acetonitrile/water+ 0.1% TFA over 30 min).

Part C: Preparation of 6-(((6-(((1-aza-2-(2-sulfophenyl)vinyl)amino)(3-pyridyl)carbonylamino)-2-((1-((N-methyl-N-(2-phenylethyl)carbamoyl)methyl)-5-(phenylmethoxy)-indol-2-yl)carbonylamino)hexanoic acid A solution of 6-amino-2-((1-((N-methyl-N-(2-phenylethyl)carbamoyl)methyl)-5-(phenylmethoxy)indol-2-yl)carbonylamino)hexanoic acid (68 mg, 0.119 mmol) in DMF (1.5 mL) was added triethylamine (50 mL, 0.357 mmol) and stirred at room temperature for 15 min. 2-[[[5-[[(2,5-Dioxo-1-pyrrolidinyl)oxy]carbonyl]-2-pyridinyl]hydrazono]methyl-benzenesulfonic acid, monosodium salt (63 mg, 0.143 mmol) was added and the mixture was stirred for 24 h. The mixture was concentrated under high vacuum and purified by reverse-phase HPLC (water-acetonitrile gradient containing 0.1% TFA) to afford (48%) of a white powdered solid. ESMS: Calculated for $C_{46}H_{47}N_7O_9S$, 873.31 Found 872.3 [M–H]–1; $R_t$=11.569 min (100% pure, Vydac C18 column; gradient 20 to 100% acetonitrile/water+ 0.1% TFA over 30 min).

Example 70

Synthesis of 1-(3-((6-((1-aza-2-(2-sulfophenyl)vinyl)amino)-(3-pyridyl)carbonylamino)-3-(N-(6-(4,6-diphenyl(2-pyridyloxy))-2,2-dimethylhexyl)carbamoyl)propanoylamino)-ethane-1,2-dicarboxylic acid.

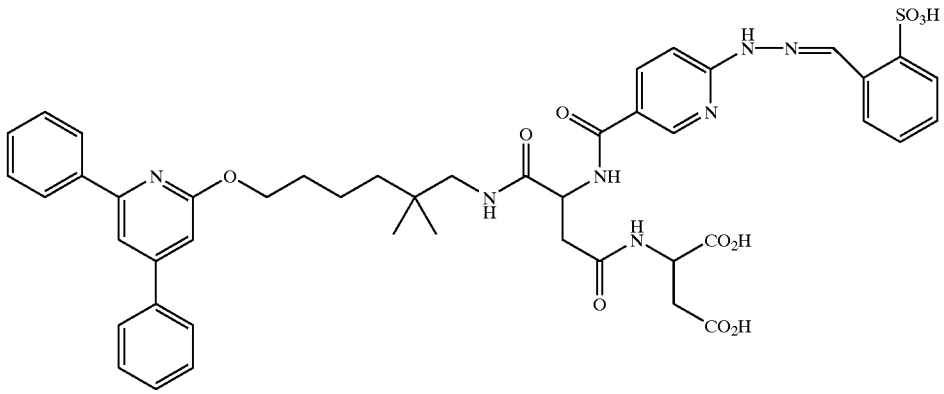

A mixture of 3-((tert-butoxy)carbonylamino-3-(N-(6-(4,6-diphenyl(2-pyridyloxy))-2,2-dimethylhexyl)carbamloyl)-propanoic acid (50 mg, 0.0847 mmol), N,N-dimethylformamide (2 mL), diisopropylethylamine (45 mL, 0.254 mmol) and 2-(1H-benzotriazole-1-yl)-1,1,3,3-tetramethyluronium hexafluorophosphate (32 mg, 0.0847 mmol) was stirred at room temperature for 10 min. H-Asp-OH (11.4 mg, 0.0847 mmol) was added in portions and the mixture was stirred for 18 h. The mixture was concentrated under high vacuum and purified by reverse-phase HPLC (water-acetonitrile gradient containing 0.1% TFA) to provide the intermediate product. A solution of this intermediate in dichloromethane (4 mL) was treated with trifluoroacetic acid (4 mL) and stirred at room temperature for 1 h. The solution was concentrated under high vacuum, and the residue was lyophilized to give the deprotected amine salt. To a solution of this amine salt in DMF (1.5 mL) was added triethylamine (35 mL). After stirring for 10 min, 2-[[[5-[[(2,5-Dioxo-1-pyrrolidinyl)oxy]carbonyl]-2-pyridinyl]hydrazono]methyl]-benzenesulfonic acid, monosodium salt (44.76 mg, 0.102 mmol) was added. The mixture was stirred for 24 h and concentrated under high vacuum. Purification by reverse-phase HPLC (water-acetonitrile gradient containing 0.1% TFA) yielded 7 mg (9.1%) of a white powdered solid. ESMS: Calculated for $C_{46}H_{49}N_7O_{11}S$, 907.32 Found 908.3 [M+H]+1; $R_t$=14.158 min (100% pure, Vydac C18 column; gradient 20 to 100% acetonitrile/water+0.1% TFA over 30 min).

Example 71

Synthesis of 1-(2-(3-((6-((1-aza-2-(2-sulfophenyl)vinyl)-amino)(3-pyridyl)carbonylamino)-3-(N-(6-(4,6-diphenyl(2-pyridyloxy))-2,2-dimethylhexyl)carbamoyl)propanoylamino)-3-carboxypropanoylamino)ethane-1,2-dicarboxylic acid

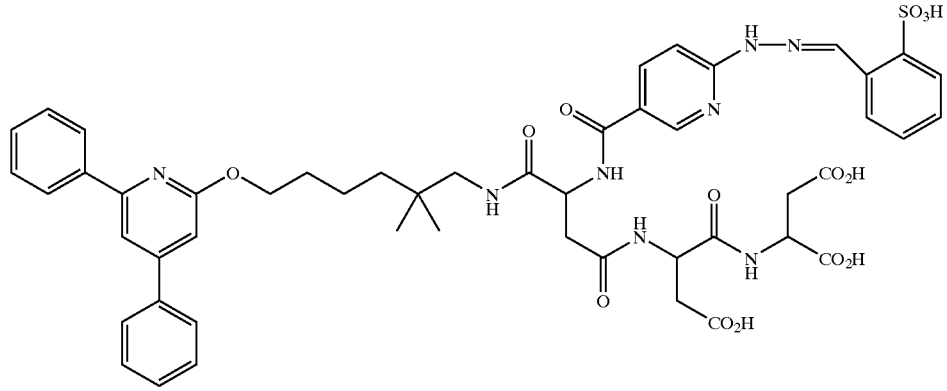

A mixture of 3-((tert-butoxy)carbonylamino-3-(N-(6-(4,6-diphenyl(2-pyridyloxy))-2,2-dimethylhexyl)carbamoyl)-propanoic acid (50 mg, 0.0847 mmol), N,N-dimethylformamide (2 mL), diisopropylethylamine (45 mL, 0.254 mmol) and 2-(1H-benzotriazole-1-yl)-1,1,3,3-tetramethyluronium hexafluorophosphate (32 mg, 0.0847 mmol) was stirred at room temperature for 10 min. H-Asp-Asp-OH (11.4 mg, 0.0847 mmol) was added in portions and the mixture was stirred for 18 h. The mixture was concentrated under high vacuum and purified by reverse-phase HPLC (water-acetonitrile gradient containing 0.1% TFA) to provide the desired intermediate product. A solution of this intermediate in dichloromethane (4 mL) was treated with trifluoroacetic acid (4 mL) and stirred at room temperature for 1 h. The solution was concentrated under high vacuum, and the residue was lyophilized to give the deprotected amine salt. To a solution of this amine salt in DMF (1.5 mL) was added triethylamine (35 mL). After stirring for 10 min, 2-[[[5-[[(2,5-Dioxo-1-pyrrolidinyl)oxy]carbonyl]-2-pyridinyl]hydrazono]methyl]-benzenesulfonic acid, monosodium salt (44.76 mg, 0.102 mmol) was added. The mixture was stirred for 24 h and concentrated under high vacuum. Purification by reverse-phase HPLC (water-acetonitrile gradient containing 0.1% TFA) to give 13 mg (15.1%) of a white powdered solid. ESMS: Calculated for $C_{50}H_{54}N_8O_{14}S$, 1022.35 Found 1023.3 [M+H]+1; $R_t$=13.570 min (90.6% pure, Vydac C18 column; gradient 20 to 100% acetonitrile/water+0.1% TFA over 30 min).

Example 72

Synthesis of 2-(2-aza-2-((5-(N-(1-(N-(6-(4,6-diphenyl(2-pyridyloxy))-2,2-dimethylhexyl)carbamoyl)-2-(3-(((4,5,6-trihydroxy-3-(hydroxymethyl)(2-oxanyl))amino)carbonylamino)-propanoylamino)ethyl)carbamoyl(2-pyirdyl))amino)vinyl)-benzenesulfonic acid

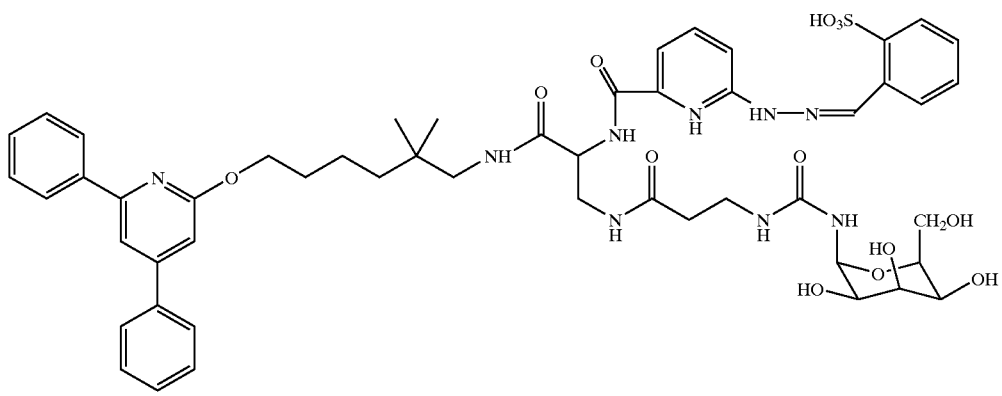

Part A: Preparation of 2-((tert-butoxy)carbonylamino)-N-(6-(4,6-diphenyl(2-pyridyloxy))-2,2-dimethylhexyl)-3-((fluoren-9-ylmethoxy)carbonylamino)propanamide

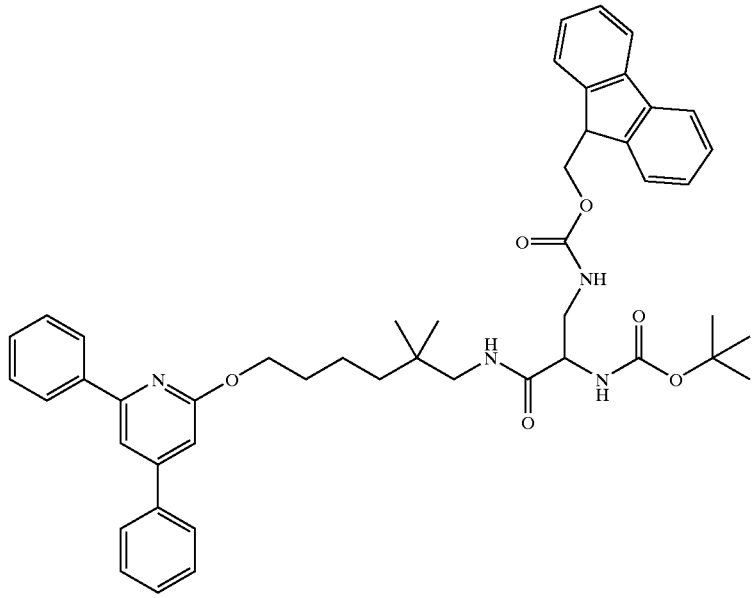

To a solution of 6-(4,6-diphenyl(2-pyridyloxy))-2,2-dimethylhexylamine (130 mg, 0.347 mmol) in DMF (6 mL) was added diisopropylethylamine (0.18 mL, 1.04 mmol) followed by 2-(1H-Benzotriazole-1-yl)-1,1,3,3-tetramethyluronium hexafluorophosphate (158 mg, 0.416 mmol). After stirring at room temperature for 15 min, Boc-DAP(Fmoc)-OH (178 mg, 0.416 mmol) was added. The mixture was stirred for 24 h, concentrated under high vacuum and purified by reverse-phase HPLC (water-acetonitrile gradient containing 0.1% TFA) to afford 171 mg (63%) of a white powdered solid. ESMS: Calculated for $C_{48}H_{54}N_4O_6$, 782.40 Found 783.5 [M+H]+1; $R_t$=23.382 min (87.9% pure, Vydac C18 column; gradient 20 to 100% acetonitrile/water+0.1% TFA over 30 min).

Part B: Preparation of 3-amino-2-((tert-butoxy)-carbonylamino)-N-(6-(4,6-diphenyl(2-pyridyloxy))-2,2-dimethylhexyl)propanamide A solution of 2-((tert-butoxy)carbonylamino)-N-(6-(4,6-diphenyl(2-pyridyloxy))-2,2-dimethylhexyl)-3-((fluoren-9-ylmethoxy)carbonylamino)propanamide (171 mg, 0.218 mmol) in DMF (5 mL) was added piperidine (1.25 mL) and stirred at room temperature for 1.5 h. The solution was concentrated under high vacuum, and the residue was purified by reverse-phase HPLC (water-acetonitrile containing 0.1% TFA) to give 70 mg (57%) of product. ESMS: Calculated for $C_{33}H_{44}N_4O_4$, 560.34 Found 561.4 [M+H]+1; $R_t$=17.715 min (98.3% pure, Vydac C18 column; gradient 20 to 100% acetonitrile/water+0.1% TFA over 30 min).

Part C: Preparation of 2-((tert-butoxy)carbonylamino)-N-(6-(4,6-diphenyl(2-pyridyloxy))-2,2-dimethylhexyl)-3-(3-(((4,5,6-trihydroxy-3-(hydroxymethyl)(2-oxanyl))amino)-carbonylamino)propanoylamino)propanamide

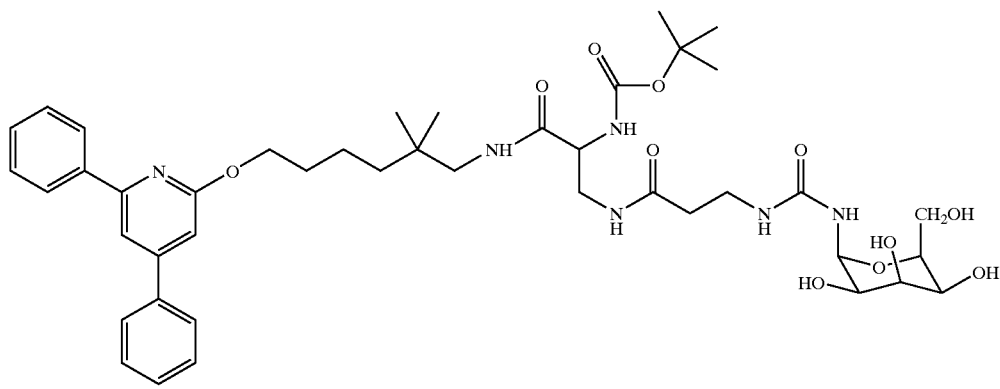

A solution of 3-amino-2-((tert-butoxy)carbonylamino)-N-(6-(4,6-diphenyl(2-pyridyloxy))-2,2-dimethylhexyl)propanamide (70 mg, 0.125 mmol) in DMF (2 mL) was added triethylamine (52 mL, 0.375 mmol) and stirred for 5 min. (b-D-Glucoseamido)-carbonyl-b-alanine-Osu (58.7 mg, 0.15 mmol) was added and the mixture was stirred for 18 h. The mixture was concentrated under high vacuum, and the residue was lyophilized to provide 93 mg (89%) of product which was used without further purification. ESMS: Calculated for $C_{43}H_{60}N_6O_{11}$, 836.43 Found 835.3 [M−H]−1; $R_t$=16.154 min (74.0% pure, Vydac C18 column; gradient 20 to 100% acetonitrile/water+0.1% TFA over 30 min).

Part D: Preparation of 2-amino-N-(6-(4,6-diphenyl(2-pyridyloxy))-2,2-dimethylhexyl)-3-(3-(((4,5,6-trihydroxy-3-(hydroxymethyl)(2-oxanyl))amino)carbonylamino) propanoyl-amino)propanamide (trifluoroacetic acid salt)

A solution of 2-((tert-butoxy)carbonylamino)-N-(6-(4,6-diphenyl(2-pyridyloxy))-2,2-dimethylhexyl)-3-(3-(((4,5,6-trihydroxy-3-(hydroxymethyl)(2-oxanyl))amino) carbonylamino)-propanoylamino)propanamide (93 mg, 0.111 mmol) in dichloromethane (4 mL) was treated with trifluoroacetic acid (5 mL) was added and stirred at room temperature for 1 h. The solution was concentrated under high vacuum, and the residue was lyophilized to give 82 mg (100%) of product. The product was used without further purification. ESMS: Calculated for $C_{38}H_{52}N_6O_9$, 736.38 Found 737.5 [M+H]+1; $R_t$=13.320 min (80.5% pure, Vydac C18 column; gradient 20 to 100% acetonitrile/water+0.1% TFA over 30 min).

Part E: Preparation of 2-(2-aza-2-((5-(N-(1-(N-(6-(4,6-diphenyl(2-pyridyloxy))-2,2-dimethylhexyl)carbamoyl)-2-(3-(((4,5,6-trihydroxy-3-(hydroxymethyl)(2-oxanyl))-amino)carbonylamino)propanoylamino)ethyl)carbamoyl(2-pyridyl))amino)vinyl)benzenesulfonic acid A solution of 2-amino-N-(6-(4,6-diphenyl(2-pyridyloxy))-2,2-dimethylhexyl)-3-(3-(((4,5,6-trihydroxy-3-(hydroxymethyl)(2-oxanyl))amino)carbonylamino) propanoyl-amino)propanamide (82 mg, 0.111 mmol) in DMF (2 mL) was added triethylamine (46 mL, 0.333 mmol) and stirred at room temperature for 10 min. 2-[[[5-[[(2,5-Dioxo-1-pyrrolidinyl)-oxy]carbonyl]-2-pyridinyl] hydrazono]methyl]-benzenesulfonic acid, monosodium salt (68 mg, 0.155 mmol) was added and the mixture was stirred for 24 h. The mixture was concentrated under high vacuum and purified by reverse-phase HPLC (water-acetonitrile gradient containing 0.1% TFA) to afford 20 mg (17%) of a white powdered solid. ESMS: Calculated for $C_{51}H_{61}N_9O_{13}S$, 1039.41 Found 1038.2 [M−H]−1; $R_t$=13.149 min (92.5% pure, Vydac C18 column; gradient 20 to 100% acetonitrile/water+0.1% TFA over 30 min).

Example 73

Synthesis of 3-(N-(6-(4,6-diphenyl(2-pyridyloxy))-2,2-dimethylhexyl)carbamoyl)-3-(3-pyridylcarbonylamino)propanoic acid.

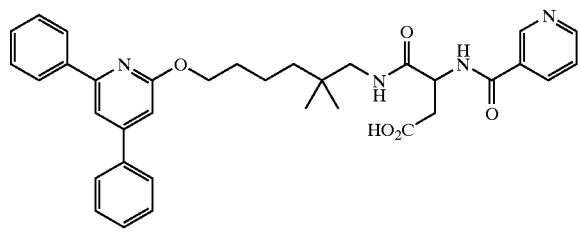

A mixture of 3-amino-3-(N-(6-(4,6-diphenyl(2-pyridyloxy))-2,2-dimethylhexyl)carbamoyl)propanoic acid (100 mg, 0.204 mmol), N,N-dimethylformamide (2 mL), and triethylamine (0.1 mL) was stirred at room temperature for 5 min. Succinimidyl nicotinate (69 mg, 0.315 mmol) was added, and the mixture was stirred for 18 h. The mixture was concentrated under high vacuum, and the residue was purified using reverse-phase HPLC (water-acetonitrile gradient containing 0.1% TFA) to afford 23 mg (19%) of a white powdered solid. ESMS: Calculated for $C_{35}H_{38}N_4O_5$, 594.2842 Found 595.2 [M+H]+1; $R_t$=15.597 min (100% pure, Vydac C18 column; gradient 20 to 100% acetonitrile/water+0.1% TFA over 30 min).

Example 74

Synthesis of N-(6-(4,6-diphenyl(2-pyridyloxy))-2,2-dimethylhexyl)-3-pyridylformamide

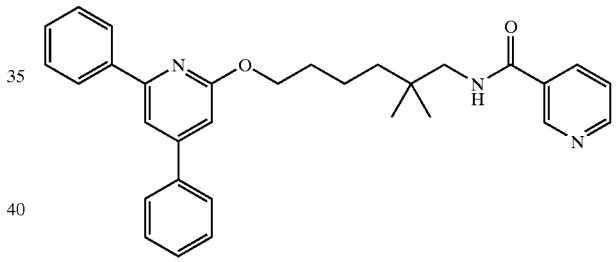

A mixture of 6-(4,6-diphenyl(2-pyridyloxy))-2,2-dimethylhexylamine (0.14 g, 0.373 mmol), N,N-dimethylformamide (4 mL), and triethylamine (0.3 mL) was stirred at room temperature for 10 min. Succinimidyl nicotinate (0.1 g, 0.447 mmol) was added, and the mixture was stirred for 18 h. The mixture was concentrated under high vacuum, and the residue was purified using reverse-phase HPLC (water-acetonitrile containing 0.1 TFA) to afford 0.114 mg (64%) of a white powdered solid. $^1$H NMR (CDCl$_3$): 8.12–6.80 (m, 16H), 4.54 (t, 2H), 3.43 (t, 2H), 1.90 (m, 6H), 1.05 (s, 6H); ESMS: Calculated for $C_{31}H_{33}N_3O_2$, 479.2573 Found 480.2 [M+H]+1; $R_t$=17.096 min (100% pure, Vydac C18 column; gradient 20 to 100% acetonitrile/water+0.1% TFA over 30 min).

Example 75

Synthesis of 2-(2-aza-2-((5-((6-(4-benzo[d]1,3-dioxolan-5-yl-6-phenyl(2-pyridyloxy))-2,2-dimethylhexanoyl-amino)sulfonyl)-(2-pyridyl))amino)vinyl)benzenesulfonic acid

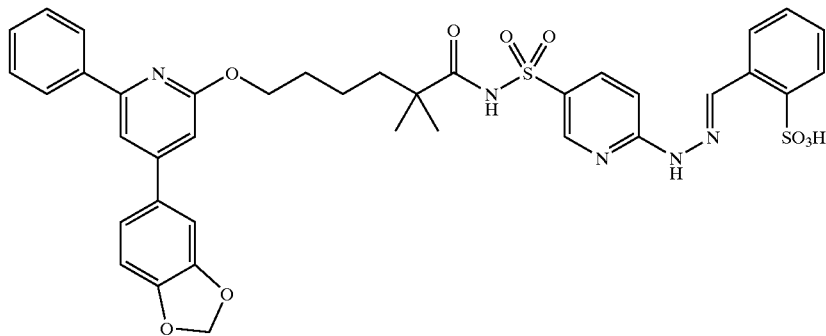

Part A: Preparation of 6-(4-benzo[d]1,3-dioxolan-5-yl-6-phenyl (2-pyridyloxy))-N-((6-chloro(3-pyridyl))sulfonyl)-2,2-dimethyhexanamide

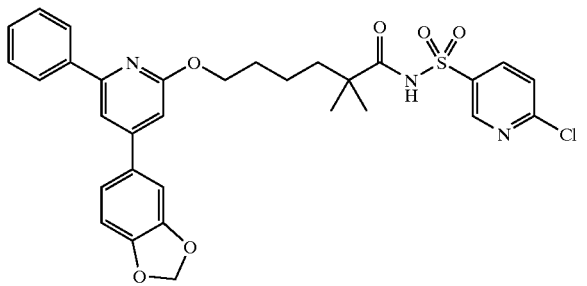

To a solution of 6-(4-benzo[d]1,3-dioxolan-5-yl-6-phenyl (2-pyridyloxy))-2,2-dimethylhexanoic acid (0.100 g, 0.231 mmol) in methylene chloride, was added 2-chloropyridine-5-sulfonamide (0.0466 g, 0.243 mmol), dimethylaminopyridine (0.0367 g, 0.300 mmol), 1-(3-dimethylaminopropyl)-3-ethyl carbodiimide hydrochloride (0.0443 g, 0.231 mmol), and 4 A molecular sieves. The reaction mixture was stirred overnight for 18 h and then filtered. The filtrate was washed with 1N HCl, water, brine. The organic layer was dried over magnesium sulfate, filtered, and concentrated to a small volume. The resulting concentrated solution was triturated with hexane. The product was filtered, washed with hexane and dried under high vacuum to give 51.7 mgs (37%) of product. ESMS: Calcd. For $C_{31}H_{30}N_3O_6S$, 607.15; Found, 608.4 [M+H+1] HPLC Method 5. $R_t$=19.226 min Purity=78%

Part B: Preparation of 6-(4-benzo[d]1,3-dioxolan-5-yl-6-phenyl(2-pyridyloxy))-N-((6-hydrazino(3-pyridyl))sulfonyl)-2,2-dimethylhexanamide 6-(4-Benzo[d]1,3-dioxolan-5-yl-6-phenyl(2-pyridyloxy))-N-((6-chloro(3-pyridyl))sulfonyl)-2,2-dimethylhexanamide (0.100 g, 0.164 mmol) was brought up in hydrazine hydrate (5 mL). The reaction was heated to 70° C. for 18 h. A precipitate was still in the reaction so ethanol (10 mL) was added. The precipitate dissolved and the reaction was heated at 80° C. for another 20 h. The reaction was then concentrated under high vacuum to give the crude product. The crude product was purified by flash chromatography (7:1 chloroform:methanol) to give 54.8 mgs (55%) of product. ESMS: Calcd. For $C_{31}H_{33}N_5O_6S$, 603.21; Found, 604.4 [M+H+1] HPLC Method 5.$R_t$=15.285 min Purity=98%

Part C: Preparation of 2-(2-aza-2-((5-((6-(4-benzo[d]1,3-dioxolan-5-yl-6-phenyl(2-pyridyloxy))-2,2-dimethylhexanoyl-amino)sulfonyl)(2-pyridyl))amino)vinyl)benzenesulfonic acid 6-(4-Benzo[d]1,3-dioxolan-5-yl-6-phenyl(2-pyridyloxy))-N-((6-hydrazino(3-pyridyl))sulfonyl)-2,2-dimethylhexanamide (0.050 g, 0.0828 mmol) was dissolved in dimethylformamide (1 mL). Triethylamine (34.6 μL, 0.248 mmol) was added, and the reaction was stirred for 5 min. 2-Formylbenzenesulfonic acid monosodium salt (0.0181 g, 0.0869 mmol) was added, and the reaction was stirred overnight for 18 h. The reaction was concentrated to an oil under high vacuum. The crude product was purified by preparative HPLC Method 2 to give 6.4 mg (10%) of product. ESMS: Calcd. For $C_{38}H_{37}N_5O_9S2$, 771.20; Found, 772.3 [M+H+1] HPLC Method 5.$R_t$=15.431 min Purity=97%

Example 76

Synthesis of 6-(4-benzo[d]1,3-dioxolan-5-yl-6-phenyl(2-pyridyloxy))-N-(1-(N-((6-hydrazino(3-pyridyl))sulfonyl)cabamoyl)-2-(4-hydroxyphenyl)ethyl)-2,2-dimethylhexanamide

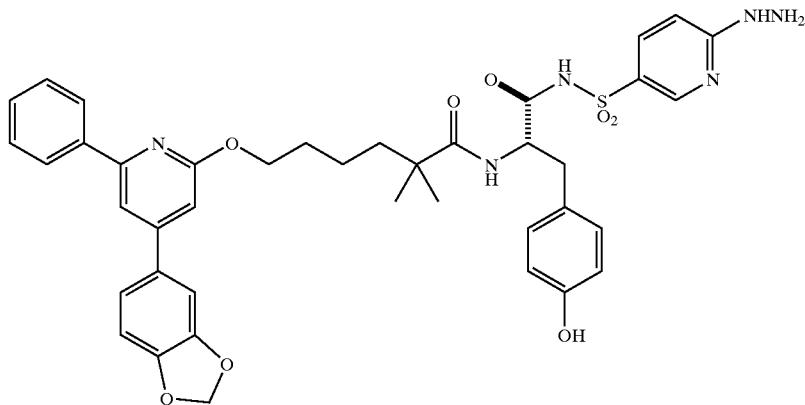

Part A: Preparation of tert-butyl 2-(6-(4-benzo[d]1,3-dioxolan-5-yl-6-phenyl(2-pyridyloxy))-2,2-dimethylhexanoyl-amino)-3-(4-(tert-butoxy)phenyl)propanoate

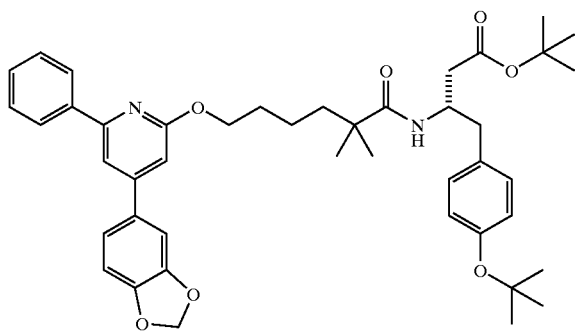

6-(4-Benzo[d]1,3-dioxolan-5-yl-6-phenyl(2-pyridyloxy))-2,2-dimethylhexanoic acid (0.100 g, 0.231 mmol) was dissolved in dimethylformamide (5 mL). Diisopropylethylamine (100.5 µL, 0.578 mmol) was added, and the reaction was stirred for 5 min. H-Tyr(OtBu)-OtBu.HCl (0.0838 g, 0.254 mmol) and 2(1H-benzotriazole-1-yl)-1,1,3,3-tetramethyluronium hexafluorophosphate (0.0964 g, 0.254 mmol) were added, and the reaction was stirred under nitrogen for 24 h. The reaction was concentrated to a residue under high vacuum to give 190.5 mg (116%) of product. The crude product was utilized in the next step. ESMS: Calcd. For $C_{43}H_{52}N_2O_7$, 708.38; Found 709.5 [M+H]+1 HPLC Method 5.$R_t$=23.043 min Purity=87%

Part B: Preparation of 2-(6-(4-benzo[d]1,3-dioxolan-5-yl-6-phenyl(2-pyridyloxy))-2,2-dimethylhexanoyl-amino)-3-(4-hydroxyphenyl)propanoic acid Tert-butyl 2-(6-(4-benzo[d]1,3-dioxolan-5-yl-6-phenyl(2-pyridyloxy))-2,2-dimethylhexanoyl-amino)-3-(4-(tert-butoxy)phenyl)propanoate (0.144 g, approx.0.223 mmol) was dissolved in methylene chloride (3.0 mL). Trifluoroacetic acid (3.0 mL) was added, and the reaction was stirred for 2 h. The reaction was concentrated under high vacuum. The resulting oil was brought up in 50:50 acetonitrile/water and lyophilized to give the product as an oil. The product was purified by preparative HPLC Method 2 to give 119.1 mg (98%) of product. HRMS: Calcd. For $C_{35}H_{36}N_2O_7$+H, 597.2600; Found, 597.2617. HPLC Method 5.$R_t$=15.729 min Purity=100%

Part C Preparation of 6-(4-benzo[d]1,3-dioxolan-5-yl-6-phenyl(2-pyridyloxy))-N-(1-(N-((6-hydrazino(3-pyridyl))sulfonyl)cabamoyl)-2-(4-hydroxyphenyl)ethyl)-2,2-dimethylhexanamide To a solution of 2-(6-(4-benzo[d]1,3-dioxolan-5-yl-6-phenyl(2-pyridyloxy))-2,2-dimethylhexanoyl-amino)-3-(4-hydroxyphenyl)propanoic acid (0.231 mmol) in methylene chloride, is added 2-chloro-pyridine-5-sulfonamide (0.243 mmol), dimethylaminopyridine (0.300 mmol), 1-(3-dimethylaminopropyl)-3-ethyl carbodiimide hydrochloride (0.231 mmol), and 4 A molecular sieves. The reaction mixture is stirred overnight for 18 h and is then filtered. The filtrate is washed with 1N HCl, water, brine. The organic layer is dried over magnesium sulfate, filtered, and concentrated to a small volume. The resulting concentrated solution is triturated with hexane. The product is filtered, washed with hexane and dried under high vacuum to give the chloropyridine intermediate. This intermediate (0.164 mmol) is brought up in hydrazine hydrate (5 mL). The reaction is heated to 70° C. for 18 h. The precipitate is dissolved in ethanol (10 mL) and the reaction is heated at 80° C. for another 20 h. The reaction is then concentrated under high vacuum to give the crude product, which is purified by flash chromatography.

Example 77

Synthesis of 4-(4,6-diphenyl(2-pyridyloxy))-N-(1-(N-(1-(N-((6-hydrazino(3-pyridyl))sulfonyl)cabamoyl)-2-(4-hydroxyphenyl)ethyl)-carbamoyl)-isopropyl)butanamide

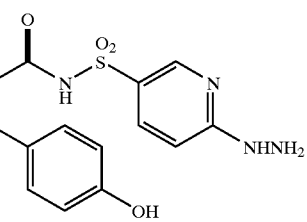

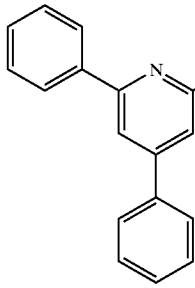

Part A: Preparation of 4-(4,6-diphenyl-2-pyridyloxy)butanenitrile 4,6-Diphenyl-pyridone (1.5 g, 6.07 mmol) was dissolved in dimethylformamide (40 mL). 4-Bromobutyronitrile (1.81 mL, 18.2 mmol) and silver carbonate (1.67 g, 6.07 mmol) were added, and the reaction was refluxed in the dark for 72 h. The reaction was then cooled, filtered, and concentrated under high vacuum. The residue was brought up in ethyl acetate and passed through silica gel. The filtrate was concentrated under high vacuum. The resulting residue was purified by flash chromatography (5:1 hexane:ethyl acetate) to give 1.77 g (93%) of product. ESMS: Calcd. For $C_{21}H_{18}N_2O$, 314.14; Found 315.3 [M+H]+1HPLC Method 5.$R_t$=18.715 min Purity=97%

Part B: Preparation of 4-(4,6-diphenyl-2-pyridyloxy)butanoic acid 4-(4,6-Diphenyl-2-pyridyloxy)butanenitrile (0.813 g, 2.59 mmol) was dissolved in conc. Hydrochloric acid (10 mL), glacial acetic acid (6 mL), and water (4 mL), and heated to reflux for 20 h. The reaction was diluted with water, and extracted with methylene chloride. The organic layer was washed with water, brine, dried over magnesium sulfate, filtered, and evaporated. The resulting oil was purified by flash chromatography (1. 4:1 hexane:ethyl acetate, 2.2:1 methylene chloride:ethyl acetate) to give 109.1 mg (13%) of product. ESMS: Calcd. For $C_{21}H_{19}NO_3$, 333.14; Found 332.3 [M–H]–1 HPLC Method 5. $R_t$=15.884 min Purity=100%

Part C: Preparation of 2-(2-(4-(4,6-diphenyl-2-pyridyloxy)butanoylamino)-2-methylpropanoylamino)-3-(4-hydroxyphenyl)propanoic acid

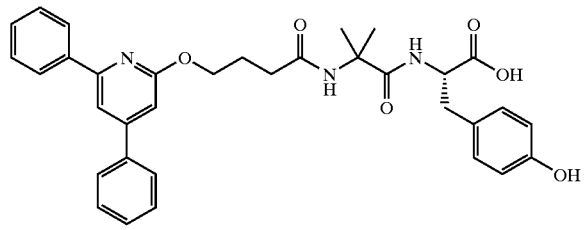

To a teabag (5×5 cm polypropylene filter, 0.75 μm mesh) was added 0.50 g of Fmoc-Tyr(OtBu)-wang resin. The teabag was washed with the following (10 ml/bag) DMF 2×3 min, 20% piperidine in DMF solution 1×3 min, 20% piperidine in DMF solution 1×30 min, DCM 8×3 min, and DMF 3×3 min. To the reactor was added five equivalents of each of the following; Fmoc-Aib-OH, HBTU, HOBT, diisopropylethylamine (DIEA) and DMF (10 ml/bag). The bag was shaken overnight for about 16 h. The bag was then washed with the following (10 ml/bag): DMF 3×3 min, DCM 8×3 min. and dried under high vacuum. The coupling yield (99%) was determined using the picric acid assay. Then 0.200 g of this Fmoc-Aib-Tyr(OtBu)-wang resin was transfered to a teabag (5×5 cm polypropylene filter, 0.75 μm mesh). The teabag was washed with the following (10 ml/bag) DMF 2×3 min, 20% piperidine in DMF solution 1×3 min, 20% piperidine in DMF solution 1×30 min, DCM 8×3 min, and DMF 3×3 min. To the reactor was added 2.5 equivalents of 4-(4,6-diphenyl-2-pyridyloxy)-butanoic acid and five equivalents of each of the following; HBTU, HOBT, diisopropylethylamine (DIEA) and DMF (10 ml/bag). The bag was then shaken overnight for about 18 h. The bag was then washed with the following (10 ml/bag): DMF 3×3 min, DCM 8×3 min. The bag was dried under high vacuum. The contents of the bag was then placed in a small erlenmeyer flask and a cleavage cocktail (10 mL) (95% trifluoroacetic acid, 2.5% triisopropylsilane, and 2.5% water) added. The resin was allowed to sit for two hours while occasionally being swirled. After each swirl the side of the flask was rinsed with additional cocktail until the total volume of cocktail added was 15 mL. After two hours, the resin was filtered and washed with TFA (2×4 mL). The filtrate was concentrated to an oil under high vacuum. The oil was purified by preparative HPLC Method 2 to give 14.1 mg of product. HRMS: Calcd. For $C_{34}H_{35}N_3O_6$+H, 582.2604; Found, 582.2606. HPLC Method 5. $R_t$=13.912 min Purity=98%

Part D Preparation of Preparation of 4-(4,6-diphenyl(2-pyridyloxy))-N-(1-(N-(1-(N-((6-hydrazino(3-pyridyl))sulfonyl)cabamoyl)-2-(4-hydroxyphenyl)ethyl)-carbamoyl)-isopropyl)butanamide To a solution of 2-(2-(4-(4,6-diphenyl-2-pyridyloxy)-butanoylamino)-2-methylpropanoylamino)-3-(4-hydroxyphenyl)propanoic acid (0.231 mmol) in methylene chloride, is added 2-chloro-pyridine-5-sulfonamide (0.243 mmol), dimethylaminopyridine (0.300 mmol), 1-(3-dimethylaminopropyl)-3-ethyl carbodiimide hydrochloride (0.231 mmol), and 4 A molecular sieves. The reaction mixture is stirred overnight for 18 h and is then filtered. The filtrate is washed with 1N HCl, water, brine. The organic layer is dried over magnesium sulfate, filtered, and concentrated to a small volume. The resulting concentrated solution is triturated with hexane. The product is filtered, washed with hexane and dried under high vacuum to give the chloropyridine intermediate. This intermediate (0.164 mmol) is brought up in hydrazine hydrate (5 mL). The reaction is heated to 70° C. for 18 h. The precipitate is dissolved in ethanol (10 mL) and the reaction is heated at

Example 78

Synthesis of 3-(4-(3-((6-((1-aza-2-(2-sulfophenyl)vinyl)amino)(3-pyridyl))carbonylamino)-propoxy)phenyl)-2-(2,2-dimethyl-6-(5-oxo-1-prop-2-enyl (2-6,7,8-trihydronaphthyloxy))hexanoylamino)propanoic acid

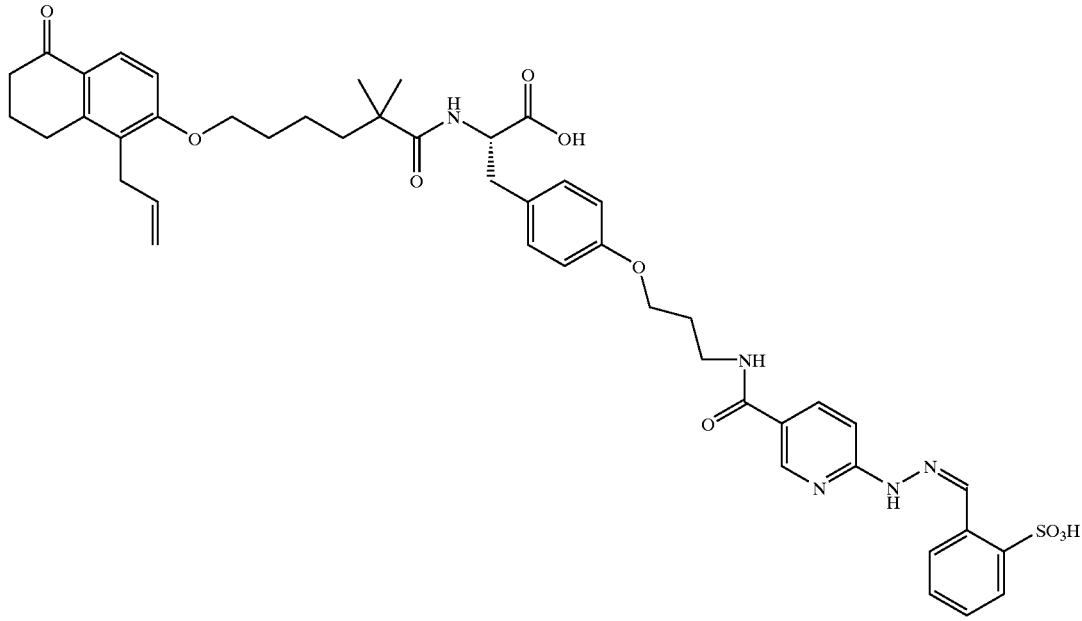

Part A: Preparation of tert-butyl 3-(4-(tert-butoxy)phenyl)-2-(2,2-dimethyl-6-(5-oxo-1-prop-2-enyl(2-6,7,8-trihydronaphthyloxy))hexanoylamino)propanoate

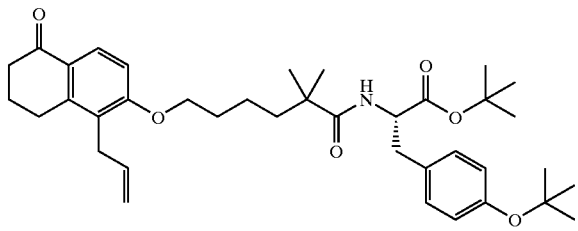

H-Tyr(OtBu)-OtBu.HCl (0.115 g, 0.348 mmol) was dissolved in dimethylformamide (5 mL). Diisopropylethylamine (126.3 μL, 0.725 mmol) was added, and the reaction was stirred for 5 min. 2,2-Dimethyl-6-(5-oxo-1-prop-2-enyl (2-6,7,8-trihydronaphthyloxy))hexanoic acid(0.100 g, 0.290 mmol) and 2 (1H-benzotriazole-1-yl)-1,1,3,3-tetramethyluronium hexafluorophosphate (0.121 g, 0.319 mmol) were added, and the reaction was stirred under nitrogen for 60 h. The reaction was concentrated to a residue under high vacuum. The oil was dissolved in 50:50 ACN:H2O and lyophilized to give 0.457 g of product, however, as an oil. ESMS: Calcd. For $C_{38}H_{53}NO_6$, 619.39, Found 620.5 [M+H]+1HPLC Method 5. $R_t$=21.882 min Purity=94%

Part B: Preparation of 2-(2,2-dimethyl-6-(5-oxo-1-prop-2-enyl(2-6,7,8-trihydronaphthyloxy))hexanoylamino)-3-(4-hydroxyphenyl)propanoic acid tert-Butyl 3-(4-(tert-butoxy)phenyl)-2-(2,2-dimethyl-6-(5-oxo-1-prop-2-enyl(2-6,7,8-trihydronaphthyloxy))-hexanoylamino)propanoate (0.457 g) was dissolved in methylene chloride (3.0 mL). Trifluoroacetic acid (3.0 mL) was added, and the reaction was stirred for 2 h. The reaction was concentrated under high vacuum. The resulting oil was purified by preparative HPLC Method 2 to give 126.5 mg (86% over 2 steps) of product. HRMS: Calcd. For $C_{30}H_{37}NO_6$+H, 508.2699; Found, 508.2703. HPLC Method 5. $R_t$=13.743 min Purity=98%

Part C Preparation of 3-(4-(3-((6-((1-aza-2-(2-sulfophenyl)vinyl)amino)(3-pyridyl))carbonylamino)-propoxy)phenyl)-2-(2,2-dimethyl-6-(5-oxo-1-prop-2-enyl(2-6,7,8-trihydronaphthyloxy))hexanoylamino)propanoic acid H-Tyr(O—CH$_2$—CH$_2$—CH$_2$—NH-boc)-OtBu (0.348 mmol) is dissolved in dimethylformamide (5 mL). Diisopropylethylamine (0.725 mmol) is added, and the reaction is stirred for 5 min. 2,2-Dimethyl-6-(5-oxo-1-prop-2-enyl(2-6,7,8-trihydro-naphthyloxy))hexanoic acid (0.290 mmol) and 2(1H-benzo-triazole-1-yl)-1,1,3,3-tetramethyluronium hexafluorophosphate (0.319 mmol) is added, and the reaction is stirred under nitrogen for 60 h. The reaction mixture is concentrated to a residue under high vacuum and is dissolved in methylene chloride (5 mL). Trifluoroacetic acid (5.0 mL) is added, and the reaction is stirred for 2 h. The reaction is concentrated under high vacuum to give the amine product. A mixture of this product (0.0805 mmol), N,N-dimethyl formamide (2 mL), and triethylamine (0.2478 mmol) is stirred at room temperature for 15 min. 2-[[[5-[[(2,5-Dioxo-1-pyrrolidinyl)oxy]carbonyl]-2-pyridinyl]hydrazono]methyl]-benzenesulfonic acid, monosodium salt (0.0991 mmol) is added and the mixture is stirred under nitrogen. After 24 h, the mixture is concentrated under high vacuum. Purification by reverse-phase HPLC (water-acetonitrile gradient containing 0.1% TFA) yields the desired product.

Example 79

Synthesis of 3-((6-((1-aza-2-(2-sulfophenyl)vinyl)amino)(3-pyridyl)carbonylamino)-3-(N-(6-(4-benzo[d]1,3-dioxolan-5-yl-6-phenyl(2-pyridyloxy))-2,2-dimethylhexyl)carbamoyl)propanoic acid

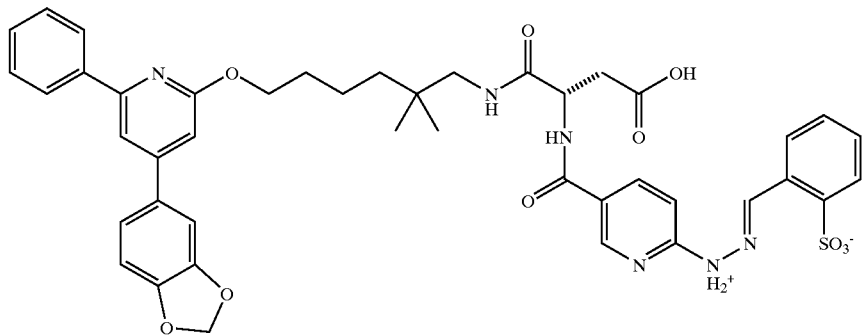

Part A: Preparation of tert-butyl 3-(N-(6-(4-benzo[d]1,3-dioxolan-5-yl-6-phenyl(2-pyridyloxy))-2,2-dimethylhexyl)carbamoyl)-3-((tertbutoxy)carbonylamino)-propanoate

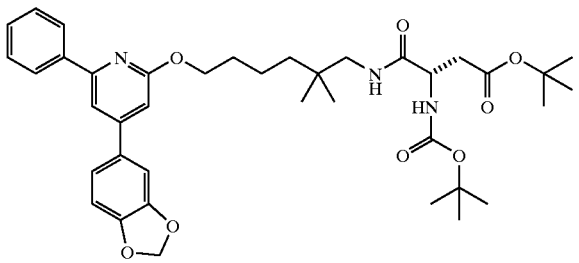

1-Amino-2,2-dimethyl-6-[(4-(3,4-methylenedioxyphenyl)-6-phenyl-2-pyridinyl)oxy]-hexane (0.100 g, 0.239 mmol) was dissolved in dimethylformamide (5 mL). Triethylamine (0.100 mL, 0.717 mmol) was added, and the reaction was stirred for 5 min. Boc-Asp(OtBu)-Osu (0.110 g, 0.287 mmol) was added, and the reaction was stirred under nitrogen for 48 h. The reaction was concentrated to an oil under high vacuum. The oil was dissolved in 50:50 ACN/H2O and lyophilized to give 0.219 g (133%) of product. ESMS: Calcd. For $C_{39}H_{51}N_3O_8$, 689.37; Found 690.5 [M+H]+1. HPLC Method 5. $R_t$=21.930 min Purity 97%

Part B: Preparation of 3-amino-3-(N-(6-(4-benzo[d]1,3-dioxolan-5-yl-6-phenyl(2-pyridyloxy))-2,2-dimethylhexyl)carbamoyl)propanoic acid Tert-butyl 3-(N-(6-(4-benzo[d]1,3-dioxolan-5-yl-6-phenyl(2-pyridyloxy))-2,2-dimethylhexyl)carbamoyl)-3-((tertbutoxy)carbonylamino)propanoate (0.145 g, 0.210 mmol) was dissolved in methylene chloride (3.0 mL). Trifluoroacetic acid (3.0 mL) was added, and the reaction was stirred for 2 h. The reaction was concentrated under high vacuum. The resulting oil was brought up 50:50 acetonitrile/water and lyophilized to give 242.0 mg (177%) of product. ESMS: Calcd. For $C_{30}H_{35}N_3O_6$, 533.25; Found 532.3 [M−H]−1HPLC Method 5. $R_t$=13.921 min Purity=96%

Part C: Preparation of 3-((6-((1-aza-2-(2-sulfophenyl)vinyl)amino)(3-pyridyl)carbonylamino)-3-(N-(6-(4-benzo[d]1,3-dioxolan-5-yl-6-phenyl(2-pyridyloxy))-2,2-dimethylhexyl)carbamoyl)propanoic acid 3-Amino-3-(N-(6-(4-benzo[d]1,3-dioxolan-5-yl-6-phenyl(2-pyridyloxy))-2,2-dimethylhexyl)carbamoyl)propanoic acid (0.100 g, 0.154 mmol) was dissolved in dimethylformamide (5 mL). Triethylamine (64.4 µL, 0.462 mmol) was added and the reaction was stirred for 5 min. 2-[-[5-[[(2,5-Dioxo-1-pyrrolidinyl)oxy]carbonyl]-2-pyridinyl]hydrazono]methyl]-benzenesulfonic acid, monosodium salt (0.082 g, 0.185 mmol) was added and the reaction was stirred for 24 hours under nitrogen. The reaction was then concentrated to an oil under high vacuum. The oil was triturated with ethyl acetate. The crude product was then purified by preparative HPLC Method 2 to give 31.1 mg (24%) of product. HRMS: Calcd. For $C_{43}H_{44}N_6O_{10}S$+H, 837.2917; Found, 837.2901. HPLC Method 5. $R_t$=14.279 min Purity=93%

Example 80

Synthesis of 2-(2-aza-2-((5-(N-(1-(N-(6-(4-benzo[d]1,3-dioxolan-5-yl-6-phenyl(2-pyridyloxy))-2,2-dimethyl-hexyl)carbamoyl)-2-(4-hydroxyphenyl)ethyl)carbamoyl(2-pyridyl))amino)vinyl)-benzenesulfonic acid

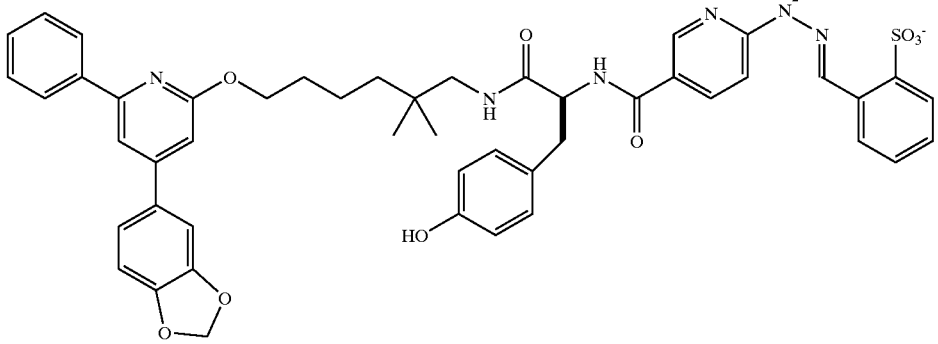

Part A: Preparation of N-(6-(4-benzo[d]1,3-dioxolan-5-yl-6-phenyl(2-pyridyloxy))-2,2-dimethylhexyl)-2-((tert-butoxy)carbonylamino)-3-(4-hydroxyphenyl)propanamide

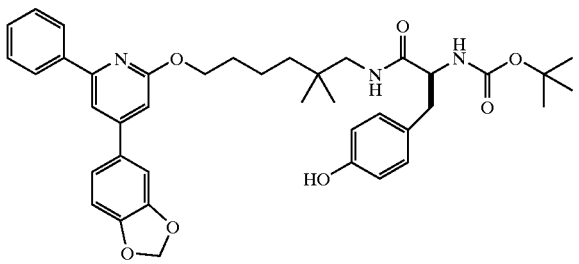

1-Amino-2,2-dimethyl-6-[(4-(3,4-methylenedioxy-phenyl)-6-phenyl-2-pyridinyl)oxy]-hexane (0.100 g, 0.239 mmol) was dissolved in dimethylformamide (5 mL). Diisopropylethylamine (104.1 µL, 0.598 mmol) was added, and the reaction was stirred for 5 min. Boc-Tyr-OH (0.081 g, 0.287 mmol) and 2(1H-benzotriazole-1-yl)-1,1,3,3-tetramethyluronium hexafluorophosphate (0.100 g, 0.263 mmol) were added, and the reaction was stirred under nitrogen for 24 h. The reaction was concentrated to an oil under high vacuum. The oil was dissolved in 50:50 ACN/H₂O and lyophilized. The crude product was then purified by preparative HPLC Method 2 to give 67.9 mg (42%) of product. ESMS: Calcd. For $C_{40}H_{47}N_3O_7$, 681.34; Found, 680.3 [M−H]−1 HPLC Method 5. $R_t$=19.238 min Purity=98%

Part B: Preparation of 2-amino-N-(6-(4-benzo[d]1,3-dioxolan-5-yl-6-phenyl(2-pyridyloxy))-2,2-dimethylhexyl)-3-(4-hydroxyphenyl)propanamide N-(6-(4-Benzo[d]1,3-dioxolan-5-yl-6-phenyl(2-pyridyloxy))-2,2-dimethylhexyl)-2-((tert-butoxy)carbonyl-amino)-3-(4-hydroxyphenyl)propanamide (0.058 g, 0.0851 mmol) was dissolved in methylene chloride (3.0 mL). Trifluoroacetic acid (3.0 mL) was added, and the reaction was stirred for 2 h. The reaction was concentrated under high vacuum. The resulting oil was brought up in 50:50 acetonitrile/water and lyophilized to give 53.6 mg (91%) of product. ESMS: Calcd for $C_{35}H_{39}N_3O_5$, 581.29; Found, 582.5 [M+H]+1 HPLC Method 5.$R_t$=14.920 min Purity=98%

Part C: Preparation of 2-(2-aza-2-((5-(N-(1-(N-(6-(4-benzo[d]1,3-dioxolan-5-yl-6-phenyl(2-pyridyloxy))-2,2-dimethylhexyl)carbamoyl)-2-(4-hydroxyphenyl)ethyl)-carbamoyl(2-pyridyl))amino)vinyl)benzenesulfonic acid 2-Amino-N-(6-(4-benzo[d]1,3-dioxolan-5-yl-6-phenyl(2-pyridyloxy))-2,2-dimethylhexyl)-3-(4-hydroxyphenyl)-propanamide (0.020 g, 0.0287 mmol) was dissolved in dimethylformamide (2 mL). Triethylamine (12 µL, 0.861 mmol) was added and the reaction was stirred for 5 min. 2-[[[5-[[(2,5-Dioxo-1-pyrrolidinyl)oxy]carbonyl]-2-pyridinyl]-hydrazono]methyl]benzenesulfonic acid, monosodium salt (0.0152 g, 0.0344 mmol) was added and the reaction was stirred for 48 h under nitrogen. The reaction was then concentrated to an oil under high vacuum. The oil was then purified by preparative HPLC Method 2 to give 15.6 mg (61%) of product. HRMS: Calcd. For $C_{48}H_{48}N_6O_9S$+H, 885.3282; Found, 885.3268. HPLC Method 5.$R_t$=15.453 min Purity=94%

Example 81

Synthesis of 2-((6-((1-aza-2-(2-sulfophenyl)vinyl)amino)(3-pyridyl)carbonylamino)-2-(2,2-dimethyl-6-(5-oxo-1-prop-2-enyl(2-6,7,8-trihydronaphthyloxy))hexanoylamino)acetic acid

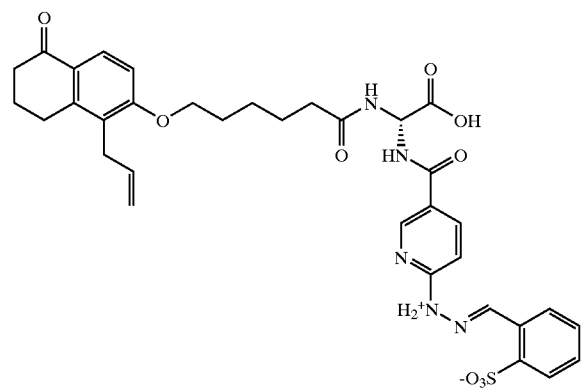

Part A: Preparation of ethyl 6-(5-oxo-1-prop-2-enyl(2-6,7,8-trihydronaphthyloxy))hexanoate 6-Hydroxy-5-prop-2-enyl-2,3,4-trihydronaphthalen-1-one (1.0 g, 4.97 mmol) was dissolved in dimethylformamide (15 mL). Ethyl-6-bromohexanoate (1.33 mL, 7.45 mmol) was dissolved in dimethylformamide (15 mL), and added to the reaction. Potassium carbonate (1.20 g, 8.70 mmol) and potassium iodide (0.206 g, 1.24 mmol) were added, and the reaction was heated to 100° C. for 16 h. The reaction was concentrated under high vacuum. The resulting oil was brought up in ethyl acetate and washed with water, brine, dried over magnesium sulfate, filtered, and evaporated. The resulting crude product was dissolved in 90:10 hexane:ethyl acetate and passed through silica gel. The filtrate was then concentrated to give 1.218 g (71%) of product. ESMS: Calcd. For $C_{21}H_{28}O_4$, 344.20; Found, 345.2 [M+H]+1 HPLC Method 5. $R_t$=17.662 min Purity=96%

Part B: Preparation of 6-(5-oxo-1-prop-2-enyl(2-6,7,8-trihydronaphthyloxy))hexanoic acid Ethyl 6-(5-oxo-1-prop-2-enyl(2-6,7,8-trihydronaphthyloxy))hexanoate (1.10 g, 3.19 mmol) was dissolved in ethanol (20 mL). Potassium hydroxide pellets (0.268 g, 4.78 mmol) were dissolved in water (1 mL), and added to the reaction. The reaction mixture was heated to reflux for 18 h then concentrated to an oil under high vacuum. The residue was brought up in water. The solution was adjusted to pH 5 with 1N hydrochloric acid. The solution was extracted with ethyl acetate. The organic layer was washed with water, brine, dried over magnesium sulfate, filtered, and concentrated to an oil under high vacuum. The oil was recrystallized from hexane:ethyl acetate to give 0.842 g (83%) of product. ESMS: Calcd. For $C_{19}H_{24}O_4$, 316.17; Found, 315.2 [M–H]–1HPLC Method 5. $R_t$=13.339 min Purity 98%

Part C: Preparation of 2-amino-2-(6-(5-oxo-1-prop-2-enyl (2-6,7,8-trihydronaphthyloxy))hexanoylamino)acetic acid To a teabag (5×5 cm polypropylene filter, 0.75 μm mesh) was added 0.50 g of Fmoc-Gly(NH-Boc)-Wang Resin. The teabag was washed with the following (10 ml/bag) DMF 2×3 min, 20% piperidine in DMF solution 1×3 min, 20% piperidine in DMF solution 1×30 min, DCM 8×3 min, and DMF 3×3 min. To the reactor was added 3 equivalents of the 6-(5-oxo-1-prop-2-enyl(2-6,7,8-trihydronaphthyloxy)) hexanoic acid, five equivalents of each of the following; HBTU, HOBT, diisopropylethylamine(DIEA) and DMF (10 ml/bag). The bag was then shaken overnight for about 20 h. The bag was then washed with the following (10 ml/bag): DMF 3×3 min, DCM 8×3 min. The bag was dried under high vacuum. The contents of the bag was then placed in a small erlenmeyer flask. To the flask was added cleavage cocktail (10 mL) (95% trifluoroacetic acid, 2.5% triisopropylsilane, and 2.5% water). The resin was allowed to sit for two hours while occasionally being swirled. After each swirl the side of the flask was rinsed with additional cocktail until the total volume of cocktail added was 15 mL. After two hours, the resin was filtered and washed with TFA (2×4 mL). The filtrate was concentrated to an oil under high vacuum. The oil was triturated with ether to give 0.0792 g of product. ESMS: Calcd. For $C_{21}H_{28}N_2O_5$, 388.20; Found, 389.2 [M+H]+1 HPLC Method 5. $R_t$=9.020 min Purity-95%

Part D: Preparation of 2-((6-((1-aza-2-(2-sulfophenyl)-vinyl)amino)(3-pyridyl)carbonylamino)-2-(6-(5-oxo-1-prop-2-enyl(2-6,7,8-trihydronaphthyloxy))hexanoylamino) acetic acid 2-Amino-2-(6-(5-oxo-1-prop-2-enyl(2-6,7,8-trihydronaphthyloxy))hexanoylamino)acetic acid (0.040 g, 0.0796 mmol) was dissolved in dimethylformamide (3 mL). Triethylamine (33.2 μL, 0.239 mmol) was added and the reaction was stirred for 5 minutes. 2-[[[5-[[(2,5-Dioxo-1-pyrrolidinyl)oxy]-carbonyl]-2-pyridinyl]hydrazono]-methyl]benzenesulfonic acid, monosodium salt (0.0421 g, 0.0955 mmol) was added and the reaction was stirred for 24 hours under nitrogen. The reaction was then concentrated to an oil under high vacuum. The oil was then purified by preparative HPLC Method 2 to give 14.9 mg (27%) of product. HRMS: Calcd. For $C_{34}H_{37}N_5O_9S$+H, 692.2390; Found, 692.2404. HPLC Method 5. $R_t$=9.976 min Purity=92%

Example 82

Synthesis of 2-((6-((1-aza-2-(2-sulfophenyl)vinyl) amino)(3-pyridyl)carbonylamino)-2-(2,2-dimethyl-6-(5-oxo-1-prop-2-enyl(2-6,7,8-trihydronaphthyloxy))hexanoylamino)acetic acid

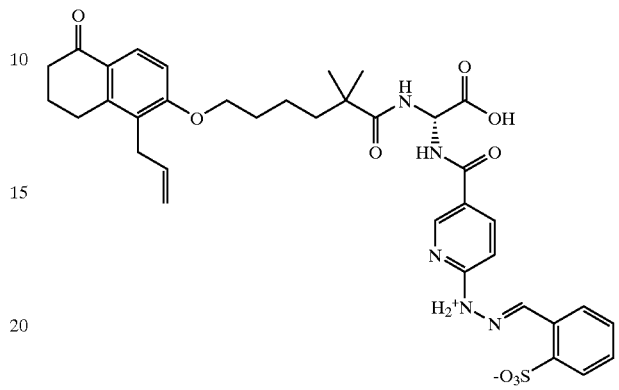

Part A: Preparation of ethyl 2,2-dimethyl-6-(5-oxo-1-prop-2-enyl(2-6,7,8-trihydronaphthyloxy))hexanoate 6-Hydroxy-5-prop-2-enyl-2,3,4-trihydronaphthalen-1-one (1.0 g, 4.97 mmol) was dissolved in dimethylformamide (15 mL). Ethyl 6-bromo-2,2-dimethylhexanoate (1.87 g, 7.45 mmol) was dissolved in dimethylformamide (15 mL), and added to the reaction. Potassium carbonate (1.20 g, 8.70 mmol) and potassium iodide (0.206 g, 1.24 mmol) were added, and the reaction was heated to 100° C. for 16 h. The reaction was concentrated under high vacuum. The resulting oil was brought up in ethyl acetate and washed with water, brine, dried over magnesium sulfate, filtered, and evaporated. The resulting crude product was dissolved in 90:10 hexane:ethyl acetate and passed through silica gel. The filtrate was then concentrated to give 1.595 g (86%) of product. ESMS: Calcd. For $C_{23}H_{32}O_4$, 372.23; Found, 373.3 [M+H]+1HPLC Method 5. $R_t$=19.756 min Purity=98%

Part B: Preparation of 2,2-dimethyl-6-(5-oxo-1-prop-2-enyl (2-6,7,8-trihydronaphthyloxy))hexanoic acid Ethyl 2,2-dimethyl-6-(5-oxo-1-prop-2-enyl(2-6,7,8-trihydronaphthyloxy))hexanoate (1.40 g, 3.76 mmol) was dissolved in ethanol (20 mL). Potassium hydroxide pellets (0.316 g, 5.64 mmol) were dissolved in water (1 mL), and added to the reaction. The reaction was heated to reflux for 4 days. The reaction was concentrated to an oil under high vacuum. The residue was brought up in water. The solution was adjusted to pH 5 with 1N hydrochloric acid. The solution was extracted with ethyl acetate. The organic layer was washed with water, brine, dried over magnesium sulfate, filtered, and concentrated to an oil under high vacuum. The oil was purified by flash chromatography 7:1 methylene chloride:ethyl acetate to give 0.635 g (49%) of product as an oil. ESMS: Calcd. For $C_{21}H_{28}O_4$, 344.20; Found, 345.2 [M+H]+1HPLC Method 5. $R_t$=15.644 min Purity=92%

Part C: Preparation of 2-amino-2-(2,2-dimethyl-6-(5-oxo-1-prop-2-enyl(2-6,7,8-trihydronaphthyloxy))hexanoylamino) acetic acid To a teabag (5×5 cm polypropylene filter, 0.75 μm mesh) was added 0.50 g of Fmoc-Gly(NH-Boc)-Wang Resin. The teabag was washed with the following (10 ml/bag) DMF 2×3 min, 20% piperidine in DMF solution 1×3 min, 20% piperidine in DMF solution 1×30 min, DCM 8×3 min, and DMF 3×3 min. To the reactor was added 3 equivalents of the 2,2-dimethyl-6-(5-oxo-1-prop-2-enyl(2-6,7,8-trihydronaphthyloxy))hexanoic acid, five equivalents of each of the following; HBTU, HOBT, diisopropylethylamine(DIEA) and DMF (10 ml/bag). The bag was then shaken overnight for about 20 h. The bag was then washed with the following (10 ml/bag): DMF 3×3 min, DCM 8×3 min. The bag was dried under high vacuum. The contents of the bag was then placed in a small erlenmeyer flask. To the flask was added cleavage cocktail (10 mL) (95% trifluoroacetic acid, 2.5% triisopropylsilane, and 2.5% water). The resin was allowed to sit for two hours while occasionally being swirled. After each swirl the side of the flask was rinsed with additional cocktail until the total volume of cocktail added was 15 mL. After two hours, the resin was filtered and washed with TFA (2×4 mL). The filtrate was concentrated to an oil under high vacuum. The oil was triturated with ether to give 0.0560 g of product. ESMS: Calcd. For $C_{23}H_{32}N_2O_5$, 416.23; Found, 417.3 [M+H]+1 HPLC Method 5. $R_t$=10.429 min Purity=97%

Part D: Preparation of 2-((6-((1-aza-2-(2-sulfophenyl)vinyl) amino)(3-pyridyl)carbonylamino)-2-(2,2-dimethyl-6-(5-oxo-1-prop-2-enyl(2-6,7,8-trihydronaphthyloxy)) hexanoylamino)acetic acid 2-Amino-2-(2,2-dimethyl-6-(5-oxo-1-prop-2-enyl(2-6,7,8-trihydronaphthyloxy))hexanoylamino)acetic acid (0.025 g, 0.0471 mmol) was dissolved in dimethylformamide (2 mL). Triethylamine (19.7 μL, 0.141 mmol) was added and the reaction was stirred for 5 minutes. 2-[[[5-[[(2,5-Dioxo-1-pyrrolidinyl)oxy]-carbonyl]-2-pyridinyl]hydrazono] methyl]-benzenesulfonic acid, monosodium salt (0.0249 g, 0.0565 mmol) was added and the reaction was stirred for 24 hours under nitrogen. The reaction was then concentrated to an oil under high vacuum. The oil was then purified by preparative HPLC Method 2 to give 8.9 mg (26%) of product. HRMS: Calcd. For $C_{36}H_{41}N_5O_9S+H$, 720.2703; Found, 720.2727. HPLC Method 5. $R_t$=11.243 min Purity=100%

Example 83

Synthesis of 3-((6-((1-aza-2-(2-sulfophenyl)vinyl) amino)(3-pyridyl)carbonylamino)-3-(N-(6-(6-ethyl-3-hydroxy-4-phenylphenoxy)-2,2-dimethylhexyl) carbamoyl)propanoic acid Part A: Preparation of 6-(2-ethyl-4-phenyl-5-(benzyloxy) phenoxy)-2,2-dimethylhexanenitrile

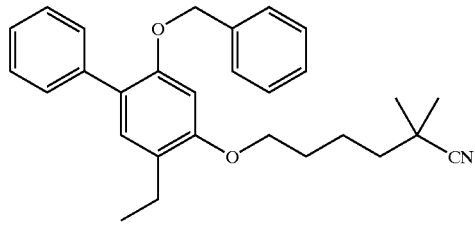

Benzene boronic acid (0.851 g, 6.98 mmol) was dissolved in ethanol (5.82 mL) (1.2 mM solution). 6-(4-Bromo-2-ethyl-5-(benzyloxy)phenoxy)-2,2-dimethylhexanenitrile (1.5 g, 3.49 mmol) was dissolved in toluene (17.4 mL) (0.2 mM solution), and added to the ethanol solution. Sodium bicarbonate was dissolved in water (5.24 mL) (2 mM solution), and added to the reaction. The reaction was heated to reflux overnight. The reaction was cooled to room temp and diluted with ethyl acetate. The organic layer was washed with sat. ammonium chloride. The organic layer was concentrated to an oil and purified by flash column chromatography (10:1 hexane:ethyl acetate) to give 1.24 g (83%) of product. ESMS: Calcd. For $C_{29}H_{33}NO_2$, 427.25; Found, 445.3 [M+NH$_4$]+1 HPLC Method 5.$R_t$=21.888 min Purity=95%

Part B: Preparation of 6-(2-ethyl-4-phenyl-5-(benzyloxy) phenoxy)-2,2-dimethylhexylamine To a dry flask was added aluminum chloride (0.589 g, 4.11 mmol). The flask was cooled to less than 0° C. with an ice/ethanol bath. Ether (10 mL) was added, and the reaction was stirred for 5 minutes until the aluminum chloride dissolved. Lithium aluminum hydride (0.156 g, 4.11 mmol) was then added, and the reaction was heated to reflux. 6-(2-Ethyl-4-phenyl-5-(benzyloxy)phenoxy)-2,2-dimethylhexane-nitrile (0.800 g, 1.87 mmol) was dissolved in ether (5 mL) and added dropwise to the refluxing solution. After addition was complete, the reaction was stirred for 5 hours at room temperature. The reaction was then quenched with water. 5N Hydrosulfuric acid was added until a clear solution formed. This mixture was then extracted with ether (3×). The aqueous layer was then cooled in an ice bath and basified to pH 14 with 50% aq. Sodium hydroxide. The resulting solution was then extracted with ether (4×). The organic layer was washed with saturated NaCl, dried over magnesium sulfate, and evaporated to give 0.982 g (121%) of product as an oil.

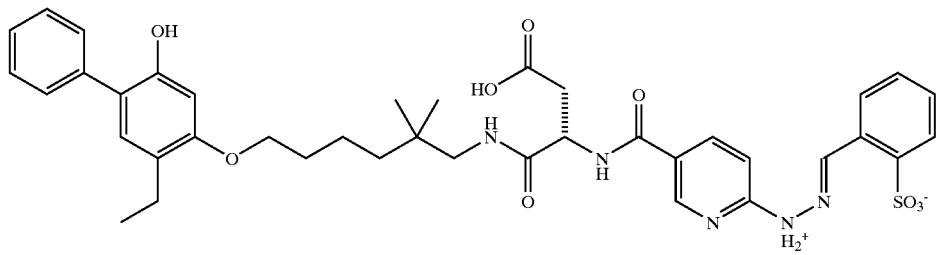

ESMS: Calcd. For $C_{29}H_{37}NO_2$, 431.28; Found, 432.3 [M+H]+1 HPLC Method 5. $R_t$=17.226 min Purity=91%

Part C: Preparation of tert-butyl 3-((tert-butoxy) carbonylamino)-3-(N-(6-(2-ethyl-4-phenyl-5-(benzyloxy) phenoxy)-2,2-dimethylhexyl)carbamoyl)-propanoate

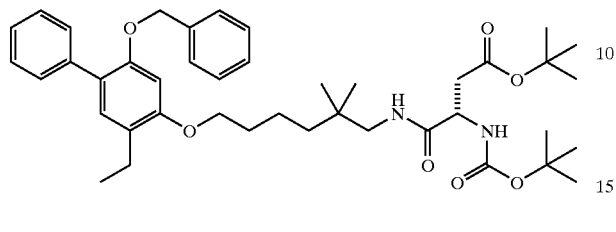

6-(2-Ethyl-4-phenyl-5-(benzyloxy)phenoxy)-2,2-dimethylhexylamine(0.100 g, 0.232 mmol) was dissolved in dimethylformamide (5 mL). Triethylamine (0.097 mL, 0.696 mmol) was added, and the reaction was stirred for 5 min. Boc-Asp(OtBu)-Osu (0.107 g, 0.278 mmol) was added, and the reaction was stirred under nitrogen for 60 h. The reaction was concentrated to an oil under high vacuum. The oil was dissolved in 50:50 ACN/H$_2$O and lyophilized to give 0.239 g (147%) of product as an oil. ESMS: Calcd. For $C_{42}H_{58}N_2O_7$, 702.42; Found, 703.5 [M+H]+1 HPLC Method 5. $R_t$=24.125 min Purity=89%

Part D: Preparation of 3-amino-3-(N-(6-(6-ethyl-3-hydroxy-4-phenylphenoxy)-2,2-dimethylhexyl)carbamoyl)propanoic acid tert-Butyl 3-((tert-butoxy)carbonylamino)-3-(N-(6-(2-ethyl-4-phenyl-5-(benzyloxy)phenoxy)-2,2-dimethylhexyl)-carbamoyl)propanoate (0.200 g, 0.284 PH-7202 mmol) was dissolved in anisole (0.937 mL, 8.63 mmol), and cooled to 0° C. in an ice bath. Trifluoroacetic acid (6.25 mL, 81.1 mmol) was added, and the reaction was stirred for 10 min at 0° C. Trifluoromethanesulfonic acid (0.625 mL, 7.06 mmol) was added dropwise. The reaction was stirred at 0° C. for 1.5 h. The reaction was concentrated under high vacuum. The resulting oil was purified using the following method to give 48.5 mg (30%) of product. ESMS: Calcd. For $C_{26}H_{36}N_2O_5$, 456.26; Found, 455.3 [M−H]−1 HPLC Method 5. $R_t$=13.395 min Purity=87%

Part E: Preparation of 3-((6-((1-aza-2-(2-sulfophenyl)vinyl) amino)(3-pyridyl)carbonylamino)-3-(N-(6-(6-ethyl-3-hydroxy-4-phenylphenoxy)-2,2-dimethylhexyl)-carbamoyl) propanoic acid 3-Amino-3-(N-(6-(6-ethyl-3-hydroxy-4-phenylphenoxy)-2,2-dimethylhexyl)carbamoyl)propanoic acid (0.0315 g, 0.0533 mmol) was dissolved in dimethylformamide (5 mL). Triethylamine (22.3 μL, 0.160 mmol) was added and the reaction was stirred for 5 min. 2-[[[5-[[(2,5-Dioxo-1-pyrrolidinyl)oxy]carbonyl]-2-pyridinyl]hydrazono]-methyl] benzenesulfonic acid, monosodium salt (0.0281 g, 0.0640 mmol) was added and the reaction was stirred for 24 hours under nitrogen. The reaction was then concentrated to an oil under high vacuum. The oil was then purified by preparative HPLC Method 2 to give 14.4 mg (35%) of product. HRMS: Calcd. For $C_{40}H_{45}N_5O_9S$+H, 760.3016; Found, 760.2997. HPLC Method 5. $R_t$=13.874 min Purity=83%

Example 84
Synthesis of 2-((6-((1-aza-2-(2-sulfophenyl)vinyl) amino)(3-pyridyl)carbonylamino)-2-(6-(4-benzo[d] 1,3-dioxolan-5-yl-6-phenyl(2-pyridyloxy))-2,2-dimethylhexanoylamino)acetic acid

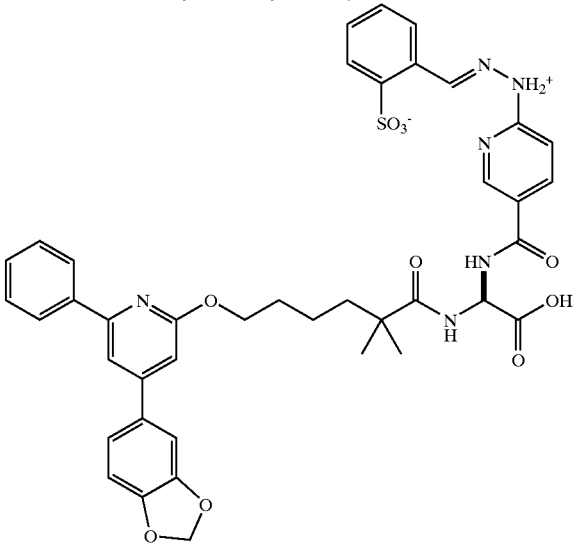

Part A: Preparation of 2-amino-2-(6-(4-benzo[d]1,3-dioxolan-5-yl-6-phenyl (2-pyridyloxy))-2,2-dimethylhexanoylamino) acetic acid

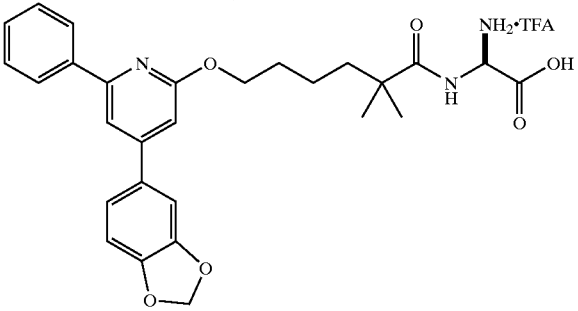

To a teabag (5×5 cm polypropylene filter, 0.75 μm mesh) was added 0.50 g of Fmoc-Gly(NH-Boc)-Wang Resin. The teabag was washed with the following (10 ml/bag) DMF 2×3 min, 20% piperidine in DMF solution 1×3 min, 20% piperidine in DMF solution 1×30 min, DCM 8×3 min, and DMF 3×3 min. To the reactor was added 2 equivalents of the 6-(4-benzo[d]1,3-dioxolan-5-yl-6-phenyl (2-pyridyloxy))-2, 2-dimethylhexanoic acid, five equivalents of each of the following; HBTU, HOBT, diisopropylethylamine(DIEA) and DMF (10 ml/bag). The bag was then shaken overnight for about 20 h. The bag was then washed with the following (10 ml/bag): DMF 3×3 min, DCM 8×3 min. The bag was dried under high vacuum. The contents of the bag was then placed in a small erlenmeyer flask. To the flask was added cleavage cocktail (10 mL) (95% trifluoroacetic acid, 2.5% triisopropylsilane, and 2.5% water). The resin was allowed to sit for two hours while occasionally being swirled. After each swirl the side of the flask was rinsed with additional cocktail until the total volume of cocktail added was 15 mL. After two hours, the resin was filtered and washed with TFA (2×4 mL). The filtrate was concentrated to an oil under high vacuum. The oil was triturated with ether to give 0.0460 g of product. ESMS: Calcd. For $C_{28}H_{31}N_3O_6$, 505.22; Found, 506.3 [M+H]+1 HPLC Method 5. $R_t$=13.477 min Purity 90%

Part B: Preparation of 2-((6-((1-aza-2-(2-sulfophenyl)vinyl) amino)(3-pyridyl)carbonylamino)-2-(6-(4-benzo[d]1,3-dioxolan-5-yl-6-phenyl(2-pyridyloxy))-2,2-dimethylhexanoylamino)acetic acid 2-Amino-2-(6-(4-benzo[d]1,3-dioxolan-5-yl-6-phenyl(2-pyridyloxy))-2,2-dimethylhexanoylamino)acetic acid (0.035 g, 0.0560 mmol) was dissolved in dimethylformamide (3 mL). Triethylamine (23.4 μL, 0.168 mmol) was added and the reaction was stirred for 5 minutes. 2-[[[5-[[(2,5-Dioxo-1-pyrrolidinyl)oxy]carbonyl]1-2-pyridinyl]hydrazono]methyl]-benzenesulfonic acid, monosodium salt (0.030 g, 0.0672 mmol) was added and the reaction was stirred for 24 hours under nitrogen. The reaction was then concentrated to an oil under high vacuum. The oil was then purified by preparative HPLC Method 2 to give 11.2 mg (25%) of product. HRMS: Calcd. For $C_{41}H_{40}N_6O_{10}S+H$, 809.2605; Found, 809.2578. HPLC Method 5.$R_t$=13.711 min Purity=98%

Example 85

Synthesis of 2-(2-aza-2-((5-(N-(5-((3-((N-(6-(4,6-diphenyl(2-pyridyloxy))-2,2-dimethylhexanoylamino)-3-(4-hydroxyphenyl)propanoylamino)-1-(N-(2,3,4,5,6-pentahydroxyhexyl)carbamoyl)pentyl)carbamoyl(2-pyridyl))amino)vinyl)benzenesulfonic acid 6-(4,6-Diphenyl(2-pyridyloxy))-2,2-dimethylhexanoic acid (0.200 g, 0.513 mmol) was dissolved in dimethylformamide (5 mL). Diisopropylethylamine (223 μL, 1.53 mmol) was added, and the reaction was stirred for 5 min. H-Tyr(Obzl)-Ome (0.198 g, 0.616 mmol) and 2(1H-benzotriazole-1-yl)-1,1,3,3-tetramethyluronium hexafluorophosphate (0.214 g, 0.564 mmol) were added, and the reaction was stirred under nitrogen for 60 h. The reaction was concentrated to an oil under high vacuum. The oil was dissolved in 50:50 ACN/$H_2O$ and lyophilized. The crude product was then purified by preparative HPLC Method 2 to give 322.9 mg (96%) of product. ESMS: Calcd. For $C_{42}H_{44}N_2O_5$, 656.33; Found, 657.5 [M+H]+1 HPLC Method 5.$R_t$=22.768 min Purity=100%

Part B: Preparation of 2-(6-(4,6-diphenyl(2-pyridyloxy))-2,2-dimethylhexanoylamino)-3-(4-hydroxyphenyl)propanoic acid Methyl 2-(6-(4,6-diphenyl(2-pyridyloxy))-2,2-dimethylhexanoylamino)-3-(4-hydroxyphenyl)propanoate (0.150 g, 0.228 mmol) was dissolved in tetrahydrofuran (10 mL). Lithium hydroxide monohydrate (0.0958 g, 2.28 mmol) was dissolved in water (2 mL) and added to the reaction. The reaction was stirred for 18 h. The reaction was

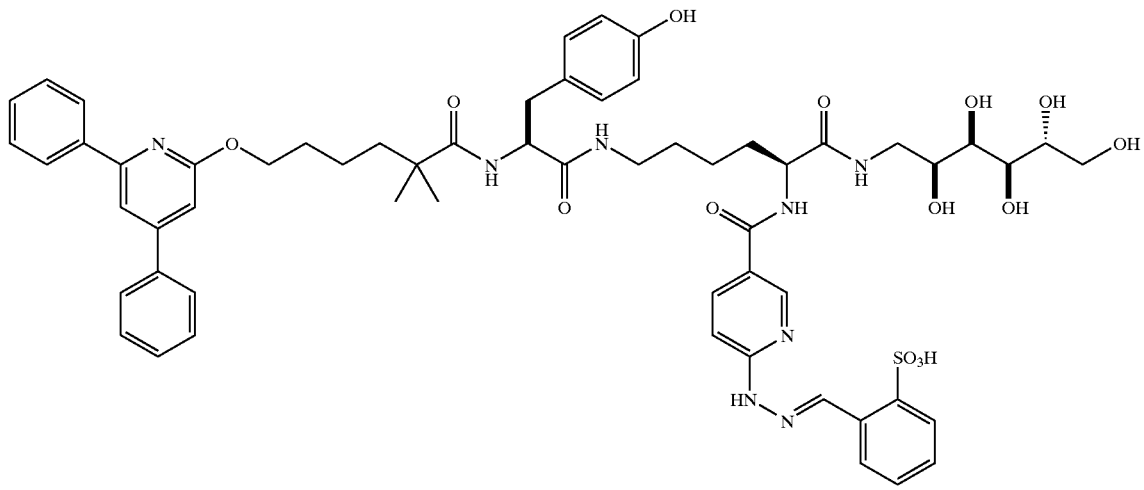

Part A: Preparation of methyl 2-(6-(4,6-diphenyl(2-pyridyloxy))-2,2-dimethylhexanoylamino)-3-(4-hydroxyphenyl)propanoate then concentrated, brought up in water, acidified to pH 5 with 1N HCl, and extracted with ethyl acetate. The organic layer was washed with water, brine, dried over magnesium

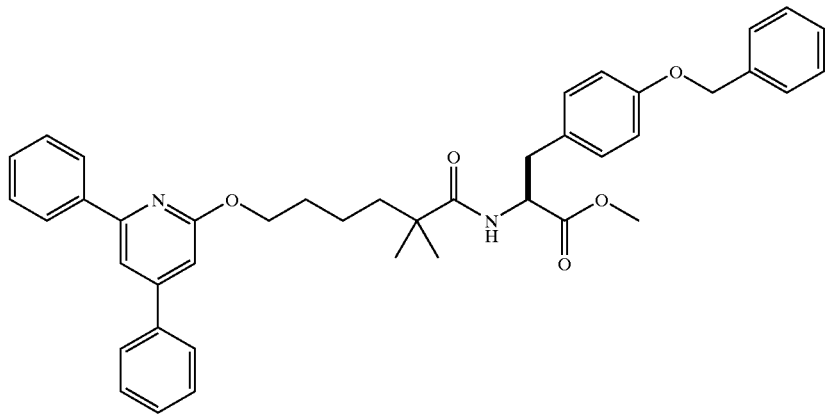

sulfate, filtered, and evaporated to give 138.6 mg (95%) of product. ESMS: Calcd. For $C_{41}H_{42}N_2O_5$, 642.31; Found, 643.4 [M+H]+1 HPLC Method 5.$R_t$=21.258 min Purity= 95%

Part C: Preparation of N-(1-(N-(5-((tert-butoxy) carbonylamino)-5-(N-(2,3,4,5,6-pentahydroxyhexyl) carbamoyl)pentyl)carbamoyl)-2-(4-benzyloxyphenyl) ethyl)-6-(4,6-diphenyl(2-pyridyloxy))-2,2-dimethylhexanamide

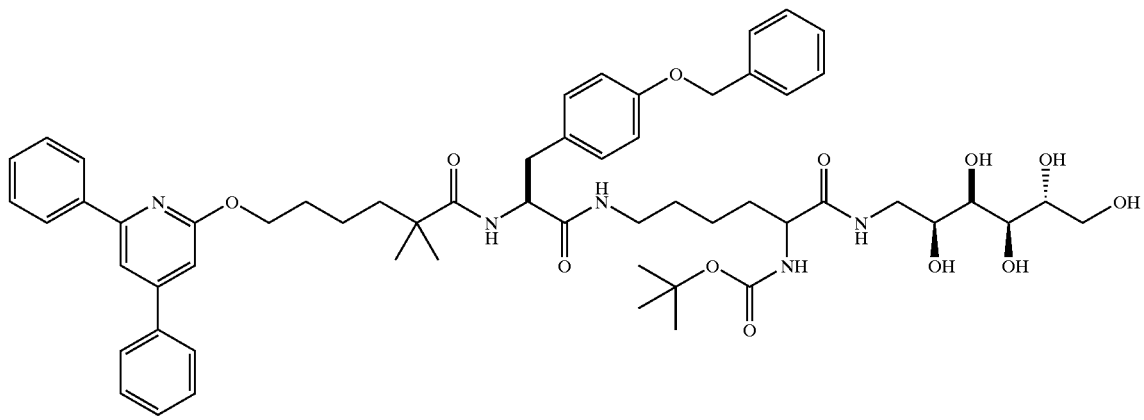

6-Amino-2-((tert-butoxy)carbonylamino)-(N-(2,3,4,5,6-pentahydroxyhexyl)hexanamide (0.050 g, 0.122 mmol) was dissolved in dimethylformamide (3 mL). Diisopropylethylamine (63.8 µL, 0.366 mmol) was added, and the reaction was stirred for 5 min. 2-(6-(4,6-Diphenyl(2-pyridyloxy))-2,2-dimethylhexanoylamino)-3-(4-hydroxyphenyl)propanoic acid (0.0942 g, 0.146 mmol) and 2(1H-benzotriazole-1-yl)-1,1,3,3-tetramethyluronium hexafluorophosphate (0.050 g, 0.134 mmol) were added, and the reaction was stirred under nitrogen for 72 h. The reaction was concentrated to an oil under high vacuum. The oil was then purified by preparative HPLC Method 2 to give 79.2 mg (63%) of product. ESMS: Calcd. For $C_{58}H_{75}N_5O_{12}$, 1033.54; Found, 1034.5 [M+H]+ 1HPLC Method 5. $R_t$=19.290 min Purity=84%

Part D: Preparation of N-(1-(N-(5-((tert-butoxy) carbonylamino)-5-(N-(2,3,4,5,6-pentahydroxyhexyl) carbamoyl)pentyl)carbamoyl)-2-(4-hydroxyphenyl)ethyl)-6-(4,6-diphenyl(2-pyridyloxy))-2,2-dimethylhexanamide A small round bottom was purged with nitrogen. To this was added palladium on carbon (30 mg, 10%w/w) followed by methanol (5 mL). N-(1-(N-(5-((Tert-butoxy) carbonylamino)-5-(N-(2,3,4,5,6-pentahydroxyhexyl) carbamoyl)pentyl)carbamoyl)-2-(4-benzyloxyphenyl) ethyl)-6-(4,6-diphenyl(2-pyridyloxy))-2,2-dimethylhexanamide (0.065 g, 0.0628 mmol) was dissolved in methanol (5 mL) and added to the reaction. The reaction was evacuated and purged with nitrogen twice, and then evacuated and opened to hydrogen twice. The reaction was stirred under hydrogen for 4 h. The reaction was not complete so more palladium on carbon was added (30 mg). The reaction was stirred overnight for 18 h. The reaction was filtered through celite, washed with methanol. The filtrate was concentrated to an oil under high vacuum to give 57.0 mg (96%) of product. ESMS: Calcd. For $C_{51}H_{69}N_5O_{12}$, 943.49; Found, 944.5 [M+H]+1HPLC Method 5. $R_t$=15.990 min Purity=85%

Part E: Preparation of N-(1-(N-(5-amino-5-(N-(2,3,4,5,6-pentahydroxyhexyl)carbamoyl)pentyl)carbamoyl)-2-(4-hydroxyphenyl)ethyl)-6-(4,6-diphenyl(2-pyridyloxy))-2,2-dimethylhexanamide N-(1-(N-(5-((Tert-butoxy)carbonylamino)-5-(N-(2,3,4,5,6-pentahydroxyhexyl)carbamoyl)pentyl)carbamoyl)-2-(4-hydroxyphenyl)ethyl)-6-(4,6-diphenyl(2-pyridyloxy))-2,2-dimethylhexanamide (0.054 g, 0.0572 mmol) was dissolved in methylene chloride (1.5 mL). Trifluoroacetic acid (1.5 mL) was added, and the reaction was stirred for 2 h. The reaction was concentrated under high vacuum. The resulting oil was triturated with ether to give 40 mg (73%) of product. ESMS: Calcd. For $C_{46}H_{61}N_5O_{10}$, 843.44; Found, 844.6 [M+H]+1HPLC Method 5. $R_t$=13.804 min Purity=89%

Part F: Preparation of 2-(2-aza-2-((5-(N-(5-((3-((N-(6-(4,6-diphenyl(2-pyridyloxy))-2,2-dimethylhexanoylamino)-3-(4-hydroxyphenyl)propanoylamino)-1-(N-(2,3,4,5,6-pentahydroxyhexyl)carbamoyl)pentyl)carbamoyl(2-pyridyl))amino)vinyl)benzenesulfonic acid N-(1-(N-(5-Amino-5-(N-(2,3,4,5,6-pentahydroxyhexyl)-carbamoyl)pentyl)carbamoyl)-2-(4-hydroxyphenyl)ethyl)-6-(4,6-diphenyl(2-pyridyloxy))-2,2-dimethylhexanamide (0.040 g, 0.0418 mmol) was dissolved in dimethylformamide (3 mL). Triethylamine (17.5 µL, 0.125 mmol) was added and the reaction was stirred for 5 minutes. 2-[[[5-[[(2,5-Dioxo-1-pyrrolidinyl)oxy]carbonyl]-2-pyridinyl] hydrazono]methyl]-benzenesulfonic acid, monosodium salt (0.0221 g, 0.0501 mmol) was added and the reaction was stirred for 24 hours under nitrogen. The reaction was then concentrated to an oil under high vacuum. The oil was then purified by preparative HPLC Method 2 to give 12.1 mg (25%) of product. HRMS: Calcd. For $C_{59}H_{70}N_8O_{14}S+H$, 1147.4810; Found, 1147.4826. HPLC Method 5.$R_t$=13.358 min Purity=90%

Example 86

Synthesis of 2-(2-aza-2-((5-(N-(5-((3-((N-(6-(4-benzo[d]1,3-dioxolan-5-yl-6-phenyl(2-pyridyloxy))-2,2-dimethylhexyl)-carbamoyl)-2-(N-(2,3,4,5,6-pentahydroxyhexyl)carbamoyl)-ehtyl)carbamoyl(2-pyridyl))amino)vinyl)benxenesulfonic acid

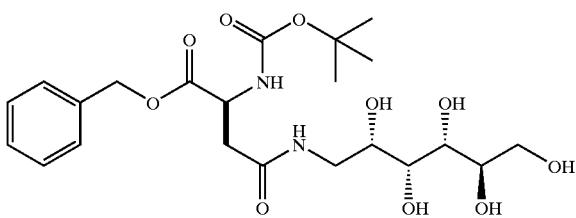

Part A: Preparation of benzyl 2-((tert-butoxy)carbonylamino)-3-(N-(2,3,4,5,6-pentahydroxyhexyl)carbamoyl)propanoate

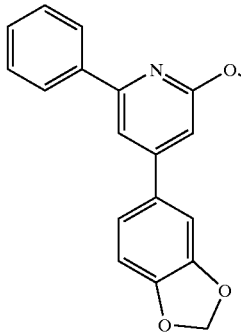

Boc-Asp(Osu)-Obzl (2.00 g, 4.76 mmol) was dissolved in tetrahydrofuran (25 mL). 1-Amino-desoxysorbitol (0.948 g, 5.24 mmol) was dissolved in water (5 mL), and added to the reaction. Triethylamine (0.265 mL, 1.90 mmol) was added, and the reaction was stirred for 3 h under nitrogen. The reaction was concentrated under high vacuum. The residue was brought up in water and extracted with ethyl acetate. The ethyl acetate was washed with 0.1 N hydrochloric acid, water, brine, dried over magnesium sulfate, and filtered. As the filtrate was evaporated the product precipitated out of the solution. The precipitate was filtered, washed with hexane, and dried under high vacuum to give 0.384 g (17%) of

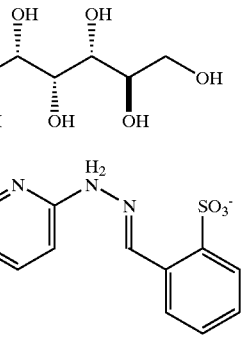

product. ESMS: Calculated for $C_{22}H_{34}N_2O_{10}$, 486.22; Found, 487.3 [M+H]+1HPLC Method 5.$R_t$=8.724 min Purity=100%

Part B: Preparation of 2-((tert-butoxy)carbonylamino)-3-(N-(2,3,4,5,6-pentahydroxyhexyl)carbamoyl)propanoic acid A small round bottom was purged with nitrogen. To this was added palladium on carbon (100 mg, 10%w/w) followed by ethanol (5 mL). Benzyl 2-((tert-butoxy)carbonylamino)-3-(N-(2,3,4,5,6-pentahydroxyhexyl)carbamoyl)propanoate (0.300 g, 0.617 mmol) was dissolved in ethanol (5 mL) and added to the reaction. The reaction was evacuated and purged with nitrogen twice, and then evacuated and opened to hydrogen twice. The reaction was stirred under hydrogen for 20 h. The reaction was filtered through celite, washed with ethanol. The filtrate was concentrated to an oil under high vacuum to give 266 mg (109%) of product. ESMS: Calcd. For $C_{15}H_{28}N_2O_{10}$, 396.17; Found, 397.2 [M+H]+1

Part C: Preparation of N-(6-(4-benzo[d]1,3-dioxolan-5-yl-6-phenyl(2-pyridyloxy))-2,2-dimethylhexyl)-2-((tert-butoxy)carbonylamino)-N'-(2,3,4,5,6-pentahydroxyhexyl)butane-1,4-diamide

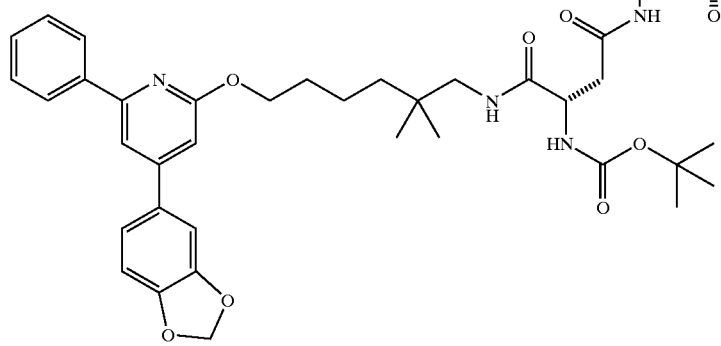

1-Amino-2,2-dimethyl-6-[(4-(3,4-methylenedioxy-phenyl)-6-phenyl-2-pyridinyl)oxy]-hexane (0.100 g, 0.239 mmol) was dissolved in dimethylformamide (5 mL). Diisopropylethylamine (124.9 µL, 0.717 mmol) was added, and the reaction was stirred for 5 min. 2-((Tert-butoxy)carbonylamino)-3-(N-(2,3,4,5,6-pentahydroxyhexyl)carbamoyl)propanoic acid(0.114 g, 0.287 mmol) and 2(1H-benzotriazole-1-yl)-1,1,3,3-tetramethyluronium hexafluorophosphate (0.109 g, 0.287 mmol) were added, and the reaction was stirred under nitrogen for 48 h. The reaction was concentrated to an oil under high vacuum. The oil was then purified by preparative HPLC Method 3 to give 98.9 mg (52%) of product. ESMS: Calcd. For $C_{41}H_{56}N_4O_{12}$, 796.39; Found, 797.5 [M+H]+1 HPLC Method 5.$R_t$=15.813 min Purity=100%

Part D: Preparation of 2-amino-N-(6-(4-benzo[d]1,3-dioxolan-5-yl-6-phenyl(2-pyridyloxy))-2,2-dimethylhexyl)-N'-(2,3,4,5,6-pentahydroxyhexyl)butane-1,4-diamide N-(6-(4-Benzo[d]1,3-dioxolan-5-yl-6-phenyl(2-pyridyloxy))-2,2-dimethylhexyl)-2-((tert-butoxy)carbonyl-amino)-N'-(2,3,4,5,6-pentahydroxyhexyl)butane-1,4-diamide (0.090 g, 0.113 mmol) was dissolved in methylene chloride (1.5 mL). Trifluoroacetic acid (1.5 mL) was added, and the reaction was stirred for 2 h. The reaction was concentrated under high vacuum. The resulting oil was triturated with ether to give 80.5 mg (88%) of product. ESMS: Calcd. For $C_{36}H_{48}N_4O_{10}$, 696.34; Found, 697.4 [M+H]+1 HPLC Method 5. $R_t$=12.776 min Purity=88%

Part E: Preparation of 2-(2-aza-2-((5-(N-(5-((3-((N-(6-(4-benzo[d]1,3-dioxolan-5-yl-6-phenyl(2-pyridyloxy))-2,2-dimethylhexyl)carbamoyl)-2-(N-(2,3,4,5,6-pentahydroxyhexyl)carbamoyl)ethyl)carbamoyl(2-pyridyl))amino)vinyl)benzenesulfonic acid 2-Amino-N-(6-(4-benzo[d]1,3-dioxolan-5-yl-6-phenyl(2-pyridyloxy))-2,2-dimethylhexyl)-N'-(2,3,4,5,6-pentahydroxyhexyl)butane-1,4-diamide(0.047 g, 0.0580 mmol) was dissolved in dimethylformamide (3 mL). Triethylamine (24.3 µL, 0.174 mmol) was added and the reaction was stirred for 5 minutes. 2-[[[5-[[(2,5-Dioxo-1-pyrrolidinyl)oxy]-carbonyl]-2-pyridinyl]hydrazono]methyl]-benzenesulfonic acid, monosodium salt (0.0306 g, 0.0696 mmol) was added and the reaction was stirred for 72 hours under nitrogen. The reaction was then concentrated to an oil under high vacuum. The oil was then purified by preparative HPLC Method 3 to give 25.2 mg (43%) of product. HRMS: Calcd. For $C_{49}H_{57}N_7O_{14}S+H$, 1000.3762; Found, 1000.3732. HPLC Method 5.$R_t$=12.730 min Purity=96%

Example 87

Synthesis of 2-(2-aza-2-((5-(N-(5-((3-((N-(6-(4-benzo[d]1,3-dioxolan-5-yl-6-phenyl(2-pyridyloxy))-2,2-dimethylhexyl)carbamoyl)amino)phenyl)carbonylamino)-1-(N-(2,3,4,5,6-pentahydroxyhexyl)carbamoyl)pentyl)carbamoyl(2-pyridyl))amino)vinyl)benzenesulfonic acid

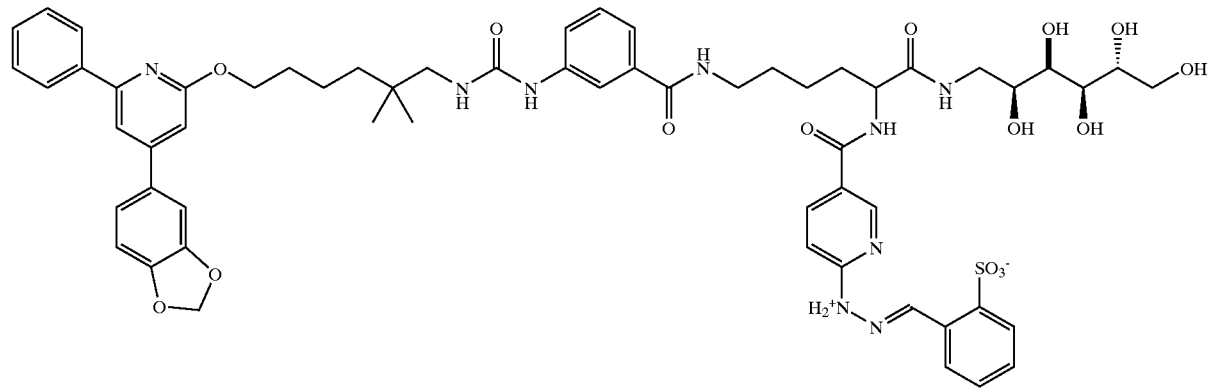

Part A: Preparation of methyl 3-((N-(6-(4-benzo[d]1,3-dioxolan-5-yl-6-phenyl(2-pyridyloxy))-2,2-dimethylhexyl)carbamoyl)amino)benzoate

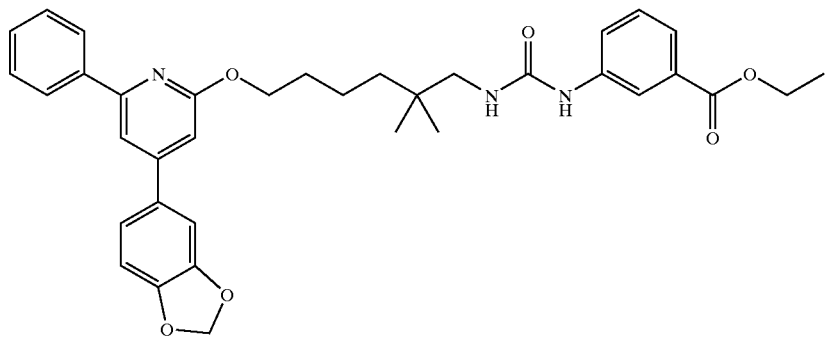

1-Amino-2,2-dimethyl-6-[(4-(3,4-methylenedioxyphenyl)-6-phenyl-2-pyridinyl)oxy]-hexane (0.300 g, 0.717 mmol) was dissolved in dimethylformamide (10 mL). Diisopropylethylamine (642 μL, 3.58 mmol) was added, and the reaction was stirred for 5 min. 3-Ethoxycarbonylphenyl isocyanate (0.548 g, 2.87 mmol) was added, and the reaction was stirred under nitrogen for 36 h. The reaction was concentrated to an oil under high vacuum. The oil was then purified by preparative HPLC Method 3 to give 431.6 mg (98%) of product. ESMS: Calcd. For $C_{36}H_{39}N_3O_6$, 609.28; Found, 610.4 [M+H]+1 HPLC Method 5.$R_t$=20.452 min Purity=99%

Part B: Preparation of 3-((N-(6-(4-benzo[d]1,3-dioxolan-5-yl-6-phenyl(2-pyridyloxy))-2,2-dimethylhexyl)carbamoyl)amino)-benzoic acid Methyl 3-((N-(6-(4-benzo[d]1,3-dioxolan-5-yl-6-phenyl(2-pyridyloxy))-2,2-dimethylhexyl)carbamoyl)amino)-benzoate(0.400 g, 0.656 mmol) was dissolved in ethanol (10 mL). Potassium hydroxide pellets (0.0736 g, 1.31 mmol) were dissolved in water (1 mL), and added to the reaction. The reaction was heated to reflux for 16 h. The reaction was concentrated to an oil under high vacuum. The residue was brought up in water. The solution was adjusted to pH 5 with 1N hydrochloric acid. The solution was extracted with ethyl acetate. The organic layer was washed with water, brine, dried over magnesium sulfate, filtered, and concentrated to an oil under high vacuum. The oil was recrystallized from hexane:ethyl acetate to give 0.212 g (56%) of product. HRMS: Calcd. For $C_{34}H_{35}N_3O_6+H$, 582.2604; Found, 582.2604. HPLC Method 5.$R_t$=17.966 min Purity 100%

Part C: Preparation of 6-((3-((N-(6-(4-benzo[d]1,3-dioxolan-5-yl-6-phenyl(2-pyridyloxy))-2,2-dimethylhexyl)carbamoyl)-amino)phenyl)carbonylamino)-2-((tert-butoxy)carbonylamino)-(N-(2,3,4,5,6-pentahydroxyhexyl)hexanamide Part D: Preparation of 2-amino-6-((3-((N-(6-(4-benzo[d]1,3-dioxolan-5-yl-6-phenyl(2-pyridyloxy))-2,2-dimethylhexyl)carbamoyl)amino)phenyl)carbonylamino)-N-(2,3,4,5,6-pentahydroxyhexyl)hexanamide 6-((3-((N-(6-(4-Benzo[d]1,3-dioxolan-5-yl-6-phenyl(2-pyridyloxy))-2,2-dimethylhexyl)carbamoyl)amino)phenyl)carbonylamino)-2-((tert-butoxy)carbonylamino)-(N-(2,3,4,5,6-pentahydroxyhexyl)hexanamide (0.045 g, 0.0462 mmol) was dissolved in methylene chloride (3.0 mL). Trifluoroacetic acid (3.0 mL) was added, and the reaction was stirred for 2 h. The reaction was concentrated under high vacuum. The resulting oil was triturated with ether to give 34.2 mg (75%) of product. ESMS: Calcd. For $C_{46}H_{60}N_6O_{11}$, 872.43;Found, 873.6 [M+H]+1 HPLC Method 5.$R_t$=14.610 min Purity=91%

Part E: Preparation of 2-(2-aza-2-((5-(N-(5-((3-((N-(6-(4-benzo[d]1,3-dioxolan-5-yl-6-phenyl(2-pyridyloxy))-2,2-dimethylhexyl)carbamoyl)amino)phenyl)carbonylamino)-1-(N-(2,3,4,5,6-pentahydroxyhexyl)carbamoyl)pentyl)carbamoyl(2-pyridyl))amino)vinyl)benzenesulfonic acid 2-Amino-6-((3-((N-(6-(4-benzo[d]1,3-dioxolan-5-yl-6-phenyl(2-pyridyloxy))-2,2-dimethylhexyl)carbamoyl)amino)-phenyl)carbonylamino)-N-(2,3,4,5,6-pentahydroxyhexyl)-hexanamide (0.029 g, 0.0294 mmol) was dissolved in dimethylformamide (3 mL). Triethylamine (12.3 μL, 0.0882 mmol) was added and the reaction was stirred for 5 minutes. 2-[[[5-[[(2,5-Dioxo-1-pyrrolidinyl)oxy]carbonyl]-2-pyridinyl]hydrazono]methyl]-benzenesulfonic acid, monosodium salt (0.0155 g, 0.0353 mmol) was added and the reaction was stirred for 72 hours under nitrogen. The reaction was then concentrated to an oil under high vacuum. The oil was then purified by the preparative HPLC Method 4 to give 4.0 mg (12%) of product. ESMS: Calcd. For $C_{59}H_{69}N_9O_{15}S$, 1175.46; Found, 1176.4 [M+H]+1 HPLC Method 5.$R_t$=13.898 min Purity=94%

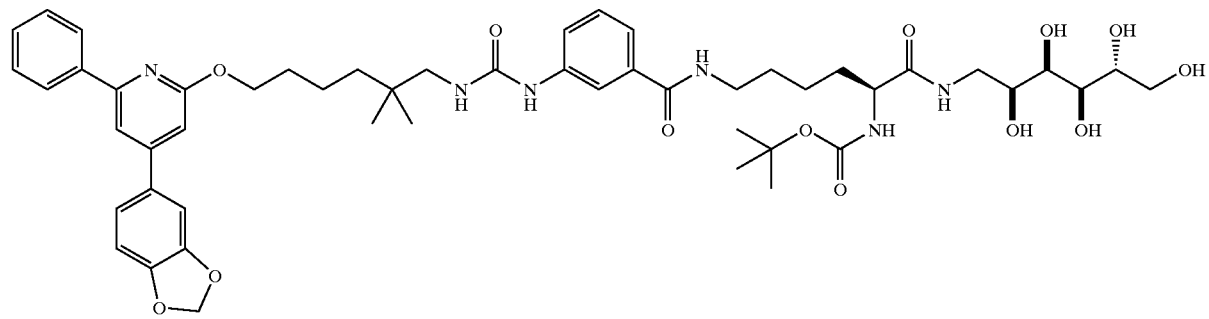

6-Amino-2-((tert-butoxy)carbonylamino)-(N-(2,3,4,5,6-pentahydroxyhexyl)hexanamide (0.040 g, 0.0977 mmol) was dissolved in dimethylformamide (2 mL). Diisopropylethylamine (46.4 μL, 0.266 mmol) was added, and the reaction was stirred for 5 min. 3-((N-(6-(4-Benzo[d]1,3-dioxolan-5-yl-6-phenyl(2-pyridyloxy))-2,2-dimethylhexyl)carbamoyl)amino)-benzoic acid (0.0516 g, 0.0888 mmol) and 2(1H-benzotriazole-1-yl)-1,1,3,3-tetramethyluronium hexafluorophosphate (0.0404 g, 0.106 mmol) were added, and the reaction was stirred under nitrogen for 48 h. The reaction was concentrated to an oil under high vacuum. The oil was then purified by preparative HPLC Method 3 to give 55.0 mg (64%) of product. ESMS: Calcd. For $C_{51}H_{68}N_6O_{13}$, 972.48; Found, 973.6 [M+H]+1 HPLC Method 5.$R_t$=16.354 min Purity=97%

| Preparative HPLC Method 4 | |
|---|---|
| Instrument | Rainin Rabbit; Dynamax software |
| Column | Vyadac C-18 (21.2 mm × 25 cm) |
| Detector | Knauer VWM |
| Flow Rate | 15 ml/min |
| Column Temp | RT |
| Mobile Phase | A: 0.1% TFA in $H_2O$ |
| | B: 0.1% TFA in ACN/$H_2O$ (9:1) |
| Gradient | Time (min)　　% A　　% B |
| | 0　　60　　40 |
| | 12　　32　　68 |

-continued

Preparative HPLC Method 4

| 32 | 20 | 80 |
| 33 | 60 | 40 |

Example 88

Synthesis of 2-((6-((1-aza-2-(2-sulfophenyl)vinyl)amino)(3-pyridyl))carbonylamino)-3-(N-(6-(4-benzo[d]1,3-dioxolan-5-yl-6-phenyl(2-pyridyloxy))-2,2-dimethylhexyl)carbamoyl)-propanoylamino)-3-carboxypropanoylamino)-3-carboxypropanoylamino)-ethane-1,2-dicarboxylic acid 3-((6-((1-Aza-2-(2-sulfophenyl)vinyl)amino)(3-pyridyl)carbonylamino)-3-(N-(6-(4-benzo[d]1,3-dioxolan-5-yl-6-phenyl(2-pyridyloxy))-2,2-dimethylhexyl)carbamoyl)propanoic acid (0.044 g, 0.0526 mmol) was dissolved in dimethylformamide (3 mL). Diisopropylethylamine (27.5 μL, 0.158 mmol) was added, and the reaction was stirred for 5 min. Triaspartic acid (Asp-Asp-Asp-OH, 0.0229 g, 0.0631 mmol) and 2(1H-benzotriazole-1-yl)-1,1,3,3-tetramethyluronium hexafluorophosphate (0.0239 g, 0.0631 mmol) were added, and the reaction was stirred under nitrogen for 18 h. The reaction was concentrated to an oil under high vacuum. The oil was then purified by preparative HPLC Method 3 to give 22.6 mg (36%) of product. HRMS: Calcd. For $C_{55}H_{59}N_9O_{19}S+H$, 1182.3726; Found 1182.3765. HPLC Method 5.$R_t$=12.612 min Purity=95%

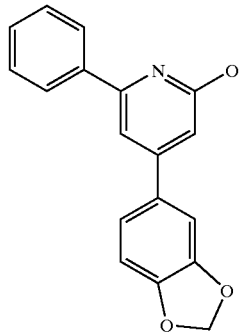
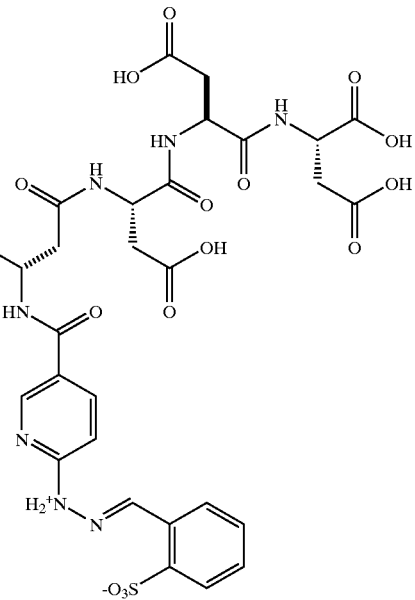

Example 89

Synthesis of 2-((6-((1-aza-2-(2-sulfophenyl)vinyl)amino)(3-pyridyl))carbonylamino)-3-(2-(5-(4-benzo[d]1,3-dioxolan-5-yl-6-phenyl(2-pyridyloxy))pentyloxy)phenyl)propanoic acid

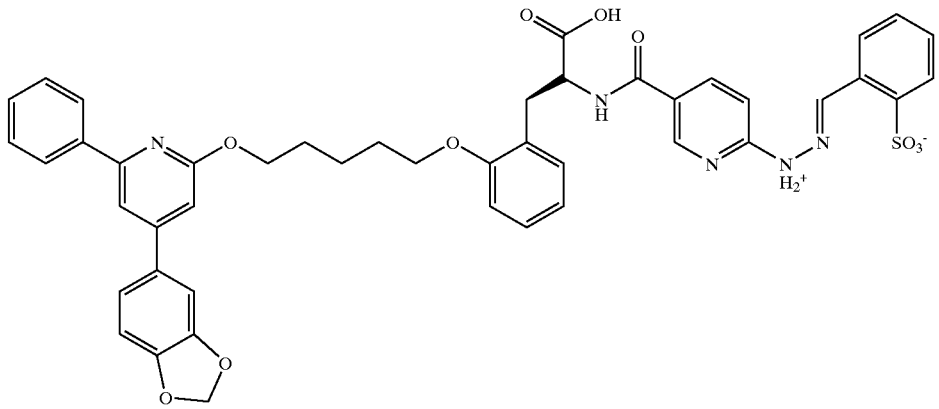

Part A: Preparation of 4-benzo[d]1,3-dioxolan-5-yl-6-phenyl-2-(5-(1,1,2,2-tetramethyl-1-silapropoxy)pentyloxy)pyridine

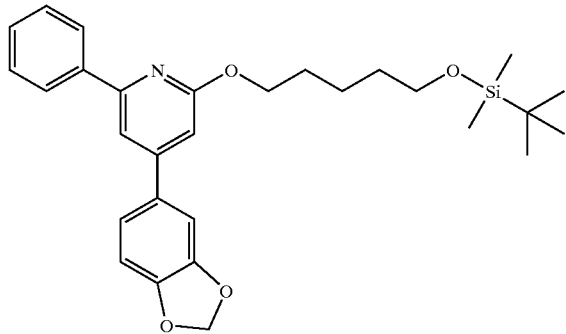

4-(3,4-Methylenedioxyphenyl)-6-phenyl-2-pyridone (0.585 g, 2.01 mmol) and 5-(t-butyldimethylsilyloxy)-1-pentanol (0.877 g, 4.02 mmol) were brought up in tetrahydrofuran (15 mL). Triphenylphosphine (1.05 g, 4.02 mmol) and diethylazodicarboxylate (0.700 g, 4.02 mmol) were added, and the reaction was stirred for 4 h. The reaction was quenched with sat. ammonium chloride. The reaction was concentrated under high vacuum. The remaining aqueous layer was extracted with ethyl acetate. The organic layer was washed with brine, dried over magnesium sulfate, filtered, and concentrated to an oil under high vacuum. The oil was brought up in 90:10 hexane:ethyl acetate and passed through silica gel. The filtrate was concentrated to an oil under high vacuum to give 1.068 g (108%) of product. ESMS matches if TBDMS group ionizes during mass spec. Calcd. For $C_{23}H_{22}NO_4$, 376.15; Found, 377.3 [M+H]+1 HPLC Method 5.$R_t$=25.623 min Purity=50%

Part B: Preparation of 5-(4-benzo[d]1,3-dioxolan-5-yl-6-phenyl-2-pyridyloxy)pentan-1-ol A small round bottom was purged with nitrogen. To this was added palladium on carbon (200 mg, 10%w/w) followed by ethyl acetate (7 mL). 4-Benzo[d]1,3-dioxolan-5-yl-6-phenyl-2-(5-(1,1,2,2-tetramethyl-1-silapropoxy)pentyloxy)pyridine (1.04 g, 2.12 mmol) was dissolved in ethyl acetate (8 mL) and added to the reaction. The reaction was evacuated and purged with nitrogen twice, and then evacuated and opened to hydrogen twice. The reaction was stirred under hydrogen for 3 h. The reaction was not complete so more palladium on carbon was added (200 mg), and the reaction was stirred for 3 h more. The reaction was still not complete so more palladium on carbon was added (500 mg) was added, and the reaction was stirred overnight for 16 h. The reaction still was not done, so more palladium on carbon (600 mg) was added, and the reaction was stirred for 3 h. The reaction was filtered through celite, washed with ethyl acetate. The filtrate was concentrated to an oil under high vacuum. The oil was recrystallized from hexane:ether to give 421.8 mg (53%) of product. ESMS: Calcd. For $C_{23}H_{23}NO_4$, 377.16; Found, 378.2 [M+H]+1 HPLC Method 5. $R_t$=16.203 min Purity=99%

Part C: Preparation of methyl 3-(2-(5-(4-benzo[d]1,3-dioxolan-5-yl-6-phenyl(2-pyridyloxy))pentyloxy)phenyl)-2-((tert-butoxy)carbonylamino)propanoate 5-(4-Benzo[d]1,3-dioxolan-5-yl-6-phenyl-2-pyridyloxy)-pentan-1-ol (0.153 g, 0.406 mmol) and methyl 2-((tert-butoxy)-carbonylamino)-3-(2-hydroxyphenyl)propanoate (0.100 g, 0.338 mmol) were brought up in tetrahydrofuran (10 mL). Triphenylphosphine (0.177 g, 0.676 mmol) and diethylazodicarboxylate (0.118 g, 0.676 mmol) were added, and the reaction was stirred for 3 h. The reaction was quenched with sat. ammonium chloride. The reaction was concentrated under high vacuum. The remaining aqueous layer was extracted with ethyl acetate. The organic layer was washed with brine, dried over magnesium sulfate, filtered, and concentrated to an oil under high vacuum. The oil was purified by flash chromatography (5:1 hexane:ethyl acetate) to give 0.111 g (50%) of product. ESMS: Calcd. For $C_{38}H_{42}N_2O_8$, 654.29; Found, 655.4 [M+H]+1 HPLC Method 5.$R_t$=21.986 min Purity=95%

Part D: Preparation of 3-(2-(5-(4-benzo[d]1,3-dioxolan-5-yl-6-phenyl(2-pyridyloxy))pentyloxy)phenyl)-2-((tert-butoxy)carbonylamino)propanoic acid

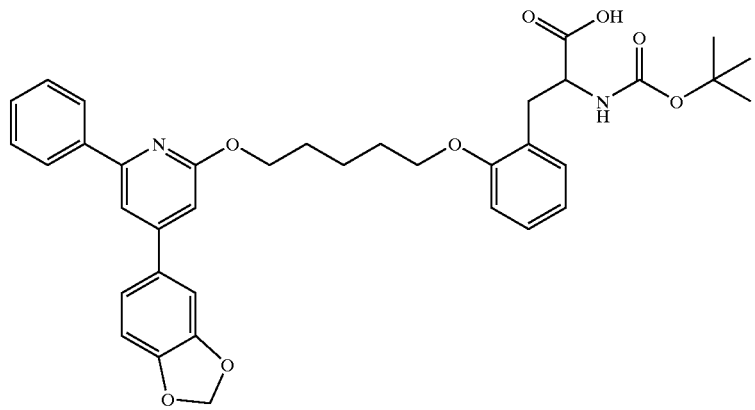

Methyl 3-(2-(5-(4-benzo[d]1,3-dioxolan-5-yl-6-phenyl(2-pyridyloxy))pentyloxy)phenyl)-2-((tert-butoxy)carbonyl-amino)propanoate (0.098 g, 0.150 mmol) was dissolved in tetrahydrofuran (5 mL). Lithium hydroxide monohydrate (0.0628 g, 1.50 mmol) was dissolved in water (1 mL) and added to the reaction. The reaction was stirred for 18 h. The reaction was then concentrated, brought up in water, acidified to pH 5 with 1N HCl, and extracted with ethyl acetate. The organic layer was washed brine, dried over magnesium sulfate, filtered, and evaporated to give 93.9 mg (98%) of product. ESMS: Calcd. For $C_{37}H_{40}N_2O_8$, 640.27; Found, 641.4. [M+H]+1 HPLC Method 5. $R_t$=20.109 min Purity=91%

Part E: Preparation of 2-amino-3-(2-(5-(4-benzo[d]1,3-dioxolan-5-yl-6-phenyl(2-pyridyloxy))pentyloxy)phenyl)propanoic acid To a solution of 3-(2-(5-(4-Benzo[d]1,3-dioxolan-5-yl-6-phenyl(2-pyridyloxy))pentyloxy)phenyl)-2-((tert-butoxy)-carbonylamino)-propanoic acid (0.083 g, 0.130 mmol) in methylene chloride (3.0 mL) was added trifluoroacetic acid (3.0 mL), and the reaction stirred for 2 h. The reaction was concentrated under high vacuum to give 85 mg (100%) of product as an oil. ESMS: Calcd. For $C_{32}H_{32}N_2O_6$, 540.23; Found, 541.3 [M+H]+1 HPLC Method 5.$R_t$=15.041 min Purity=96%

Part F: Preparation of 2-((6-((1-aza-2-(2-sulfophenyl)vinyl)amino)(3-pyridyl))carbonylamino)-3-(2-(5-(4-benzo[d]1,3-dioxolan-5-yl-6-phenyl(2-pyridyloxy))pentyloxy)phenyl)propanoic acid To a solution of 2-amino-3-(2-(5-(4-benzo[d]1,3-dioxolan-5-yl-6-phenyl(2-pyridyloxy))pentyloxy)phenyl)propanoic acid (0.080 g, 0.122 mmol) in dimethylformamide (3 mL) was added triethylamine (85.0 μL, 0.610 mmol) and the reaction stirred for 5 min. 2-[[[5-[[(2,5-Dioxo-1-pyrrolidinyl)oxy]carbonyl]-2-pyridinyl]hydrazono]methyl]-benzenesulfonic acid, monosodium salt (0.0646 g, 0.146 mmol) was added and the reaction was stirred for 96 hours under nitrogen. The reaction was concentrated to an oil under high vacuum. The oil was then purified by preparative HPLC Method 3 to give 36.4 mg (35%) of product. HRMS: Calcd. For $C_{45}H_{41}N_5O_{10}S$+H, 844.2652; Found, 844.2667. HPLC Method 5.$R_t$=15.161 min Purity=96%

HPLC Method 5

| | |
|---|---|
| Instrument | HP1050 |
| Column | Vydac C18 (4.6 × 250 mm) |
| Detector | Diode array detector 220 nm/500 ref |
| Flow Rate | 1.0 mL/min. |
| Column Temp | 50 ° C. |
| Sample Size | 15 uL |
| Mobile Phase | A: 0.1% TFA in water |
| | B: 0.1% TFA in ACN/Water (9:1) |
| Gradient | Time (min)   % A   % B |
| | 0    80    20 |
| | 20    0    100 |
| | 30    0    100 |
| | 31    80    20 |

Examples 90–166

The reagents of examples 1–58, 61–72, and 75–89 are LTB4 antagonist compounds which incorporate a chelator or bonding unit for Tc-99m. The following procedures (A–D) describe the synthesis of radiopharmaceuticals of the present invention (Examples 90–166). The reagents comprised of a hydrazinonicotinamide group, present either as the free hydrazine or in protected form as a hydrazone react to form ternary ligand complexes with Tc-99m, designated by the formulae $^{99m}$Tc(LTB4)(tricine)(phosphine) and $^{99m}$Tc(LTB4)(tricine)(L) (L=Imine-Nitrogen Containing Heterocycle), in which (LTB4) represents the LTB4 antagonist compound bonded to the Tc through a diazenido (—N═N—) or hydrazido (═N—NH—) moiety. The other two ligands in the Tc coordination sphere are tricine and either a phosphine or an imine-nitrogen containing heterocycle. The reagents comprised of a diamidedithiol or monoamidemonoaminedithiol chelator form complexes with Tc-99m of the formula $^{99m}$Tc(O) (LTB4) in which the designation (LTB4) represents the LTB4 antagonist compound bonded to the Tc through two nitrogen donors and two sulfur donors forming a Tc(O) ($N_2S_2$) coordination sphere.

Procedure A

Synthesis of Tc-99m LTB4 Antagonist Complexes of the Formula $^{99m}$Tc(LTB4)(tricine)(phosphine) Using Stannous Reducing Agent (Examples 90–93, 95–97, 99, 100, 105, 111, 126, and 145–150.)

10–30 μg (0.2–0.4 mL) of LTB4 antagonist in saline or 50% aqueous ethanol, 40 mg (0.4 mL) of tricine in water, 1–7 mg (0.10–0.30 mL) of phosphine dissolved in water or ethanol, 25 μg (25 μL) $SnCl_2.2H_2O$ dissolved in 0.1 M HCl, 0–0.25 mL ethanol and 50–150 mCi $^{99m}TcO_{4-}$ in saline were combined in a 10 cc vial. The kit was heated in a 100° C. water bath for 10–20 minutes, then a 50 μL sample analyzed by HPLC Method 6. If necessary, the complex was purified by performing a 300–400 μL injection on the HPLC and collecting the fraction into a shielded flask. The collected fraction was evaporated to dryness, redissolved with a 0.05–5% solution of Tween 80 in saline, and then re-analyzed using HPLC Method 6.

Procedure B

Synthesis of Tc-99m LTB4 Antagonist Complexes of the Formula $^{99m}$Tc(LTB4)(tricine)(TPPTS) without Using Stannous Reducing Agent (Examples 93, 97, 100–103, 105 –109, 111–124, 126–143.)

To a lyophilized vial containing 4.84 mg TPPTS, 6.3 mg tricine, 40 mg mannitol and 0.25 M succinate buffer, pH 4.8, was added 0.2–0.4 mL (20–40 μg) LTB4 antagonist in saline or 50% aqueous ethanol, 50–100 mCi $^{99m}TcO_{4-}$ in saline, and additional saline to give a total volume of 1.3–1.5 mL. The kit is heated in an 100° C. water bath for 10–15 minutes, and a sample was then analyzed by HPLC Method 6 or 7. If necessary, the complex was purified by performing a 300–400 μL injection on the HPLC and collecting the fraction into a shielded flask. The collected fraction was evaporated to dryness, redissolved with a 0.05–5% solution of Tween 80 in saline, and then re-analyzed using HPLC Method 6 or 7.

Procedure C

Synthesis of Tc-99m LTB4 Antagonist Complexes of the Formula $^{99m}$Tc(LTB4)(tricine)(L) (L=Imine-Nitrogen Containing Heterocycle) (Examples 151–164)

To a 10 mL vial was added 0.4 mL of tricine solution (100 mg/mL in 25 mM succinate buffer, pH 5.0), 0.2 mL of LTB4 antagonist solution (100μ/mL in EtOH), 0.2–0.4 mL of coligand solution (10–50 mg/mL in 25 mM succinate buffer, pH=5.0, depending on the type of coligand (for pyridine analogs, the coligand concentration was 5–10 mg/mL while the concentration of imidazole, thiazole or triazole analogs was 1–5 mg/mL), 0.2–0.5 mL of $^{99m}TcO_{4-}$ solution (100–200 mCi/mL in saline), and 25 μL of $SnCl_2.2H_2O$ solution (1.0 mg/mL in 0.1 N HCl). The reaction mixture was heated at 100° C. for 10–15 min. After cooling at room temperature, the reaction mixture was analyzed by HPLC Method 6 If necessary, the complex was purified by performing a 300–400 μL injection on the HPLC and collecting the fraction into a shielded flask. The collected fraction was evaporated to dryness, redissolved with a 0.05–5% solution of Tween 80 in saline, and then re-analyzed using HPLC Method 6.

Procedure D

Synthesis of Tc-99m LTB4 Antagonist Complexes of the Formula $^{99m}$Tc(O)(LTB4) (Examples 165, 166)

A commercial Glucoscan® kit (containing 200 mg sodium glucoheptonate and ~60 μg stannous chloride dihydrate) was reconstitituted with 1.25 mL saline. To 0.5 mL of the reconstituted Glucoscan® was added: 150 μL 1:7 glacial acetic acid: 0.2 M HCl(aq), 0.25 mg (0.5 mL) of the respective conjugate dissolved in ethanol and ca. 50–150 mCi $^{99m}TcO_{4-}$ in saline. The kit was heated in an 80° C. water bath for 30 minutes, then a 50 μL sample analyzed by HPLC Method 6. If necessary, the complexes were purified by performing a 300–400 μL injection on the HPLC and collecting the fraction into a shielded flask. The collected fraction is evaporated to dryness, redissolved with 0.05–5% solution of Tween 80 in saline, and then re-analyzed by HPLC Method 6.

Analytical Methods

HPLC Method 6

Column: Zorbax C18, 25 cm×4.6 mm or Vydac C18, 25 cm×4.6 mm
Column Temperature: ambient
Flow: 1.0 mL/min
Solvent A: 10 mM sodium phosphate buffer pH 6
Solvent B: 100% Acetonitrile
Detector: sodium iodide (NaI) radiometric probe Gradient A (Ex. 99, 100):

| t (min) | 0 | 20 | 30 | 31 | 40 |
|---|---|---|---|---|---|
| % B | 15 | 50 | 75 | 15 | 15 |

Gradient B (Ex. 90–93, 95, 96):

| t (min) | 0 | 20 | 30 | 31 | 40 |
|---|---|---|---|---|---|
| % B | 0 | 90 | 90 | 0 | 0 |

Gradient C (Ex. 94, 97, 98, 101–109, 111–144, 147–166):

| t (min) | 0 | 20 | 30 | 31 | 40 |
|---|---|---|---|---|---|
| % B | 0 | 75 | 75 | 0 | 0 |

Gradient D (Ex. 145, 146):

| t (min) | 0 | 20 | 30 | 31 | 40 |
|---|---|---|---|---|---|
| % B | 0 | 80 | 80 | 0 | 0 |

HPLC Method 7 (Ex. 110)
Column: Cosmosil C18, 25 cm×4.6 mm
Column Temperature: 50° C.
Flow: 1.0 mL/min
Solvent A: 25 mM sodium phosphate pH 6
Solvent B: 100% Acetonitrile
Detector: NaI radiometric probe Gradient:

| t (min) | 0 | 20 | 30 | 31 | 40 |
|---|---|---|---|---|---|
| % B | 40 | 80 | 80 | 40 | 40 |

TABLE 1

Analytical and Yield Data for $^{99m}Tc$ (LTB4) (tricine) (TPPTS) Complexes

| Complex Ex. No. | Reagent Ex. No. | % Yield | RT (min) |
|---|---|---|---|
| 90 | 1 | 75 | 12.7 |
| 91 | 2 | 92 | 12.0 |
| 92 | 3 | 83 | 12.4 |
| 93 | 4 | 88 | 15.2 |
| 94 | 6 | 91 | 12.8 |
| 95 | 7 | 91 | 15.1 |
| 96 | 8 | 59 | 12.9 |
| 97 | 10 | 70 | 15.0 |
| 98 | 12 | 68 | 16.0 |
| 99 | 14 | 60 | 18.7 |
| 100 | 15 | 83 | 15.0 |
| 101 | 17 | 47 | 12.4 |
| 102 | 18 | 60 | 15.3 |
| 103 | 19 | 77 | 16.0 |
| 104 | 20 | 72 | 14.1 |
| 105 | 21 | 54 | 12.1 |
| 106 | 23 | 73 | 13.5 |
| 107 | 26 | 41 | 15.6 |
| 108 | 27 | 80 | 16.4 |
| 109 | 28 | 83 | 15.0 |
| 110 | 31 | 51 | 16.0 |
| 111 | 32 | 58 | 15.8 |
| 112 | 33 | 83 | 16.0 |
| 113 | 34 | 80 | 13.3 |
| 114 | 35 | 85 | 14.1 |
| 115 | 36 | 47 | 13.8 |
| 116 | 37 | 44 | 15.7 |
| 117 | 38 | 90 | 14.0 |
| 118 | 39 | 76 | 14.6 |
| 119 | 40 | 85 | 13.8 |
| 120 | 41 | 79 | 12.8 |
| 121 | 42 | 82 | 13.6 |
| 122 | 43 | 87 | 13.3 |
| 123 | 44 | 87 | 12.2 |
| 124 | 45 | 87 | 12.6 |
| 125 | 49 | 92 | 10.9 |
| 126 | 54 | 85 | 17.5 |
| 127 | 56 | 33 | 13.9 |
| 128 | 58 | 46 | 13.3 |
| 129 | 64 | 86 | 13.9 |
| 130 | 65 | 94 | 13.9 |
| 131 | 67 | 79 | 12.9 |
| 132 | 67 | 82 | 13.2 |
| 133 | 68 | 83 | 14.5 |
| 134 | 70 | 67 | 12.9 |
| 135 | 72 | 57 | 11.7 |
| 136 | 75 | 87 | 12.5 |
| 137 | 79 | 82 | 13.3 |
| 138 | 80 | 47 | 15.7 |
| 139 | 84 | 94 | 12.8 |
| 140 | 85 | 50 | 14.7 |
| 141 | 86 | 93 | 14.2 |
| 142 | 87 | 44 | 15.7 |
| 143 | 88 | 94 | 12.2 |
| 144 | 89 | 82 | 13.8 |

TABLE 2

Analytical and Yield Data for $^{99m}Tc$ (LTB4) (tricine) (TPPDS) and $^{99m}Tc$ (LTB4) (tricine) (TPPMS) Complexes Using the Reagent of Example 1

| Complex Ex. No. | Phosphine | % Yield | RT (min) |
|---|---|---|---|
| 145 | TPPDS | 96 | 17.7 |
| 146 | TPPMS | 97 | 20.9 |

TABLE 3

Analytical and Yield Data for
$^{99m}$Tc (LTB4) (tricine) (TFP) Complexes

| Complex Ex. No. | Reagent Ex. No. | % Yield | RT (min) |
|---|---|---|---|
| 147 | 15 | 70 | 19.6 |
| 148 | 33 | 62 | 19.5 |
| 149 | 34 | 75 | 18.7 |
| 150 | 79 | 75 | 18.1 |

TABLE 4

HPLC and Yield Data $^{99m}$Tc (LTB4) (tricine) (L)
Complexes (L = Imine-Nitrogen Containing Heterocycle)

| Complex Ex. No. | Reagent Ex. No. | Imine Ligand (L) | % Yield | RT (min) |
|---|---|---|---|---|
| 151 | 1 | A | 75 | 16.7 |
| 152 | 14 | A | 90 | 16.6 |
| 153 | 14 | B | 88 | 17.1 |
| 154 | 15 | B | 57 | 13.8 |
| 155 | 15 | C | 89 | 14.5 |
| 156 | 15 | D | 28 | 13.8 |
| 157 | 15 | A | 67 | 14.8 |
| 158 | 15 | E | 64 | 16.0 |
| 159 | 15 | F | 25 | 15.6 |
| 160 | 15 | G | 62 | 16.1 |
| 161 | 15 | H | 86 | 17.5 |
| 162 | 15 | I | 66 | 14.8 |
| 163 | 21 | A | 64 | 13.9 |
| 164 | 34 | H | 71 | 16.4 |

Imine-nitrogen Containing Coligands, L
A 3-pyridinesulfonic acid
B 3,5-pyridinedicarboxylic acid
C Isonicotinic acid
D Nicotinic acid
E Hydroxyyethylisonicotinamide
F 4-Methyl-5-imidazolemethanol
G 4-Methyl-5-thiazoleethanol
H pyridine
I 4-pyridylethylsulfonic acid

TABLE 5

Analytical and Yield Data for $^{99m}$TcO (LTB4) Complexes

| Complex Ex. No. | Reagent Ex. No. | % Yield | RT (min) |
|---|---|---|---|
| 165 | 9 | 80 | 16.0 |
| 166 | 55 | 81 | 13.9 |

Reported retention times are the average of the two diastereomeric complexes when resolvable.

Example 167

2-({2-[((2S)-2-[Bis(carboxymethyl)amino]-3-{4-[({
[3-(2-{2-[3-(5-{5-[5-(4,6-diphenyl(2-pyridyloxy))-1,
1-dimethylpentyl](5H-1,2,3,4-tetraazolyl)}
pentanoylamino)propoxy]ethoxy}ethoxy)propyl]
amino}thioxomethyl)amino]phenyl}propyl)
(carboxymethyl)amino]ethyl}(carboxymethyl)
amino)acetic Acid

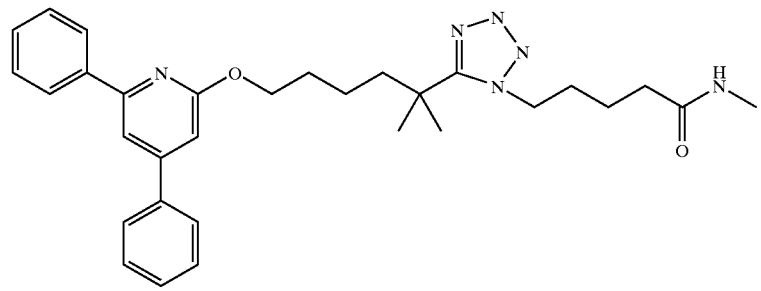

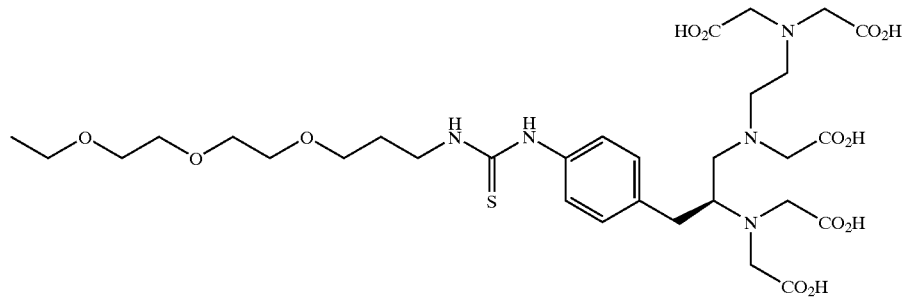

N-(3-(2-(2-(3-((tert-Butoxy)carbonylamino)propoxy) ethoxy)ethoxy)propyl)-5-(4-(5-(4,6-diphenyl(2-pyridyloxy))-1,1-dimethylpentyl)(1,2,3,5-tetraazolyl)) pentanamide (80 mg, 0.098 mmol) was dissolved in 50/50 TFA/DCM and allowed to stand at ambient temperatures under nitrogen for 10 min. The TFA was removed under reduced pressure and the resulting thick oil was dissolved in anhydrous DMF (3.0 mL) and the solution was made basic to pH paper with DIEA (87 µL, 0.50 mmol). The solution was treated with 2-{[2-({(2S)-2-[bis(carboxymethyl) amino]-3-(4-isothiocyanatophenyl)propyl}- (carboxymethyl)amino)ethyl](carboxymethyl)amino}acetic acid (63.4 mg, 0.117 mmol) and stirred at ambient temperatures for 18 h. Additional isothiocyanate (30.0 mg, 0.056 mmol) was added and stirring was continued an additional 5 h. The DMF was removed under vacuum, and the resulting oil was dissolved in 50/50 0.01 M NH4O ac, pH 7.0/ACN and purified by preparative HPLC on a Varian Microsorb C-18, 8 micron particle size column (41.4×250 mm) using a 1.0%/min gradient of 10 to 50% ACN containing 0.01 M NH4Oac, pH 7.0 at a flow rate of 80 mL/min. The main product peak eluting at 30.0 min was collected and lyophilized to give the title compound as a colorless powder (27.5 mg, 22.3%). MS: 1256.4 [M+H], 628.9 [M+2H].

Example 168

Approximately 5–20 mCi of one of the Tc99m labeled LTB4-targeted compounds of examples 90–166 is administered to a mammal 5–60 minutes following reperfusion of an ischemic territory of the heart (e.g. following angioplasty of an occluded coronary artery) along with the administration of 2–4 mCi of Tl-201. Allowing 5–60 minutes for adequate blood clearance an image is acquired detecting principally the 70–80 keV photons of Tl-201 and the 140 keV photons of Tc99m. Following spectral separation and color coding the simultaneous display of the two isotope images provides a scintigram of both the cardiac perfusion (Tl-201) and cardiac inflammation (Tc99m-LTB4 reagent) images in one display.

Example 169

Approximately 2–5 mCi of an In-111 labeled LTB4-targeted compound of Example 167 is administered to a mammal having active inflammatory atherosclerosis in the heart (e.g in a patient with acute coronary disease) along with the administration of 10–30 mCi of Tc-99m-Sestamibi. Allowing 15–120 minutes for adequate blood clearance an image is acquired with the camera detecting principally the 160 and 250 keV photons of In-111, and the 140 keV photons of Tc99m. The simultaneous imaging of the In-111 labeled LTB4 antagonist and Tc99m perfusion agent is carried out by a method such as that reported by White (White, S A, Mueller, D H, Smith H E, et al. J Nucl Med Tech 1984, 12: 124–125) or Hillel (Hillel P G, Tindale W B, Taylor C J, et al. Nucl Med Commun 1998, 19, 761–769). The images are displayed side-by-side or are overlayed to faciliate interpretation of the $^{111}$In-LTB4 antagonist localization in the heart in relation to the $^{99m}$Tc perfusion agent distribution in the heart.

Utility

The radiopharmaceuticals of this invention are useful for imaging sites of infection and/or inflammation in mammals. The reagents of this invention are useful in the treatment of diseases associated with infection and inflammation. Representative compounds were tested in the in vitro and in vivo tests described below and found to be active.

LTB4 Human Neutrophil (PMN) Binding Assay

Heparinized blood was placed on a ficol gradient followed by its sedimentation with dextran. This resulted in preparations containing >95% neutrophils (PMN). The PMN solution was adjusted to achieve a concentration of $8 \times 10^6$ PMN/ml. In this assay the test agent will actively compete with 3[H] LTB4 for the PMN LTB4 receptor. Very briefly, the assay was performed as follows; [3H]LTB4 (1 nM) and test agent were placed into a 96 well microplate with filters (0.65 µm pore size). PMN solution ($8 \times 10^6$/ml) was added and the microplate incubated for 10 min at 4° C. The microplate was then placed on Millipore filtration system; the wells washed with cold saline (3×) and dried. The filters were removed from the microplate; placed into scintillation fluid and the concentration of [3H]LTB4 determined.

The compounds of Examples 1–89 were tested in this assay and all were found to be active.

Guinea Pig Focal Infection Model

The function of the model is to rapidly assess an agent's ability to detect inflammation/infection as well as determine the biodistribution. Very briefly, the procedure was as follows: A #10 trochar needle was used to introduce a piece of umbilical tape immersed in a 6% sodium caseinate solution into the right flank and placed on the left side of the peritoneal cavity of anesthetized guinea pigs. The placement of the immersed string served as the focal site for white blood cell recruitment over the next eighteen hours. Eighteen hours later the guinea pigs were anesthetized and the test agent administered via the lateral saphenous vein. At the appropriate time postinjection, the animals were euthanized and the focal uptake determined. Throughout the course of the study blood was withdrawn via cardiac puncture. Uptake and target/background ratios were determined via well counting.

The radiopharmaceuticals of Examples 90, 92–95, 97, 99, 100, 102, 106–118, 126, 130, 133–134, 137 –141, 143 and 166 were evaluated in this model and all were found to have focal uptake at the site of the sterile inflammation ranging from 0.1 to 2.1%i.d./g.

Rabbit Focal Infection Model

The function of the model is to rapidly assess an agent's ability to detect inflammation/infection via scintigraphy as well as determine the biodistribution. The protocol takes place over 2 days and is comprised of induction of an infection, imaging, followed by a biodistribution. Very briefly, the procedure was as follows: On day 1, $2 \times 10^9$ colonies of *E.coli* was administered intramuscularly in the thigh to anesthetized rabbits. The infection was permitted to fulminate for 24 hrs prior to the intravenous administration of the test agent. Prior to the administration of the test agent, the animal was anesthetized, intubated and monitored to assess arterial pressure and heart rate and hematology. Anterior 5 min serial images were performed over a 4 hr period. At the end of the protocol the animal was euthanized with a pentobarbital overdose and the uptake of the test agent in various organs assessed via well counting.

The radiopharmaceuticals of Examples 90, 93, 94, 97, 99, 100, 102, 107, 108, 113, 114, 118, 127, 129, 130, 133, 137, 140, and 157 were evaluated in this model and all were found to give a target-to-background ratio (infection site to contralateral muscle regions of interest) of ranging from 1.3 to 15.9.

Dosage and Formulation

The anti-infection and anti-inflamation compounds of this invention can be administered as treatment for infection and inflamation by any means that produces contact of the active agent with the agent's site of action. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

We claim:

1. A method of concurrent imaging in a mammal comprising:
   a) administering to said mammal a radiolabeled LTB4 binding agent and a radiolabeled perfusion imaging agent; and
   b) concurrently detecting the radiolabeled LTB4 binding agent bound at the LTB4 receptor and the radiolabeled perfusion imaging agent;
   wherein said radiolabeled agents have spectrally separable energies.

2. The method according to claim 1, for use in concurrent imaging sites of inflammation and organ perfusion.

3. The method according to claim 1, for use in diagnosing and localizing sites of inflammation and perfusion abnormalities.

4. The method according to claim 1, for use in concurrent detection and localization of sites of ischemic tissue injury and perfusion abnormalities.

5. The method according to claim 1, for use in concurrent detection and localization of sites of ischemic tissue injury, vulnerable plaque, bacterial endocarditis or cardiac transplant rejection.

6. The method according to claim 1, for use in the concurrent detection and localization of sites of vulnerable plaque and perfusion abnormalities.

7. The method according to claim 1, for use in the concurrent detection and localization of sites of cardiac infection and perfusion abnormalities.

8. The method according to claim 1, for use in the concurrent detection and localization of sites of cardiac transplant rejection and perfusion abnormalities.

9. The method according to claim 1, wherein the method of detecting the radiolabeled agents is by scintigraphic imaging.

10. The method according to claim 1, wherein the method of detecting the radiolabeled agents is by radiation detecting probe.

11. The method according to claim 1, wherein the method of detecting the radiolabeled agents is by planar or ring gamma camera.

12. The method according to claim 1, wherein administering said radiolabeled LTB4 binding agent and radiolabeled perfusion imaging agent is concurrent.

13. The method according to claim 1, wherein administering said radiolabeled LTB4 binding agent and radiolabeled perfusion imaging agent is sequential.

14. The method according to claim 1, wherein the radiolabeled LTB4 binding agent is administered in a synergystically effective amount.

15. The method according to claim 1, wherein said concurrent detection of the radiolabeled LTB4 binding agent and the radiolabeled perfusion imaging agent provides improved accuracy of the image registration, as compared to serial or sequential imaging of radiolabeled LTB4 binding agent and a radiolabeled perfusion imaging agent.

16. The method according to claim 1, wherein the energies of the radiolabeled agents are spectrally separable by pulse-height analysis.

17. The method according to claim 1, wherein the difference in spectral energies of the radiolabeled agents is >10 Kev.

18. The method of claim 1 wherein the radiolabeled LTB4 binding agent is radiolabeled with a radioisotope selected from the group consisting of $^{99m}$Tc, $^{111}$In, $^{95}$Tc, $^{62}$Cu, $^{67}$Ga, $^{68}$Ga, $^{123}$I, $^{125}$I, $^{18}$F, $^{11}$C, $^{13}$N, $^{15}$O, and $^{75}$Br.

19. The method of claim 1 wherein the LTB4 binding agent is radiolabeled with In-111, Tc-99m or I-123.

20. The method of claim 1 wherein the perfusion imaging agent is radiolabeled with Tc-99m or Tl-201.

21. The method of claim 1 wherein the perfusion imaging agent is hexakis methoxyisobutyl isonitrile Technetium(I) ($^{99m}$Tc-Sestamibi), $^{210}$Tl, $^{99m}$Tc-tetrofosmin, $^{99m}$Tc-furifosmin, or $^{99m}$Tc-NOET.

22. A method according to claim 1, wherein the radiolabeled LTB4 binding agent is reagent which undergoes direct transformation into a compound radiolabeled with a radioisotope selected from the group consisting of $^{99m}$Tc, $^{111}$In, $^{95}$Tc, $^{62}$Cu, $^{67}$Ga, and $^{68}$Ga and said reagent having the formula:

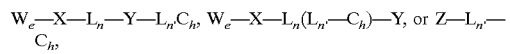

wherein, $W_e$ is selected from the group:

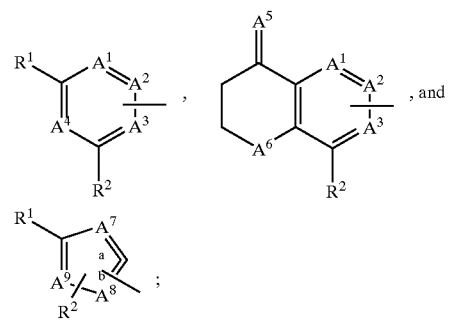

wherein, $A^1$ is N, C—OH, or CH;

$A^2$ and $A^3$ are i dependently N or CH;

$A^4$ is N or $CR^3$;

$A^5$ is O or S $A^6$ is O, $CH_2$ or S;

$A^7$ is C—OH, N, NH, O or S;

$A^8$ is NH, $CH_2$, O, S, N, or CH;

$A^9$ is N or CH;

a and b indicate the alternative positions of a double bond;

$R^1$ is selected f m the group: H, —C(=NH)NH$_2$, $C_1$–$C_6$ alkyl substituted with 0–3 $R^4$, $C_1$–$C_6$ alkoxy substituted with 0–3 $R^4$, aryl substituted with 0–3 $R^5$, and heterocycle substituted with 0–3 $R^5$;

$R^2$ is selected m the group: H, $C_1$–$C_3$ alkyl, $C_2$–$C_3$ alkenyl, cyclopropyl, cyclopropylmethyl, and aryl substituted with 0–3 $R^5$;

$R^3$ is —H, —OH or $C_1$–$C_3$ alkoxy;

or alternatively $R^1$ and $R^3$ can be taken together with the atoms to which they are attached to form a fused phenyl ring substituted with 0–3 $R^5$;

$R^4$ is independently selected from the group: —F, —Cl, —Br, —I, =O, —N($R^6$)($R^7$), and —CF;

$R^5$ is independently selected from the group: —F, —Cl, —Br, —I, —N($R^6$)($R^7$), —CF$_3$, $C_1$–$C_3$ alkyl, $C_1$–$C_3$ alkoxy, and methylenedioxy;

$R^6$ and $R^7$ are independently H or $C_1$–$C_3$ alkyl;

provided that when $A^1$ and $A^2$ are CH, $A^3$ is C—X, and $A^4$ is $CR^3$, $R^1$ is selected from the group: $C_1$–$C_5$ alkyl substituted with 1–3 $R^4$, $C_1$–$C_5$ alkoxy substituted with 0–3 $R^4$, and aryl substituted with 0–3 $R^5$;

X is O, S, $CH_2$ or CH=CH;

$L_n$ is a linking group having the formula

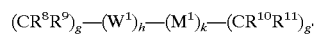

wherein,

R[8], R[9], R[10] an R[11] are independently selected at each occurrence from the group: bond to $L_{n'}$, H, $C_1$–$C_5$ alkyl, and $C_1$–$C_5$ alkoxy, or alternatively, R[8] and R[9] or R[10] and R[11] may be taken together to form a 3–6 membered cycloalkyl or heterocycle;

W[1] is independently selected from the group: O, S, C(=O)O, OC(=O), CH=CH, $(OCH_2CH_2)_p$ and $(CH_2CH_2O)_{p'}$, wherein p and p' are independently 1–3;

M[1] is selected from the group:
  phenyl substituted with 0–3 R[12], heterocycle substituted with 0–3 R[12], benzophenone substituted with 0–3 R[12], and diphenylether substituted with 0–3 R[12];

R[12] is independently selected from the group: a bond to $L_{n'}$, —COOR[13], $C_1$–$C_5$ alkyl substituted with 0–3 R[14], and $C_1$–$C_5$ alkoxy substituted with 0–3 R[14];

R[13] is H or $C_1$–$C_5$ alkyl;

R[14] is independently selected from the group: a bond to $L_{n'}$, and —COOH;

g is 0–10;
h is 0–3,
k is 0–1;
g' is 0–5;
  provided that when h is 0 and k is 0, g is >1;
  and provided that when W[1] is O or S and k is 0, g+g' is ≧1;

Y is selected from C(=O)NH, NHC(=O), C=O, C(=O)O, OC(=O), NHS(=O)$_2$, C(=O)NHS(=O)$_2$, COOH, C(=O)NH$_2$, NH(C=O)NH, or tetrazole;

provided that from 0–1 of R[9], R[10], R[11], R[12], and R[14] is a bond to $L_{n'}$ and when one of these variables is a bond to $L_{n'}$, then Y is COOH, C(=O)NH$_2$, or tetrazole;

$L_{n'}$ is a linking group having the formula:

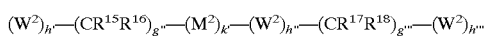

wherein,

W[2] is independently selected at each occurrence from the group: O, S, NH, NHC(=O), NHC(=O)M[2], C(=O)NH, C(=O), C(=O)O, OC(=O), NHC(=O)NH, SO$_2$, $(OCH_2CH_2)_s$, $(CH_2CH_2O)_{s'}$, $(OCH_2CH_2CH_2)_{s''}$, $(CH_2C_2CH_2O)_t$, and $(aa)_{t'}$, wherein aa is independently at each occurrence an amino acid, and s, s', s", t, and t' are independently 1–10;

M[2] is selected from the group: aryl substituted with 0–3 R[19], cycloalkyl substituted with 0–3 R[19], and heterocycle substituted with 0–3 R[19];

R[15], R[16], R[17] and R[18] are independently selected at each occurrence from the group: =O, COOH, SO$_3$H, PO$_3$H, $C_1$–$C_5$ alkyl substituted with 0–3 R[19], aryl substituted with 0–3 R[19], benzyl substituted with 0–3 R[19], and $C_1$–$C_5$ alkoxy substituted with 0–3 R[19], NHC(=O)R[20], C(=O)NHR[20], NHC(=O)NHR[20], NHR[20], R[20], and a bond to $C_h$;

R[19] is independently selected at each occurrence from the group: COOR[20], OH, NHR[20], SO$_3$H, PO$_3$H, aryl substituted with 0–3 R[20], heterocycle substituted with 0–3 R[20], $C_1$–$C_5$ alkyl substituted with 0–1 R[21], $C_1$–$C_5$ alkoxy substituted with 0–1 R[21], and a bond to $C_h$;

R[20] is independently selected at each occurrence from the group: H, aryl substituted with 0–1 R[21], heterocycle substituted with 0–1 R[21], cycloalkyl substituted with 0–1 R[21], polyalkylene glycol substituted with 0–1 R[21], carbohydrate substituted with 0–1 R[21], cyclodextrin substituted with 0–1 R[21], amino acid substituted with 0–1 R[21], polycarboxyalkyl substituted with 0–1 R[21], polyazaalkyl substituted with 0–1 R[21], peptide substituted with 0–1 R[21], wherein said peptide is comprised of 2–10 amino acids, and a bond to $C_h$;

R[21] is a bond to $C_h$;

k' is 0–2;
h' is 0–2;
h" is 0–5;
h'" is 0–2;
g" is 0–10;
g'" is 0–10;

$C_h$ is a metal bonding unit having a formula selected from the group:

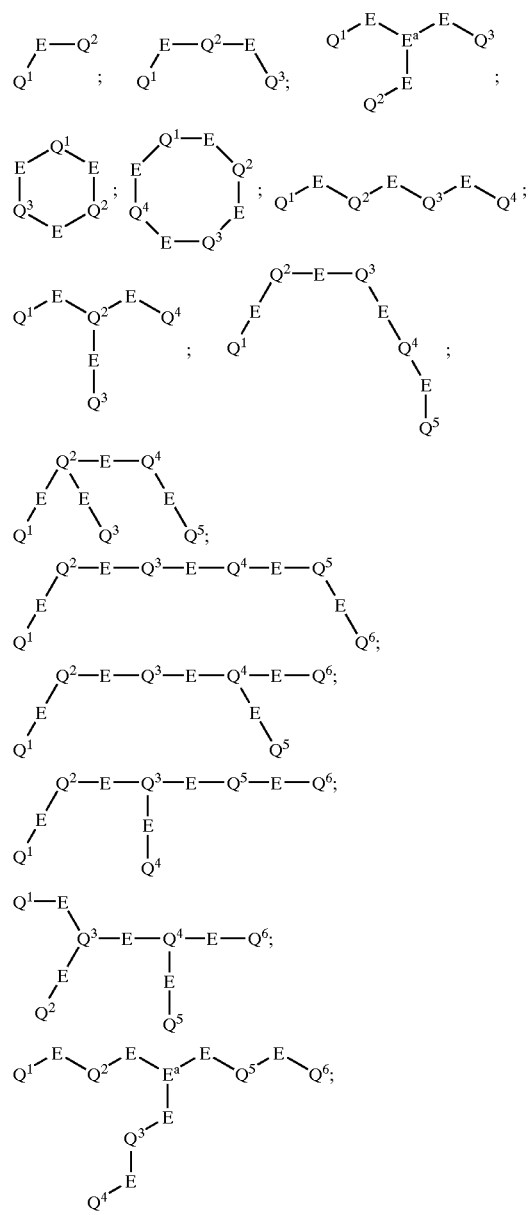

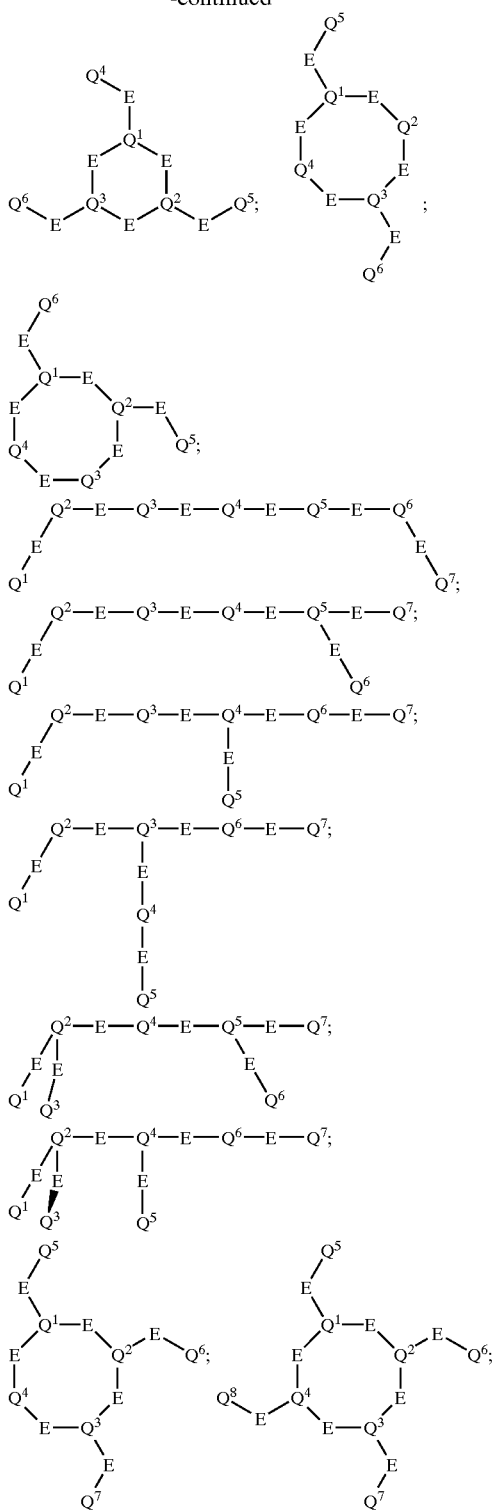

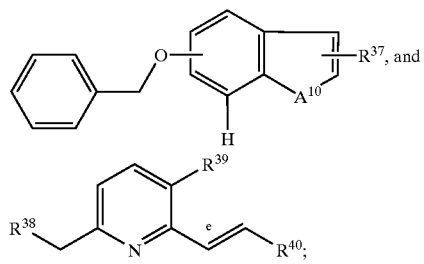

wherein:

$Q^1$, $Q^2$, $Q^3$, $Q^4$, $Q^5$, $Q^6$, $Q^7$, and $Q^8$ are independently selected at each occurrence from the group: $NR^{22}$, $NR^{22}R^{23}$, S, SH, O, OH, $PR^{22}$, $PR^{22}R^{23}$, $P(NR^{24})R^{25}R^{26}$, $P(O)R^{25}R^{26}$, and $P(S)R^{25}R^{26}$;

E is a bond, CH, or a spacer group selected from the group: $C_1$–$C_{10}$ alkyl substituted with 0–3 $R^{27}$, aryl substituted with 0–3 $R^{27}$, cycloalkyl substituted with 0–3 $R^{27}$, heterocycloalkyl substituted with 0–3 $R^{27}$, aralkyl substituted with 0–3 $R^{27}$, and alkaryl substituted with 0–3 $R^{27}$;

$E^a$ is a $C_1$–$C_{10}$ alkyl group or a $C_3$–$C_{14}$ carbocycle;

$R^{22}$, $R^{23}$, and $R^{24}$ are each independently selected from the group: a bond to $L_{n''}$, hydrogen, $C_1$–$C_{10}$ alkyl substituted with 0–3 $R^{27}$, aryl substituted with 0–3 $R^{27}$, cycloalkyl substituted with 0–3 $R^{27}$, heterocycloalkyl substituted with 0–3 $R^{27}$, aralkyl substituted with 0–3 $R^{27}$, alkaryl substituted with 0–3 $R^{27}$, heterocycle substituted with 0–3 $R^{27}$, and an electron, provided that when one of $R^{22}$ or $R^{23}$ is an electron, then the other is also an electron;

$R^{25}$ and $R^{26}$ are each independently selected from the group: a bond to $L_{n''}$, —OH, $C_1$–$C_{10}$ alkyl substituted with 0–3 $R^{27}$, $C_1$–$C_{10}$ alkyl substituted with 0–3 $R^{27}$, aryl substituted with 0–3 $R^{27}$, cycloalkyl substituted with 0–3 $R^{27}$, heterocycloalkyl substituted with 0–3 $R^{27}$, aralkyl substituted with 0–3 $R^{27}$, alkaryl substituted with 0–3 $R^{27}$, and heterocycle substituted with 0–3 $R^{27}$;

$R^{27}$ is independently selected at each occurrence from the group: a bond to $L_{n'}$, =O, F, Cl, Br, I, —$CF_3$, —CN, —$CO_2R^{28}$, —C(=O)$R^{28}$, —C(=O)N($R^{28}$)$_2$, —CHO, —$CH_2OR^{28}$, —OC(=O)$R^{28}$, —OC(=O)O$R^{28a}$, —O$R^{28}$, —OC(=O)N($R^{28}$)$_2$, —$NR^{29}$C(=O)$OR^{28}$, —$NR^{29}$C(=O)$OR^{28a}$, —$NR^{29}$C(=O)N($R^{28}$)$_2$, —$NR^{29}SO_2$N($R^{28}$)$_2$, —$NR^{29}SO_2R^{28a}$, —$SO_3H$, —$SO_2R^{28a}$, —$SR^{28}$, —S(=O)$R^{28a}$, —$SO_2$N($R^{28}$)$_2$, —N($R^{28}$)$_2$, —NHC(=NH)$NHR^{28}$, —C(=NH)$NHR^{28}$, =$NOR^{28}$, $NO_2$, —C(=O)$NHOR^{28}$, —C(=O)$NHNR^{28}R^{28a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{28}$, and a 5–10-membered heterocyclic ring system containing 1–4 heteroatoms independently selected from N, S, and O;

$R^{28}$, $R^{28a}$, and $R^{29}$ are independently selected at each occurrence from the group: a bond to $L_{n'}$, H, $C_1$–$C_6$ alkyl, phenyl, benzyl, $C_1$–$C_6$ alkoxy, halide, nitro, cyano, and trifluoromethyl;

Z is selected from the group:

wherein, $A^{10}$ is $NR^{41}$ or —C($R^{41}$)=CH—;

$R^{37}$ is selected from the group: C(=O)—$R^{42}$, CH=$CR^{43}$C(=O)—$R^{42}$, $CH_2$C(=O)—$R^{42}$, and $CH_2CH_2$C(=O)—$R^{42}$;

$R^{38}$ is selected from the group: $SR^{44}$, $SCH_2R^{44}$, and S(=O)$R^{44}$; $R^{39}$ is selected from the group: $C_1$–$C_{10}$ alkyl substituted with 0–3 $R^{44}$, and $C_1$–$C_{10}$ alkoxy substituted with 0–3 $R^{44}$;

$R^{40}$ is C(=O)—$R^{42}$;

$R^{41}$ is $CH_2$C(=O)N($CH_3$)$CH_2CH_2C_6H_5$;

$R^{42}$ is a bond to $L_{n'}$;

$R^{43}$ is selected from the group: H and $C_1$–$C_3$ alkyl $R^{44}$ is phenyl substituted with 0–4 $R^{45}$;

$R^{45}$ is independently selected at each occurrence from the group: $C_1$–$C_4$ alkyl $OR^{46}$, $C(=O)OR^{46}$, —Cl, —Br, —F, and $N(R^{46})_2$;

$R^{46}$ is independently selected at each occurrence from the group: H, and $C_1$–$C_{10}$ alkyl; and e indicates the position of an optional double bond; and pharmaceutically acceptable salts thereof.

23. A method according to claim 22 wherein:

$W_e$ is selected from the group:

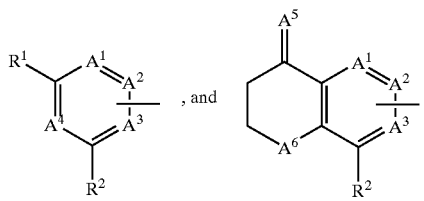

wherein, $A^1$ is N, C—OH, or CH;

$A^2$ and $A^3$ are CH;

$A^4$ is $CR^3$;

$A^5$ is O;

$A^6$ is O or $CH_2$;

$R^4$ is independently selected from the group:
—F, —Cl, =O, —N($R^6$)($R^7$), and —$CF_3$;

$R^5$ is independently selected from the group:
—F, —Cl, —$CF_3$, $C_1$–$C_3$ alkyl, $C_1$–$C_3$ alkoxy, and methylenedioxy;

X is O, $CH_2$ or CH=CH;

$R^8$, $R^9$, $R^{10}$ and $R^{11}$ are independently selected at each occurrence from the group: a bond to $L_{n'}$, H, $C_1$–$C_5$ alkyl, and $C_1$–$C_5$ alkoxy;

or alternatively, $R^8$ and $R^9$ or $R^{10}$ and $R^{11}$ may be taken together to form a 3–6 membered cycloalkyl;

$C_h$ is selected from the group:

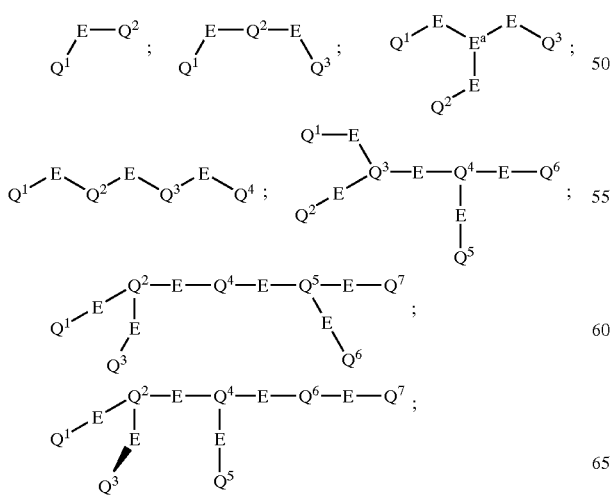

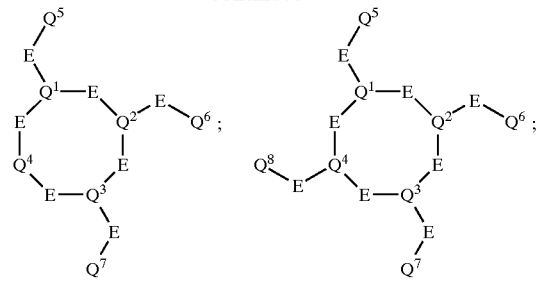

wherein:

$Q^1$, $Q^2$, $Q^3$, $Q^4$, $Q^5$, $Q^6$, $Q^7$, and $Q^8$ are independently selected at each occurrence from the group: $NR^{22}$, $NR^{22}R^{23}$, S, SH, OH;

E is a bond, CH, or a spacer group selected from the group: $C_1$–$C_{10}$ alkyl substituted with 0–3 $R^{27}$, aryl substituted with 0–3 $R^{27}$, cycloalkyl substituted with 0–3 $R^{27}$, and heterocycle substituted with 0–3 $R^{27}$;

$E^a$ is CH or a $C_3$–$C_6$ carbocycle;

$R^{22}$ and $R^{23}$ are each independently selected from the group: a bond to $L_{n'}$, hydrogen, $C_1$–$C_{10}$ alkyl substituted with 0–3 $R^{27}$, aryl substituted with 0–3 $R^{27}$, heterocycle substituted with 0–3 $R^{27}$, and an electron, provided that when one of $R^{22}$ or $R^{23}$ is an electron;

$R^{27}$ is independently selected at each occurrence from the group: a bond to L, =O, F, Cl, Br, I, —$CF_3$, —CN, —$CO_2R^{28}$, —C(=O)$R^{28}$, —C(=O)N($R^{28}$)$_2$, —$CH_2OR^{28}$, —OC(=O)$R^{28}$, —OC(=O)$OR^{28a}$, —$OR^{28}$, —OC(=O)N($R^{28}$)$_2$, —$NR^{29}$C(=O)$R^{28}$, —$NR^{29}$C(=O)$OR^{28a}$, —$NR^{29}$C(=O)N($R^{28}$)$_2$, —$NR^{29}SO_2N(R^{28})_2$, —$NR^{29}SO_2R^{28a}$, —$SO_3H$, —$SO_2R^{28a}$, —$SR^{28}$, —$SR^{28a}$, —S(=O)$R^{28a}$, —$SO_2N(R^{28})_2$, —N($R^{28}$)$_2$, —NHC(=NH)$NHR^{28}$, —C(=NH)$NHR^{28}$, =$NOR^{28}$, $NO_2$, —C(=O)$NHOR^{28}$, —C(=O)$NHNR^{28}R^{28a}$, —$OCH_2CO_2H$, and 2-(1-morpholino)ethoxy;

$R^{28}$, $R^{28a}$, and $R_{29}$ are independently selected at each occurrence from the group: a bond to $L_{n'n'}$, H, and $C_1$–$C_6$ alkyl;

$R^{39}$ is selected from the group: $C_1$–$C_{10}$ alkyl substituted with 0–1 $R^{44}$, and $C_1$–$C_{10}$ alkoxy substituted with 0–1 $R^{44}$;

$R^{43}$ is H; and $R^{46}$ is independently selected at each occurrence from the group: H, and $C_1$–$C_5$ alkyl.

24. A reagent of claim 22, wherein:

$R^1$ is selected from the group:
H, —C(=NH)$NH_2$, $C_1$–$C_6$ alkyl substituted with 0–2 $R^4$, $C_1$–$C_6$ alkoxy substituted with 0–2 $R^4$, aryl substituted with 0–2 $R^5$, and heterocycle substituted with 0–2 $R^5$;

$R^3$ is —H, —OH or $C_1$–$C_3$ alkoxy;

or alternatively, $R^1$ and $R^3$ can be taken together with the atoms to which they are attached to form a fused phenyl ring substituted with 0–2 $R^5$;

$R^4$ is independently selected from the group:
=O, and —N($R^6$ $R^7$);

$R^5$ is independently selected from the group:
—F, $C_1$–$C_3$ alkyl, $C_1$–$C_3$ alkoxy, and methylenedioxy;

X is O, $CH_2$ or CH=CH;

$R^8$, $R^9$, $R^{10}$ and $R^{11}$ are independently selected at each occurrence from the group: a bond to $L_{n'}$, H, and $C_1$–$C_3$ alkyl;

or alternatively, $R^8$ and $R^9$ or $R^{10}$ and $R^{11}$ may be taken together to form a 3–6 membered cycloalkyl;

$W^1$ is O;

$M^1$ is selected from the group:
phenyl substituted with 0–1 $R^{12}$, heterocycle substituted with 0–1 $R^{12}$, benzophenone substituted with 0–1 $R^{12}$, and diphenylether substituted with 0–1 $R^{12}$;

$R^{12}$ is independently selected from the group: a bond to $L_{n'}$, —COOR$^{13}$, $C_1$–$C_5$ alkyl substituted with 0–1 $R^{14}$, and $C_1$–$C_5$ alkoxy substituted with 0–1 $R^{14}$;

$M^2$ is selected from the group: aryl substituted with 0–1 $R^{19}$, cycloalkyl substituted with 0–3 $R^{19}$, and heterocycle substituted with 0–1 $R^{19}$;

$C_h$ is selected from:

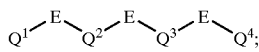

wherein,
$Q^1$ and $Q^4$ are SH;
$Q^2$ and $Q^3$ are $N^{22}$;
E is independently selected from the group: CHR$^{27}$, CH$_2$CHR$^{27}$, CH$_2$CH$_2$CHR$^{27}$, and CHR$^{27}$C(=O);
$R^{22}$ is selected from the group: H, $C_1$–$C_6$ alkyl substituted with 0–1 $R^{27}$; and
$R^{27}$ are independently selected from H and a bond to $L_{n'}$, and,

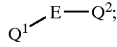

wherein,
E is a bond;
$Q^2$ is NHR$^{23}$, wherein $R^{23}$ is heterocycle substituted with $R^{27}$, wherein the heterocycle is selected from pyridine and thiazole, $R^{27}$ is selected from C(=O)NHR$^{28}$ and C(=O)R$^{28}$, and $R^{28}$ is a bond to $L_{n'}$;
$A^{10}$ is NR$^{41}$;
$R^{39}$ is $C_1$–$C_{10}$ alkoxy substituted with 1 $R^{44}$; and
$R^{45}$ is independently selected at each occurrence from the group: $C_1$–$C_4$ alkyl, OH, C(=O)OH, —Cl, —F, and NH$_2$.

25. The method of claim 22, wherein the reagent is selected from the group:

4-ethyl-2-(4-fluorophenyl)-[5-[5,5-dimethyl-6-[[6-[[[(2-sulfonylphenyl)methylene]hydrazino]-3-pyridinyl]carbonyl]amino]hexyl]oxy]phenol;

4-ethyl-2-(4-fluorophenyl)-[5-[-4-[[6-[[[(2-sulfonylphenyl)methylene]hydrazino]-3-pyridinyl]carbonyl]amino]butyl]oxy]phenol;

2-[[[5-[[(6-[(4,6-diphenyl-2-pyridinyl)oxy]-1-hexanamino]carbonyl]-2-pyridinyl]hydrazono]methyl]-benzenesulfonic acid;

2-[[[5-[[2,2-dimethyl-6-[(6-fluorophenyl-4-phenyl-2-pyridinyl)oxy]-1-hexanamino]carbonyl]-2-pyridinyl]hydrazono]methyl]-benzenesulfonic acid;

2-[[[5-[[N-[6-[(6-(4-fluorophenyl)-4-phenyl-2-pyridinyl)oxy]-hexanoyl]-tyrosine-O-[3-propanamino]]carbonyl]-2-pyridinyl]hydrazono]-methyl]-benzenesulfonic acid;

2-[[[5-[[N-[6-[(4,6-diphenyl-2-pyridinyl)oxy]-hexanoyl]-tyrosine-O-[3-propanamino]]]carbonyl]-2-pyridinyl]hydrazono]-methyl]-benzenesulfonic acid;

2-[[[5-[[N-[6-[(4-(3,4-methylenedioxyphenyl)-6-phenyl-2-pyridinyl)oxy]-hexanoyl]-tyrosine-O-[3-propanamino]]-carbonyl]-2-pyridinyl]hydrazono]-methyl]-benzenesulfonic acid;

2-[[[5-[[alpha-N-[6-[(4,6-diphenyl-2-pyridinyl)oxy]-hexanoyl]-lysine-epsilon-N-amino]carbonyl]-2-pyridinyl]hydrazono]-methyl]-benzenesulfonic acid;

4-ethyl-2-(4-fluorophenyl)-5-[(5,5-dimethyl-6-aminohexyl)oxy]phenol N-[4-(carboxy)benzyl]-N,N'-bis[2-thioethyl]-glycinamide conjugate;

Benzenesulfonic Acid, 2-[[[5-[[[6-[(4,6-diphenyl-2-pyridinyl)oxy]-2,2-dimethyl-1-hexyl]aza]carbonyl]-2-pyridinyl]hydrazono]methyl];

2-[[[5-[[[[6-[(4,6-Diphenyl-2-pyridinyl)oxy]-hexanoyl]-4-sulfonamidyl]benzylamino]carbonyl]-2-pyridinyl]-hydrazono]methyl]-benzenesulfonic acid;

4-ethyl-2-(4-fluorophenyl)-[5-[6,6-dimethyl-7-[[6-[[[(2-sulfonylphenyl)methylene]hydrazino]-3-pyridinyl]carbonyl]amino]heptyl]oxy]phenol;

4-ethyl-2-(5-pyrazolyl)-[5-[5,5 dimethyl-6-[[6-[[[(2-sulfonylphenyl)methylene]hydrazino]-3-pyridinyl]carbonyl]amino]hexyl]oxy]phenol;

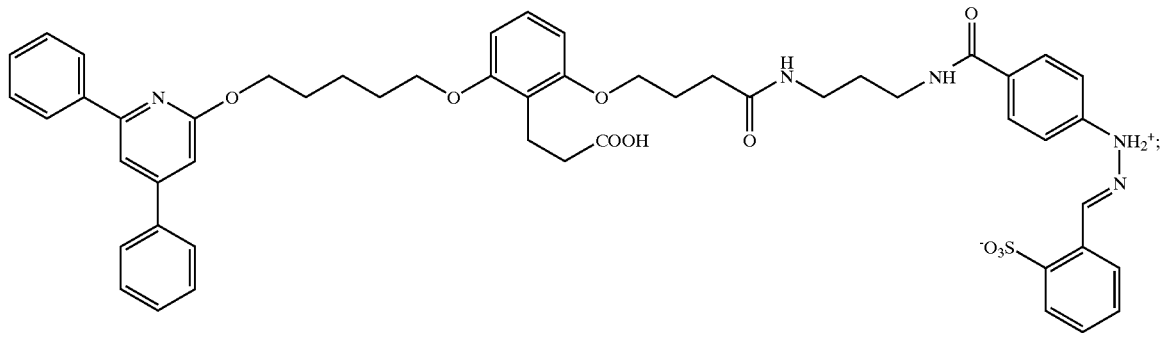

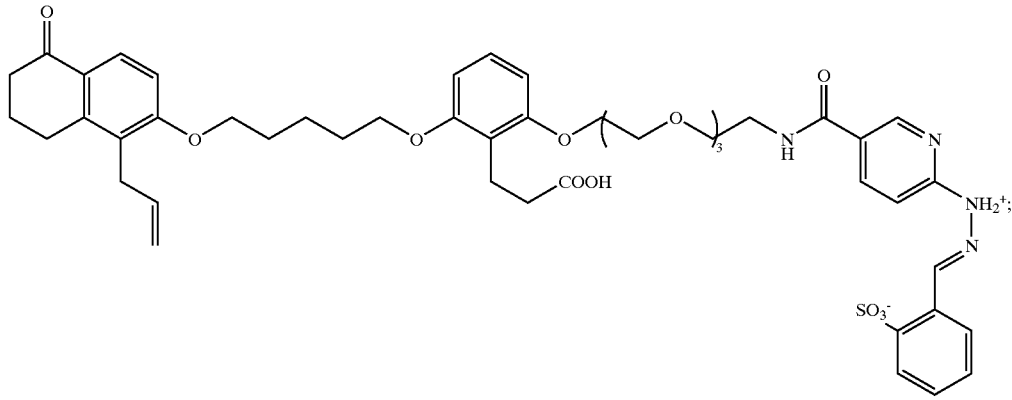

4-ethyl-2-(4-fluorophenyl)-[5-[6,6-dimethyl-7-[[6-[[[phenylmethylene[hydrazino]-3-pyridinyl]carbonyl]amino]heptyl]oxy]phenol;

N-((6-((1-aza-2-phenylvinyl)amino)(3-pyridyl))sulfonyl)-3-(1-((N-(2-phenylethyl)carbamoyl)methyl)-5-(phenylmethoxy)indol-3-yl)prop-2-enamide;

propyl 3-((7-(3-(6-ethyl-4-(4-fluorophenyl)-3-hydroxyphenoxy)propoxy)-8-propylchroman-2-yl)carbonylamino)propanoate, 2-(2-aza-2-((5-carbamoyl(2-pyridyl)amino)vinyl)benzenesulfonic acid;

3-((7-(-(6-ethyl-4-(4-fluorophenyl)-3-hydroxyphenoxy)propoxy)-8-propylchroman-2-yl)carbonylamino)propyl-2-methylpropanoate, 2-(2-aza-2((5-carbamoyl(2-pyridyl)amino)vinyl)-benzenesulfonic acid;

N-(3-((7-(3-(6-ethyl-4-(4-fluorophenyl)-3-hydroxyphenoxy)propoxy)-8-propylchroman-2-yl)carbonylamino)propyl)-2-methylpropanamide, 2-(2-aza-2-((5-carbamoyl(2-pyridyl))amino)vinyl)-benzenesulfonic acid;

2-(2-aza-2-((5-(N-(6-(6-ethyl-3-hydroxy-4-(1-methylpyrazol-5-yl)phenoxy)-2,2-dimethylhexyl)carbamoyl)(2-pyridyl))amino)vinyl)-benzenesulfonic acid;

2-(2-aza-2-((5-(N-(6-(6-ethyl-3-hydroxy-4-(1-methylpyrazol-5-yl)phenoxy)-2,2-dimethylhexyl)carbamoyl)(2-pyridyl))amino)vinyl)-benzenesulfonic acid;

2-(2-aza-2-((5-((3-((6-ethyl-4-(4-fluorophenyl)-3-hydroxyphenoxy)methyl)piperidyl)carbonyl)(2-pyridyl))amino)vinyl)benzenesulfonic acid;

2-(((4-(N-(6-(4,6-Diphenyl(2-pyridyloxy))-2,2-dimethylhexyl)carbamoyl)phenyl)methyl)(2-sulfanylethyl)amino)-N-(2-sulfanylethyl)ethanamide;

2-(2-Aza-2-((5-(N-(3-(2-(2-(3-(5-(4-(5-(4,6-diphenyl(2-pyridyloxy))-1,1-dimethylpentyl)(1,2,3,5 tetraazolyl))pentanoylamino)propoxy)ethoxy)ethoxy)propyl)-carbamoyl) (2-pyridyl))amino)vinyl)-benzenesulfonic Acid;

2-(2-Aza-2-((5-(N-(3-(2-(2-(3-5-(5-(4,6-diphenyl(2-pyridyloxy))-1,1-dimethylpentyl)(1,2,3,4-tetraazolyl))pentanoylamino) propoxy)ethoxy)ethoxy propyl)carbamoyl)(2-pyridyl))amino)vinyl)benzenesulfonic Acid;

2-(2-Aza-2-((5-(N-(2-(2-(2-(2-(2-(2-(2-(2-(5-(4-(5-(4,6-diphenyl(2-pyridyloxy))-1,1-dimethylpentyl) (1,2,3,5-tetraazolyl))pentanoylamino)-ethoxy)ethoxy)ethoxy)ethoxy)-ethoxy) ethoxy)ethoxy)ethyl)carbamoyl)(2-pyridyl))amino)vinyl)benzenesulfonic Acid;

2-(2-Aza-2-((5-(N-(5-(4-(5-(4,6-diphenyl(2-pyridyloxy))-1,1-dimethylpentyl)(1,2,3,5-tetraazolyl))-pentanoylamino)-1-(6-deoxy-β-cyclodextryl)carbamoyl)pentyl)carbamoyl)(2-pyridyl))amino)vinyl)benzenesulfonic Acid;

2-(2-Aza-2-((5-(N-(3-(2-(2-(3-(2-(5-(5-(4,6-diphenyl(2-pyridyloxy))-1,1-dimethylpentyl) (1,2,3,4-tetraazolyl))acetylamino)propoxy)ethoxy)ethoxy)propyl)carbamoyl)(2-pyridyl))amino)vinyl)-benzenesulfonic Acid;

2-(2-Aza-2-((5-(N-(3-(2-(2-(3-(2-(4-(5-(4,6-diphenyl(2-pyridyloxy))-1,1-dimethylpentyl)(1,2,3,5-tetraazolyl))acetylamino)propoxy)ethoxy)ethoxy)propyl)-carbamoyl) (2-pyridyl))amino)vinyl)-benzenesulfonic Acid;

3-(6-(3-(N-(5-((6-((1-Aza-2-(sulfophenyl)vinyl)amino)(3-pyridyl))carbonylamino)-5-(N-(□-methoxypolyethylene(750)glycoxyethyl)carbamoyl)pentyl)carbamoyl)propoxy)2-(5-(4,6-diphenyl(2-pyridyloxy))pentyloxy)phenyl)propanoic Acid;

3-(6-(3-(N-(3-(2-(2-(3-((6-((1-Aza-2-(2-sulfophenyl)vinyl)amino)(3-pyridyl))carbonylamino)-propoxy)ethoxy)ethoxy)propyl)carbamoyl)propoxy)2-(5-(4,6-diphenyl(2-pyridyloxy))pentyloxy)-phenyl)propanoic Acid;

3-(6-(3-(N-(5-((6-((1-Aza-2-(2 sulfophenyl)vinyl)amino)-(3-pyridyl))carbonylamino)-5-(N-(2,3,4,5,6-pentahydroxyhexyl)carbamoyl)-pentyl)carbamoyl)propoxy)2-(5-(4,6-diphenyl(2-pyridyloxy))pentyloxy)phenyl)propanoic Acid;

3-(6-(3-(N-(3-((6-((1-Aza-2-(2 sulfophenyl)vinyl)amino)-(3-pyridyl))carbonylamino)propyl)carbamoyl)-propoxy)-2-(5-(5-oxo-1-prop-2-enyl(2-6,7,8-trihydronaphthyloxy))pentyloxy)phenyl)propanoic Acid;

3-(6-(3-N-(2-(2-(2-(2-(2-(2-(2-(2-((6-((1-Aza-2-(2-sulfophenyl)vinyl)amino)(3-pyridyl))carbonylamino-ethoxy)ethoxy)ethoxy)ethoxy)ethoxy)-ethoxy)ethoxy)ethyl)carbamoyl)propoxy)-2-(5-(5-oxo-1-prop-2-enyl(2-6,7,8-trihydronaphthyloxy))-pentyloxy)phenyl)propanoic Acid;

3-(6-(3-N-(5-((6-((1-Aza-2-(2-sulfophenyl)vinyl)amino)(3-pyridyl))carbonylamino)-5-(N-(2,3,4,5,6-pentahydroxyhexyl)carbamoyl)-pentyl)carbamoyl)propoxy-2-(5-(5-oxo-1-prop-2-enyl(2-6,7,8-trihydronaphthyloxy))-pentyloxy)phenyl)propanoic Acid;

3-(6-(3-N-(5-((6-((1-Aza-2-(2-sulfophenyl)vinyl)amino)
(3-pyridyl))carbonylamino)-5-(N-(6-deoxy-☐-
cyclodextryl)carbamoyl)-pentyl)carbamoyl)propoxy-
2-(5-(5-oxo-1-prop-2-enyl(2-6,7,8-
trihydronaphthyloxy))-pentyloxy)phenyl)propanoic
Acid;

3-(6-(3-(N-(3-((6-((1-Aza-2-(2 sulfophenyl)vinyl)
amino)-(3-pyridyl))-Gly-Lys-Lys-Lys)aminopropyl)-
carbamoyl)propoxy)-2-(5-(5-oxo-1-prop-2-enyl(2-6,7,
8-trihydronaphthyloxy))-pentyloxy)phenyl)propanoic
Acid;

2-Sulfobenzaldehyde (E)-N-[3-(6-Hydrazinonic-
otinamido)-propyl]-3-[6-[[(2,6-dichlorophenyl)thio]
methyl]-3-(2-phenylethoxy)-2-pyridinyl]-2-
propenamide Hydrazone;

2-Sulfobenzaldehyde (E)-N-[3-(6-Hydrazinonic-
otinamido)-propyl]-3-[6-[(phenylthio)methyl]-3-(2-
phenylethoxy)-2-pyridinyl]-2-propenamide Hydra-
zone;

2-Sulfobenzaldehyde (E)-N-[3-(6-Hydrazinonic-
otinamido)-propyl]-3-[6-[[(2-chlorophenyl)thio]
methyl]-3-(2-phenylethoxy)-2-pyridinyl]-2-
propenamide Hydrazone;

2-Sulfobenzaldehyde (E)-N-[3-(6-Hydrazinonic-
otinamido)-propyl]-3-[6-[[(2,6-dimethylphenyl)thio]
methyl]-3-(2-phenylethoxy)-2-pyridinyl]-2-
propenamide Hydrazone;

2-Sulfobenzaldehyde (E)-N-[3-(6-Hydrazinonic-
otinamido)propyl]-3-[6-[[(2,3,5,6-tetrafluorophenyl)
thio]methyl]-3-(2-phenylethoxy)-2-pyridinyl]-2-
propenamide Hydrazone;

2-Sulfobenzaldehyde (E)-N-[3-(6-Hydrazinonic-
otinamido)propyl]-3-[6-[[(4-hydroxyphenyl)thio]
methyl]-3-(2-phenylethoxy)-2-pyridinyl]-2-
propenamide Hydrazone;

2-Sulfobenzaldehyde (E)-N-[2-(6-Hydrazinonic-
otinamido)-ethyl]-3-[6-[[(2,6-dichlorophenyl)thio]
methyl]-3-(2-phenylethoxy)-2-pyridinyl]-2-
propanamide Hydrazone;

2-Sulfobenzaldehyde N-[3-(6-Hydrazinonicotinamido)-
propyl]-1-[3-([1,1'-biphenyl]-4-ylmethyl)-2H-1-
benzopyran-7-yl]-cyclopentanecarboxamide Hydra-
zone;

2-Sulfobenzaldehyde 6-[5-(6-Hydrazinonicotinamido)-
pentyloxy]-5-(2-propenyl)-1,2,3,4-tetrahydro-
naphthalen-1 one Hydrazone;

2-Sulfobenzaldehyde 6-[6-(6-Hydrazinonicotinamido)-
hexyloxy]-5-(2-propenyl)-1,2,3,4-tetrahydro-
naphthalen-1 one Hydrazone;

2-Sulfobenzaldehyde 6-[6-(6-Hydrazinonicotinamido)-4,
4-dimethylpentyloxy]-5-(2-propenyl)-1,2,3,4-
tetrahydronaphthalen-1-one Hydrazone;

2-Sulfobenzaldehyde 6-[6-(6-Hydrazinonicotinamido)-5,
5-dimethylhexyloxy]-5-(2-propenyl)-1,2,3,4-
tetrahydronaphthalen-1-one Hydrazone;

2-Sulfobenzaldehyde 6-[4-(6-Hydrazinonicotinamido)-
butoxy]-5-(2-propenyl)-1,2,3,4-tetrahydronaphthalen-
1-one Hydrazone;

2-Sulfobenzaldehyde 6-[3-(6-Hydrazinonicotinamido)-
propoxy]-5-(2-propenyl)-1,2,3,4-tetrahydro-
naphthalen-1-one Hydrazone;

2-Sulfobenzaldehyde 6-[2-(6-Hydrazinonicotinamido)-
ethoxy]-5-(2-propenyl)-1,2,3,4-tetrahydro-
naphthalen-1 one Hydrazone;

2-[[[5-[[2,2-Dimethyl-6-[(4-(3,4-methylenedioxy-
phenyl)-6-phenyl-2-pyridinyl)oxy]-1-hexanamino]
carbonyl]-2-pyridinyl]hydrazono]methyl]-
benzenesulfonic acid;

N-[2,2-Dimethyl-6-[(4-(3,4-methylenedioxyphenyl)-6-
phenyl-2-pyridinyl)oxy]-hexyl]-bis-S-(1-
ethoxyethylmercapto-acetyl)pentanoate;

2-[[[5-[[N-[6-[(4,6-diphenyl-2-pyridinyl)oxy]-hexanoyl]-
glycine-alpha-amino]carbonyl]-2-pyridinyl]
hydrazono]-methyl]-benzenesulfonic acid;

2-Acetyl-4-ethyl-[5-[6-[[[(2-sulfonylphenyl)
methylene]hydrazino]-3-pyridinyl]carbonyl]amino]
hexyl]oxy]phenol;

2,4-Diethyl-[5-[5,5-dimethyl-6-[[6-[[[(2-sulfonylphenyl)
methylene]hydrazino]-3-pyridinyl]carbonyl]amino]
hexyl]oxy]phenol;

3-(4-(5-(4,6-diphenyl(2-pyridyloxy))pentyloxy)-3-
ethoxyphenyl)-N-((6-hydrazino(3-pyridyl))sulfonyl)
prop-2-enamide;

2-((6-((1-aza-2-(2-sulfophenyl vinyl)-amino)(3-pyridyl))
carbonyl)-7-(5-(4,6-diphenyl(2-pyridyl-oxy))
pentyloxy-1,2,3,4-tetrahydro-isoquinoline-3-
carboxylic acid;

2-((6-((1-aza-2-(2-sulfophenyl vinyl)-amino)(3-pyridyl)
carbonylamino)-3-(4-(5-(4,6-diphenyl(2-pyridyloxy)
pentyloxy)phenyl)propanoic acid;

2-((6-((1-aza-2-(2-sulfophenyl vinyl)-amino)(3-pyridyl)
carbonylamino)-3-(2-(5-(4,6-diphenyl(2-pyridyloxy)
pentyloxy)phenyl)propanoic acid;

3-((6-((1-aza-2-(2-sulfophenyl vinyl)amino)(3-pyridyl)
carbonylamino)-3-(N-(6-(4,6-diphenyl(2-pyridyloxy)-
2,2-dimethylhexyl)carbamoyl)propanoic acid;

2-(2-aza-2-((5-(N-(3-(2-(2-(3-((1-((N-methyl-N-(2-
phenylethyl)carbamoyl)methyl)-5-(phenylmethoxy)-
indol-2-yl)carbonylamino)-propoxy)ethoxy)ethoxy)-
propyl)-carbamoyl)(2-pyridyl))amino)vinyl)-
benzenesulfonic acid;

2-(2-((6-((1-aza-2-(2-sulfophenyl)vinyl)-amino)(3-
pyridyl)carbonylamino)-3-carboxypropanoylamino)-3-
(2-(5-(4,6-diphenyl(2-pyridyloxy))pentyloxy)-phenyl)
propanoic acid;

2-(2-aza-2-((5-(N-(2-(N-(3-(2-(2-(3-(2-(2,5-
dioxoimidazolidin-4-yl)acetylamino)-propoxy)ethoxy)
ethoxy)-propyl)carbamoyl)-1-(N-(6-(4,6-diphenyl(2-
pyridyloxy))-2,2-dimethylhexyl)carbamoyl)-ethyl)
carbamoyl(2-pyridyl))amino)-vinyl)benzenesulfonic
acid;

6-((6-((1-aza-2-(2-sulfophenyl)-vinyl)amino)(3-pyridyl)
carbonylamino)-2-((1-((N-methyl-N-(2-phenylethyl)
carbamoyl)methyl)-5-(phenylmethoxy)indol-2-yl)
carbonylamino)hexanoic acid;

1-(3-((6-((1-aza-2-(2-sulfophenyl)vinyl)amino)-(3-
pyridyl)carbonylamino)-3-(N-(6-(4,6-diphenyl(2-
pyridyloxy)-2,2-dimethylhexyl)carbamoyl)-
propanoylamino)-ethane-1,2-dicarboxylic acid;

1-(2-(3-((6-((1-aza-2-(2-sulfophenyl)vinyl)-amino)(3-
pyridyl)carbonylamino)-3-(N-(6-(4,6-diphenyl(2-
pyridyloxy)-2,2-dimethylhexyl)carbamoyl)-
propanoylamino)-3-carboxypropanoylamino)ethane-1,
2-dicarboxylic acid;

2-(2-aza-2-((5-(N-(1-(N-(6-(4,6-diphenyl(2-
pyridyloxy))-2,2-dimethylhexyl)carbamoyl)-2-(3-(((4,
5,6-trihydroxy-3-(hydroxymethyl)(2-oxanyl))amino)-
carbonylamino)-propanoylamino)ethyl)carbamoyl(2-
pyirdyl))amino)vinyl)-benzenesulfonic acid;

2-(2-aza-2-((5-((6-(4-benzo[d]1,3-dioxolan-5-yl-6-phenyl(2-pyridyloxy))-2,2-dimethylhexanoyl-amino)sulfonyl)-(2-pyridyl))amino)-vinyl)benzenesulfonic acid;

6-(4-benzo[d]1,3-dioxolan-5-yl-6-phenyl(2-pyridyloxy))-N-(1-(N-((6-hydrazino(3-pyridyl))sulfonyl)-cabamoyl)-2-(4-hydroxyphenyl)ethyl)-2,2-dimethylhexanamide;

4-(4,6-diphenyl(2-pyridyloxy))-N-(1-(N-(1-(N-((6-hydrazino(3-pyridyl))sulfonyl)cabamoyl)-2-(4-hydroxyphenyl)ethyl)-carbamoyl)-isopropyl)butanamide;

3-(4-(3-((6-((1-aza-2-(2-sulfophenyl)vinyl)amino)(3-pyridyl))carbonylamino)-propoxy)phenyl)-2-(2,2 dimethyl-6-(5-oxo-1-prop-2-enyl(2-6,7,8-trihydronaphthyloxy))hexanoylamino)propanoic acid;

3-((6-((1-aza-2-(2-sulfophenyl vinyl)amino)(3-pyridyl)carbonylamino)-3-(N-(6-(4-benzo[d]1,3-dioxolan-5 yl-6-phenyl(2-pyridyloxy))-2,2-dimethylhexyl)carbamoyl)propanoic acid;

2-(2-aza-2-((5-(N-(1-(N-(6-(4-benzo[d]1,3-dioxolan-5-yl-6-phenyl(2-pyridyloxy))-2,2-dimethyl-hexyl)carbamoyl)-2-(4-hydroxyphenyl)ethyl)-carbamoyl(2-pyridyl))amino)vinyl)-benzenesulfonic acid;

2-((6-((1-aza-2-(2-sulfophenyl vinyl)amino)(3-pyridyl) carbonylamino)-2-(2,2-dimethyl-6-(5-oxo-1-prop-2-enyl(2-6,7,8-trihydronaphthyloxy))-hexanoylamino)acetic acid;

2-((6-((1-aza-2-(2-sulfophenyl vinyl)amino)(3-pyridyl) carbonylamino)-2-(2,2-dimethyl-6-(5-oxo-1-prop-2-enyl(2-6,7,8-trihydronaphthyloxy))-hexanoylamino)acetic acid;

3-((6-((1-aza-2-(2-sulfophenyl vinyl)amino)(3-pyridyl) carbonylamino)-3-(N-(6-(6-ethyl-3-hydroxy-4-phenylphenoxy)-2,2-dimethylhexyl)-carbamoyl)propanoic acid;

2-((6-((1-aza-2-(2-sulfophenyl vinyl)amino)(3-pyridyl) carbonylamino)-2-(6-(4-benzo[d]1,3-dioxolan-5-yl-6-phenyl(2-pyridyloxy))-2,2-dimethylhexanoylamino)acetic acid;

2-(2-aza-2-((5-(N-(5-((3-((N-(6-(4,6-diphenyl(2-pyridyloxy))-2,2-dimethylhexanoylamino)-3-(4-hydroxyphenyl)propanoylamino)-1-(N-(2,3,4,5,6-pentahydroxyhexyl)carbamoyl)pentyl)carbamoyl(2-pyridyl))amino)vinyl)benzenesulfonic acid;

2-(2-aza-2-((5-(N-(5-((3-((N-(6-(4-benzo[d]1,3-dioxolan-5-yl-6-phenyl(2-pyridyloxy))-2,2-dimethylhexyl)-carbamoyl)-2-(N-(2,3,4,5,6-pentahydroxyhexyl)-carbamoyl)-ethyl)carbamoyl(2-pyridyl))amino)vinyl)benzenesulfonic acid;

2-(2-aza-2-((5-(N-(5-((3-((N-(6-(4-benzo[d]1,3-dioxolan-5-yl-6-phenyl(2-pyridyloxy))-2,2-dimethylhexyl)-carbamoyl)amino)phenyl)carbonylamino)-1-(N-(2,3,4,5,6-pentahydroxyhexyl)-carbamoyl)pentyl)carbamoyl(2-pyridyl))amino)vinyl)benzenesulfonic acid;

2-((6-((1-aza-2-(2-sulfophenyl vinyl)amino)(3-pyridyl)) carbonylamino)-3-(N-(6-(4-benzo[d]1,3-dioxolan-5-yl-6-phenyl(2-pyridyloxy))-2,2-dimethylhexyl)carbamoyl)-propanoylamino)-3-carboxypropanoylamino)-3-carboxypropanoylamino)-ethane-1,2-dicarboxylic acid;

2-((6-((1-aza-2-(2-sulfophenyl vinyl)amino)(3-pyridyl)) carbonylamino)-3-(2-(5-(4-benzo[d]1,3-dioxolan-5-yl-6-phenyl(2-pyridyloxy))pentyloxy)-phenyl)propanoic acid; and 2-({2-[((2S)-2-[Bis(carboxymethyl)amino]-3-{4-[({[3-(2-{2-[3-(5-{5-[5-(4,6-diphenyl(2-pyridyloxy))-1,1-dimethylpentyl](5H-1,2,3,4-tetraazolyl)}-pentanoylamino)propoxy]ethoxy}ethoxy)propyl]amino}thioxomethyl)amino]phenyl}propyl) (carboxymethyl)amino]ethyl}-(carboxymethyl)amino) acetic acid.

26. The method according to claim 1, wherein the radio-labeled LTB4 binding agent is elected from the group consisting of:

$^{99m}$Tc(tricine)(TPPTS)(4-ethyl-2-(4-fluorophenyl)-[5-[5,5-dimethyl-6-[[[6-diazenido-3-pyridinyl]carbonyl]amino]hexyl]oxy]phenol);

$^{99m}$Tc(tricine)(TPPDS)(4-ethyl-2-(4-fluorophenyl)-[5-[5,5-dimethyl-6-[[[6-diazenido-3-pyridinyl]carbonyl]-amino]hexyl]oxy]phenol);

$^{99m}$Tc(tricine)(TPPMS)(4-ethyl-2-(4-fluorophenyl)-[5-[5,5-dimethyl-6-[[[6-diazenido-3-pyridinyl]carbonyl]-amino]hexyl]oxy]phenol);

$^{99m}$Tc(tricine)(3-sulfonatopyridine))(4-ethyl-2-(4-fluorophenyl)-[5-[5,5-dimethyl-6-[[[6-diazenido-3-pyridinyl]carbonyl]amino]hexyl]oxy]phenol);

$^{99m}$Tc(tricine)(TPPTS)(4-ethyl-2-(4-fluorophenyl)-[5-[4-[[[6-diazenido-3-pyridinyl]carbonyl]amino]-butyl]oxy]phenol);

$^{99m}$Tc(tricine)(TPPTS)(2-[[5-[[(6-[(4,6-diphenyl-2-pyridinyl)oxy]-1-hexanamino]carbonyl]-2-pyridinyl]diazenido]);

$^{99m}$Tc(tricine)(TPPTS)(2-[[5-[[2,2-dimethyl-6-[(6-fluorophenyl-4-phenyl-2-pyridinyl)oxy]-1-hexanamino]carbonyl]-2-pyridinyl]diazenido]);

$^{99m}$Tc(tricine)(TPPTS)(2-[[5-[[N-[6-[(4,6-diphenyl-2-pyridinyl)oxy]-hexanoyl]-tyrosine-O-[3-propanamino]]carbonyl]-2-pyridinyl]diazenido]);

$^{99m}$Tc(tricine)(TPPTS)(2-[[[5-[[N-[6-[(4-(3,4-methylenedioxyphenyl)-6-phenyl-2-pyridinyl)oxy]-hexanoyl]-tyrosine-O-[3-propanamino]]-carbonyl]-2-pyridinyl]diazenido]);

$^{99m}$Tc(tricine)(TPPTS)(2-[[[5-[[alpha-N-[6-[(4,6-diphenyl-2-pyridinyl)oxy]-hexanoyl]-lysine-epsilon-N-amino]carbonyl]-2-pyridinyl]diazenido]);

$^{99m}$Tc(tricine)(TPPTS)(2-[[[5-[[[6-[(4,6-diphenyl-2-pyridinyl)oxy]-2,2-dimethyl-1-hexyl]aza]carbonyl]-2-pyridinyl]diazenido]);

$^{99m}$Tc(tricine)(TPPTS)(4-ethyl-2-(4-fluorophenyl)-[5-[6,6-dimethyl-7-[[6-[[6-diazenido]-3-pyridinyl]carbonyl]amino]heptyl]oxy]phenol);

$^{99m}$Tc(tricine)(TPPTS)(2[6-[(4,6-Diphenyl-2-pyridinyl)oxy]pentyl]-6-(8-[[[6-diazenido]-3-pyridinyl]carbonyl]amino-5-aza-4-oxooctyloxy) benzenepropanoic Acid);

$^{99m}$Tc(tricine)(3-pyridinesulfonic acid))(2-[6-[(4,6-Diphenyl-2-pyridinyl)oxy]pentyl]-6-(8-[[[6-diazenido]-3-pyridinyl]carbonyl]amino-5-aza-4-oxooctyloxy)benzenepropanoic Acid);

$^{99m}$Tc(tricine)(3,5-pyridinedicarboxylic acid)(2-[6-[(4,6-Diphenyl-2-pyridinyl)oxy]pentyl]-6-(8-[[[6-diazenido]-3-pyridinyl]carbonyl]amino-5-aza-4-oxooctyloxy)-benzenepropanoic Acid;

$^{99m}$Tc(tricine)(TPPTS)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(TFP)(6-(11-[[[6 diazenido]-3-pyridinyl]carbonyl]amino-3,6,9-trioxaundecyl-oxy)-2-[5-[(5- oxo-1-(2-propenyl)-5,6,7,8-tetrahydro-2-naphthalenyl) oxy]pentyloxy]-benzenepropanoic Acid;

$^{99m}$Tc(tricine)(3,5-pyridinedicarboxylic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(isonicotinic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyoxy]benzenepropanoic Acid);

$^{99m}$Tc(tricine)(nicotinic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyoxy]benzenepropanoic Acid);

$^{99m}$Tc(tricine)(3-pyridinesulfonic acid)(6-(11-[[[6-diazenido]-3-pyridinyl]carbonyl]amino-3,6,9-trioxaundecylox-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(hydroxyethylisonicotinamide)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(4-methyl-5-imidazolemethanol)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(4-methyl-5-thiazoleethanol)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(pyridine)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyloxy]benzenepropanoic Acid);

$^{99m}$Tc(tricine)(4-pyridylethylsulfonic acid)(6-(11-[[[6-diazenido]-3-pyridinyl]carbonyl]amino-3,6,9-trioxaundecyloxy)-2-[5-[(5-oxo-1-(2-propenyl)-5,6,7,8-tetrahydro-2-naphthalenyl)oxy]pentyl]oxy]benzenepropanoic Acid);

$^{99m}$Tc(tricine)(TPPTS)(N-((6-(diazenido)(3-pyridyl))sulfonyl)-3-(1-((N-(2-phenylethyl)carbamoyl)methyl)-5-(phenylmethoxy)indol-3-yl)prop-2-enamide);

$^{99m}$Tc(tricine)(TPPTS)((2-((5-carbamoyl(2-pyridyl)diazenido)ethyl 3-((7-(3-(6-ethyl-4-(4-fluorophenyl)-3-hydroxyphenoxy)propoxy)-8-propylchroman-2-yl)carbonylamino)propanoate);

$^{99m}$Tc(tricine)(TPPTS)(3-((7-(-(6-ethyl-4-(4-fluorophenyl)-3-hydroxyphenoxy)propoxy)8-propylchroman-2-yl)carbonylamino)propyl-2-methylpropanoate, 2-(2((5-carbamoyl(2-pyridyl)diazenido));

$^{99m}$Tc(tricine)(TPPTS)(N-(3-((7-(3-(6-ethyl-4-(4-fluorophenyl)-3-hydroxyphenoxy)propoxy)-8-propylchroman-2-yl)carbonylamino)propyl)-2 methylpropanamide, 2-(2-((5-carbamoyl(2-pyridyl))diazenido);

$^{99m}$Tc(tricine)(TPPTS)(2-(2-((5-(N-(6-(6-ethyl-3-hydroxy-4-(1-methylpyrazol-5-yl)phenoxy)-2,2-dimethylhexyl)carbamoyl)(2-pyridyl))diazenido);

$^{99m}$Tc(tricine)(3-pyridinesulfonic acid)(2-(2-((5-(N-(6-(6-ethyl-3-hydroxy-4-(1-methylpyrazol-5-yl)phenoxy)-2,2-dimethylhexyl)carbamoyl)(2-pyridyl))diazenido);

$^{99m}$Tc(tricine)(TPPTS)(2-(2-((5-((3-((6-ethyl-4-(4-fluorophenyl)-3-hydroxyphenoxy)methyl)-piperidyl)carbonyl)(2-pyridyl))diazenido)

$^{99m}$Tc(tricine)(TPPTS)(2-(2-((5-(N-(3-(2-(2-(3-(5-(5-(5-(4,6-diphenyl(2-pyridyloxy))-1,1-dimethylpentyl)(1,2,3,4-tetraazolyl))-pentanoylamino)propoxy)ethoxy)ethoxy)propyl)carbamoyl)(2-pyridyl))diazenido);

$^{99m}$Tc(tricine)(TPPTS)(2-(2-((5-(N-(2-(2-(2-(2-(2-(2-(2-(5-(4-(5-(4,6-diphenyl(2-pyridyloxy))-1,1-dimethylpentyl)(1,2,3,5-tetraazolyl))pentanoylamino)-ethoxy)ethoxy)ethoxy)ethoxy)ethoxy)ethoxy)ethyl)carbamoyl)(2-pyridyl))diazenido);

$^{99m}$Tc(tricine)(TPPTS)(2-(2-((5-(N-(5-(4-(5-(4,6-diphenyl(2-pyridyloxy))-1,1-dimethylpentyl)(1,2,3,5-tetraazolyl))-pentanoylamino)-1-(6-deoxy-☐-cyclodextryl)-carbamoyl)pentyl)carbamoyl)(2-pyridyl))diazenido);

$^{99m}$Tc(tricine)(TPPTS)(3-(6-(3-N-(5-((6-(diazenido)(3-pyridyl))carbonylamino)-5-(N-(☐-methoxypolyethylene(750)glycoxyethyl)carbamoyl)pentyl)carbamoyl)propoxy)2-(5-(4,6-diphenyl(2-pyridyloxy))pentyloxy)phenyl)propanoic Acid);

$^{99m}$Tc(tricine)(TPPTS)(3-(6-(3-(N-(3-(2-(2-(3-((6-(diazenido)(3-pyridyl))carbonylamino)-propoxy)ethoxy)ethoxy)propyl)carbamoyl)propoxy)2-(5-(4,6-diphenyl(2-pyridyloxy))pentyloxy)-phenyl)propanoic Acid);

$^{99m}$Tc(tricine)(TPPTS)(3-(6-(3-(N-(5-((6-(diazenido)(3-pyridyl))carbonylamino)-5-(N-(2,3,4,5,6-pentahydroxyhexyl)carbamoyl)pentyl)carbamoyl)propoxy)2-(5(4,6-diphenyl(2-pyridyloxy))pentyloxy)phenyl)propanoic Acid);

$^{99m}$Tc(tricine)(TFP)(3-(6-(3-(N-(5-((6-(diazenido)(3-pyridyl))carbonylamino)-5-(N-(2,3,4,5,6-pentahydroxyhexyl)carbamoyl)pentyl)carbamoyl)propoxy)2-(5-(4,6-diphenyl(2-pyridyloxy))pentyloxy)phenyl)propanoic Acid);

$^{99m}$Tc(tricine)(TPPTS)(3-(6-(3-(N-(3-((6-(diazenido)(3-pyridyl))carbonylamino)-propyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(TFP)(3-(6-(3-(N-(3-((6-(diazenido)(3-pyridyl))carbonylamino)-propyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(pyridine)(3-(6-(3-(N-(3-((6-(diazenido)(3-pyridyl))carbonylamino)-propyl)carbamoyl)propoxy)-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6(3-N-(2-(2-(2-(2-(2-(2-(2-((6-(diazenido)(3-pyridyl))carbonylamino)ethoxy)ethoxy)ethoxy)ethoxy)ethoxy)ethoxy)ethyl)-carbamoyl)propoxy)-2-5-(5-oxo-1-prop-2-enyl(2-6,7,8-trihydronaphthyloxy))-pentyloxy)phenyl)propanoic Acid);

$^{99m}$Tc(tricine)(TPPTS)(3-(6-(3-N-(5-((6-(diazenido)(3-pyridyl))carbonylamino)-5-(N-(2,3,4,5,6-pentahydroxyhexyl)carbamoyl)pentyl)carbamoyl)propoxy-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6-(3-N-(5-((6-(diazenido)(3-pyridyl))carbonylamino)-5-(N-(6-deoxy-☐- cyclodextryl)carbamoyl)pentyl)carbamoyl)propoxy-2-(5-(5-oxo-1-prop-2-enyl(2-6,7,8-trihydronaphthyloxy))pentyloxy)phenyl)propanoic Acid);

$^{99m}$Tc(tricine)(TPPTS)(3-(6-(3-(N-(3-((6-((diazenido)(3-pyridyl))-Gly-Lys-Lys-Lys)aminopropyl)carbamoyl)-propoxy)-2-(5-(5-oxo-1-prop-2-enyl(2-6,7,8-trihydronaphthyloxy))pentyloxy)phenyl)propanoic Acid);

$^{99m}$Tc(tricine)(TPPTS)((E)N-[3-(6-diazenidonicotinamido)-propyl]-3-[6-[[(2,6-dichlorophenyl)thio]methyl]-3-(2-phenylethoxy)-2-pyridinyl]-2-propenamide);

$^{99m}$Tc(tricine)(TPPTS)((E)-N-[3-(6-diazenidonicotinamido)-propyl]-3-[6-[(phenylthio)methyl]-3-(2-phenylethoxy)-2-pyridinyl]-2-propenamide);

$^{99m}$Tc(tricine)(TPPTS)((E)-N-[3-(6-diazenidonicotinamido)-propyl]-3-[6-[[(2-chlorophenyl)thio]methyl]-3-(2-phenylethoxy)-2-pyridinyl]-2-propenamide);

$^{99m}$Tc(tricine)(TPPTS)((E)-N-[3-(6-diazenidonicotinamido)-propyl]-3-[6-[[(2,6-dimethylphenyl)thio]methyl]-3-(2-phenylethoxy)-2-pyridinyl]-2-propenamide)

$^{99m}$Tc(tricine)(TPPTS)((E)-N-[3-(6-diazenidonicotinamido)-propyl]-3-[6-[[(2,3,5,6-tetrafluorophenyl)-thio]methyl]-3-(2-phenylethoxy)-2-pyridinyl]-2-propenamide);

$^{99m}$Tc(tricine)(TPPTS)((E)-N-[3-(6-diazenidonicotinamido)-propyl]-3-[6-[[(2,3,5,6-tetrafluorophenyl)thio]methyl]-3-(2-phenylethoxy)-2-pyridinyl]-2-propenamide);

$^{99m}$Tc(tricine)(TPPTS)((E)-N-[2-(6-diazenidonicotinamido)-ethyl]-3-[6-[[(2,6-dichlorophenyl)thio]methyl]-3-(2-phenylethoxy)-2-pyridinyl]-2-propanamide);

$^{99m}$Tc(tricine)(TPPTS)(6-[6-(6-diazenidonicotinamido)-4,4-dimethylpentyloxy]-5-(2-propenyl)-1,2,3,4-tetrahydronaphthalen-1-one);

$^{99m}$Tc(tricine)(TPPTS)(2-[[[5-[[2,2-Dimethyl-6-[(4-(3,4-methylenedioxyphenyl)-6-phenyl-2-pyridinyl)oxy]-1-hexanamino]carbonyl]-2-pyridinyl]diazenido);

$^{99m}$Tc(tricine)(TPPTS)(2-[[[5-[[N-[6-[(4,6-diphenyl-2-pyridinyl)oxy]-hexanoyl]-glycine-alpha-amino]carbonyl]-2-pyridinyl]diazenido);

$^{99m}$Tc(tricine)(TPPTS)(2,4-Diethyl-[5-[5,5-dimethyl-6-[[6-[[diazenido]-3-pyridinyl]carbonyl]-amino]hexyl]oxy]phenol);

$^{99m}$Tc(tricine)(TPPTS)(2-((6-diazenido)(3-pyridyl)carbonylamino)-3-(2-(5-(4,6-diphenyl(2-pyridyloxy))pentyloxy)phenyl)propanoic acid);

$^{99m}$Tc(tricine)(TPPTS)(3-((6-diazenido)(3-pyridyl)carbonylamino)-3-(N-(6-(4,6-diphenyl(2-pyridyloxy))-2,2-dimethylhexyl)carbamoyl)propanoic acid);

$^{99m}$Tc(tricine)(TPPTS)(2-(2-((6-(diazenido)(3-pyridyl)carbonylamino)-3-carboxypropanoylamino)-3-(2-(5-(4,6-diphenyl(2-pyridyloxy))pentyloxy)-phenyl)propanoic acid);

$^{99m}$Tc(tricine)(TPPTS)(2-(2-((5-(N-(2-(N-(3-(2-(2-(3-(2-(2,5-dioxoimidazolidin-4-yl)acetylamino)-propoxy)ethoxy)ethoxy)-propyl)carbamoyl)-1-(N-(6-(4,6-diphenyl(2-pyridyloxy))-2,2-dimethylhexyl)carbamoyl)-ethyl)carbamoyl(2-pyridyl))diazenido);

$^{99m}$Tc(tricine)(TPPTS)(1-(3-((6-(diazenido)-(3-pyridyl)carbonylamino)-3-(N-(6-(4,6-diphenyl(2-pyridyloxy))-2,2-dimethylhexyl)carbamoyl)-propanoylamino)-ethane-1,2-dicarboxylic acid);

$^{99m}$Tc(tricine)(TPPTS)(2-(2-((5-(N-(1-(N-(6-(4,6-diphenyl(2-pyridyloxy))-2,2-dimethylhexyl)-carbamoyl)-2-(3-(((4,5,6-trihydroxy-3-(hydroxymethyl)(2-oxanyl))amino)carbonylamino)-propanoylamino)ethyl)carbamoyl(2-pyridyl))diazenido);

$^{99m}$Tc(tricine)(TPPTS)(2-(2-((5-((6-(4-benzo[d]1,3-dioxolan-5-yl-6-phenyl(2-pyridyloxy))-2,2-dimethylhexanoyl-amino)sulfonyl)-(2-pyridyl))diazenido);

$^{99m}$Tc(tricine)(TPPTS)(3-((6-(diazenido)(3-pyridyl)carbonylamino)-3-(N-(6-(4-benzo[d]1,3-dioxolan-5-yl-6-phenyl(2-pyridyloxy))-2,2-dimethylhexyl)carbamoyl)propanoic acid);

$^{99m}$Tc(tricine)(TFP)(3-((6-((diazenido)(3-pyridyl)carbonylamino)-3-(N-(6-(4-benzo[d]1,3-dioxolan-5-yl-6-phenyl(2-pyridyloxy))-2,2-dimethylhexyl)carbamoyl)propanoic acid);

$^{99m}$Tc(tricine)(TPPTS)(2-(2-((5-(N-(1-(N-(6-(4-benzo[d]1,3-dioxolan-5-yl-6-phenyl(2-pyridyloxy))-2,2-dimethyl-hexyl)carbamoyl)-2-(4-hydroxyphenyl)ethyl)carbamoyl(2-pyridyl))diazenido);

$^{99m}$Tc(tricine)(TPPTS)(2-((6-(diazenido)(3-pyridyl)carbonylamino)-2-(6-(4-benzo[d]1,3-dioxolan-5-yl-6-phenyl(2-pyridyloxy))-2,2-dimethylhexanoylamino)acetic acid);

$^{99m}$Tc(tricine)(TPPTS)(2-(2-((5-(N-(5-((3-((N-(6-(4,6-diphenyl(2-pyridyloxy))-2,2-dimethylhexanoyl-amino)-3-(4-hydroxyphenyl)propanoylamino)-1-(N-(2,3,4,5,6-pentahydroxyhexyl)carbamoyl)pentyl)carbamoyl(2-pyridyl))diazenido);

$^{99m}$Tc(tricine)(TPPTS)(2-(2-((5-(N-(5-((3-((N-(6-(4-benzo[d]1,3-dioxolan-5-yl-6-phenyl(2-pyridyloxy))-2,2-dimethylhexyl)-carbamoyl)-2-(N-(2,3,4,5,6-pentahydroxyhexyl)carbamoyl)-ethyl)carbamoyl(2-pyridyl))diazenido);

$^{99m}$Tc(tricine)(TPPTS)(2-(2-((5-(N-(5-((3-((N-(6-(4-benzo[d]1,3-dioxolan-5-yl-6-phenyl(2-pyridyloxy))-2,2-dimethylhexyl)carbamoyl)amino)-phenyl)carbonylamino)-1-(N-(2,3,4,5,6-pentahydroxyhexyl)carbamoyl)pentyl)carbamoyl(2-pyridyl))diazenido);

$^{99m}$Tc(tricine)(TPPTS)(2-((6-diazenido)(3-pyridyl))carbonylamino)-3-(N-(6-(4-benzo[d]1,3-dioxolan-5-yl-6-phenyl(2-pyridyloxy))-2,2-dimethylhexyl)carbamoyl)-propanoylamino)-3-carboxypropanoylamino)-3-carboxypropanoylamino)-ethane-1,2-dicarboxylic acid);

$^{99m}$Tc(tricine)(TPPTS)(2-((6-diazenido)(3-pyridyl))carbonylamino)-3-(2-(5-(4-benzo[d]1,3-dioxolan-5-yl-6-phenyl(2-pyridyloxy))pentyloxy)-phenyl)propanoic acid);

$^{99m}$TcO(4-ethyl-2-(4-fluorophenyl)-5-[(5,5-dimethyl-6-aminohexyl)oxy]phenol N-[4-(carboxy)benzyl]-N,N'-bis[2-thiolatoethyl]-glycinamide);

$^{99m}$TcO(N-[2,2-Dimethyl-6[(4-(3,4-methylenedioxyphenyl)-6-phenyl-2-pyridinyl)oxy]-hexyl]-bis (mercapto-acetyl)pentanoate); and $^{111}$In(2-({2-[((2S)-2-[Bis(carboxymethyl)amino]-3-{4-[({[3-(2-{2-[3-(5-{5-[5-(4,6-diphenyl(2-pyridyloxy)-1,1-dimethylpentyl](5H-1,2,3,4 tetrazolyl)}pentanoyl-amino)-propoxy]ethoxy}ethoxy)propyl]- amino}thioxomethyl)amino]phenyl}propyl)(carboxymethyl)amino]ethyl}-(carboxymethyl)amino)acetate).

27. A kit comprising a reagent of claim 22 and a perfusion imaging agent.

28. The kit of claim 27 further comprising a reducing agent.

29. The kit of claim 28 wherein the reducing agent is tin(II).

30. The kit of claim 29 further comprising one or more ancillary ligands.

31. The kit of claim 30 wherein the ancillary ligands are tricine and TPPTS.

32. A kit co rising radiolabeled LTB4 binding agent of claim 18 and a perfusion imaging agent.

33. The kit of claim 32 further comprising a reducing agent.

34. The kit of claim 33 wherein the reducing agent is tin(II).

35. The kit of claim 34 further comprising one or more ancillary ligands.

36. The kit of claim 35 wherein the ancillary ligands are tricine and TPPTS.

37. A kit comprising radiolabeled LTB4 binding agent of claim 18 and a radiolabeled perfusion imaging agent of claim 22.

38. The kit of claim 37 further comprising a reducing agent.

39. The kit of claim 38 wherein the reducing agent is tin(II).

40. The kit of claim 39 further comprising one or more ancillary ligands.

41. The kit of claim 40 wherein the ancillary ligands are tricine and TPPTS.

42. The method according to claim 1, further comprising forming an image from the detection of said agents.

43. The method according to claim 42, wherein the images are displayed side-by-side to faciliate interpretation of the localization of the radiolabeled LTB4 binding agent in the body, relative to the distribution of the radiolabeled perfusion agent in the body.

44. The method according to claim 42, wherein the images are are overlayed to faciliate interpretation of the localization of the radiolabeled LTB4 binding agent in the body, relative to the distribution of the radiolabeled perfusion agent in the body.

45. A method according to claim 1, wherein the radiolabeled LTB4 binding agent is a reagent of which undergoes direct transformation into a compound radiolabeled with a radioisotope selected from the group consisting of, $^{123}$I, $^{125}$I, $^{18}$F, $^{11}$C, $^{13}$N, $^{15}$O, and $^{75}$Br, and said reagent having the formula:

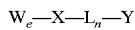

wherein, $W_e$ is selected from the group:

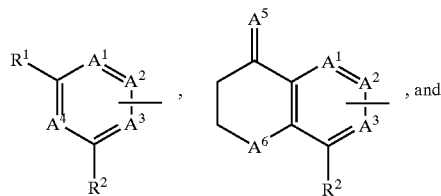

-continued

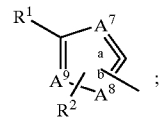

wherein, $A^1$ is N, C—OH, or CH;

$A^2$ and $A^3$ are independently N or CH;

$A^4$ is N or $CR^3$;

$A^5$ is O or S;

$A^6$ is O, $CH_2$ or S;

$A^7$ is C—OH, N, NH, O or S;

$A^8$ is NH, $CH_2$, O, S, N, or CH;

$A^9$ is N or CH;

a and b indicate the alternative positions of a double bond;

$R^1$ is selected from the group: H, —C(=NH)$NH_2$, $C_1$-$C_6$ alkyl substituted with 0–3 $R^4$, $C_1$-$C_6$ alkoxy substituted with 0–3 $R^4$, aryl substituted with 0–3 $R^5$, and heterocycle substituted with 0–3 $R^5$;

$R^2$ is selected from the group: H, $C_1$-$C_3$ alkyl, $C_2$-$C_3$ alkenyl, cyclopropyl, cyclopropylmethyl, and aryl substituted with 0–3 $R^5$;

$R^3$ is —H, —OH or $C_1$-$C_3$ alkoxy;

or alternatively, $R^1$ and $R^3$ can be taken together with the atoms to which they are attached to form a fused phenyl ring substituted with 0–3 $R^5$;

$R^4$ is independently selected from the group: —F, —Cl, —Br, —I, =O, —N($R^6$)($R^7$), and —$CF_3$;

$R^5$ is independently selected from the group: —F, —Cl, —Br, —I, —N($R^6$)($R^7$), —$CF_3$, $C_1$-$C_3$ alkyl, $C_1$-$C_3$ alkoxy, and methylenedioxy;

$R^6$ and $R^7$ are independently H or $C_1$-$C_3$ alkyl;

provided that when $A^1$ and $A^2$ are CH, $A^3$ is C—X, and $A^4$ is $CR^3$, $R^1$ is selected from the group: $C_1$-$C_5$ alkyl substituted with 1–3 $R^4$, $C_1$-$C_5$ alkoxy substituted with 0–3 $R^4$, and aryl substituted with 0–3 $R^5$;

X is O, S, $CH_2$ or CH=CH;

$L_n$ is a linking group having the formula

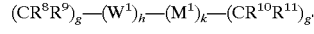

wherein, $R^8$, $R^9$, $R^{10}$ an are independently selected at each occurrence from the group: H, $C_1$-$C_5$ alkyl, and $C_1$-$C_5$ alkoxy, or alternatively, $R^8$ and $R^9$ or $R^{10}$ and $R^{11}$ may be taken together to form a 3–6 membered cycloalkyl or heterocycle;

$W^1$ is independently selected from the group: O, S, C(=O), OC(=O), CH=CH (OCH$_2$CH$_2$)$_p$ and (CH$_2$CH$_2$O)$_{p'}$, wherein p and p' are independently 1–3;

$M^1$ is selected from the group:
phenyl substituted with 0–3 $R^{12}$, heterocycle substituted with 0–3 $R^{12}$, benzophenone substituted with 0–3 $R^{12}$, and diphenylether substituted with 0–3 $R^{12}$;

$R^{12}$ is independently selected from the group: —COOR$^{13}$, $C_1$-$C_5$ alkyl substituted with 0–3 $R^{14}$, and $C_1$-$C_5$ alkoxy substituted with 0–3 $R^{14}$;

$R^{13}$ is H or $C_1$-$C_5$alkyl;

$R^{14}$ is —COOH;

g is 0–10;

h is 0–3;

k is 0–1;

g' is 0–5;

provided that when h is 0 and k is 0, g is >1;

and provided that when $W^1$ is O or S and k is 0, g+g' is ≧1; and

Y is selected from C(=O)NH, NHC(=O), C=O, C(=O)O, OC(=O), NHS(=O)$_2$, C(=O)NHS(=O)$_2$, COOH, C(=O)NH$_2$, NH(C=O)NH, or tetrazole; or a pharmaceutically acceptable salts thereof.

46. A method according to claim 45 wherein:

$W_e$ is selected from the group:

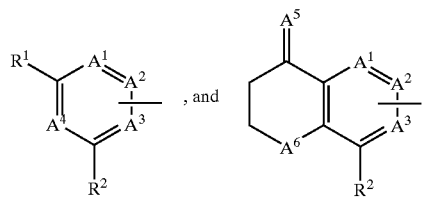
, and wherein, $A^1$ is N, C—OH, or CH;

$A^2$ and $A^3$ are CH;

$A^4$ is $CR^3$;

$A^5$ is O;

$A^6$ is O or $CH_2$;

$R^4$ is independently selected from the group:
—F, —Cl, =O, —N($R^6$)($R^7$), and —CF$_3$;

$R^5$ is independently selected from the group:
—F, —Cl, —CF$_3$, C$_1$–C$_3$ alkyl, C$_1$–C$_3$ alkoxy, and methylenedioxy;

X is O, CH$_2$ or CH=CH; and $R^8$, $R^9$, $R^{10}$ and $R^{11}$ are independently selected at each occurrence from the group: H, C$_1$–C$_5$ alkyl, and C$_1$–C$_5$ alkoxy;

or alternatively, $R^8$ and $R^9$ or $R^{10}$ and $R^{11}$ may be taken together to form a 3–6 membered cycloalkyl.

47. A reagent of claim 45, wherein:

$R^1$ is selected from the group:
H, —C(=NH)NH$_2$, C$_1$–C$_6$ alkyl substituted with 0–2 $R^4$, C$_1$–C$_6$ alkoxy substituted with 0–2 $R^4$, aryl substituted with 0–2 $R^5$, and heterocycle substituted with 0–2 $R^5$;

$R^3$ is —H, —OH or C$_1$–C$_3$ alkoxy;

or alternatively, $R^1$ and $R^3$ can be taken together with the atoms to which they are attached to form a fused phenyl ring substituted with 0–2 $R^5$;

$R^4$ is independently selected from the group:
=O, and —N($R^6$)($R^7$);

$R^5$ is independently selected from the group:
—F, C$_1$–C$_3$ alkyl, C$_1$–C$_3$ alkoxy, and methylenedioxy;

X is O, CH$_2$ or CH=CH;

$R^8$, $R_9$, $R^{10}$ an $R^{11}$ are independently selected at each occurrence from the group: H and C$_1$–C$_3$ alkyl;

or alternatively, $R^8$ and $R^9$ or $R^{10}$ and $R^{11}$ may be taken together to form a 3–6 membered cycloalkyl;

$W^1$ is O;

M1 is selected from the group:
phenyl substituted with 0–1 $R^{12}$, heterocycle substituted with 0–1 $R^{12}$, benzophenone substituted with 0–1 $R^{12}$, and diphenylether substituted with 0–1 $R^{12}$;

$R^{12}$ is independently selected from the group:
—COOR$^{13}$, C$_1$–C$_5$ alkyl substituted with 0–1 $R^{14}$, and C$_1$–C$_5$ alkoxy substituted with 0–1 $R^{14}$; and $M^2$ is selected from the group: aryl substituted with 0–1 $R^{19}$, cycloalkyl substituted with 0–3 $R^{19}$, and heterocycle substituted with 0–1 $R^{19}$.

48. A kit comprising a reagent of claim 45 and a perfusion imaging agent.

49. The method according to claim 5, wherein said ischemic tissue injury comprises reperfusion injury.

* * * * *